(12) United States Patent
Chu et al.

(10) Patent No.: US 12,024,528 B2
(45) Date of Patent: *Jul. 2, 2024

(54) BRIDGED TRICYCLIC CARBAMOYLPYRIDONE COMPOUNDS AND USES THEREOF

(71) Applicant: Gilead Sciences, Inc., Foster City, CA (US)

(72) Inventors: Hang Chu, Foster City, CA (US); Ana Z. Gonzalez Buenrostro, San Mateo, CA (US); Xiaochun Han, San Jose, CA (US); Anna E. Hurtley, San Mateo, CA (US); Lan Jiang, Foster City, CA (US); Jiayao Li, Foster City, CA (US); Gregg M. Schwarzwalder, Redwood City, CA (US); Devleena M. Shivakumar, Menlo Park, CA (US); Matthew J. Von Bargen, Redwood City, CA (US); Qiaoyin Wu, Foster City, CA (US); Hong Yang, Fremont, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/334,611

(22) Filed: Jun. 14, 2023

(65) Prior Publication Data
US 2023/0339972 A1    Oct. 26, 2023

Related U.S. Application Data

(63) Continuation of application No. 18/296,285, filed on Apr. 5, 2023, now abandoned.

(60) Provisional application No. 63/476,873, filed on Dec. 22, 2022, provisional application No. 63/328,061, filed on Apr. 6, 2022.

(51) Int. Cl.
| | |
|---|---|
| *C07D 498/20* | (2006.01) |
| *A61K 45/06* | (2006.01) |
| *A61P 31/18* | (2006.01) |
| *C07D 471/22* | (2006.01) |
| *C07D 491/22* | (2006.01) |
| *C07D 497/22* | (2006.01) |
| *C07D 498/22* | (2006.01) |
| *C07D 513/22* | (2006.01) |
| *C07D 515/22* | (2006.01) |

(52) U.S. Cl.
CPC ............ *C07D 498/20* (2013.01); *A61K 45/06* (2013.01); *A61P 31/18* (2018.01); *C07D 471/22* (2013.01); *C07D 491/22* (2013.01); *C07D 497/22* (2013.01); *C07D 498/22* (2013.01); *C07D 513/22* (2013.01); *C07D 515/22* (2013.01); *C07B 2200/05* (2013.01)

(58) Field of Classification Search
None
See application file for complete search history.

(56) References Cited

U.S. PATENT DOCUMENTS

| | | | |
|---|---|---|---|
| 9,522,912 B2 | 12/2016 | Bacon et al. | |
| 10,087,178 B2 | 10/2018 | Miyazaki et al. | |
| 11,084,832 B2 | 8/2021 | Chu et al. | |
| 11,492,352 B2 | 11/2022 | Ishii et al. | |
| 11,548,902 B1 | 1/2023 | Chu et al. | |
| 11,613,546 B2 | 3/2023 | Chu et al. | |
| 11,697,652 B2 | 7/2023 | Jiang et al. | |
| 11,884,683 B2 | 1/2024 | Yu et al. | |
| 11,897,892 B2 | 2/2024 | Chu et al. | |
| 2009/0253681 A1 | 10/2009 | Summa et al. | |
| 2009/0270412 A1 | 10/2009 | Hung et al. | |
| 2013/0171214 A1 | 7/2013 | Mundhra et al. | |
| 2018/0155365 A1 | 6/2018 | Graham et al. | |
| 2019/0284208 A1 | 9/2019 | Johns et al. | |
| 2019/0315769 A1 | 10/2019 | Graham et al. | |

(Continued)

FOREIGN PATENT DOCUMENTS

| | | |
|---|---|---|
| CN | 104995198 | 10/2015 |
| CN | 116390924 | 7/2023 |

(Continued)

OTHER PUBLICATIONS

Patani et al (Chem Rev 96:3147-3176, 1996) (Year: 1996).*

(Continued)

*Primary Examiner* — Craig D Ricci
(74) *Attorney, Agent, or Firm* — Fish & Richardson P.C.

(57) ABSTRACT

The present disclosure relates generally to compounds, of Formula I:

Also disclosed are pharmaceutical compositions comprising said compounds and methods of making said compounds. The compounds of the disclosure are useful in treating or preventing human immunodeficiency virus (HIV) infection.

28 Claims, No Drawings

(56) References Cited

U.S. PATENT DOCUMENTS

| | | |
|---|---|---|
| 2019/0322666 A1 | 10/2019 | Yu et al. |
| 2020/0317689 A1 | 10/2020 | Chu et al. |
| 2021/0284642 A1 | 9/2021 | Jiang et al. |
| 2022/0135565 A1 | 5/2022 | Chu et al. |
| 2022/0267343 A1 | 8/2022 | Chu et al. |
| 2023/0058677 A1 | 2/2023 | Tomida et al. |
| 2023/0203061 A1 | 6/2023 | Chu et al. |
| 2023/0257389 A1 | 8/2023 | Chu et al. |
| 2024/0010650 A1 | 1/2024 | Jiang et al. |

FOREIGN PATENT DOCUMENTS

| | | |
|---|---|---|
| EP | 3938047 A1 | 1/2022 |
| JP | 2006342115 A | 12/2006 |
| TW | 200716635 A | 5/2007 |
| TW | 202106689 A | 2/2021 |
| TW | 202120510 A | 6/2021 |
| WO | WO-2006/088173 A1 | 8/2006 |
| WO | WO-2006/116764 A1 | 11/2006 |
| WO | WO-2007/019098 A2 | 2/2007 |
| WO | WO-2007/049675 A1 | 5/2007 |
| WO | WO-2007/050510 A2 | 5/2007 |
| WO | WO-2007/148780 A1 | 12/2007 |
| WO | WO-2008/010964 A1 | 1/2008 |
| WO | WO-2008/048538 A1 | 4/2008 |
| WO | WO-2009/088729 A1 | 7/2009 |
| WO | WO-2009/117540 A1 | 9/2009 |
| WO | WO-2009/154870 A1 | 12/2009 |
| WO | WO-2010/000030 A1 | 1/2010 |
| WO | WO-2010/011812 A1 | 1/2010 |
| WO | WO-2010/011814 A1 | 1/2010 |
| WO | WO-2010/011815 A1 | 1/2010 |
| WO | WO-2010/011816 A1 | 1/2010 |
| WO | WO-2010/011818 A1 | 1/2010 |
| WO | WO-2010/011819 A1 | 1/2010 |
| WO | WO-2010/042391 A3 | 4/2010 |
| WO | WO-2010/068253 A1 | 6/2010 |
| WO | WO-2010/088167 A1 | 8/2010 |
| WO | WO-2010/147068 A1 | 12/2010 |
| WO | WO-2011/011483 A1 | 1/2011 |
| WO | WO-2011/025683 A1 | 3/2011 |
| WO | WO-2011/045330 A1 | 4/2011 |
| WO | WO-2011/094150 A1 | 8/2011 |
| WO | WO-2011/105590 A1 | 9/2011 |
| WO | WO-2011/121105 A1 | 10/2011 |
| WO | WO-2011/129095 A1 | 10/2011 |
| WO | WO-2012/018065 A1 | 2/2012 |
| WO | WO-2012/058173 A1 | 5/2012 |
| WO | WO-2012/078834 A1 | 6/2012 |
| WO | WO-2013/054862 A1 | 4/2013 |
| WO | WO-2014/008636 A1 | 1/2014 |
| WO | WO-2014/014933 A1 | 1/2014 |
| WO | WO-2014/028384 A1 | 2/2014 |
| WO | WO-2014/099586 A1 | 6/2014 |
| WO | WO-2014/100323 A1 | 6/2014 |
| WO | WO-2014/172188 A2 | 10/2014 |
| WO | WO-2014/183532 A1 | 11/2014 |
| WO | WO-2014/200880 A1 | 12/2014 |
| WO | WO-2015/006731 A1 | 1/2015 |
| WO | WO-2015/006733 A1 | 1/2015 |
| WO | WO-2015/039348 A1 | 3/2015 |
| WO | WO-2015/048363 A1 | 4/2015 |
| WO | WO-2015/089847 A1 | 6/2015 |
| WO | WO-2015/095258 A1 | 6/2015 |
| WO | WO-2015/196116 A1 | 12/2015 |
| WO | WO-2016/027879 A1 | 2/2016 |
| WO | WO-2016/033009 A1 | 3/2016 |
| WO | WO-2016/090545 A1 | 6/2016 |
| WO | WO-2016/094197 A1 | 6/2016 |
| WO | WO-2016/094198 A1 | 6/2016 |
| WO | WO-2016/106237 A1 | 6/2016 |
| WO | WO-2016/154527 A1 | 9/2016 |
| WO | WO-2016/161382 A1 | 10/2016 |
| WO | WO-2016/187788 A1 | 12/2016 |
| WO | WO-2017/087256 A1 | 5/2017 |
| WO | WO-2017/087257 A1 | 5/2017 |
| WO | WO-2017/106071 A1 | 6/2017 |
| WO | WO-2017/113288 A1 | 7/2017 |
| WO | WO-2017/116928 A1 | 7/2017 |
| WO | WO-2017/223280 A2 | 12/2017 |
| WO | WO-2018/102485 A1 | 6/2018 |
| WO | WO-2018/102634 A1 | 6/2018 |
| WO | WO-2018/109786 A1 | 6/2018 |
| WO | WO-2018/140368 A1 | 8/2018 |
| WO | WO-2019/058393 A1 | 3/2019 |
| WO | WO-2019/160783 A1 | 8/2019 |
| WO | WO-2019/209667 A1 | 10/2019 |
| WO | WO-2019/223408 A1 | 11/2019 |
| WO | WO-2019/230857 A1 | 12/2019 |
| WO | WO-2019/230858 A1 | 12/2019 |
| WO | WO-2019/232216 A1 | 12/2019 |
| WO | WO-2019/236396 A1 | 12/2019 |
| WO | WO-2019/244066 A2 | 12/2019 |
| WO | WO-2020/003093 A1 | 1/2020 |
| WO | WO-2020/086555 A1 | 4/2020 |
| WO | WO-2020/112931 A1 | 6/2020 |
| WO | WO-2020/197991 A1 | 10/2020 |
| WO | WO-2020/221294 A1 | 11/2020 |
| WO | WO-2020/246910 A1 | 12/2020 |
| WO | WO-2021/093846 A1 | 5/2021 |
| WO | WO-2021/107066 A1 | 6/2021 |
| WO | WO 2022089562 | 5/2022 |
| WO | WO-2022/177840 A1 | 8/2022 |

OTHER PUBLICATIONS (2020) "Product Monograph Including Patient Medication Information" ViiV Healthcare ULC, 51 pages.

Akiyama, T. et al. (2013) "Discovery of Novel HIV Integrase Inhibitors Part 2. Selection and Evaluation of an Azabicyclic Carbamoyl Pyridone as a Pre-clinical Candidate", 245th ACS National Meeting and Exposition, Poster MEDI 403.

Andersson, V. et al. (2016) "Macrocyclic Prodrugs of a Selective Nonpeptidic Direct Thrombin Inhibitor Display High Permeability, Efficient Bioconversion but Low Bioavailability", J Med Chem, 59(14):6658-6670.

Anonymous (2013) "Thomson Reuters Drug News: Results from phase III trials of dolutegravir presented", Thomson Reuters. Retrieved from the Internet Jul. 5, 2013 <URL: http://drugnews.thomsonpharma.com/ddn/article.do?printerFriendlyFormat=true>.

Bari, H. (2010) "A Prolonged Release Parenteral Drug Delivery System—An Overview", Int J Pharm Sci Rev Res, 3(1):1-11.

Benn, P. et al. (2021) "Long-Acting Cabotegravir + Rilpivirine in Older Adults: Pooled Phase 3 Week 48 Results" CROI 2021, Science Spotlight, 1-11.

Bocedi, A. et al. (2004) "Binding of Anti-HIV Drugs to Human Serum Albumin", IUBMB Life, 56(10):609-614.

Bowers, G. et al. (2016) "Disposition and metabolism of cabotegravir: a comparison of biotransformation and excretion between different species and routes of administration in humans" Xenobiotica, 46(2):147-162.

Brinson, C. et al. (2013) "Dolutegravir Treatment Response and Safety by Key Subgroups in Treatment Naive HIV Infected Individuals", 20th CROI, Poster 554.

Brooks, K. et al. (2019) "Integrase Inhibitors: After 10 Years of Experience, Is the Best Yet to Come?" Pharmacotherapy, 1-23.

Burns, J. et al. (2020) "No overall change in the rate of weight gain after switching to an integrase-inhibitor in virologically suppressed adults with HIV" AIDS, 34:109-114.

Castellino, S. et al. (2013) "Metabolism, Excretion, and Mass Balance of the HIV-1 Integrase Inhibitor Dolutegravir in Humans" 57(8):3536-3546.

Cook, N. et al. (2019) "Structural basis of second-generation HIV Integrase inhibitor action and viral resistance" Science, 1-9.

Correll, C. et al. (2021) "Pharmacokinetic Characteristics of Long-Acting Injectable Antipsychotics for Schizophrenia: An Overview" CNS Drugs, 35: 39-59.

Cottrell, M. et al. (2013) "Clinical Pharmacokinetic, Pharmacodynamic and Drug-Interaction Profile of the Integrase Inhibitor Dolutegravir", Clin Pharmacokinet, 52(11):981-994.

(56) References Cited

OTHER PUBLICATIONS

Cottura, N. (2021) "In-Silico Prediction of Long-Acting Cabotegravir PK in Liver Impaired Patients" CROI 2021, Science Spotlight, 6 pages.

Curley, P. et al. (2019) "Long-Acting Emtricitabine Prodrugs Provide Protection From HIV Infection In Vivo", 2019 CROI, Poster 2262.

Del Mar Gutierrez, M. et al. (2014) "Drug safety profile of integrase strand transfer inhibitors", Expert Opin Drug Saf, 13(4):431-445.

Dicker, I. et al. (2011) "Simple and Accurate In Vitro Method for Predicting Serum Protein Binding of HIV Integrase Strand Transfer Inhibitors", HIV-1 Integrase: Mechanism and Inhibitor Design, First Edition.

EFSA (European Food Safety Authority), (2005) "Opinion of the Scientific Panel on Dietetic Products, Nutrition and Allergies on a request from the Commission related to the Tolerable Upper Intake Level of Potassium", EFSA Journal 2005, 3(3):193, 19 pp.

Flexner, C. (2020) "Novel Approaches to HIV Treatment and Prevention using Long Acting Drug Delivery" Johns Hopkins University, Division of Clinical Pharmacology, 45 pages.

Friedman, E. et al. (2016) "A Single Monotherapy Dose of MK-8591, a Novel NRTI, Suppresses HIV for 10 Days" CROI 2016, Poster, Abstract #437LB.

Gallant, J. et al. (2017) "Antiviral Activity, Safety, and Pharmacokinetics of Bictegravir as 10-Day Monotherapy in HIV-1-Infected Adults" J Acquir Immune Defic Syndr, 75(1):61-66.

Gelé, T. et al. (2020) "Characteristics of Dolutegravir and Bictegravir Plasma Protein Binding: a First Approach for the Study of Pharmacologic Sanctuaries", Antimicrob Agents Chemother, 64(11):e00895-20.

Grobler, J. et al. (2016) "Efficacy of once-weekly MK-8591 in SIV infected rhesus macaques", Merck & Co., Inc., 7th International Workshop on Clinical Pharmacology of HIV & Hepatitis Therapy.

Grobler, J. et al. (2019) "MK-8591 Potency and PK Provide High Inhibitory Quotients at Low Doses QD and QW" CROI 2019, Poster, Abstract #481.

Groseclose, M. et al. (2019) "Intramuscular and subcutaneous drug depot characterization of a long-acting abotegravir nanoformulation by Maldi IMS" International Journal of Mass Spectometry, 437:92-98.

Gurevich, K. (2013) "Effect of blood protein concentrations on drug-dosing regimes: practical guidance", Theor Biol Med Model, 10:20.

Günthard, H. et al. (2016) "Antiretroviral Drugs for Treatment and Prevention of HIV Infection in Adults: 2016 Recommendations of the International Antiviral Society—USA Panel", JAMA, 316(2):191-210.

Han, K. et al. (2021) "Cabotegravir Population Pharmacokinetic (PPK) Simulation to Inform Q2M Strategies Following Dosing Interruptions" CROI 2021, Science Spotlight, 9 pages.

Hare, S. et al. (2011) "Structural and Functional Analyses of the Second-Generation Integrase Strand Transfer Inhibitor Dolutegravir (S/GSK1349572)", Mol Pharmacol, 80(4):565-572.

Hill, L. et al. (2018) "Profile of bictegravir/emtricitabine/tenofovir alafenamide fixed dose combination and its potential in the treatment of HIV-1 infection: evidence to date" HIV/AIDS—Research and Palliative Care, 10:203-213.

Hughes, D. (2019) "Review of Synthetic Routes and Final Forms of Integrase Inhibitors Dolutegravir, Cabotegravir, and Bictegravir" Organic Process Research & Development, 23:716-729.

Hurt, C. et al. (2013) "Characterization of Resistance to Integrase Strand Transfer Inhibitors among Clinical Specimens in the United States, 2009-2012", 20th CROI, Poster 591.

Jaeger, H. et al. (2021) "Week 96 Efficacy and Safety of Long-Acting Cabotegravir + Rilpivirine Every 2 Months: ATLAS-2M" CROI 2021, Science Spotlight, 1-9.

Jiskoot, W. (2020) "Long-actinginjectables& implantables: immunogenicityconcerns" Third Long-Acting Injectables & Implantables Conference, 32 pages.

Jogiraju, V. (2021) "Pharmacokinetics of Lenacapavir, an HIV-1 Capsid Inhibitor, in Hepatic Impairment" CROI 2021, Science Spotlight, 6 pages.

Johns, B. et al. (2010) "The Discovery of S/GSK1349572: A Once Daily Next Generation Integrase Inhibitor with a Superior Resistance Profile", 17th CROI.

Johns, B. et al. (2013) "Carbamoyl Pyridone HIV?1 Integrase Inhibitors 3. A Diastereomeric Approach to Chiral Nonracemic Tricyclic Ring Systems and the Discovery of Dolutegravir (S/GSK1349572) and (S/GSK1265744)" J. Med. Chem., 56:5901-5916.

Jucker, B. et al. (2021) "Multiparametric magnetic resonance imaging to characterize cabotegravir long-acting formulation depot kinetics in healthy adult volunteers" Br J Clin Pharmacol., 1-12.

Kalicharan, R. et al. (2017) "New Insights Into Drug Absorption From Oil Depots" University Medical Center Utrecht, Utrecht, the Netherlands, Thesis, 152 pages.

Kalicharan, R. et al. (2016) "Fundamental understanding of drug absorption from a parenteral oil depot" European Journal of Pharmaceutical Sciences, 83: 19-27.

Kandala, B. et al. (2021) "Model-informed dose selection for Islatravir/MK-8507 oral once-weekly phase 2B study" CROI 2021, Science Spotlight, 6 pages.

Kandel, C. et al. (2015) "Dolutegravir—a review of the pharmacology, efficacy, and safety in the treatment of HIV" Drug Design, Development and Therapy, 9:3547-3555.

Kinvig, H. (2021) "In-Silico Prediction of Monthly Bictegravir Microneedle Array Patches" CROI 2021, Science Spotlight, 6 pages.

Klooster, G. et al. (2010) "Pharmacokinetics and Disposition of Rilpivirine (TMC278) Nanosuspension as a Long-Acting Injectable Antiretroviral Formulation" Antimicrobial Agents and Chemotherapy, 54(5): 2042-2050.

Kochansky, C. et al. (2008) "Impact of pH on Plasma Protein Binding in Equilibrium Dialysis", Mol Pharm, 5(3): 438-448.

Kulkarni, T. et al. (2019) "Prodrugs extend the half life and potency of Cabotegravir", CROI, Poster 489.

Kulkarni, T. et al. (2020) "A Year-Long Extended Release Nanoformulated Cabotegravir Prodrug", Nat Mater, 19(8):910-920.

Lalezari, J. et al. (2009) "Potent Antiviral Activity of S/GSK1349572, A Next Generation Integrase Inhibitor (INI), in INI-Naïve HIV-1-Infected Patients: ING111521 Protocol" IAS 2009, 5th Conference on HIV Pathogenesis, Abstract TUAB105, 15 pages.

Landovitz, R. et al. (2018) "Safety, tolerability, and pharmacokinetics of long-acting injectable cabotegravir in low-risk HIV-uninfected individuals: HPTN 077, a phase 2a randomized controlled trial" PLoS Med, 15(11):1-22.

Landovitz, R. et al. (2020) "Cabotegravir Is Not Associated With Weight Gain in Human Immunodeficiency Virus-uninfected Individuals in HPTN 077", Clin Infect Dis, 70(2):319-322.

Le Hingrat, Q. et al. (2018) "A New Mechanism of Resistance of Human Immunodeficiency Virus Type 2 to Integrase Inhibitors: A 5-Amino-Acid Insertion in the Integrase C-Terminal Domain" Clinical Infectious Diseases, 1-11.

Letendre, S. et al. (2013) "Distribution and Antiviral Activity in Cerebrospinal Fluid (CSF) of the Integrase Inhibitor, Dolutegravir (DTG): ING116070 Week 16 Results", 20th CROI, Poster 178LB.

Liu, S. et al. (2019) "Mechanistic Assessment of Extrahepatic Contributions to Glucuronidation of Integrase Strand Transfer Inhibitors" Drug Metabolism and Disposition, 47(5) 535-544.

Markowitz, M. (2017) "Weekly Oral MK-8591 Protects Male Rhesus Macaques against Repeated Low Dose Intrarectal Challenge with SHIV109CP3", 9th IAS Conference on HIV Science (IAS 2017), PowerPoint Presentation.

Martin, C. et al. (2021) "Bictegravir and Cabotegravir: in Vitro Phenotypic Susceptibility of HIV-1 Nongroup M" CROI 2021, Science Spotlight, 1-6.

Matthews, R. et al. (2017) "Single doses as low as 0.5 mg of the novel NRTTI MK-8591 suppress HIV for at least seven days", IAS 2017: Conference on HIV Pathogenesis, Poster.

Mcelnay, J. & D'arcy, P. (1983) "Protein Binding Displacement Interactions and their Clinical Importance", Drugs, 25(5):495-513.

(56) References Cited

OTHER PUBLICATIONS

Mcmillan, J. et al. (2019) "Pharmacokinetic testing of a first generation cabotegravir prodrug in rhesus macaques" AIDS, 33(3):585-588.
Menéndez-Arias, L. & Alvarez, M. (2014) "Antiretroviral therapy and drug resistance in human immunodeficiency virus type 2 infection", Antiviral Res, 102:70-86.
Min, S. et al. (2011) "Antiviral activity, safety, and pharmacokinetics/pharmacodynamics of dolutegravir as 10-day monotherapy in HIV-1-infected adults" AIDS 25(14):1737-1745.
Muller, R. et al. (2011) "State of the art of nanocrystals—Special features, production, nanotoxicology aspects and intracellular delivery" European Journal of Pharmaceuticals and Biopharmaceutics, 78:1-9.
Mullokandov, E. et al. (2014) "Protein Binding Drug-Drug Interaction between Warfarin and Tizoxanide in Human Plasma", Austin J Pharmacol Ther, 2(7):id1038.
Métifiot, M. et al. (2013) "HIV Integrase Inhibitors: 20-Year Landmark and Challenges", Adv Pharmacol, 67:75-105.
Nair, V. et al. (2014) "Pharmacokinetics and Dose-range Finding Toxicity of a Novel anti-HIV Active Integrase Inhibitor" Supplementary Materials.
Nair, V. et al. (2014) "Pharmacokinetics and Dose-range Finding Toxicity of a Novel anti-HIV Active Integrase Inhibitor", Antiviral Res, 108:25-29.
Neary, M. (2021) "In Vitro / In Vivo Development of Long Acting Biodegradable Emtricitabine Implants" CROI 2021, Science Spotlight, 6 pages.
Orkin, C. et al. (2019) "Long-Acting Cabotegravir + Rilpivirine for HIV Maintenance: Flair Week 48 Results", CROI 2019, PowerPoint Presentation.
Orkin, C. et al. (2020) "Long-Acting Cabotegravir + Rilpivirine for HIV Treatment: Flair Week 96 Results" Conference on Retroviruses and Opportunistic Infections, Poster 0482, 1 page.
Park, B. et al. (2001) "Metabolism of Fluorine-Containing Drugs" Annu. Rev. Pharmacol. Toxicol. 41:443-470.
Passos, D. et al. (2020) "Structural basis for strand transfer inhibitor binding to HIV intasomes" Science, 1-9.
Passos, D. et al. (2020) Supplementary Materials for "Structural basis for strand transfer inhibitor binding to HIV intasomes" Science, Supplementary Text, 38 pages.
Podany, A. et al. (2017) "Comparative Clinical Pharmacokinetics and Pharmacodynamics of HIV-1 Integrase Strand Transfer Inhibitors", Clin Pharmacokinet, 56(1):25-40.
Pozniak, A. et al. (2013) "Dolutegravir (DTG) Versus Raltegravir (RAL) in ART-Experienced, Integrase-Naive Subjects: 24-Week Interim Results From Sailing (ING111762)", 20th CROI.
Quashie, P. et al. (2013) "Evolution of HIV integrase resistance mutations", Curr Opin Infect Dis, 26(1):43-49.
Raffi, F. et al. (2013) "Once-daily dolutegravir versus raltegravir in antiretroviral-naive adults with HIV-1 infection: 48 week results from the randomised, double-blind, non-inferiority SPRING-2 study", Lancet, 381(9868): 735-743.
Raheem, I. et al. (2015) "Discovery of 2-Pyridinone Aminals: A Prodrug Strategy to Advance a Second Generation of HIV?1 Integrase Strand Transfer Inhibitors" J. Med. Chem., 58:8154-8165.
Rahnfeld, L. et al. (2020) "Injectable Lipid-Based Depot Formulations: Where Do We Stand?" Pharmaceutics 12(0567):1-28.
Rajoli, R. et al. (2019) "In Silico Simulation Of Long-Acting Tenofovir Alafenamide Subcutaneous Implant", CROI 2019, Poster 487.
Rautio, J. et al. (2018), "The expanding role of prodrugs in contemporary drug design and development", Nat Rev Drug Discov, 17(8):559-587.
Reese, M. et al. (2013) "In Vitro Investigations into the Roles of Drug Transporters and Metabolizing Enzymes in the Disposition and Drug Interactions of Dolutegravir, a HIV Integrase Inhibitor" Drug Metab Dispos 41:353-361.
Rhodes, M. et al. (2012) "Assessing a Theoretical Risk of Dolutegravir-Induced Developmental Immunotoxicity in Juvenile Rats", Toxicol Sci, 130(1):70-81.
Roberts, J. et al. (2013) "The Clinical Relevance of Plasma Protein Binding Changes", Clin Pharmacokinet, 52(1):1-8.
Rossenu, S. et al. (2021) "Population PK Modeling of Every 2 Months IM RPV LA for Managing Dosing Interruptions in HIV-1 Patients" CROI 2021, Science Spotlight, 1-7.
Rudd, D. et al. (2020) "Modeling-Supported Islatravir Dose Selection for Phase 3" CROI 2020, Poster, Abstract #462.
Scarsi, K. et al. (2020) "HIV-1 Integrase Inhibitors: A Comparative Review of Efficacy and Safety" Drugs, 80(16):1649-1676.
Shaik, J. et al. (2019) "A Phase 1 Study to Evaluate the Pharmacokinetics and Safety of Cabotegravir in Patients With Hepatic Impairment and Healthy Matched Controls" Clinical Pharmacology in Drug Development, 00(0):1-10.
Shi, Y. et al. (2021) "A review of existing strategies for designing longacting parenteral formulations: Focus on underlying mechanisms, and future perspectives" Acta Pharmaceutica Sinica B, 11(8): 2396-2415.
Song, I. et al. (2013) "Dolutegravir Has No Effect on the Pharmacokinetics of Methadone or Oral Contraceptives With Norgestimate and Ethinyl Estradiol", 20th CROI.
Spreen, W. et al. (2013) "Pharmacokinetics, Safety, and Monotherapy Antiviral Activity of GSK1265744, an HIV Integrase Strand Transfer Inhibitor" HIV Clinical Trials, 14(5): 192-203.
Spreen, W. et al. (2014) "GSK1265744 Pharmacokinetics in Plasma and Tissue After Single-Dose Long-Acting Injectable Administration in Healthy Subjects" J Acquir Immune Defic Syndr, 67(5):481-486.
Taoada, Y. et al. (2013) "Discovery of Novel HIV Integrase Inhibitors Part 1. Molecular Design and SAR of Azabicyclic Carbamoyl Pyridone Inhibitors", 245th ACS National Meeting and Exposition, Poster MEDI 402.
Tian, H. et al. (2018) "Effects of Plasma Albumin on the Pharmacokinetics of Esomeprazole in ICU Patients", Biomed Res Int, 2018:6374374.
Trezza, C. et al. (2015) "Formulation and pharmacology of long-acting cabotegravir" Current Opinion—HIV and AIDS, 10(4):239-245.
Van Der Galiën, R. et al. (2019) "Pharmacokinetics of HIV-Integrase Inhibitors During Pregnancy: Mechanisms, Clinical Implications and Knowledge Gaps", Clin Pharmacokinet, 58(3):309-323.
Walji, A. et al. (2015) "Discovery of MK-8970: An Acetal Carbonate Prodrug of Raltegravir with Enhanced Colonic Absorption" ChemMedChem, 10:245-252.
Wang, Y. C. et al. (2002) "Switch in asymmetric induction sense in cycloadditions using camphor-based nitroso dienophiles", Tetrahedron: Asymmetry, 13(7):691-695.
Weaving, G. et al. (2016) "Age and sex variation in serum albumin concentration: an observational study", Ann Clin Biochem, 53(1):106-111.
Weller, S. et al. (2014) "Pharmacokinetics of dolutegravir in HIV-seronegative subjects with severe renal impairment" Eur J Clin Pharmacol 70:29-35.
Wilkinson, J. et al. (2022) "Lipid based intramuscular long-acting injectables: Current state of the art" European Journal of Pharmaceutical Sciences, 178(106253): 1-20.
Williams, D. & Lemke, T. (2002), Foye's Principles of Medicinal Chemistry, 5th Ed., pp. 59-63.
Wolkowicz, U. et al. (2014) "Structural Basis of Mos1 Transposase Inhibition by the Anti-retroviral Drug Raltegravir", ACS Chem Biol, 9(3):743-751.
Wu, J. et al. (2012) "Implications of Plasma Protein Binding for Pharmacokinetics and Pharmacodynamics of the γ-Secretase Inhibitor RO4929097", Clin Cancer Res, 18(7):2066-2079.
Yoshinaga, T. et al. (2015) "Antiviral Characteristics of GSK1265744, an HIV Integrase Inhibitor Dosed Orally or by Long-Acting Injection" 59(1):397-406.
Yoshinaga, T. et al. (2018) "Novel secondary mutations C56S and G149A confer resistance to HIV-1 integrase strand transfer inhibitors" Antiviral Research, 152:1-9.

(56) References Cited

OTHER PUBLICATIONS

Zhang, W. et al. (2018) "Accumulation of Multiple Mutations In Vivo Confers Cross-Resistance to New and Existing Integrase Inhibitors" The Journal of Infectious Diseases, 218:1773-1776.
Zhao, X. et al. (2014) "4-Amino-1-hydroxy-2-oxo-1,8-naphthyridine-Containing Compounds Having High Potency against Raltegravir-Resistant Integrase Mutants of HIV-1", J Med Chem, 57(12):5190-5202.
Intl. Search Report and Written Opinion dated Jun. 1, 2023 for Intl. Appl. No. PCT/US2023/065401.
U.S. Appl. No. 17/489,406, filed Sep. 29, 2021, Hang Chu et al.
U.S. Appl. No. 18/050,650, filed Oct. 28, 2022, Hang Chu et al.
U.S. Appl. No. 18/164,317, filed Feb. 3, 2023, Hang Chu et al.
U.S. Appl. No. 18/296,285, filed Apr. 5, 2023, Hang Chu et al.
U.S. Appl. No. 18/316,579, filed May 12, 2023, Lan Jiang et al.
U.S. Appl. No. 18/334,588, filed Jun. 14, 2023, Hang Chu et al.
Fulmali et al., "Phosphate moiety in FDA-approved pharmaceutical salts and prodrugs," Drug Dev. Res., Jun. 2, 2022, 83(5):1059-1074.
Levine et al., "Trimethyl lock: A trigger for molecular release in chemistry, biology, and pharmacology," Chem. Sci., Jan. 2012, 3(8):2412-2420.
Randolph et al., "Prodrug Strategies to Improve the Solubility of the HCV NS5A Inhibitor Pibrentasvir (ABT-530)," J. Med. Chem., Sep. 3, 2020, 63:11034-11044.
Tantra et al., "Phosphate Prodrugs: An Approach to Improve the Bioavailability of Clinically Approved Drugs," Curr. Med. Chem., Mar. 21, 2023, 31(3):336-357.
Voight et al., "Desymmetrization of pibrentasvir for efficient prodrug synthesis," Chem. Sci., Jun. 29, 2021, 12(29):10076-10082.
Ivashchenko et al., "Synthesis, biological evaluation and in silico modeling of novel integrase strand transfer inhibitors (INSTIs)," European Journal of Medicinal Chemistry, Mar. 1, 2020, 189:112064.
Thierry et al., "Different Pathways Leading to Integrase Inhibitors Resistance," Front. Microbiol., Jan. 11, 2017, 7:2165, 13 pages.
Office Action in TW Appln. No. 112112594, dated Oct. 30, 2023, 13 pages (with machine translation).

* cited by examiner

BRIDGED TRICYCLIC CARBAMOYLPYRIDONE COMPOUNDS AND USES THEREOF

CROSS REFERENCE

This Application is a continuation of U.S. Ser. No. 18/296,285, filed on Apr. 5, 2023, which claims priority to U.S. Provisional Application No. 63/328,061 filed Apr. 6, 2022 and U.S. Provisional Application No. 63/476,873 filed Dec. 22, 2022. The entire contents of these applications are incorporated herein in their entirety for all purposes.

FIELD

Compounds, compositions, and methods that may be used for treating or preventing human immunodeficiency virus (HIV) infection are disclosed. In particular, novel spirocyclic substituted bridged tricyclic carbamoylpyridone compounds and methods for their preparation and use as therapeutic or prophylactic agents are disclosed.

BACKGROUND

Human immunodeficiency virus infection and related diseases are a major public health problem worldwide. Human immunodeficiency virus encodes three enzymes which are required for viral replication: reverse transcriptase, protease, and integrase. Although drugs targeting reverse transcriptase and protease are in wide use and have shown effectiveness, particularly when employed in combination, toxicity and development of resistant strains may limit their usefulness (Palella, et al. *N. Engl. J Med.* (1998) 338:853-860; Richman, D. D. *Nature* (2001) 410:995-1001). Accordingly, there is a need for new agents that inhibit the replication of HIV.

A goal of antiretroviral therapy is to achieve viral suppression in the HIV infected patient. Current treatment guidelines published by the United States Department of Health and Human Services provide that achievement of viral suppression requires the use of combination therapies, i.e., several drugs from at least two or more drug classes (Panel on Antiretroviral Guidelines for Adults and Adolescents. Guidelines for the Use of Antiretroviral Agents in Adults and Adolescents Living with HIV. Department of Health and Human Services. Available at http://www.aidsinfo.nih.gov/ContentFiles/AdultandAdolescentGL.pdf. Accessed Feb. 12, 2019). In addition, decisions regarding the treatment of HIV infected patients are complicated when the patient requires treatment for other medical conditions (Id. at F-8). Because the standard of care requires the use of multiple different drugs to suppress HIV, as well as to treat other conditions the patient may be experiencing, the potential for drug interaction is a criterion for selection of a drug regimen. As such, there is a need for antiretroviral therapies having a decreased potential for drug interactions.

In addition, the HIV virus is known to mutate in infected subjects (Tang, et al. Drugs (2012) 72 (9) e1-e25). Because of the proclivity of the HIV virus to mutate, there is a need for anti-HIV drugs to be effective against a range of known HIV variants (Hurt, et al. *HIV/AIDS CID* (2014) 58, 423-431).

For certain patients, for example, those with difficult or limited access to health care, adherence to daily oral treatment or prophylactic regimens can be challenging. Drugs that offer favorable pharmaceutical properties (for example, improved potency, long-acting pharmacokinetics, low solubility, low clearance, and/or other properties) are amenable to less frequent administration and provide for better patient compliance. Such improvements can, in turn, optimize drug exposure and limit the emergence of drug resistance.

SUMMARY

The present disclosure is directed to novel compounds having antiviral activity and pharmaceutically acceptable salts thereof. In some embodiments, the compounds may be used to treat HIV infections, to inhibit the activity of HIV integrase and/or to reduce HIV replication. In some embodiments, compounds disclosed herein may be effective against a range of known drug-resistant HIV mutants. In some embodiments, compounds disclosed herein may have a decreased propensity to cause drug-drug interactions when co-administered with other drugs. In some embodiments, compounds disclosed herein may be administered with less than daily frequency, for example, at weekly, monthly, once every three months, once every six months, or longer intervals.

In one embodiment, the disclosure provides a compound of Formula (I):

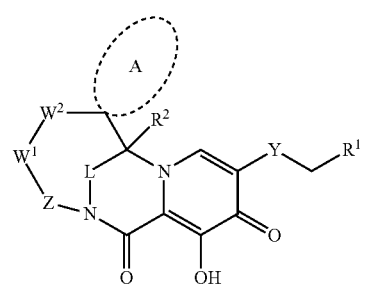

I or a pharmaceutically acceptable salt thereof, wherein:
$R^1$ is H, $C_{6-10}$aryl or 5 to 10 membered heteroaryl containing 1, 2, 3, or 4 heteroatoms independently selected from N, O, and S,
  wherein the $C_{6-10}$aryl or 5 to 10 membered heteroaryl is optionally substituted with one, two, three or four $R^{41}$, wherein each $R^{41}$ is independently halo, $C_{1-6}$ alkyl, $C_{1-4}$ haloalkyl, cyano, —O—$C_{1-4}$ alkyl, or $C_{1-4}$ alkyl-O—$C_{1-4}$ alkyl;
$R^2$ is H, $C_{1-6}$ alkyl, or $C_{1-4}$ haloalkyl;
L is —$CR^{3a}R^{3b}$—, —C(O)—, —$SO_2$—, —$CH_2$—$CH_2$—, or —N($R^a$)—;
$W^1$ is a bond or —$CR^{4a}R^{4b}$—;
$W^2$ is —$CR^{5a}R^{5b}$—, —$CR^{5a}R^{5b}CR^{5c}R^{5d}$—, —$CR^{6a}$=$CR^{6b}$—, —N($R^7$)—, —O—, —S(O)$_n$—, —C(O)—, —C(O)O—, —C(O)NH—, —$CR^{5a}R^{5b}$—N($R^7$)—, —$CR^{5a}R^{5b}$—O—, —$CR^{5a}R^{5b}$—S(O)$_n$—, —$CR^{5a}R^{5b}$—C(O)—, —$CR^{5a}R^{5b}$—C(O)O—, —$CR^{5a}R^{5b}$—OC(O)—, —$CR^{5a}R^{5b}$—C(O)NH—, or —$CR^{5a}R^{5b}$—NHC(O)—;
Y is —C(O)NH—,

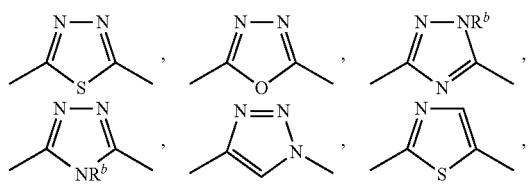

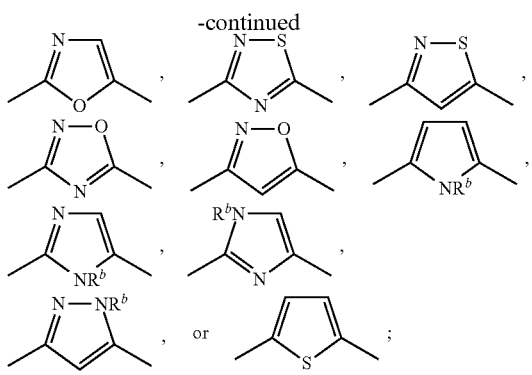

is a three to seven membered spiro ring containing 1, 2 or 3 heteroatoms selected from N, O, and S; wherein the spiro ring is optionally substituted with one, two, three, or four $R^8$ groups;

Z is —$CR^{9a}R^{9b}$—, —$CR^{9a}R^{9b}CR^{9c}R^{9d}$—, or —$CR^{10a}$=$CR^{10b}$—;

$R^{3a}$ and $R^{3b}$ are independently H, $C_{1-6}$ alkyl, $C_{1-4}$ haloalkyl, or —O—$C_{1-4}$ alkyl; or $R^{3a}$ and $R^{3b}$ together with the carbon atom to which they are attached form a 3- to 7-membered spiro ring containing 0, 1, or 2 heteroatoms selected from N, O, and S, wherein the spiro ring is optionally substituted with one, two or three $R^{42}$, wherein each $R^{42}$ is independently halo, $C_{1-4}$ alkyl or $C_{1-4}$ haloalkyl;

$R^{4a}$ and $R^{4b}$ are independently H, $C_{1-6}$ alkyl, $C_{1-4}$ haloalkyl, or halo;

$R^{5a}$, $R^{5b}$, $R^{5c}$, and $R^{5d}$ are independently H, $C_{1-6}$ alkyl, $C_{1-4}$ haloalkyl, halo, hydroxyl, cyano, —O—$C_{1-4}$ alkyl, or $C_{1-4}$ alkylene-O—$C_{1-4}$ alkyl; or $R^{5a}$ and $R^{5b}$ or $R^{5c}$ and $R^{5d}$ together with the carbon atom to which they are attached form a 3- to 7-membered spiro ring containing 0, 1, or 2 heteroatoms selected from N, O, and S, wherein the spiro ring is optionally substituted with one, two or three $R^{43}$, wherein each $R^{43}$ is independently halo, $C_{1-4}$ alkyl or $C_{1-4}$ haloalkyl; or $R^{5a}$ and $R^{5c}$ or $R^{5b}$ and $R^{5d}$ together with the carbon atoms to which each is attached form a 3- to 7-membered fused ring containing 0 or 1 heteroatom selected from N, O, and S, wherein the fused ring is optionally substituted with one to three $R^{43}$, wherein each $R^{43}$ is independently halo, $C_{1-4}$ alkyl or $C_{1-4}$ haloalkyl;

each $R^{6a}$ and $R^{6b}$ is independently H, halo, $C_{1-4}$ haloalkyl, or $C_{1-6}$ alkyl; or $R^{6a}$ and $R^{6b}$ together with the carbon atoms to which each is attached form a 5- to 10-membered partially unsaturated fused ring containing 0 or 1 heteroatom selected from N, O, and S, or a 5- to 10-membered fused aromatic ring, or a 5- to 10-membered fused heteroaromatic ring containing 1 or 2 heteroatoms selected from N, O and S, wherein the partially unsaturated fused ring, fused aromatic ring, or fused heteroaromatic ring is optionally substituted with one, two, three or four $R^{44}$, wherein each $R^{44}$ is independently halo or $C_{1-4}$ alkyl;

$R^7$ is H, $C_{1-6}$ alkyl, $C_{1-4}$ haloalkyl, C(O)$R^c$, or SO$_2R^c$;

each $R^8$ is independently selected from the group consisting of:

(i) halo, (ii) $C_{1-6}$ alkyl optionally substituted with OH, $C_{1-6}$ alkoxy, $C_{6-10}$ aryl or 5- to 10-membered heteroaryl comprising 1, 2, or 3 heteroatoms independently selected from N, O, and S,
wherein the $C_{6-10}$ aryl or 5- to 10-membered heteroaryl is optionally substituted with 1 to 4 substituents selected independently from $C_1$-$C_3$ alkyl, $C_1$-$C_3$ alkoxy, halo, CN, $C_1$-$C_3$ haloalkyl, $C_3$-$C_7$ cycloalkyl, and three to seven membered halocycloalkyl containing 1, 2, or 3 heteroatoms selected from N, O, and S, (iii) $C_{1-6}$haloalkyl optionally substituted with OH, $C_{1-6}$ alkoxy, $C_{6-10}$ aryl or 5- to 10-membered heteroaryl comprising 1, 2, or 3 heteroatoms independently selected from N, O, and S,
wherein the $C_{6-10}$ aryl or 5- to 10-membered heteroaryl is optionally substituted with 1 to 4 substituents selected from $C_1$-$C_3$ alkyl, $C_1$-$C_3$ alkoxy, halo, CN, $C_1$-$C_3$ haloalkyl, $C_3$-$C_7$ cycloalkyl, and three to seven membered halocycloalkyl containing 1, 2, or 3 heteroatoms selected from N, O, and S, (iv) CN, (v) oxo, (vi) —X—$R^{45}$
wherein X is O or S; and $R^{45}$ is H, $C_{1-6}$ alkyl or 3- to 7-membered ring containing 0, 1, or 2 heteroatoms selected from N, O and S;
wherein the $C_1$-$C_6$ alkyl or the 3- to 7-membered ring is optionally substituted with 1, 2, or 3 groups selected independently from CN, halo, $C_1$-$C_6$ alkoxy, $C_{6-10}$ aryl and 5- to 10-membered heteroaryl containing 1, 2, or 3 heteroatoms independently selected from N, O, and S, (vii) NH$R^{46}$,
wherein $R^{46}$ is $C_1$-$C_6$ alkyl;

(viii) N$R^{47}R^{48}$,
wherein $R^{47}$ is $C_1$-$C_6$ alkyl; and
$R^{48}$ is $C_1$-$C_6$ alkyl, (ix) $C_{6-10}$ aryl optionally substituted with 1, 2, 3, or 4 substituents independently selected from $C_{1-6}$ alkyl, $C_{1-6}$ haloalkyl, halo, CN, $C_{3-7}$ cycloalkyl, and $C_{1-6}$ alkoxy;
wherein the $C_{3-7}$ cycloalkyl is optionally substituted with 1, 2, 3, or 4 independent halo groups, (x) 3- to 7-membered ring containing 0, 1, or 2 heteroatoms selected independently from N, O and S,
wherein the 3- to 7-membered ring is optionally substituted with one, two or three substituents selected independently from halo, $C_{1-6}$ alkyl, $C_{1-6}$ haloalkyl, $C_{1-6}$ alkoxy, and $C_{3-7}$ cycloalkyl, and (xi) 5- to 10-membered heteroaryl ring containing 1, 2, or 3 heteroatoms independently selected from N, O, and S,
wherein the 5- to 10-membered heteroaryl ring is optionally substituted with one, two or three substituents selected independently from halo, $C_{1-6}$ alkyl, $C_{1-6}$ haloalkyl, $C_{1-6}$ alkoxy, and $C_{3-7}$ cycloalkyl, (xii) —SO$_2R^{413}$,
$R^{413}$ is $C_1$-$C_6$ alkyl or 3 to 7 membered ring containing 0, 1, or 2 heteroatoms selected from N, O and S;

wherein the $C_1$-6 alkyl or the 3 to 7 membered ring is optionally substituted with 1, 2, or 3 groups selected from CN, halo and $C_1$-$C_6$ alkoxy, (xiii) —SON($R^{A14}$)$_2$, each $R^{A14}$ is independently H, $C_{1-6}$ alkyl or 3 to 7 membered ring containing 0, 1, or 2 heteroatoms independently selected from N, O and S;

wherein the $C_{1-6}$ alkyl or the 3- to 7-membered ring is optionally substituted with 1, 2, or 3 groups selected from CN, halo and $C_1$-$C_6$ alkoxy, (xiv) $C_{2-6}$ alkynyl optionally substituted with one, two, three, or four substituents independently selected from $C_{1-6}$ alkoxy, OH, —SO$_2$—($C_{1-3}$ alkyl), or two $R^8$ groups are joined to form a fused, spiro, or bridged 3- to 7-membered ring containing 0, 1, 2, or 3 heteroatoms selected from N, O and S;

wherein the 3- to 7-membered ring is optionally substituted with one, two or three substituents selected independently from halo, OH, $C_{1-6}$ alkyl, $C_{1-6}$ haloalkyl, $C_{1-6}$ alkoxy, and $C_{3-7}$ cycloalkyl; or two $R^8$ groups on adjacent carbon atoms are joined to form a fused 6- to 10-membered aromatic ring containing 0, 1, 2, or 3 heteroatoms selected from N, O and S, wherein the fused 6- to 10-membered aromatic ring is optionally substituted with one, two or three substituents selected independently from halo, OH, $C_{1-6}$ alkyl, $C_{1-6}$ haloalkyl, $C_{1-6}$ alkoxy, and $C_{3-7}$ cycloalkyl;

$R^{9a}$, $R^{9b}$, $R^{9c}$, and $R^{9d}$ are each independently H, $C_{1-6}$ alkyl, $C_{1-4}$ haloalkyl, or halo; or $R^{9a}$ and $R^{9b}$ or $R^{9c}$ and $R^{9d}$ together with the carbon atom to which they are attached form a 3- to 7-membered spiro ring containing 0, 1, or 2 heteroatoms selected from N, O, and S, wherein the spiro ring is optionally substituted with one, two or three $R^{A9}$, wherein each $R^{A9}$ is independently halo, $C_{1-4}$ alkyl or $C_{1-4}$ haloalkyl; or $R^{9a}$ and $R^{9c}$ or $R^{9b}$ and $R^{9d}$ together with the carbon atoms to which each is attached form a 3- to 7-membered fused ring containing 0 or 1 heteroatom selected from N, O, and S, wherein the fused ring is optionally substituted with one, two or three $R^{A11}$, wherein each $R^{A10}$ is independently halo, $C_{1-4}$ alkyl, or $C_{1-4}$ haloalkyl; or one of $R^{9a}$, $R^{9b}$, $R^{9c}$, and $R^{9d}$ and one of $R^{4a}$, $R^{4b}$, $R^{5a}$, $R^{5b}$, and $R^7$ together with the atoms to which each is attached form a 3- to 7-membered fused ring containing 0, 1, or 2 heteroatoms selected from N, O and S, wherein the fused ring is optionally substituted with one, two, three or four $R^{A11}$, wherein each $R^{A11}$ is independently halo or $C_{1-4}$ alkyl;

$R^{10a}$ and $R^{10b}$ are independently H, halo, $C_{1-4}$haloalkyl, or $C_{1-6}$ alkyl; or $R^{10a}$ and $R^{10b}$ together with the carbon atoms to which each is attached form a 5- to 10-membered partially unsaturated fused ring containing 0 or 1 heteroatom selected from N, O, and S, or a 5- to 10-membered fused aromatic ring, or a 5- to 10-membered fused heteroaromatic ring containing 1 or 2 heteroatoms selected from N, O and S, wherein the partially unsaturated fused ring, fused aromatic ring, or fused heteroaromatic ring is optionally substituted with one to four $R^{A12}$, wherein each $R^{A12}$ is independently halo or $C_{1-4}$ alkyl;

$R^a$ is independently H, $C_{1-6}$ alkyl, $C_{1-6}$ haloalkyl, C(O)$R^c$, or SO$_2R^c$;

$R^b$ is H or $C_{1-4}$ alkyl;

$R^c$ is $C_{1-4}$ alkyl or $C_{1-4}$ alkyloxy; and each n is independently 0, 1, or 2.

In one embodiment, a pharmaceutical composition is provided comprising a therapeutically effective amount of a compound of Formula I or a pharmaceutically acceptable salt thereof, and a pharmaceutically acceptable excipient.

In another embodiment, a kit or an article of manufacture comprising a compound of Formula I, or a pharmaceutically acceptable salt thereof, and instructions for use.

In another embodiment, a method of treating an HIV infection in a human having or at risk of having the infection, by administering to the human a therapeutically effective amount of a compound of Formula I or a pharmaceutically acceptable salt thereof, or a pharmaceutical composition of a compound of Formula I, or a pharmaceutically acceptable salt thereof, is provided.

In another embodiment, use of a compound of Formula I, or a pharmaceutically acceptable salt thereof, or a pharmaceutical composition of a compound of Formula I or a pharmaceutically acceptable salt thereof, for treating an HIV infection in a human having or at risk of having the infection is provided.

In another embodiment, use of a compound of Formula I, or a pharmaceutically acceptable salt thereof, or a pharmaceutical composition of a compound of Formula I or a pharmaceutically acceptable salt thereof, in the manufacture of a medicament for treating an HIV infection in a human having or at risk of having the infection is provided.

In another embodiment, a compound of Formula I or a pharmaceutically acceptable salt thereof, or a pharmaceutical composition of a compound of formula I or a pharmaceutically acceptable salt thereof, for use in medical therapy is provided.

In another embodiment, a compound of Formula I or a pharmaceutically acceptable salt thereof, or a pharmaceutical composition of a compound of formula I or a pharmaceutically acceptable salt thereof, for use in treating an HIV infection is provided.

Other embodiments, objects, features, and advantages may be set forth in the detailed description of the embodiments that follows, and in part may be apparent from the description, or may be learned by practice, of the claimed embodiments. These objects and advantages may be realized and attained by the processes and compositions particularly pointed out in the description and claims thereof. The foregoing Summary has been made with the understanding that it is to be considered as a brief and general synopsis of some of the embodiments disclosed herein, is provided for the benefit and convenience of the reader, and is not intended to limit in any manner the scope, or range of equivalents, to which the appended claims are lawfully entitled.

DETAILED DESCRIPTION

In the following description, certain specific details are set forth in order to provide a thorough understanding of various embodiments disclosed herein. However, one skilled in the art will understand that the embodiments disclosed herein may be practiced without these details. The description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments

I. DEFINITIONS

Unless the context requires otherwise, throughout the present disclosure and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment disclosed herein. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —$NH_2$ radical.

"Hydroxy" or "hydroxyl" refers to the —OH radical.

The term "$C_{1-n}$ alkyl" as used herein, wherein n is an integer, either alone or in combination with another radical, is intended to mean acyclic, straight or branched chain alkyl radicals containing from 1 to n carbon atoms. "$C_{1-6}$ alkyl" includes, but is not limited to, methyl, ethyl, propyl (n-propyl), butyl (n-butyl), 1methylethyl (isopropyl), 1methylpropyl (sec-butyl), 2methylpropyl (iso-butyl), 1,1dimethylethyl (tertbutyl), pentyl and hexyl. The abbreviation Me denotes a methyl group; Et denotes an ethyl group, Pr denotes a propyl group, iPr denotes a 1-methylethyl group, Bu denotes a butyl group and tBu denotes a 1,1-dimethylethyl group.

"Alkyl" is hydrocarbon containing normal, secondary or tertiary atoms. For example, an alkyl group can have 1 to 20 carbon atoms (i.e., $C_{1-20}$ alkyl), 1 to 10 carbon atoms (i.e., $C_{1-10}$ alkyl), 1 to 8 carbon atoms (i.e., $C_{1-8}$ alkyl) or 1 to 6 carbon atoms (i.e., $C_{1-6}$ alkyl). Examples of suitable alkyl groups include, but are not limited to, methyl (Me, —$CH_3$), ethyl (Et, $CH_2CH_3$), 1-propyl (n-Pr, n-propyl, —$CH_2CH_2CH_3$), 2-propyl (i-Pr, ipropyl, $CH(CH_3)_2$), 1-butyl (n-Bu, n-butyl, —$CH_2CH_2CH_2CH_3$), 2methyl1-propyl (i-Bu, ibutyl, —$CH_2CH(CH_3)_2$), 2butyl (s-Bu, s-butyl, $CH(CH_3)CH_2CH_3$), 2-methyl-2-propyl (t-Bu, tbutyl, —$C(CH_3)_3$), 1-pentyl (n-pentyl, $CH_2CH_2CH_2CH_2CH_3$), 2-pentyl ($CH(CH_3)CH_2CH_2CH_3$), 3pentyl ($CH(CH_2CH_3)_2$), 2-methyl-2-butyl ($C(CH_3)_2CH_2CH_3$), 3methyl2-butyl ($CH(CH_3)CH(CH_3)_2$), 3methyl1butyl ($CH_2CH_2CH(CH_3)_2$), 2-methyl-1-butyl ($CH_2CH(CH_3)CH_2CH_3$), 1-hexyl ($CH_2CH_2CH_2CH_2CH_2CH_3$), 2-hexyl ($CH(CH_3)CH_2CH_2CH_2CH_3$), 3hexyl ($CH(CH_2CH_3)(CH_2CH_2CH_3)$), 2methyl-2-pentyl ($C(CH_3)_2CH_2CH_2CH_3$), 3methyl2pentyl ($CH(CH_3)CH(CH_3)CH_2CH_3$), 4-methyl-2-pentyl ($CH(CH_3)CH_2CH(CH_3)_2$), 3-methyl-3-pentyl (—$C(CH_3)(CH_2CH_3)_2$), 2methyl-3-pentyl (—$CH(CH_2CH_3)CH(CH_3)_2$), 2,3-dimethyl-2-butyl ($C(CH_3)_2CH(CH_3)_2$), 3,3dimethyl2butyl (—$CH(CH_3)C(CH_3)_3$, and octyl (($CH_2)_7CH_3$). "Alkyl" also refers to a saturated, branched or straight chain hydrocarbon radical having two monovalent radical centers derived by the removal of two hydrogen atoms from the same or two different carbon atoms of a parent alkane. For example, an alkyl group can have 1 to 10 carbon atoms (i.e., $C_{1-10}$ alkyl), or 1 to 6 carbon atoms (i.e., $C_{1-6}$ alkyl) or 1-3 carbon atoms (i.e., $C_{1-3}$ alkyl). Typical alkyl radicals include, but are not limited to, methylene ($CH_2$), 1,1ethyl ($CH(CH_3)$), 1,2ethyl ($CH_2CH_2$), 1,1-propyl ($CH(CH_2CH_3)$), 1,2-propyl ($CH_2CH(CH_3)$), 1,3propyl ($CH_2CH_2CH_2$), 1,4-butyl ($CH_2CH_2CH_2CH_2$), and the like.

The term "alkenyl" as used herein refers to a straight or branched hydrocarbon containing normal, secondary or tertiary carbon atoms with at least one site of unsaturation, i.e., a carbon-carbon, $sp^2$ double bond. For example, an alkenyl group can have 2 to 20 carbon atoms (i.e., $C_2$-$C_{20}$ alkenyl, or $C_{2-20}$ alkenyl), 2 to 8 carbon atoms (i.e., $C_2$-$C_8$ alkenyl or $C_{2-8}$), or 2 to 6 carbon atoms (i.e., $C_2$-$C_6$ alkenyl, or $C_{2-6}$ alkenyl). Examples of suitable alkenyl groups include, but are not limited to, ethylene or vinyl (CH=$CH_2$), allyl ($CH_2$CH=$CH_2$), cyclopentenyl ($C_5H_7$), and 5-hexenyl ($CH_2CH_2CH_2CH_2$CH=$CH_2$).

The term "$C_{2-n}$alkenyl", as used herein, wherein n is an integer, either alone or in combination with another radical, is intended to mean an unsaturated, acyclic straight or branched chain radical containing two to n carbon atoms, at least two of which are bonded to each other by a double bond. Examples of such radicals include, but are not limited to, ethenyl (vinyl), 1propenyl, 2propenyl, and 1butenyl. Unless specified otherwise, the term "$C_{2-n}$alkenyl" is understood to encompass individual stereoisomers where possible, including but not limited to (E) and (Z) isomers, and mixtures thereof. When a $C_{2-n}$alkenyl group is substituted, it is understood to be substituted on any carbon atom thereof which would otherwise bear a hydrogen atom, unless specified otherwise, such that the substitution would give rise to a chemically stable compound, such as are recognized by those skilled in the art.

"Alkynyl" is a straight or branched hydrocarbon containing normal, secondary or tertiary carbon atoms with at least one site of unsaturation, i.e., a carbon-carbon, sp triple bond. For example, an alkynyl group can have 2 to 20 carbon atoms (i.e., $C_{2-20}$ alkynyl), 2 to 8 carbon atoms (i.e., $C_{2-8}$ alkyne,), or 2 to 6 carbon atoms (i.e., $C_{2-6}$ alkynyl). Examples of suitable alkynyl groups include, but are not limited to, acetylenic (C≡CH), propargyl ($CH_2$C≡CH), and the like.

The term "$C_{2-n}$ alkynyl", as used herein, wherein n is an integer, either alone or in combination with another radical, is intended to mean an unsaturated, acyclic straight or branched chain radical containing two to n carbon atoms, at least two of which are bonded to each other by a triple bond. Examples of such radicals include, but are not limited to, ethynyl, 1propynyl, 2propynyl, and 1butynyl. When a $C_{2-n}$ alkynyl group is substituted, it is understood to be substituted on any carbon atom thereof which would otherwise bear a hydrogen atom, unless specified otherwise, such that the substitution would give rise to a chemically stable compound, such as are recognized by those skilled in the art.

"Cyano" or "carbonitrile" refers to the group —CN.

The term "halo" or "halogen" as used herein refers to fluoro, chloro, bromo and iodo.

The term "haloalkyl" as used herein refers to an alkyl as defined herein, wherein one or more hydrogen atoms are each replaced by a halo substituent. For example, a $C_{1-6}$ haloalkyl is a $C_{1-6}$ alkyl wherein one or more of the hydrogen atoms have been replaced by a halo substituent. Such a range includes one halo substituent on the alkyl group to complete halogenation of the alkyl group.

The term "$C_{1-n}$ haloalkyl" as used herein, wherein n is an integer, either alone or in combination with another radical, is intended to mean an alkyl radical having 1 to n carbon atoms as defined above wherein one or more hydrogen atoms are each replaced by a halo substituent. Examples of $C_{1-n}$ haloalkyl include but are not limited to chloromethyl, chloroethyl, dichloroethyl, bromomethyl, bromoethyl, dibromoethyl, fluoromethyl, difluoromethyl, trifluoromethyl, fluoroethyl and difluoroethyl.

The term "aryl" as used herein refers to a single aromatic ring or a bicyclic or multicyclic ring. For example, an aryl group can have 6 to 20 carbon atoms, 6 to 14 carbon atoms, or 6 to 12 carbon atoms. Aryl includes a phenyl radical or an ortho-fused bicyclic or multicyclic radical having about 9 to 14 atoms in which at least one ring is aromatic (e.g., an aryl fused to one or more aryl or carbocycle). Such bicyclic or multicyclic rings may be optionally substituted with one or more (e.g., 1, 2 or 3) oxo groups on any carbocycle portion of the bicyclic or multicyclic ring. It is to be understood that the point of attachment of a bicyclic or multicyclic radical, as defined above, can be at any position of the ring including an aryl or a carbocycle portion of the ring. Typical aryl groups include, but are not limited to, phenyl, indenyl, naphthyl, 1, 2, 3, 4-tetrahydronaphthyl, anthracenyl, and the like.

The term "heteroaryl", "heteroaryl ring" or "heteroaromatic ring" as used herein refer to a single aromatic ring or a multiple condensed ring. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g., ring systems comprising 2 or 3 rings) wherein a heteroaryl group, as defined above, can be fused with one or more heteroaryls (e.g., naphthyridinyl), carbocycles (e.g., 5,6,7,8-tetrahydroquinolyl) or aryls (e.g., indazolyl) to form a multiple condensed ring. Such multiple condensed rings may be optionally substituted with one or more (e.g., 1, 2 or 3) oxo groups on the carbocycle portions of the condensed ring. It is to be understood that the point of attachment of a heteroaryl multiple condensed ring, as defined above, can be at any position of the ring including a heteroaryl, aryl or a carbocycle portion of the ring. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl and thianaphthenyl.

The term "heterocyclyl", "heterocycle", or "halocycloalkyl" as used herein refers to a single saturated or partially unsaturated ring or a multiple condensed ring. The term includes single saturated or partially unsaturated ring (e.g., 3, 4, 5, 6 or 7-membered ring) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Such rings include but are not limited to azetidinyl, tetrahydrofuranyl or piperidinyl. The term also includes multiple condensed ring systems (e.g., ring systems comprising 2 or 3 rings) wherein a heterocycle group (as defined above) can be connected to two adjacent atoms (fused heterocycle) with one or more heterocycles (e.g., decahydronapthyridinyl), heteroaryls (e.g., 1,2,3,4-tetrahydronaphthyridinyl), carbocycles (e.g., decahydroquinolyl) or aryls. It is to be understood that the point of attachment of a heterocycle multiple condensed ring, as defined above, can be at any position of the ring including a heterocycle, heteroaryl, aryl or a carbocycle portion of the ring. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl and 1,4-benzodioxanyl.

The term "ring" as used herein referes to cycloalkyl or heterocyclyl group. The term ring as used herein include, but are not limited, to spiro, bridged and fused rings. The ring can be fully saturated or partially unsaturated.

The term "fused ring" as used herein "Fused" refers to a carbocyclic, heterocyclic, aromatic, or heteroaromatic ring structure described herein which is connected to an existing ring structure in the compounds disclosed herein via two adjacent atoms that are shared by the fused ring structure and the existing ring structure. For example, the bicyclic compounds depicted below incorporate fused cyclopropane (i.e., a cyclopropane ring fused to a cyclohexane ring), a fused pyrrolidine (i.e., a pyrrolidine ring fused to a benzene ring), and fused thiophene (i.e., a thiene ring fused to a furan ring), respectively:

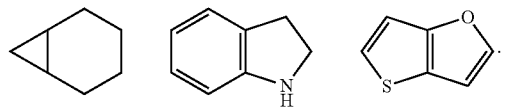

The term "$C_{3-m}$ cycloalkyl" as used herein, wherein m is an integer, either alone or in combination with another radical, is intended to mean a cycloalkyl substituent containing from 3 to m carbon atoms and includes, but is not limited to, cyclopropyl, cyclobutyl, cyclopentyl, cyclohexyl and cycloheptyl. The term includes fully saturated as well as partially unsaturated rings.

It is to be understood that when a variable is substituted, for example, as described by the phrase "$C_{1-6}$ alkyl, either alone or as part of a group, is optionally substituted", the phrase means that the variable $C_{1-6}$ alkyl can be substituted when it is alone and that it can also be substituted when the variable "$C_{1-6}$ alkyl" is part of a larger group. Similarly, when stated, other variables (e.g., $C_{2-6}$ alkynyl, aryl, heteroaryl, heterocycle, etc.) can also be substituted "either alone or as part of a group."

It is to be understood that certain variables of Formula I that connect two chemical groups may be oriented in either direction. Thus, for the X group of Formula I (e.g., O, C(O), C(O)O, S, S(O), $SO_2$, ($C_1$-$C_6$)alkylO-, ($C_1$-$C_6$)alkylC(O), ($C_1$-$C_6$)alkylC(O)O, ($C_1$-$C_6$)alkylS, ($C_1$-$C_6$)alkylS(O) and ($C_1$-$C_6$)alkylSO$_2$) certain values of X that are not symmetric can be oriented in either direction. For example, the C(O)O, can be oriented as either C(O)O or OC(O), relative to the groups it connects.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers or axes of chirality and whose molecules are not mirror images of one another. Diastereomers typically have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The term "treatment" or "treating," to the extent it relates to a disease or condition includes preventing the disease or condition from occurring, inhibiting the disease or condition, eliminating the disease or condition, and/or relieving one or more symptoms of the disease or condition.

The term "treating" with respect to the treatment of a disease-state in a patient include (i) inhibiting or ameliorating the disease-state in a patient, e.g., arresting or slowing its development; or (ii) relieving the disease-state in a patient, i.e., causing regression or cure of the disease-state. In the case of HIV, treatment includes reducing the level of HIV viral load in a patient.

The term "treatment" as used herein is intended to mean the administration of a compound or composition according to the present invention to alleviate or eliminate symptoms of HIV infection and/or to reduce viral load in a patient. The term "treatment" also encompasses the administration of a compound or composition according to the present invention postexposure of the individual to the virus but before the appearance of symptoms of the disease, and/or prior to the detection of the virus in the blood, to prevent the appearance of symptoms of the disease and/or to prevent the virus from reaching detectible levels in the blood, and the administration of a compound or composition according to the present invention to prevent perinatal transmission of HIV from mother to baby, by administration to the mother before giving birth and to the child within the first days of life.

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Protecting groups are available, commonly known and used, and are optionally used to prevent side reactions with the protected group during synthetic procedures, i.e., routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. PGs do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether-nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene (John Wiley & Sons, Inc., New York, 1991, ISBN 0-471-62301-6) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below.

The term "protecting group" as used herein is intended to mean protecting groups that can be used during synthetic transformation, including but not limited to examples which are listed in Greene, "Protective Groups in Organic Chemistry", John Wiley & Sons, New York (1981), and more recent editions thereof.

The term "solvate" refers to a crystalline solid containing amounts of a solvent incorporated within the crystal structure. As used herein, the term "solvate" includes hydrates.

The term "non-solvate" refers to a crystalline solid in which no solvent molecules occupy a specific crystallographic site.

The term "pharmaceutically acceptable" with respect to a substance as used herein means that substance which is, within the scope of sound medical judgment, suitable for use in contact with the tissues of humans and lower animals without undue toxicity, irritation, allergic response, and the like, commensurate with a reasonable benefit/risk ratio, and effective for the intended use when the substance is used in a pharmaceutical composition.

The term "pharmaceutically acceptable salt" as used herein is intended to mean a salt of a compound according to the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, for example, S. M. Birge et al., J. Pharm. Sci., 1977, 66, pp. 1-19.

The term "pharmaceutically-acceptable acid addition salt" as used herein is intended to mean those salts which retain the biological effectiveness and properties of the free bases and which are not biologically or otherwise undesirable, formed with inorganic acids including but not limited to hydrochloric acid, hydrobromic acid, sulfuric acid, sulfamic acid, nitric acid, phosphoric acid and the like, and organic acids including but not limited to acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid and the like.

The term "pharmaceutically-acceptable base addition salt" as used herein is intended to mean those salts which retain the biological effectiveness and properties of the free acids and which are not biologically or otherwise undesirable, formed with inorganic bases including but not limited to ammonia or the hydroxide, carbonate, or bicarbonate of ammonium or a metal cation such as sodium, potassium, lithium, calcium, magnesium, iron, zinc, copper, manganese, aluminum and the like. Particularly preferred are the ammonium, potassium, sodium, calcium, and magnesium salts. Salts derived from pharmaceutically-acceptable organic nontoxic bases include but are not limited to salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins and the like. Particularly preferred organic nontoxic bases are isopropylamine, diethylamine, ethanolamine, trimethylamine, dicyclohexylamine, choline, and caffeine.

The term "antiviral agent" as used herein is intended to mean an agent that is effective to inhibit the formation and/or replication of a virus in a human, including but not limited to agents that interfere with either host or viral mechanisms necessary for the formation and/or replication of a virus in a human. The term "antiviral agent" includes, for example, an HIV integrase catalytic site inhibitor selected from the group consisting of: raltegravir (ISENTRESS®; Merck); elvitegravir (Gilead); soltegravir (GSK; ViiV); GSK 1265744 (GSK; ViiV) and dolutegravir; an HIV nucleoside reverse transcriptase inhibitor selected from the group consisting of: abacavir (ZIAGEN®; GSK); didanosine (VIDEX®; BMS); tenofovir (VIREAD®; Gilead); emtricitabine (EMTRIVA®; Gilead); lamivudine (EPIVIR®; GSK/Shire); stavudine (ZERIT®; BMS); zidovudine (RETROVIR®; GSK); elvucitabine (Achillion); and festinavir (Oncolys); an HIV non-nucleoside reverse transcriptase inhibitor selected from the group consisting of: nevirapine (VIRAMUNE®; BI); efavirenz (SUSTIVA®; BMS); etravirine (INTELENCE®; J&J); rilpivirine (TMC278, R278474; J&J); fosdevirine (GSK/ViiV); and lersivirine (Pfizer/ViiV); an HIV protease inhibitor selected from the group consisting of: atazanavir (REYATAZ®; BMS); darunavir (PREZISTA®; J&J); indinavir (CRIXIVAN®; Merck); lopinavir (KELETRA®; Abbott); nelfinavir (VIRACEPT®; Pfizer); saquinavir (INVIRASE®; Hoffmann-LaRoche); tipranavir (APTIVUS®; BI); ritonavir (NORVIR®; Abbott); and fosamprenavir (LEXIVA®; GSK/Vertex); an HIV entry inhibitor selected from: maraviroc (SELZENTRY®; Pfizer); enfuvirtide (FUZEON®; Trimeris); and BMS-663068 (BMS); and an HIV maturation inhibitor selected from: bevirimat (Myriad Genetics).

The term "antiviral agent" as used herein is intended to mean an agent that is effective to inhibit the formation and/or replication of a virus in a mammal, including but not limited to agents that interfere with either host or viral mechanisms necessary for the formation and/or replication of a virus in a mammal.

The term "inhibitor of HIV replication" as used herein is intended to mean an agent capable of reducing or eliminating the ability of HIV to replicate in a host cell, whether in vitro, ex vivo or in vivo.

The term "substituent", as used herein and unless specified otherwise, is intended to mean an atom, radical or group which may be bonded to a carbon atom, a heteroatom or any other atom which may form part of a molecule or fragment thereof, which would otherwise be bonded to at least one hydrogen atom. Substituents contemplated in the context of a specific molecule or fragment thereof are those which give rise to chemically stable compounds, such as are recognized by those skilled in the art.

The term "heteroatom" as used herein is intended to mean O, S or N.

The terms "O—$C_{1-n}$ alkyl" or "$C_{1-n}$ alkoxy" as used herein interchangeably, wherein n is an integer, either alone or in combination with another radical, is intended to mean an oxygen atom further bonded to an alkyl radical having 1 to n carbon atoms as defined above. Examples of $C_{1-n}$ alkoxy include but are not limited to methoxy ($CH_3O$—), ethoxy ($CH_3CH_2O$—), propoxy ($CH_3CH_2CH_2O$—), 1-methylethoxy (iso-propoxy; $(CH_3)_2CHO$) and 1,1-dimethylethoxy (tert-butoxy; $(CH_3)_3CO$). When an $C_{1-n}$ alkoxy is substituted, it is understood to be substituted on the alkyl portion thereof, such that the substitution would give rise to a chemically stable compound, such as are recognized by those skilled in the art.

The term "oxo" as used herein is intended to mean an oxygen atom attached to a carbon atom as a substituent by a double bond (=O).

The term "mammal" as used herein is intended to encompass humans, as well as non-human mammals which are susceptible to infection by HIV. Non-human mammals include but are not limited to domestic animals, such as cows, pigs, horses, dogs, cats, rabbits, rats and mice, and non-domestic animals.

The embodiments disclosed herein are also meant to encompass all pharmaceutically acceptable compounds of Formula I being isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$ $^{15}O$, $^{17}O$, $^{18}O$, $^{31}P$, $^{32}P$, $^{35}S$, $^{18}F$, $^{36}Cl$, $^{123}I$, and $^{125}I$, respectively. In certain embodiments, these radiolabeled compounds are useful to help determine or measure the effectiveness of the compounds, by characterizing, for example, the site or mode of action, or binding affinity to pharmacologically important site of action. Certain isotopically-labeled compounds of Formula I, for example, those incorporating a radioactive isotope, are useful in drug and/or substrate tissue distribution studies. The radioactive isotopes tritium, i.e., $^3H$, and carbon-14, i.e., $^{14}C$, are particularly useful for this purpose in view of their ease of incorporation and ready means of detection.

In certain embodiments, substitution with heavier isotopes such as deuterium, i.e., 2H, may afford certain therapeutic advantages resulting from greater metabolic stability. For example, in vivo half-life may increase or dosage requirements may be reduced. Thus, heavier isotopes may be preferred in some circumstances.

Substitution with positron emitting isotopes, such as $^{11}C$, $^{18}F$, $^{15}O$, and $^{13}N$, can be useful in Positron Emission Topography (PET) studies for examining substrate receptor occupancy. Isotopically-labeled compounds of the compounds disclosed herein can be prepared by techniques known to those skilled in the art or by processes analogous to those described in the Examples as set out below using an appropriate isotopically-labeled reagent in place of the non-labeled reagent previously employed.

The methods, compositions, kits and articles of manufacture provided herein use or include compounds (e.g., a compound of Formula I) or pharmaceutically acceptable salts thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds increase resistance to metabolism, and thus are useful for increasing the half-life of compounds or pharmaceutically acceptable salts thereof, when administered to a mammal. See, e.g., Foster, "Deuterium Isotope Effects in Studies of Drug Metabolism", Trends Pharmacol. Sci., 5(12):524-527 (1984). Such compounds can be synthesized by means known in the art, for example by employing starting materials in which one or more hydrogen atoms have been replaced by deuterium.

The embodiments disclosed herein are also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the embodiments disclosed herein include compounds produced by a process comprising administering a compound according to the embodiments disclosed herein to a mammal for a period of time sufficient to yield a metabolic product thereof. Such products are typically identified by administering a radiolabeled compound according to the embodiments disclosed herein in a detectable dose to an animal, such as rat, mouse, guinea pig, monkey, or to human, allowing sufficient time for metabolism to occur, and isolating its conversion products from the urine, blood or other biological samples.

The compounds disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic, scalemic, and optically pure forms. Optically active (+) and (−), (R)- and (S)-, or (D)- and (L)-isomers may be prepared using chiral synthons or chiral reagents, or resolved using methods such as chromatography and fractional crystallization. Techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

Optional" or "optionally" means that the subsequently described event or circumstances may or may not occur, and that the description includes instances where said event or circumstance occurs and instances in which it does not. For example, "optionally substituted heterocyclyl" means that the heterocyclyl radical may or may not be substituted and that the description includes both substituted heterocyclyl radicals and heterocyclyl radicals having no substitution.

II. COMPOUNDS

In some embodiments, the disclosure provides a compound of Formula I:

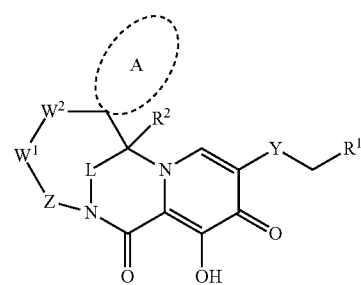

I or a pharmaceutically acceptable salt thereof, wherein:
$R^1$ is H, $C_{6-10}$ aryl or 5 to 10 membered heteroaryl containing 1, 2, 3, or 4 heteroatoms independently selected from N, O, and S,
  wherein the $C_{6-10}$ aryl or 5 to 10 membered heteroaryl is optionally substituted with one, two, three or four $R^{41}$, wherein each $R^{41}$ is independently halo, $C_{1-6}$ alkyl, $C_{1-4}$ haloalkyl, cyano, —O—$C_{1-4}$ alkyl, or $C_{1-4}$ alkyl-O—$C_{1-4}$ alkyl;
$R^2$ is H, $C_{1-6}$ alkyl, or $C_{1-4}$ haloalkyl;
L is —$CR^{3a}R^{3b}$—, —C(O)—, —$SO_2$—, —$CH_2$—$CH_2$—, or —$N(R^a)$—;
$W^1$ is a bond or —$CR^{4a}R^{4b}$—;

$W^2$ is —$CR^{5a}R^{5b}$—, —$CR^{5a}R^{5b}CR^{5c}R^{5d}$—, —$CR^{6a}$=$CR^{6b}$—, —$N(R^7)$—, —O—, —$S(O)_n$—, —C(O)—, —C(O)O—, —C(O)NH—, —$CR^{5a}R^{5b}$—$N(R^7)$—, —$CR^{5a}R^{5b}$—O—, —$CR^{5a}R^{5b}$—$S(O)_n$—, —$CR^{5a}R^{5b}$—C(O)—, —$CR^{5a}R^{5b}$—C(O)O—, —$CR^{5a}R^{5b}$—OC(O)—, —$CR^{5a}R^{5b}$—C(O)NH—, or —$CR^{5a}R^{5b}$—NHC(O)—;

Y is —C(O)NH—,

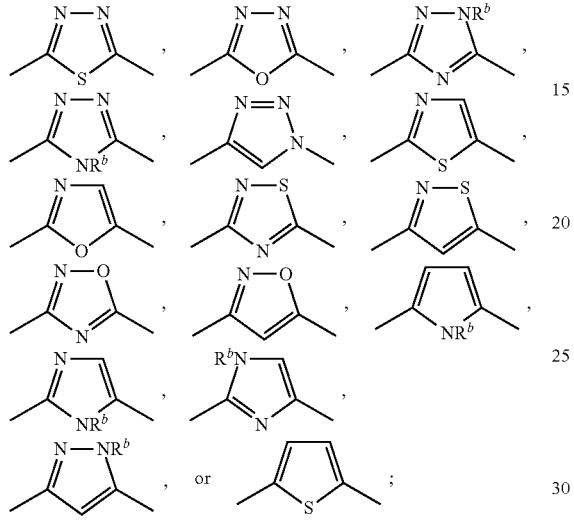

is a three to seven membered spiro ring containing 1, 2 or 3 heteroatoms selected from N, O, and S; wherein the spiro ring is optionally substituted with one, two, three, or four $R^8$ groups;

Z is —$CR^{9a}R^{9b}$—, —$CR^{9a}R^{9b}CR^{9c}R^{9d}$—, or —$CR^{10a}$=$CR^{10b}$—;

$R^{3a}$ and $R^{3b}$ are independently H, $C_{1-6}$ alkyl, $C_{1-4}$ haloalkyl, or —O—$C_{1-4}$ alkyl; or $R^{3a}$ and $R^{3b}$ together with the carbon atom to which they are attached form a 3- to 7-membered spiro ring containing 0, 1, or 2 heteroatoms selected from N, O, and S, wherein the spiro ring is optionally substituted with one, two or three $R^{42}$, wherein each $R^{42}$ is independently halo, $C_{1-4}$ alkyl or $C_{1-4}$ haloalkyl;

$R^{4a}$ and $R^{4b}$ are independently H, $C_{1-6}$ alkyl, $C_{1-4}$ haloalkyl, or halo;

$R^{5a}$, $R^{5b}$, $R^{5c}$, and $R^{5d}$ are independently H, $C_{1-6}$ alkyl, $C_{1-4}$ haloalkyl, halo, hydroxyl, cyano, —O—$C_{1-4}$ alkyl, or $C_{1-4}$ alkylene-O—$C_{1-4}$ alkyl; or $R^{5a}$ and $R^{5b}$ or $R^{5c}$ and $R^{5d}$ together with the carbon atom to which they are attached form a 3- to 7-membered spiro ring containing 0, 1, or 2 heteroatoms selected from N, O, and S, wherein the spiro ring is optionally substituted with one, two or three $R^{43}$, wherein each $R^{43}$ is independently halo, $C_{1-4}$ alkyl or $C_{1-4}$ haloalkyl; or $R^{5a}$ and $R^{5c}$ or $R^{5b}$ and $R^{5d}$ together with the carbon atoms to which each is attached form a 3- to 7-membered fused ring containing 0 or 1 heteroatom selected from N, O, and S, wherein the fused ring is optionally substituted with one to three $R^{43}$, wherein each $R^{43}$ is independently halo, $C_{1-4}$ alkyl or $C_{1-4}$ haloalkyl;

each $R^{6a}$ and $R^{6b}$ is independently H, halo, $C_{1-4}$ haloalkyl, or $C_{1-6}$ alkyl; or $R^{6a}$ and $R^{6b}$ together with the carbon atoms to which each is attached form a 5- to 10-membered partially unsaturated fused ring containing 0 or 1 heteroatom selected from N, O, and S, or a 5- to 10-membered fused aromatic ring, or a 5- to 10-membered fused heteroaromatic ring containing 1 or 2 heteroatoms selected from N, O and S, wherein the partially unsaturated fused ring, fused aromatic ring, or fused heteroaromatic ring is optionally substituted with one, two, three or four $R^{44}$, wherein each $R^{44}$ is independently halo or $C_{1-4}$ alkyl;

$R^7$ is H, $C_{1-6}$ alkyl, $C_{1-4}$ haloalkyl, $C(O)R^c$, or $SO_2R^c$;

each $R^8$ is independently selected from the group consisting of:

(i) halo, (ii) $C_{1-6}$ alkyl optionally substituted with OH, $C_{1-6}$ alkoxy, $C_{6-10}$ aryl or 5- to 10-membered heteroaryl comprising 1, 2, or 3 heteroatoms independently selected from N, O, and S, wherein the $C_{6-10}$ aryl or 5- to 10-membered heteroaryl is optionally substituted with 1 to 4 substituents selected independently from $C_1$-$C_3$ alkyl, $C_1$-$C_3$ alkoxy, halo, CN, $C_1$-$C_3$ haloalkyl, $C_3$-$C_7$ cycloalkyl, and three to seven membered halocycloalkyl containing 1, 2, or 3 heteroatoms selected from N, O, and S, (iii) $C_{1-6}$ haloalkyl optionally substituted with OH, $C_{1-6}$ alkoxy, $C_{6-10}$ aryl or 5- to 10-membered heteroaryl comprising 1, 2, or 3 heteroatoms independently selected from N, O, and S, wherein the $C_{6-10}$ aryl or 5- to 10-membered heteroaryl is optionally substituted with 1 to 4 substituents selected from $C_1$-$C_3$ alkyl, $C_1$-$C_3$ alkoxy, halo, CN, $C_1$-$C_3$ haloalkyl, $C_3$-$C_7$ cycloalkyl, and three to seven membered halocycloalkyl containing 1, 2, or 3 heteroatoms selected from N, O, and S, (iv) CN, (v) oxo, (vi) —X—$R^{45}$ wherein X is O or S; and $R^{45}$ is H, $C_{1-6}$ alkyl or 3- to 7-membered ring containing 0, 1, or 2 heteroatoms selected from N, O and S;

wherein the $C_1$-$C_6$ alkyl or the 3- to 7-membered ring is optionally substituted with 1, 2, or 3 groups selected independently from CN, halo, $C_1$-$C_6$ alkoxy, $C_{6-10}$ aryl and 5- to 10-membered heteroaryl containing 1, 2, or 3 heteroatoms independently selected from N, O, and S, (vii) $NHR^{46}$, wherein $R^{46}$ is $C_1$-$C_6$ alkyl;

(viii) $NR^{47}R^{48}$, wherein $R^{47}$ is $C_1$-$C_6$ alkyl;

and $R^{48}$ is $C_1$-$C_6$ alkyl, (ix) $C_{6-10}$ aryl optionally substituted with 1, 2, 3, or 4 substituents independently selected from $C_{1-6}$ alkyl, $C_{1-6}$ haloalkyl, halo, CN, $C_{3-7}$ cycloalkyl, and $C_{1-6}$ alkoxy;

wherein the $C_{3-7}$ cycloalkyl is optionally substituted with 1, 2, 3, or 4 independent halo groups, (x) 3- to 7-membered ring containing 0, 1, or 2 heteroatoms selected independently from N, O and S, wherein the 3- to 7-membered ring is optionally substituted with one, two or three substituents selected independently from halo, $C_{1-6}$ alkyl, $C_{1-6}$ haloalkyl, $C_{1-6}$ alkoxy, and $C_{3-7}$ cycloalkyl, and (xi) 5- to 10-membered heteroaryl ring containing 1, 2, or 3 heteroatoms independently selected from N, O, and S, wherein the 5- to 10-membered heteroaryl ring is optionally substituted with one, two or three substituents selected independently from halo, $C_{1-6}$ alkyl, $C_{1-6}$ haloalkyl, $C_{1-6}$ alkoxy, and $C_{3-7}$ cycloalkyl, (xii) —$SO_2R^{413}$, $R^{413}$ is $C_1$-$C_6$ alkyl or 3 to 7 membered ring containing 0, 1, or 2 heteroatoms selected from N, O and S;

wherein the $C_{1-6}$ alkyl or the 3 to 7 membered ring is optionally substituted with 1, 2, or 3 groups selected from CN, halo and $C_1$-$C_6$ alkoxy, (xiii) —$SO(NR^{414})_2$, each $R^{414}$ is independently H, $C_{1-6}$ alkyl or 3 to 7 membered ring containing 0, 1, or 2 heteroatoms independently selected from N, O and S;

wherein the $C_{1-6}$ alkyl or the 3 to 7 membered ring is optionally substituted with 1, 2, or 3 groups selected from CN, halo and $C_1$-$C_6$ alkoxy, (xiv) $C_{2-6}$ alkynyl optionally substituted with one, two, three, or four substituents independently selected from $C_{1-6}$ alkoxy, OH, —$SO_2$—($C_{1-3}$ alkyl), or two $R^8$ groups are joined to form a fused, spiro, or bridged 3- to 7-membered ring containing 0, 1, 2, or 3 heteroatoms selected from N, O and S;

wherein the 3- to 7-membered ring is optionally substituted with one, two or three substituents selected independently from halo, OH, $C_{1-6}$ alkyl, $C_{1-6}$ haloalkyl, $C_{1-6}$ alkoxy, and $C_{3-7}$ cycloalkyl; or two $R^8$ groups on adjacent carbon atoms are joined to form a fused 6- to 10-membered aromatic ring containing 0, 1, 2, or 3 heteroatoms selected from N, O and S, wherein the fused 6- to 10-membered aromatic ring is optionally substituted with one, two or three substituents selected independently from halo, OH, $C_{1-6}$ alkyl, $C_{1-6}$ haloalkyl, $C_{1-6}$ alkoxy, and $C_{3-7}$ cycloalkyl;

$R^{9a}$, $R^{9b}$, $R^{9c}$, and $R^{9d}$ are each independently H, $C_{1-6}$ alkyl, $C_{1-4}$ haloalkyl, or halo; or $R^{9a}$ and $R^{9b}$ or $R^{9c}$ and $R^{9d}$ together with the carbon atom to which they are attached form a 3- to 7-membered spiro ring containing 0, 1, or 2 heteroatoms selected from N, O, and S, wherein the spiro ring is optionally substituted with one, two or three $R^{49}$, wherein each $R^{49}$ is independently halo, $C_{1-4}$ alkyl or $C_{1-4}$ haloalkyl; or $R^{9a}$ and $R^{9c}$ or $R^{9b}$ and $R^{9d}$ together with the carbon atoms to which each is attached form a 3- to 7-membered fused ring containing 0 or 1 heteroatom selected from N, O, and S, wherein the fused ring is optionally substituted with one, two or three $R^{411}$, wherein each $R^{410}$ is independently halo, $C_{1-4}$ alkyl, or $C_{1-4}$ haloalkyl; or one of $R^{9a}$, $R^{9b}$, $R^{9c}$, and $R^{9d}$ and one of $R^{4a}$, $R^{4b}$, $R^{5a}$, $R^{5s}$, and $R^7$ together with the atoms to which each is attached form a 3- to 7-membered fused ring containing 0, 1, or 2 heteroatoms selected from N, O and S, wherein the fused ring is optionally substituted with one, two, three or four $R^{411}$, wherein each $R^{411}$ is independently halo or $C_{1-4}$ alkyl;

$R^{10a}$ and $R^{10b}$ are independently H, halo, $C_{1-4}$haloalkyl, or $C_{1-6}$ alkyl; or $R^{10a}$ and $R^{10b}$ together with the carbon atoms to which each is attached form a 5- to 10-membered partially unsaturated fused ring containing 0 or 1 heteroatom selected from N, O, and S, or a 5- to 10-membered fused aromatic ring, or a 5- to 10-membered fused heteroaromatic ring containing 1 or 2 heteroatoms selected from N, O and S, wherein the partially unsaturated fused ring, fused aromatic ring, or fused heteroaromatic ring is optionally substituted with one to four $R^{412}$, wherein each $R^{412}$ is independently halo or $C_{1-4}$ alkyl;

$R^a$ is independently H, $C_{1-6}$ alkyl, $C_{1-6}$ haloalkyl, $C(O)R^c$, or $SO_2R^c$;

$R^b$ is H or $C_{1-4}$ alkyl;

$R^c$ is $C_{1-4}$ alkyl or $C_{1-4}$ alkyloxy; and each n is independently 0, 1, or 2.

In some embodiments of the compound of Formula I, or the pharmaceutically acceptable salt thereof,  is substituted with one, two, three, or four $R^8$ groups; and at least one $R^8$ group is selected from the group consisting of:

(i) $C_{1-6}$ alkyl substituted with OH, $C_{1-6}$ alkoxy, $C_{6-10}$ aryl or 5- to 10-membered heteroaryl comprising 1, 2, or 3 heteroatoms independently selected from N, O, and S, wherein the $C_{6-10}$ aryl or 5- to 10-membered heteroaryl is optionally substituted with 1 to 4 substituents selected independently from $C_1$-$C_3$ alkyl, $C_1$-$C_3$ alkoxy, halo, CN, $C_1$-$C_3$ haloalkyl, $C_3$-$C_7$ cycloalkyl, and three to seven membered halocycloalkyl containing 1, 2, or 3 heteroatoms selected from N, O, and S, (ii) $C_{1-6}$haloalkyl substituted with OH, $C_{1-6}$ alkoxy, $C_{6-10}$ aryl or 5- to 10-membered heteroaryl comprising 1, 2, or 3 heteroatoms independently selected from N, O, and S, wherein the $C_{6-10}$ aryl or 5- to 10-membered heteroaryl is optionally substituted with 1 to 4 substituents selected from $C_1$-$C_3$ alkyl, $C_1$-$C_3$ alkoxy, halo, CN, $C_1$-$C_3$ haloalkyl, $C_3$-$C_7$ cycloalkyl, and three to seven membered halocycloalkyl containing 1, 2, or 3 heteroatoms selected from N, O, and S, (iii) CN, (iv) oxo, (v) —X—$R^{45}$ wherein X is O or S; and $R^{4}$s is H, $C_{1-6}$ alkyl or 3- to 7-membered ring containing 0, 1, or 2 heteroatoms selected from N, O and S;

wherein the $C_1$-$C_6$ alkyl or the 3- to 7-membered ring is optionally substituted with 1, 2, or 3 groups selected independently from CN, halo, $C_1$-$C_6$ alkoxy, $C_{6-10}$ aryl and 5- to 10-membered heteroaryl containing 1, 2, or 3 heteroatoms independently selected from N, O, and S, (vi) $NHR^{46}$, wherein $R^{46}$ is $C_1$-$C_6$ alkyl;

(vii) $NR^{47}R^{48}$, wherein $R^{47}$ is $C_1$-$C_6$ alkyl and $R^{48}$ is $C_1$-$C_6$ alkyl;

(viii) $C_{6-10}$ aryl optionally substituted with 1, 2, 3, or 4 substituents independently selected from $C_{1-6}$ alkyl, $C_{1-6}$ haloalkyl, halo, CN, $C_{3-7}$ cycloalkyl, and $C_{1-6}$ alkoxy; wherein the $C_{3-7}$ cycloalkyl is optionally substituted with 1, 2, 3, or 4 independent halo groups, (ix) 3 to 7 membered ring containing 0, 1, or 2 heteroatoms selected independently from N, O and S, wherein the 3- to 7-membered ring is optionally substituted with one, two or three substituents selected independently from halo, $C_{1-6}$ alkyl, $C_{1-6}$ haloalkyl, $C_{1-6}$ alkoxy, and $C_{3-7}$ cycloalkyl, and
(x) 5- to 10 membered heteroaryl ring containing 1, 2, or 3 heteroatoms independently selected from N, O, and S,
wherein the 5- to 10 membered heteroaryl ring is optionally substituted with one, two or three substituents selected independently from halo, $C_{1-6}$ alkyl, $C_{1-6}$ haloalkyl, $C_{1-6}$ alkoxy, and $C_{3-7}$ cycloalkyl,
(xi) —$SO_2R^{413}$,
$R^{413}$ is $C_1$-$C_6$ alkyl or 3 to 7 membered ring containing 0, 1, or 2 heteroatoms selected from N, O and S;
wherein the $C_{1-6}$ alkyl or the 3 to 7 membered ring is optionally substituted with 1, 2, or 3 groups selected from CN, halo and $C_1$-$C_6$ alkoxy,
(xii) —$SO(NR^{414})_2$,
each $R^{414}$ is independently H, $C_{1-6}$ alkyl or 3 to 7 membered ring containing 0, 1, or 2 heteroatoms independently selected from N, O and S;
wherein the $C_{1-6}$ alkyl or the 3 to 7 membered ring is optionally substituted with 1, 2, or 3 groups selected from CN, halo and $C_1$-$C_6$ alkoxy,
(xiii) $C_{2-6}$ alkynyl optionally substituted with one, two, three, or four substituents independently selected from $C_{1-6}$ alkoxy, OH, —$SO_2$—($C_{1-3}$ alkyl), or
two $R^8$ groups are joined to form a fused, spiro, or bridged 3- to 7-membered ring containing 0, 1, 2, or 3 heteroatoms selected from N, O and S;
wherein the 3- to 7-membered ring is optionally substituted with one, two or three substituents selected independently from halo, OH, $C_{1-6}$ alkyl, $C_{1-6}$ haloalkyl, $C_{1-6}$ alkoxy, and $C_{3-7}$ cycloalkyl; or
two $R^8$ groups on adjacent carbon atoms are joined to form a fused 6- to 10-membered aromatic ring containing 0, 1, 2, or 3 heteroatoms selected from N, O and S,
wherein the fused 6- to 10-membered aromatic ring is optionally substituted with one, two or three substituents selected independently from halo, OH, $C_{1-6}$ alkyl, $C_{1-6}$ haloalkyl, $C_{1-6}$ alkoxy, and $C_{3-7}$ cycloalkyl.

In some embodiments of the compound of Formula I, or the pharmaceutically acceptable salt thereof,  is a six membered spiro ring containing 1 or 2 heteroatoms selected from N, O, and S; wherein the spiro ring is optionally substituted with one, two, three, or four $R^8$ groups. In some embodiments of the compound of Formula I, or the pharmaceutically acceptable salt thereof,  is a six membered spiro ring containing 1 or 2 heteroatoms selected from N, O, and S; wherein the spiro ring is optionally substituted with one, two, or three $R^8$ groups. In some embodiments of the compound of Formula I, or the pharmaceutically acceptable salt thereof,  is a six membered spiro ring containing 1 or 2 heteroatoms selected from N, O, and S; wherein the spiro ring is optionally substituted with one or two $R^8$ groups.

In some embodiments of the compound of Formula I, or the pharmaceutically acceptable salt thereof,  is a six membered spiro ring containing 1 or 2 heteroatoms selected from N and O; wherein the spiro ring is optionally substituted with one, two, three, or four $R^8$ groups. In some embodiments of the compound of Formula I, or the pharmaceutically acceptable salt thereof,  is a six membered spiro ring containing 1 or 2 heteroatoms selected from N and O; wherein the spiro ring is optionally substituted with one, two, or three $R^8$ groups. In some embodiments of the compound of Formula I, or the pharmaceutically acceptable salt thereof,  is a six membered spiro ring containing 1 or 2 heteroatoms selected from N and O; wherein the spiro ring is optionally substituted with one or two $R^8$ groups.

In some embodiments of the compound of Formula I, or the pharmaceutically acceptable salt thereof  is a five membered spiro ring containing 1 or 2 heteroatoms selected from N, O, and S; wherein the spiro ring is optionally substituted with one, two, three, or four $R^8$ groups. In some embodiments of the compound of Formula I, or the pharmaceutically acceptable salt thereof  is a five membered spiro ring containing 1 or 2 heteroatoms selected from N, O, and S; wherein the spiro ring is optionally substituted with one, two, or three $R^8$ groups. In some embodiments of the compound of Formula I, or the pharmaceutically acceptable salt thereof  is a five membered spiro ring containing 1 or 2 heteroatoms selected from N, O, and S; wherein the spiro ring is optionally substituted with one or two $R^8$ groups.

In some embodiments of the compound of Formula I, or the pharmaceutically acceptable salt thereof  is a five membered spiro ring containing 1 or 2 heteroatoms selected from N and O; wherein the spiro ring is optionally substituted with one, two, three, or four $R^8$ groups. In some embodiments of the compound of Formula I, or the pharmaceutically acceptable salt thereof  is a five membered spiro ring containing 1 or 2 heteroatoms selected from N and O; wherein the spiro ring is optionally substituted with one, two, or three $R^8$ groups. In some embodiments of the compound of Formula I, or the pharmaceutically acceptable salt thereof  is a five membered spiro ring containing 1 or 2 heteroatoms selected from N and O; wherein the spiro ring is optionally substituted with one or two $R^8$ groups.

In some embodiments of the compound of Formula I, or the pharmaceutically acceptable salt thereof,  is a four membered spiro ring containing 1 or 2 heteroatoms selected from N, O, and S; wherein the spiro ring is optionally substituted with one, two, three, or four R⁸ groups. In some embodiments of the compound of Formula I, or the pharmaceutically acceptable salt thereof,  is a four membered spiro ring containing 1 or 2 heteroatoms selected from N, O, and S; wherein the spiro ring is optionally substituted with one, two, or three R⁸ groups. In some embodiments of the compound of Formula I, or the pharmaceutically acceptable salt thereof,  is a four membered spiro ring containing 1 or 2 heteroatoms selected from N, O, and S; wherein the spiro ring is optionally substituted with one or two R⁸ groups.

In some embodiments of the compound of Formula I, or the pharmaceutically acceptable salt thereof,  is a four membered spiro ring containing 1 or 2 heteroatoms selected from N and S; wherein the spiro ring is optionally substituted with one, two, three, or four R⁸ groups. In some embodiments of the compound of Formula I, or the pharmaceutically acceptable salt thereof,  is a four membered spiro ring containing 1 or 2 heteroatoms selected from N and S, wherein the spiro ring is optionally substituted with one, two, or three R⁸ groups. In some embodiments of the compound of Formula I, or the pharmaceutically acceptable salt thereof,  is a four membered spiro ring containing 1 or 2 heteroatoms selected from N and S; wherein the spiro ring is optionally substituted with one or two R⁸ groups.

In some embodiments of the compound of Formula I, or the pharmaceutically acceptable salt thereof,  is selected from the group consisting of

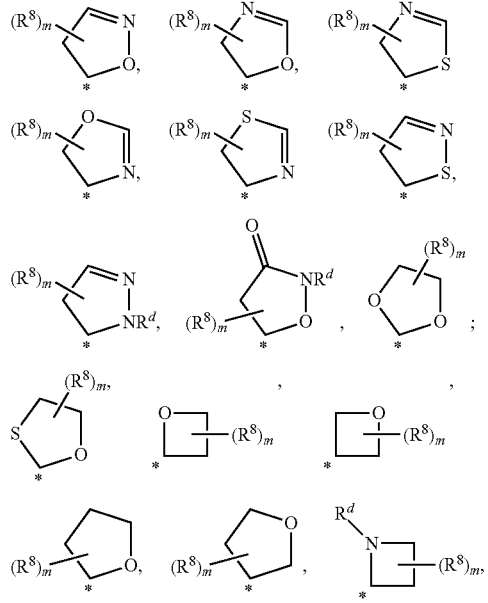

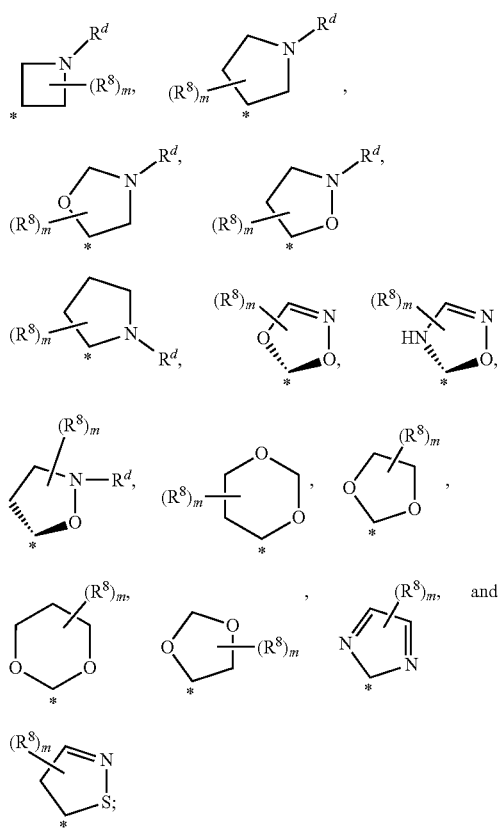

wherein * indicates the point of attachment of  to the remaining Formula I; $R^d$ is H, $C_{1-4}$alkyl or $C_{1-4}$haloalkyl; and m is 0, 1, 2, 3 or 4.

In some embodiments of the compound of Formula I, or the pharmaceutically acceptable salt thereof,  is selected from the group consisting of

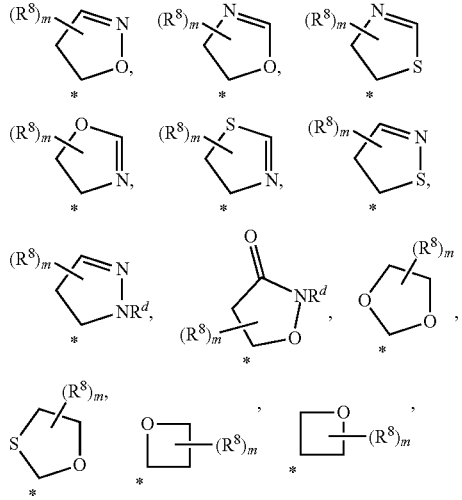

-continued

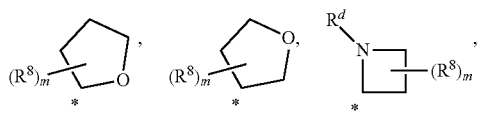

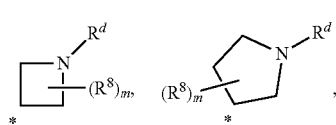

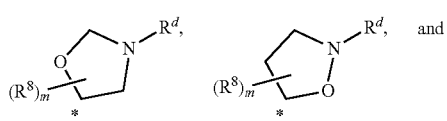

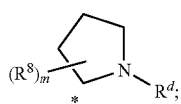

wherein * indicates the point of attachment of (A) to the remaining Formula I; $R^d$ is H, $C_{1-4}$alkyl or $C_{1-4}$haloalkyl; and m is 0, 1, 2, 3, or 4.

In some embodiments of the compound of Formula I, or the pharmaceutically acceptable salt thereof (A) is selected from the group consisting of

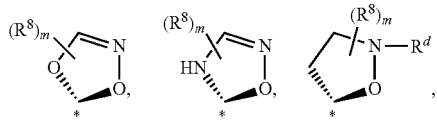

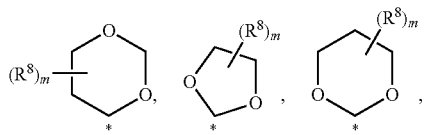

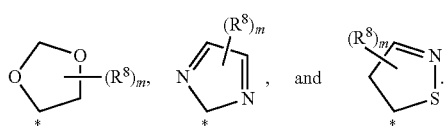

In some embodiments of the compound of Formula I, or the pharmaceutically acceptable salt thereof (A) is

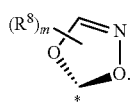

In some embodiments of the compound of Formula I, or the pharmaceutically acceptable salt thereof (A) is

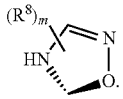

In some embodiments of the compound of Formula I, or the pharmaceutically acceptable salt thereof (A) is

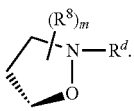

In some embodiments of the compound of Formula I, or the pharmaceutically acceptable salt thereof (A) is

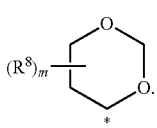

In some embodiments of the compound of Formula I, or the pharmaceutically acceptable salt thereof (A) is

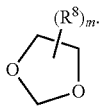

In some embodiments of the compound of Formula I, or the pharmaceutically acceptable salt thereof (A) is

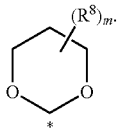

In some embodiments of the compound of Formula I, or the pharmaceutically acceptable salt thereof (A) is

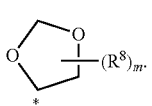

In some embodiments of the compound of Formula I, or the pharmaceutically acceptable salt thereof  is

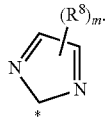

In some embodiments of the compound of Formula I, or the pharmaceutically acceptable salt thereof  is

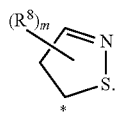

In some embodiments of the compound of Formula I, or the pharmaceutically acceptable salt thereof  is selected from the group consisting of

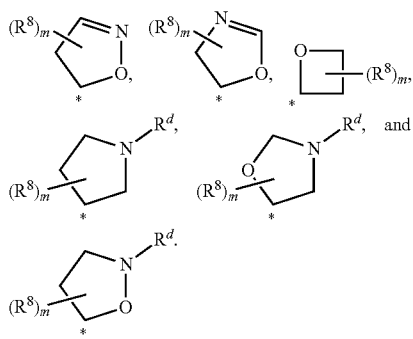

In some embodiments of the compound of Formula I, or the pharmaceutically acceptable salt thereof,  is

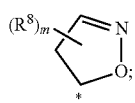

wherein m is 0, 1, 2 or 3. In some embodiments of the compound of Formula I, or the pharmaceutically acceptable salt thereof,  is

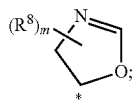

wherein m is 0, 1, 2, 3 or 4. In some embodiments of the compound of Formula I, or the pharmaceutically acceptable salt thereof,  is

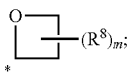

In some embodiments of the compound of Formula I, or the pharmaceutically acceptable salt thereof,  is

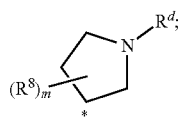

wherein m is 0, 1, 2 or 3. In some embodiments of the compound of Formula I, or the pharmaceutically acceptable salt thereof,  is

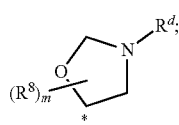

wherein m is 0, 1, 2 or 3. In some embodiments of the compound of Formula I, or the pharmaceutically acceptable salt thereof,  is

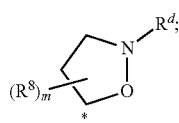

wherein m is 0, 1, 2 or 3.

In some embodiments of the compound of Formula I, or the pharmaceutically acceptable salt thereof, the compound has a Formula I-A:

I-A

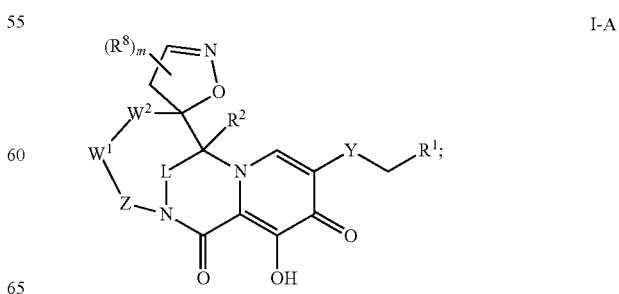

I-A; wherein m is 0, 1 or 2 or 3.

In some embodiments of the compound of Formula I, or the pharmaceutically acceptable salt thereof, the compound has a Formula I-B:

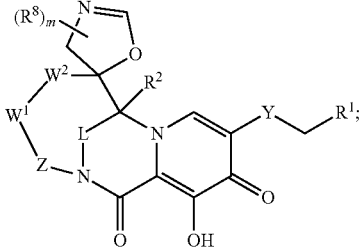

I-B; wherein m is 0, 1, 2 or 3.

In some embodiments of the compound of Formula I, or the pharmaceutically acceptable salt thereof, the compound has a Formula I-C:

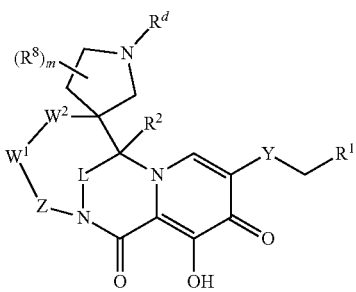

wherein $R^d$ is H, $C_{1-4}$alkyl or $C_{1-4}$haloalkyl; and m is 0, 1, 2 or 3.

In some embodiments of the compound of Formula I, or the pharmaceutically acceptable salt thereof, the compound has a Formula I-D:

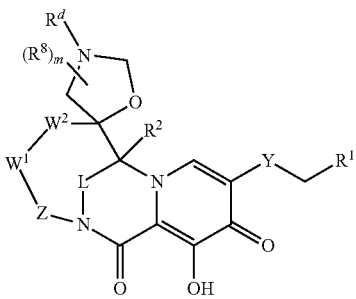

wherein $R^d$ is H, $C_{1-4}$alkyl or $C_{1-4}$haloalkyl; and m is 0, 1, 2 or 3.

In some embodiments of the compound of Formula I, or the pharmaceutically acceptable salt thereof, the compound has a Formula I-E:

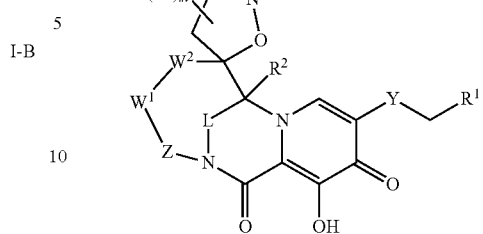

wherein $R^d$ is H, $C_{1-4}$alkyl or $C_{1-4}$haloalkyl; and m is 0, 1, 2 or 3.

In some embodiments of the compound of Formula I, or the pharmaceutically acceptable salt thereof, the compound has a Formula I-F:

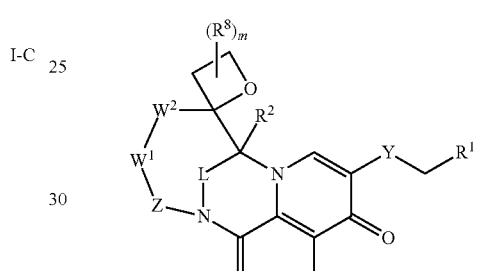

wherein m is 0, 1, 2, 3, or 4.

In some embodiments of the compound of Formula I, I-A, I-B, I-C, I-D, I-E, or I-F, or the pharmaceutically acceptable salt thereof, $R^2$ is H or $C_{1-6}$ alkyl. In some embodiments, $R^2$ is H. In some embodiments, $R^2$ is $C_{1-6}$ alkyl. In some embodiments, $R^2$ is $C_{1-3}$ alkyl. In some embodiments, $R^2$ is $C_{1-4}$haloalkyl.

In some embodiments of the compound of Formula I, I-A, I-B, I-C, I-D, I-E, or I-F, or the pharmaceutically acceptable salt thereof, Y is selected from the group consisting of —C(O)NH—,

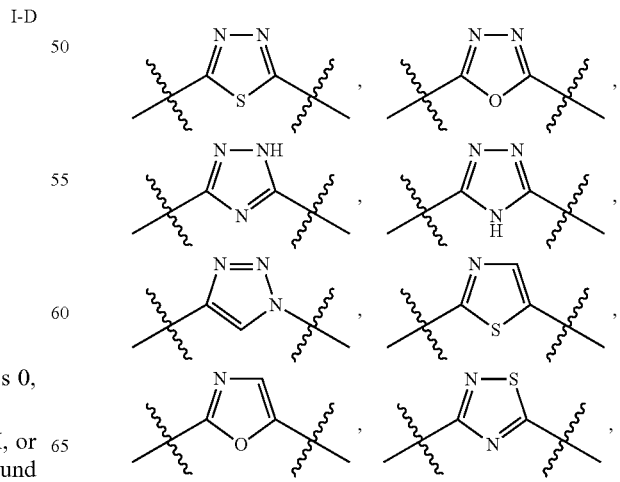

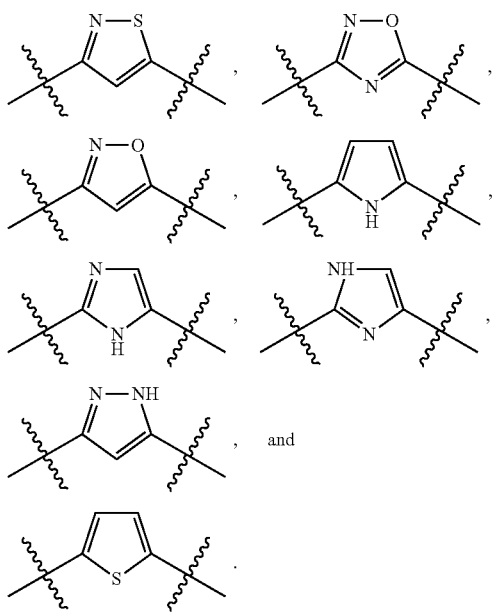
In some embodiments, Y is —C(O)NH—. In some embodiments, Y is
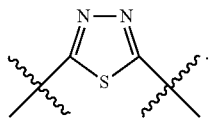 [SMILES: *c1nnc(*)s1]
In some embodiments, Y is
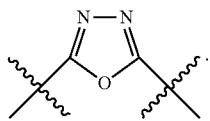 [SMILES: *c1nnc(*)o1]
In some embodiments, Y is
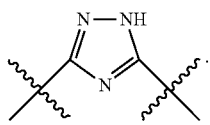 [SMILES: *c1n[nH]c(*)n1]
In some embodiments, Y is
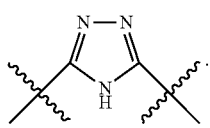 [SMILES: *c1nnc(*)[nH]1]
In some embodiments, Y is
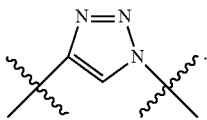 [SMILES: *c1cn(*)nn1]
In some embodiments, Y is
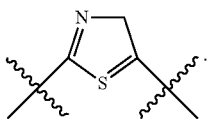
In some embodiments, Y is
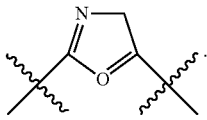
In some embodiments, Y is
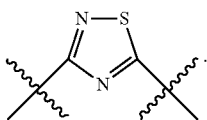 [SMILES: *c1nsc(*)n1]
In some embodiments, Y is
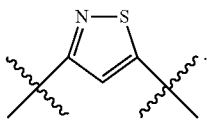 [SMILES: *c1cc(*)sn1]
In some embodiments, Y is
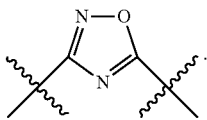 [SMILES: *c1noc(*)n1]
In some embodiments, Y is
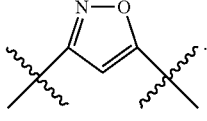 [SMILES: *c1cc(*)on1]

In some embodiments, Y is

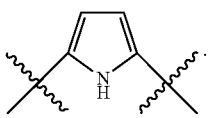 [SMILES: *c1ccc(*)[nH]1]

In some embodiments, Y is

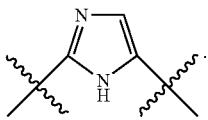 [SMILES: *c1cnc(*)[nH]1]

In some embodiments, Y is

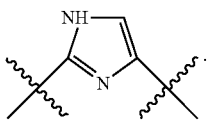 [SMILES: *c1c[nH]c(*)n1]

In some embodiments, Y is

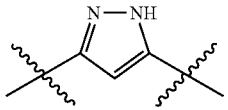

In some embodiments, Y is

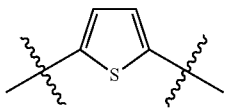

In some embodiments of the compound of Formula I, I-A, I-B, I-C, I-D, I-E, or I-F, or the pharmaceutically acceptable salt thereof, Y is -C(O)NH— and $R^2$ is H or $C_{1-6}$ alkyl.

In some embodiments of the compound of Formula I or I-A, or the pharmaceutically acceptable salt thereof, the compound has a Formula II-A:

Formula II-A

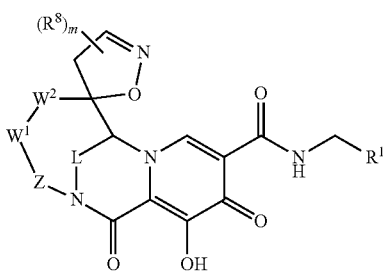

wherein m is 0, 1, 2 or 3.

In some embodiments of the compound of Formula I, I-A, I-B, I-C, I-D, I-E, I-F, or II-A, or the pharmaceutically acceptable salt thereof, $R^1$ is phenyl, optionally substituted with one, two, three, or four $R^{41}$, wherein each $R^{41}$ is independently halo, $C_{1-4}$ alkyl, $C_{1-4}$ haloalkyl, cyano, —O—$C_{1-4}$ alkyl, or $C_{1-4}$ alkyl-O—$C_{1-4}$ alkyl. In some embodiments, $R^1$ is phenyl, optionally substituted with one, two, three, or four $R^{41}$, wherein each $R^{41}$ is independently halo, $C_{1-4}$ alkyl, $C_{1-4}$ haloalkyl, or —O—$C_{1-4}$ alkyl. In some embodiments, $R^1$ is phenyl substituted with one, two, three, or four $R^{41}$, wherein each $R^{41}$ is independently halo or —O—$C_{1-4}$ alkyl. In some embodiments, $R^1$ is phenyl substituted with one, two, three, or four halogens. In some embodiments, $R^1$ is phenyl substituted with two or three halogens selected from chloro and fluoro. In some embodiments, $R^1$ is

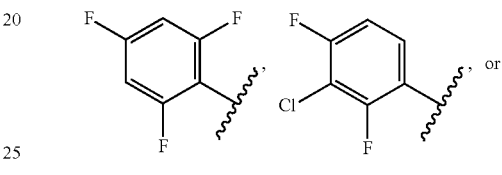

In some embodiments, $R^1$ is

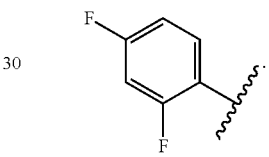

In some embodiments, $R^1$ is

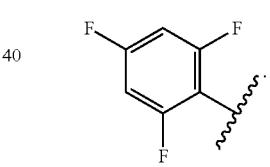

In some embodiments, $R^1$ is

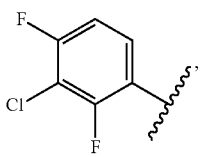

In some embodiments, $R^1$ is

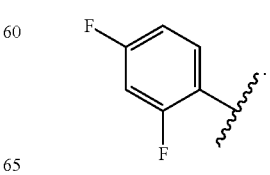

In some embodiments, $R^1$ is

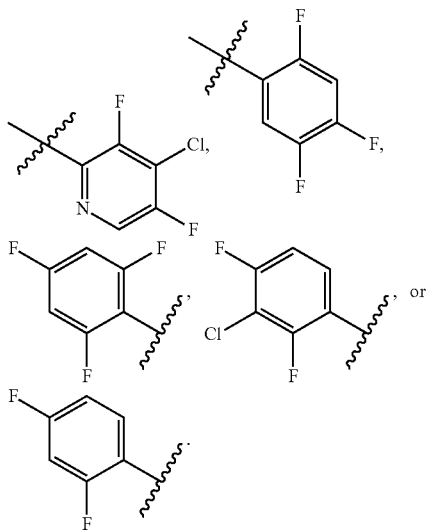

In some embodiments, $R^1$ is

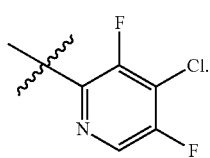 [SMILES: *c1ncc(F)c(Cl)c1F]

In some embodiments, $R^1$ is

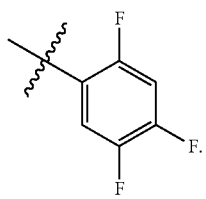 [SMILES: *c1cc(F)c(F)cc1F]

In some embodiments, $R^1$ is

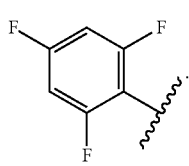

In some embodiments, $R^1$ is

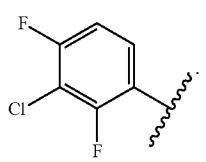

In some embodiments, $R^1$ is

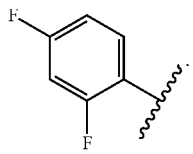

In some embodiments, $R^1$ is

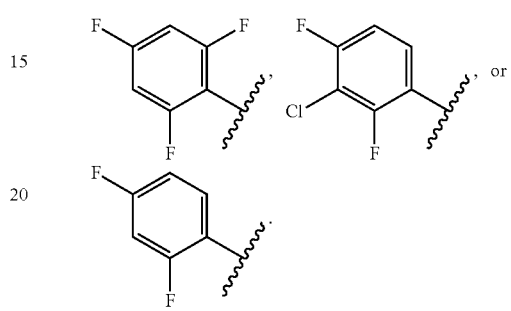

In some embodiments, $R^1$ is

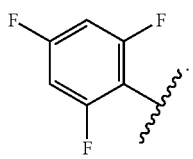

In some embodiments, $R^1$ is

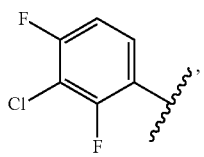 [SMILES: *c1ccc(F)c(Cl)c1F]

In some embodiments, $R^1$ is

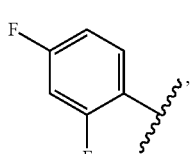

In some embodiments of the compound of Formula I, I-A, I-B, I-C, I-D, I-E, I-F, or II-A, or the pharmaceutically acceptable salt thereof, $R^1$ is pyridyl optionally substituted with one, two, three, or four $R^{41}$, wherein each $R^{41}$ is independently halo, $C_{1-4}$ alkyl, $C_{1-4}$ haloalkyl, cyano, —O—$C_{1-4}$ alkyl, or $C_{1-4}$ alkyl-O—$C_{1-4}$ alkyl. In some embodiments, $R^1$ is pyridyl optionally substituted with one, two, three, or four $R^{41}$, wherein each $R^{41}$ is independently halo, $C_{1-4}$ alkyl, $C_{1-4}$ haloalkyl, or —O—$C_{1-4}$ alkyl. In some embodiments, $R^1$ is pyridyl substituted with one, two, three, or four $R^{41}$, wherein each $R^{41}$ is independently halo or —O—$C_{1-4}$ alkyl. In some embodiments, $R^1$ is pyridyl substituted with one, two, three, or four halogens. In some embodiments, $R^1$ is pyridyl substituted with two or three halogens selected from chloro and fluoro. In some embodiments, $R^1$ is

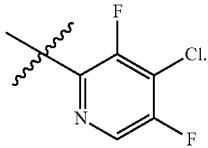

In some embodiments of the compound of Formula I, I-A or II-A, or the pharmaceutically acceptable salt thereof, the compound has a Formula II-Aa or II-Ab:

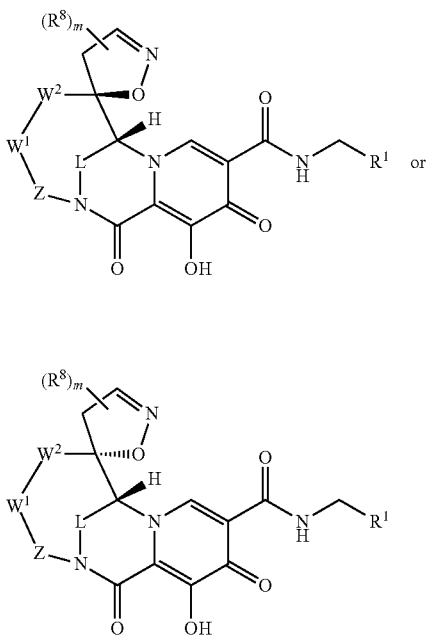

wherein m is 0, 1, 2 or 3.

In some embodiments of the compound of Formula I, I-A or II-A, or the pharmaceutically acceptable salt thereof, the compound has a Formula II-Aa. In some embodiments of the compound of Formula I, I-A or II-A, or the pharmaceutically acceptable salt thereof, the compound has a Formula II-Ab.

In some embodiments of the compound of Formula I, I-A, I-B, I-C, I-D, I-E, I-F, II-A, II-Aa, or II-Ab, or the pharmaceutically acceptable salt thereof L is —$CR^{3a}R^{3b}$—; wherein $R^{3a}$ and $R^{3b}$ are independently H, $C_{1-6}$ alkyl, $C_{1-4}$ haloalkyl, or —O—$C_{1-4}$ alkyl. In some embodiments, L is —$CR^{3a}R^{3b}$—; wherein $R^{3a}$ and $R^{3b}$ are independently H, $C_{1-6}$ alkyl or $C_{1-4}$haloalkyl. In some embodiments, L is —$CR^{3a}R^{3b}$—; wherein $R^{3a}$ and $R^{3b}$ are independently H or $C_{1-6}$ alkyl. In some embodiments, L is —$CR^{3a}R^{3b}$—; wherein $R^{3a}$ and $R^{3b}$ are both H. In some embodiments, L is —C(O)—. In some embodiments, L is —$SO_2$—. In some embodiments, L is —$CH_2$—$CH_2$—. In some embodiments, L is or —N($R^a$)—. In some embodiments, L is NH.

In some embodiments of the compound of Formula I, I-A, II-A, II-Aa, or II-Ab, the compound has a Formula III:

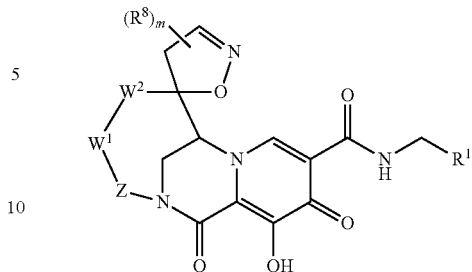

wherein m is 0, 1, 2 or 3.

In some embodiments of the compound of Formula I, I-A, II-A, II-Aa, II-Ab, or III, the compound has a Formula IIIa or IIIb:

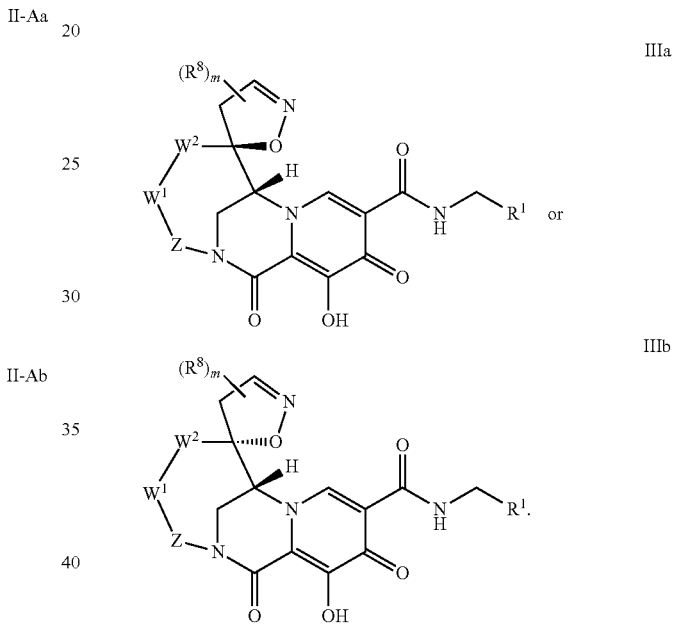

wherein m is 0, 1, 2 or 3.

In some embodiments of the compound of Formula I, I-A, II-A, II-Aa, or III, the compound has a Formula IIIa. In some embodiments of the compound of Formula I, I-A, II-A, II-Ab, or III, the compound has a Formula IIIb.

In some embodiments of the compound of Formula I, I-A, I-B, I-C, I-D, I-E, I-F, II-II-A, II-Aa, II-Ab, III, IIIa, or IIIb, or the pharmaceutically acceptable salt thereof, $W^1$ is a bond or —$CR^{4a}R^{4b}$—; wherein $R^{4a}$ and $R^{4b}$ are independently H, $C_{1-6}$ alkyl, $C_{1-4}$ haloalkyl, or halo. In some embodiments, $W^1$ is a bond or —$CR^{4a}R^{4b}$—; wherein $R^{4a}$ and $R^{4b}$ are independently H, $C_{1-6}$ alkyl, or halo. In some embodiments, $W^1$ is a bond or —$CR^{4a}R^{4b}$—; wherein $R^{4a}$ and $R^{4b}$ are independently H, —$CH_3$, or halo. In some embodiments, $W^1$ is a bond or —$CR^{4a}H$—; wherein $R^{4a}$ is H, $C_{1-6}$ alkyl, or halo. In some embodiments, $W^1$ is bond, —$CH_2$— or —CH(F)—.

In some embodiments of the compound of Formula I, I-A, I-B, I-C, I-D, I-E, I-F, II-A, IIAa, II-Ab, III, IIIa, or IIIb or the pharmaceutically acceptable salt thereof, Y is-C(O) NH—; $R^2$ is H or $C_{1-6}$ alkyl; and $W^1$ is a bond or —$CR^{4a}R^{4b}$—; wherein $R^{4a}$ and $R^{4b}$ are independently H, $C_{1-6}$ alkyl, $C_{1-4}$ haloalkyl, or halo. In some embodiments, Y is-C(O)NH—; $R^2$ is H or $C_{1-6}$ alkyl; and $W^1$ is a bond or —$CR^{4a}R^{4b}$—; wherein $R^{4a}$ and $R^{4b}$ are independently H, $C_{1-6}$ alkyl, or halo. In some embodiments, Y is-C(O)NH—; $R^2$ is H or $C_{1-6}$ alkyl; and $W^1$ is a bond or —$CR^{4a}R^{4b}$—; wherein $R^{4a}$ and $R^{4b}$ are independently H, —$CH_3$, or halo. In some embodiments, Y is-C(O)NH—; $R^2$ is H or $C_{1-6}$ alkyl; and $W^1$ is a bond or —$CR^{4a}H$—; wherein $R^{4a}$ is H, $C_{1-6}$ alkyl, or halo. In some embodiments, Y is-C(O)NH—; $R^2$ is H or $C_{1-6}$ alkyl; and $W^1$ is bond, —$CH_2$— or —CH(F)—.

In some embodiments of the compound of Formula I, I-A, I-B, I-C, I-D, I-E, I-F, II-II-A, II-Aa, II-Ab, III, IIIa, or IIIb, or the pharmaceutically acceptable salt thereof, Z is —$CR^{9a}R^{9b}$—; wherein $R^{9a}$ and $R^{9b}$ are each independently H, $C_{1-6}$ alkyl, $C_{1-4}$ haloalkyl, or halo. In some embodiments, Z is —$CR^{9a}R^{9b}$—; wherein $R^{9a}$ and $R^{9b}$ are each independently H, $C_{1-6}$ alkyl, or $C_{1-4}$ haloalkyl. In some embodiments, Z is —$CH(CH_3)$— or —$CH(CH_2F)$—.

In some embodiments of the compound of Formula I, I-A, I-B, I-C, I-D, I-E, I-F, II-II-A, Aa, II-Ab, III, IIIa, or IIIb or the pharmaceutically acceptable salt thereof, Y is-C(O)NH—; $R^2$ is H or $C_{1-6}$ alkyl; $W^1$ is a bond or —$CR^{4a}R^{4b}$—; wherein $R^{4a}$ and $R^{4b}$ are independently H, $C_{1-6}$ alkyl, $C_{1-4}$ haloalkyl, or halo; and Z is —$CR^{9a}R^{9b}$—; wherein $R^{9a}$ and $R^{9b}$ are each independently H, $C_{1-6}$ alkyl, $C_{1-4}$ haloalkyl, or halo. In some embodiments, Y is-C(O)NH—; $R^2$ is H or $C_{1-6}$ alkyl; $W^1$ is a bond or —$CR^{4a}R^{4b}$—; wherein $R^{4a}$ and $R^{4b}$ are independently H, $C_{1-6}$ alkyl, or halo; and Z is —$CR^{9a}R^{9b}$—; wherein $R^{9a}$ and $R^{9b}$ are each independently H, $C_{1-6}$ alkyl, or $C_{1-4}$ haloalkyl. In some embodiments, Y is-C(O)NH—; $R^2$ is H or $C_{1-6}$ alkyl; $W^1$ is a bond or —$CR^{4a}R^{4b}$—; wherein $R^{4a}$ and $R^{4b}$ are independently H, —$CH_3$, or halo; and Z is —$CR^{9a}R^{9b}$—; wherein $R^{9a}$ and $R^{9b}$ are each independently H, $C_{1-6}$ alkyl, or $C_{1-4}$ haloalkyl. In some embodiments, Y is-C(O)NH—; $R^2$ is H or $C_{1-6}$ alkyl; and $W^1$ is a bond or —$CR^{4a}H$—; wherein $R^{4a}$ is H, $C_{1-6}$ alkyl, or halo; and Z is —$CR^{9a}R^{9b}$—; wherein $R^{9a}$ and $R^{9b}$ are each independently H, $C_{1-6}$ alkyl, or $C_{1-4}$ haloalkyl. In some embodiments, Y is-C(O)NH—; $R^2$ is H or $C_{1-6}$ alkyl; $W^1$ is bond, —$CH_2$— or —CH(F)—; and Z is —$CH(CH_3)$— or —$CH(CH_2F)$—.

In some embodiments of the compound of Formula I, I-A, I-B, I-C, I-D, I-E, I-F, II-II-A, Aa, II-Ab, III, IIIa, or IIIb, or the pharmaceutically acceptable salt thereof, $W^2$ is —$CR^{5a}R^{5b}$— or —$CR^{6a}$=$CR^{6b}$—; wherein $R^{5a}$ and $R^{5b}$ are independently H, $C_{1-6}$ alkyl, $C_{1-4}$ haloalkyl, halo, hydroxyl, cyano, —O—$C_{1-4}$ alkyl, or $C_{1-4}$ alkylene-O—$C_{1-4}$ alkyl; and $R^{6a}$ and $R^{6b}$ are independently H, halo, $C_{1-4}$ haloalkyl, or $C_{1-6}$ alkyl. In some embodiments, $W^2$ is —$CR^{5a}R^{5b}$— or —$CR^{6a}$=$CR^{6b}$—; wherein $R^{5a}$ and $R^{5b}$ are independently H, $C_{1-6}$ alkyl, $C_{1-4}$ haloalkyl, halo, or —O—$C_{1-4}$ alkyl; and $R^{6a}$ and $R^{6b}$ are independently H, halo, $C_{1-4}$ haloalkyl, or $C_{1-6}$ alkyl. In some embodiments, $W^2$ is —$CR^{5a}R^{5b}$— or —$CR^{6a}$=$CR^{6b}$—; wherein $R^{5a}$ and $R^{5b}$ are independently H, $C_{1-6}$ alkyl, or halo; and $R^{6a}$ and $R^{6b}$ are independently H, halo or $C_{1-6}$ alkyl. In some embodiments, $W^2$ is —$CH_2$— or —CH=CH—. In some embodiments, $W^2$ is —$CH_2$—. In some embodiments, $W^2$ is —CH=CH—.

In some embodiments of the compound of Formula I, I-A, I-B, I-C, I-D, I-E, I-F, II-II-A, Aa, II-Ab, III, IIIa, or IIIb, or the pharmaceutically acceptable salt thereof, Y is-C(O)NH—; $R^2$ is H or $C_{1-6}$ alkyl; $W^1$ is a bond or —$CR^{4a}R^{4b}$—; wherein $R^{4a}$ and $R^{4b}$ are independently H, $C_{1-6}$ alkyl, $C_{1-4}$ haloalkyl, or halo; Z is —$CR^{9a}R^{9b}$—; wherein $R^{9a}$ and $R^{9b}$ are each independently H, $C_{1-6}$ alkyl, $C_{1-4}$ haloalkyl, or halo; and $W^2$ is —$CR^{5a}R^{5b}$— or —$CR^{6a}$=$CR^{6b}$—; wherein $R^{5a}$ and $R^{5b}$ are independently H, $C_{1-6}$ alkyl, $C_{1-4}$ haloalkyl, halo, hydroxyl, cyano, —O—$C_{1-4}$ alkyl, or $C_{1-4}$ alkylene-O—$C_{1-4}$ alkyl; and $R^{6a}$ and $R^{6b}$ are independently H, halo, $C_{1-4}$ haloalkyl, or $C_{1-6}$ alkyl.

In some embodiments of the compound of Formula I, I-A, I-B, I-C, I-D, I-E, I-F, II-II-A, Aa, II-Ab, III, IIIa, or IIIb, or the pharmaceutically acceptable salt thereof, Y is-C(O)NH—; $R^2$ is H or $C_{1-6}$ alkyl; $W^1$ is a bond or —$CR^{4a}R^{4b}$—; wherein $R^{4a}$ and $R^{4b}$ are independently H, $C_{1-6}$ alkyl, or halo; Z is —$CR^{9a}R^{9b}$—; wherein $R^{9a}$ and $R^{9b}$ are each independently H, $C_{1-6}$ alkyl, or $C_{1-4}$ haloalkyl; and $W^2$ is —$CR^{5a}R^{5b}$— or —$CR^{6a}$=$CR^{6b}$—; wherein $R^{5a}$ and $R^{5b}$ are independently H, $C_{1-6}$ alkyl, $C_{1-4}$ haloalkyl, halo, or —O—$C_{1-4}$ alkyl; and $R^{6a}$ and $R^{6b}$ are independently H, halo, $C_{1-4}$ haloalkyl, or $C_{1-6}$ alkyl.

In some embodiments of the compound of Formula I, I-A, I-B, I-C, I-D, I-E, I-F, II-II-A, Aa, II-Ab, III, IIIa, or IIIb, or the pharmaceutically acceptable salt thereof, Y is-C(O)NH—; $R^2$ is H or $C_{1-6}$ alkyl; $W^1$ is a bond or —$CR^{4a}R^{4b}$—; wherein $R^{4a}$ and $R^{4b}$ are independently H, —$CH_3$, or halo; Z is —$CR^{9a}R^{9b}$—; wherein $R^{9a}$ and $R^{9b}$ are each independently H, $C_{1-6}$ alkyl, or $C_{1-4}$ haloalkyl; and $W^2$ is —$CR^{5a}R^{5b}$— or —$CR^{6a}$=$CR^{6b}$—; wherein $R^{5a}$ and $R^{5b}$ are independently H, $C_{1-6}$ alkyl, or halo; and $R^{6a}$ and $R^{6b}$ are independently H, halo or $C_{1-6}$ alkyl.

In some embodiments of the compound of Formula I, I-A, I-B, I-C, I-D, I-E, I-F, II-II-A, Aa, II-Ab, III, IIIa, or IIIb, or the pharmaceutically acceptable salt thereof, Y is-C(O)NH—; $R^2$ is H or $C_{1-6}$ alkyl; and $W^1$ is a bond or —$CR^{4a}H$—; wherein $R^{4a}$ is H, $C_{1-6}$ alkyl, or halo; Z is —$CR^{9a}R^{9b}$—; wherein $R^{9a}$ and $R^{9b}$ are each independently H, $C_{1-6}$ alkyl, or $C_{1-4}$ haloalkyl; and $W^2$ is —$CH_2$— or —CH=CH—.

In some embodiments of the compound of Formula I, I-A, I-B, I-C, I-D, I-E, I-F, II-II-A, Aa, II-Ab, III, IIIa, or IIIb, or the pharmaceutically acceptable salt thereof, Y is-C(O)NH—; $R^2$ is H or $C_{1-6}$ alkyl; and $W^1$ is a bond or —$CR^{4a}H$—; wherein $R^{4a}$ is H, $C_{1-6}$ alkyl, or halo; Z is —$CR^{9a}R^{9b}$—; wherein $R^{9a}$ and $R^{9b}$ are each independently H, $C_{1-6}$ alkyl, or $C_{1-4}$ haloalkyl; and $W^2$ is —$CH_2$—.

In some embodiments of the compound of Formula I, I-A, I-B, I-C, I-D, I-E, I-F, II-II-A, Aa, II-Ab, III, IIIa, or IIIb, or the pharmaceutically acceptable salt thereof, Y is-C(O)NH—; $R^2$ is H or $C_{1-6}$ alkyl; and $W^1$ is a bond or —$CR^{4a}H$—; wherein $R^{4a}$ is H, $C_{1-6}$ alkyl, or halo; Z is —$CR^{9a}R^{9b}$—; wherein $R^{9a}$ and $R^{9b}$ are each independently H, $C_{1-6}$ alkyl, or $C_{1-4}$ haloalkyl; and $W^2$ is —CH=CH—.

In some embodiments of the compound of Formula I, I-A, I-B, I-C, I-D, I-E, I-F, II-II-A, Aa, II-Ab, III, IIIa, or IIIb, or the pharmaceutically acceptable salt thereof, Y is-C(O)NH—; $R^2$ is H or $C_{1-6}$ alkyl; $W^1$ is bond, —$CH_2$— or —CH(F)—; Z is —$CH(CH_3)$— or —$CH(CH_2F)$—; and $W^2$ is —$CH_2$— or —CH=CH—.

In some embodiments of the compound of Formula I, I-A, I-B, I-C, I-D, I-E, or I-F, II-II-A, Aa, II-Ab, III, IIIa, or IIIb, or the pharmaceutically acceptable salt thereof, Y is-C(O)NH—; $R^2$ is H or $C_{1-6}$ alkyl; $W^1$ is bond, —$CH_2$— or —CH(F)—; Z is —$CH(CH_3)$— or —$CH(CH_2F)$—; and $W^2$ is —$CH_2$—.

In some embodiments of the compound of Formula I, I-A, I-B, I-C, I-D, I-E, or I-F, II-II-A, Aa, II-Ab, III, IIIa, or IIIb, or the pharmaceutically acceptable salt thereof, Y is-C(O)NH—; $R^2$ is H or $C_{1-6}$ alkyl; $W^1$ is bond, —$CH_2$— or —CH(F)—; Z is —$CH(CH_3)$— or —$CH(CH_2F)$—; and $W^2$ is —CH=CH—.

In some embodiments of the compound of Formula I, I-A, II-A, II-Aa, II-Ab, III, IIIa, or IIIb, or the pharmaceutically acceptable salt thereof, the compound has a Formula IV:

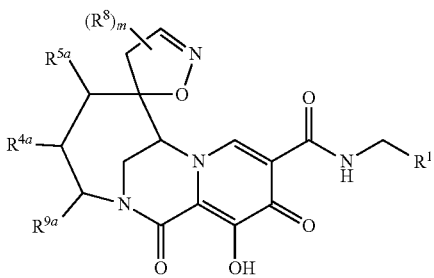

wherein m is 0, 1, 2 or 3.

In some embodiments of the compound of Formula I, I-A, II-A, II-Aa, III, IIIa, or IV, or the pharmaceutically acceptable salt thereof, the compound has a Formula IVa:

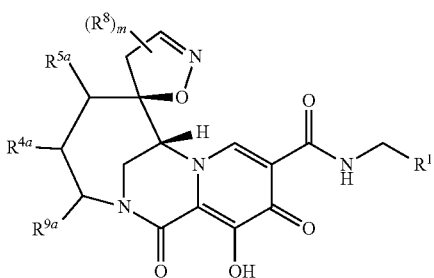

wherein m is 0, 1, 2 or 3.

In some embodiments of the compound of Formula I, I-A, II-A, II-Ab, III, IIIb, or IV, or the pharmaceutically acceptable salt thereof, wherein the compound has a Formula IVb:

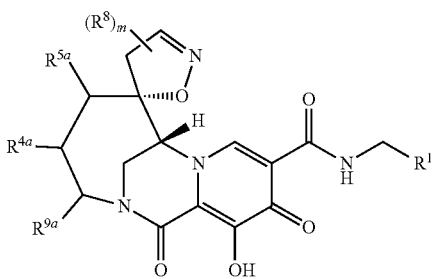

wherein m is 0, 1, 2 or 3.

In some embodiments of the compound of Formula I, I-A, II-A, II-Aa, II-Ab, III, IIIa, IIIb, IV, IVa, or IVb, or the pharmaceutically acceptable salt thereof, $R^{4a}$ is H, $C_{1-6}$ alkyl, or $C_{1-4}$haloalkyl.

In some embodiments of the compound of Formula I, I-A, II-A, II-Aa, II-Ab, III, IIIa, IIIb, IV, IVa, or IVb, or the pharmaceutically acceptable salt thereof, $R^{5a}$ is H, halo, $C_{1-4}$ haloalkyl, or $C_{1-6}$ alkyl.

In some embodiments of the compound of Formula I, I-A, II-A, II-Aa, II-Ab, III, IIIa, IIIb, IV, IVa, or IVb, or the pharmaceutically acceptable salt thereof, $R^{4a}$ is H, $C_{1-6}$ alkyl, or $C_{1-4}$haloalkyl; and $R^{5a}$ is H, halo, $C_{1-4}$haloalkyl, or $C_{1-6}$ alkyl.

In some embodiments of the compound of Formula I, I-A, II-A, II-Aa, II-Ab, III, IIIa, IIIb, IV, IVa, or IVb, or the pharmaceutically acceptable salt thereof, $R^{9a}$ is H, $C_{1-6}$ alkyl, $C_{1-4}$ haloalkyl, or halo. In some embodiments, $R^{9a}$ is $C_{1-6}$ alkyl, $C_{1-4}$haloalkyl, or halo. In some embodiments, $R^{9a}$ is $C_{1-6}$ alkyl or $C_{1-4}$haloalkyl. In some embodiments, $R^{9a}$ is —$CH_3$ or —$CH_2F$.

In some embodiments of the compound of Formula I, I-A, II-A, II-Aa, II-Ab, III, IIIa, IIIb, IV, IVa, or IVb, or the pharmaceutically acceptable salt thereof, $R^{4a}$ is H, $C_{1-6}$ alkyl, or $C_{1-4}$ haloalkyl; $R^{5a}$ is H, halo, $C_{1-4}$ haloalkyl, or $C_{1-6}$ alkyl; and $R^{9a}$ is H, $C_{1-6}$ alkyl, $C_{1-4}$ haloalkyl, or halo. In some embodiments, $R^{4a}$ is H, $C_{1-6}$ alkyl, or $C_{1-4}$ haloalkyl; $R^{5a}$ is H, halo, $C_{1-4}$ haloalkyl, or $C_{1-6}$ alkyl; and $R^{9a}$ is $C_{1-6}$ alkyl, $C_{1-4}$ haloalkyl, or halo. In some embodiments, $R^{4a}$ is H, $C_{1-6}$ alkyl, or $C_{1-4}$ haloalkyl; $R^{5a}$ is H, halo, $C_{1-4}$haloalkyl, or $C_{1-6}$ alkyl; and $R^{9a}$ is $C_{1-6}$ alkyl or $C_{1-4}$haloalkyl. In some embodiments, $R^{4a}$ is H, $C_{1-6}$ alkyl, or $C_{1-4}$haloalkyl; $R^{5a}$ is H, halo, $C_{1-4}$haloalkyl, or $C_{1-6}$ alkyl; and $R^{9a}$ is —$CH_3$ or —$CH_2F$.

In some embodiments of the compound of Formula I, I-A, I-B, I-C, I-D, I-E, I-F, II-A, II-Aa, II-Ab, III, IIIa, IIIb, IV, IVa, or IVb, or the pharmaceutically acceptable salt thereof, each $R^8$ is independently:
(i) halo,
(ii) $C_{1-6}$ alkyl optionally substituted with OH, $C_{1-6}$ alkoxy, $C_{6-10}$ aryl or 5- to 10-membered heteroaryl comprising 1, 2, or 3 heteroatoms independently selected from N, O, and S,
(iii) $C_{1-6}$haloalkyl,
(iv) CN,
(v) oxo,
(vi) —X—$R^{45}$
wherein X is O or S; and $R^{45}$ is H, $C_{1-6}$ alkyl or 3- to 7-membered ring containing 0, 1, or 2 heteroatoms selected from N, O and S; wherein the $C_1$-$C_6$ alkyl or the 3- to 7-membered ring is optionally substituted with 1, 2, or 3 groups selected independently from CN, halo, $C_1$-$C_6$ alkoxy, $C_{6-10}$ aryl and 5- to 10-membered heteroaryl containing 1, 2, or 3 heteroatoms independently selected from N, O, and S,
(vii) $NHR^{46}$,
wherein $R^{46}$ is $C_1$-$C_6$ alkyl;
(viii) $NR^{47}R^{48}$,
wherein $R^{47}$ is $C_1$-$C_6$ alkyl;
and $R^{48}$ is $C_1$-$C_6$ alkyl,
(ix) $C_{6-10}$ aryl optionally substituted with 1, 2, 3, or 4 substituents independently selected from $C_{1-6}$ alkyl, $C_{1-6}$ haloalkyl, halo, CN, $C_{3-7}$ cycloalkyl, and $C_{1-6}$ alkoxy;
wherein the $C_{3-7}$ cycloalkyl is optionally substituted with 1, 2, 3, or 4 independent halo groups,
(x) 3 to 7 membered ring containing 0, 1, or 2 heteroatoms selected independently from N, O and S,
wherein the 3- to 7-membered ring is optionally substituted with one, two or three substituents selected independently from halo, $C_{1-6}$ alkyl, $C_{1-6}$ haloalkyl, $C_{1-6}$ alkoxy, and $C_{3-7}$ cycloalkyl, or
(xi) 5- to 10 membered heteroaryl ring containing 1, 2, or 3 heteroatoms independently selected from N, O, and S, or
wherein the 5- to 10 membered heteroaryl ring is optionally substituted with one, two or three substituents selected independently from halo, $C_{1-6}$ alkyl, $C_{1-6}$ haloalkyl, $C_{1-6}$ alkoxy, and $C_{3-7}$ cycloalkyl, or
two $R^8$ groups are joined to form a fused, spiro, or bridged 3 to 7 membered ring containing 0, 1, 2, or 3 heteroatoms selected from N, O and S.

wherein the 3- to 7-membered ring is optionally substituted with one, two or three substituents selected independently from halo, OH, $C_{1-6}$ alkyl, $C_{1-6}$ haloalkyl, $C_{1-6}$ alkoxy, and $C_{3-7}$ cycloalkyl; or two $R^8$ groups on adjacent carbon atoms are joined to form a fused 6 to 10 membered aromatic ring containing 0, 1, 2, or 3 heteroatoms selected from N, O and S, wherein the fused 6 to 10 membered aromatic ring is optionally substituted with one, two or three substituents selected independently from halo, OH, $C_{1-6}$ alkyl, $C_{1-6}$ haloalkyl, $C_{1-6}$ alkoxy, and $C_{3-7}$ cycloalkyl.

In some embodiments of the compound of Formula I, I-A, I-B, I-C, I-D, I-E, I-F, II-A, II-Aa, II-Ab, III, IIIa, IIIb, IV, IVa, or IVb, or the pharmaceutically acceptable salt thereof, each $R^8$ is independently:

(i) halo,
(ii) $C_{1-6}$ alkyl optionally substituted with OH, $C_{1-6}$ alkoxy, $C_{6-10}$ aryl or 5- to 10-membered heteroaryl comprising 1, 2, or 3 heteroatoms independently selected from N, O, and S,
(iii) $C_{1-6}$ haloalkyl,
(iv) CN,
(v) oxo,
(vi) —X—$R^{45}$
  wherein X is O or S; and $R^{45}$ is H, $C_{1-6}$ alkyl or 3- to 7-membered ring containing 0, 1, or 2 heteroatoms selected from N, O and S;
  wherein the $C_1$-$C_6$ alkyl or the 3- to 7-membered ring is optionally substituted with 1, 2, or 3 groups selected independently from CN, halo, $C_1$-$C_6$ alkoxy, $C_{6-10}$ aryl and 5- to 10-membered heteroaryl containing 1, 2, or 3 heteroatoms independently selected from N, O, and S
(vii) NH$R^{46}$,
  wherein $R^{46}$ is $C_1$-$C_6$ alkyl;
(viii) N$R^{47}R^{48}$,
  wherein $R^{47}$ is $C_1$-$C_6$ alkyl;
  and $R^{48}$ is $C_1$-$C_6$ alkyl,
(ix) $C_{6-10}$ aryl,
(x) 3 to 7 membered ring containing 0, 1, or 2 heteroatoms selected independently from N, O and S, or
(xi) 5- to 10 membered heteroaryl ring containing 1, 2, or 3 heteroatoms independently selected from N, O, and S, or two $R^8$ groups are joined to form a fused, spiro, or bridged 3 to 7 membered ring containing 0, 1, 2, or 3 heteroatoms selected from N, O and S.

In some embodiments of the compound of Formula I, I-A, I-B, I-C, I-D, I-E, I-F, II-A, II-Aa, II-Ab, III, IIIa, IIIb, IV, IVa, or IVb, or the pharmaceutically acceptable salt thereof, each $R^8$ is independently $C_1$, F, Br, oxo, CN, methyl, ethyl, propyl, $CH_2Ph$, $CH_2OH$, $CH_2OMe$, NHMe, NMe$_2$, OH, OMe, $OCH_2CF_3$, $OCH_2CHF_2$, $OCH_2CH_2OMe$, SMe, $CHF_2$, $CH_2CF_3$, $(CH_2)_4Cl$, $CH_2F$, $CH_2CH_2F$, $CH(CH_3)F$, $CF_2CH_3$, $CF_3$,

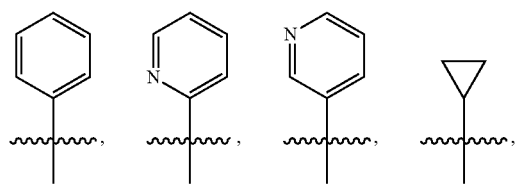

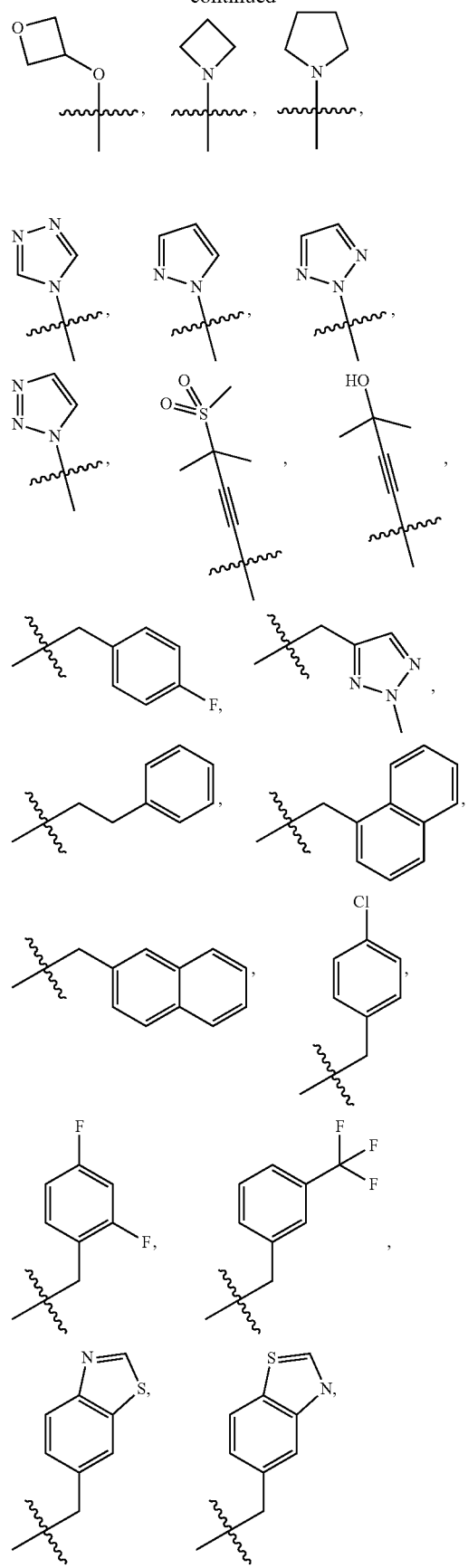

-continued

[chemical structures shown]

In some embodiments of the compound of Formula I, I-A, I-B, I-C, I-D, I-E, I-F, II-A, II-Aa, II-Ab, III, IIIa, IIIb, IV, IVa, or IVb, or the pharmaceutically acceptable salt thereof, each $R^8$ is independently $C_1$, F, Br, oxo, CN, methyl, ethyl, propyl, $CH_2Ph$, $CH_2OH$, $CH_2OMe$, NHMe, $NMe_2$, OH, OMe, $OCH_2CF_3$, $OCH_2CHF_2$, $OCH_2CH_2OMe$, SMe, $CH_2F$, $CHF_2$, $CH_2CF_3$, $(CH_2)_4Cl$,

[chemical structures shown]

In some embodiments of the compound of Formula I, I-A, II-A, II-Aa, II-Ab, III, IIIa, IIIb, IV, IVa, or IVb, or the pharmaceutically acceptable salt thereof,
 $R^{4a}$ is H, $C_{1-6}$ alkyl, or $C_{1-4}$ haloalkyl;
 $R^{5a}$ is H, halo, $C_{1-4}$ haloalkyl, or $C_{1-6}$ alkyl;
 $R^{9a}$ is H, $C_{1-6}$ alkyl, $C_{1-4}$ haloalkyl, or halo; and each $R^8$ is independently
  (i) halo,
  (ii) $C_{1-6}$ alkyl optionally substituted with OH, $C_{1-6}$ alkoxy, $C_{6-10}$ aryl or 5- to 10-membered heteroaryl comprising 1, 2, or 3 heteroatoms independently selected from N, O, and S,
  (iii) $C_{1-6}$ haloalkyl,
  (iv) CN,
  (v) oxo,
  (vi) —X—$R^{45}$
    wherein X is O or S; and $R^4S$ is H, $C_{1-6}$ alkyl or 3- to 7-membered ring containing 0, 1, or 2 heteroatoms selected from N, O and S;
    wherein the $C_1$-$C_6$ alkyl or the 3- to 7-membered ring is optionally substituted with 1, 2, or 3 groups selected independently from CN, halo, $C_1$-$C_6$ alkoxy, $C_{6-10}$ aryl and 5- to 10-membered heteroaryl containing 1, 2, or 3 heteroatoms independently selected from N, O, and S
  (vii) $NHR^{46}$,
    wherein $R^{46}$ is $C_1$-$C_6$ alkyl;
  (viii) $NR^{47}R^{48}$,
    wherein $R^{47}$ is $C_1$-$C_6$ alkyl;
    and $R^{48}$ is $C_1$-$C_6$ alkyl,
  (ix) $C_{6-10}$ aryl,
  (x) 3 to 7 membered ring containing 0, 1, or 2 heteroatoms selected independently from N, O and S, or
  (xi) 5- to 10 membered heteroaryl ring containing 1, 2, or 3 heteroatoms independently selected from N, O, and S, or two $R^8$ groups are joined to form a fused, spiro, or bridged 3 to 7 membered ring containing 0, 1, 2, or 3 heteroatoms selected from N, O and S.

In some embodiments of the compound of Formula I, I-A, II-A, II-Aa, II-Ab, III, IIIa, IIIb, IV, IVa, or IVb, or the pharmaceutically acceptable salt thereof,
 $R^{4a}$ is H, $C_{1-6}$ alkyl, or $C_{1-4}$ haloalkyl;
 $R^{5a}$ is H, halo, $C_{1-4}$ haloalkyl, or $C_{1-6}$ alkyl;
 $R^{9a}$ is $C_{1-6}$ alkyl, $C_{1-4}$ haloalkyl, or halo; and
 each $R^8$ is independently
  (i) halo,
  (ii) $C_{1-6}$ alkyl optionally substituted with OH, $C_{1-6}$ alkoxy, $C_{6-10}$ aryl or 5- to 10-membered heteroaryl comprising 1, 2, or 3 heteroatoms independently selected from N, O, and S,
  (iii) $C_{1-6}$ haloalkyl,
  (iv) CN,
  (v) oxo,
  (vi) —X—$R^{45}$
    wherein X is O or S; and $R^4S$ is H, $C_{1-6}$ alkyl, or 3- to 7-membered ring containing 0, 1, or 2 heteroatoms selected from N, O and S;
    wherein the $C_1$-$C_6$ alkyl or the 3- to 7-membered ring is optionally substituted with 1, 2, or 3 groups selected independently from CN, halo, $C_1$-$C_6$ alkoxy, $C_{6-10}$ aryl and 5- to 10-membered heteroaryl containing 1, 2, or 3 heteroatoms independently selected from N, O, and S
  (vii) $NHR^{46}$,
    wherein $R^{46}$ is $C_1$-$C_6$ alkyl;
  (viii) $NR^{47}R^{48}$,
    wherein $R^{47}$ is $C_1$-$C_6$ alkyl;
    and $R^{48}$ is $C_1$-$C_6$ alkyl,
  (ix) $C_{6-10}$ aryl,
  (x) 3 to 7 membered ring containing 0, 1, or 2 heteroatoms selected independently from N, O and S, or
  (xi) 5- to 10 membered heteroaryl ring containing 1, 2, or 3 heteroatoms independently selected from N, O, and S, or
   two $R^8$ groups are joined to form a fused, spiro, or bridged 3 to 7 membered ring containing 0, 1, 2, or 3 heteroatoms selected from N, O and S.

In some embodiments of the compound of Formula I, I-A, II-A, II-Aa, II-Ab, III, IIIa, IIIb, IV, IVa, or IVb, or the pharmaceutically acceptable salt thereof,
$R^{4a}$ is H, $C_{1-6}$ alkyl, or $C_{1-4}$ haloalkyl;
$R^{5a}$ is H, halo, $C_{1-4}$haloalkyl, or $C_{1-6}$ alkyl;
$R^{9a}$ is $C_{1-6}$ alkyl or $C_{1-4}$ haloalkyl and each $R^8$ is independently
(i) halo,
(ii) $C_{1-6}$ alkyl optionally substituted with OH, $C_{1-6}$ alkoxy, $C_{6-10}$ aryl or 5- to 10-membered heteroaryl comprising 1, 2, or 3 heteroatoms independently selected from N, O, and S,
(iii) $C_{1-6}$haloalkyl,
(iv) CN,
(v) oxo,
(vi) —X—$R^{45}$
wherein X is O or S; and $R^4$S is H, $C_{1-6}$ alkyl or 3- to 7-membered ring containing 0, 1, or 2 heteroatoms selected from N, O and S;
wherein the $C_1$-$C_6$ alkyl or the 3- to 7-membered ring is optionally substituted with 1, 2, or 3 groups selected independently from CN, halo, $C_1$-$C_6$ alkoxy, $C_{6-10}$ aryl and 5- to 10-membered heteroaryl containing 1, 2, or 3 heteroatoms independently selected from N, O, and S
(vii) NHR$^{46}$,
wherein $R^{46}$ is $C_1$-$C_6$ alkyl;
(viii) NR$^{47}$R$^{48}$,
wherein $R^{47}$ is $C_1$-$C_6$ alkyl;
and $R^{48}$ is $C_1$-$C_6$ alkyl,
(ix) $C_{6-10}$ aryl,
(x) 3 to 7 membered ring containing 0, 1, or 2 heteroatoms selected independently from N, O and S, or
(xi) 5- to 10 membered heteroaryl ring containing 1, 2, or 3 heteroatoms independently selected from N, O, and S, or
two $R^8$ groups are joined to form a fused, spiro, or bridged 3 to 7 membered ring containing 0, 1, 2, or 3 heteroatoms selected from N, O and S.

In some embodiments of the compound of Formula I, I-A, II-A, II-Aa, II-Ab, III, IIIa, IIIb, IV, IVa, or IVb, or the pharmaceutically acceptable salt thereof,
$R^{4a}$ is H, $C_{1-6}$ alkyl, or $C_{1-4}$ haloalkyl;
$R^{5a}$ is H, halo, $C_{1-4}$haloalkyl, or $C_{1-6}$ alkyl;
$R^{9a}$ is —CH$_3$ or —CH$_2$F.
each $R^8$ is independently
(i) halo,
(ii) $C_{1-6}$ alkyl optionally substituted with OH, $C_{1-6}$ alkoxy, $C_{6-10}$ aryl or 5- to 10-membered heteroaryl comprising 1, 2, or 3 heteroatoms independently selected from N, O, and S,
(iii) $C_{1-6}$ haloalkyl,
(iv) CN,
(v) oxo,
(vi) —X—$R^{45}$
wherein X is O or S; and $R^4$S is H, $C_{1-6}$ alkyl or 3- to 7-membered ring containing 0, 1, or 2 heteroatoms selected from N, O and S;
wherein the $C_1$-$C_6$ alkyl or the 3- to 7-membered ring is optionally substituted with 1, 2, or 3 groups selected independently from CN, halo, $C_1$-$C_6$ alkoxy, $C_{6-10}$ aryl and 5- to 10-membered heteroaryl containing 1, 2, or 3 heteroatoms independently selected from N, O, and S
(vii) NHR$^{46}$,
wherein $R^{46}$ is $C_1$-$C_6$ alkyl;
(viii) NR$^{47}$R$^{48}$,
wherein $R^{47}$ is $C_1$-$C_6$ alkyl;
and $R^{48}$ is $C_1$-$C_6$ alkyl,
(ix) $C_{6-10}$ aryl,
(x) 3 to 7 membered ring containing 0, 1, or 2 heteroatoms selected independently from N, O and S, or
(xi) 5- to 10 membered heteroaryl ring containing 1, 2, or 3 heteroatoms independently selected from N, O, and S, or
two $R^8$ groups are joined to form a fused, spiro, or bridged 3 to 7 membered ring containing 0, 1, 2, or 3 heteroatoms selected from N, O and S.

In some embodiments of the compound of Formula I, I-A, I-B, I-C, I-D, I-E, I-F, II-A, II-Aa, II-Ab, III, IIIa, IIIb, IV, IVa, or IVb, or the pharmaceutically acceptable salt thereof, each $R^8$ is independently $C_1$, F, Br, oxo, CN, methyl, ethyl, propyl, CH$_2$Ph, CH$_2$OH, CH$_2$OMe, NHMe, NMe$_2$, OH, OMe, OCH$_2$CF$_3$, OCH$_2$CHF$_2$, OCH$_2$CH$_2$OMe, SMe, CH$_2$F, CHF$_2$, CH$_2$CF$_3$, (CH$_2$)$_4$Cl,

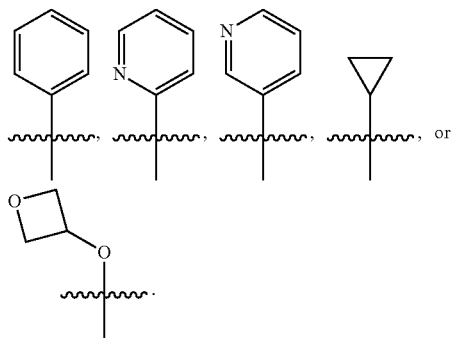

In some embodiments of the compound of Formula I, I-A, I-B, I-C, I-D, I-E, I-F, II-A, II-Aa, II-Ab, III, IIIa, IIIb, IV, IVa, or IVb, or the pharmaceutically acceptable salt thereof, each $R^8$ is independently —Cl, —F, —Br, oxo, —CN, methyl, ethyl, propyl, —CH$_2$Ph, —CH$_2$ CH$_2$Ph, —CH(CH$_3$)Ph, —CH$_2$C(CH$_3$)$_2$, —CH$_2$OH, —CH$_2$OMe, —NHMe, —NMe$_2$, —OH, —OMe, —OCD$_3$, —OCD$_3$OCH$_2$CF$_3$, —OCH$_2$CHF$_2$, —OCH$_2$C(CH$_3$)$_2$, —OCH$_2$CH$_2$OMe, —SMe, —CH$_2$F, —CHF$_2$, —CF$_3$, —CH$_2$CF$_3$, —(CH$_2$)$_4$Cl, —SMe, —SO$_2$Me, —CH$_2$CH$_2$F, —CH(CH$_3$)F, —C(F)$_2$CH$_3$, —CF$_3$, —OCH$_2$CF$_3$, —C≡CC(CH$_3$)$_2$SO$_2$CH$_3$, —C≡CC(CH$_3$)$_2$OH,

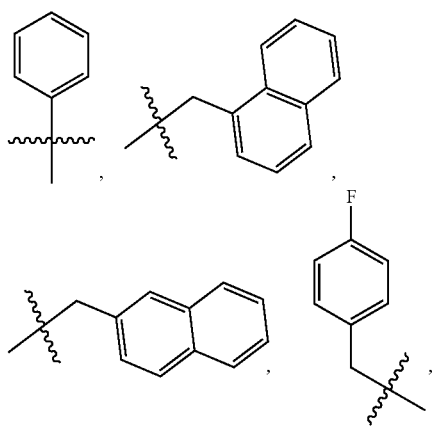

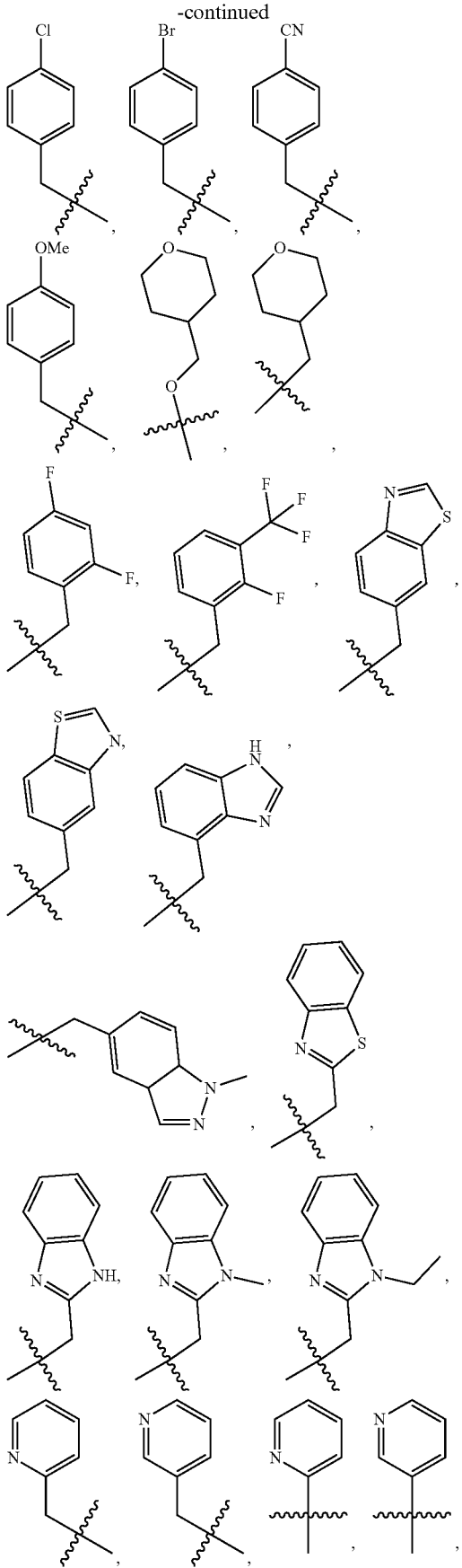

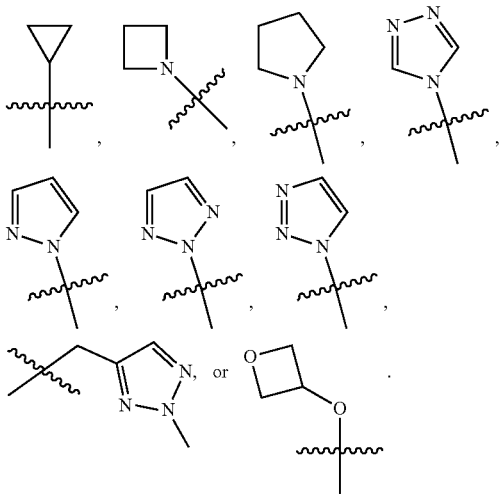

In some embodiments of the compound of Formula I, I-A, I-B, I-C, I-D, I-E, I-F, II-A, II-Aa, II-Ab, III, IIIa, IIIb, IV, IVa, or IVb, or the pharmaceutically acceptable salt thereof, two $R^8$ are joined to form a fused 6 membered ring containing one O.

In some embodiments of the compound of Formula I, I-A, II-A, II-Aa, II-Ab, III, IIIa, IIIb, IV, IVa, or IVb, or the pharmaceutically acceptable salt thereof, $R^{4a}$ is H, $C_{1-6}$ alkyl, or $C_{1-4}$ haloalkyl;

$R^{5a}$ is H, halo, $C_{1-4}$ haloalkyl, or $C_{1-6}$ alkyl;

$R^{9a}$ is H, $C_{1-6}$ alkyl, $C_{1-4}$ haloalkyl, or halo; and each $R^8$ is independently $C_1$, F, Br, oxo, CN, methyl, ethyl, propyl, $CH_2Ph$, $CH_2OH$, $CH_2OMe$, NMe, $NMe_2$, OH, OMe, $OCH_2CF_3$, $OCH_2CHF_2$, $OCH_2CH_2OMe$, SMe, $CH_2F$, $CHF_2$, $CH_2CF_3$, $(CH_2)_4Cl$,

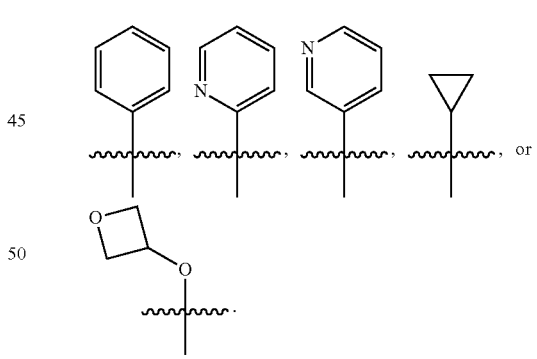

In some embodiments of the compound of Formula I, I-A, II-A, II-Aa, II-Ab, III, IIIa, IIIb, IV, IVa, or IVb, or the pharmaceutically acceptable salt thereof, $R^{4a}$ is H, $C_{1-6}$ alkyl, or $C_{1-4}$ haloalkyl;

$R^{5a}$ is H, halo, $C_{1-4}$ haloalkyl, or $C_{1-6}$ alkyl;

$R^{9a}$ is $C_{1-6}$ alkyl or $C_{1-4}$ haloalkyl and each $R^8$ is independently $C_1$, F, Br, oxo, CN, methyl, ethyl, propyl, $CH_2Ph$, $CH_2OH$, $CH_2OMe$, NMe, $NMe_2$, OH, OMe, $OCH_2CF_3$, $OCH_2CHF_2$, $OCH_2CH_2OMe$, SMe, $CH_2F$, $CHF_2$, $CH_2CF_3$, $(CH_2)_4Cl$,

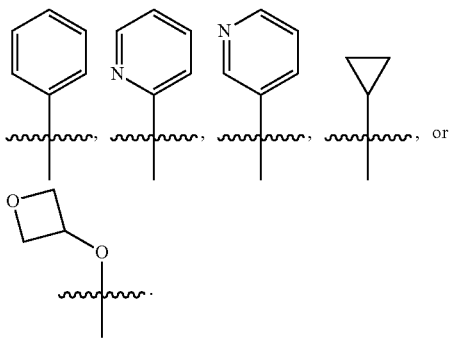, or

In some embodiments of the compound of Formula I, I-A, II-A, II-Aa, II-Ab, III, IIIa, IIIb, IV, IVa, or IVb, or the pharmaceutically acceptable salt thereof,
$R^{4a}$ is H, $C_{1-6}$ alkyl, or $C_{1-4}$ haloalkyl;
$R^{5a}$ is H, halo, $C_{1-4}$ haloalkyl, or $C_{1-6}$ alkyl;
$R^{9a}$ is $C_{1-6}$ alkyl or $C_{1-4}$ haloalkyl and
each $R^8$ is independently $C_1$, F, Br, oxo, CN, methyl, ethyl, propyl, $CH_2Ph$, $CH_2OH$, $CH_2OMe$, $NMe$, $NMe_2$, OH, OMe, $OCH_2CF_3$, $OCH_2CHF_2$, $OCH_2CH_2OMe$, SMe, $CH_2F$, $CHF_2$, $CH_2CF_3$, $(CH_2)_4Cl$,

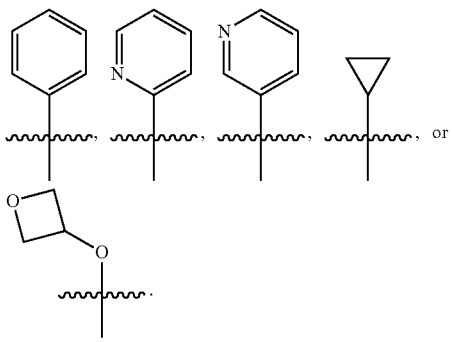, or

In some embodiments of the compound of Formula I, I-A, II-A, II-Aa, II-Ab, III, IIIa, IIIb, IV, IVa, or IVb, or the pharmaceutically acceptable salt thereof,
$R^{4a}$ is H, $C_{1-6}$ alkyl, or $C_{1-4}$ haloalkyl;
$R^{5a}$ is H, halo, $C_{1-4}$ haloalkyl, or $C_{1-6}$ alkyl;
$R^{9a}$ is $C_{1-6}$ alkyl or $C_{1-4}$ haloalkyl and
each $R^8$ is independently Cl, F, Br, oxo, CN, methyl, ethyl, propyl, $CH_2Ph$, $CH_2OH$, $CH_2OMe$, $NMe$, $NMe_2$, OH, OMe, $OCH_2CF_3$, $OCH_2CHF_2$, $OCH_2CH_2OMe$, SMe, $CH_2F$, $CHF_2$, $CH_2CF_3$, $(CH_2)_4Cl$, I

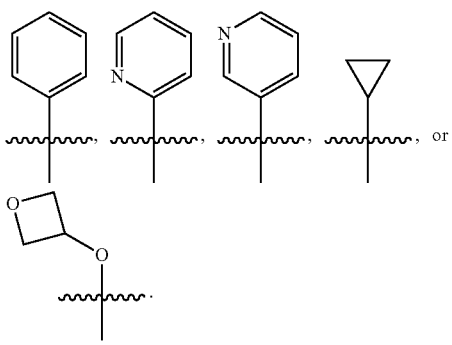, or

In some embodiments of the compound of Formula I, I-A, I-B, I-C, I-D, I-E, I-F, II-A, II-Aa, II-Ab, III, IIIa, IIIb, IV, IVa, or IVb, or the pharmaceutically acceptable salt thereof, m is 0, 1, or 2. In some embodiments, m is 0. In some embodiments, m is 1. In some embodiments, m is 2.

In some embodiments of the compound of Formula I, I-A, II-A, II-Aa, II-Ab, III, IIIa, IIIb, IV, IVa, or IVb, or the pharmaceutically acceptable salt thereof, the compound has a Formula V:

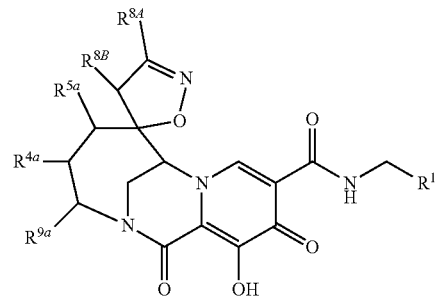

V wherein $R^{5A}$ and $R^{5B}$ are each independently H, halo, $C_{1-4}$ alkyl or $C_{1-4}$ haloalkyl.

In some embodiments of the compound of Formula I, I-A, II-A, II-Aa, III, IIIa, IV, IVa, or V, or the pharmaceutically acceptable salt thereof, the compound has a Formula Va:

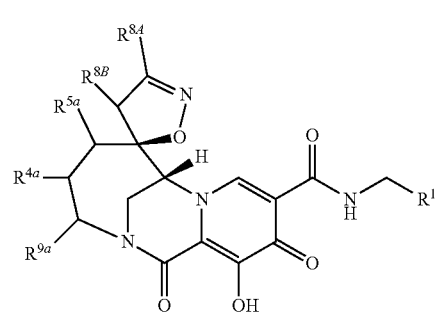

Va wherein $R^{8A}$ and $R^{8B}$ are each independently H, halo, $C_{1-4}$ alkyl or $C_{1-4}$ haloalkyl.

In some embodiments of the compound of Formula I, I-A, II-A, II-Ab, III, IIIb, IV, IVb, or V, or the pharmaceutically acceptable salt thereof, the compound has a Formula Vb:

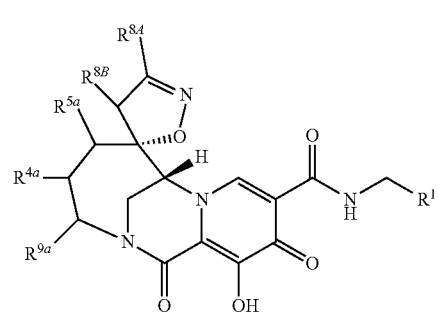

Vb wherein $R^{8A}$ and $R^{8B}$ are each independently H, halo, $C_{1-4}$ alkyl or $C_{1-4}$ haloalkyl.

In some embodiments of the compounds of Formula V, Va, or Vb, or the pharmaceutically acceptable salt thereof, $R^{8A}$ is halo, $C_{1-4}$ alkyl or $C_{1-4}$ haloalkyl and $R^{8B}$ is H, halo, $C_{1-4}$ alkyl or $C_{1-4}$ haloalkyl. In some embodiments, $R^{8A}$ is halo, $C_{1-4}$ alkyl or $C_{1-4}$ haloalkyl and $R^{8B}$ is H. In some embodiments, $R^{8A}$ is H, halo, $C_{1-4}$ alkyl or $C_{1-4}$ haloalkyl and $R^{8B}$ is halo, $C_{1-4}$ alkyl or $C_{1-4}$ haloalkyl. In some embodiments, $R^{8A}$ is H and $R^{8B}$ is halo, $C_{1-4}$ alkyl or $C_{1-4}$ haloalkyl.

In some embodiments of the compound of Formula V, Va, or Vb, or the pharmaceutically acceptable salt thereof, $R^{4a}$ is H, $C_{1-6}$ alkyl, or $C_{1-4}$ haloalkyl.

In some embodiments of the compound of Formula V, Va, or Vb, or the pharmaceutically acceptable salt thereof, $R^{5a}$ is H, halo, $C_{1-4}$ haloalkyl, or $C_{1-6}$ alkyl.

In some embodiments of the compound of Formula V, Va, or Vb, or the pharmaceutically acceptable salt thereof, $R^{9a}$ is H, $C_{1-6}$ alkyl, $C_{1-4}$ haloalkyl, or halo. In some embodiments, $R^{9a}$ is $C_{1-6}$ alkyl, $C_{1-4}$ haloalkyl, or halo. In some embodiments, $R^{9a}$ is $C_{1-6}$ alkyl.

In some embodiments of the compound of Formula V, Va, or Vb, or the pharmaceutically acceptable salt thereof, $R^{4a}$ is H, $C_{1-6}$ alkyl, or $C_{1-4}$ haloalkyl.

In some embodiments of the compound of Formula V, Va, or Vb, or the pharmaceutically acceptable salt thereof, $R^{5a}$ is H, halo, $C_{1-4}$ haloalkyl, or $C_{1-6}$ alkyl.

In some embodiments of the compound of Formula V, Va, or Vb, or the pharmaceutically acceptable salt thereof, $R^{9a}$ is H, $C_{1-6}$ alkyl, $C_{1-4}$ haloalkyl, or halo. In some embodiments, $R^{9a}$ is $C_{1-6}$ alkyl, $C_{1-4}$ haloalkyl, or halo. In some embodiments, $R^{9a}$ is $C_{1-6}$ alkyl.

In some embodiments of the compounds of Formula V, Va, or Vb, or the pharmaceutically acceptable salt thereof, $R^{5A}$ is halo, $C_{1-4}$ alkyl or $C_{1-4}$ haloalkyl; $R^{5B}$ is H, halo, $C_{1-4}$ alkyl or $C_{1-4}$ haloalkyl; $R^{4a}$ is H, $C_{1-6}$ alkyl, or $C_{1-4}$ haloalkyl; $R^{5a}$ is H, halo, $C_{1-4}$ haloalkyl, or $C_{1-6}$ alkyl; and $R^{9a}$ is H, $C_{1-6}$ alkyl, $C_{1-4}$ haloalkyl, or halo.

In some embodiments of the compounds of Formula V, Va, or Vb, or the pharmaceutically acceptable salt thereof, $R^{5A}$ is halo, $C_{1-4}$ alkyl or $C_{1-4}$ haloalkyl; $R^{5B}$ is H; $R^{4a}$ is H, $C_{1-6}$ alkyl, or $C_{1-4}$ haloalkyl; $R^{5a}$ is H, halo, $C_{1-4}$ haloalkyl, or $C_{1-6}$ alkyl; and $R^{9a}$ is H, $C_{1-6}$ alkyl, $C_{1-4}$ haloalkyl, or halo.

In some embodiments of the compounds of Formula V, Va, or Vb, or the pharmaceutically acceptable salt thereof, $R^{5A}$ is H, halo, $C_{1-4}$ alkyl or $C_{1-4}$ haloalkyl; $R^{5B}$ is halo, $C_{1-4}$ alkyl or $C_{1-4}$ haloalkyl; $R^{4a}$ is H, $C_{1-6}$ alkyl, or $C_{1-4}$ haloalkyl; $R^{5a}$ is H, halo, $C_{1-4}$ haloalkyl, or $C_{1-6}$ alkyl; and $R^{9a}$ is H, $C_{1-6}$ alkyl, $C_{1-4}$ haloalkyl, or halo.

In some embodiments of the compounds of Formula V, Va, or Vb, or the pharmaceutically acceptable salt thereof, $R^{5A}$ is H; $R^{5B}$ is halo, $C_{1-4}$ alkyl or $C_{1-4}$ haloalkyl; $R^{4a}$ is H, $C_{1-6}$ alkyl, or $C_{1-4}$ haloalkyl; $R^{5a}$ is H, halo, $C_{1-4}$ haloalkyl, or $C_{1-6}$ alkyl; and $R^{9a}$ is H, $C_{1-6}$ alkyl, $C_{1-4}$ haloalkyl, or halo.

In some embodiments of the compounds of Formula V, Va, or Vb, or the pharmaceutically acceptable salt thereof, $R^{5A}$ is halo, $C_{1-4}$ alkyl or $C_{1-4}$ haloalkyl; $R^{5B}$ is H, halo, $C_{1-4}$ alkyl or $C_{1-4}$ haloalkyl; $R^{4a}$ is H, $C_{1-6}$ alkyl, or $C_{1-4}$ haloalkyl; $R^{5a}$ is H, halo, $C_{1-4}$ haloalkyl, or $C_{1-6}$ alkyl; and $R^{9a}$ is $C_{1-6}$ alkyl, $C_{1-4}$ haloalkyl, or halo.

In some embodiments of the compounds of Formula V, Va, or Vb, or the pharmaceutically acceptable salt thereof, $R^{5A}$ is H; $R^{5B}$ is halo, $C_{1-4}$ alkyl or $C_{1-4}$ haloalkyl; $R^{4a}$ is H, $C_{1-6}$ alkyl, or $C_{1-4}$ haloalkyl; $R^{5a}$ is H, halo, $C_{1-4}$ haloalkyl, or $C_{1-6}$ alkyl; and $R^{9a}$ is $C_{1-6}$ alkyl, $C_{1-4}$ haloalkyl, or halo.

In some embodiments of the compounds of Formula V, Va, or Vb, or the pharmaceutically acceptable salt thereof, $R^{5A}$ is halo, $C_{1-4}$ alkyl or $C_{1-4}$ haloalkyl; $R^{5B}$ is H, halo, $C_{1-4}$ alkyl or $C_{1-4}$ haloalkyl; $R^{4a}$ is H, $C_{1-6}$ alkyl, or $C_{1-4}$ haloalkyl; $R^{5a}$ is H, halo, $C_{1-4}$ haloalkyl, or $C_{1-6}$ alkyl; and $R^{9a}$ is $C_{1-6}$ alkyl.

In some embodiments of the compounds of Formula V, Va, or Vb, or the pharmaceutically acceptable salt thereof, $R^{5A}$ is halo, $C_{1-4}$ alkyl or $C_{1-4}$ haloalkyl; $R^{5B}$ is H; $R^{4a}$ is H, $C_{1-6}$ alkyl, or $C_{1-4}$ haloalkyl; $R^{5a}$ is H, halo, $C_{1-4}$ haloalkyl, or $C_{1-6}$ alkyl; and $R^{9a}$ is $C_{1-6}$ alkyl.

In some embodiments of the compounds of Formula V, Va, or Vb, or the pharmaceutically acceptable salt thereof, $R^{5A}$ is H, halo, $C_{1-4}$ alkyl or $C_{1-4}$ haloalkyl; $R^{5B}$ is halo, $C_{1-4}$ alkyl or $C_{1-4}$ haloalkyl; $R^{4a}$ is H, $C_{1-6}$ alkyl, or $C_{1-4}$ haloalkyl; $R^{5a}$ is H, halo, $C_{1-4}$ haloalkyl, or $C_{1-6}$ alkyl; and $R^{9a}$ is $C_{1-6}$ alkyl.

In some embodiments of the compounds of Formula V, Va, or Vb, or the pharmaceutically acceptable salt thereof, $R^{5A}$ is H; $R^{5B}$ is halo, $C_{1-4}$ alkyl or $C_{1-4}$ haloalkyl; $R^{4a}$ is H, $C_{1-6}$ alkyl, or $C_{1-4}$ haloalkyl; $R^{5a}$ is H, halo, $C_{1-4}$ haloalkyl, or $C_{1-6}$ alkyl; and $R^{9a}$ is $C_{1-6}$ alkyl.

In some embodiments of the compounds of Formula V, Va, or Vb, or the pharmaceutically acceptable salt thereof, $R^{5A}$ is H; $R^{5B}$ is halo, $C_{1-4}$ alkyl or $C_{1-4}$ haloalkyl; $R^{4a}$ is H, $C_{1-6}$ alkyl, or $C_{1-4}$ haloalkyl; $R^{5a}$ is H, halo, $C_{1-4}$ haloalkyl, or $C_{1-6}$ alkyl; $R^{9a}$ is $C_{1-6}$ alkyl; and $R^1$ is phenyl, optionally substituted with one, two, three, or four $R^{41}$, wherein each $R^{41}$ is independently halo, $C_{1-4}$ alkyl, $C_{1-4}$ haloalkyl, or —O—$C_{1-4}$ alkyl.

In some embodiments of the compounds of Formula V, Va, or Vb, or the pharmaceutically acceptable salt thereof, $R^{5A}$ is H; $R^{5B}$ is halo, $C_{1-4}$ alkyl or $C_{1-4}$ haloalkyl; $R^{4a}$ is H, $C_{1-6}$ alkyl, or $C_{1-4}$ haloalkyl; $R^{5a}$ is H, halo, $C_{1-4}$ haloalkyl, or $C_{1-6}$ alkyl; $R^{9a}$ is $C_{1-6}$ alkyl; and $R^1$ is phenyl substituted with one, two, three, or four $R^{41}$, wherein each $R^{41}$ is independently halo or —O—$C_{1-4}$ alkyl.

In some embodiments of the compounds of Formula V, Va, or Vb, or the pharmaceutically acceptable salt thereof, $R^{5A}$ is H; $R^{5B}$ is halo, $C_{1-4}$ alkyl or $C_{1-4}$ haloalkyl; $R^{4a}$ is H, $C_{1-6}$ alkyl, or $C_{1-4}$ haloalkyl; $R^{5a}$ is H, halo, $C_{1-4}$ haloalkyl, or $C_{1-6}$ alkyl; $R^{9a}$ is $C_{1-6}$ alkyl; and $R^1$ is phenyl substituted with one, two, three, or four halogens.

In some embodiments of the compounds of Formula V, Va, or Vb, or the pharmaceutically acceptable salt thereof, $R^{5A}$ is H; $R^{5B}$ is halo, $C_{1-4}$ alkyl or $C_{1-4}$ haloalkyl; $R^{4a}$ is H, $C_{1-6}$ alkyl, or $C_{1-4}$ haloalkyl; $R^{5a}$ is H, halo, $C_{1-4}$ haloalkyl, or $C_{1-6}$ alkyl; $R^{9a}$ is $C_{1-6}$ alkyl; and $R^1$ is phenyl substituted with two or three halogens selected from chloro and fluoro.

In some embodiments of the compounds of Formula V, Va, or Vb, or the pharmaceutically acceptable salt thereof, $R^{5A}$ and $R^{5B}$ are each independently H, halo, $C_{1-4}$ alkyl, $C_{1-4}$ haloalkyl or —X—$R^{48}$; wherein X is O and $R^AS$ is H, $C_{1-6}$ alkyl, $C_{1-6}$ haloalkyl or 3- to 7-membered ring containing 0, 1, or 2 heteroatoms selected from N, O and S.

In some embodiments of the compounds of Formula V, Va, or Vb, or the pharmaceutically acceptable salt thereof: $R^{8A}$ and $R^{8B}$ are each independently H, halo, $C_{1-4}$ alkyl, $C_{1-4}$ haloalkyl or —X—$R^{48}$; wherein X is O and $R^AS$ is H, C$_{1-6}$ alkyl, C$_{1-6}$ haloalkyl or 3- to 7-membered ring containing 0, 1, or 2 heteroatoms selected from N, O and S;

R$^1$ is phenyl substituted with two or three halogens selected from chloro and fluoro;

R$^{4a}$ is R$^{4a}$ is H, halo, C$_{1-6}$ alkyl, or C$_{1-4}$ haloalkyl;

R$^{5a}$ is H, halo, C$_{1-4}$ haloalkyl, or C$_{1-6}$ alkyl; and

R$^{9a}$ is C$_{1-6}$ alkyl or C$_{1-4}$ haloalkyl.

In some embodiments of the compounds of Formula V, Va, or Vb, or the pharmaceutically acceptable salt thereof, R$^{5A}$ and R$^{5B}$ are each independently H, halo, C$_{1-4}$ alkyl, C$_{1-4}$ haloalkyl or —X—R$^{45}$; wherein X is O and R$^{4S}$ is C$_{1-6}$ alkyl or C$_{1-6}$ haloalkyl.

In some embodiments of the compounds of Formula V, Va, or Vb, or the pharmaceutically acceptable salt thereof:

R$^{8A}$ and R$^{8B}$ are each independently H, halo, C$_{1-4}$ alkyl, C$_{1-4}$haloalkyl or —X—R$^{45}$; wherein X is O and R$^{45}$ is C$_{1-6}$ alkyl or C$_{1-6}$ haloalkyl;

R$^1$ is phenyl substituted with two or three halogens selected from chloro and fluoro;

R$^{4a}$ is R$^{4a}$ is H, halo, C$_{1-6}$ alkyl, or C$_{1-4}$ haloalkyl;

R$^{5a}$ is H, halo, C$_{1-4}$haloalkyl, or C$_{1-6}$ alkyl; and

R$^{9a}$ is C$_{1-6}$ alkyl or C$_{1-4}$ haloalkyl.

In some embodiments of the compounds of Formula V, Va, or Vb, or the pharmaceutically acceptable salt thereof, R$^{5A}$ and R$^{5B}$ are each independently H, halo, C$_{1-4}$ alkyl, C$_{1-4}$haloalkyl or —X—R$^{48}$; wherein X is O and R$^{4S}$ is C$_{1-6}$ alkyl.

In some embodiments of the compounds of Formula V, Va, or Vb, or the pharmaceutically acceptable salt thereof:

R$^{8A}$ and R$^{8B}$ are each independently H, halo, C$_{1-4}$ alkyl, C$_{1-4}$haloalkyl or —X—R$^{45}$; wherein X is O and R$^{45}$ is C$_{1-6}$ alkyl;

R$^1$ is phenyl substituted with two or three halogens selected from chloro and fluoro;

R$^{4a}$ is R$^{4a}$ is H, halo, C$_{1-6}$ alkyl, or C$_{1-4}$ haloalkyl;

R$^{5a}$ is H, halo, C$_{1-4}$haloalkyl, or C$_{1-6}$ alkyl; and

R$^{9a}$ is C$_{1-6}$ alkyl or C$_{1-4}$ haloalkyl.

In some embodiments of the compounds of Formula I, I-A, II-A, II-Aa, II-Ab, III, IIIa, IIIb, IV, V, Va, or Vb, or the pharmaceutically acceptable salt thereof, the compound is:

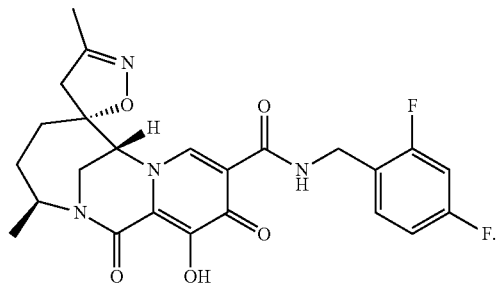 [SMILES: CC1=NO[C@]2(CC[C@H](C)N3C[C@H]2n2cc(C(=O)NCc4ccc(F)cc4F)c(=O)c(O)c2C3=O)C1]

In some embodiments of the compounds of Formula I, I-A, II-A, II-Aa, II-Ab, III, IIIa, IIIb, IV, V, Va, or Vb, or the pharmaceutically acceptable salt thereof, the compound is:

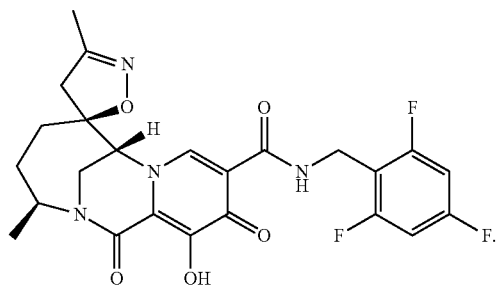 [SMILES: CC1=NO[C@@]2(CC[C@H](C)N3C[C@H]2n2cc(C(=O)NCc4c(F)cc(F)cc4F)c(=O)c(O)c2C3=O)C1]

In some embodiments of the compounds of Formula I, I-A, II-A, II-Aa, II-Ab, III, IIIa, IIIb, IV, V, Va, or Vb, or the pharmaceutically acceptable salt thereof, the compound is:

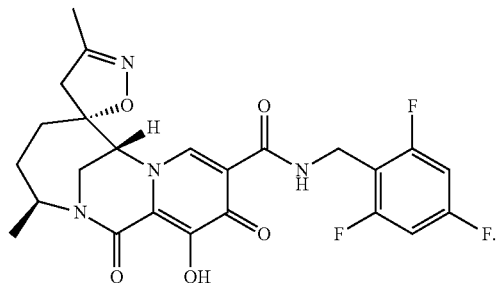 [SMILES: CC1=NO[C@]2(CC[C@H](C)N3C[C@H]2n2cc(C(=O)NCc4c(F)cc(F)cc4F)c(=O)c(O)c2C3=O)C1]

In some embodiments of the compounds of Formula I, I-A, II-A, II-Aa, II-Ab, III, IIIa, IIIb, IV, V, Va, or Vb, or the pharmaceutically acceptable salt thereof, the compound is:

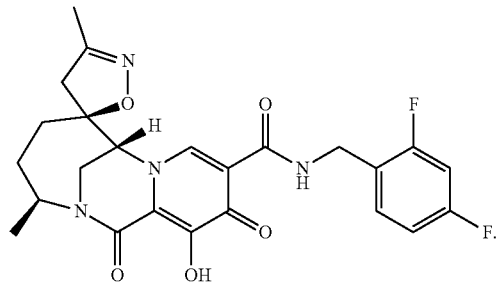

In some embodiments of the compounds of Formula I, I-A, II-A, II-Aa, II-Ab, III, IIIa, IIIb, IV, V, Va, or Vb, or the pharmaceutically acceptable salt thereof, the compound is:

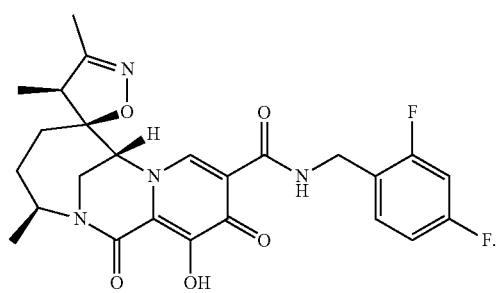 [SMILES: CC1=NO[C@@]2(CC[C@H](C)N3C[C@H]2n2cc(C(=O)NCc4ccc(F)cc4F)c(=O)c(O)c2C3=O)[C@H]1C]

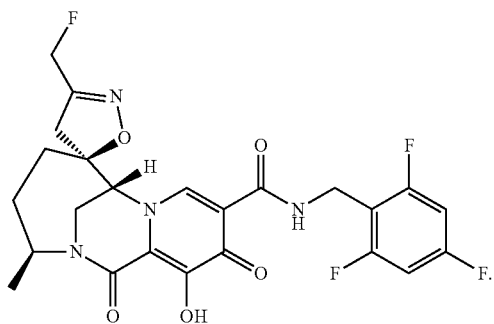 [SMILES: C[C@H]1CC[C@]2(CC(CF)=NO2)[C@H]2CN1C(=O)c1c(O)c(=O)c(C(=O)NCc3c(F)cc(F)cc3F)cn12]

In some embodiments of the compounds of Formula I, I-A, II-A, II-Aa, II-Ab, III, IIIa, IIIb, IV, V, Va, or Vb, or the pharmaceutically acceptable salt thereof, the compound is:

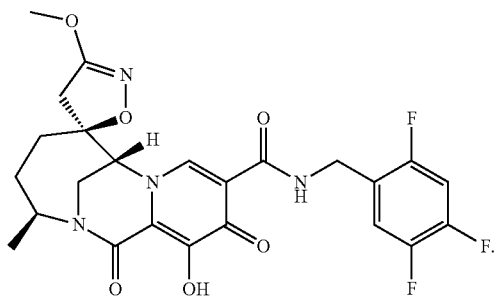 [SMILES: COC1=NO[C@@]2(CC[C@H](C)N3C[C@H]2n2cc(C(=O)NCc4cc(F)c(F)cc4F)c(=O)c(O)c2C3=O)C1]

In some embodiments of the compounds of Formula I, I-A, II-A, II-Aa, II-Ab, III, IIIa, IIIb, IV, V, Va, or Vb, or the pharmaceutically acceptable salt thereof, the compound is:

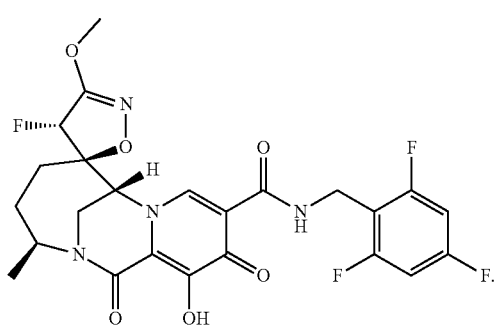 [SMILES: COC1=NO[C@@]2(CC[C@H](C)N3C[C@H]2n2cc(C(=O)NCc4c(F)cc(F)cc4F)c(=O)c(O)c2C3=O)[C@@H]1F]

In some embodiments of the compounds of Formula I, I-A, II-A, II-Aa, II-Ab, III, IIIa, IIIb, IV, V, Va, or Vb, or the pharmaceutically acceptable salt thereof, the compound is:

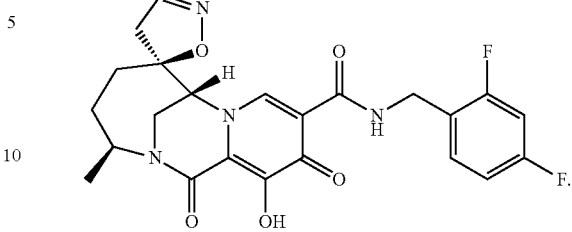

In some embodiments of the compounds of Formula I, I-A, II-A, II-Aa, II-Ab, III, IIIa, IIIb, IV, V, Va, or Vb, or the pharmaceutically acceptable salt thereof, the compound is selected from the group consisting of:

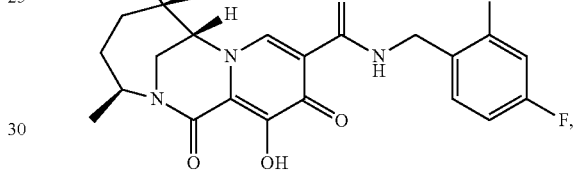

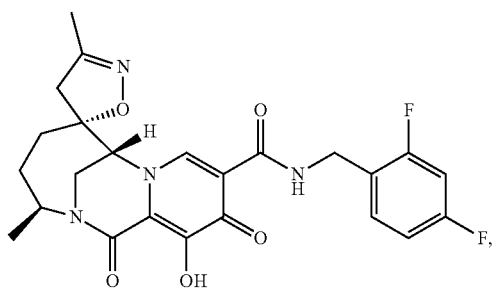

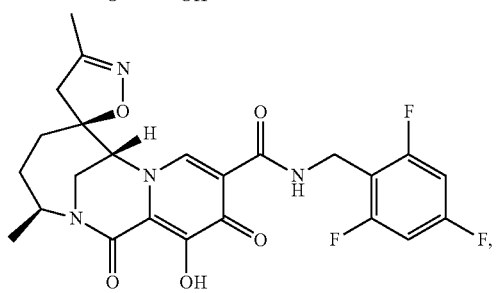

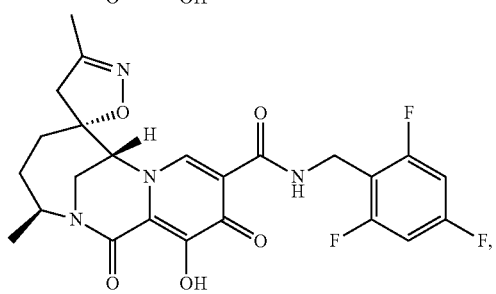

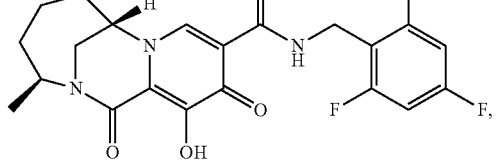

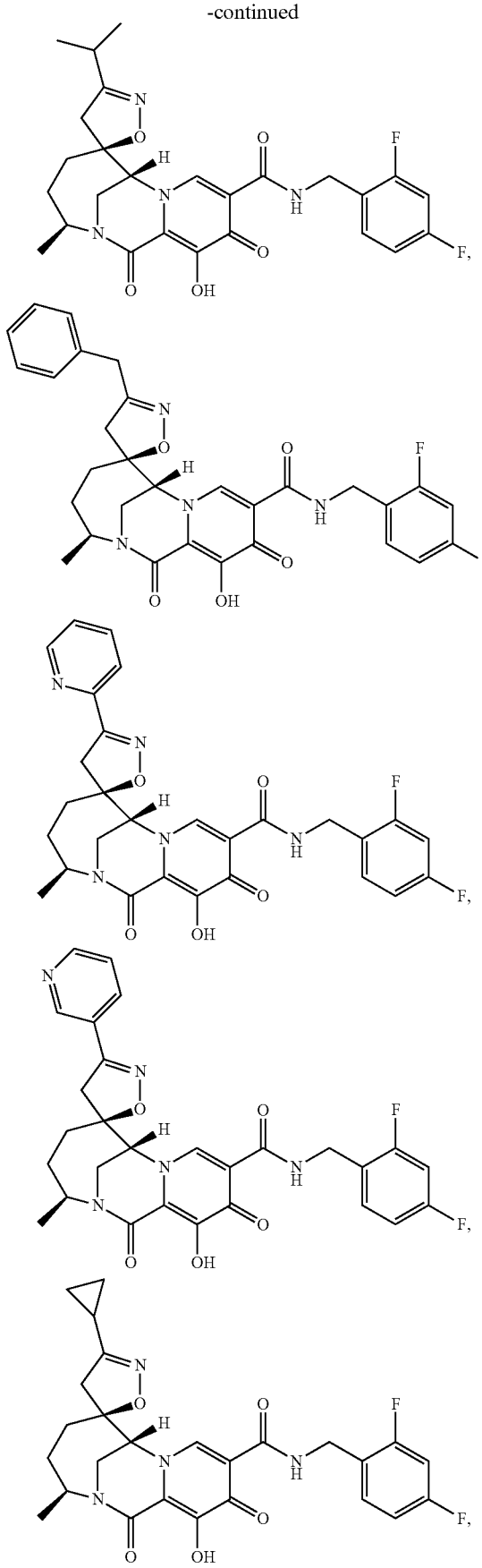
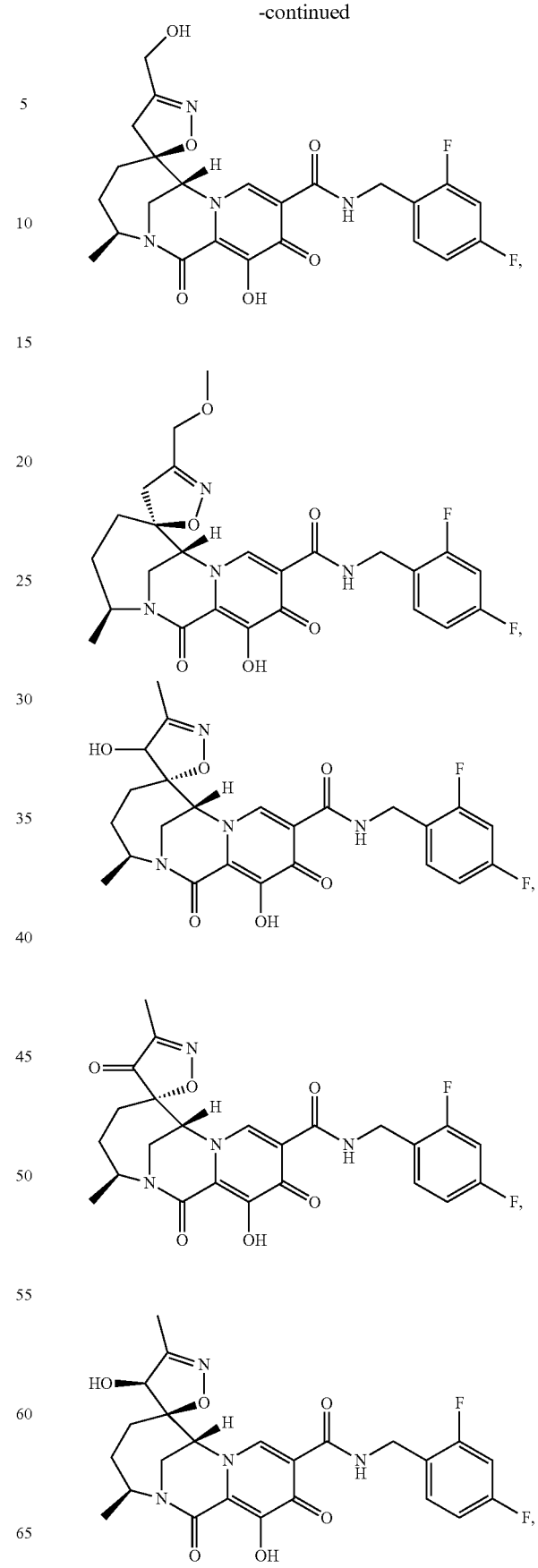

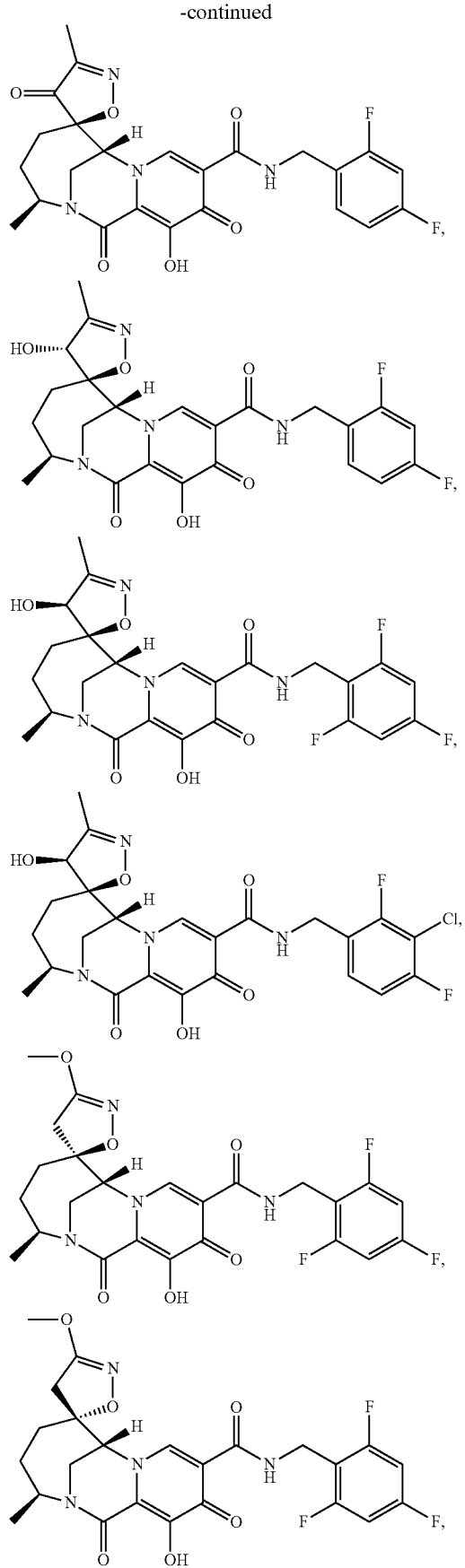
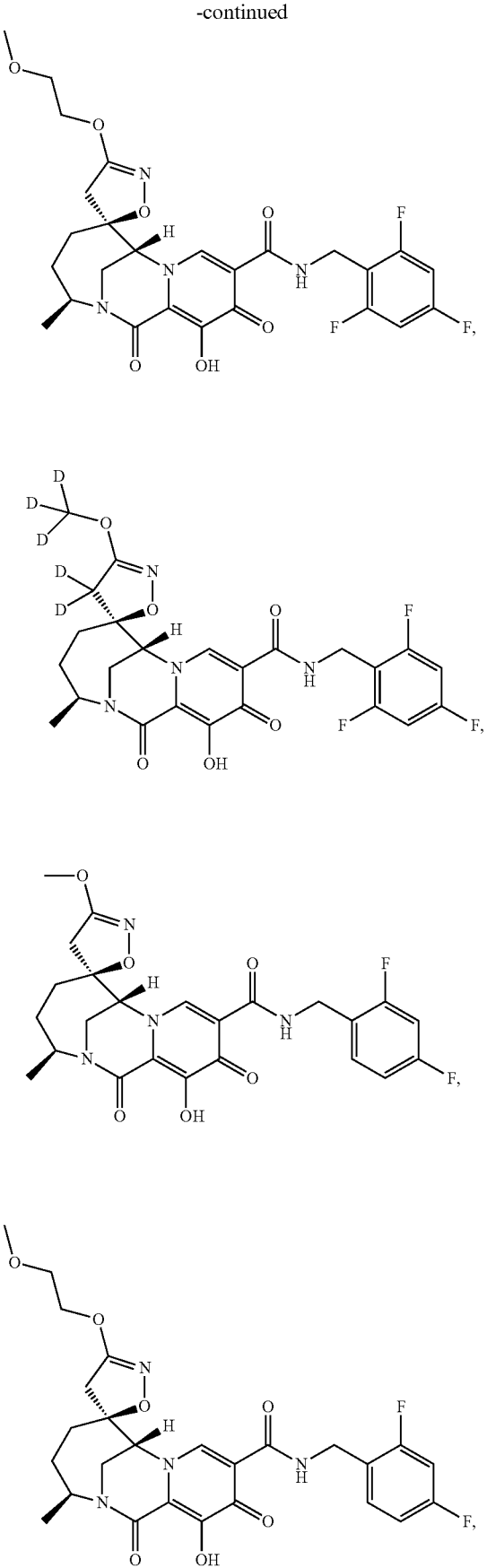

63
-continued
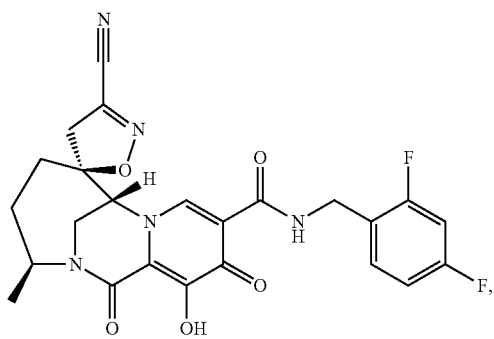
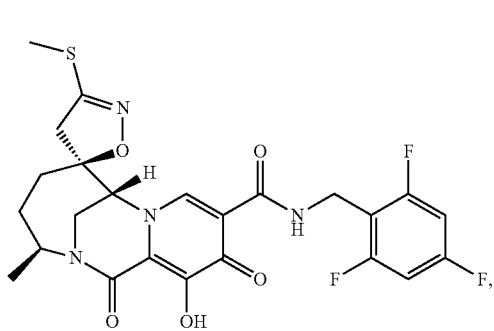
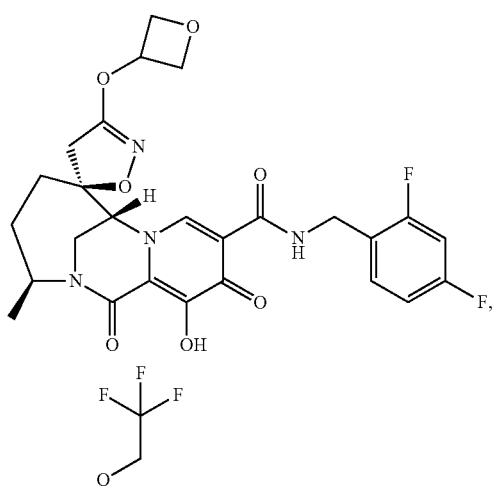
64
-continued
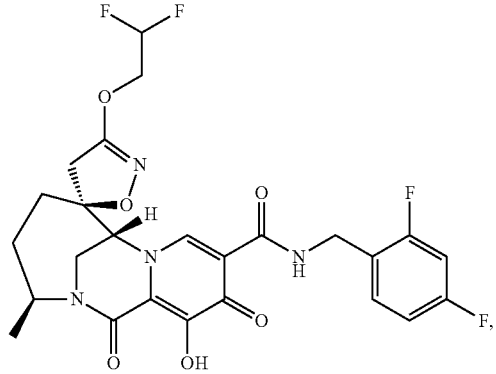
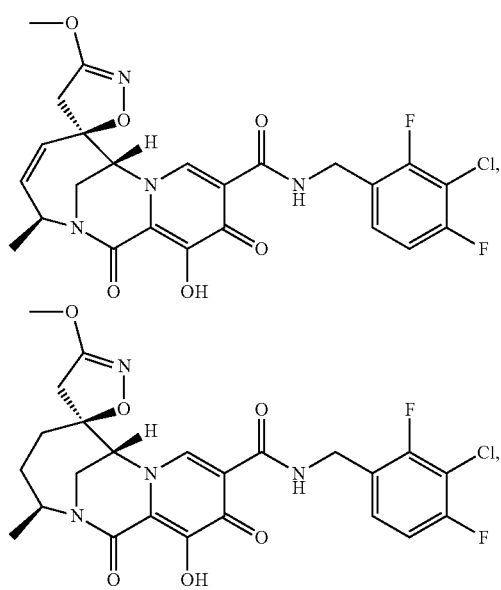
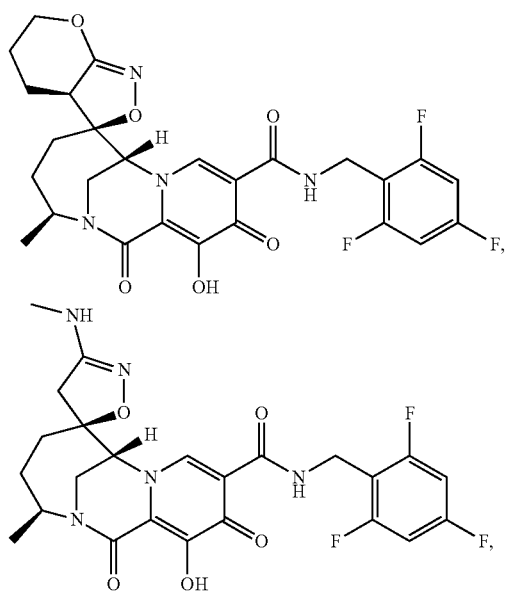

65
-continued
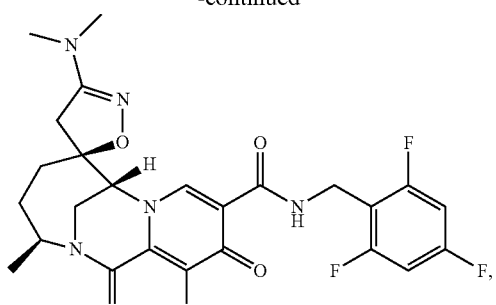
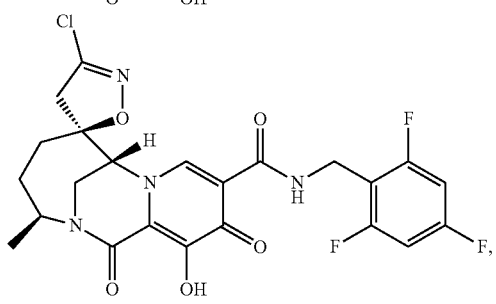
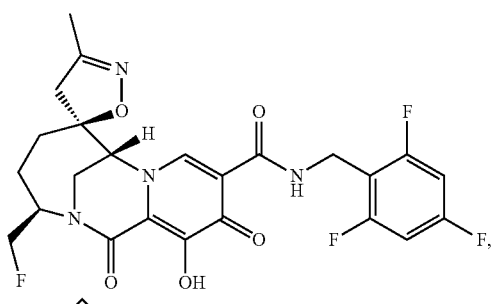
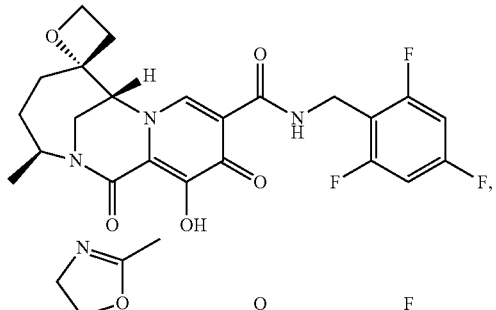
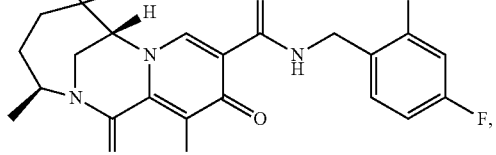
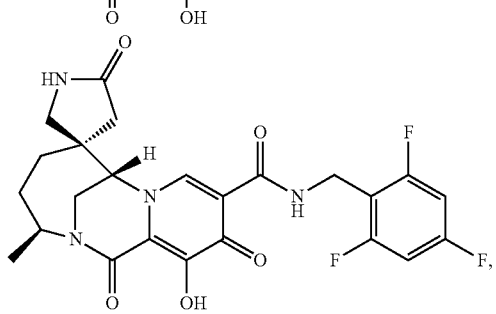
66
-continued
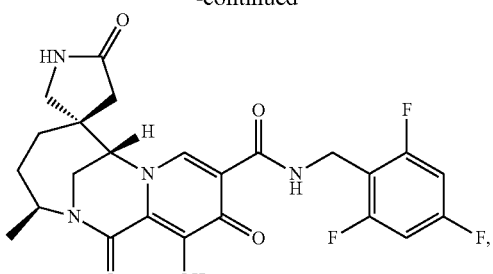
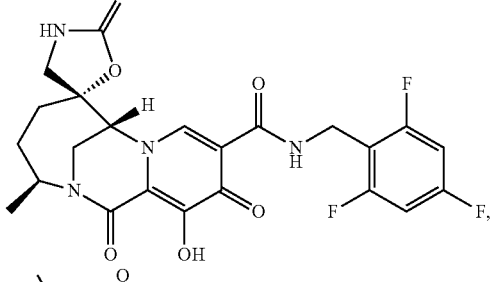
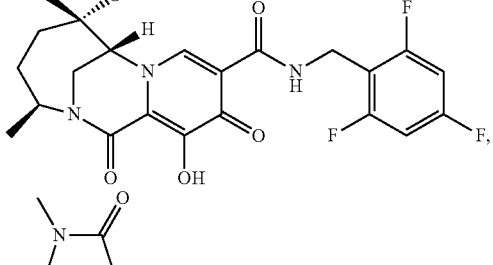
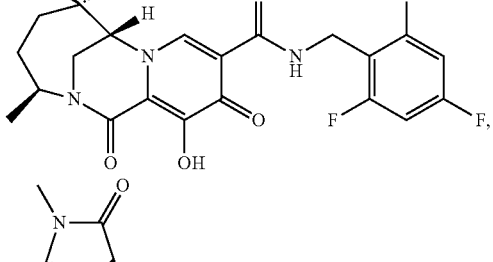
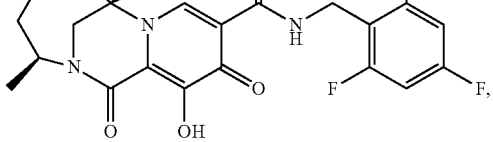
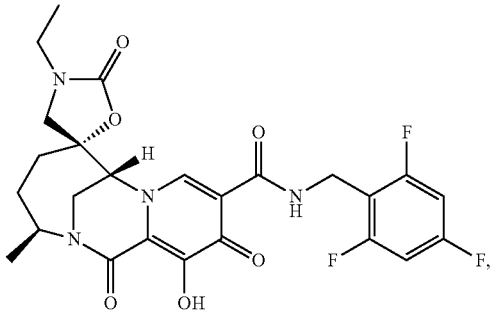

67
-continued
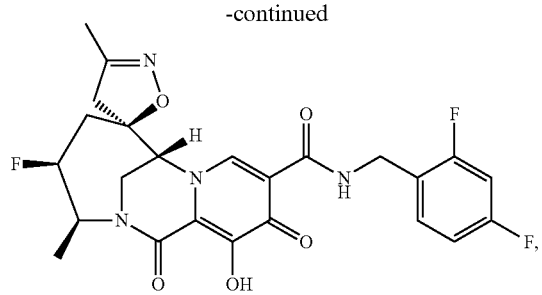
68
-continued
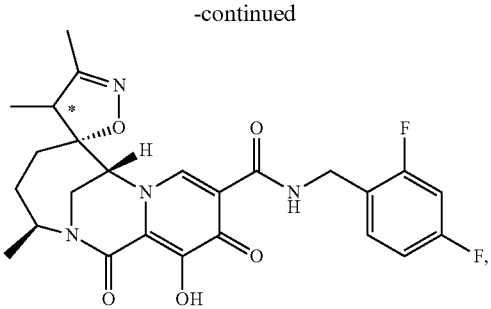
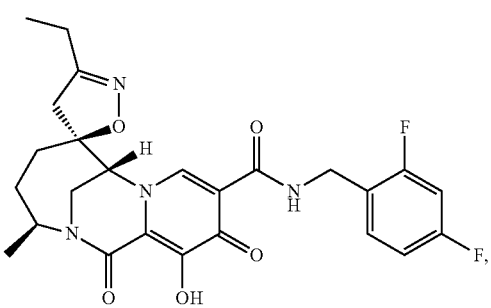
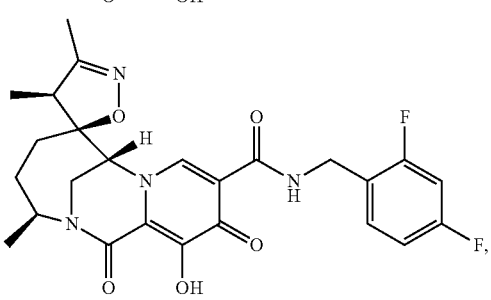
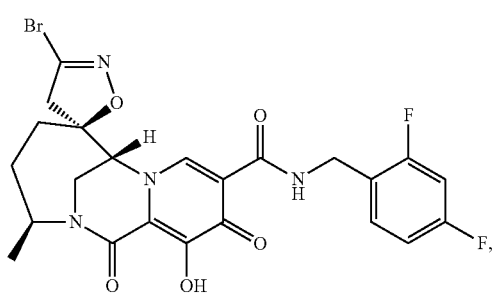
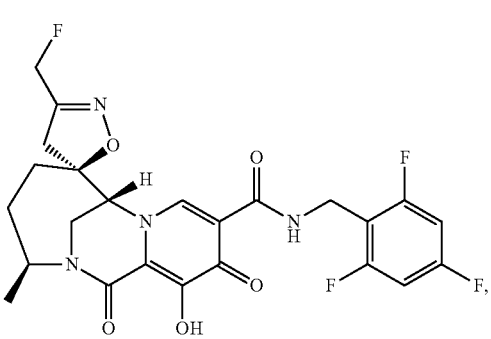
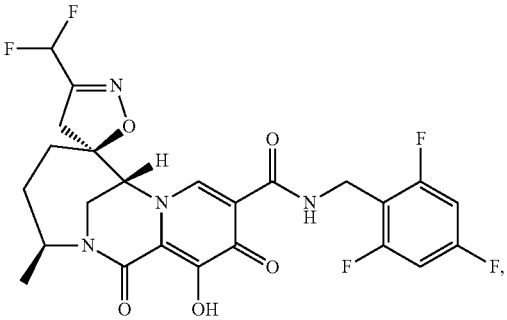

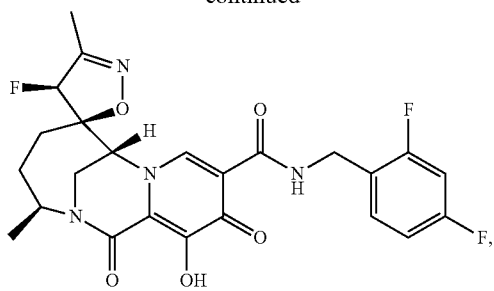
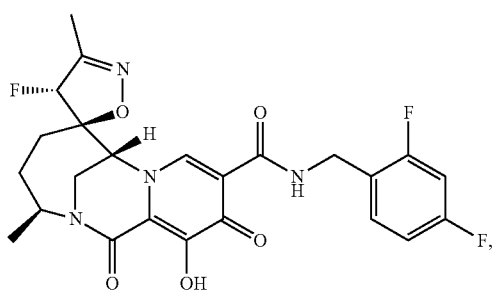
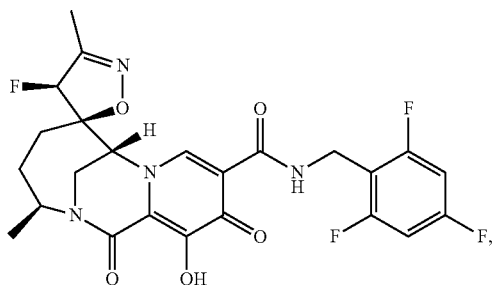
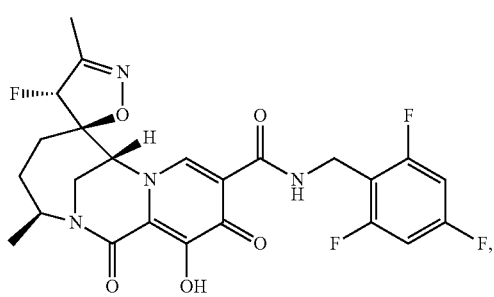
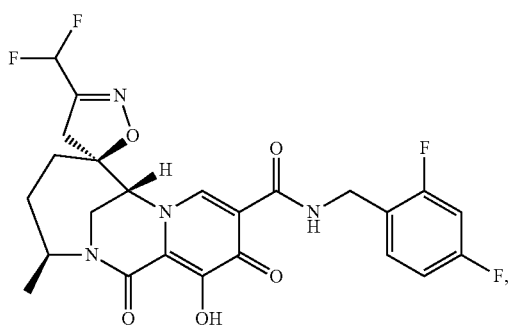
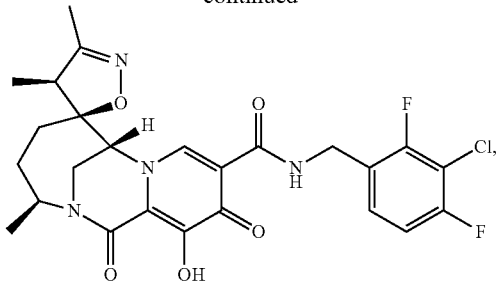
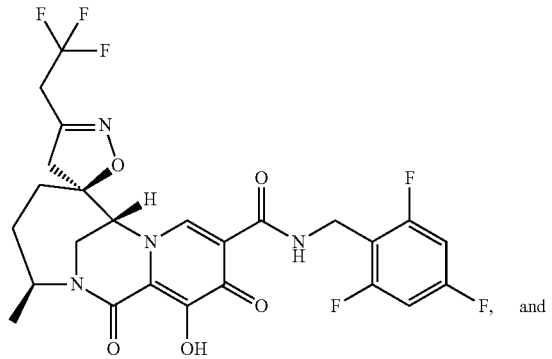
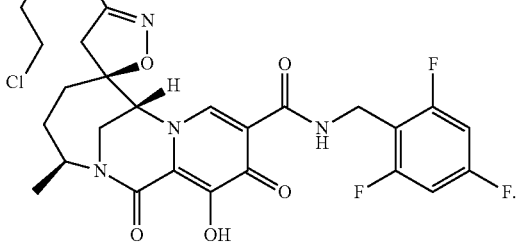
In some embodiments of the compounds of Formula I, I-A, II-A, II-Aa, II-Ab, III, IIIa, IIIb, IV, V, Va, or Vb, or the pharmaceutically acceptable salt thereof, the compound is selected from the group consisting of:
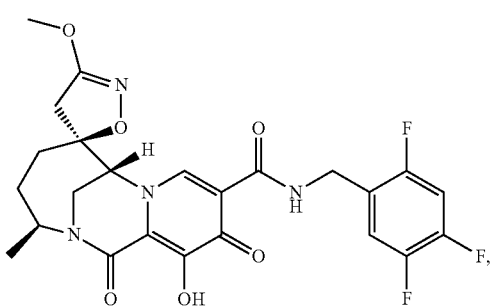

71
-continued
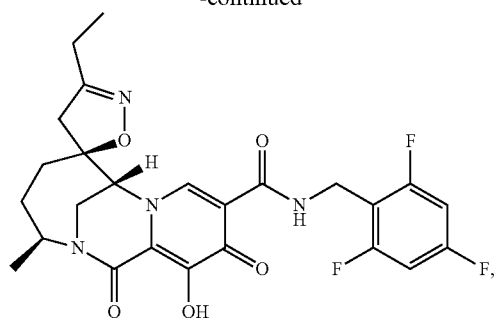
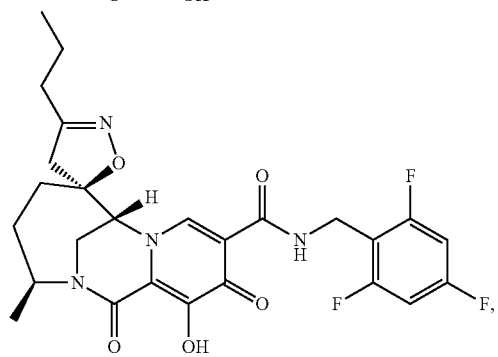
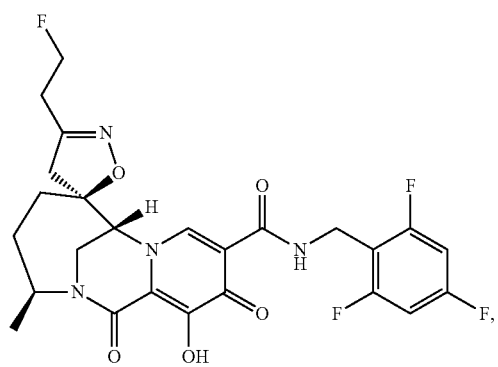
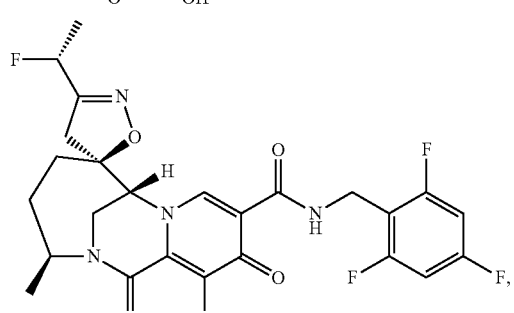
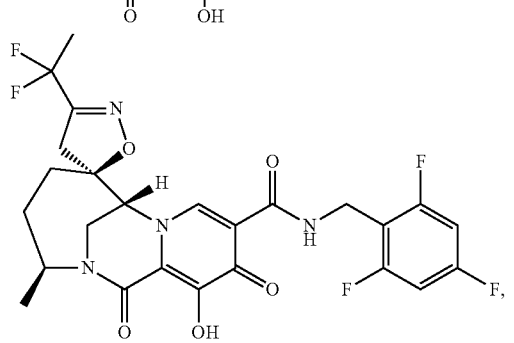
72
-continued
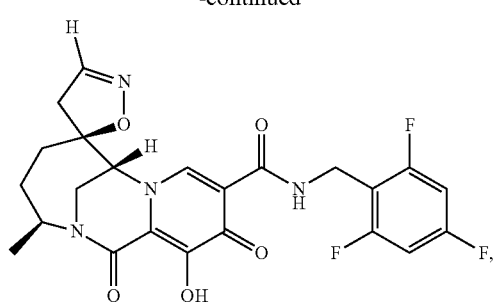
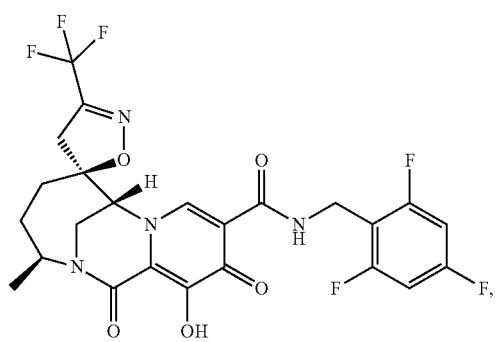
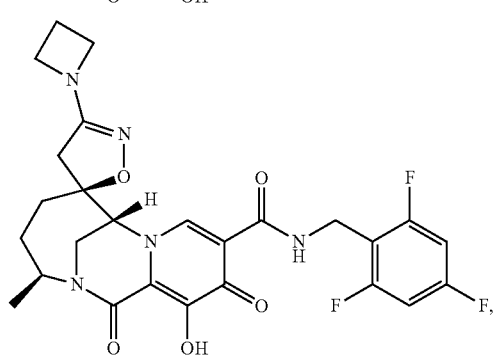
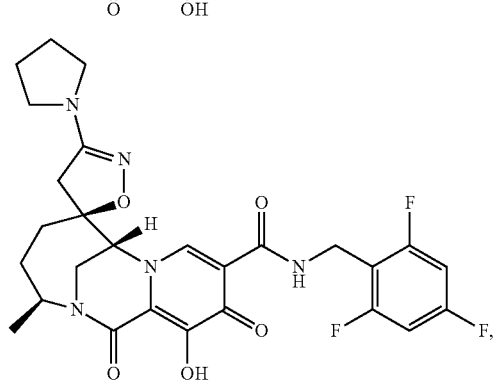
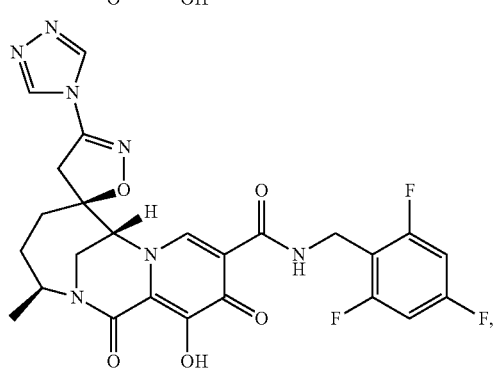

73
-continued
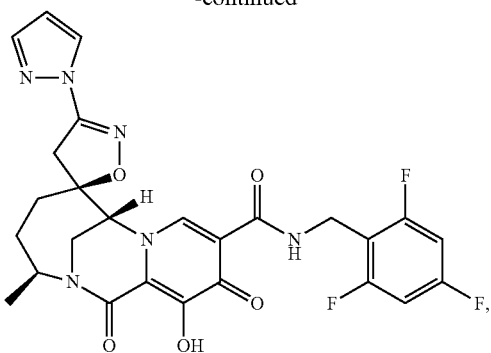
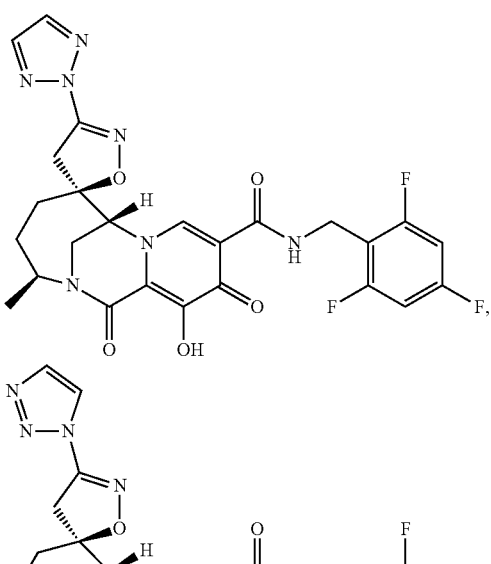
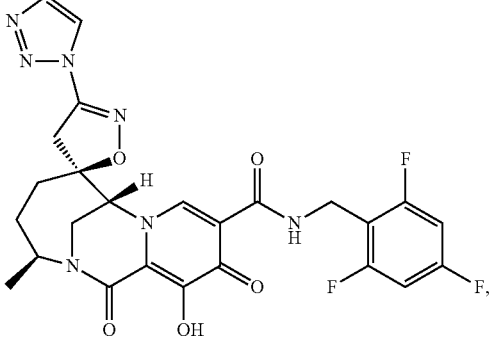
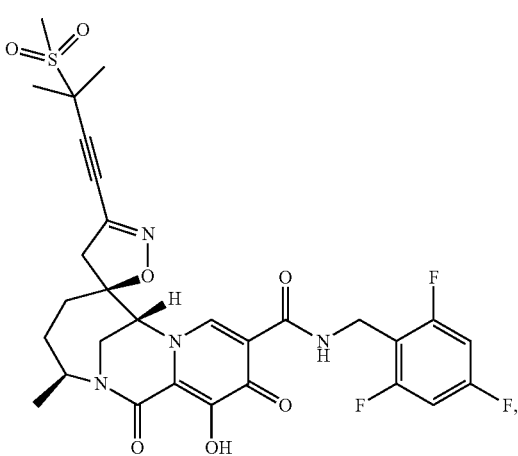
74
-continued
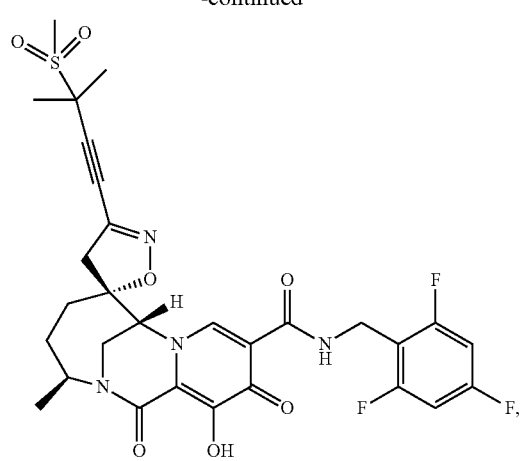
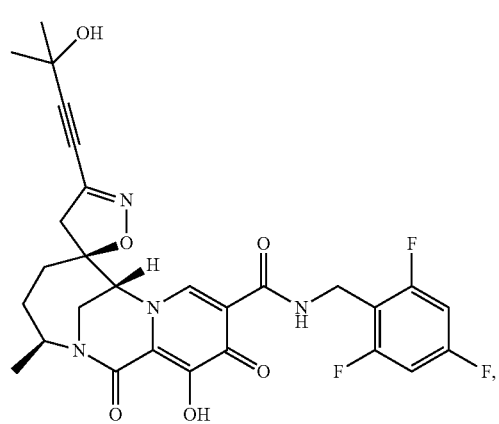
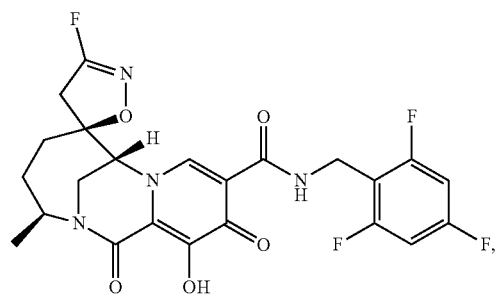
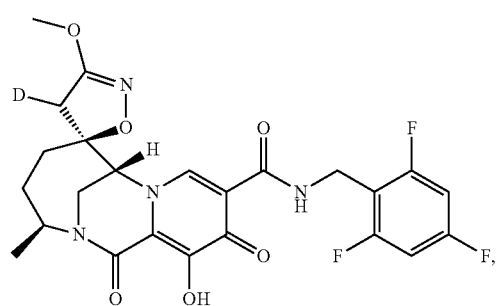

75
-continued
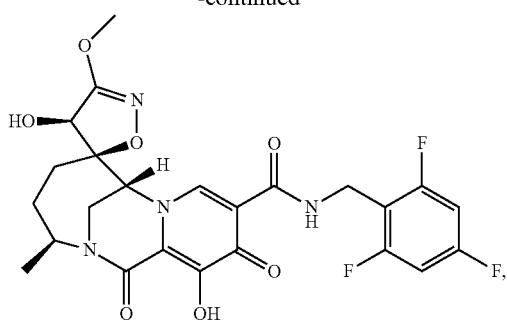
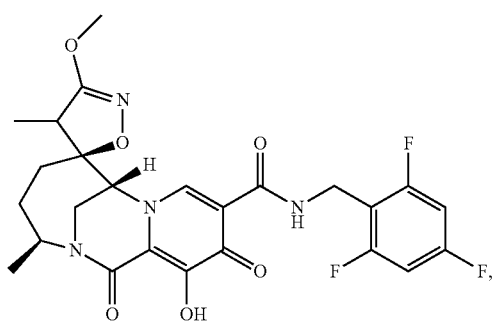
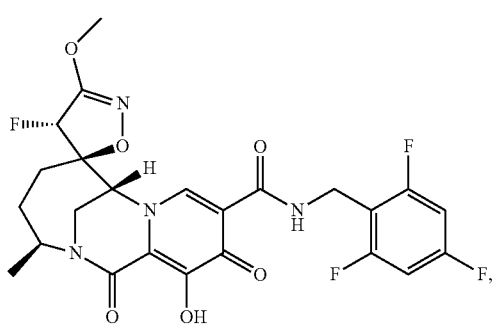
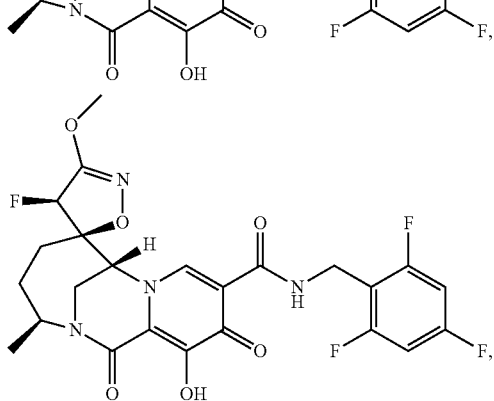
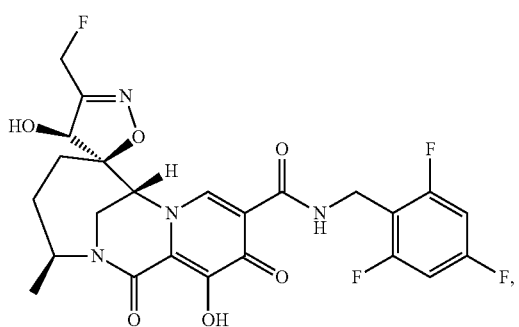
76
-continued
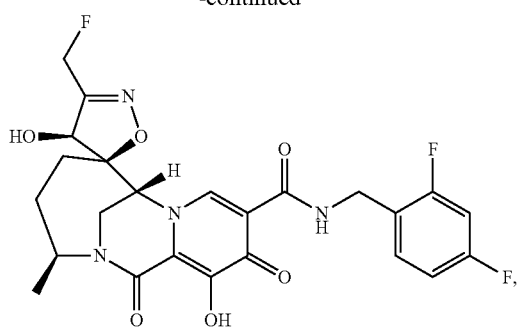
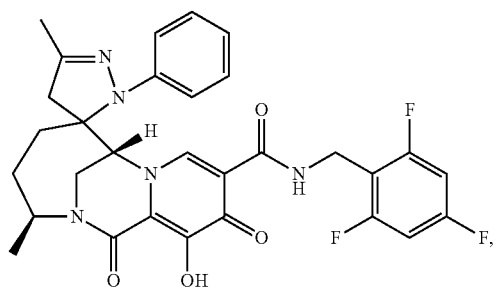
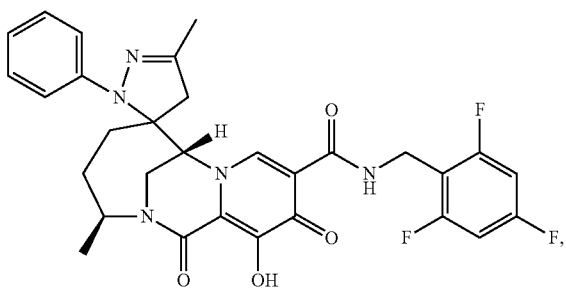
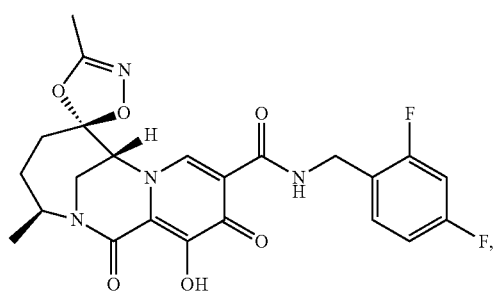
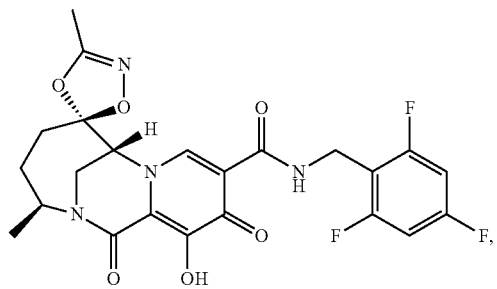

77
-continued
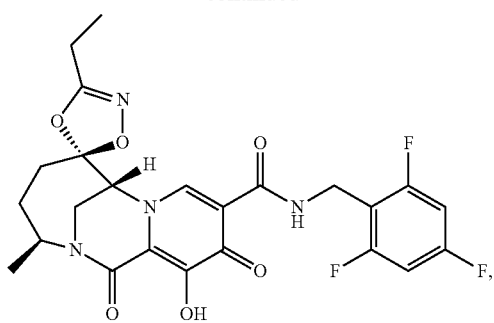
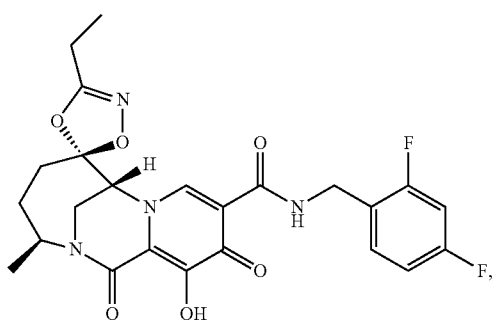
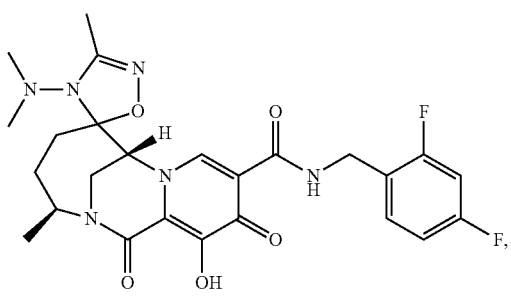
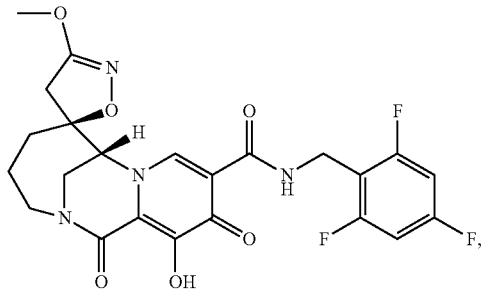
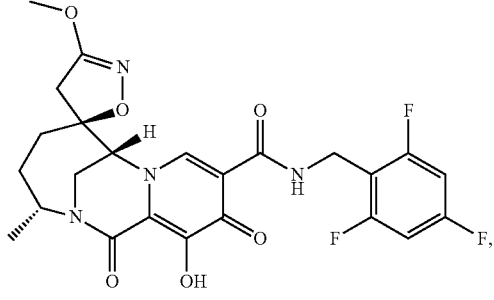
78
-continued
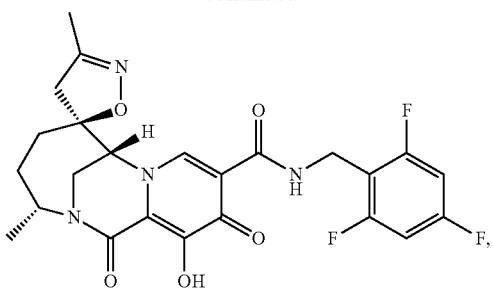
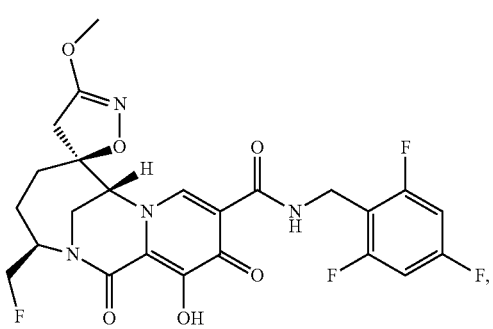
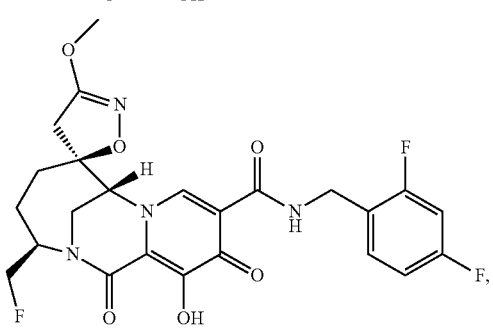
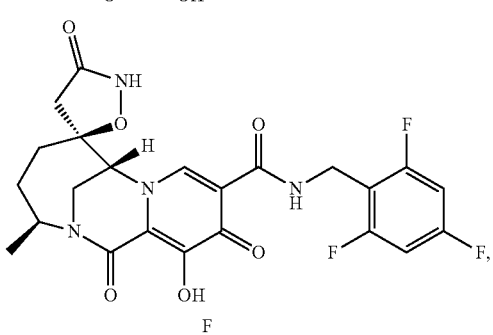
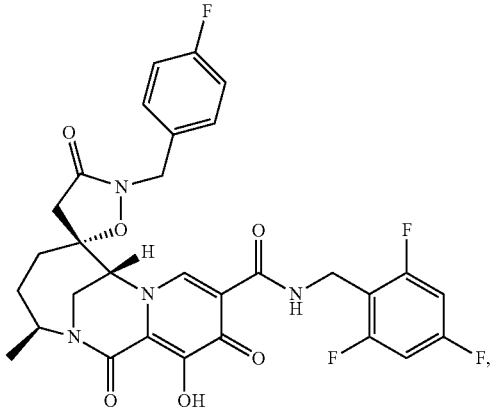

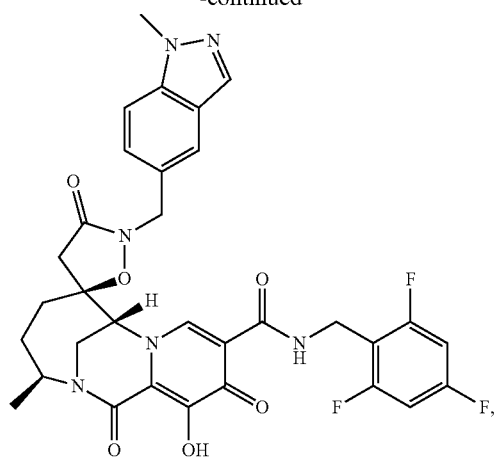
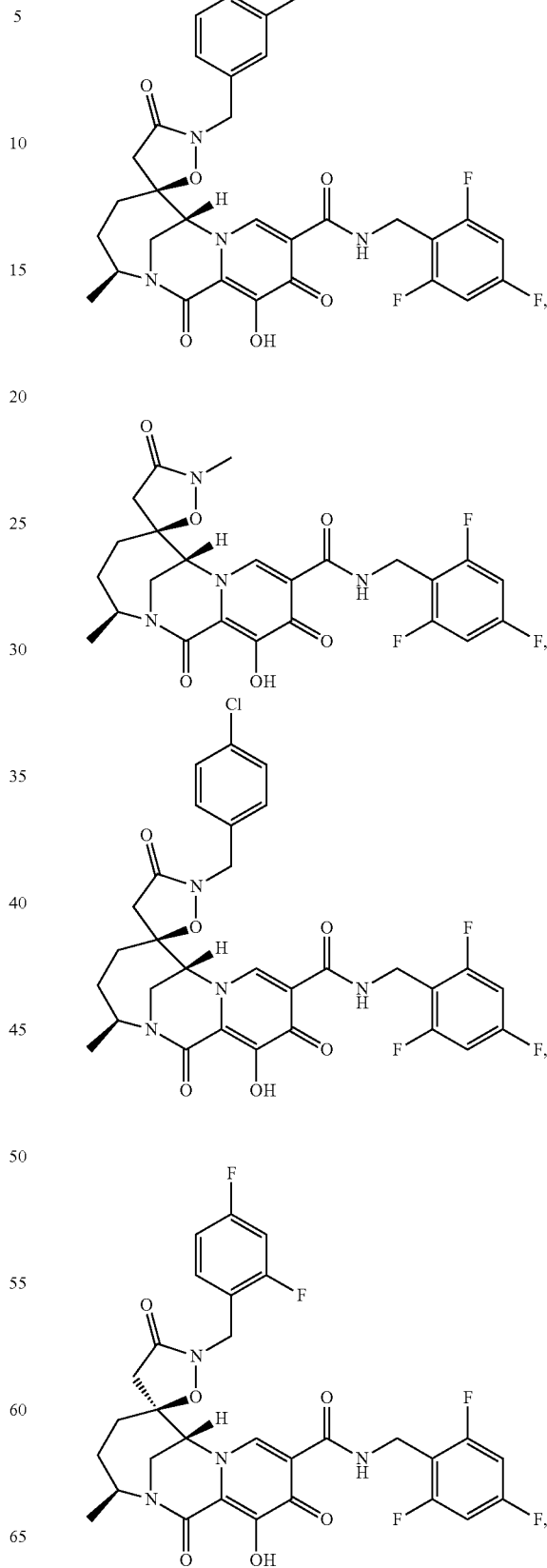

81
-continued
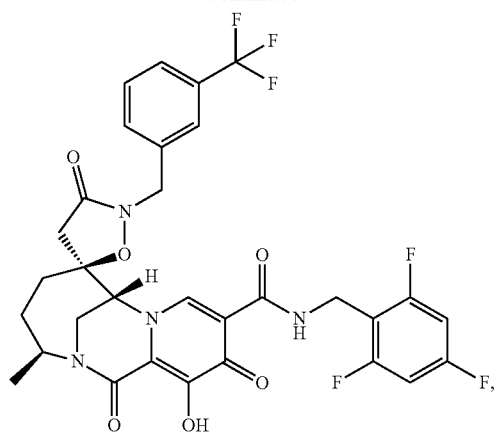
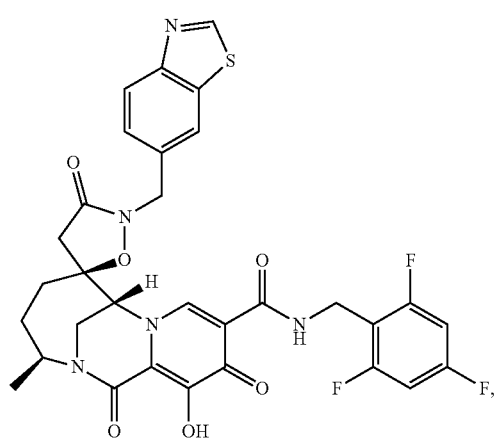
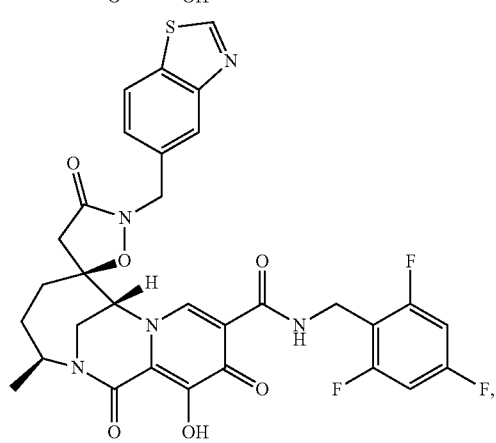
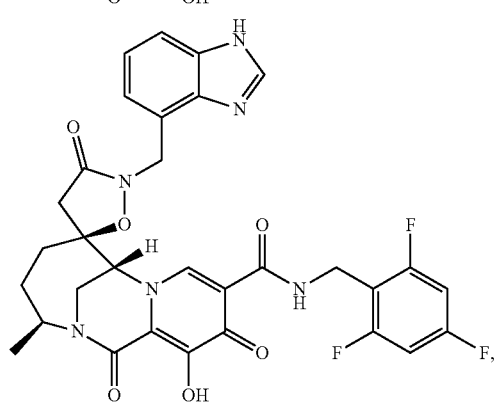
82
-continued
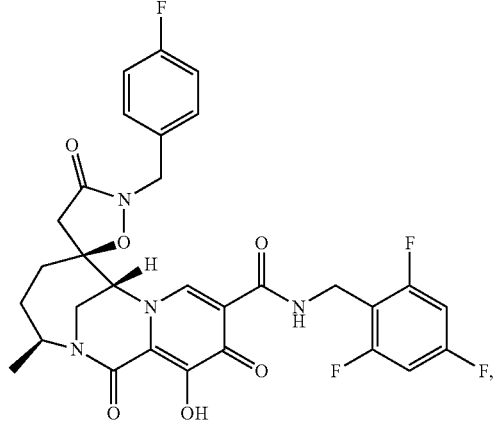
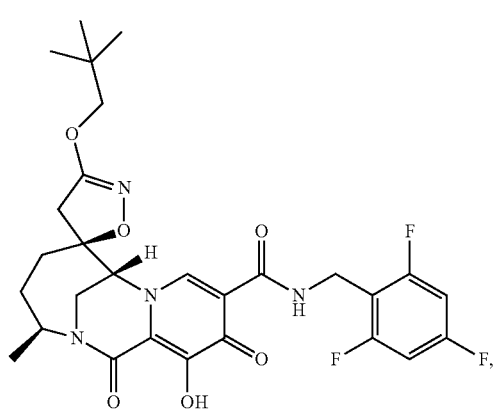
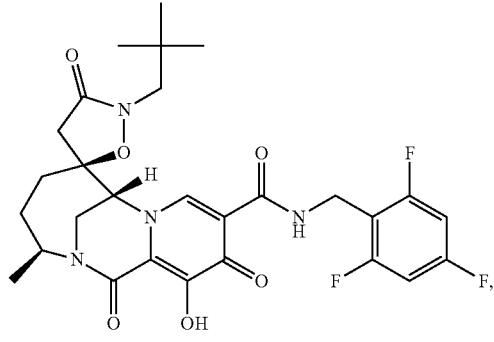
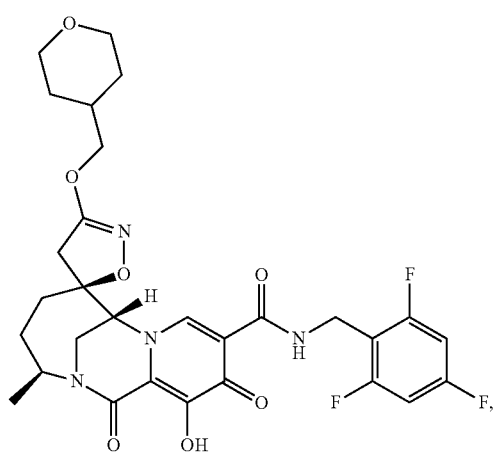

83
-continued
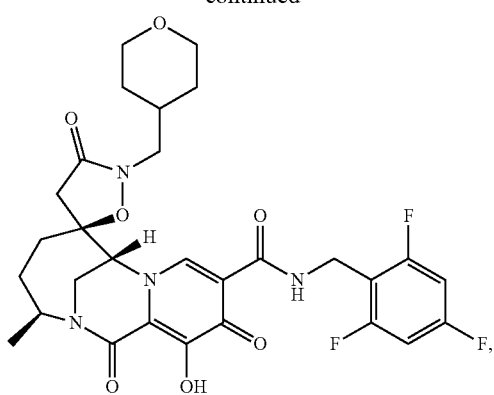
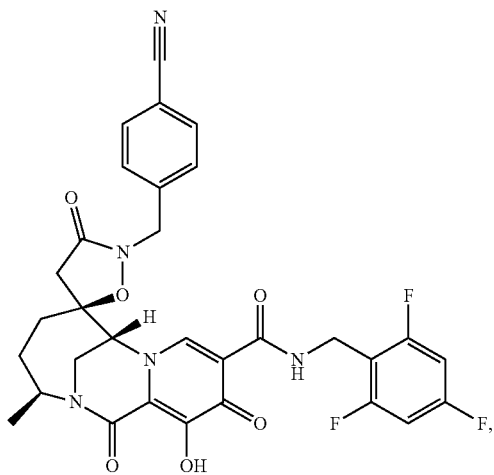
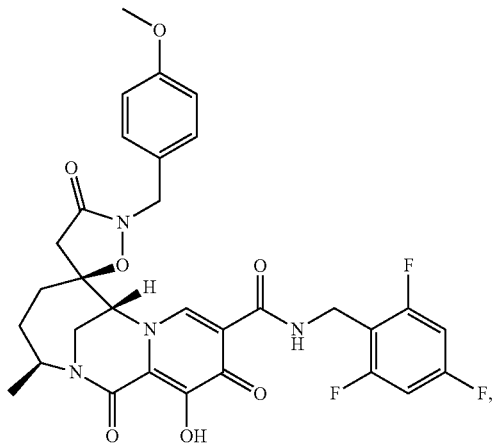
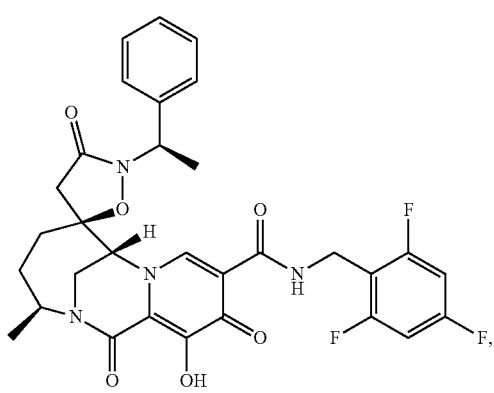
84
-continued
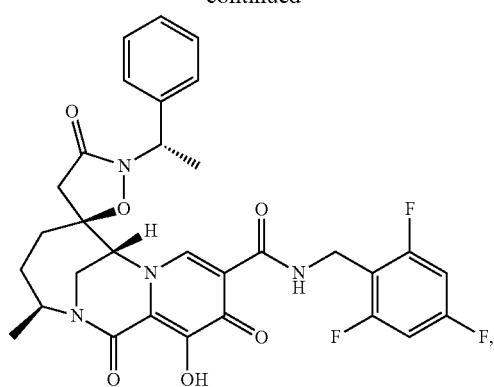
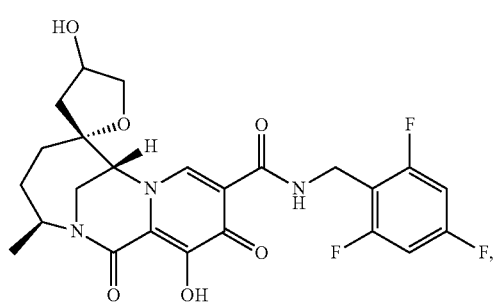
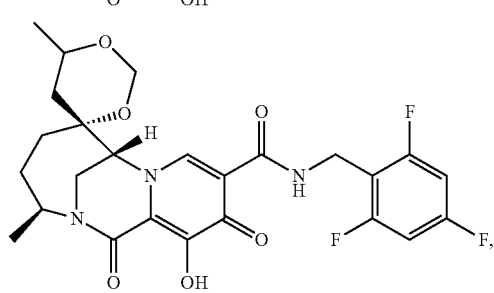
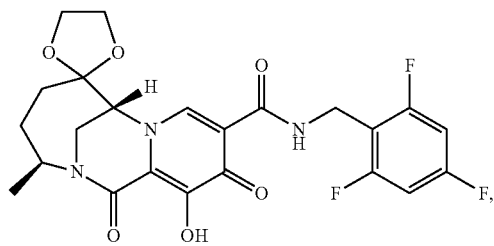
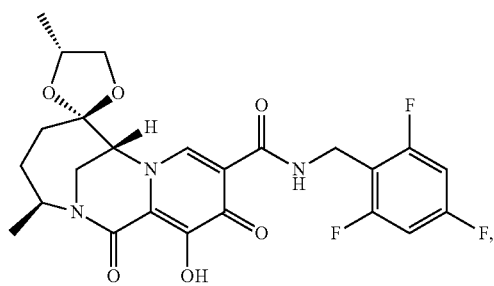

-continued
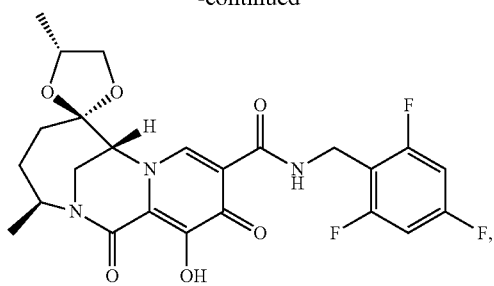
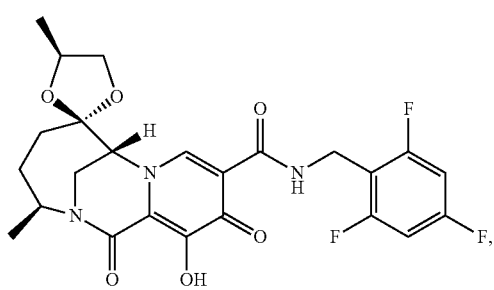
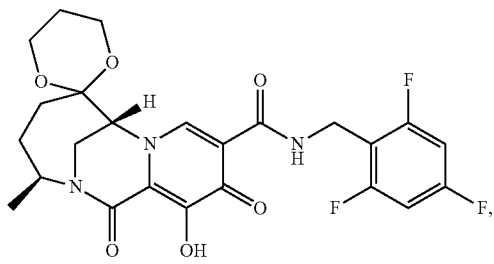

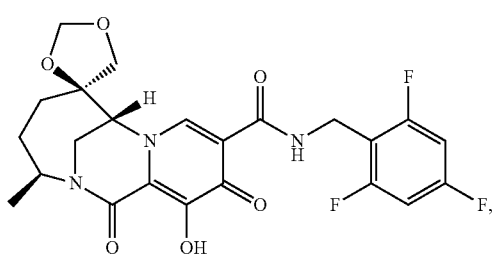
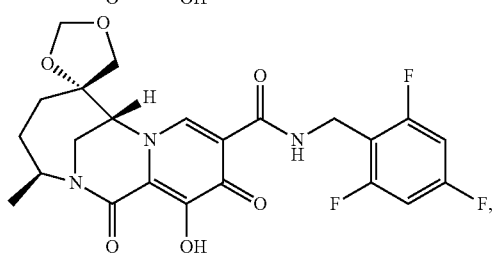
-continued
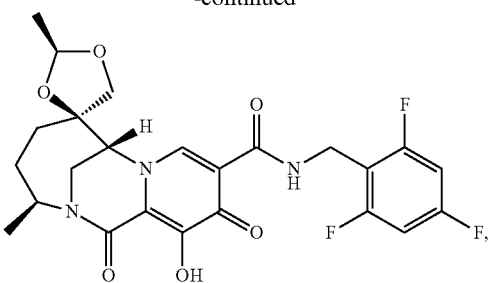
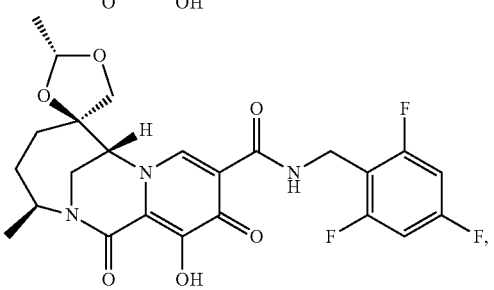
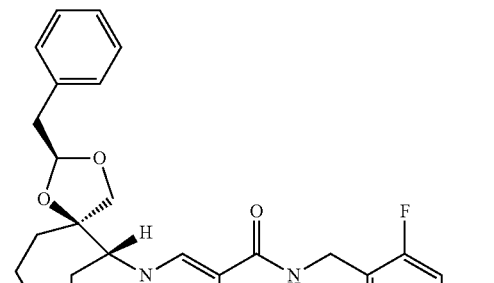
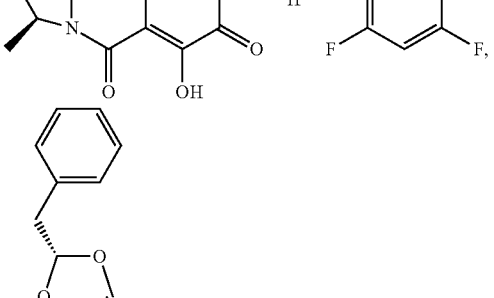
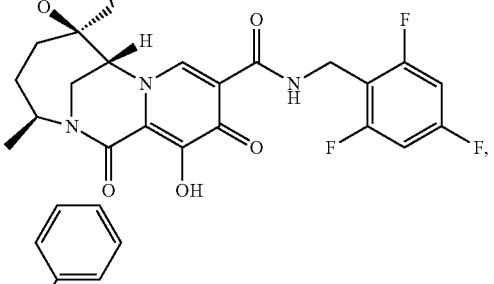
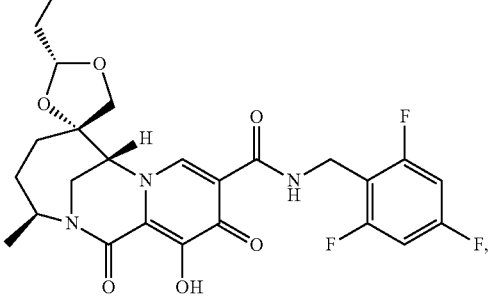

87
-continued
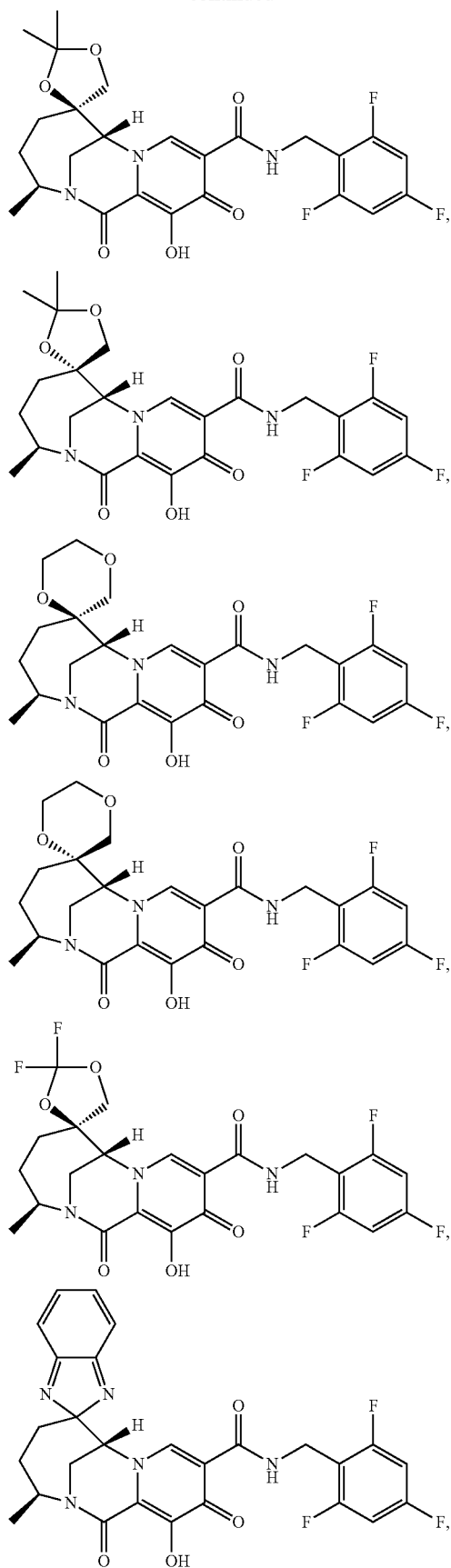
88
-continued
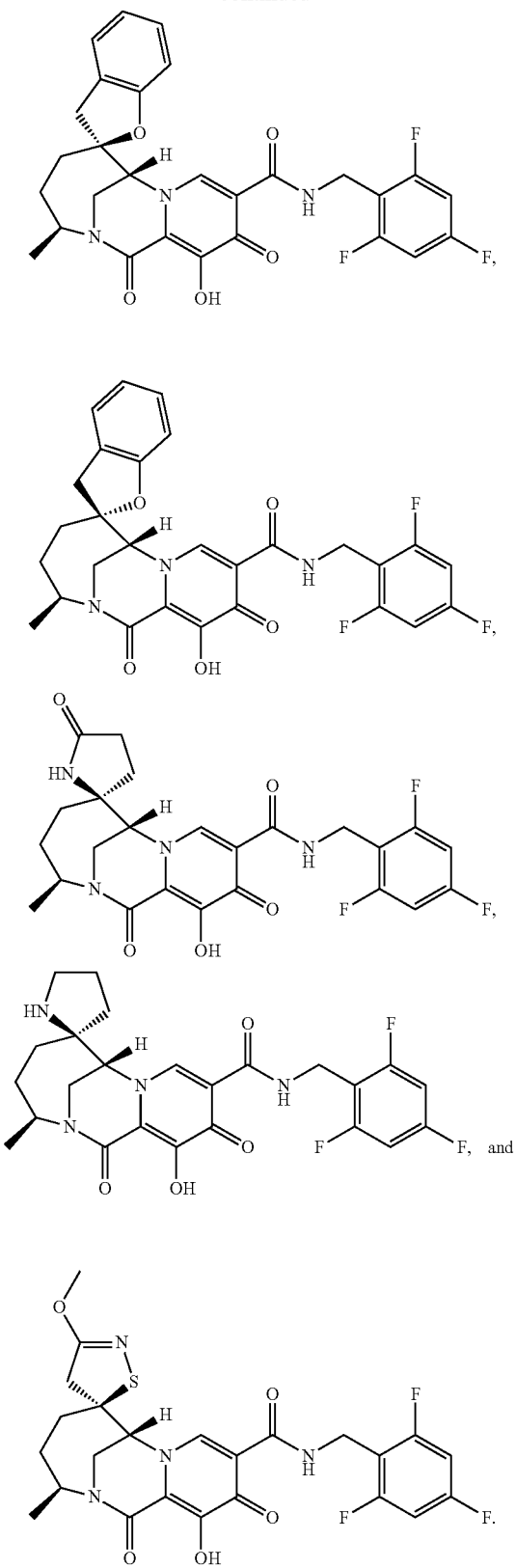
In some embodiments of the compounds of Formula I, I-A, II-A, II-Aa, II-Ab, III, IIIa, IIIb, IV, V, Va, or Vb, or the pharmaceutically acceptable salt thereof, the compound is:

89
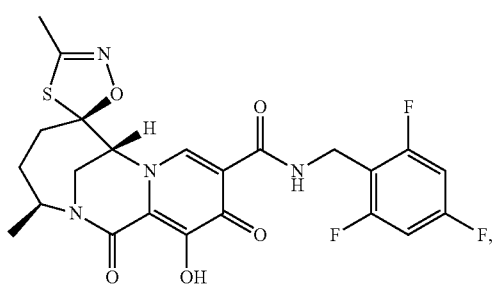
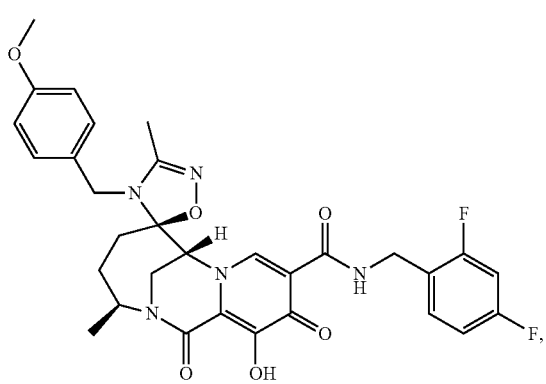
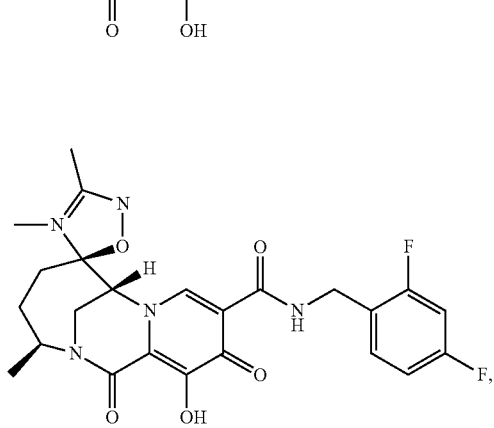
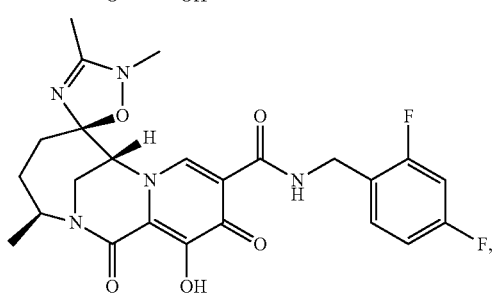
90
-continued
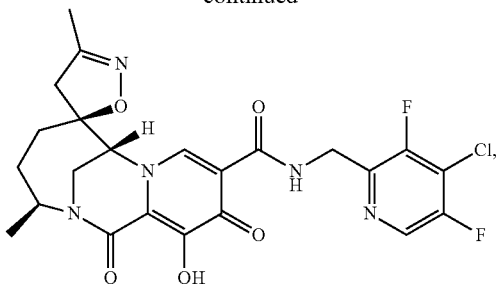
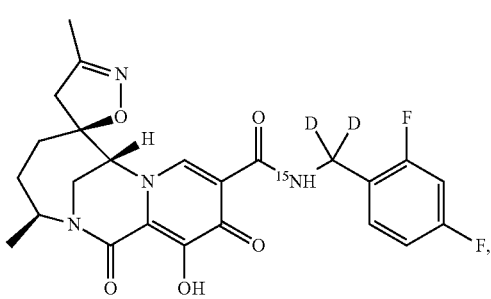
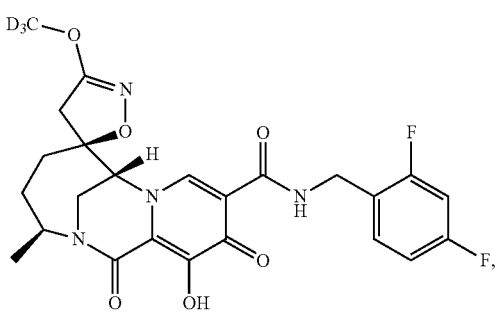
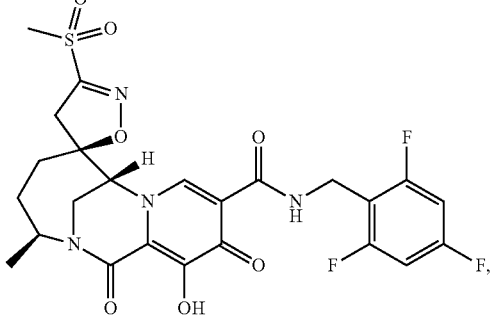

91
-continued
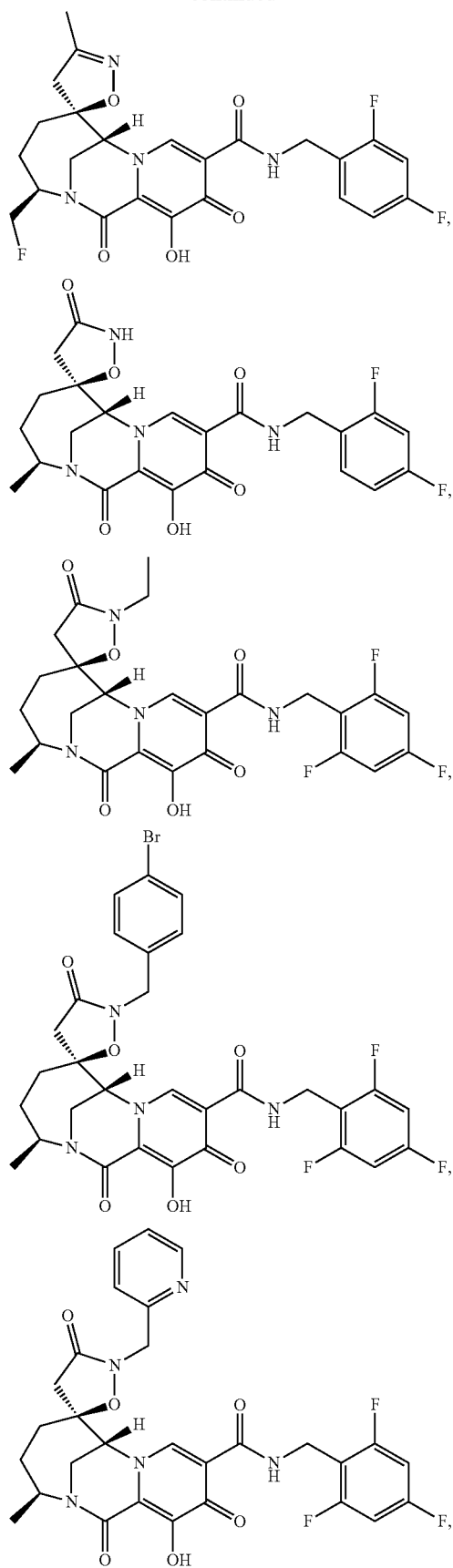
92
-continued
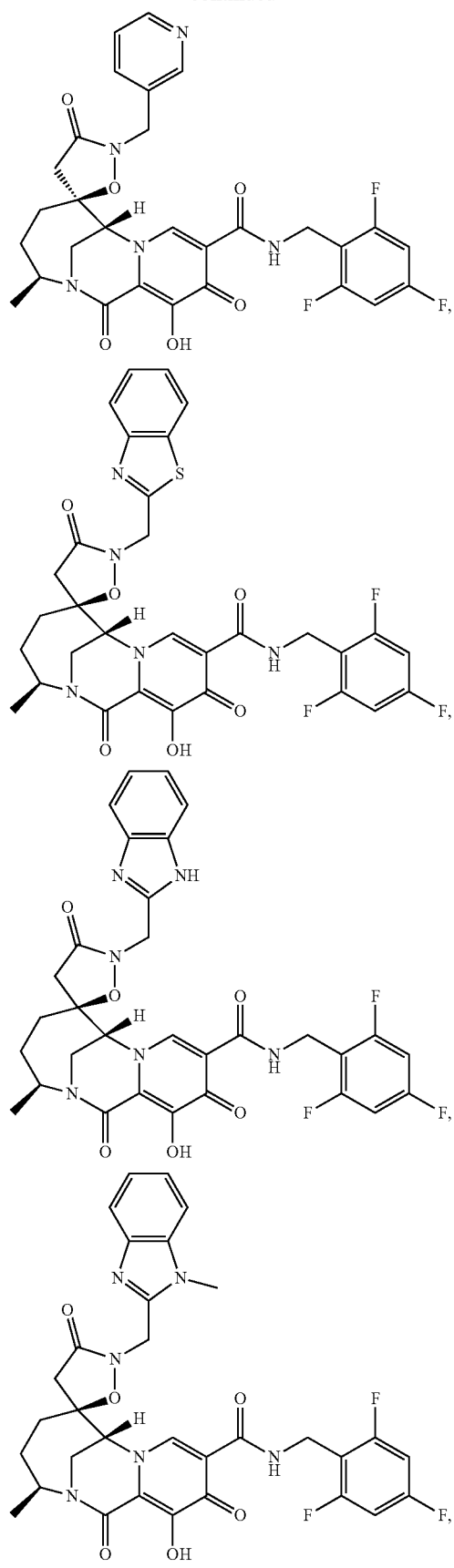

93
-continued
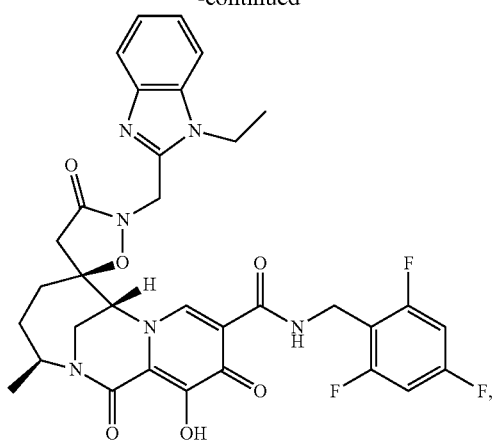
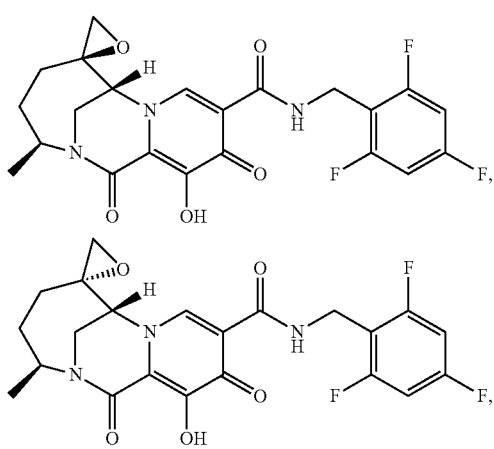
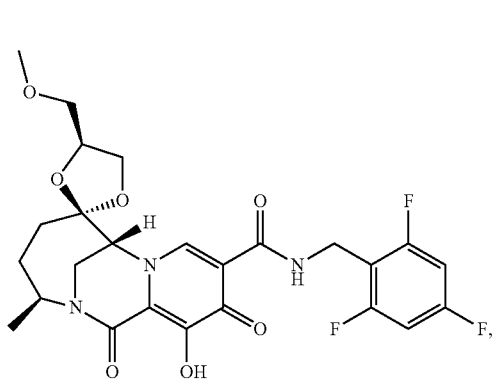
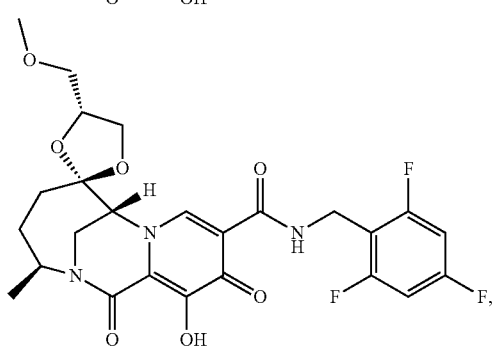
94
-continued
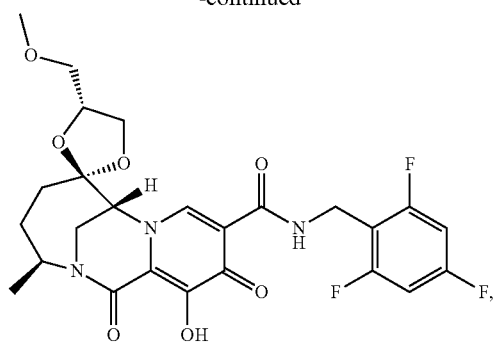
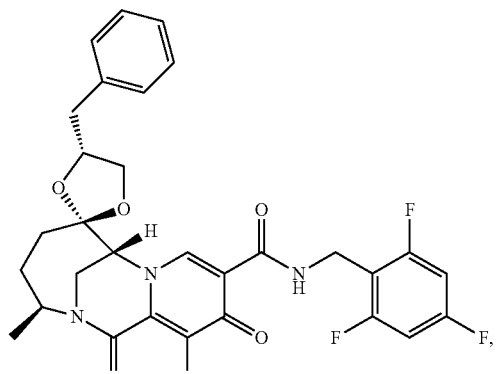
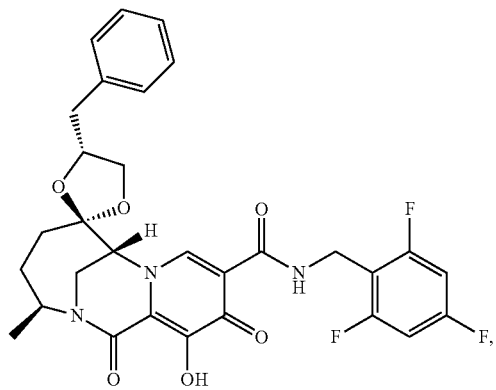
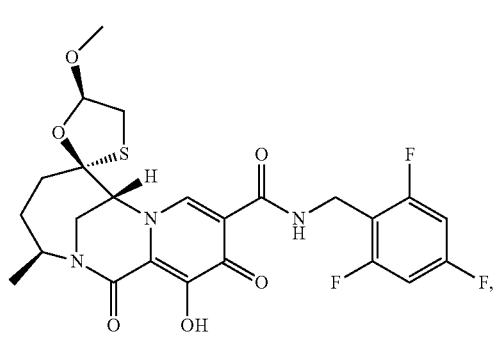

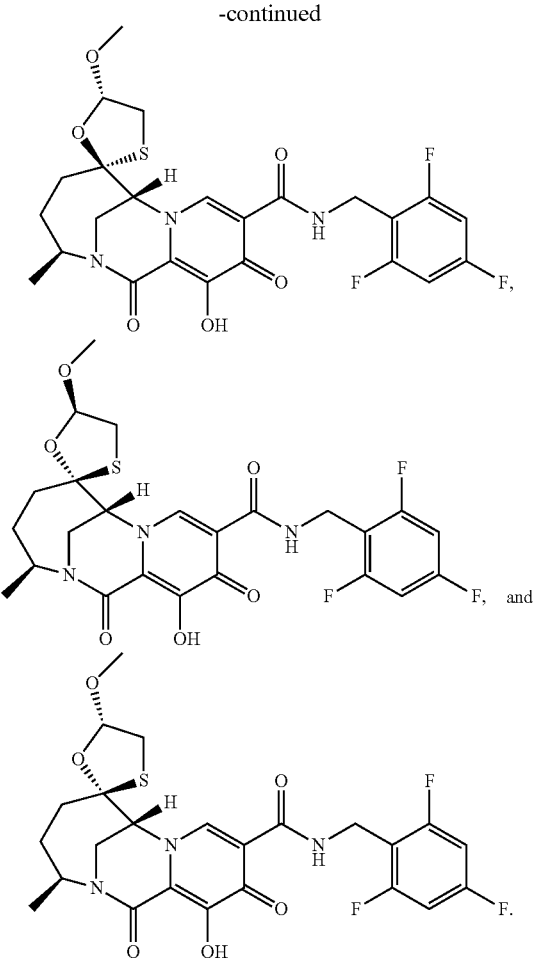

III. PHARMACEUTICAL COMPOSITIONS

Compounds provided herein are usually administered in the form of pharmaceutical compositions. Thus, provided herein are also pharmaceutical compositions that comprise one or more of the compounds provided herein or pharmaceutically acceptable salts, isomer, or a mixture thereof and one or more pharmaceutically acceptable vehicles selected from carriers, adjuvants and excipients. The compounds provided herein may be the sole active ingredient or one of the active ingredients of the pharmaceutical compositions. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

In one aspect, provided herein are pharmaceutical compositions comprising a compound provided herein (e.g., a compound of Formula I, I-A, I-B, I-C, I-D, I-E, I-F, II-A, II-Aa, II-Ab, III, IIIa, IIIb, IV, V, Va, or Vb), or a pharmaceutically acceptable salt thereof, and a pharmaceutically acceptable excipient or carrier. In some embodiments, the pharmaceutical compositions comprise a therapeutically effective amount of a compound provided herein, or a pharmaceutically acceptable salt thereof, and a pharmaceutically acceptable excipient or carrier.

In some embodiments, the pharmaceutical compositions provided herein further comprise one or more (e.g., one, two, three, four, one or two, one to three, or one to four) additional therapeutic agents, or a pharmaceutically acceptable salt thereof. In some embodiments, the pharmaceutical compositions further comprise a therapeutically effective amount of the one or more (e.g., one, two, three, four, one or two, one to three, or one to four) additional therapeutic agents, or a pharmaceutically acceptable salt thereof.

The pharmaceutical compositions may be administered in either single or multiple doses. The pharmaceutical compositions may be administered by various methods including, for example, rectal, buccal, intranasal and transdermal routes. In some embodiments, the pharmaceutical compositions may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds provided herein. Administration may be via, for example, capsule or enteric coated tablets. In making the pharmaceutical compositions that include at least one compound provided herein or pharmaceutically acceptable salts, isomer, or a mixture thereof, the active ingredient (such as a compound provided herein) is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the pharmaceutical compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose or any combinations thereof. The pharmaceutical compositions can additionally include lubricating agents such as talc, magnesium stearate, and mineral oil; wetting agents; emulsifying and suspending agents; preserving agents such as methyl and propylhydroxy-benzoates; sweetening agents; and flavoring agents; or any combinations thereof.

The pharmaceutical compositions that include at least one compound described herein or pharmaceutically acceptable salts, isomer, or a mixture thereof can be formulated so as to provide quick, sustained or delayed release of the active ingredient (such as a compound provided herein) after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices ("patches"). Such transdermal patches may be used to provide continuous or discontinuous infusion of the compounds provided herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or pharmaceutically acceptable salts, isomer, or a mixture thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with materials such as shellac, cetyl alcohol, and cellulose acetate.

Pharmaceutical compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

IV. METHODS OF TREATMENT

In one embodiment, methods of treating an HIV (e.g., HIV-1 and/or HIV-2) infection in a human having or at risk of having the infection comprising administering to the human a therapeutically effective amount of a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof, or a pharmaceutical composition of a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof, are provided.

In some embodiments, the methods further comprise administering to the human a therapeutically effective amount of one, two, three, or four additional therapeutic agents. In certain embodiments, the additional therapeutic agent or agents are anti-HIV agents. In particular embodiments, the additional therapeutic agent or agents are HIV protease inhibitors, HIV non-nucleoside or non-nucleotide inhibitors of reverse transcriptase, HIV nucleoside or nucleotide inhibitors of reverse transcriptase, HIV capsid inhibitors, gp41 inhibitors, CXCR4 inhibitors, gp120 inhibitors, CCR5 inhibitors, latency reversing agents, capsid polymerization inhibitors, HIV bNAbs (broadly neutralizing HIV antibodies), TLR7 agonists, pharmacokinetic enhancers, other drugs for treating HIV, or combinations thereof. In one embodiment, the additional therapeutic agent or agents are abacavir, tenofovir alafenamide, tenofovir disoproxil, lenacapavir, or a pharmaceutically acceptable salt thereof. In one embodiment, the additional therapeutic agent or agents are abacavir, tenofovir alafenamide, tenofovir disoproxil, lenacapavir, GS-5894, islatravir, or a pharmaceutically acceptable salt thereof. In some embodiments, the additional therapeutic agent or agents are lenacapavir, islatravir. In some embodiments, the additional therapeutic agent is lenacapavir. In some embodiments, the additional therapeutic agent is islatravir.

In another embodiment, a use of a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof, or a pharmaceutical composition of a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof, for treating an HIV (e.g., HIV-1 and/or HIV-2) infection in a human having or at risk of having the infection is provided.

In another embodiment, a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof, or a pharmaceutical composition of a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof, for use in medical therapy is provided.

In another embodiment, a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof, or a pharmaceutical composition of Formula I, I-A, I-B, I-C, I-D, I-E, I-F, II-A, II-Aa, II-Ab, III, IIIa, IIIb, IV, IVa, IVb, V, Va, or pharmaceutically acceptable salt thereof, for use in treating an HIV infection is provided.

In another embodiment, a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof, or a pharmaceutical composition of a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof for use in a method of treating an HIV infection in a human having or at risk of having the infection, is provided.

In another embodiment, a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof, or a pharmaceutical composition of a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof for use in a method of treating an HIV infection in a human having or at risk of having the infection, is provided wherein said method further comprises administering to the human one, two, three, or four additional therapeutic agents.

In another embodiment, a compound of I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof, or a pharmaceutical composition of a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof for use in a method of treating an HIV infection in a human having or at risk of having the infection, is provided wherein said method further comprises administering to the human one, two, three, or four additional therapeutic agents selected from the group consisting of HIV protease inhibitors, HIV non-nucleoside or non-nucleotide inhibitors of reverse transcriptase, HIV nucleoside or nucleotide inhibitors of reverse transcriptase, HIV capsid inhibitors, gp41 inhibitors, CXCR4 inhibitors, gp120 inhibitors, CCR5 inhibitors, latency reversing agents, capsid polymerization inhibitors, HIV bNAbs, TLR7 agonists, pharmacokinetic enhancers, other drugs for treating HIV, or combinations thereof. In one embodiment, the one, two, three, or four additional therapeutic agents are selected from HIV protease inhibitors, HIV non-nucleoside inhibitors of reverse transcriptase, HIV nucleoside or nucleotide inhibitors of reverse transcriptase, latency reversing agents, HIV capsid inhibitors, HIV bNAbs, TLR7 agonists, and combinations thereof.

In another embodiment, a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof, or a pharmaceutical composition of a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof for use in a method of treating an HIV infection in a human having or at risk of having the infection, is provided wherein said method further comprises administering to the human a therapeutically effective amount of tenofovir disoproxil and emtricitabine.

In another embodiment, a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof, or a pharmaceutical composition of a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof for use in a method of treating an HIV infection in a human having or at risk of having the infection, is provided wherein said method further comprises administering to the human a therapeutically effective amount of tenofovir alafenamide and emtricitabine.

In another embodiment, a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof, or a pharmaceutical composition of a compound of I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof for use in a method of treating an HIV infection in a human having or at risk of having the infection, is provided wherein said method further comprises administering to the human a therapeutically effective amount of tenofovir disoproxil.

In another embodiment, a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof, or a pharmaceutical composition of a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof for use in a method of treating an HIV infection in a human having or at risk of having the infection, is provided wherein said method further comprises administering to the human a therapeutically effective amount of tenofovir alafenamide.

In another embodiment, a method of using a compound of Formula I, I-A, I-B, I-C, I-D, I-E, I-F, II-A, II-Aa, II-Ab, III, IIIa, IIIb, IV, IVa, IVb, V, Va, or Vb in therapy is provided. In particular, a method of treating the proliferation of the HIV virus, treating AIDS, or delaying the onset of AIDS or ARC symptoms in a mammal (e.g., a human) is provided, comprising administering to the mammal a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof, and a pharmaceutically acceptable excipient.

In another embodiment, a composition comprising a compound of Formula I, I-A, I-B, I-C, I-D, I-E, I-F, II-A, II-Aa, II-Ab, III, IIIa, IIIb, IV, IVa, IVb, V, Va, or Vb, or pharmaceutically acceptable salt thereof, and a pharmaceutically acceptable excipient, for use in a method of treating the proliferation of the HIV virus, treating AIDS, or delaying the onset of AIDS or ARC symptoms in a mammal (e.g., a human) is provided.

In one embodiment, a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof, or a pharmaceutical composition of a compound of Formula I, I-A, I-B, I-C, I-D, I-E, I-F, II-A, II-Aa, II-Ab, III, IIIa, IIIb, IV, IVa, IVb, V, Va, or Vb or a pharmaceutically acceptable salt thereof, is provided for use in preventing HIV infection.

For example, in one embodiment, a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof, or a pharmaceutical composition of a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof, is provided for use in pre-exposure prophylaxis (PrEP), i.e., before the exposure of the individual to the HIV virus to prevent HIV infection from taking hold if the individual is exposed to the virus and/or to keep the virus from establishing a permanent infection and/or to prevent the appearance of symptoms of the disease and/or to prevent the virus from reaching detectable levels in the blood.

In another embodiment, the use of a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof, for the manufacture of a medicament for treating an HIV infection in a human being having or at risk of having the infection is disclosed.

In another embodiment, the use of a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof, as a research tool is disclosed.

In another embodiment, an article of manufacture comprising a composition effective to treat an HIV infection; and packaging material comprising a label which indicates that the composition can be used to treat infection by HIV is disclosed. Exemplary compositions comprise a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof.

In still another embodiment, a method of inhibiting the replication of HIV is disclosed. The method comprises exposing the virus to an effective amount of the compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof, under conditions where replication of HIV is inhibited.

In another embodiment, the use of a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof, to inhibit the activity of the HIV integrase enzyme is disclosed.

In another embodiment, the use of a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt thereof, to inhibit the replication of HIV is disclosed.

V. ADMINISTRATION

The compounds of the present disclosure (for example, a compound of Formula I, I-A, I-B, I-C, I-D, I-E, I-F, II-A, II-Aa, II-Ab, III, IIIa, IIIb, IV, IVa, IVb, V, Va, or Vb), can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the preferred route may vary with, for example, the condition of the recipient. An advantage of certain compounds disclosed herein is that they are orally bioavailable and can be dosed orally.

A compound of the present disclosure may be administered to an individual in accordance with an effective dosing regimen for a desired period of time or duration, such as at least about one month, at least about 2 months, at least about 3 months, at least about 6 months, or at least about 12 months or longer. In some embodiments, the compound is administered on a daily or intermittent schedule for the duration of the individual's life.

The specific dose level of a compound of the present disclosure for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The dosage may also be described as a total amount of a compound described herein administered per dose. Dosage of a compound of Formula I, I-A, I-B, I-C, I-D, I-E, I-F, II-A, II-Aa, II-Ab, III, IIIa, IIIb, IV, IVa, IVb, V, Va, or Vb, or a pharmaceutically acceptable salt or pharmaceutically acceptable tautomer thereof, may be between about 1 mg and 4,000 mg, between about 2,000 to 4,000 mg, between about 1 to 2,000 mg, between about 1 to 1,000 mg, between about 10 to 500 mg, between about 20 to 500 mg, between about 50 to 300 mg, between about 75 to 200 mg, or between about 15 to 150 mg.

The dosage or dosing frequency of a compound of the present disclosure may be adjusted over the course of the treatment, based on the judgment of the administering physician.

The compounds of the present disclosure may be administered to an individual (e.g., a human) in a therapeutically effective amount. In some embodiments, the compound is administered once daily. In some embodiments, the compound is administered once every week. In some embodiments, the compound is administered once every month. In some embodiments, the compound is administered every two months. In some embodiments, the compound is administered every three months. In some embodiments, the compound is administered every four months. In some embodiments, the compound is administered every five months. In some embodiments, the compound is administered every six months. In some embodiments, the compound is administered every seven months. In some embodiments, the compound is administered every eight months. In some embodiments, the compound is administered every nine months. In some embodiments, the compound is administered every ten months. In some embodiments, the compound is administered every eleven months. In some embodiments, the compound is administered every year.

The compounds provided herein can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day. In some embodiments, a therapeutically effective amount of the compounds provided herein include from about 0.3 mg to about 30 mg per dose, or from about 30 mg to about 300 mg per dose, or from about 0.3 µg to about 30 mg per dose, or from about g to about 300 µg per dose.

A compound of the present disclosure may be combined with one or more additional therapeutic agents in any dosage amount of the compound of the present disclosure (e.g., from 1 mg to 1000 mg of compound). Therapeutically effective amounts may include from about 0.1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose, or such as from about 0.01 mg per dose to about 1000 mg per dose, or such as from about 0.01 mg per dose to about 100 mg per dose, or such as from about 0.1 mg per dose to about 100 mg per dose, or such as from about 1 mg per dose to about 100 mg per dose, or such as from about 1 mg per dose to about 10 mg per dose, or such as from about 1 mg per dose to about 1000 mg per dose. Other therapeutically effective amounts of the compound of Formula I are about 1 mg per dose, or about 2, 3, 4, 5, 6, 7, 8, 9, 10, 15, 20, 25, 30, 35, 40, 45, 50, 55, 60, 65, 70, 75, 80, 85, 90, 95, or about 100 mg per dose. Other therapeutically effective amounts of the compound of the present disclosure are about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or about 1000 mg per dose.

In some embodiments, the methods described herein comprise administering to the subject an initial daily dose of about 1 to 500 mg of a compound p herein and increasing the dose by increments until clinical efficacy is achieved. Increments of about 5, 10, 25, 50, or 100 mg can be used to increase the dose. The dosage can be increased daily, every other day, twice per week, once per week, once every two weeks, once every three weeks, or once a month.

When administered orally, the total daily dosage for a human subject may be between about 1 mg and 1,000 mg, between about 10-500 mg/day, between about 50-300 mg/day, between about 75-200 mg/day, or between about 100-150 mg/day. In some embodiments, the total daily dosage for a human subject may be about 100, 200, 300, 400, 500, 600, 700, 800, 900, or 1000 mg/day administered in a single dose. In some embodiments, the total daily dosage for a human subject may be about 200, 300, 400, 500, 600, 700, or 800 mg/day administered in a single dose. In some embodiments, the total daily dosage for a human subject may be about 300, 400, 500, or 600 mg/day administered in a single dose.

In some embodiments, the total daily dosage for a human subject may be about 100 mg/day administered in a single dose. In some embodiments, the total daily dosage for a human subject may be about 150 mg/day administered in a single dose. In some embodiments, the total daily dosage for a human subject may be about 200 mg/day administered in a single dose. In some embodiments, the total daily dosage for a human subject may be about 250 mg/day administered in a single dose. In some embodiments, the total daily dosage for a human subject may be about 300 mg/day administered in a single dose. In some embodiments, the total daily dosage for a human subject may be about 350 mg/day administered in a single dose. In some embodiments, the total daily dosage for a human subject may be about 400 mg/day administered in a single dose. In some embodiments, the total daily dosage for a human subject may be about 450 mg/day administered in a single dose. In some embodiments, the total daily dosage for a human subject may be about 500 mg/day administered in a single dose. In some embodiments, the total daily dosage for a human subject may be about 550 mg/day administered in a single dose. In some embodiments, the total daily dosage for a human subject may be about 600 mg/day administered in a single dose. In some embodiments, the total daily dosage for a human subject may be about 650 mg/day administered in a single dose. In some embodiments, the total daily dosage for a human subject may be about 700 mg/day administered in a single dose. In some embodiments, the total daily dosage for a human subject may be about 750 mg/day administered in a single dose. In some embodiments, the total daily dosage for a human subject may be about 800 mg/day administered in a single dose. In some embodiments, the total daily dosage for a human subject may be about 850 mg/day administered in a single dose. In some embodiments, the total daily dosage for a human subject may be about 900 mg/day administered in a single dose. In some embodiments, the total daily dosage for a human subject may be about 950 mg/day administered in a single dose. In some embodiments, the total daily dosage for a human subject may be about 1000 mg/day administered in a single dose.

A single dose can be administered hourly, daily, weekly, or monthly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In certain embodiments, a single dose can be administered once every week. A single dose can also be administered once every month. In some embodiments, a compound disclosed herein is administered once daily in a method disclosed herein. In some embodiments, a compound disclosed herein is administered twice daily in a method disclosed herein.

In some embodiments, a compound disclosed herein is administered once every 10 days. In some embodiments, a compound disclosed herein is administered once every 15 days. In some embodiments, a compound disclosed herein is administered once every 20 days. In some embodiments, a compound disclosed herein is administered once every 10-15 days. In some embodiments, a compound disclosed herein is administered once every 15-20 days. In some embodiments, a compound disclosed herein is administered once every 10-20 days. In some embodiments, a compound disclosed herein is administered once every month. In some embodiments, a compound disclosed herein is administered once every 2 months. In some embodiments, a compound disclosed herein is administered once every 3 months. In some embodiments, a compound disclosed herein is administered once every 4 months. In some embodiments, a compound disclosed herein is administered once every 5 months. In some embodiments, a compound disclosed herein is administered once every 6 months. In some embodiments, a compound disclosed herein is administered once every 8 months. In some embodiments, a compound disclosed herein is administered once every 10 months. In some embodiments, a compound disclosed herein is administered once every year.

The frequency of dosage of the compound of the present disclosure will be determined by the needs of the individual patient and can be, for example, once per day, once per week, once per two weeks, once per month, once per two months, once per three months, once per four months, once per six months, or less. Administration of the compound continues for as long as necessary to treat the HIV infection.

VI. KITS AND ARTICLES OF MANUFACTURE

In one aspect, provided herein are kits that comprise a compound provided herein, (e.g., a compound of Formula I, I-A, I-B, I-C, I-D, I-E, I-F, II-A, II-Aa, II-Ab, III, IIIa, IIIb, IV, IVa, IVb, V, Va, or Vb), or a pharmaceutically acceptable salt, stereoisomer, prodrug, or solvate thereof, and suitable packaging. In some embodiments, the kit further comprises instructions for use. In some embodiments, the kit comprises a compound provided herein (e.g., a compound of Formula I, I-A, I-B, I-C, I-D, I-E, I-F, II-A, II-Aa, II-Ab, III, IIIa, IIIb, IV, IVa, IVb, V, Va, or Vb), or a pharmaceutically acceptable salt, stereoisomer, prodrug, or solvate thereof, and a label and/or instructions for use of the compounds in the treatment of the indications, including the diseases or conditions, described herein.

In some embodiments, the kits further comprise one or more (e.g., one, two, three, four, one or two, one to three, or one to four) additional therapeutic agents, or a pharmaceutically acceptable salt thereof.

In one aspect, provided herein are articles of manufacture that comprise a compound described herein or pharmaceutically acceptable salts, isomer, or a mixture thereof in a suitable container. In some embodiments, the container may be a vial, jar, ampoule, preloaded syringe, or intravenous bag.

VII. COMBINATION THERAPY

In certain embodiments, a method for treating an HIV infection is provided, comprising administering to the human a therapeutically effective amount of a compound disclosed herein, or a pharmaceutically acceptable salt thereof, in combination with a therapeutically effective amount of one, two, three, or four additional therapeutic agents. In one embodiment, a method for treating an HIV infection is provided, comprising administering to the human a therapeutically effective amount of a compound disclosed herein, or a pharmaceutically acceptable salt thereof, in combination with a therapeutically effective amount of one, two, three, or four additional therapeutic agents.

In one embodiment, pharmaceutical compositions comprising a compound disclosed herein, or a pharmaceutically acceptable salt thereof, in combination with one, two, three, or four additional therapeutic agents, and a pharmaceutically acceptable carrier, diluent, or excipient are provided.

In certain embodiments, the present disclosure provides a method for treating an HIV infection, comprising administering to a subject in need thereof a therapeutically effective amount of a compound disclosed herein, or a pharmaceutically acceptable salt thereof, in combination with a therapeutically effective amount of one, two, three, or four additional therapeutic agents which are suitable for treating an HIV infection.

In certain embodiments, a compound disclosed herein, or a pharmaceutically acceptable salt thereof, is combined with one, two, three, four, or more additional therapeutic agents. In certain embodiments, a compound disclosed herein, or a pharmaceutically acceptable salt thereof, is combined with one, two, three, or four additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.

Administration of HIV Combination Therapy

In certain embodiments, a compound disclosed herein is administered with one, two, three, or four additional therapeutic agents. Co-administration of a compound disclosed herein with one, two, three, or four additional therapeutic agents generally refers to simultaneous or sequential administration of a compound disclosed herein and one, two, three, or four additional therapeutic agents, such that therapeutically effective amounts of the compound disclosed herein and the one, two, three, or four additional therapeutic agents are both present in the body of the patient. When administered sequentially, the combination may be administered in two or more administrations.

Co-administration includes administration of unit dosages of the compounds disclosed herein before or after administration of unit dosages of one, two, three, or four additional therapeutic agents. For example, the compound disclosed herein may be administered within seconds, minutes, or hours of the administration of the one, two, three, or four additional therapeutic agents. In some embodiments, a unit dose of a compound disclosed herein is administered first, followed within seconds or minutes by administration of a unit dose of one, two, three, or four additional therapeutic agents. Alternatively, a unit dose of one, two, three, or four additional therapeutic agents is administered first, followed by administration of a unit dose of a compound disclosed herein within seconds or minutes. In other embodiments, a unit dose of a compound disclosed herein is administered first, followed, after a period of hours (e.g., 1-12 hours), by administration of a unit dose of one, two, three, or four additional therapeutic agents. In yet other embodiments, a unit dose of one, two, three, or four additional therapeutic agents is administered first, followed, after a period of hours (e.g., 1-12 hours), by administration of a unit dose of a compound disclosed herein.

In certain embodiments, a kit comprising a compound disclosed herein (e.g., a compound of Formula I, I-A, I-B, I-C, I-D, I-E, I-F, II-II-A, Aa, II-Ab, III, IIIa, IIIb, IV, IVa, IVb, V, Va, or Vb), or a pharmaceutically acceptable salt thereof, in combination with one or more (e.g., one, two, three, or four) additional therapeutic agents is provided.

In a specific embodiment, the kit includes a compound disclosed herein, or a pharmaceutically acceptable salt thereof, an HIV nucleoside or nucleotide inhibitor of reverse transcriptase and an HIV capsid inhibitor or an HIV capsid polymerization inhibitor.

HIV Combination Therapy

In the above embodiments, the additional therapeutic agent or agents may be an anti-HIV agent. In some instances, the additional therapeutic agent can be HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, HIV capsid inhibitors, nucleocapsid protein 7 (NCp7) inhibitors, HIV Tat or Rev inhibitors, inhibitors of Tat-TAR-P-TEFb, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T-cell receptors, TCR-T, autologous T-cell therapies, engineered B cells, NK cells), latency reversing agents, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement $C_5$a receptor antagonists, DNA methyltransferase inhibitor, Fatty acid synthase inhibitor, HIV vif gene modulators, Vif dimerization antagonists, HIV-1 viral infectivity factor inhibitors, HIV-1 Nef modulators, TNF alpha ligand inhibitors, HIV Nef inhibitors, Hck tyrosine kinase modulators, mixed lineage kinase-3 (MLK-3) inhibitors, HIV-1 splicing inhibitors, integrin antagonists, nucleoprotein inhibitors, splicing factor modulators, COMM domain containing protein 1 modulators, HIV ribonuclease H inhibitors, IFN antagonists, retrocyclin modulators, CD3 antagonists, CDK-4 inhibitors, CDK-6 inhibitors, CDK-9 inhibitors, Cytochrome P450 3 inhibitors, CXCR4 modulators, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, HPK1 (MAP4K1) inhibitors, proprotein convertase PC9 stimulators, ATP dependent RNA helicase DDX3X inhibitors, reverse transcriptase priming complex inhibitors, G6PD and NADH-oxidase inhibitors, mTOR complex 1 inhibitors, mTOR complex 2 inhibitors, P-Glycoprotein modulators, RNA polymerase modulators, TAT protein inhibitors, Prolyl endopeptidase inhibitors, Phospholipase A2 inhibitors, pharmacokinetic enhancers, HIV gene therapy, HIV vaccines, anti-HIV peptides, and combinations thereof.

In some embodiments, the additional therapeutic agent or agents are selected from combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In some embodiments, the additional therapeutic agent or agents are chosen from HIV protease inhibitors, HIV non-nucleoside or non-nucleotide inhibitors of reverse transcriptase, HIV nucleoside or nucleotide inhibitors of reverse transcriptase, HIV integrase inhibitors, HIV capsid inhibitors, gp41 inhibitors, CXCR4 inhibitors, gp120 inhibitors, CCR5 inhibitors, Nef inhibitors, latency reversing agents, HIV bNAbs, agonists of TLR7, TLR8, and TLR9, HIV vaccines, cytokines, immune checkpoint inhibitors, FLT3 ligands, T cell and NK cell recruiting bispecific antibodies, chimeric T cell receptors targeting HIV antigens, pharmacokinetic enhancers, and other drugs for treating HIV, and combinations thereof.

In some embodiments, the additional therapeutic agent or agents are chosen from dolutegravir, cabotegravir, islatravir, darunavir, bictegravir, elsulfavirine, rilpivirine, and lenacapavir, and combinations thereof.

HIV Combination Drugs

Examples of combination drugs include, but are not limited to, ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; tenofovir analog; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); BIKTARVY® (bictegravir+emtricitabine+tenofovir alafenamide), DOVATO® (dolutegravir+lamivudine), TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine, lopinavir+ritonavir+abacavir+lamivudine, lamivudine, cabotegravir+rilpivirine, 3-BNC117+albuvirtide, elpida (elsulfavirine, VM-1500), and VM-1500A, lenacapavir+islatravir (oral, injectable), and dual-target HIV-1 reverse transcriptase/nucleocapsid protein 7 inhibitors.

Other HIV Drugs

Examples of other drugs for treating HIV include, but are not limited to, aspernigrin C, acemannan, alisporivir, BanLec, deferiprone, Gamimune, metenkefalin, naltrexone, Prolastin, REP 9, RPI-MN, VSSP, Hlviral, SB-728-T, 1,5-dicaffeoylquinic acid, rHIV7-shl-TAR-CCR5RZ, AAV-eCD4-Ig gene therapy, MazF gene therapy, BlockAide, bevirimat derivatives, ABBV-382, ABX-464, AG-1105, APH-0812, APH0202, bryostatin-1, bryostatin analogs, BIT-225, BRII-732, BRII-778, CYT-107, CS-TATI-1, fluoro-beta-D-arabinose nucleic acid (FANA)-modified antisense oligonucleotides, FX-101, griffithsin, GSK-3739937, GSK-3739937 (long-acting), HGTV-43, HPH-116, HS-10234, hydroxychloroquine, IMB-10035, IMO-3100, IND-02, JL-18008, LADAVRU, MK-1376, MK-2048, MK-4250, MK-8507, MK-8558, MK-8591 (islatravir), NOV-205, OB-002H, ODE-Bn-TFV, PA-1050040 (PA-040), PC-707, PGN-007, QF-036, S-648414, SCY-635, SB-9200, SCB-719, TR-452, TEV-90110, TEV-90112, TEV-90111, TEV-90113, RN-18, DIACC-1010, Fasnall, Immuglo, 2-CLIPS peptide, HRF-4467, thrombospondin analogs, TBL-1004HI, VG-1177, xl-081, AVI-CO-004, rfhSP-D, [18F]-MC-225, URMC-099-C, RES-529, Verdinexor, IMC-M113V, IML-106, antiviral fc conjugate (AVC), WP-1096, WP-1097, Gammora, ISR-CO48, ISR-48, ISR-49, MK-8527, cannabinoids, ENOB-HV-32, HiviCide-I, T-1144, VIR-576, nipamovir, Covimro, and ABBV-1882.

HIV Protease Inhibitors

Examples of HIV protease inhibitors include, but are not limited to, amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, ASC-09+ritonavir, AEBL-2, DG-17, GS-1156, TMB-657 (PPL-100), T-169, BL-008, MK-8122, TMB-607, GRL-02031, and TMC-310911.

Additional examples of HIV protease inhibitors are described, e.g., in U.S. Pat. No. 10,294,234, and U.S. Patent Application Publication Nos. US2020030327 and US2019210978.

HIV Gag Protein Inhibitors

Examples of HIV Gag protein inhibitors include, but are not limited to, HRF-10071.

HIV Ribonuclease H Inhibitors

Examples of HIV ribonuclease H inhibitors include, but are not limited to, NSC-727447.

HIV Nef Inhibitors

Examples of HIV Nef inhibitors include, but are not limited to, FP-1.

HIV Reverse Transcriptase Inhibitors

Examples of HIV non-nucleoside or non-nucleotide inhibitors of reverse transcriptase include, but are not limited to, dapivirine, delavirdine, delavirdine mesylate, doravirine, efavirenz, etravirine, lentinan, nevirapine, rilpivirine, ACC-007, ACC-008, AIC-292, F-18, KM-023, PC-1005, M1-TFV, M2-TFV, VM-1500A-LAI, PF-3450074, elsulfavirine (sustained release oral, HIV infection), doravirine+islatravir (fixed dose combination/oral tablet formulation, HIV-1 infection), elsulfavirine (long acting injectable nanosuspension, HIV infection), and elsulfavirine (VM-1500).

Examples of HIV nucleoside or nucleotide inhibitors of reverse transcriptase include, but are not limited to, adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir octadecyloxyethyl ester (AGX-1009), tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, rovafovir etalafenamide (GS-9131), GS-9148, MK-8504, islatravir, MK-8583, VM-2500, and KP-1461.

Additional examples of HIV nucleoside or nucleotide inhibitors of reverse transcriptase include, but are not limited to, those described in patent publications US2007049754, US2016250215, US2016237062, US2016251347, US2002119443, US2013065856, US2013090473, US2014221356, and WO04096286.

HIV Integrase Inhibitors

Examples of HIV integrase inhibitors include, but are not limited to, elvitegravir, elvitegravir (extended-release microcapsules), curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, PEGylated raltegravir, dolutegravir, JTK-351, bictegravir, AVX-15567, cabotegravir (long acting injectable), diketo quinolin-4-1 derivatives, integrase-LEDGF inhibitor, ledgins, M-522, M-532, MK-0536, NSC-310217, NSC-371056, NSC-48240, NSC-642710, NSC-699171, NSC-699172, NSC-699173, NSC-699174, stilbenedisulfonic acid, T169, STP-0404, VM-3500, XVIR-110, and ACC-017.

Examples of HIV non-catalytic site, or allosteric, integrase inhibitors (NCINI) include, but are not limited to, CX-05045, CX-05168, and CX-14442.

Additional examples of HIV capsid inhibitors include, but are not limited to, those described in U.S. Patent Application Publication Nos. US20200317689, US20210284642, US2014221356 and US2016016973.

HIV Viral Infectivity Factor Inhibitors

Examples of HIV viral infectivity factor inhibitors include, but are not limited to, 2-amino-N-(2-methoxyphenyl)-6-((4-nitrophenyl)thio)benzamide derivatives, and Irino-L.

HIV Entry Inhibitors

Examples of HIV entry (fusion) inhibitors include, but are not limited to, AAR-501, LBT-5001, cenicriviroc, CCR5 inhibitors, gp41 inhibitors, CD4 attachment inhibitors, gp120 inhibitors, gp160 inhibitors, and CXCR4 inhibitors.

Examples of CCR5 inhibitors include, but are not limited to, aplaviroc, vicriviroc, maraviroc, maraviroc (long acting injectable nanoemulsion), cenicriviroc, leronlimab (PRO-140), adaptavir (RAP-101), nifeviroc (TD-0232), anti-GP120/CD4 or CCR5 bispecific antibodies, B-07, MB-66, polypeptide $C_{25}P$, TD-0680, thioraviroc and vMIP (Haimipu).

Examples of gp41 inhibitors include, but are not limited to, albuvirtide, enfuvirtide, griffithsin (gp41/gp120/gp160 inhibitor), BMS-986197, enfuvirtide biobetter, enfuvirtide biosimilar, HIV-1 fusion inhibitors (P26-Bapc), ITV-1, ITV-2, ITV-3, ITV-4, CPT-31, Cl3hmAb, lipuvirtide, PIE-12 trimer and sifuvirtide.

Examples of CD4 attachment inhibitors include, but are not limited to, ibalizumab and CADA analogs.

Examples of gp120 inhibitors include, but are not limited to, anti-HIV microbicide, Radha-108 (receptol) 3B3-PE38, BMS818251, BanLec, bentonite-based nanomedicine, fostemsavir tromethamine, IQP-0831, VVX-004, and BMS-663068.

Examples of gp160 inhibitors include, but are not limited to, fangchinoline.

Examples of CXCR4 inhibitors include, but are not limited to, plerixafor, ALT-1188, N15 peptide, and vMIP (Haimipu).

HIV Maturation Inhibitors

Examples of HIV maturation inhibitors include, but are not limited to, BMS-955176, GSK-3640254 and GSK-2838232.

Latency Reversing Agents

Examples of latency reversing agents include, but are not limited to, toll-like receptor (TLR) agonists (including TLR7 agonists, e.g., GS-9620, TLR8 agonists, and TLR9 agonists), histone deacetylase (HDAC) inhibitors, proteasome inhibitors such as velcade, protein kinase C (PKC) activators, Smyd2 inhibitors, BET-bromodomain 4 (BRD4) inhibitors (such as ZL-0580, apabetalone), ionomycin, IAP antagonists (inhibitor of apoptosis proteins, such as APG-1387, LBW-242), SMAC mimetics (including TL32711, LCL161, GDC-0917, HGS1029, AT-406, Debio-1143), PMA, SAHA (suberanilohydroxamic acid, or suberoyl, anilide, and hydroxamic acid), NIZ-985, IL-15 modulating antibodies (including IL-15, IL-15 fusion proteins, and IL-15 receptor agonists), JQ1, disulfiram, amphotericin B, and ubiquitin inhibitors such as largazole analogs, APH-0812, and GSK-343. Examples of PKC activators include, but are not limited to, indolactam, prostratin, ingenol B, and DAG-lactones.

Additional examples of TLR7 agonists include, but are not limited to, those described in U.S. Patent Application Publication No. US2010143301.

Additional examples of TLR8 agonists include, but are not limited to, those described in U.S. Patent Application Publication No. US2017071944.

Histone Deacetylase (HDAC) Inhibitors

In some embodiments, the agents as described herein are combined with an inhibitor of a histone deacetylase, e.g., histone deacetylase 1, histone deacetylase 9 (HDAC9, HD7, HD7b, HD9, HDAC, HDAC7, HDAC7B, HDAC9B, HDAC9FL, HDRP, MITR; Gene ID: 9734). Examples of HDAC inhibitors include without limitation, abexinostat, ACY-241, AR-42, BEBT-908, belinostat, CKD-581, CS-055

(HBI-8000), CT-101, CUDC-907 (fimepinostat), entinostat, givinostat, mocetinostat, panobinostat, pracinostat, quisinostat (JNJ-26481585), resminostat, ricolinostat, romidepsin, SHP-141, TMB-ADC, valproic acid (VAL-001), vorinostat, tinostamustine, remetinostat, and entinostat.

Capsid Inhibitors

Examples of capsid inhibitors include, but are not limited to, capsid polymerization inhibitors or capsid disrupting compounds, HIV nucleocapsid p7 (NCp7) inhibitors such as azodicarbonamide, HIV p24 capsid protein inhibitors, lenacapavir (GS-6207), GS-CA1, AVI-621, AVI-101, AVI-201, AVI-301, and AVI-CAN1-15 series, PF-3450074, HIV-1 capsid inhibitors (HIV-1 infection, Shandong University), and compounds described in (GSK WO2019/087016).

Additional examples of capsid inhibitors include, but not limited to, those described in U.S. Patent Application Publication Nos. US2018051005 and US2016108030.

Cytochrome P450 3 Inhibitors

Examples of Cytochrome P450 3 inhibitors include, but are not limited to, those described in U.S. Pat. No. 7,939,553.

RNA Polymerase Modulators

Examples of RNA polymerase modulators include, but are not limited to, those described in U.S. Pat. Nos. 10,065,958 and 8,008,264.

Immune Checkpoint Modulators

In various embodiments, the agents as described herein, are combined with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of infected cells. Activation or stimulation of stimulatory immune check points can augment the effect of immune checkpoint inhibitors in infective therapeutics. In various embodiments, the immune checkpoint proteins or receptors regulate T cell responses (e.g., reviewed in Xu et al., J Exp Clin Cancer Res. (2018) 37:110). In various embodiments, the immune checkpoint proteins or receptors regulate NK cell responses (e.g., reviewed in Davis et al., Semin Immunol. (2017) 31:64-75 and Chiossone et al., Nat Rev Immunol. (2018) 18(11):671-688).

Examples of immune checkpoint proteins or receptors include without limitation CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSFi4 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMFI, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); lymphocyte activating 3 (CD223); killer cell immunoglobulin like receptor, three Ig domains and long cytoplasmic tail 1 (KIR, CD158E1); killer cell lectin like receptor $C_1$ (KLRC1, NKG2A, CD159A); killer cell lectin like receptor K1 (KLRK1, NKG2D, CD314); killer cell lectin like receptor $C_2$ (KLRC2, CD159c, NKG2C); killer cell lectin like receptor $C_3$ (KLRC3, NKG2E); killer cell lectin like receptor $C_4$ (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); SLAM family member 7 (SLAMF7); and Hematopoietic Progenitor Kinase 1 (HPK1, MAP4K1).

In various embodiments, the agents described herein are combined with one or more blockers or inhibitors of one or more T-cell inhibitory immune checkpoint proteins or receptors. Illustrative T-cell inhibitory immune checkpoint proteins or receptors include without limitation CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSFI4 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In various embodiments, the agents, as described herein, are combined with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu et al., *J Exp Clin Cancer Res*. (2018) 37:110.

In various embodiments, the agents as described herein, are combined with one or more blockers or inhibitors of one or more NK-cell inhibitory immune checkpoint proteins or receptors. Illustrative NK-cell inhibitory immune checkpoint proteins or receptors include without limitation killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor $C_1$ (KLRC1, NKG2A, CD159A); and killer cell lectin like receptor D1 (KLRD1, CD94). In various embodiments, the agents as described herein, are combined with one or more agonist or activators of one or more NK-cell stimulatory immune checkpoint proteins or receptors. Illustrative NK-cell stimulatory immune checkpoint proteins or receptors include without limitation CD16, CD226 (DNAM-1); CD244 (2B4, SLAMF4); killer cell lectin like receptor K1 (KLRK1, NKG2D, CD314); SLAM family member 7 (SLAMF7). See, e.g., Davis et al., Semin Immunol. (2017) 31: 64-75; Fang et al., Semin Immunol. (2017) 31:37-54; and Chiossone et al., Nat Rev Immunol. (2018) 18(11):671-688.

In some embodiments, the one or more immune checkpoint inhibitors comprises a proteinaceous (e.g., antibody or fragment thereof, or antibody mimetic) inhibitor of PD-L1 (CD274), PD-1 (PDCD1) or CTLA4. In some embodiments, the one or more immune checkpoint inhibitors comprises a small organic molecule inhibitor of PD-L1 (CD274), PD-1 (PDCD1) or CTLA4. In some embodiments, the small molecule inhibitor of CD274 or PDCD1 is selected from the group consisting of GS-4224, GS-4416, INCB086550 and MAX10181. In some embodiments, the small molecule inhibitor of CTLA4 comprises BPI-002.

Examples of inhibitors of CTLA4 that can be co-administered include without limitation ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors of PD-L1 (CD274) or PD-1 (PDCD1) that can be co-administered include without limitation pembrolizumab, nivolumab, cemiplimab, pidilizumab, AMP-224, MEDI0680 (AMP-514), spartalizumab, atezolizumab, avelumab, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181(budigalimab), PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, GS-4224, GS-4416, INCB086550, MAX10181, as well as multi-specific inhibitors FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), and INBRX-105 (4-1BB/PDL1).

In various embodiments, the agents as described herein are combined with anti-TIGIT antibodies, such as BMS-986207, RG-6058, and AGEN-1307.

TNF Receptor Superfamily (TNFRSF) Member Agonists or Activators

In various embodiments, the agents as described herein are combined with an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Examples of anti-TNFRSF4 (OX40) antibodies that can be co-administered include without limitation, MEDI6469, MEDI6383, MEDI0562 (tavolixizumab), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628.

Examples of anti-TNFRSF5 (CD40) antibodies that can be co-administered include without limitation RG7876, SEA-CD40, APX-005M and ABBV-428.

In some embodiments, the anti-TNFRSF7 (CD27) antibody varlilumab (CDX-1127) is co-administered.

Examples of anti-TNFRSF9 (4-1BB, CD137) antibodies that can be co-administered include without limitation urelumab, utomilumab (PF-05082566), AGEN2373 and ADG-106.

Examples of anti-TNFRSF18 (GITR) antibodies that can be co-administered include without limitation, MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Bi- and Tri-Specific Natural Killer (NK)-Cell Engagers

In various embodiments, the agents as described herein, are combined with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcTR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BB). As appropriate, the anti-CD16 binding bi-specific molecules may or may not have an Fc. Illustrative bi-specific NK-cell engagers that can be co-administered target CD16 and one or more HIV-associated antigens as described herein. BiKEs and TriKEs are described, e.g., in Felices et al., Methods Mol Biol. (2016) 1441:333-346; Fang et al., Semin Immunol. (2017) 31:37-54. Examples of trispecific NK cell engagers (TRiKE) include, but are not limited to, OXS-3550, HIV-TriKE, and CD16-IL-15-B7H3 TriKe.

Indoleamine-Pyrrole-2,3-Dioxygenase (IDO1) Inhibitors

In various embodiments, the agents as described herein are combined with an inhibitor of indoleamine 2,3-dioxygenase 1 (IDO1; NCBI Gene ID: 3620). Examples of IDO1 inhibitors include without limitation, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, shIDO-ST, EOS-200271, KHK-2455, and LY-3381916.

Toll-Like Receptor (TLR) Agonists

In various embodiments, the agents as described herein are combined with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793). Example TLR7 agonists that can be co-administered include without limitation AL-034, DSP-0509, GS-9620 (vesatolimod), vesatolimod analog, LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7854, RG-7795, and the compounds disclosed in US20100143301 (Gilead Sciences), US20110098248 (Gilead Sciences), and US20090047249 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). TLR7/TLR8 agonists include without limitation NKTR-262, telratolimod and BDB-001. TLR8 agonists include without limitation E-6887, IMO-4200, IMO-8400, IMO-9200, MCT-465, MEDI-9197, motolimod, resiquimod, GS-9688, VTX-1463, VTX-763, 3M-051, 3M-052, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). TLR9 agonists include without limitation AST-008, cobitolimod, CMP-001, IMO-2055, IMO-2125, S-540956, litenimod, MGN-1601, BB-001, BB-006, IMO-3100, IMO-8400, IR-103, IMO-9200, agatolimod, DIMS-9054, DV-1079, DV-1179, AZD-1419, lefitolimod (MGN-1703), CYT-003, CYT-003-QbG10, tilsotolimod and PUL-042. Examples of TLR3 agonist include rintatolimod, poly-ICLC, RIBOXXON®, Apoxxim, RIBOXXIM®, IPH-33, MCT-465, MCT-475, and ND-1.1. TLR4 agonists include, but are not limited to, G-100 and GSK-1795091.

CDK inhibitors or antagonists

In some embodiments, the agents described herein are combined with an inhibitor or antagonist of CDK. In some embodiments, the CDK inhibitor or antagonist is selected from the group consisting of VS2-370.

STING agonists, RIG-I and NOD2 modulators

In some embodiments, the agents described herein are combined with a stimulator of interferon genes (STING). In some embodiments, the STING receptor agonist or activator is selected from the group consisting of ADU-S100 (MIW-815), SB-11285, MK-1454, SR-8291, AdVCA0848, GSK-532, SYN-STING, MSA-1, SR-8291, STING agonist (latent HIV), 5,6-dimethylxanthenone-4-acetic acid (DMXAA), cyclic-GAMP (cGAMP) and cyclic-di-AMP. In some embodiments, the agents described herein are combined with a RIG-I modulator such as RGT-100, or NOD2 modulator, such as SB-9200, and IR-103.

LAG-3 and TIM-3 Inhibitors

In certain embodiments, the agents as described herein are combined with an anti-TIM-3 antibody, such as TSR-022, LY-3321367, MBG-453, INCAGN-2390.

In certain embodiments, the antibodies or antigen-binding fragments described herein are combined with an anti LAG-3 (Lymphocyte-activation) antibody, such as relatlimab (ONO-4482), LAG-525, MK-4280, REGN-3767, INCAGN2385.

Interleukin Agonists

In certain embodiments, the agents described herein are combined with an interleukin agonist, such as IL-2, IL-7, IL-15, IL-10, IL-12 agonists; examples of IL-2 agonists such as proleukin (aldesleukin, IL-2); BC-IL (Cel-Sci), pegylated IL-2 (e.g., NKTR-214); modified variants of IL-2 (e.g., THOR-707), bempegaldesleukin, AIC-284, ALKS-4230, CUI-101, Neo-2/15; examples of IL-15 agonists, such as ALT-803, NKTR-255, and hetIL-15, interleukin-15/Fc fusion protein, AM-0015, NIZ-985, SO-C101, IL-15 Synthorin (pegylated 11-15), P-22339, and a IL-15-PD-1 fusion protein N-809; examples of IL-7 include without limitation CYT-107.

Examples of additional immune-based therapies that can be combined with an agent of this disclosure include, but are not limited to, interferon alfa, interferon alfa-2b, interferon alfa-n3, pegylated interferon alfa, interferon gamma; FLT3 agonists such as CDX-301, GS-3583, gepon, normferon, peginterferon alfa-2a, peginterferon alfa-2b, and RPI-MN.

Phosphatidylinositol 3-kinase (PI3K) Inhibitors

Examples of PI3K inhibitors include, but are not limited to, idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

Alpha-4/Beta-7 Antagonists

Examples of Integrin alpha-4/beta-7 antagonists include, but are not limited to, PTG-100, TRK-170, abrilumab, etrolizumab, carotegrast methyl, and vedolizumab.

HPK1 Inhibitors

Examples of HPK1 inhibitors include, but are not limited to, ZYF-0272, and ZYF-0057.

HIV Targeting Antibodies

Examples of HIV antibodies, bispecific antibodies, and "antibody-like" therapeutic proteins include, but are not limited to, DARTs®, DUOBODIES®, BITES®, XmAbs®, TandAbs®, Fab derivatives, bNAbs (broadly neutralizing HIV-1 antibodies), TMB-360, TMB-370, and those targeting HIV gp120 or gp41, antibody-Recruiting Molecules targeting HIV, anti-CD63 monoclonal antibodies, anti-GB virus C antibodies, anti-GP120/CD4, gp120 bispecific monoclonal antibody, CCR5 bispecific antibodies, anti-Nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), PGT121.414.LS, ibalizumab, ibalizumab (second generation), Immuglo, MB-66, clone 3 human monoclonal antibody targeting KLIC (HIV infection), GS-9721, BG-HIV, VRC-HIVMAB091-00-AB.

Various bNAbs may be used. Examples include, but are not limited to, those described in U.S. Pat. Nos. 8,673,307; 9,493,549; 9,783,594; 10,239,935; US2018371086, US2020223907; WO2014/063059; WO2012/158948; WO2015/117008, and PCT/US2015/41272, and WO2017/096221, including antibodies 12A12, 12A21, NIH45-46, bANC131, 8ANC134, 1B2530, INC9, 8ANC195. 8ANC196, 10-259, 10-303, 10-410, 10-847, 10-996, 10-1074, 10-1121, 10-1130, 10-1146, 10-1341, 10-1369, and 10-1074GM. Additional examples include those described in Klein et al., Nature, 492(7427): 118-22 (2012), Horwitz et al., Proc Natl Acad Sci USA, 110(41): 16538-43 (2013), Scheid et al., Science, 333: 1633-1637 (2011), Scheid et al., Nature, 458:636-640 (2009), Eroshkin et al, Nucleic Acids Res., 42 (Database issue):D1 133-9 (2014), Mascola et al., Immunol Rev., 254(1):225-44 (2013), such as 2F5, 4E10, M66.6, CAP206-CH12, 10E81 (all of which bind the MPER of gp41); PG9, PG16, CH01-04 (all of which bind V1V2-glycan), 2G12 (which binds to outer domain glycan); b12, HJ16, CH103-106, VRC01-03, VRC-PG04, 04b, VRC-CH30-34, 3BNC62, 3BNC89, 3BNC91, 3BNC95, 3BNC104, 3BNC176, and 8ANC131 (all of which bind to the CD4 binding site).

Additional broadly neutralizing antibodies that can be used as a second therapeutic agent in a combination therapy are described, e.g., in U.S. Pat. Nos. 8,673,307; 9,493,549; 9,783,594; and WO 2012/154312; WO2012/158948; WO 2013/086533; WO 2013/142324; WO2014/063059; WO 2014/089152, WO 2015/048462; WO 2015/103549; WO 2015/117008; WO2016/014484; WO 2016/154003; WO 2016/196975; WO 2016/149710; WO2017/096221; WO 2017/133639; WO 2017/133640, which are hereby incorporated herein by reference in their entireties for all purposes. Additional examples include, but are not limited to, those described in Sajadi et al., Cell. (2018) 173(7):1783-1795; Sajadi et al., J Infect Dis. (2016) 213(1):156-64; Klein et al., Nature, 492(7427): 118-22 (2012), Horwitz et al., Proc Natl Acad Sci USA, 110(41): 16538-43 (2013), Scheid et al., Science, 333: 1633-1637 (2011), Scheid et al., Nature, 458:636-640 (2009), Eroshkin et al., Nucleic Acids Res., 42 (Database issue):D1 133-9 (2014), Mascola et al., Immunol Rev., 254(1):225-44 (2013), such as 2F5, 4E10, M66.6, CAP206-CH12, 10E8, 10E8v4, 10E8-5R-100° F., DH511.11P, 7b2, 10-1074, and LN01 (all of which bind the MPER of gp41).

Examples of additional antibodies include, but are not limited to, bavituximab, UB-421, BF520.1, BiIA-SG, CHO1, CH59, $C_2F5$, $C_4E10$, $C_2F5+C_2G12+C4E10$, CAP256V2LS, 3BNC117, 3BNC117-LS, 3BNC60, DH270.1, DH270.6, D1D2, 10-1074-LS, Cl3hmAb, GS-9722 (elipovimab), DH411-2, BG18, GS-9721, GS-9723, PGT145, PGT121, PGT-121.60, PGT-121.66, PGT122, PGT-123, PGT-124, PGT-125, PGT-126, PGT-151, PGT-130, PGT-133, PGT-134, PGT-135, PGT-128, PGT-136, PGT-137, PGT-138, PGT-139, MDX010 (ipilimumab), DH511, DH511-2, N6, N6LS, N49P6, N49P7, N49P7.1, N49P9, N49P11, N60P1.1, N60P25.1, N60P2.1, N60P31.1, N60P22, NIH 45-46, PGC14, PGG14, PGT-142, PGT-143, PGT-144, PGDM1400, PGDM12, PGDM21, PCDN-33A, 2Dm2m, 4Dm2m, 6Dm2m, PGDM1400, MDX010 (ipilimumab), VRC01, VRC-01-LS, A32, 7B2, 10E8, VRC-07-523, VRC07-523LS, VRC24, VRC41.01, 10E8VLS, 3810109, 10E8v4, IMC-HIV, iMabm36, eCD4-Ig, IOMA, CAP256-VRC26.25, DRVIA7, VRC-HIVMAB080-00-AB, VRC-HIVMAB060-00-AB, P2G12, VRC07, 354BG8, 354BG18, 354BG42, 354BG33, 354BG129, 354BG188, 354BG411, 354BG426, VRC29.03, CAP256, CAP256-VRC26.08, CAP256-VRC26.09, CAP256-VRC26.25, PCT64-24E and VRC38.01, PGT-151, CAP248-2B, 35022, ACS202, VRC34 and VRC34.01, 10E8, 10E8v4, 10E8-5R-100° F., 4E10, DH511.11P, 2F5, 7b2, and LN01.

Examples of HIV bispecific and trispecific antibodies include without limitation MGD014, B12BiTe, BiIA-SG, TMB-bispecific, SAR-441236, VRC-01/PGDM-1400/10E8v4, 10E8.4/iMab, 10E8v4/PGT121-VRCO1.

Examples of in vivo delivered bNAbs include without limitation AAV8-VRC07; mRNA encoding anti-HIV antibody VRCO1; and engineered B-cells encoding 3BNC117 (Hartweger et al., J. Exp. Med. 2019, 1301).

Pharmacokinetic Enhancers

Examples of pharmacokinetic enhancers include, but are not limited to, cobicistat and ritonavir.

Additional Therapeutic Agents

Examples of additional therapeutic agents include, but are not limited to, the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

HIV Vaccines

Examples of HIV vaccines include, but are not limited to, peptide vaccines, recombinant subunit protein vaccines, live vector vaccines, DNA vaccines, HIV MAG DNA vaccine, CD4-derived peptide vaccines, vaccine combinations, adenoviral vector vaccines (an adenoviral vector such as Ad5, Ad26 or Ad35), simian adenovirus (chimpanzee, gorilla, rhesus i.e., rhAd), adeno-associated virus vector vaccines, Chimpanzee adenoviral vaccines (e.g., ChAdOX1, ChAd68, ChAd3, ChAd63, ChAd83, ChAd155, ChAd157, Pan5, Pan6, Pan7, Pan9), Coxsackieviruses based vaccines, enteric virus based vaccines, Gorilla adenovirus vaccines, lentiviral vector based vaccine, arenavirus vaccines (such as LCMV, Pichinde), bi-segmented or tri-segmented arenavirus based vaccine, trimer-based HIV-1 vaccine, measles virus based vaccine, flavivirus vector based vaccines, tobacco mosaic virus vector based vaccine, Varicella-zoster virus based vaccine, Human parainfluenza virus 3 (PIV3) based vaccines, poxvirus based vaccine (modified vaccinia virus Ankara (MVA), orthopoxvirus-derived NYVAC, and avipoxvirus-derived ALVAC (canarypox virus) strains); fowlpox virus based vaccine, rhabdovirus-based vaccines, such as VSV and marabavirus; recombinant human CMV (rhCMV) based vaccine, alphavirus-based vaccines, such as semliki forest virus, venezuelan equine encephalitis virus and sindbis virus; (see Lauer, Clinical and Vaccine Immunology, 2017, DOI: 10.1128/CVI.00298-16); LNP formulated mRNA based therapeutic vaccines; LNP-formulated self-replicating RNA/self-amplifying RNA vaccines.

Examples of vaccines include: AAVLP-HIV vaccine, AE-298p, anti-CD40.Env-gp140 vaccine, Ad4-EnvC150, BG505 SOSIP.664 gp140 adjuvanted vaccine, BG505 SOSIP.GT1.1 gp140 adjuvanted vaccine, ChAdOx1.tHIVconsv1 vaccine, CMV-MVA triplex vaccine, ChAdOx1.HTI, Chimigen HIV vaccine, ConM SOSIP.v7 gp140, ALVAC HIV (vCP1521), AIDSVAX B/E (gp120), monomeric gp120 HIV-1 subtype C vaccine, MPER-656 liposome subunit vaccine, Remune, ITV-1, Contre Vir, Ad5-ENVA-48, DCVax-001 (CDX-2401), Vacc-4x, Vacc-C5, VAC-3S, multiclade DNA recombinant adenovirus-5 (rAd5), rAd5 gag-pol env A/B/C vaccine, Pennvax-G, Pennvax-GP, Pennvax-G/MVA-CMDR, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multiHIV (FIT-06), ChAdV63.HIVconsv, gp140 [delta]V2.TV1+MF-59, rVSVIN HIV-1 gag vaccine, SeV-EnvF, SeV-Gag vaccine, AT-20, DNK-4, ad35-Grin/ENV, TBC-M4, HIVAX, HIVAX-2, N123-VRC-34.01 inducing epitope-based HIV vaccine, NYVAC-HIV-PT1, NYVAC-HIV-PT4, DNA-HIV-PT123, rAAV1-PG9DP, GOVX-B11, GOVX-B21, GOVX-C55, TVI-HIV-1, Ad-4 (Ad4-env Clade C+Ad4-mGag), Paxvax, EN41-UGR7C, EN41-FPA2, ENOB-HV-11, ENOB-HV-12, PreVaxTat, AE-H, MYM-V101, CombiHIVvac, ADVAX, MYM-V201, MVA-CMDR, MagaVax, DNA-Ad5 gag/pol/nef/nev (HVTN505), MVATG-17401, ETV-01, CDX-1401, DNA and Sev vectors vaccine expressing SCaVII, rcAD26.MOS1.HIV-Env, Ad26.Mod.HIV vaccine, Ad26.Mod.HIV+MVA mosaic vaccine+gp140, AGS-004, AVX-101, AVX-201, PEP-6409, SAV-001, ThV-01, TL-01, TUTI-16, VGX-3300, VIR-1111, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines (such as DermaVir), gag-based DNA vaccine, GI-2010, gp41 HIV-1 vaccine, HIV vaccine (PIKA adjuvant), i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, rgp160 HIV vaccine, RNActive HIV vaccine, SCB-703, Tat Oyi vaccine, TBC-M4, UBI HIV gp120, Vacc-4x+romidepsin, variant gp120 polypeptide vaccine, rAd5 gag-pol env A/B/C vaccine, DNA.HTI and MVA.HTI, VRC-HIVDNA016-00-VP+VRC-HIVADV014-00-VP, INO-6145, JNJ-9220, gp145 C.6980; eOD-GT8 60mer based vaccine, PD-201401, env (A, B, C, A/E)/gag (C) DNA Vaccine, gp120 (A,B,C,A/E) protein vaccine, PDPHV-201401, Ad4-EnvCN54, EnvSeq-1 Envs HIV-1 vaccine (GLA-SE adjuvanted), HIV p24gag prime-boost plasmid DNA vaccine, HIV-1 iglb12 neutralizing VRC-01 antibody-stimulating anti-CD4 vaccine, arenavirus vector-based vaccines (Vaxwave, TheraT), MVA-BN HIV-1 vaccine regimen, mRNA based prophylactic vaccines, VPI-211, multimeric HIV gp120 vaccine (Fred Hutchinson cancer center), TBL-1203HI, CH505 TF chTrimer, CD40.HIVRI.Env vaccine, Drep-HIV-PT-1, mRNA-1644, and mRNA-1574.

Birth Control (Contraceptive) Combination Therapy

In certain embodiments, the agents described herein are combined with a birth control or contraceptive regimen. Therapeutic agents used for birth control (contraceptive) that can be combined with an agent of this disclosure include without limitation cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

In a particular embodiment, a compound disclosed herein, or a pharmaceutically acceptable salt thereof, is combined with one, two, three, or four additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); BIKTARVY® (bictegravir+emtricitabine+tenofovir alafenamide), adefovir; adefovir dipivoxil; cobicistat; emtricitabine; tenofovir; tenofovir alafenamide and elvitegravir; tenofovir alafenamide+elvitegravir (rectal formulation, HIV infection); tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; PEGylated raltegravir; raltegravir and lamivudine; lamivudine+lopinavir+ritonavir+abacavir; maraviroc; tenofovir+emtricitabine+maraviroc, enfuvirtide; ALUVIA®

(KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In some embodiments, an agent disclosed herein, or a pharmaceutical composition thereof, is combined with an HIV nucleoside or nucleotide inhibitor of reverse transcriptase and an HIV non-nucleoside inhibitor of reverse transcriptase. In another specific embodiment, an agent disclosed herein, or a pharmaceutical composition thereof, is combined with an HIV nucleoside or nucleotide inhibitor of reverse transcriptase, and an HIV protease inhibiting compound. In an additional embodiment, an agent disclosed herein, or a pharmaceutical composition thereof, is combined with an HIV nucleoside or nucleotide inhibitor of reverse transcriptase, an HIV non-nucleoside inhibitor of reverse transcriptase, and a pharmacokinetic enhancer. In certain embodiments, an agent disclosed herein, or a pharmaceutical composition thereof, is combined with at least one HIV nucleoside inhibitor of reverse transcriptase, an integrase inhibitor, and a pharmacokinetic enhancer. In another embodiment, an agent disclosed herein, or a pharmaceutical composition thereof, is combined with two HIV nucleoside or nucleotide inhibitors of reverse transcriptase.

In another embodiment, an agent disclosed herein, or a pharmaceutical composition thereof, is combined with a first additional therapeutic agent chosen from dolutegravir, cabotegravir, islatravir, darunavir, bictegravir, elsulfavirine, rilpivirine, and lenacapavir and a second additional therapeutic agent chosen from emtricitabine and lamivudine.

In some embodiments, an agent disclosed herein, or a pharmaceutical composition thereof, is combined with a first additional therapeutic agent (a contraceptive) selected from the group consisting of cyproterone acetate, desogestrel, dienogest, drospirenone, estradiol valerate, ethinyl Estradiol, ethynodiol, etonogestrel, levomefolate, levonorgestrel, lynestreno, medroxyprogesterone acetate, mestranol, mifepristone, misoprostol, nomegestrol acetate, norelgestromin, norethindrone, noretynodrel, norgestimate, ormeloxifene, segesterone acetate, ulipristal acetate, and any combinations thereof.

Gene Therapy and Cell Therapy

In certain embodiments, the agents described herein are combined with a gene or cell therapy regimen. Gene therapy and cell therapy include without limitation the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection. Examples of cell therapy include without limitation LB-1903, ENOB-HV-01, ENOB-HV-21, ENOB-HV-31, GOVX-B01, HSPCs overexpressing ALDH1 (LV-800, HIV infection), AGT103-T, and SupT1 cell based therapy. Examples of dendritic cell therapy include without limitation AGS-004. CCR5 gene editing agents include without limitation SB-728T, SB-728-HSPC. CCR5 gene inhibitors include without limitation Cal-1, and lentivirus vector CCR5 shRNA/TRIM5alpha/TAR decoy-transduced autologous CD34-positive hematopoietic progenitor cells (HIV infection/HIV-related lymphoma). In some embodiments, C34-CCR5/C34-CXCR4 expressing CD4-positive T-cells are co-administered with one or more multi-specific antigen binding molecules. In some embodiments, the agents described herein are co-administered with AGT-103-transduced autologous T-cell therapy or AAV-eCD4-Ig gene therapy.

Gene Editors

In certain embodiments, the agents described herein are combined with a gene editor, e.g., an HIV targeted gene editor. In various embodiments, the genome editing system can be selected from the group consisting of: a CRISPR/Cas9 complex, a zinc finger nuclease complex, a TALEN complex, a homing endonucleases complex, and a meganuclease complex. An illustrative HIV targeting CRISPR/Cas9 system includes without limitation EBT-101.

CAR-T Cell Therapy

In some embodiments, the agents described herein can be co-administered with a population of immune effector cells engineered to express a chimeric antigen receptor (CAR), wherein the CAR comprises an HIV antigen binding domain. The HIV antigen include an HIV envelope protein or a portion thereof, gp120 or a portion thereof, a CD4 binding site on gp120, the CD4-induced binding site on gp120, N glycan on gp120, the V2 of gp120, the membrane proximal region on gp41. The immune effector cell is a T-cell or an NK cell. In some embodiments, the T-cell is a CD4+ T-cell, a CD8+ T-cell, or a combination thereof. Cells can be autologous or allogeneic. Examples of HIV CAR-T include A-1801, A-1902, convertible CAR-T, VC-CAR-T, CMV-N6-CART, anti-HIV duoCAR-T, anti-CD4 CART-cell therapy, CD4 CAR+C34-CXCR4+CCR5 ZFN T-cells, dual anti-CD4 CART-T cell therapy (CD4 CAR+C34-CXCR4 T-cells), anti-CD4 MicAbody antibody+anti-MicAbody CAR T-cell therapy (iNKG2D CAR, HIV infection), GP-120 CAR-T therapy, autologous hematopoietic stem cells genetically engineered to express a CD4 CAR and the $C_{46}$ peptide.

TCR T-Cell Therapy

In certain embodiments, the agents described herein are combined with a population of TCR-T-cells. TCR-T-cells are engineered to target HIV derived peptides present on the surface of virus-infected cells, for example, ImmTAV.

B-Cell Therapy

In certain embodiments, the antibodies or antigen-binding fragments described herein are combined with a population of B cells genetically modified to express broadly neutralizing antibodies, such as 3BNC117 (Hartweger et al., *J. Exp. Med.* 2019, 1301, Moffett et al., *Sci. Immunol.* 4, eaax0644 (2019) 17 May 2019.

A compound as disclosed herein (e.g., any compound of Formula I) may be combined with one, two, three, or four additional therapeutic agents in any dosage amount of the compound of Formula I (e.g., from 1 mg to 500 mg of compound).

In one embodiment, kits comprising a compound disclosed herein, or a pharmaceutically acceptable salt thereof, in combination with one or more (e.g., one, two, three, one or two, or one to three) additional therapeutic agents are provided.

In one embodiment, the additional therapeutic agent or agents of the kit is an anti-HIV agent, selected from HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T cell receptors, TCR-T, autologous T cell therapies), compounds that target the HIV capsid, latency reversing agents, HIV bNAbs, immune-based therapies, phosphatidylinositol 3-kinase (PI3K) inhibitors, HIV antibodies, broadly neutralizing HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement $C_5a$ receptor antagonists, DNA methyltransferase inhibitor, HIV vif gene modulators, Vif dimerization antagonists, HIV viral infectivity factor inhibitors, TAT protein inhibitors, HIV Nef modulators, Hck tyrosine kinase modulators, mixed lineage kinase-3 (MLK-3) inhibitors, HIV splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

In some embodiments, the additional therapeutic agent or agents of the kit are selected from combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In a specific embodiment, the kit includes a compound disclosed herein, or a pharmaceutically acceptable salt thereof, and an HIV nucleoside or nucleotide inhibitor of reverse transcriptase. In a specific embodiment, the kit includes a compound disclosed herein, or a pharmaceutically acceptable salt thereof, and an HIV nucleoside or nucleotide inhibitor of reverse transcriptase and an HIV non-nucleoside inhibitor of reverse transcriptase. In another specific embodiment, the kit includes a compound disclosed herein, or a pharmaceutically acceptable salt thereof, and an HIV nucleoside or nucleotide inhibitor of reverse transcriptase, and an HIV protease inhibiting compound. In an additional embodiment, the kit includes a compound disclosed herein, or a pharmaceutically acceptable salt thereof, an HIV nucleoside or nucleotide inhibitor of reverse transcriptase, an HIV non-nucleoside inhibitor of reverse transcriptase, and a pharmacokinetic enhancer. In certain embodiments, the kit includes a compound disclosed herein, or a pharmaceutically acceptable salt thereof, at least one HIV nucleoside inhibitor of reverse transcriptase, an integrase inhibitor, and a pharmacokinetic enhancer. In another embodiment, the kit includes a compound disclosed herein, or a pharmaceutically acceptable salt thereof, and two HIV nucleoside or nucleotide inhibitors of reverse transcriptase. In a specific embodiment, the kit includes a compound disclosed herein, or a pharmaceutically acceptable salt thereof, an HIV nucleoside or nucleotide inhibitor of reverse transcriptase and an HIV capsid inhibitor. In a specific embodiment, the kit includes a compound disclosed herein, or a pharmaceutically acceptable salt thereof, an HIV nucleoside inhibitor of reverse transcriptase and an HIV capsid inhibitor. In a specific embodiment, the kit includes a compound disclosed herein, or a pharmaceutically acceptable salt thereof, and an HIV capsid inhibitor. In a specific embodiment, the kit includes a compound disclosed herein, or a pharmaceutically acceptable salt thereof, and one, two, three or four HIV bNAbs. In a specific embodiment, the kit includes a compound disclosed herein, or a pharmaceutically acceptable salt thereof, one, two, three or four HIV bNAbs and an HIV capsid inhibitor. In a specific embodiment, the kit includes a compound disclosed herein, or a pharmaceutically acceptable salt thereof, one, two, three or four HIV bNAbs, an HIV capsid inhibitor, and an HIV nucleoside inhibitor of reverse transcriptase.

HIV Long Acting Therapy

Examples of drugs that are being developed as long acting regimens include, but are not limited to, cabotegravir, rilpivirine, any integrase LA, VM-1500 LAI, maraviroc (LAI), tenofovir implant, islatravir implant, doravirine, raltegravir, and long acting dolutegravir.

VII. EXAMPLES

Intermediate A: (3S,7R)-12-(benzyloxy)-3-methyl-1,6,11-trioxo-N-(2,4,6-trifluorobenzyl)-1,6,7,11-tetrahydro-3H-2,7-methanopyrido[1,2-a][1,4]diazonine-10-carboxamide

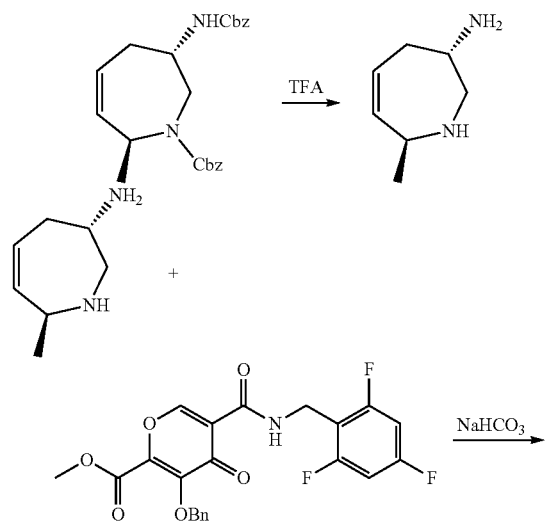

-continued

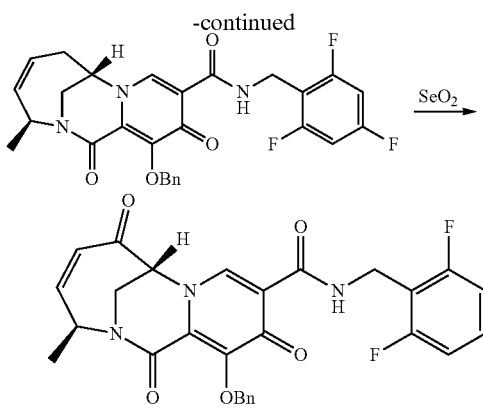

Step 1: Synthesis of (3S,7S)-7-methyl-2,3,4,7-tetrahydro-1H-azepin-3-amine

Trifluoroacetic acid (20 mL) was added to benzyl (3S,7S)-3-(((benzyloxy)carbonyl)amino)-7-methyl-2,3,4,7-tetrahydro-1H-azepine-1-carboxylate (6.2 g, 15.7 mmol) and the reaction was heated to 100° C. for 4 hours. The reaction mixture was concentrated down and the crude was used directly in next step.

Step 2: Synthesis of (3S,7S)-12-(benzyloxy)-3-methyl-1,11-dioxo-N-(2,4,6-trifluorobenzyl)-1,6,7,11-tetrahydro-3H-2,7-methanopyrido[1,2-a][1,4]diazonine-10-carboxamide Methanol (300 mL) and water (30 mL) were added to methyl 3-(benzyloxy)-4-oxo-5-((2,4,6-trifluorobenzyl)carbamoyl)-4H-pyran-2-carboxylate (6.75 g, 15.7 mmol) and (3S,7S)-7-methyl-2,3,4,7-tetrahydro-1H-azepin-3-amine (the reaction crude from the previous step). At room temperature, NaHCO$_3$ (13.2 g, 157 mmol) was added to the reaction mixture. The reaction was stirred at. room temperature overnight, then heated to 60° C. for 5 hours. The reaction mixture was concentrated down, then added ethyl acetate, washed with saturated ammonium chloride solution. The organic layer was concentrated and purified via silica chromatography (eluting with 0-10% MeOH/DCM) to give (3S,7S)-12-(benzyloxy)-3-methyl-1,11-dioxo-N-(2,4,6-trifluorobenzyl)-1,6,7,11-tetrahydro-3H-2,7-methanopyrido[1,2-a][1,4]diazonine-10-carboxamide. MS (m/z) 524.11 [M+H]+.

Step 3: Synthesis of (3S,7R)-12-(benzyloxy)-3-methyl-1,6,11-trioxo-N-(2,4,6-trifluorobenzyl)-1,6,7,11-tetrahydro-3H-2,7-methanopyrido[1,2-a][1,4]diazonine-10-carboxamide Selenium dioxide (17.4 g, 157 mmol.) was added to (3S,7S)-12-(benzyloxy)-3-methyl-1,11-dioxo-N-(2,4,6-trifluorobenzyl)-1,6,7,11-tetrahydro-3H-2,7-methanopyrido[1,2-a][1,4]diazonine-10-carboxamide (product of previous step, 15.7 mmol) in dioxane (160 mL). Then the reaction was heated to 105° C. overnight. The reaction mixture was cooled down and the solid was filtered off. The filtrate was extracted using ethyl acetate and saturated ammonium chloride solution. The organic layer was concentrated and purified via silica chromatograph (eluting with 40-100% Ethyl acetate/hexane) to give (3S,7R)-12-(benzyloxy)-3-methyl-1,6,11-trioxo-N-(2,4,6-trifluorobenzyl)-1,6,7,11-tetrahydro-3H-2,7-methanopyrido[1,2-a][1,4]diazonine-10-carboxamide. MS (m/z) 538.095 [M+H]+.

Intermediate B: (3S,6S,7R)-12-(benzyloxy)-6-hydroxy-3,6-dimethyl-1,11-dioxo-N-(2,4,6-trifluorobenzyl)-1,6,7,11-tetrahydro-3H-2,7-methanopyrido[1,2-a][1,4]diazonine-10-carboxamide

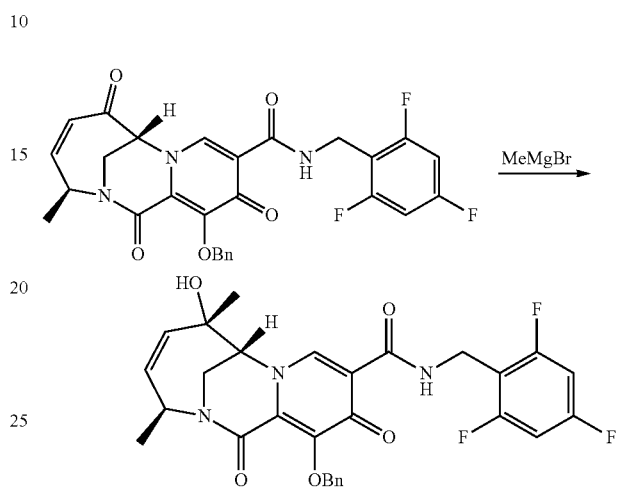

(3S,7R)-12-(benzyloxy)-3-methyl-1,6,11-trioxo-N-(2,4,6-trifluorobenzyl)-1,6,7,11-tetrahydro-3H-2,7-methanopyrido[1,2-a][1,4]diazonine-10-carboxamide (132 mg, 0.246 mmol) was dissolved in anhydrous THF (3.0 mL) and the resulting mixture was cooled to −20° C. To this stirred cold mixture was added 3.0 M ether solution of methyl magnesium bromide (0.41 mL, 1.23 mmol). After stirring for 20 minutes, the reaction was quenched with saturated NH$_4$Cl. The mixture was extracted with EtOAc, the organic layer was washed with brine, dried over sodium sulfate, filtered and concentrated. The resulting product was purified by silica gel chromatography (0-100% EtOAc/Hexanes). MS (m/z) 553.95 [M+H]+.

Intermediate C: (3S,7S)-12-(benzyloxy)-3-methyl-6-methylene-1,11-dioxo-N-(2,4,6-trifluorobenzyl)-1,4,5,6,7,11-hexahydro-3H-2,7-methanopyrido[1,2-a][1,4]diazonine-10-carboxamide

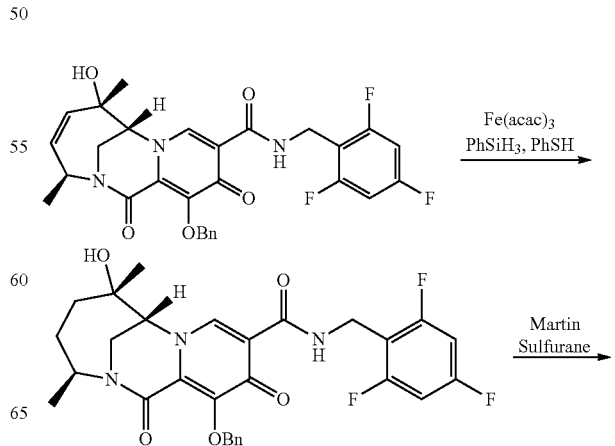

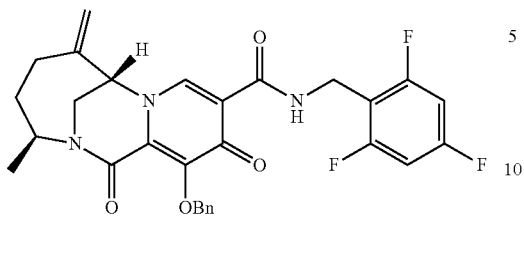

Step 1: Synthesis of (3S,6S,7R)-12-(benzyloxy)-6-hydroxy-3,6-dimethyl-1,11-dioxo-N-(2,4,6-trifluorobenzyl)-1,4,5,6,7,11-hexahydro-3H-2,7-methanopyrido[1,2-a][1,4]diazonine-10-carboxamide A round-bottom flask was charged with (3S,6S,7R)-12-(benzyloxy)-6-hydroxy-3,6-dimethyl-1,11-dioxo-N-(2,4,6-trifluorobenzyl)-1,6,7,11-tetrahydro-3H-2,7-methanopyrido[1,2-a][1,4]diazonine-10-carboxamide (3.15 g, 5.69 mmol), followed by Fe(acac)₃ (1.01 g, 2.85 mmol), EtOH (60 mL), PhSiH₃ (2.90 mL, 22.8 mmol), and PhSH (5.69 mL, 2.85 mmol, 0.5M in iPrOH). The resulting slurry was stirred at rt for 48 h. The reaction mixture was then concentrated in vacuo and the residue was purified by silica gel chromatography (20-100% ethyl acetate in hexanes) and then a second time by reverse-phase chromatography (5% to 100% acetonitrile in water buffered with 10 mM ammonium formate, pH=3.8). The corresponding fractions were combined, extracted with dichloromethane and concentrated in vacuo to afford (3S,6S,7R)-12-(benzyloxy)-6-hydroxy-3,6-dimethyl-1,11-dioxo-N-(2,4,6-trifluorobenzyl)-1,4,5,6,7,11-hexahydro-3H-2,7-methanopyrido[1,2-a][1,4]diazonine-10-carboxamide. MS (m/z) 556.4 [M+H]+.

Step 2: Synthesis of (3S,7S)-12-(benzyloxy)-3-methyl-6-methylene-1,11-dioxo-N-(2,4,6-trifluorobenzyl)-1,4,5,6,7,11-hexahydro-3H-2,7-methanopyrido[1,2-a][1,4]diazonine-10-carboxamide A round-bottom flask was charged with (3S,6S,7R)-12-(benzyloxy)-6-hydroxy-3,6-dimethyl-1,11-dioxo-N-(2,4,6-trifluorobenzyl)-1,4,5,6,7,11-hexahydro-3H-2,7-methanopyrido[1,2-a][1,4]diazonine-10-carboxamide (3.20 g, 5.76 mmol) followed by dichloromethane (90 mL). To this suspension was added Martin Sulfurane in two portions (8.91 g, 13.2 mmol) and the mixture was stirred at rt for 1 h. The resulting solution was then concentrated in vacuo and the residue was purified by reverse-phase chromatography (5-100% acetonitrile in water buffered with 10 mM ammonium fomate, pH=3.8). The corresponding fractions were combined and lyophilized to afford (3S,7S)-12-(benzyloxy)-3-methyl-6-methylene-1,11-dioxo-N-(2,4,6-trifluorobenzyl)-1,4,5,6,7,11-hexahydro-3H-2,7-methanopyrido[1,2-a][1,4]diazonine-10-carboxamide. MS (m/z) 538.4 [M+H]+.

Intermediate D: (3S,7R)-12-(benzyloxy)-N-(2,4-difluorobenzyl)-3-methyl-1,6,11-trioxo-1,6,7,11-tetrahydro-3H-2,7-methanopyrido[1,2-a][1,4]diazonine-10-carboxamide

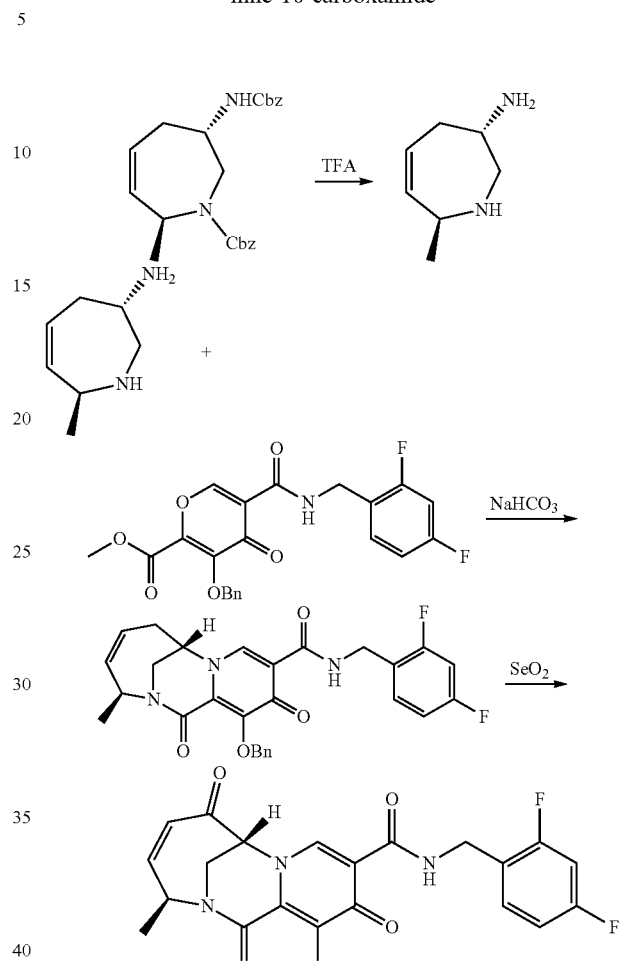

This intermediate was prepared in a manner similar to (3S,7R)-12-(benzyloxy)-3-methyl-1,6,11-trioxo-N-(2,4,6-trifluorobenzyl)-1,6,7,11-tetrahydro-3H-2,7-methanopyrido[1,2-a][1,4]diazonine-10-carboxamide (Intermediate A), except that methyl 3-(benzyloxy)-5-((2,4-difluorobenzyl)carbamoyl)-4-oxo-4H-pyran-2-carboxylate was used in the 2nd step. MS (m/z) 520.200 [M+H]+.

Intermediate E: (3S,6S,7R)-12-(benzyloxy)-N-(2,4-difluorobenzyl)-6-hydroxy-3,6-dimethyl-1,11-dioxo-1,6,7,11-tetrahydro-3H-2,7-methanopyrido[1,2-a][1,4]diazonine-10-carboxamide

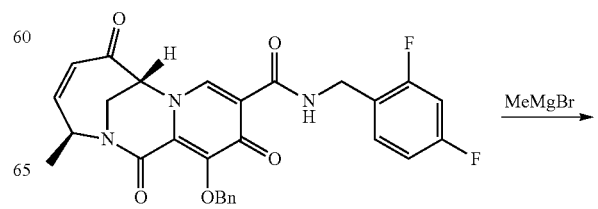

-continued

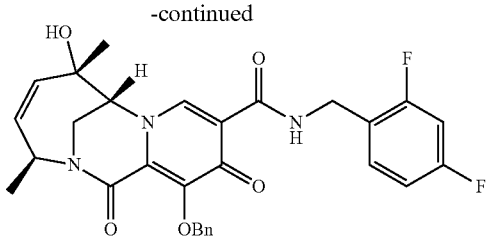

This intermediate was prepared in a manner similar to (3S,6S,7R)-12-(benzyloxy)-6-hydroxy-3,6-dimethyl-1,11-dioxo-N-(2,4,6-trifluorobenzyl)-1,6,7,11-tetrahydro-3H-2,7-methanopyrido[1,2-a][1,4]diazonine-10-carboxamide (Intermediate B), except that (3S,7R)-12-(benzyloxy)-N-(2,4-difluorobenzyl)-3-methyl-1,6,11-trioxo-1,6,7,11-tetrahydro-3H-2,7-methanopyrido[1,2-a][1,4]diazonine-10-carboxamide (Intermediate D) was used. MS (m/z) 536.4 [M+H]+.

Intermediate F: (3S,7S)-12-(benzyloxy)-N-(2,4-difluorobenzyl)-3-methyl-6-methylene-1,11-dioxo-1,4,5,6,7,11-hexahydro-3H-2,7-methanopyrido[1,2-a][1,4]diazonine-10-carboxamide

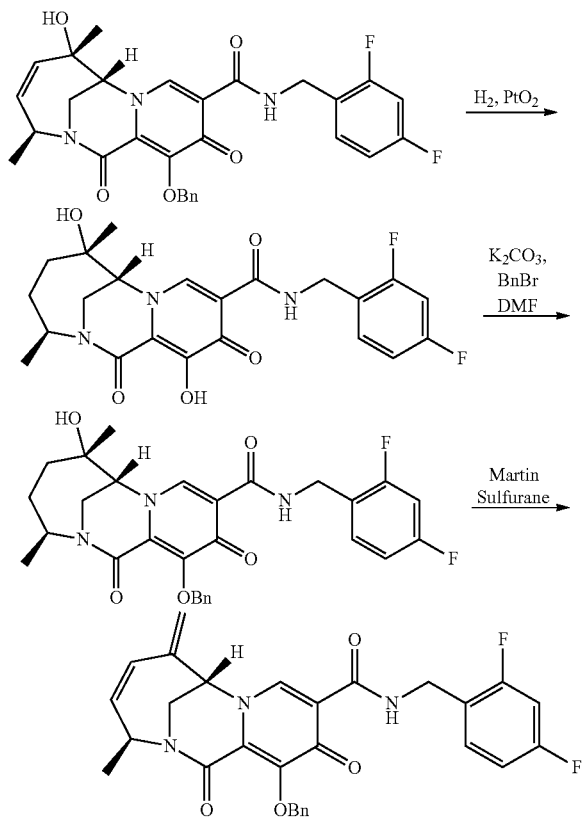

Step 1: Synthesis of (3S,6S,7R)—N-(2,4-difluorobenzyl)-6,12-dihydroxy-3,6-dimethyl-1,11-dioxo-1,4,5,6,7,11-hexahydro-3H-2,7-methanopyrido[1,2-a][1,4]diazonine-10-carboxamide To a solution of (3S,6S,7R)-12-(benzyloxy)-N-(2,4-difluorobenzyl)-6-hydroxy-3,6-dimethyl-1,11-dioxo-1,6,7,11-tetrahydro-3H-2,7-methanopyrido[1,2-a][1,4]diazonine-10-carboxamide (5.90 g, 11.0 mmol, 1 equiv.) in methanol (500 mL) and CH$_2$Cl$_2$ (170 mL) was added platinum(IV) oxide (0.72 g, 3.17 mmol, 0.29 equiv.). The flask was degassed and backfilled with nitrogen (3×), then degassed and backfilled with hydrogen gas (3×). The reaction mixture was stirred at room temperature for 16 h and diluted with CH$_2$Cl$_2$. The reaction mixture was filtered through Celite and concentrated. The residue was purified by column chromatography (0-10% MeOH/CH$_2$Cl$_2$) and fractions containing product were pooled and concentrated. The residue was triturated with MeOH and dried in a vacuum oven to afford (3S,6S,7R)—N-(2,4-difluorobenzyl)-6,12-dihydroxy-3,6-dimethyl-1,11-dioxo-1,4,5,6,7,11-hexahydro-3H-2,7-methanopyrido[1,2-a][1,4]diazonine-10-carboxamide. MS (m/z) 448.26 [M+H]+.

Step 2: Synthesis of (3S,6S,7R)-12-(benzyloxy)-N-(2,4-difluorobenzyl)-6-hydroxy-3,6-dimethyl-1,11-dioxo-1,4,5,6,7,11-hexahydro-3H-2,7-methanopyrido[1,2-a][1,4]diazonine-10-carboxamide To a suspension of (3S,6S,7R)—N-(2,4-difluorobenzyl)-6,12-dihydroxy-3,6-dimethyl-1,11-dioxo-1,4,5,6,7,11-hexahydro-3H-2,7-methanopyrido[1,2-a][1,4]diazonine-10-carboxamide (1.202 g, 2.69 mmol, 1 equiv.) and potassium carbonate (2.225 g, 16.1 mmol, 6 equiv.) in DMF (27 mL) was added benzyl bromide (0.957 mL, 8.06 mmol, 3 equiv.). The reaction mixture was stirred at rt for 16 h. The reaction mixture was diluted with EtOAc and washed with water and brine. The organic phase was dried over Na$_2$SO$_4$, filtered, and concentrated. The residue was purified by column chromatography (0-100% EtOAc/hexanes) to afford (3S,6S,7R)-12-(benzyloxy)-N-(2,4-difluorobenzyl)-6-hydroxy-3,6-dimethyl-1,11-dioxo-1,4,5,6,7,11-hexahydro-3H-2,7-methanopyrido[1,2-a][1,4]diazonine-10-carboxamide. MS (m/z) 538.11 [M+H]+.

Step 3: Synthesis of (3S,7S)-12-(benzyloxy)-N-(2,4-difluorobenzyl)-3-methyl-6-methylene-1,11-dioxo-1,4,5,6,7,11-hexahydro-3H-2,7-methanopyrido[1,2-a][1,4]diazonine-10-carboxamide To a solution of (3S,6S,7R)-12-(benzyloxy)-N-(2,4-difluorobenzyl)-6-hydroxy-3,6-dimethyl-1,11-dioxo-1,4,5,6,7,11-hexahydro-3H-2,7-methanopyrido[1,2-a][1,4]diazonine-10-carboxamide (1.258 g, 2.34 mmol, 1 equiv.) in toluene (15 mL) was added Martin sulfurane (3.933 g, 5.85 mmol, 2.5 equiv.). The reaction mixture was heated to 40° C. for 1 h and concentrated. The residue was purified by column chromatography (0-100% EtOAc/hexanes) to afford (3S,7S)-12-(benzyloxy)-N-(2,4-difluorobenzyl)-3-methyl-6-methylene-1,11-dioxo-1,4,5,6,7,11-hexahydro-3H-2,7-methanopyrido[1,2-a][1,4]diazonine-10-carboxamide. MS (m/z) 520.12 [M+H]+.

Intermediate G: (3S,7S)-12-(benzyloxy)-N-(2,4-difluorobenzyl)-3-methyl-6-methylene-1,11-dioxo-1,6,7,11-tetrahydro-3H-2,7-methanopyrido[1,2-a][1,4]diazonine-10-carboxamide

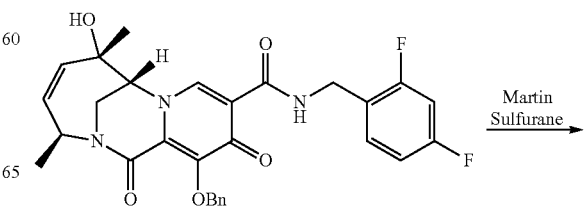

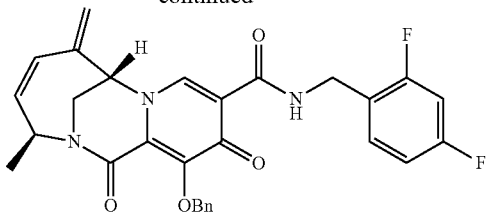

Into a suspension of (3S,6S,7R)-12-(benzyloxy)-N-(2,4-difluorobenzyl)-6-hydroxy-3,6-dimethyl-1,11-dioxo-1,6,7,11-tetrahydro-3H-2,7-methanopyrido[1,2-a][1,4]diazonine-10-carboxamide (0.525 g, 0.98 mmol) (Intermediate E) in toluene (10 ml) was added Martin Sulfurane (1.98 g, 2.94 mmol). The reaction was stirred at room temperature for 20 minutes. The reaction was diluted with EtOAc and washed with H₂O and brine. The organic phase was dried over MgSO₄, filtered, and concentrated. The residue was purified by silica gel column chromatography to afford (3S,7S)-12-(benzyloxy)-N-(2,4-difluorobenzyl)-3-methyl-6-methylene-1,11-dioxo-1,6,7,11-tetrahydro-3H-2,7-methanopyrido[1,2-a][1,4]diazonine-10-carboxamide. MS (m/z) 518.23 [M+H]+.

Example 1: Preparation of (3'S,5S,7'R)—N-(2,4-difluorobenzyl)-12'-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

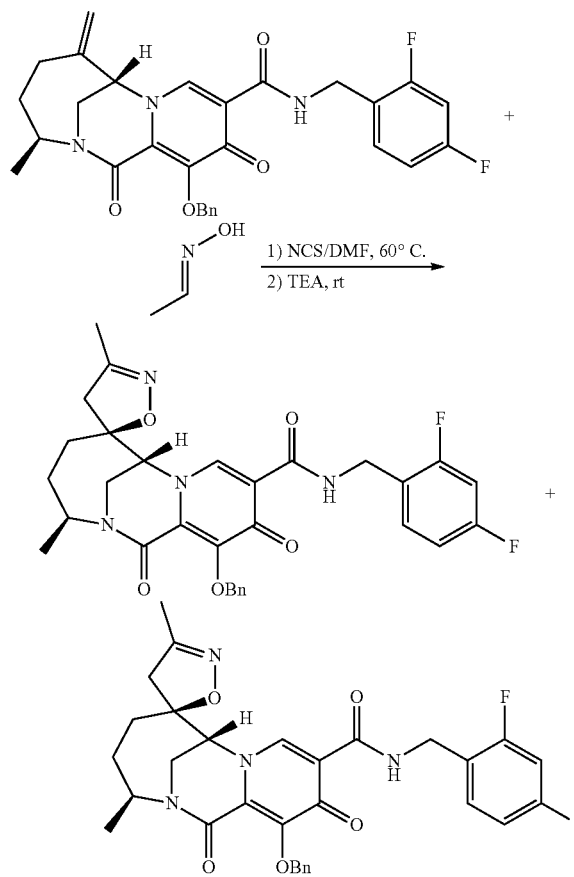

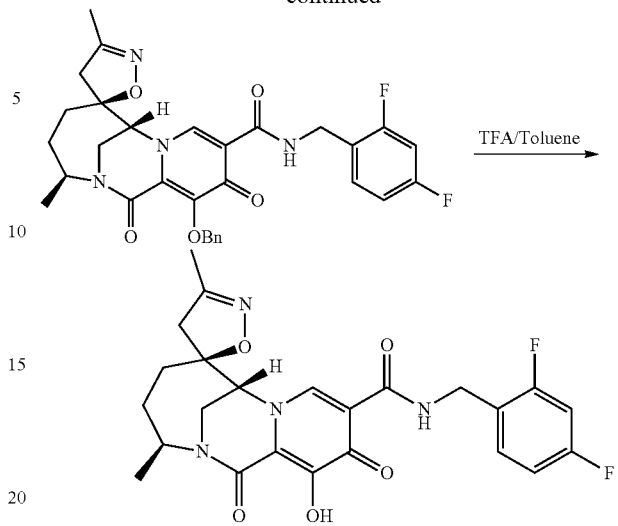

Step 1: Preparation of (3'S,5S,7'R)-12'-(benzyloxy)-N-(2,4-difluorobenzyl)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine-10'-carboxamide and (3'S,5R,7'R)-12'-(benzyloxy)-N-(2,4-difluorobenzyl)-3,3'-dimethyl-1',]'-dioxo-1',4',5',11'-tetrahydro-3'H,4H,7'H-spiro[isoxazole-5,6'-[2,7]methanopyrido[1,2-a][1,4]diazonine]-10'-carboxamide Into the solution of acetaldehyde oxime (666 mg, 11.3 mmol) in DMF (50 ml) was added N-chlorosuccinimide (1.51 g, 11.3 mmol) at rt, then heated to 60° C. for 1 h. After cooled to rt, (1S,10S)-6-benzyloxy-N-[(2,4-difluorophenyl)methyl]-10-methyl-13-methylene-5,8-dioxo-2,9-diazatricyclo[7.4.1.02,7]tetradeca-3,6-diene-4-carboxamide (Intermediate F) (1.58 g, 3.04 mmol) and triethylamine (1.539 g, 15.2 mmol) were added at rt. After the reaction mixture was stirred at rt for overnight, the reaction was quenched by adding sat. NaHCO₃ solution. The mixture was extracted with EtOAc, the organic phase was separated and dried over MgSO₄, filtered, concentrated down and purified by silica gel chromatography column (eluting with 0-100% EtOAc/hexane) to afford two separable isomers. MS (m/z) 577.135 [M+H]+(major); 577.115 [M+H]+(minor).

Step 2: Preparation of (3'S,5S,7'R)—N-(2,4-difluorobenzyl)-12'-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide To a solution of (3'S,5S,7'R)-12'-(benzyloxy)-N-(2,4-difluorobenzyl)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (64.7 mg, 0.112 mmol) in toluene (2 mL) was added TFA (0.5 mL). The reaction mixture was stirred at rt overnight. The reaction mixture was concentrated down, and the residue was purified by reverse phase HPLC, eluting with 10-90% acetonitrile in water to give title compound. MS (m/z) 487.12 [M+H]⁺. ¹H NMR (400 MHz, Chloroform-d) δ 10.53 (s, 1H), 8.43 (s, 1H), 7.37 (td, J=8.6, 6.3 Hz, 1H), 6.92-6.78 (m, 2H), 4.82-4.70 (m, 1H), 4.67 (t, J=4.8 Hz, 2H), 4.18 (d, J=2.2 Hz, 1H), 3.86 (dd, J=14.9, 1.9 Hz, 1H), 3.72 (dd, J=14.9, 2.7 Hz, 1H), 2.94 (d, J=17.8 Hz, 1H), 2.53 (d, J=17.7 Hz, 1H), 2.06 (s, 3H), 2.04-1.88 (m, 3H), 1.56 (dd, J=14.3, 11.2 Hz, 1H), 1.32 (d, J=6.6 Hz, 3H).

Example 2: Preparation of (3'S,5R,7'R)—N-(2,4-difluorobenzyl)-12'-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

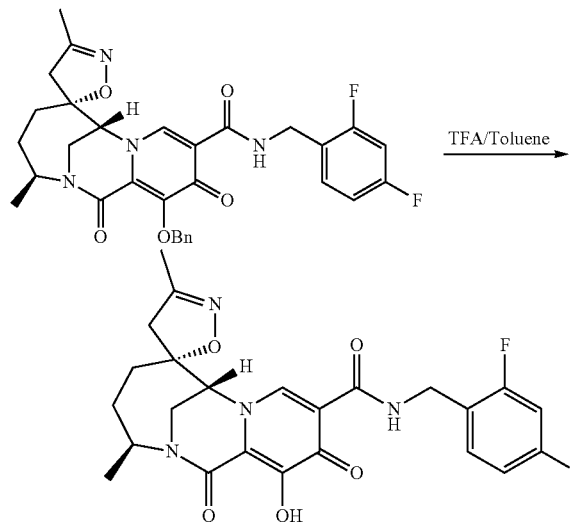

To a solution of (3'S,5R,7'R)-12'-(benzyloxy)-N-(2,4-difluorobenzyl)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (396 mg, 0.687 mmol), prepared according to Example 1, in toluene (5 mL) was added TFA (1 mL). The reaction mixture was stirred at rt overnight. The reaction mixture was concentrated down, and the residue was purified by reverse phase HPLC, eluting with 10-90% acetonitrile in water to give title compound. MS (m/z) 487.103 [M+H]+. $^1$H NMR (400 MHz, Chloroform-d) δ 10.53 (d, J=5.8 Hz, 1H), 8.41 (s, 1H), 7.38 (q, J=7.8 Hz, 1H), 6.95-6.74 (m, 2H), 4.83-4.69 (m, 1H), 4.65 (d, J=5.6 Hz, 2H), 4.25 (s, 1H), 3.77 (dd, J=15.2, 3.0 Hz, 1H), 3.44 (d, J=15.2 Hz, 1H), 3.00 (d, J=16.9 Hz, 1H), 2.83 (d, J=16.9 Hz, 1H), 2.32-2.12 (m, 1H), 2.04 (s, 3H), 1.83 (dd, J=15.3, 7.4 Hz, 1H), 1.75-1.58 (m, 1H), 1.42-1.33 (m, 1H), 1.30 (d, J=6.6 Hz, 3H).

Example 3: Preparation of (3'S,5S,7'R)-12'-hydroxy-3,3'-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

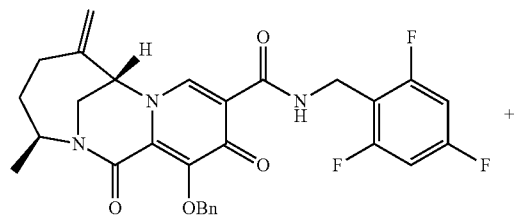

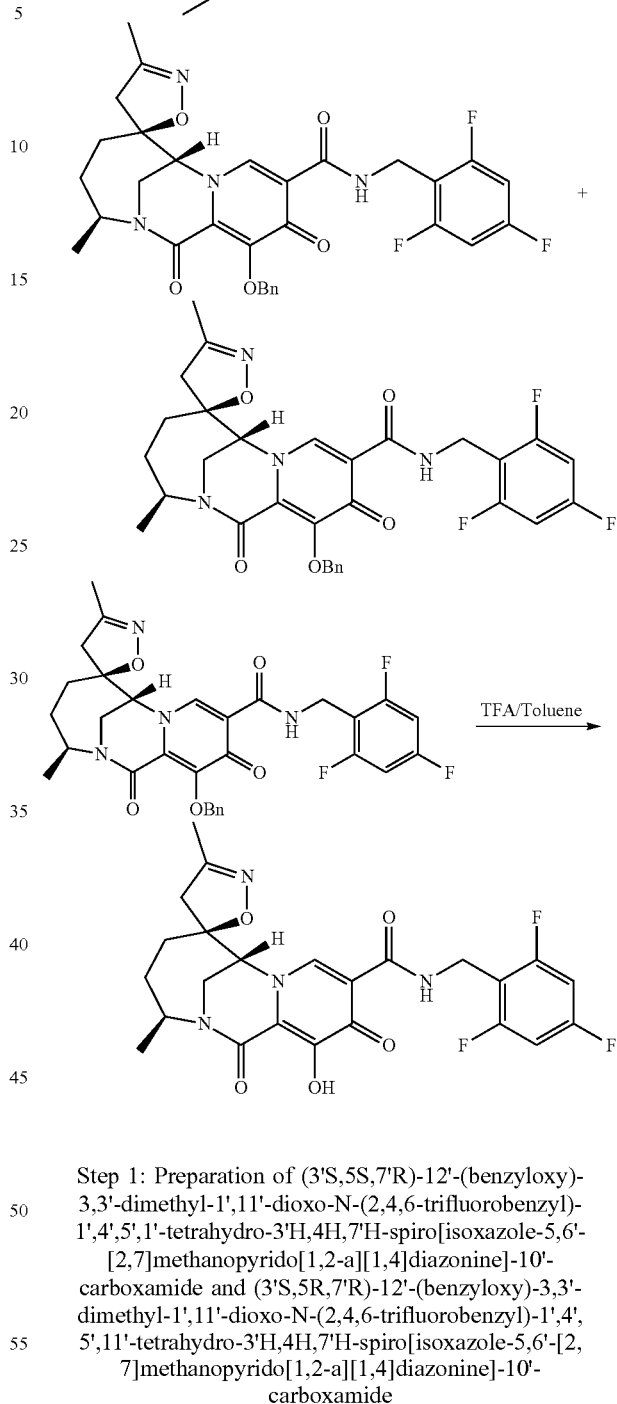

Step 1: Preparation of (3'S,5S,7'R)-12'-(benzyloxy)-3,3'-dimethyl-1',11'-dioxo-N-(2,4,6-trifluorobenzyl)-1',4',5',1'-tetrahydro-3'H,4H,7'H-spiro[isoxazole-5,6'-[2,7]methanopyrido[1,2-a][1,4]diazonine]-10'-carboxamide and (3'S,5R,7'R)-12'-(benzyloxy)-3,3'-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide Into the solution of acetaldehyde oxime (160 mg, 2.71 mmol) in DMF (5 ml) was added N-chlorosuccinimide (90.5 mg, 0.68 mmol) at rt, then heated to 60° C. for 1 h. After cooled to rt, (3S,7S)-12-(benzyloxy)-3-methyl-6-methylene-1,11-dioxo-N-(2,4,6-trifluorobenzyl)-1,4,5,6,7,11-hexahydro-3H-2,7-methanopyrido[1,2-a][1,4]diazonine-10-carboxamide (Intermediate C) (119 mg, 0.221 mmol) and triethylamine (112 mg, 1.1 mmol) was added at rt. After the reaction mixture was stirred at rt for overnight, the reaction was quenched by adding sat. NaHCO₃ solution. The mixture was extracted with EtOAc, the organic phase was separated and dried over MgSO₄, filtered, concentrated down and purified by silica gel chromatography column (eluting with 0-100% EtOAc/hexane) to afford two separable isomers. MS (m/z) 595.06 [M+H]+(major); 595.09 [M+H]+(minor).

Step 2: Preparation of (3'S,5S,7'R)-12'-hydroxy-3, 3'-dimethyl-1',11'-dioxo-N-(2,4,6-trifluorobenzyl)-1', 4',5',11'-tetrahydro-3'H,4H,7'H-spiro[isoxazole-5,6'-[2,7]methanopyrido[1,2-a][1,4]diazonine]-10'-carboxamide To a solution of (3'S,5S,7'R)-12'-(benzyloxy)-3,3'-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (72.3 mg, 0.122 mmol) in toluene (2 mL) was added TFA (0.5 mL). The reaction mixture was stirred at rt overnight. The reaction mixture was concentrated down, and the residue was purified by reverse phase HPLC, eluting with 10-90% acetonitrile in water to give title compound. MS (m/z) 505.129 [M+H]+. ¹H NMR (400 MHz, Chloroform-d) δ 10.51-10.41 (m, 1H), 8.40 (s, 1H), 6.70 (dd, J=8.7, 7.5 Hz, 2H), 4.71 (ddd, J=17.6, 11.2, 5.9 Hz, 3H), 4.13 (d, J=2.6 Hz, 1H), 3.86 (dd, J=14.9, 1.8 Hz, 1H), 3.70 (dd, J=14.9, 2.7 Hz, 1H), 2.93 (d, J=17.8 Hz, 1H), 2.52 (d, J=17.8 Hz, 1H), 2.13-1.89 (m, 6H), 1.57 (d, J=10.9 Hz, 1H), 1.31 (d, J=6.6 Hz, 3H).

Example 4: Preparation of (3'S,5R,7'R)-12'-hydroxy-3,3'-dimethyl-1',11'-dioxo-N-(2,4,6-trifluorobenzyl)-1',4',5',11'-tetrahydro-3'H,4H,7'H-spiro [isoxazole-5,6'-[2,7]methanopyrido[1,2-a][1,4] diazonine]-10'-carboxamide

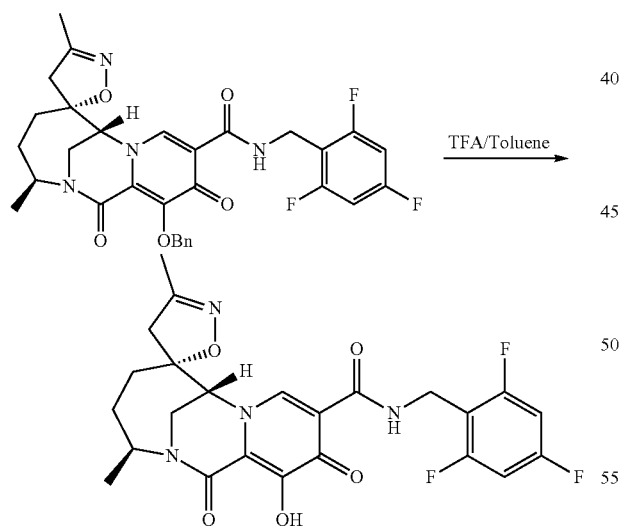

To a solution of (3'S,5R,7'R)-12'-(benzyloxy)-3,3'-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (10.8 mg, 0.018 mmol), prepared according to Example 3 in toluene (1 mL) was added TFA (0.5 mL). The reaction mixture was stirred at rt overnight. The reaction mixture was concentrated down, and the residue was purified by reverse phase HPLC, eluting with 10-90% acetonitrile in water to give title compound. MS (m/z) 505.142 [M+H]+. ¹H NMR (400 MHz, Chloroform-d) δ 10.41 (s, 1H), 8.37 (s, 1H), 6.78-6.59 (m, 2H), 4.86-4.56 (m, 3H), 4.13 (s, 1H), 3.76 (dd, J=15.2, 3.0 Hz, 1H), 3.43 (d, J=15.5 Hz, 1H), 3.02 (d, J=16.9 Hz, 1H), 2.81 (d, J=16.9 Hz, 1H), 2.27-2.17 (m, 1H), 2.06 (s, 3H), 1.82 (dd, J=15.3, 7.4 Hz, 1H), 1.74-1.63 (m, 1H), 1.40-1.32 (m, 1H), 1.30 (d, J=6.6 Hz, 3H).

Example 5: Preparation of (3'S,4'S,5R,7'R)—N-(2, 4-difluorobenzyl)-4'-fluoro-12'-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4] diazonine]-10'-carboxamide

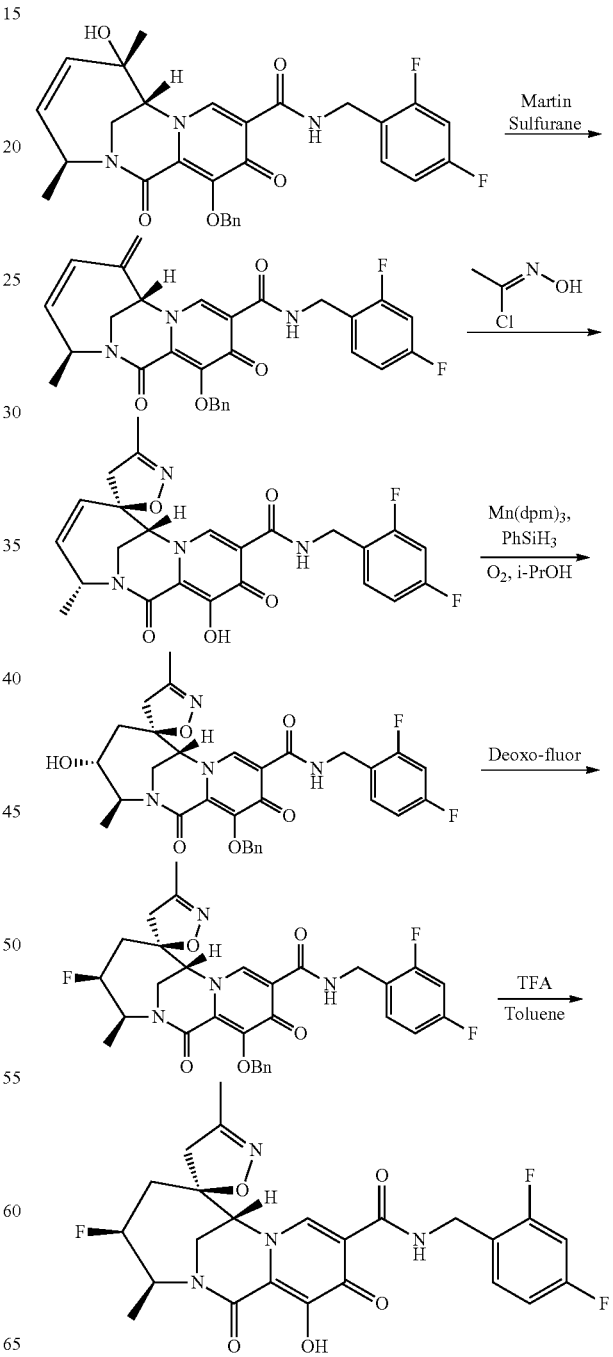

Step 1: Preparation of (3S,7S)-12-(benzyloxy)-N-(2,4-difluorobenzyl)-3-methyl-6-methylene-1,11-dioxo-1,6,7,11-tetrahydro-3H-2,7-methanopyrido[1,2-a][1,4]diazonine-10-carboxamide Into the suspension of (3S,6S,7R)-12-(benzyloxy)-N-(2,4-difluorobenzyl)-6-hydroxy-3,6-dimethyl-1,11-dioxo-1,6,7,11-tetrahydro-3H-2,7-methanopyrido[1,2-a][1,4]diazonine-10-carboxamide (Intermediate E) (0.525 g, 0.98 mmol) in toluene (10 ml) was added Martin Sulfurane (1.98 g, 2.94 mmol). Then the reaction was stirred at room temperature for 20 minutes. The reaction was diluted with EtOAc and washed with H₂O and brine. The organic phase was dried with MgSO₄. After solvent was removed in vacuo the residue was purified by silica gel chromatography to obtain the tile compound. MS (m/z) 518.23 [M+H]+.

Step 2: Preparation of (3'S,5R,7'R)-12'-(benzyloxy)-N-(2,4-difluorobenzyl)-3,3'-dimethyl-1',11'-dioxo-1',11'-dihydro-3'H,4H,7'H-spiro[isoxazole-5,6'-[2,7]methanopyrido[1,2-a][1,4]diazonine]-10'-carboxamide To solution of (3S,7S)-12-(benzyloxy)-N-(2,4-difluorobenzyl)-3-methyl-6-methylene-1,11-dioxo-1,6,7,11-tetrahydro-3H-2,7-methanopyrido[1,2-a][1,4]diazonine-10-carboxamide (0.335 g, 0.647 mmol) in DMF (2 ml) was added (1Z)—N-hydroxyacetimidoyl chloride (0.303 g, 3.24 mmol) followed by triethylamine (0.655 g, 6.47 mmol). The reaction was stirred at room temperature for 2 h. The reaction mixture was diluted with EtOAc and washed with H2O, 5% LiCl (aq), and brine. The organic phase was dried with MgSO₄. After removing solvent in vacuo the residue was purified by silica gel chromatography to obtain the tile compound. MS (m/z) 575.58 [M+H]+.

Step 3: Preparation of (3'S,4'R,5R,7'R)-12'-(benzyloxy)-N-(2,4-difluorobenzyl)-4'-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide To the solution of (3'S,5R,7'R)-12'-(benzyloxy)-N-(2,4-difluorobenzyl)-3,3'-dimethyl-1',11'-dioxo-1',11'-dihydro-3'H,4H,7'H-spiro[isoxazole-5,6'-[2,7]methanopyrido[1,2-a][1,4]diazonine]-10'-carboxamide (0.2 g, 0.353 mmol) in i-PrOH (3 ml) and DCM (2 ml) was added phenylsilane (0.11 g, 1.06 mmol), followed by tris(2,2,6,6-tetramethyl-3,5-heptanedionato)manganese(III) (0.011 g, 0.0018 mmol). Then the reaction was stirred under 02 (g) atmosphere for 24 h. Reaction was quenched by adding 10% sodium thiosulfate, then extracted with EtOAc. Organic phase was washed H₂O, brine and dried with MgSO₄. After removing solvent in vacuo the residue was purified by silica gel chromatography to obtain the tile compound. MS (m/z) 593.05 [M+H]+.

Step 4: Preparation of (3'S,4'S,5R,7'R)-12'-(benzyloxy)-N-(2,4-difluorobenzyl)-4'-fluoro-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide To a solution of (3'S,4'R,5R,7'R)-12'-(benzyloxy)-N-(2,4-difluorobenzyl)-4'-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (60 mg, 0.101 mmol) in DCM (2 mL) was added deoxofluor solution in toluene (50%, 0.375 mL, 1.01 mmol) at 0° C. The reaction mixture was stirred at 0° C. for 15 min and the reaction was quenched by adding sat. NaHCO₃ solution. The mixture was extracted with DCM, the organic phase was separated and dried over MgSO₄, filtered, concentrated down and purified by silica gel chromatography column (eluting with 0-100% hexane/EtOAc) to give the title compound. MS (m/z) 595.04 [M+H]+.

Step 5: Preparation of (3'S,4'S,5R,7'R)—N-(2,4-difluorobenzyl)-4'-fluoro-12'-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide To a solution of (3'S,4'S,5R,7'R)-12'-(benzyloxy)-N-(2,4-difluorobenzyl)-4'-fluoro-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (11 mg, 0.0185 mmol) in toluene (1 mL) was added TFA (1 mL). The reaction mixture was stirred at rt overnight. The reaction mixture was concentrated down, and the residue was purified by reverse phase HPLC, eluting with 5-100% acetonitrile in water to give title compound. MS (m/z) 505.40 [M+H]+. 1H NMR (400 MHz, Chloroform-d) δ 10.24 (t, J=5.9 Hz, 1H), 8.23 (s, 1H), 7.39 (td, J=8.6, 8.2, 6.2 Hz, 1H), 6.91-6.57 (m, 2H), 5.03 (dt, J=46.9, 5.7 Hz, 1H), 4.93-4.78 (m, 1H), 4.76-4.52 (m, 2H), 4.26 (dd, J=17.1, 2.7 Hz, 2H), 3.81 (d, J=14.4 Hz, 1H), 2.84-2.65 (m, 3H), 2.14 (s, 3H), 2.03-1.82 (m, 1H), 1.48 (dd, J=7.1, 2.3 Hz, 3H).

Example 6: Preparation of (3'S,5S,7'R)—N-(3-chloro-2,4-difluorobenzyl)-12'-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

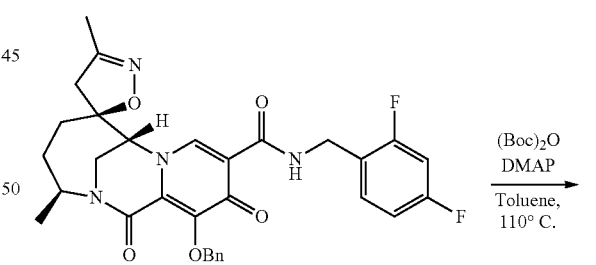

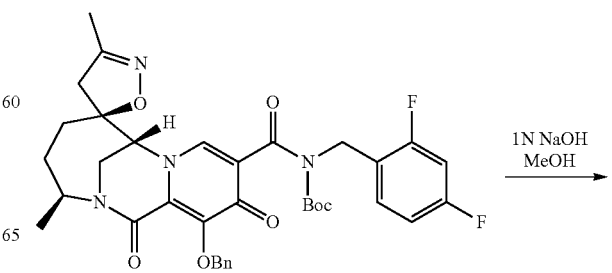

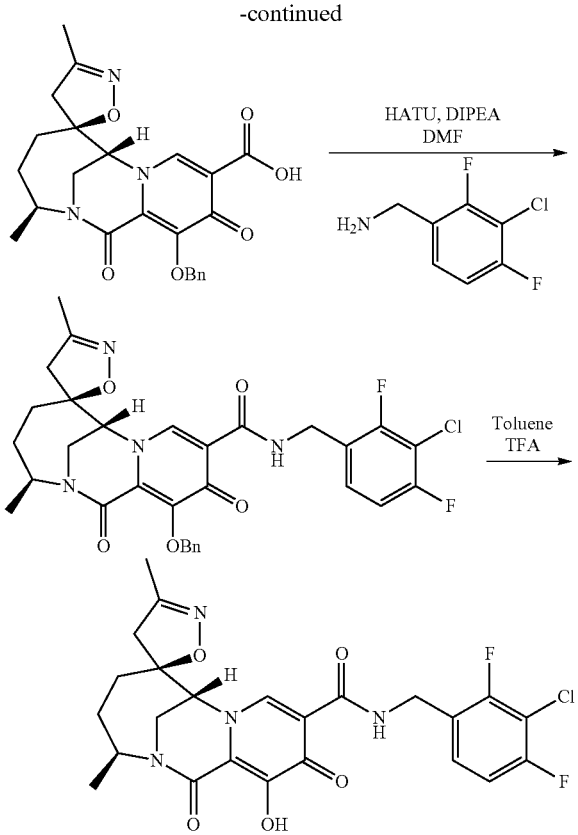

Step 1: Preparation of tert-butyl ((3'S,5S,7'R)-12'-(benzyloxy)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carbonyl)(2,4-difluorobenzyl)carbamate Into the solution of (3'S,5S,7'R)-12'-(benzyloxy)-N-(2,4-difluorobenzyl)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (631 mg, 1.11 mmol), prepared according to Example 1, in toluene (20 ml) was added di-tert-butyl dicarbonate (1.45 g, 6.64 mmol) and DMAP (608 mg, 4.98 mmol). Then the reaction mixture was heated to 110° C. for 4 h. After the reaction was cooled down to rt, the reaction was quenched by adding sat. NaHCO₃ solution. The mixture was extracted with EtOAc, the organic phase was separated and dried over MgSO₄, filtered, concentrated down and purified by silica gel column chromatography (eluting with 30-100% EtOAc/hexane) to give the title compound. MS (m/z) 676.924 [M+H]+.

Step 2: Preparation of (3'S,5S,7'R)-12'-(benzyloxy)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxylic acid Into the solution of tert-butyl ((3'S,5S,7'R)-12'-(benzyloxy)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carbonyl)(2,4-difluorobenzyl)carbamate (590 mg, 0.872 mmol) in MeOH (10 ml) was added 1N solution NaOH (3 ml) at rt. After 1 h at rt, the reaction was quenched by adding 1N HCl solution. The mixture was extracted with EtOAc, the organic phase was separated and dried over MgSO₄, filtered, concentrated to give the crude title compound which was used without purification. MS (m/z) 452.127 [M+H]+.

Step 3: Preparation of (3'S,5S,7'R)-12'-(benzyloxy)-N-(3-chloro-2,4-difluorobenzyl)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide Into the solution of (3'S,5S,7'R)-12'-(benzyloxy)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxylic acid (65 mg, 0.144 mmol) in DMF (5 ml) was added (3-chloro-2,4-difluorophenyl)methanamine (30.7 mg, 0.173 mmol). HATU (98.5 mg, 0.259 mmol) and DEA (149 mg, 1.15 mmol) at rt. After 1 h at rt, the reaction was quenched by adding sat. NaHCO₃ solution. The mixture was extracted with EtOAc, the organic phase was separated and dried over MgSO₄, filtered, concentrated down and purified by silica gel chromatography column (eluting with 50-100% EtOAc/hexane) to give the title compound. MS (m/z) 611.075 [M+H]+.

Step 4: Preparation of (3'S,5S,7'R)—N-(3-chloro-2,4-difluorobenzyl)-12'-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide To a solution of (3'S,5S,7'R)-12'-(benzyloxy)-N-(3-chloro-2,4-difluorobenzyl)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (88 mg, 0.144 mmol) in toluene (2 mL) was added TFA (0.5 mL). The reaction mixture was stirred at rt overnight. The reaction mixture was concentrated down, and the residue was purified by reverse phase HPLC, eluting with 10-90% acetonitrile in water, to give title compound. MS (m/z) 521.181 [M+H]+. ¹H NMR (400 MHz, Chloroform-d) δ 10.59-10.49 (m, 1H), 8.39 (s, 1H), 7.32-7.27 (m, 1H), 6.96 (td, J=8.5, 1.8 Hz, 1H), 4.72 (ddd, J=19.4, 7.9, 4.5 Hz, 3H), 4.15 (s, 1H), 3.87 (dd, J=14.9, 1.9 Hz, 1H), 3.71 (dd, J=14.9, 2.7 Hz, 1H), 2.93 (d, J=17.7 Hz, 1H), 2.59-2.49 (m, 1H), 2.15-1.92 (m, 6H), 1.56 (dd, J=14.2, 11.2 Hz, 1H), 1.32 (d, J=6.6 Hz, 3H).

Example 7: Preparation of (3'S,5S,7'R)—N-(2,4-difluorobenzyl)-12'-hydroxy-3-isopropyl-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

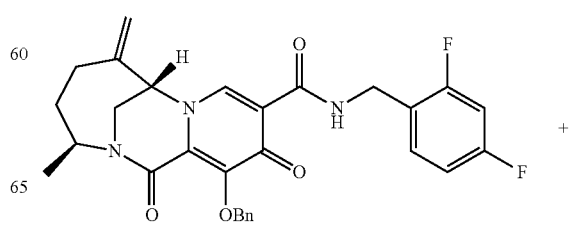

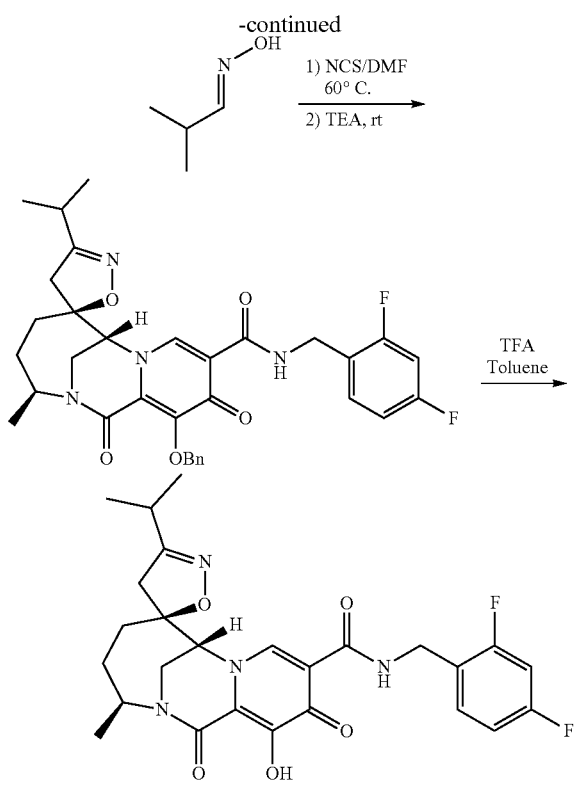

(3'S,5S,7'R)—N-(2,4-difluorobenzyl)-12'-hydroxy-3-isopropyl-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide was prepared in a manner similar to Example 1, except using isobutyraldehyde oxime in Step 1. MS (m/z) 515.152 [M+H]+. 1H NMR (400 MHz, Chloroform-d) δ 10.40 (s, 1H), 8.32 (s, 1H), 7.40 (d, J=7.2 Hz, 1H), 6.83 (q, J=9.7, 9.1 Hz, 2H), 4.84-4.75 (m, 1H), 4.67 (t, J=5.4 Hz, 2H), 4.02 (s, 1H), 3.77 (dd, J=15.2, 3.0 Hz, 1H), 3.49-3.42 (m, 1H), 3.01 (d, J=16.8 Hz, 1H), 2.83-2.71 (m, 2H), 2.24 (d, J=7.7 Hz, 1H), 1.86-1.81 (m, 2H), 1.70 (s, 1H), 1.31 (d, J=6.5 Hz, 3H), 1.23 (d, J=6.9 Hz, 6H).

Example 8: Preparation of (3'S,5S,7'R)—N-(2,4-difluorobenzyl)-3-ethyl-12'-hydroxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

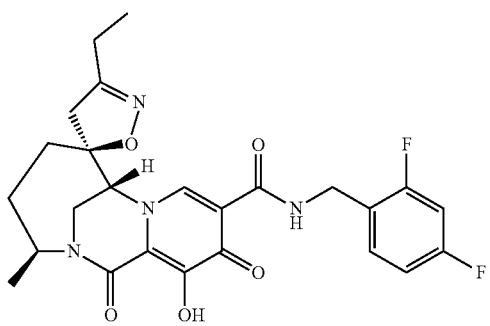 [SMILES: CCC1=NO[C@@]2(CC[C@H](C)N3C[C@H]2n2cc(C(=O)NCc4ccc(F)cc4F)c(=O)c(O)c2C3=O)C1]

The title compound was prepared in a manner similar to Example 1, except using propanal oxime instead of acetaldehyde oxime in Step 1. MS (m/z) 501.2 [M+H]+. 1H NMR (400 MHz, Chloroform-d) δ 10.76 (s, 1H), 8.61 (s, 1H), 7.38 (t, J=8.0 Hz, 1H), 6.88 (m, 2H), 4.74-4.53 (m, 5H), 3.76 (d, J=14.7 Hz, 1H), 3.56 (d, J=14.8 Hz, 1H), 2.75 (d, J=16.7 Hz, 1H), 2.47 (d, J=16.8 Hz, 1H), 1.97-1.50 (m, 7H), 1.45 (t, J=12.7 Hz, 1H), 1.31 (d, J=6.6 Hz, 3H).

Example 9: Preparation of (3'S,5S,7'R)—N-(2,4-difluorobenzyl)-12'-hydroxy-3'-methyl-1',11'-dioxo-3-(2,2,2-trifluoroethyl)-1',4',5',11'-tetrahydro-3'H,4H,7'H-spiro[isoxazole-5,6'-[2,7]methanopyrido[1,2-a][1,4]diazonine]-10'-carboxamide

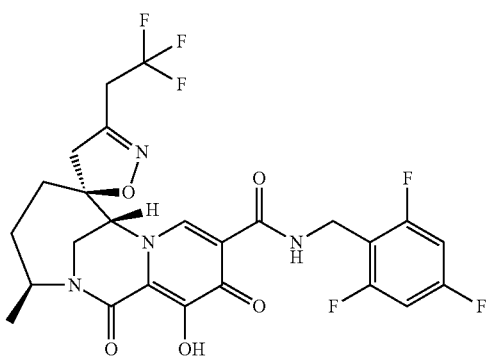 [SMILES: C[C@H]1CC[C@]2(CC(CC(F)(F)F)=NO2)[C@H]2CN1C(=O)c1c(O)c(=O)c(C(=O)NCc3c(F)cc(F)cc3F)cn12]

The title compound was prepared in a manner similar to Example 3, except using 3,3,3-trifluoropropanal oxime instead of acetaldehyde oxime in Step 1. MS (m/z) 573.09 [M+H]+. 1H NMR (400 MHz, Chloroform-d) δ 10.55 (t, J=5.8 Hz, 1H), 8.55 (s, 1H), 6.76-6.64 (m, 2H), 4.83-4.68 (m, 2H), 4.66 (dd, J=14.6, 5.6 Hz, 1H), 4.26 (d, J=2.2 Hz, 1H), 3.86 (dd, J=15.0, 1.8 Hz, 1H), 3.74 (dd, J=15.0, 2.6 Hz, 1H), 3.47-3.17 (m, 2H), 3.11 (d, J=18.0 Hz, 1H), 2.65 (d, J=18.0 Hz, 1H), 2.15-1.90 (m, 3H), 1.63-1.50 (m, 1H), 1.33 (d, J=6.6 Hz, 3H).

Example 10: Preparation of (3'S,5S,7'R)-3-(4-chlorobutyl)-12'-hydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

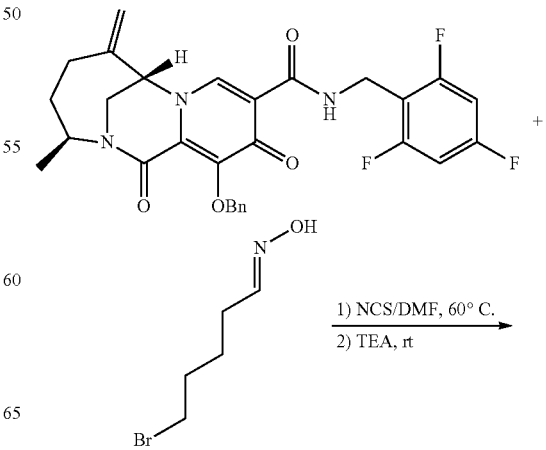

143
-continued

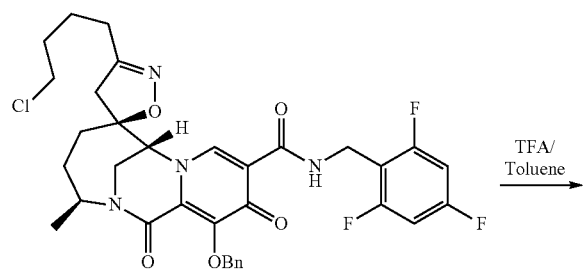

TFA/
Toluene →

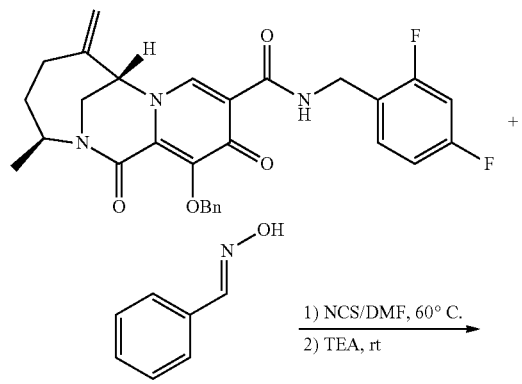

The title compound was prepared in a manner similar to Example 3, except using 5-bromopentanal oxime instead of acetaldehyde oxime in Step 1. MS (m/z) 581.223 [M+H]+. ¹H NMR (400 MHz, Chloroform-d) δ 10.35 (t, J=5.7 Hz, 1H), 8.33 (s, 1H), 6.77-6.62 (m, 2H), 4.70 (td, J=12.4, 10.4, 5.9 Hz, 3H), 4.08 (s, 1H), 3.85 (dd, J=14.9, 1.8 Hz, 1H), 3.76-3.66 (m, 1H), 3.61 (td, J=6.3, 2.4 Hz, 2H), 2.91 (d, J=17.7 Hz, 1H), 2.57 (s, 1H), 2.53 (s, 1H), 2.49-2.41 (m, 2H), 1.99 (dd, J=15.9, 9.1 Hz, 2H), 1.95-1.83 (m, 2H), 1.83-1.73 (m, 2H), 1.62-1.52 (m, 1H), 1.31 (d, J=6.6 Hz, 3H).

Example 11: Preparation of (3'S,5S,7'R)—N-(2,4-difluorobenzyl)-12'-hydroxy-3'-methyl-1',11'-dioxo-3-phenyl-1',4',5',11'-tetrahydro-3'H,4H,7'H-spiro[isoxazole-5,6'-[2,7]methanopyrido[1,2-a][1,4]diazonine]-10'-carboxamide 144
-continued

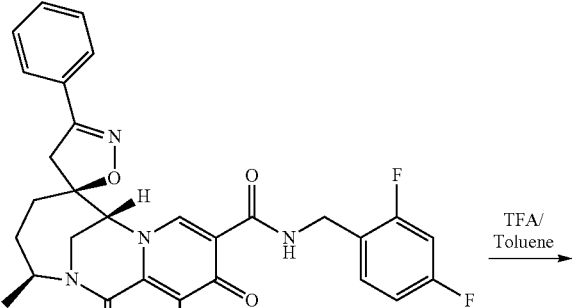

TFA/
Toluene →

The title compound was prepared in a manner similar to Example 1, except using benzaldehyde oxime instead of acetaldehyde oxime in Step 1. MS (m/z) 549.127 [M+H]+. ¹H NMR (400 MHz, Chloroform-d) δ 10.44 (t, J=5.9 Hz, 1H), 8.48 (s, 1H), 7.68-7.56 (m, 2H), 7.52-7.39 (m, 3H), 7.37 (d, J=6.4 Hz, 1H), 6.91-6.76 (m, 2H), 4.80 (d, J=6.7 Hz, 1H), 4.65 (dd, J=12.1, 5.9 Hz, 2H), 4.32 (d, J=2.3 Hz, 1H), 3.93 (dd, J=14.9, 1.9 Hz, 1H), 3.76 (dd, J=14.9, 2.7 Hz, 1H), 3.38 (d, J=17.2 Hz, 1H), 2.94 (d, J=17.2 Hz, 1H), 2.20-1.96 (m, 3H), 1.64 (dd, J=14.7, 11.5 Hz, 1H), 1.35 (d, J=6.6 Hz, 3H).

Example 12: Preparation of (3'S,5S,7'R)-3-benzyl-N-(2,4-difluorobenzyl)-12'-hydroxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

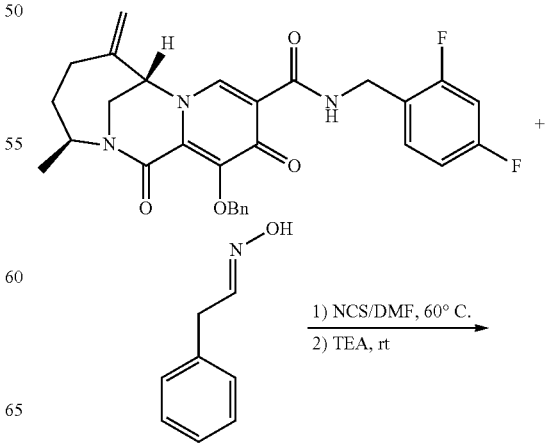

1) NCS/DMF, 60° C.
2) TEA, rt →

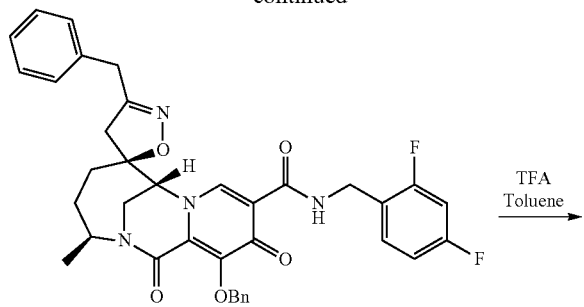

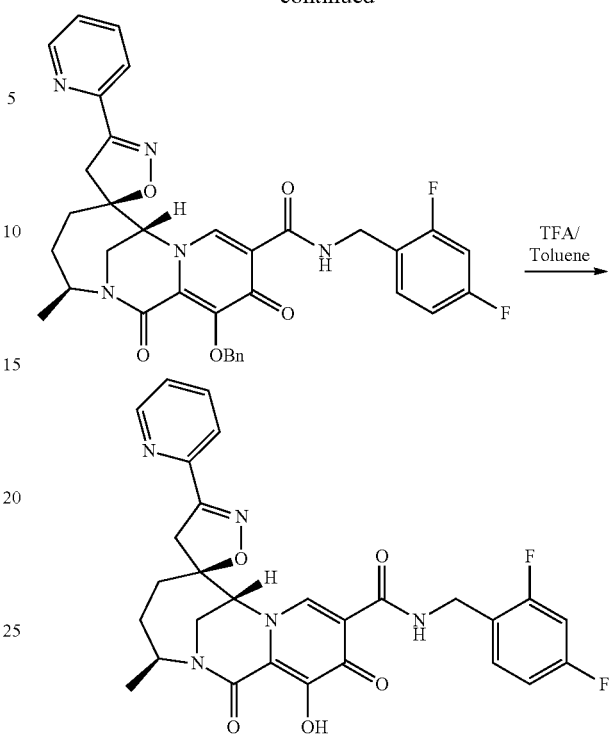

The title compound was prepared in a manner similar to Example 1, except using 2-phenylacetaldehyde oxime instead of acetaldehyde oxime in Step 1. MS (m/z) 563.165 [M+H]⁺. ¹H NMR (400 MHz, Chloroform-d) δ 10.45 (t, J=5.9 Hz, 1H), 8.36 (s, 1H), 7.39 (d, J=6.4 Hz, 1H), 7.36-7.30 (m, 2H), 7.27 (s, 1H), 7.20 (dd, J=6.9, 1.7 Hz, 2H), 6.95-6.75 (m, 2H), 4.68 (d, J=6.0 Hz, 3H), 4.18 (s, 1H), 3.93 (d, J=15.1 Hz, 1H), 3.84 (dd, J=14.9, 1.9 Hz, 1H), 3.70 (dd, J=14.9, 2.7 Hz, 1H), 3.56 (d, J=15.1 Hz, 1H), 2.85 (d, J=17.6 Hz, 1H), 2.35 (d, J=17.6 Hz, 1H), 2.11-1.89 (m, 2H), 1.80 (dd, J=15.6, 6.4 Hz, 1H), 1.48-1.35 (m, 1H), 1.31 (d, J=6.7 Hz, 3H).

The title compound was prepared in a manner similar to Example 1, except using N-hydroxypicolinimidoyl chloride instead of N-hydroxyacetimidoyl chloride in Step 1. MS (m/z) 550.177 [M+H]⁺. ¹H NMR (400 MHz, Chloroform-d) δ 10.50 (t, J=5.9 Hz, 1H), 8.66 (dd, J=4.9, 1.5 Hz, 1H), 8.43 (s, 1H), 8.16 (d, J=8.0 Hz, 1H), 7.96-7.83 (m, 1H), 7.55-7.43 (m, 1H), 7.39 (d, J=7.0 Hz, 1H), 6.93-6.74 (m, 2H), 4.89-4.75 (m, 1H), 4.67 (t, J=5.1 Hz, 1H), 4.26 (s, 1H), 3.80 (dd, J=15.3, 3.1 Hz, 1H), 3.56 (d, J=3.5 Hz, 2H), 2.36-2.26 (m, 3H), 1.95 (dd, J=15.2, 7.3 Hz, 1H), 1.81 (dd, J=15.1, 11.8 Hz, 1H), 1.52 (s, 1H), 1.34 (d, J=6.6 Hz, 3H).

Example 13: Preparation of (3'S,5S,7'R)—N-(2,4-difluorobenzyl)-12'-hydroxy-3'-methyl-1',11'-dioxo-3-(pyridin-2-yl)-1',4',5',11'-tetrahydro-3'H,4H,7'H-spiro[isoxazole-5,6'-[2,7]methanopyrido[1,2-a][1,4]diazonine]-10'-carboxamide Example 14: Preparation of (3'S,5S,7'R)—N-(2,4-difluorobenzyl)-12'-hydroxy-3'-methyl-1',11'-dioxo-3-(pyridin-3-yl)-1',4',5',11'-tetrahydro-3'H,4H,7'H-spiro[isoxazole-5,6'-[2,7]methanopyrido[1,2-a][1,4]diazonine]-10'-carboxamide

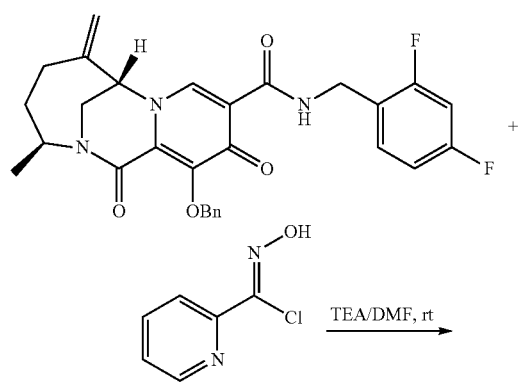

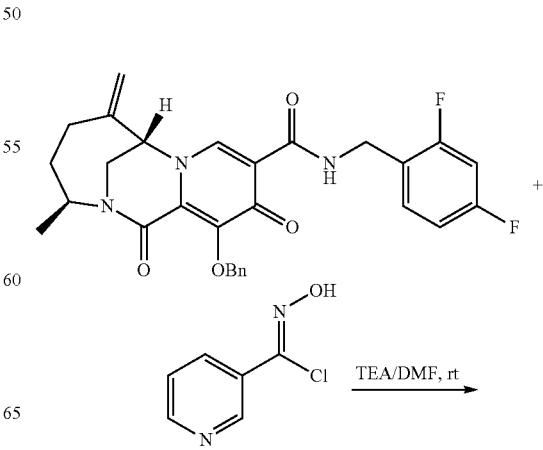

147
-continued

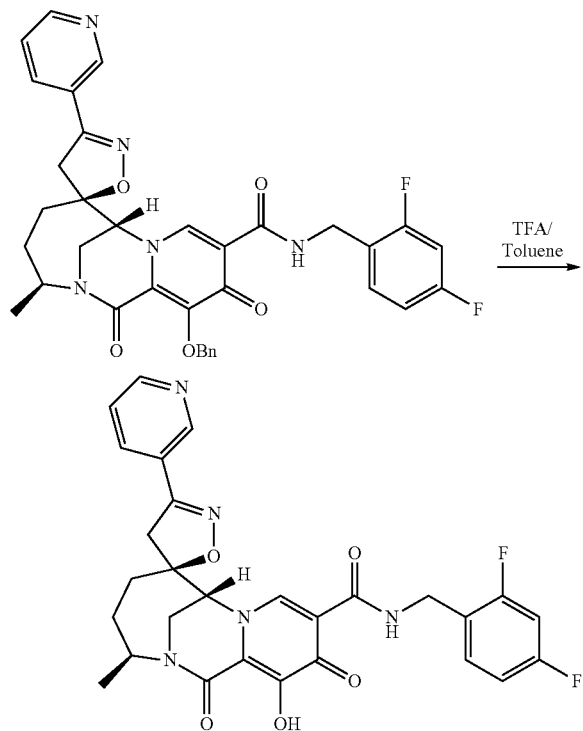

148
-continued

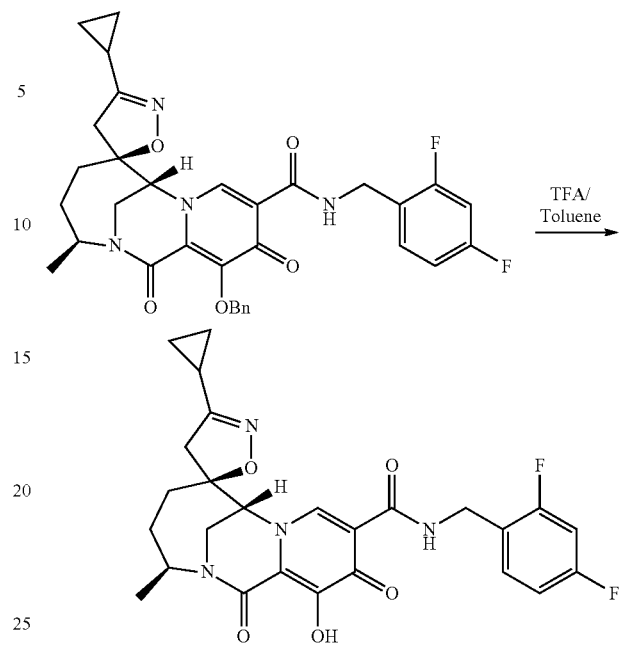

The title compound was prepared in a manner similar to Example 1, except using N-hydroxynicotinimidoyl chloride instead of N-hydroxyacetimidoyl chloride in Step 1. MS (m/z) 550.191 [M+H]+. 1H NMR (400 MHz, Chloroform-d) δ 10.41 (t, J=5.9 Hz, 1H), 8.95-8.90 (m, 1H), 8.77 (dd, J=5.1, 1.6 Hz, 1H), 8.46 (s, 1H), 8.25 (dd, J=8.1, 1.8 Hz, 1H), 7.63 (dd, J=8.1, 5.1 Hz, 1H), 7.41-7.32 (m, 1H), 6.91-6.80 (m, 2H), 4.85-4.77 (m, 1H), 4.70-4.60 (m, 2H), 4.30 (s, 1H), 3.93 (dd, J=14.9, 1.9 Hz, 1H), 3.78 (dd, J=15.0, 2.7 Hz, 1H), 3.43 (d, J=17.3 Hz, 1H), 2.99 (d, J=17.3 Hz, 1H), 2.05 (s, 2H), 1.70 (d, J=14.8 Hz, 2H), 1.36 (d, J=6.7 Hz, 3H).

The title compound was prepared in a manner similar to Example 1, except using cyclopropanecarbaldehyde oxime instead of acetaldehyde oxime in Step 1. MS (m/z) 513.16 [M+H]+. 1H NMR (400 MHz, Chloroform-d) δ 10.43 (s, 1H), 8.35 (s, 1H), 7.39 (d, J=7.4 Hz, 1H), 6.83 (q, J=10.0, 9.6 Hz, 2H), 4.83-4.71 (m, 1H), 4.67 (d, J=5.5 Hz, 2H), 4.07 (s, 1H), 3.77 (d, J=15.8 Hz, 1H), 3.42 (d, J=15.1 Hz, 1H), 2.89 (d, J=16.6 Hz, 1H), 2.63 (d, J=16.6 Hz, 1H), 2.22 (dd, J=15.0, 7.2 Hz, 2H), 1.81 (d, J=7.7 Hz, 2H), 1.70 (d, J=11.8 Hz, 1H), 1.30 (d, J=6.4 Hz, 3H), 1.00 (d, J=8.3 Hz, 2H), 0.88-0.77 (m, 2H).

Example 16: Preparation of (3'S,5S,7'R)—N-(2,4-difluorobenzyl)-12'-hydroxy-3-(hydroxymethyl)-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide Example 15: Preparation of (3'S,5S,7'R)-3-cyclopropyl-N-(2,4-difluorobenzyl)-12'-hydroxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

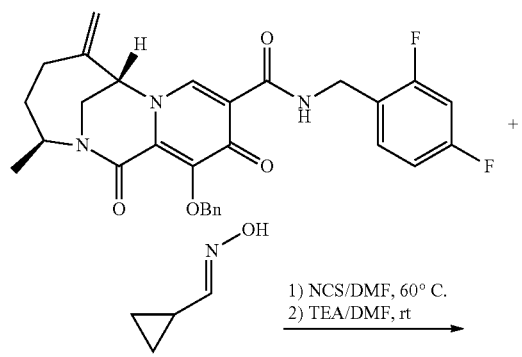

1) NCS/DMF, 60° C.
2) TEA/DMF, rt

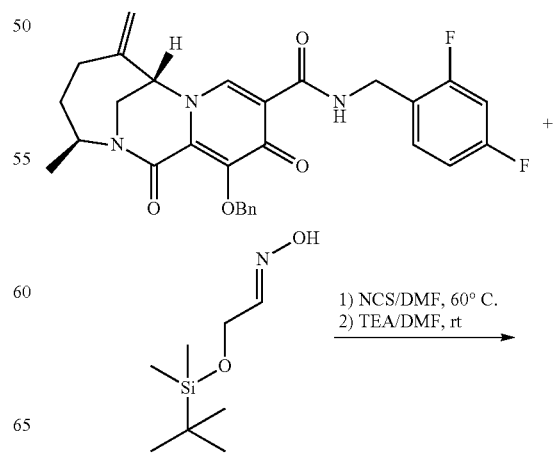

1) NCS/DMF, 60° C.
2) TEA/DMF, rt

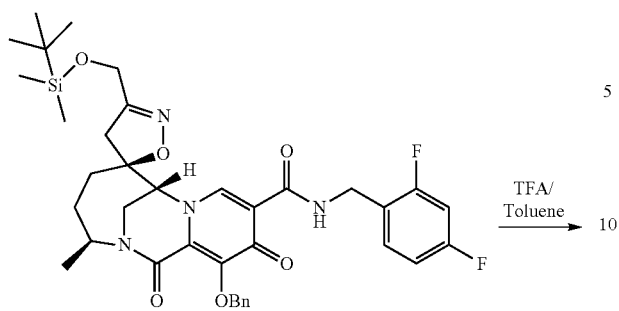

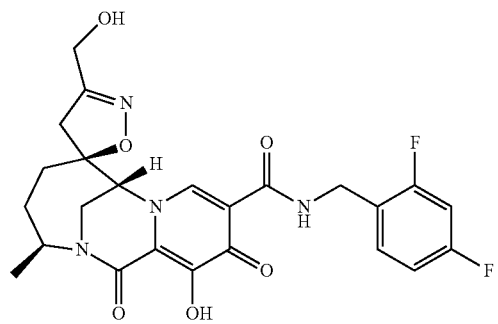

The title compound was prepared in a manner similar to Example 1, except using 2-((tert-butyldimethylsilyl)oxy)acetaldehyde oxime instead of acetaldehyde oxime in Step 1. MS (m/z) 503.154 [M+H]$^+$. $^1$H NMR (400 MHz, Chloroform-d) δ 10.63 (d, J=6.0 Hz, 1H), 8.62 (s, 1H), 7.44-7.32 (m, 1H), 6.91-6.71 (m, 2H), 4.73 (dd, J=14.8, 6.5 Hz, 2H), 4.65-4.49 (m, 2H), 4.37 (d, J=13.9 Hz, 1H), 4.28 (s, 1H), 3.87-3.78 (m, 1H), 3.66 (d, J=2.7 Hz, 1H), 3.14 (d, J=17.9 Hz, 1H), 2.67 (d, J=17.9 Hz, 1H), 2.12-1.96 (m, 3H), 1.78-1.65 (m, 1H), 1.32 (d, J=6.7 Hz, 3H).

Example 17: Preparation of (3'S,5S,7'R)—N-(2,4-difluorobenzyl)-3-(fluoromethyl)-12'-hydroxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

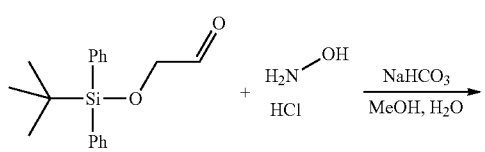

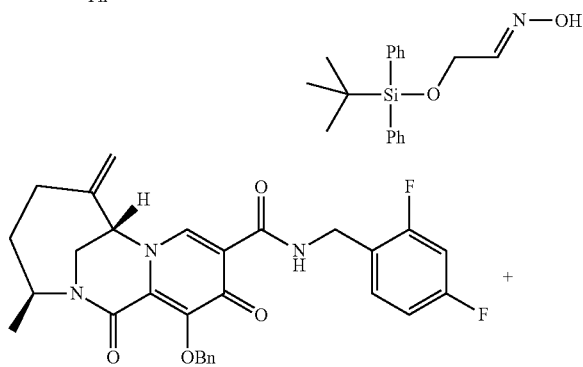

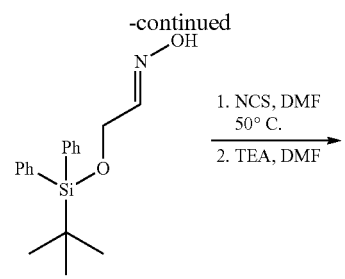

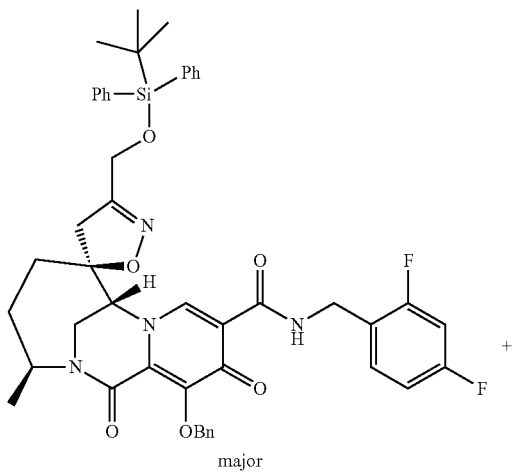

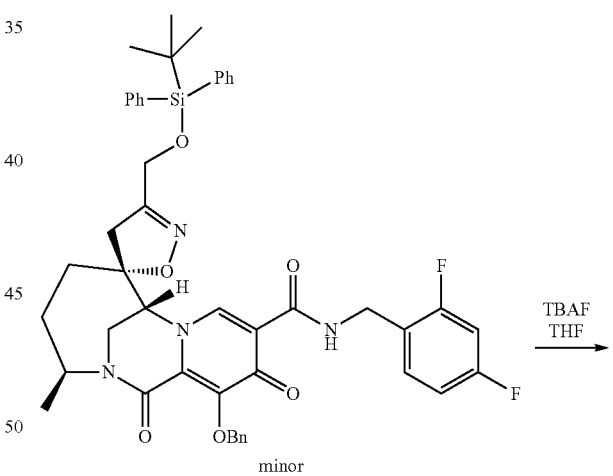

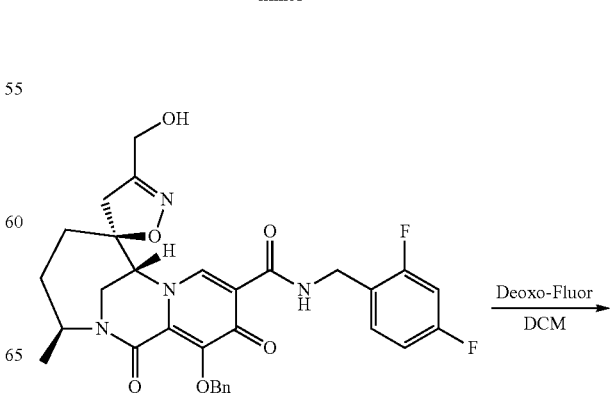

151

-continued

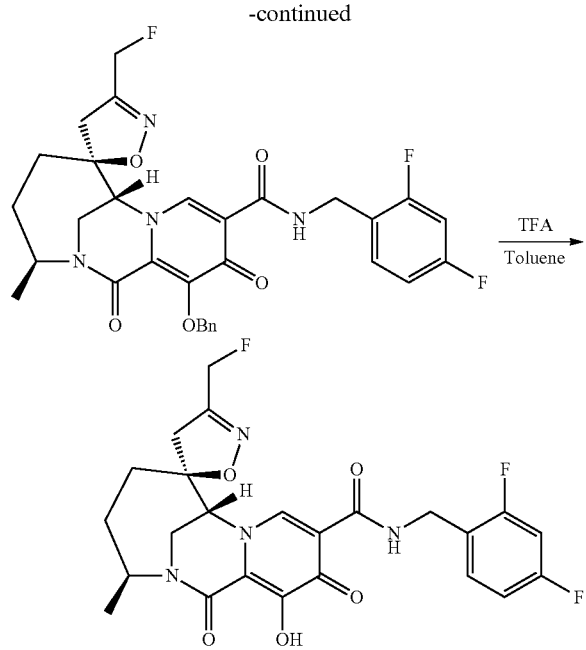

Step 1: Preparation of (E)-2-((tert-butyldiphenylsilyl)oxy)acetaldehyde oxime

To the solution of 2-[tert-butyl(diphenyl)silyl]oxyacetaldehyde (1 g, 3.35 mmol) in MeOH (15 ml) and H$_2$O (5 ml) was added hydroxylamine hydrochloride (0.28 g, 4.02 mmol) and followed by sodium bicarbonate (0.245 g, 4.02 mmol). The reaction mixture was stirred at room temperature for 2 hours. It was diluted with EtOAc and was washed with H$_2$O and brine. The organic phase was dried with MgSO$_4$ and solvent was removed in vacuo. The resulting residue was purified by silica gel chromatography to obtain the title compound. MS (m/z) 314.05 [M+H]+.

Step 2: Preparation of (3'S,5S,7'R)-12'-(benzyloxy)-3-(((tert-butyldiphenylsilyl)oxy)methyl)-N-(2,4-difluorobenzyl)-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide and (3'S,5R,7'R)-12'-(benzyloxy)-3-(((tert-butyldiphenylsilyl)oxy)methyl)-N-(2,4-difluorobenzyl)-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide The title compounds were prepared in a manner similar to Example 1, except using (E)-2-((tert-butyldiphenylsilyl)oxy)acetaldehyde oxime instead of acetaldehyde oxime. (3'S,5S,7'R)-12'-(benzyloxy)-3-(((tert-butyldiphenylsilyl)oxy)methyl)-N-(2,4-difluorobenzyl)-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide was obtained as the major stereoisomer and (3'S,5R,7'R)-12'-(benzyloxy)-3-(((tert-butyldiphenylsilyl)oxy)methyl)-N-(2,4-difluorobenzyl)-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide was obtained as the minor stereoisomer. MS (m/z) 831.12 [M+H]+(major); 831.13 [M+H]+(minor).

152

Step 3: Preparation of (3'S,5S,7'R)-12'-(benzyloxy)-N-(2,4-difluorobenzyl)-3-(hydroxymethyl)-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide To the solution of (3'S,5S,7'R)-12'-(benzyloxy)-3-(((tert-butyldiphenylsilyl)oxy)methyl)-N-(2,4-difluorobenzyl)-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (160 mg, 0.193 mmol) in THF (2 ml) was added TBAF (1N) (0.578 ml, 0.578 mmol). The reaction mixture was stirred at room temperature for 1 hour. It was diluted with EtOAc and was washed with NaHCO$_3$ (sat.) and brine. The organic phase was dried with MgSO$_4$, the solvent was removed in vacuo. The resulting residue was purified by silica gel chromatography to obtain the title compound. MS (m/z) 593.07 [M+H]+.

Step 4: Preparation of (3'S,5S,7'R)-12'-(benzyloxy)-N-(2,4-difluorobenzyl)-3-(fluoromethyl)-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide The title compound was prepared in a manner similar to Step 4 of Example 5, except using (3'S,5S,7'R)-12'-(benzyloxy)-N-(2,4-difluorobenzyl)-3-(hydroxymethyl)-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide instead of (3'S,4'R,5R,7'R)-12'-(benzyloxy)-N-(2,4-difluorobenzyl)-4'-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide. MS (m/z) 595.09 [M+H]+.

Step 5: Preparation of (3'S,5S,7'R)—N-(2,4-difluorobenzyl)-3-(fluoromethyl)-12'-hydroxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide The title compound was prepared in a manner similar to Step 2 of Example 1, except using (3'S,5S,7'R)-12'-(benzyloxy)-N-(2,4-difluorobenzyl)-3-(fluoromethyl)-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide instead of (3'S,5S,7'R)-12'-(benzyloxy)-N-(2,4-difluorobenzyl)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide. MS (m/z) 505.18 [M+H]+. $^1$H NMR (400 MHz, Chloroform-d) δ 10.49 (t, J=6.0 Hz, 1H), 8.50 (s, 1H), 7.38 (td, J=8.6, 6.4 Hz, 1H), 6.91-6.78 (m, 2H), 5.32 (s, 1H), 5.23 (s, 1H), 5.11 (s, 1H), 4.83-4.58 (m, 2H), 4.22 (s, 1H), 3.87 (dd, J=15.0, 1.8 Hz, 1H), 3.74 (dd, J=15.0, 2.6 Hz, 1H), 3.13 (dd, J=18.0, 2.1 Hz, 1H), 2.71 (dd, J=17.9, 2.4 Hz, 1H), 2.14-1.97 (m, 3H), 1.68-1.57 (m, 1H), 1.33 (d, J=6.7 Hz, 3H).

Example 18: Preparation of (3'S,5R,7'R)—N-(2,4-difluorobenzyl)-3-(fluoromethyl)-12'-hydroxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

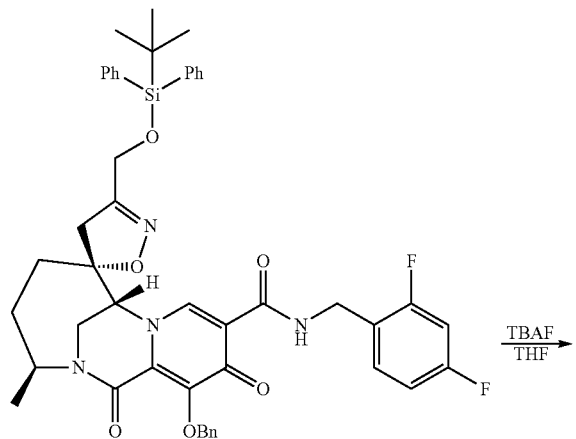

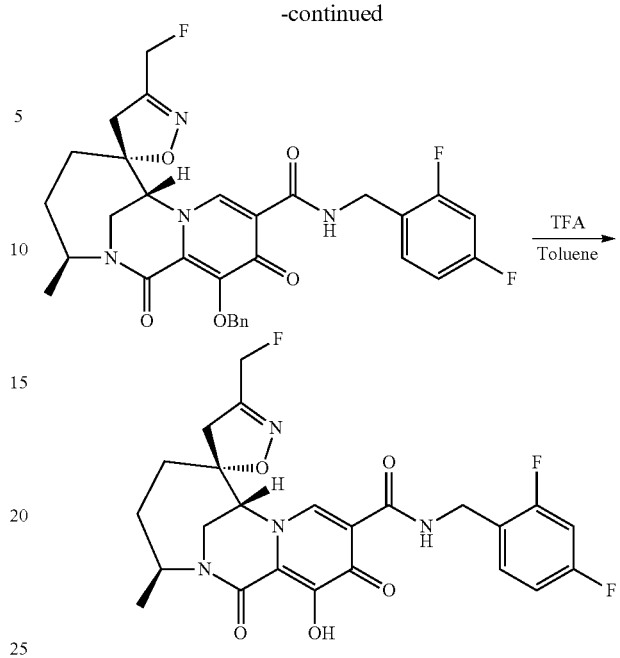

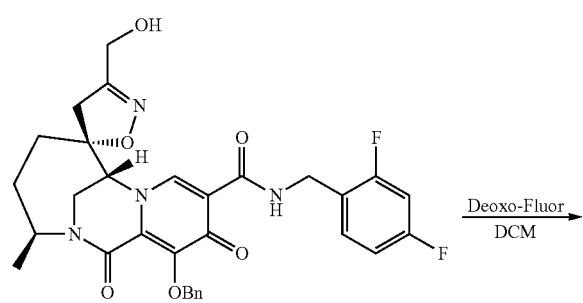

The title compound was prepared in a similar manner as (3'S,5S,7'R)—N-(2,4-difluorobenzyl)-3-(fluoromethyl)-12'-hydroxy-3'-methyl-1',11'-dioxo-1',4',5',11'-tetrahydro-3'H, 4H,7'H-spiro[isoxazole-5,6'-[2,7]methanopyrido[1,2-a][1,4]diazonine]-10'-carboxamide in Example 17, except using (3'S,5R,7'R)-12'-(benzyloxy)-3-(((tert-butyldiphenylsilyl)oxy)methyl)-N-(2,4-difluorobenzyl)-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide instead of (3'S,5S,7'R)-12'-(benzyloxy)-3-(((tert-butyldiphenylsilyl)oxy)methyl)-N-(2,4-difluorobenzyl)-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide in Step 3. MS (m/z) 505.18 [M+H]+. 1H NMR (400 MHz, Chloroform-d) δ 10.50 (t, J=6.0 Hz, 1H), 8.40 (s, 1H), 7.38 (q, J=8.1 Hz, 1H), 6.84 (q, J=9.0 Hz, 2H), 5.25 (s, 1H), 5.13 (s, 1H), 4.79 (dt, J=10.6, 6.7 Hz, 1H), 4.66 (d, J=5.8 Hz, 2H), 4.23 (s, 1H), 3.79 (dd, J=15.3, 3.1 Hz, 1H), 3.51-3.42 (m, 1H), 3.17 (d, J=16.8 Hz, 1H), 3.02 (d, J=17.2 Hz, 1H), 2.26 (dt, J=14.7, 7.0 Hz, 1H), 1.88 (dd, J=15.2, 7.4 Hz, 1H), 1.80-1.69 (m, 1H), 1.46-1.25 (m, 4H).

Example 19: Preparation of (3'S,5S,7'R)-3-(fluoromethyl)-12'-hydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

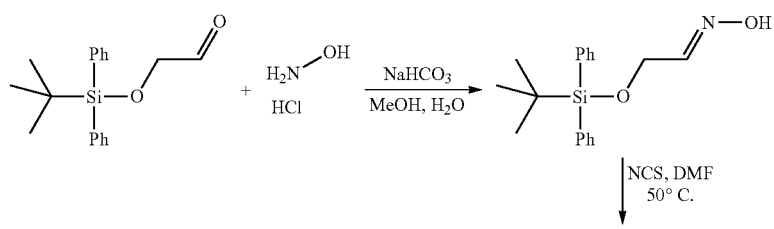

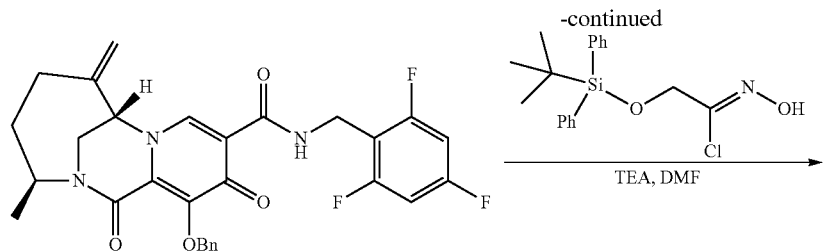

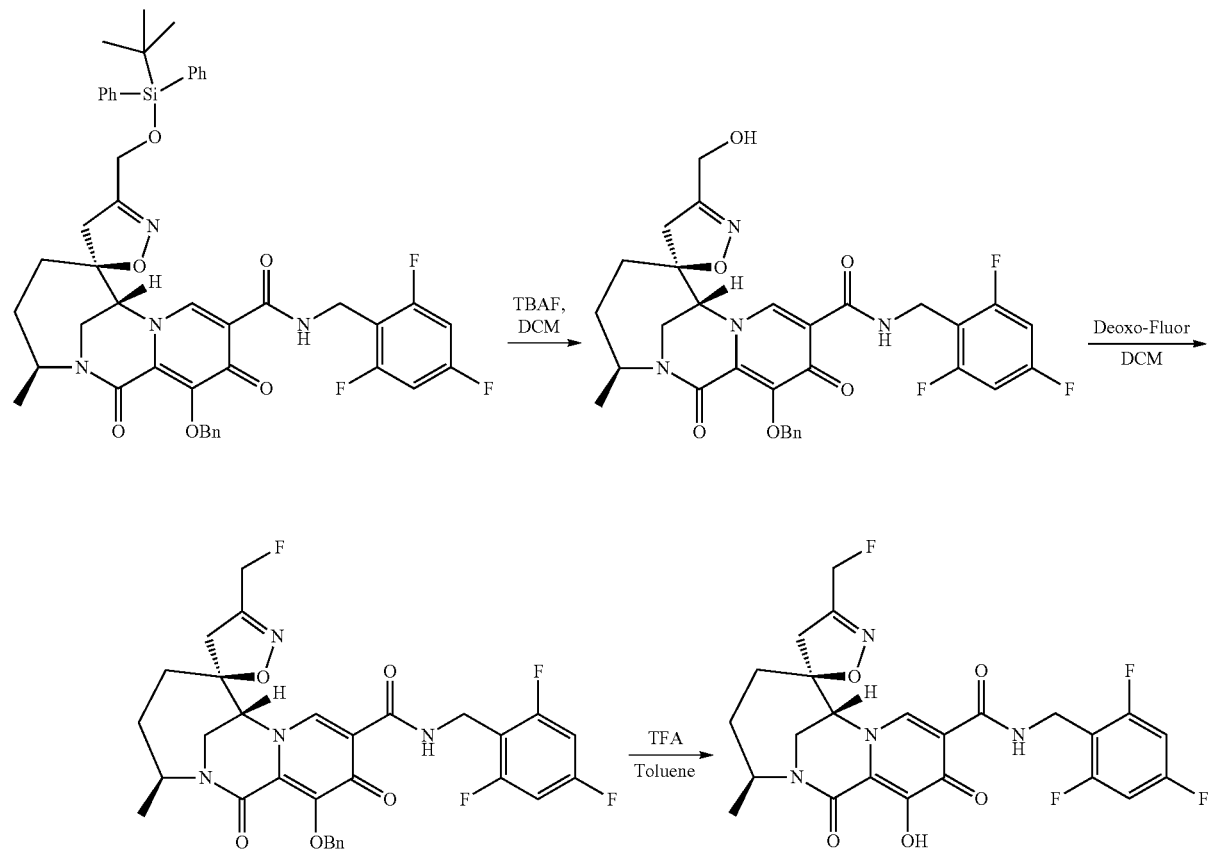

The title compound was prepared in a similar manner as (3'S,5S,7'R)—N-(2,4-difluorobenzyl)-3-(fluoromethyl)-12'-hydroxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide in Example 17, except using (3S,7S)-12-(benzyloxy)-3-methyl-6-methylene-1,11-dioxo-N-(2,4,6-trifluorobenzyl)-1,4,5,6,7,11-hexahydro-3H-2,7-methanopyrido[1,2-a][1,4]diazonine-10-carboxamide (Intermediate C) instead of (3S,7S)-12-(benzyloxy)-N-(2,4-difluorobenzyl)-3-methyl-6-methylene-1,11-dioxo-1,4,5,6,7,11-hexahydro-3H-2,7-methanopyrido[1,2-a][1,4]diazonine-10-carboxamide (Intermediate F) in Step 2. MS (m/z) 523.21 [M+H]+. 1H NMR (400 MHz, Chloroform-d) δ 10.41 (t, J=5.7 Hz, 1H), 8.52 (s, 1H), 6.81-6.57 (m, 2H), 5.16 (d, J=46.5 Hz, 2H), 4.76 (dt, J=12.0, 7.4 Hz, 2H), 4.63 (dd, J=14.5, 5.5 Hz, 1H), 4.26 (s, 1H), 3.86 (dd, J=15.0, 1.9 Hz, 1H), 3.73 (dd, J=15.0, 2.7 Hz, 1H), 3.23-3.05 (m, 1H), 2.70 (dd, J=17.8, 2.3 Hz, 1H), 2.09-1.89 (m, 3H), 1.72-1.51 (m, 1H), 1.33 (d, J=6.7 Hz, 3H).

Example 20: Preparation of (3'S,5S,7'R)-3-(difluoromethyl)-12'-hydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

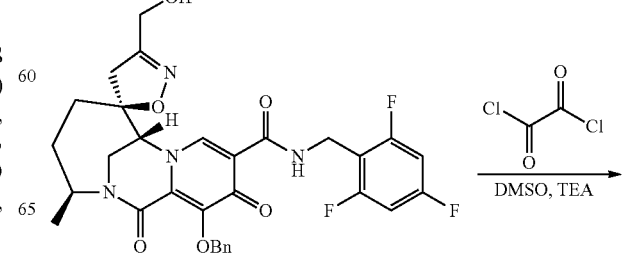

157
-continued

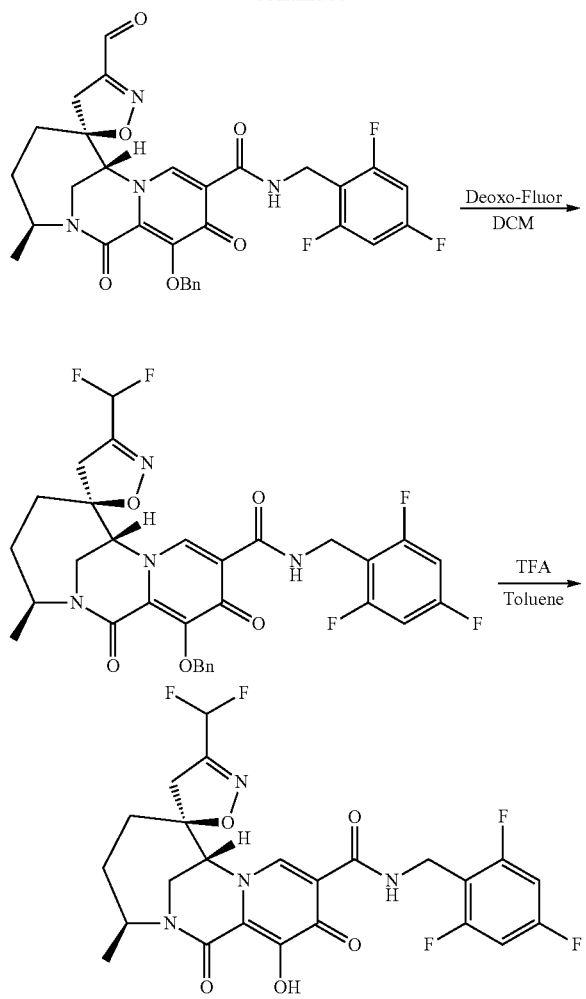

Step 1: Preparation of (3'S,5S,7'R)-12'-(benzyloxy)-3-formyl-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide To a mixture of DMSO (0.215 ml, 3.03 mmol) in DCM (2 ml) at −78° C. was added oxalyl chloride (0.118 ml, 1.39 mmol) dropwise. The mixture was stirred at −78° C. for 10 minutes, then followed by the dropwise addition of (3'S,5S,7'R)-12'-(benzyloxy)-3-(hydroxymethyl)-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (370 mg, 0.606 mmol), prepared according to Example 19, in DCM (2 mL). The resulting reaction mixture was stirred at −78° C. for 15 minutes. Triethylamine (0.426 ml, 3.03 mmol) was added to the reaction mixture and cooling bath was removed. Reaction mixture was stirred at room temperature for 30 minutes. EtOAc was added to dilute the reaction mixture, followed by H$_2$O and brine. The organic phase was dried with MgSO$_4$ and the solvent was removed under vacuo. The resulting residue was purified by silica gel chromatography to obtain the title compound. MS (m/z) 609.09 [M+H]+.

158

Step 2: Preparation of (3'S,5S,7'R)-12'-(benzyloxy)-3-(difluoromethyl)-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide The title compound was prepared in a similar manner as Step 4 of Example 5, except using (3'S,5S,7'R)-12'-(benzyloxy)-3-formyl-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide instead of (3'S,4'R,5R,7'R)-12'-(benzyloxy)-N-(2,4-difluorobenzyl)-4'-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide. MS (m/z) 631.13 [M+H]+.

Step 3: Preparation of (3'S,5S,7'R)-3-(difluoromethyl)-12'-hydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a1,4]diazonine]-10'-carboxamide The title compound was prepared in a manner similar to Step 5 of Example 5, except using (3'S,5S,7'R)-12'-(benzyloxy)-3-(difluoromethyl)-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide instead of (3'S,4'S,5R,7'R)-12'-(benzyloxy)-N-(2,4-difluorobenzyl)-4'-fluoro-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide. MS (m/z) 541.21 [M+H]+. 1H NMR (400 MHz, Chloroform-d) δ 10.55 (t, J=5.9 Hz, 1H), 8.95 (s, 1H), 6.68 (t, J=8.1 Hz, 2H), 6.57-6.30 (m, 1H), 4.89-4.73 (m, 3H), 4.50 (dd, J=14.7, 4.9 Hz, 1H), 3.87 (dd, J=15.1, 1.8 Hz, 1H), 3.78 (dd, J=15.0, 2.5 Hz, 1H), 3.22 (d, J=17.9 Hz, 1H), 2.66 (d, J=17.8 Hz, 1H), 2.02 (dq, J=20.9, 8.3, 6.4 Hz, 3H), 1.62 (dd, J=13.9, 11.0 Hz, 1H), 1.34 (d, J=6.6 Hz, 3H).

Example 21: Preparation of (3'S,5S,7'R)—N-(2,4-difluorobenzyl)-3-(difluoromethyl)-12'-hydroxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

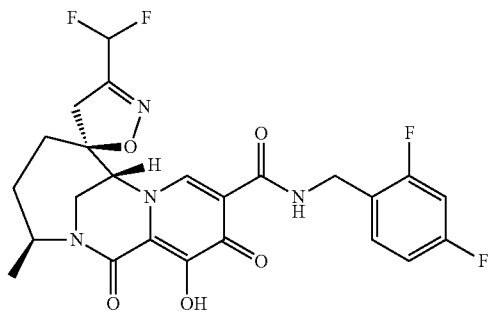 [SMILES: C[C@H]1CC[C@]2(CC(C(F)F)=NO2)[C@H]2CN1C(=O)c1c(O)c(=O)c(C(=O)NCc3ccc(F)cc3F)cn12]

The title compound was prepared in a manner similar to Example 20, except using (3'S,5S,7'R)-12'-(benzyloxy)-N-(2,4-difluorobenzyl)-3-(hydroxymethyl)-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'- carboxamide instead of (3'S,5S,7'R)-12'-(benzyloxy)-3-(hydroxymethyl)-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide in Step 1. MS (m/z) 523.10 [M+H]+. 1H NMR (400 MHz, Chloroform-d) δ 10.59 (t, J=5.8 Hz, 1H), 8.85 (s, 1H), 7.36 (q, J=8.1 Hz, 1H), 6.92-6.79 (m, 2H), 6.61-6.34 (m, 1H), 4.83-4.60 (m, 3H), 4.50 (s, 1H), 3.87 (dd, J=15.0, 1.7 Hz, 1H), 3.77 (dd, J=15.0, 2.5 Hz, 1H), 3.19 (d, J=17.9 Hz, 1H), 2.71 (d, J=17.9 Hz, 1H), 2.16-1.96 (m, 3H), 1.70-1.58 (m, 1H), 1.34 (d, J=6.6 Hz, 3H).

Example 22: Preparation of (3'S,5S,7'R)—N-(2,4-difluorobenzyl)-12'-hydroxy-3-(methoxymethyl)-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

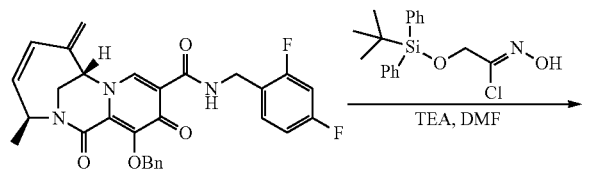

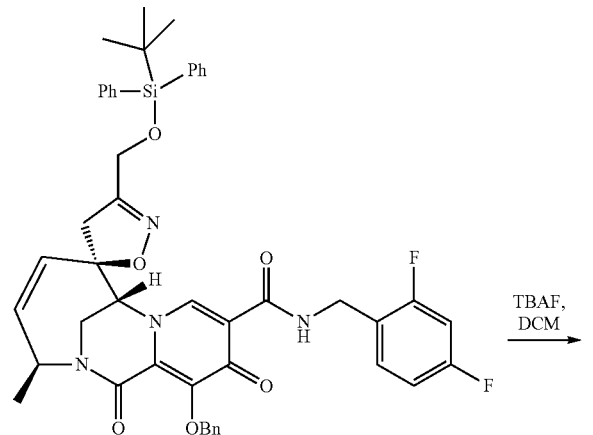

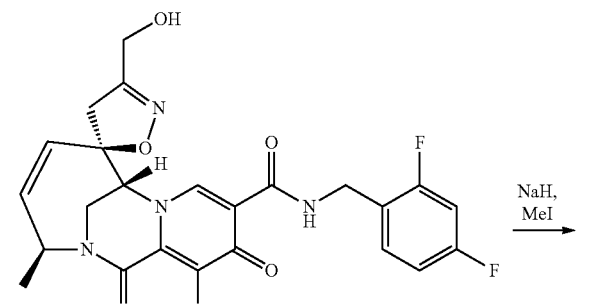

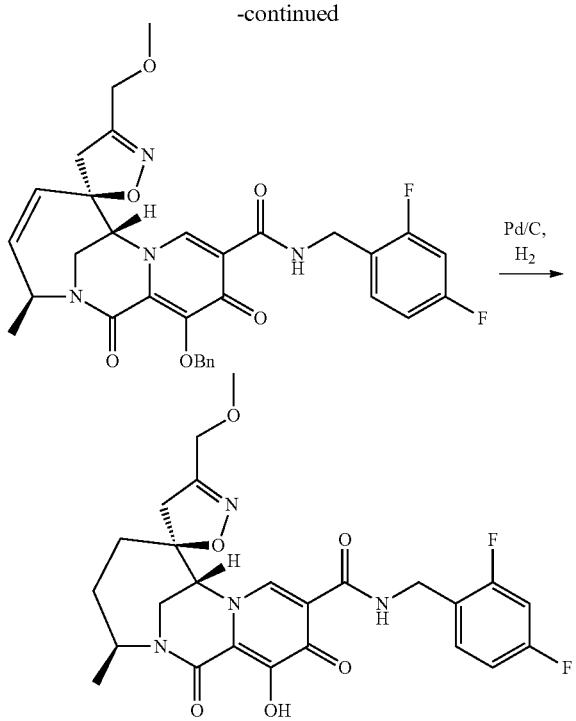

Step 1: Preparation of (3'S,5R,7'R)-12'-(benzyloxy)-3-(((tert-butyldiphenylsilyl)oxy)methyl)-N-(2,4-difluorobenzyl)-3'-methyl-1',11'-dioxo-1',11'-dihydro-3'H,4H,7'H-spiro[isoxazole-5,6'-[2,7]methanopyrido[1,2-a][1,4]diazonine]-10'-carboxamide The title compound was prepared in a manner similar to Steps 1-2 of Example 17, except using (3S,7S)-12-(benzyloxy)-N-(2,4-difluorobenzyl)-3-methyl-6-methylene-1,11-dioxo-1,6,7,11-tetrahydro-3H-2,7-methanopyrido[1,2-a][1,4]diazonine-10-carboxamide (Intermediate G) instead of (3S,7S)-12-(benzyloxy)-N-(2,4-difluorobenzyl)-3-methyl-6-methylene-1,11-dioxo-1,4,5,6,7,11-hexahydro-3H-2,7-methanopyrido[1,2-a][1,4]diazonine-10-carboxamide (Intermediate F). MS (m/z) 829.12 [M+H]+.

Step 2: Preparation of (3'S,5R,7'R)-12'-(benzyloxy)-N-(2,4-difluorobenzyl)-3-(hydroxymethyl)-3'-methyl-1',11'-dioxo-1',11'-dihydro-3'H,4H,7'H-spiro[isoxazole-5,6'-[2,7]methanopyrido[1,2-a][1,4]diazonine]-10'-carboxamide The title compound was prepared in a manner similar to Step 3 of Example 17, except using (3'S,5R,7'R)-12'-(benzyloxy)-3-(((tert-butyldiphenylsilyl)oxy)methyl)-N-(2,4-difluorobenzyl)-3'-methyl-1',11'-dioxo-1',11'-dihydro-3'H,4H,7'H-spiro[isoxazole-5,6'-[2,7]methanopyrido[1,2-a][1,4]diazonine]-10'-carboxamide instead of (3'S,5S,7'R)-12'-(benzyloxy)-3-(((tert-butyldiphenylsilyl)oxy)methyl)-N-(2,4-difluorobenzyl)-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide. MS (m/z) 591.13 [M+H]+.

Step 3: Preparation of (3'S,5R,7'R)-12'-(benzyloxy)-N-(2,4-difluorobenzyl)-3-(methoxymethyl)-3'-methyl-1',11'-dioxo-1',11'-dihydro-3'H,4H,7'H-spiro[isoxazole-5,6'-[2,7]methanopyrido[1,2-a][1,4]diazonine]-10'-carboxamide To the solution of (3'S,5R,7'R)-12'-(benzyloxy)-N-(2,4-difluorobenzyl)-3-(hydroxymethyl)-3'-methyl-1',11'-dioxo-1',11'-dihydro-3'H,4H,7'H-spiro[isoxazole-5,6'-[2,7]methanopyrido[1,2-a][1,4]diazonine]-10'-carboxamide (41 mg, 0.0694 mmol) in DMF (2 ml) was added NaH (60% in mineral oil) (5.4 mg, 0.14 mmol) followed by MeI (0.004 ml, 0.0694 mmol) at 0° C. The mixture was stirred at room temperature for 2 hours. The reaction mixture was diluted with EtOAc and was washed with H₂O and brine. The organic phase was dried with MgSO₄ and the solvent was removed in vacuo. The resulting residue was purified by silica gel column chromatography to obtain the title compound. MS (m/z) 605.09 [M+H]+.

Step 4: Preparation of (3'S,5S,7'R)—N-(2,4-difluorobenzyl)-12'-hydroxy-3-(methoxymethyl)-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide A mixture of (3'S,5R,7'R)-12'-(benzyloxy)-N-(2,4-difluorobenzyl)-3-(methoxymethyl)-3'-methyl-1',11'-dioxo-1',11'-dihydro-3'H,4H,7'H-spiro[isoxazole-5,6'-[2,7]methanopyrido[1,2-a][1,4]diazonine]-10'-carboxamide (27 mg, 0.045 mmol) and 10% Pd/C (3.8 mg) in EtOH (2 mL) was stirred at rt under 1 atm of H₂ (g). After 2 h, the reaction mixture was filtered, concentrated, and purified by reverse phase prep HPLC (5-100% MeCN/water with 0.1% TFA) to afford the title compound. MS (m/z) 517.19 [M+H]+. 1H NMR (400 MHz, Chloroform-d) δ 10.37 (s, 1H), 8.39 (s, 1H), 7.39 (q, J=8.2, 7.6 Hz, 1H), 6.84 (q, J=8.1, 7.6 Hz, 2H), 4.80-4.59 (m, 2H), 4.25 (d, J=12.3 Hz, 1H), 4.19 (d, J=12.3 Hz, 1H), 4.10 (s, 1H), 3.91-3.82 (m, 1H), 3.70 (dd, J=14.8, 2.7 Hz, 1H), 3.45 (s, 3H), 3.03 (d, J=17.9 Hz, 1H), 2.65 (d, J=17.9 Hz, 1H), 2.12-1.95 (m, 3H), 1.69-1.58 (m, 2H), 1.32 (d, J=6.7 Hz, 3H).

Example 23: Preparation of (3'S,5R,7'R)—N-(2,4-difluorobenzyl)-12'-hydroxy-3,3',4-trimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

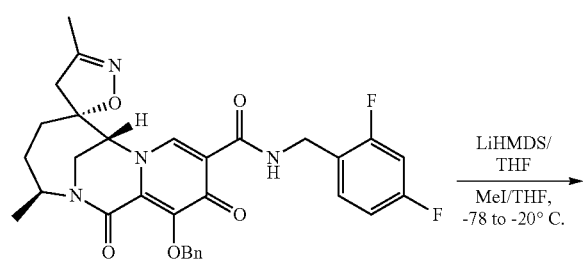

Step 1: Preparation of (3'S,5R,7'R)-12'-(benzyloxy)-N-(2,4-difluorobenzyl)-3,3',4-trimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide and (3'S,5S,7'R)-12'-(benzyloxy)-N-(2,4-difluorobenzyl)-4-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

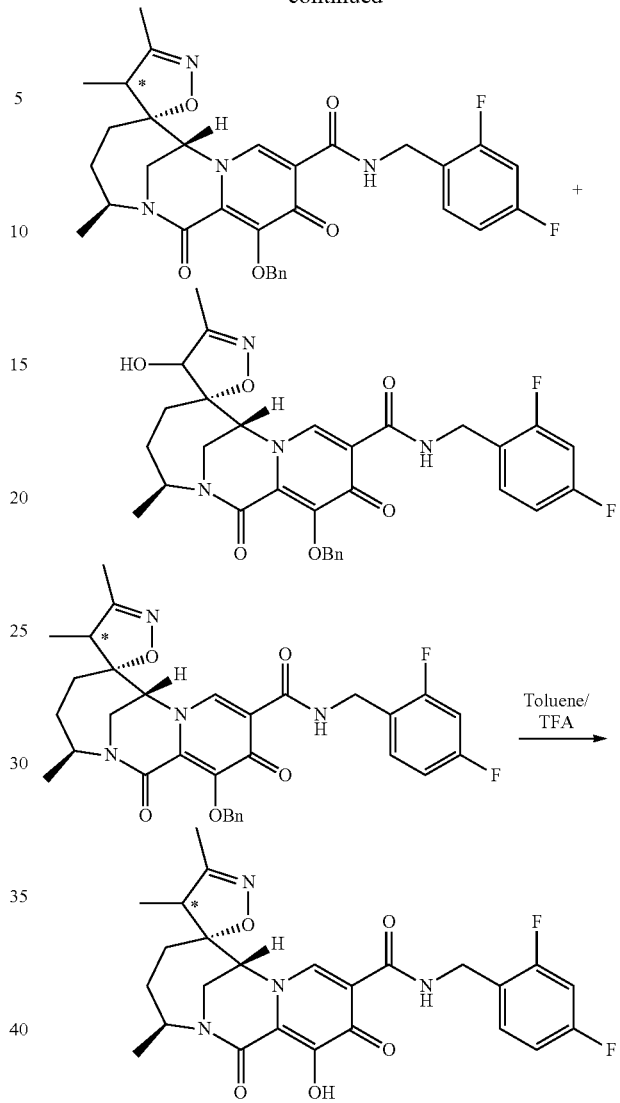

Into the solution of (3'S,5R,7'R)-12'-(benzyloxy)-N-(2,4-difluorobenzyl)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (43 mg, 0.075 mmol), prepared according to Example 1, in THF (10 ml) was added 1 M solution of LiHMDS in THF (0.373 ml) at −78° C. After 30 min., a solution MeI in THF (12.7 mg in 2 ml) was added at −78° C., then warmed to −20° C. After 2 h, the reaction was quenched by adding sat. NH₄Cl solution. The mixture was extracted with EtOAc, the organic phase was separated and dried over MgSO₄, filtered, concentrated down and purified by silica gel chromatography column (eluting with 0-5% MeOH/EtOAc) to give the title compounds. MS (m/z) 591.138 [M+H]+, and MS (m/z) 593.189 [M+H]+.

Step 2: Preparation of (3'S,5R,7'R)—N-(2,4-difluorobenzyl)-12'-hydroxy-3,3',4-trimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide To a solution of (3'S,5R,7'R)-12'-(benzyloxy)-N-(2,4-difluorobenzyl)-3,3',4-trimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (14 mg, 0.024 mmol) in toluene (1 mL) was added TFA (0.3 mL). The reaction mixture was stirred at rt overnight. The reaction mixture was concentrated down, and the residue was purified by reverse phase HPLC, eluting with 10-90% acetonitrile in water to give title compound. MS (m/z) 501.282 [M+H]+. $^1$H NMR (400 MHz, Chloroform-d) δ 10.53 (s, 1H), 8.29 (s, 1H), 7.45-7.33 (m, 1H), 6.84 (q, J=9.6, 9.0 Hz, 2H), 4.65 (t, J=5.5 Hz, 3H), 4.10 (s, 1H), 3.76 (dd, J=15.3, 3.1 Hz, 1H), 3.59-3.49 (m, 1H), 2.76 (d, J=7.1 Hz, 1H), 2.31-2.20 (m, 1H), 2.08 (s, 3H), 1.99 (dd, J=15.6, 7.9 Hz, 1H), 1.58 (dd, J=15.6, 11.6 Hz, 1H), 1.47-1.35 (m, 1H), 1.31 (d, J=6.6 Hz, 3H), 1.21 (d, J=7.1 Hz, 3H).

Example 24: Preparation of (3'S,5S,7'R)—N-(2,4-difluorobenzyl)-4,12'-dihydroxy-3,3'-dimethyl-1',11'-dioxo-1',4',5',11'-tetrahydro-3' H,4H,7'H-spiro[isoxazole-5,6'-[2,7]methanopyrido[1,2-a][1,4]diazonine]-10'-carboxamide

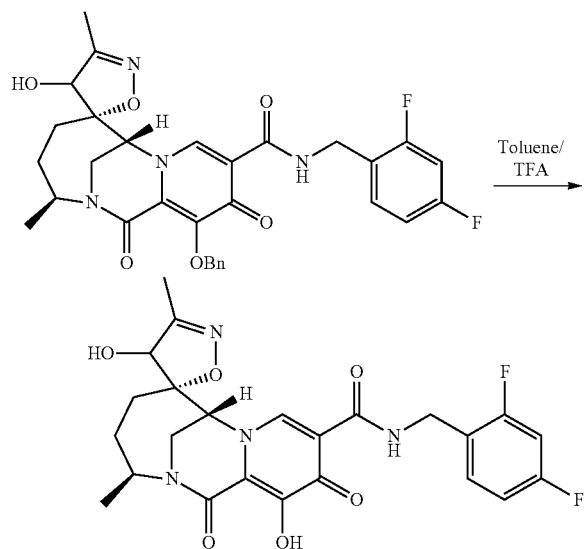

To a solution of (3'S,5S,7'R)-12'-(benzyloxy)-N-(2,4-difluorobenzyl)-4-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (14 mg, 0.024 mmol), prepared according to Example 23, in toluene (1 mL) was added TFA (0.3 mL). The reaction mixture was stirred at rt overnight. The reaction mixture was concentrated down, and the residue was purified by reverse phase HPLC, eluting with 10-90% acetonitrile in water to give title compound. MS (m/z) 503.265 [M+H]+. $^1$H NMR (400 MHz, Chloroform-d) δ 10.91 (s, 1H), 8.33 (s, 1H), 7.32 (d, J=6.8 Hz, 1H), 6.92-6.77 (m, 2H), 4.89 (s, 1H), 4.80 (s, 1H), 4.72 (d, J=7.1 Hz, 1H), 4.62 (td, J=13.3, 11.4, 5.8 Hz, 2H), 3.70-3.51 (m, 2H), 2.10 (d, J=7.1 Hz, 4H), 1.66 (s, 3H), 1.30 (d, J=6.6 Hz, 3H).

Example 25: Preparation of (3'S,5S,7'R)—N-(2,4-difluorobenzyl)-12'-hydroxy-3,3'-dimethyl-1',4,11'-trioxo-1',4',5',11'-tetrahydro-3'H,4H,7'H-spiro[isoxazole-5,6'-[2,7]methanopyrido[1,2-a][1,4]diazonine]-10'-carboxamide

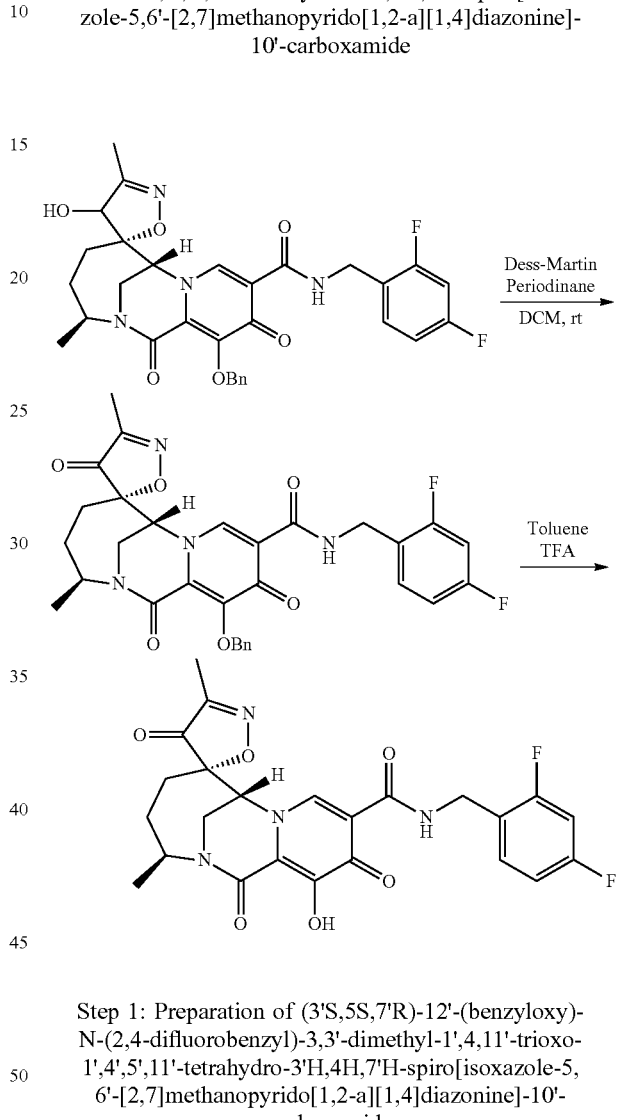

Step 1: Preparation of (3'S,5S,7'R)-12'-(benzyloxy)-N-(2,4-difluorobenzyl)-3,3'-dimethyl-1',4,11'-trioxo-1',4',5',11'-tetrahydro-3'H,4H,7'H-spiro[isoxazole-5,6'-[2,7]methanopyrido[1,2-a][1,4]diazonine]-10'-carboxamide Into the solution of (3'S,5S,7'R)-12'-(benzyloxy)-N-(2,4-difluorobenzyl)-4-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (9 mg, 0.0152 mmol), prepared according to Example 23, in DCM (3 ml) was added 1,1,1-triacetoxy-1,1-dihydro-1,2-benziodoxol-3-(1H)-one (Dess-Martin Periodinane) (10 mg, 0.023 mmol) at rt. The reaction was quenched by adding sat. NaHCO$_3$ and Na$_2$SO$_3$ solution. The mixture was extracted with EtOAc, the organic phase was separated and dried over MgSO$_4$, filtered, concentrated down and purified by silica gel column chromatography (eluting with 50-100% EtOAc/Hexane) to give the title compound. MS (m/z) 590.906 [M+H]+.

Step 2: Preparation of (3'S,5S,7'R)—N-(2,4-difluorobenzyl)-12'-hydroxy-3,3'-dimethyl-1',4,11'-trioxo-1',4',5',11'-tetrahydro-3'H,4H,7'H-spiro[isoxazole-5,6'-[2,7]methanopyrido[1,2-a][1,4]diazonine]-10'-carboxamide To a solution of (3'S,5S,7'R)-12'-(benzyloxy)-N-(2,4-difluorobenzyl)-3,3'-dimethyl-1',4,11'-trioxo-1',4',5',11'-tetrahydro-3'H,4H,7'H-spiro[isoxazole-5,6'-[2,7]methanopyrido[1,2-a][1,4]diazonine]-10'-carboxamide (8.97 mg, 0.0152 mmol) in toluene (1 mL) was added TFA (0.3 mL). The reaction mixture was stirred at rt overnight. The reaction mixture was concentrated down, and the residue was purified by reverse phase HPLC, eluting with 10-90% acetonitrile in water to give title compound. MS (m/z) 500.995 [M+H]+. 1H NMR (400 MHz, Chloroform-d) δ 10.42 (s, 1H), 8.37 (s, 1H), 7.38 (q, J=8.1 Hz, 1H), 6.84 (q, J=9.1, 8.6 Hz, 2H), 4.81 (s, 1H), 4.65 (d, J=5.8 Hz, 1H), 4.13-3.99 (m, 2H), 3.74 (dd, J=15.3, 2.8 Hz, 1H), 2.19 (s, 3H), 2.12 (d, J=15.4 Hz, 1H), 1.94-1.85 (m, 3H), 1.66-1.59 (m, 1H), 1.38 (d, J=6.7 Hz, 3H).

Example 26: Preparation of (3'S,4S,5S,7'R)—N-(2,4-difluorobenzyl)-12'-hydroxy-3,3',4-trimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

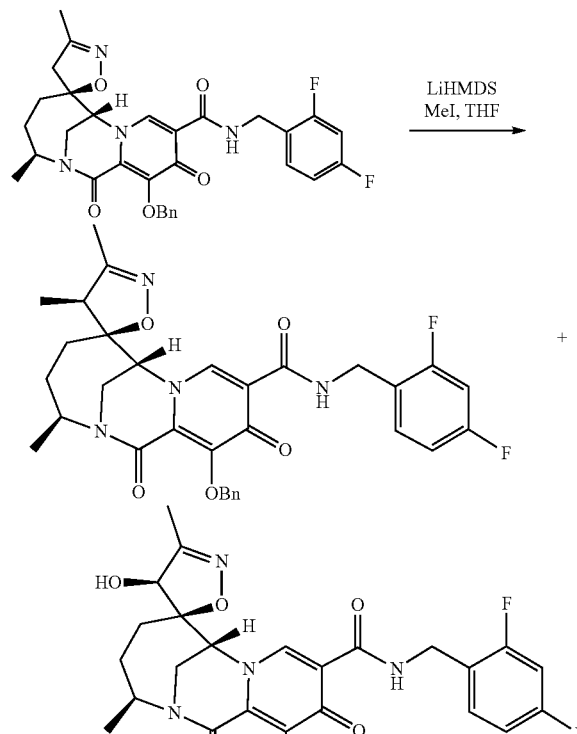

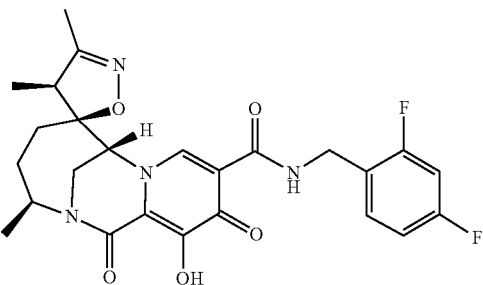

(3'S,4S,5S,7'R)—N-(2,4-difluorobenzyl)-12'-hydroxy-3,3',4-trimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide was prepared in a manner similar to Example 23, except using (3'S,4S,5S,7'R)-12'-(benzyloxy)-N-(2,4-difluorobenzyl)-3,3',4-trimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide instead of (3'S,5S,7'R)-12'-(benzyloxy)-N-(2,4-difluorobenzyl)-3,3',4-trimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide in Step 2. MS (m/z) 501.193 [M+H]+. 1H NMR (400 MHz, Chloroform-d) δ 10.47 (s, 1H), 8.40 (s, 1H), 7.47-7.34 (m, 1H), 6.93-6.75 (m, 2H), 4.69 (dt, J=14.6, 6.8 Hz, 3H), 4.18 (s, 1H), 3.85 (dd, J=14.9, 1.9 Hz, 1H), 3.76-3.61 (m, 1H), 3.18 (d, J=7.3 Hz, 1H), 2.12-1.87 (m, 6H), 1.32 (d, J=6.7 Hz, 3H), 1.23 (dd, J=14.5, 11.1 Hz, 1H), 0.82 (d, J=7.3 Hz, 3H).

Example 27: Preparation of (3'S,4S,5R,7'R)—N-(2,4-difluorobenzyl)-4-fluoro-12'-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (peak 1) and (3'S,4R,5R,7'R)—N-(2,4-difluorobenzyl)-4-fluoro-12'-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (peak 2)

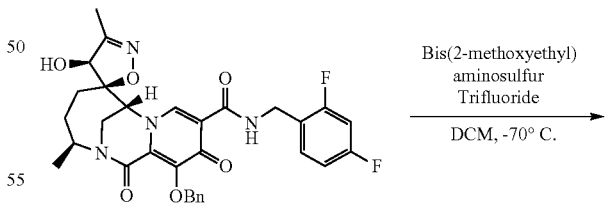

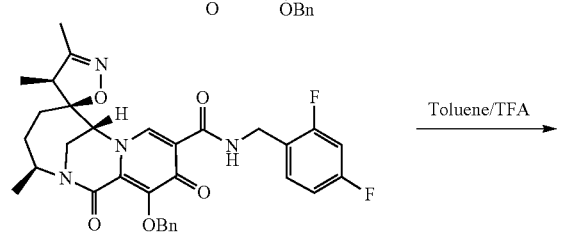

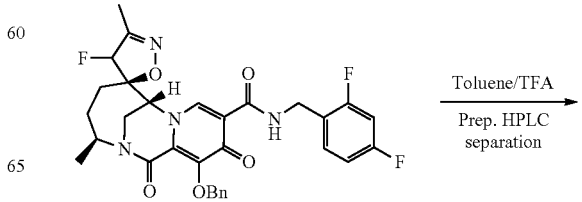

-continued

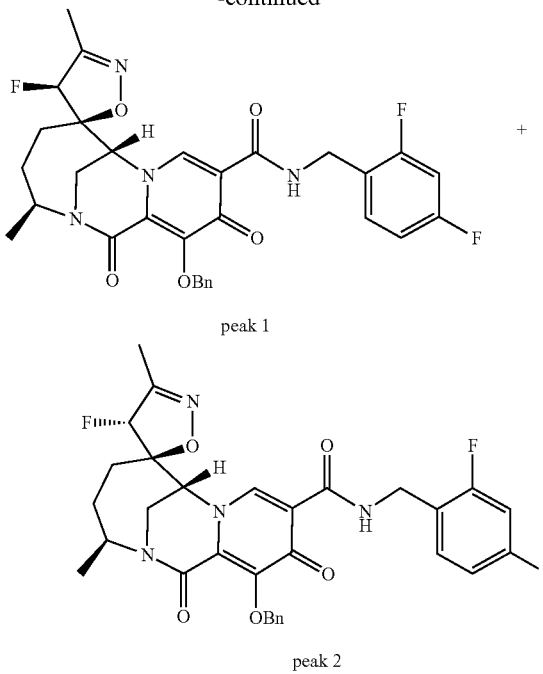

peak 1 peak 2

Step 1: Preparation of (3'S,5S,7'R)-12'-(benzyloxy)-N-(2,4-difluorobenzyl)-4-fluoro-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide Into the solution of (3'S,5S,7'R)-12'-(benzyloxy)-N-(2,4-difluorobenzyl)-4-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (82 mg, 0.138 mmol), prepared according to Example 26, in DCM (4 ml) was added bis(2-methoxyethyl)aminosulfur trifluoride (153 mg, 0.692 mmol) at 0° C. After 30 min, the reaction was quenched by adding sat. NaHCO$_3$ solution. The mixture was extracted with EtOAc, the organic phase was separated and dried over MgSO$_4$, filtered, concentrated down and purified by silica gel chromatography column (eluting with 0-100% EtOAc/hexane) to give the title compound as a mixture of stereoisomers. MS (m/z) 595.046

Step 2: Preparation of (3'S,5S,7'R)—N-(2,4-difluorobenzyl)-4-fluoro-12'-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide To a solution of the mixture of (3'S,5S,7'R)-12'-(benzyloxy)-N-(2,4-difluorobenzyl)-4-fluoro-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (25.1 mg, 0.0422 mmol) in toluene (2 mL) was added TFA (1 mL). The reaction mixture was stirred at rt overnight. The reaction mixture was concentrated down, and the residue was separated and purified by reverse phase prep HPLC, eluting with 10-90% acetonitrile in water, to give title compounds.

Peak 1: MS (m/z) 505.173 [M+H]$^+$. $^1$H NMR (400 MHz, Chloroform-d) δ 10.33 (d, J=5.9 Hz, 1H), 8.61 (d, J=6.2 Hz, 1H), 7.44-7.33 (m, 1H), 6.83 (q, J=7.9 Hz, 2H), 5.03 (d, J=53.7 Hz, 1H), 4.84 (d, J=10.5 Hz, 1H), 4.75-4.54 (m, 3H), 3.81 (dd, J=4.2, 2.3 Hz, 2H), 2.18 (d, J=3.3 Hz, 3H), 2.09-1.98 (m, 3H), 1.54 (dd, J=15.8, 6.2 Hz, 1H), 1.33 (d, J=6.7 Hz, 3H).

Peak 2: MS (m/z) 505.154 [M+H]$^+$. $^1$H NMR (400 MHz, Chloroform-d) δ 10.50 (d, J=5.9 Hz, 1H), 8.33 (s, 1H), 7.38 (q, J=8.4, 8.0 Hz, 1H), 6.92-6.78 (m, 2H), 5.34 (d, J=53.8 Hz, 1H), 4.85-4.59 (m, 3H), 3.93 (dd, J=14.9, 1.8 Hz, 1H), 3.87 (s, 1H), 3.75 (d, J=14.7 Hz, 1H), 2.21 (d, J=2.5 Hz, 3H), 2.19-2.15 (m, 1H), 2.12 (d, J=7.0 Hz, 1H), 2.06-1.99 (m, 1H), 1.53-1.44 (m, 1H), 1.35 (d, J=6.6 Hz, 3H).

Example 28: Preparation of (3'S,4S,5R,7'R)—N-(2,4-difluorobenzyl)-4,12'-dihydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

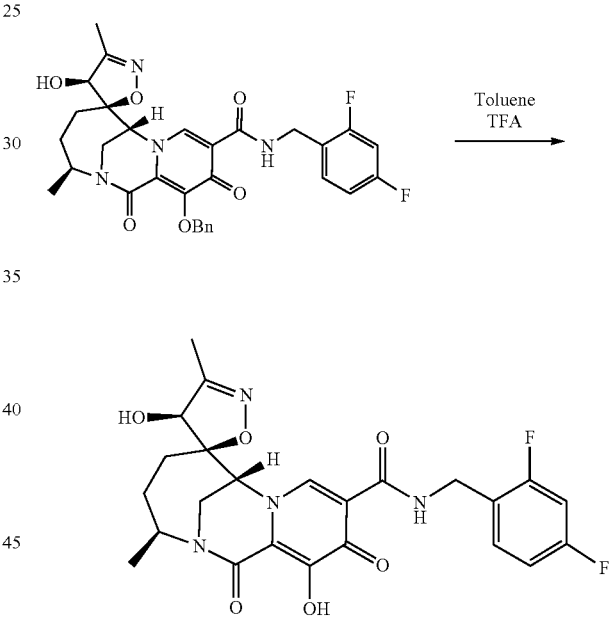

The title compound was prepared in a manner similar to Example 24, except using (3'S,4S,5R,7'R)-12'-(benzyloxy)-N-(2,4-difluorobenzyl)-4-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide, prepared according to Example 26, instead of (3'S,5S,7'R)-12'-(benzyloxy)-N-(2,4-difluorobenzyl)-4-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide. MS (m/z) 503.299 [M+H]$^+$. $^1$H NMR (400 MHz, Chloroform-d) δ 11.60 (s, 1H), 9.95-9.84 (m, 1H), 8.33 (s, 1H), 7.40 (q, J=8.3, 7.8 Hz, 1H), 6.86 (dt, J=10.2, 6.9 Hz, 2H), 5.16 (s, 1H), 4.86 (td, J=14.8, 7.2 Hz, 2H), 4.40 (dd, J=14.9, 3.9 Hz, 1H), 3.98-3.84 (m, 2H), 3.66 (dd, J=14.6, 2.7 Hz, 1H), 2.29 (dd, J=16.4, 6.3 Hz, 1H), 2.10 (s, 3H), 2.08-1.94 (m, 2H), 1.31 (d, J=6.6 Hz, 3H), 0.93 (q, J=7.5 Hz, 1H).

Example 29: Preparation of (3'S,5R,7'R)—N-(2,4-difluorobenzyl)-12'-hydroxy-3,3'-dimethyl-1',4,11'-trioxo-1',4',5',11'-tetrahydro-3'H,4H,7'H-spiro[isoxazole-5,6'-[2,7]methanopyrido[1,2-a][1,4]diazonine]-10'-carboxamide

Example 30: Preparation of (3'S,4R,5R,7'R)—N-(2,4-difluorobenzyl)-4,12'-dihydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

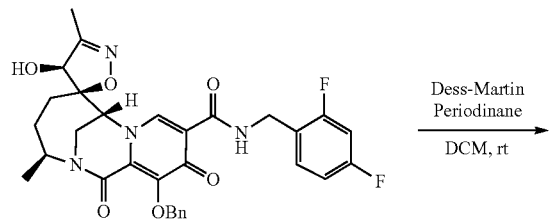

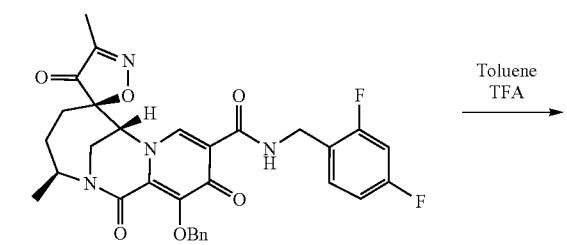

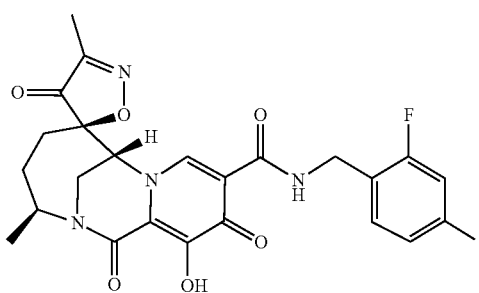

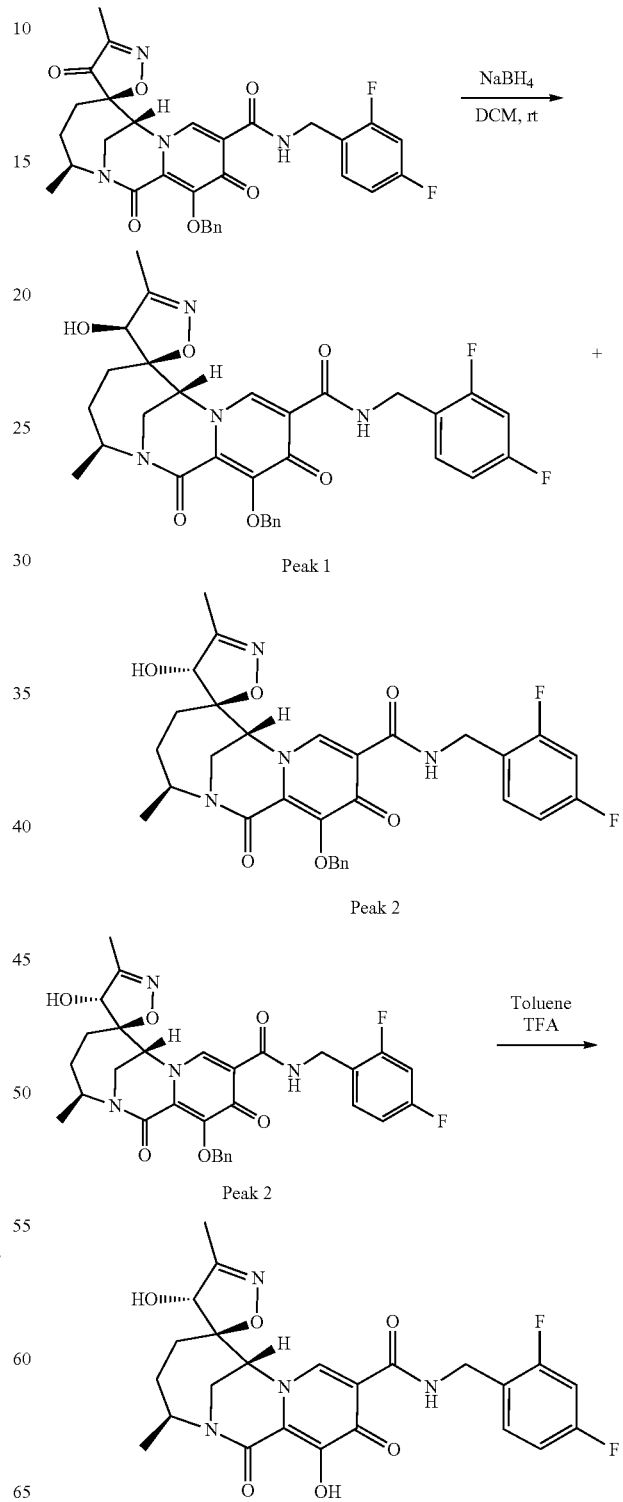

The title compound was prepared in a manner similar to Example 25, except using (3'S,4S,5R,7'R)-12'-(benzyloxy)-N-(2,4-difluorobenzyl)-4-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide, prepared according to Example 26, instead of (3'S,5S,7'R)-12'-(benzyloxy)-N-(2,4-difluorobenzyl)-4-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide. MS (m/z) 500.97 [M+H]$^+$. $^1$H NMR (400 MHz, Chloroform-d) δ 10.46 (s, 1H), 8.13 (s, 1H), 7.42-7.33 (m, 1H), 6.84 (q, J=9.4, 8.7 Hz, 2H), 4.81 (dd, J=11.3, 6.1 Hz, 1H), 4.73 (dd, J=15.4, 6.2 Hz, 1H), 4.55 (dd, J=15.4, 5.4 Hz, 1H), 4.22 (s, 1H), 3.95-3.78 (m, 2H), 2.18 (s, 3H), 2.14-2.05 (m, 2H), 1.63 (t, J=5.1 Hz, 2H), 1.37 (d, J=6.6 Hz, 3H).

Step 1: Preparation of (3'S,4S,5R,7'R)-12'-(benzyloxy)-N-(2,4-difluorobenzyl)-4-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (peak 1) and (3'S,4R,5R,7'R)-12'-(benzyloxy)-N-(2,4-difluorobenzyl)-4-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (peak 2)

Into the solution of (3'S,5R,7'R)-12'-(benzyloxy)-N-(2,4-difluorobenzyl)-3,3'-dimethyl-1',4,11'-trioxo-1',4',5',11'-tetrahydro-3'H,4H,7'H-spiro[isoxazole-5,6'-[2,7]methanopyrido[1,2-a][1,4]diazonine]-10'-carboxamide (25 mg, 0.0423 mmol), prepared according to Example 29, in DCM (3 ml) was added sodium borohydride (2.4 mg, 0.064 mmol) at rt. After completion, the reaction was quenched by adding sat. NaHCO₃ solution. The mixture was extracted with EtOAc, the organic phase was separated and dried over MgSO₄, filtered, concentrated down and purified by silica gel column chromatography (eluting with 20-100% EtOAc/Hexane) to give the title compounds as peak 1 and peak 2. MS (m/z) 593.101 [M+H]+.

Step 2: Preparation of (3'S,4R,5R,7'R)—N-(2,4-difluorobenzyl)-4,12'-dihydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide The title compound was prepared in a manner similar to Example 24, except using (3'S,4R,5R,7'R)-12'-(benzyloxy)-N-(2,4-difluorobenzyl)-4-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (peak 2 from Step 1) instead of (3'S,5S,7'R)-12'-(benzyloxy)-N-(2,4-difluorobenzyl)-4-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide. MS (m/z) 503.231 [M+H]+. ¹H NMR (400 MHz, Chloroform-d) δ 10.16 (s, 1H), 8.89 (s, 1H), 7.47-7.32 (m, 1H), 6.90-6.76 (m, 2H), 4.91-4.82 (m, 1H), 4.81 (s, 1H), 4.71 (d, J=10.4 Hz, 1H), 4.40 (d, J=17.4 Hz, 1H), 3.95-3.87 (m, 1H), 3.79 (d, J=14.6 Hz, 1H), 3.70-3.61 (m, 1H), 2.11 (d, J=5.1 Hz, 3H), 2.01 (s, 1H), 1.70 (s, 1H), 1.64-1.56 (m, 1H), 1.45 (d, J=11.8 Hz, 1H), 1.31 (dd, J=6.7, 2.3 Hz, 3H).

Example 31: Preparation of (3'S,4S,5R,7'R)-4,12'-dihydroxy-3,3'-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

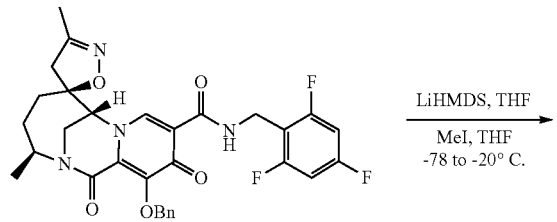

LiHMDS, THF
MeI, THF
-78 to -20° C.

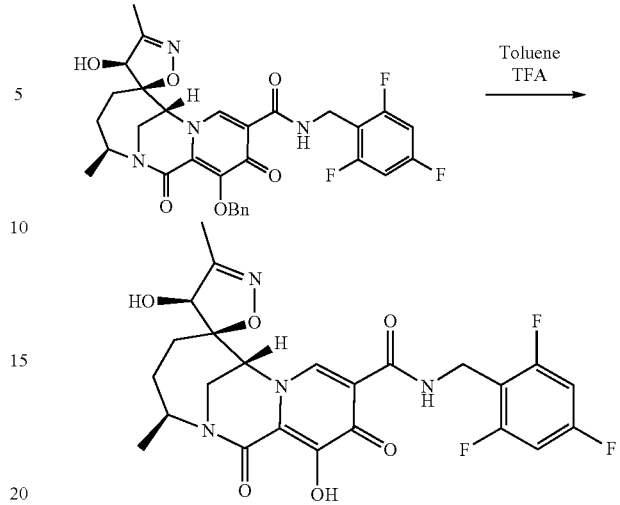

Toluene
TFA
→

Step 1: Preparation of (3'S,4S,5R,7'R)-12'-(benzyloxy)-4-hydroxy-3,3'-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide Into the solution of (3'S,5S,7'R)-12'-(benzyloxy)-3,3'-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (204 mg, 0.343 mmol), prepared according to Example 3, in THF (10 ml) was added 1N solution of LiHMDS in THF (1.2 ml, 1.2 mmol) at -40° C. under air. After 30 min., a solution MeI in THF (73 mg, 0.515 mmol) was added at -40° C., then warmed to -20° C. over 2 h. The reaction was quenched by adding sat. NH₄Cl solution. The mixture was extracted with EtOAc, the organic phase was separated and dried over MgSO₄, filtered, concentrated down and purified by silica gel column chromatography (eluting with 10-80% EtOAc/Hexane) to give the title compound. MS (m/z) 611.058 [M+H]+.

Step 2: Preparation of (3'S,4S,5R,7'R)-4,12'-dihydroxy-3,3'-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide To a solution of (3'S,4S,5R,7'R)-12'-(benzyloxy)-4-hydroxy-3,3'-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (75 mg, 0.123 mmol) in toluene (2 mL) was added TFA (0.5 mL). The reaction mixture was stirred at rt overnight. The reaction mixture was concentrated down, and the residue was separated and purified by reverse phase HPLC, eluting with 10-90% acetonitrile in water to give title compound. MS (m/z) 521.234 [M+H]+. ¹H NMR (400 MHz, Chloroform-d) δ 11.60 (s, 1H), 10.11-9.97 (m, 1H), 8.40 (s, 1H), 6.69 (t, J=8.1 Hz, 2H), 5.32 (s, 1H), 5.23 (s, 1H), 5.01 (dd, J=14.5, 8.1 Hz, 1H), 4.89-4.77 (m, 1H), 4.37 (dd, J=14.6, 3.8 Hz, 1H), 3.94 (s, 1H), 3.93-3.84 (m, 1H), 3.65 (dd, J=14.8, 2.7 Hz, 1H), 2.30 (dd, J=16.4, 6.3 Hz, 1H), 2.19 (s, 3H), 2.06 (d, J=8.2 Hz, 1H), 1.64 (dd, J=16.5, 11.2 Hz, 1H), 1.31 (d, J=6.6 Hz, 3H).

Example 32: Preparation of (3'S,4S,5R,7'R)-4-fluoro-12'-hydroxy-3,3'-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

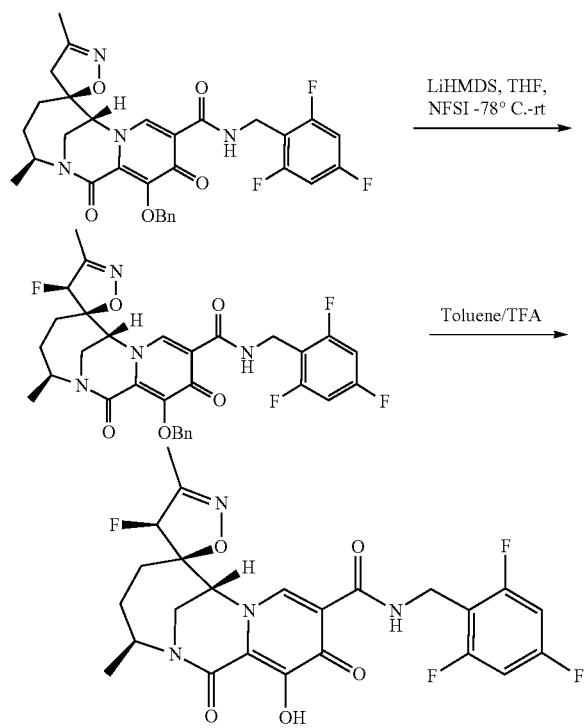

Step 1: Preparation of (3'S,4S,5R,7'R)-12'-(benzyloxy)-4-fluoro-3,3'-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide Into the solution of (3'S,5S,7'R)-12'-(benzyloxy)-N-(2,4-difluoro-6-methylbenzyl)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (35 mg, 0.059 mmol), prepared according to Example 3, and N-(benzenesulfonyl)-N-fluoro-benzenesulfonamide (22.5 mg, 0.072 mmol) in THF (10 ml) was added 1 M solution of LiHMDS in THF (0.15 ml) at −78° C. After 30 min, the reaction was allowed to warm to rt. Then the reaction was quenched by adding sat. NH$_4$Cl solution. The mixture was extracted with EtOAc, the organic phase was separated and dried over MgSO$_4$, filtered, concentrated down and purified by silica gel column chromatography (eluting with 0-80% EtOAc/hexane) to give the title compound. MS (m/z) 613.029 [M+H]+.

Step 2: Preparation of (3'S,4S,5R,7'R)-4-fluoro-12'-hydroxy-3,3'-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide To a solution of (3'S,4S,5R,7'R)-12'-(benzyloxy)-4-fluoro-3,3'-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (99 mg, 0.162 mmol) in toluene (3 mL) was added TFA (1 mL). The reaction mixture was stirred at rt overnight. The reaction mixture was concentrated down, and the residue was purified by reverse phase HPLC, eluting with 10-90% acetonitrile in water to give title compound. MS (m/z) 523.181 [M+H]+. $^1$H NMR (400 MHz, Chloroform-d) δ 10.49 (d, J=5.9 Hz, 1H), 8.44 (s, 1H), 6.70 (t, J=8.1 Hz, 2H), 5.38 (d, J=53.9 Hz, 1H), 4.83-4.70 (m, 2H), 4.63 (dd, J=14.6, 5.6 Hz, 1H), 3.98 (s, 1H), 3.92 (dd, J=15.0, 1.8 Hz, 1H), 3.80-3.72 (m, 1H), 2.18 (d, J=2.3 Hz, 3H), 2.16-2.06 (m, 2H), 2.06-1.94 (m, 1H), 1.45 (dd, J=15.2, 11.7 Hz, 1H), 1.34 (d, J=6.7 Hz, 3H).

Example 33: Preparation of (3'S,4R,5R,7'R)-4-fluoro-12'-hydroxy-3,3'-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

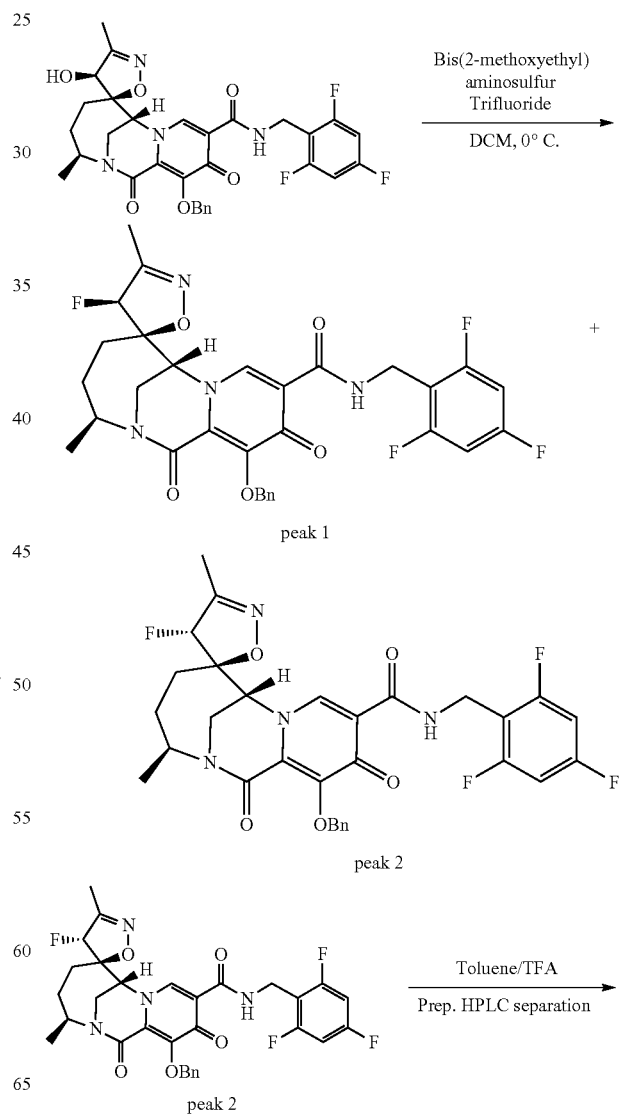

-continued

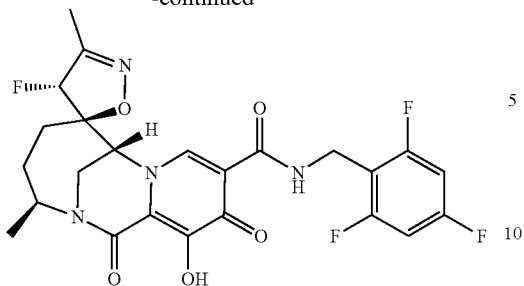

The title compound was prepared in a manner similar to Example 27, except using (3'S,4S,5R,7'R)-12'-(benzyloxy)-4-hydroxy-3,3'-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide, prepared according to Example 31, instead of (3'S,5S,7'R)-12'-(benzyloxy)-N-(2,4-difluorobenzyl)-4-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide. MS (m/z) 523.135 [M+H]+. $^1$H NMR (400 MHz, Chloroform-d) δ 10.30 (s, 1H), 8.61 (d, J=6.2 Hz, 1H), 6.76-6.63 (m, 2H), 5.04 (d, J=53.7 Hz, 1H), 4.88-4.78 (m, 1H), 4.78-4.70 (m, 1H), 4.63 (q, J=9.0, 7.3 Hz, 2H), 3.80 (dd, J=4.6, 2.3 Hz, 2H), 2.18 (d, J=3.3 Hz, 3H), 2.13-1.92 (m, 3H), 1.58-1.49 (m, 1H), 1.33 (d, J=6.8 Hz, 3H).

Example 34: Preparation of (3'S,4S,5S,7'R)—N-(3-chloro-2,4-difluorobenzyl)-12'-hydroxy-3,3',4-trimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

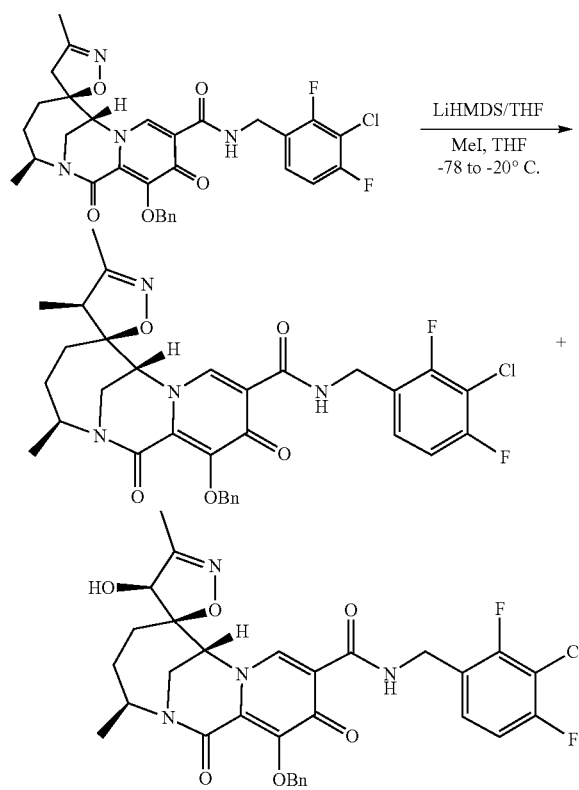

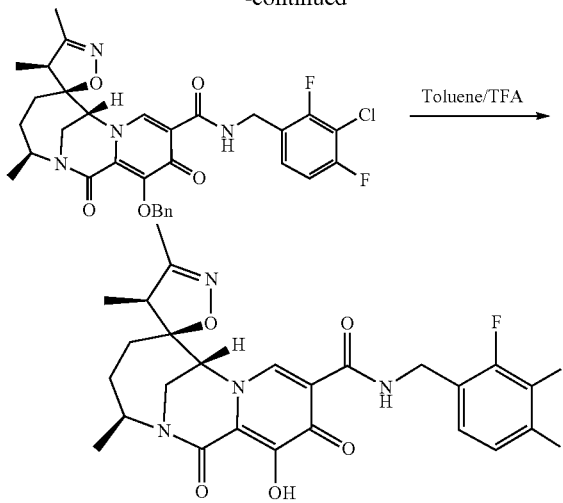

The title compound was prepared in a manner similar to Example 23, except using (3'S,5S,7'R)-12'-(benzyloxy)-N-(3-chloro-2,4-difluorobenzyl)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide, prepared according to Example 6, instead of (3'S,5S,7'R)-12'-(benzyloxy)-N-(2,4-difluorobenzyl)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide. MS (m/z) 535.208 [M+H]+. $^1$H NMR (400 MHz, Chloroform-d) δ 10.48 (s, 1H), 8.36 (s, 1H), 7.34-7.30 (m, 1H), 6.96 (t, J=8.6 Hz, 1H), 4.75-4.67 (m, 2H), 4.16 (s, 1H), 3.86 (d, J=15.0 Hz, 1H), 3.71 (d, J=2.7 Hz, 1H), 3.17 (d, J=7.4 Hz, 1H), 2.09 (d, J=8.4 Hz, 1H), 2.01 (d, J=1.0 Hz, 3H), 1.98 (d, J=7.2 Hz, 3H), 1.32 (d, J=6.6 Hz, 3H), 1.25 (d, J=12.3 Hz, 1H), 0.82 (d, J=7.3 Hz, 3H).

Example 35: Preparation of (3'S,4S,5R,7'R)—N-(3-chloro-2,4-difluorobenzyl)-4,12'-dihydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide The title compound was prepared in a manner similar to Example 24, except using (3'S,4S,5R,7'R)-12'-(benzyloxy)-N-(3-chloro-2,4-difluorobenzyl)-4-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide, prepared according to Example 34, instead of (3'S,5S,7'R)-12'-(benzyloxy)-N-(2,4-difluorobenzyl)-4-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide. MS (m/z) 537.085 [M+H]⁺. ¹H NMR (400 MHz, Chloroform-d) δ 10.00 (s, 1H), 8.34 (s, 1H), 7.30-7.25 (m, 1H), 6.97 (t, J=8.2 Hz, 1H), 5.18 (s, 1H), 4.85 (dd, J=14.6, 7.4 Hz, 2H), 4.47-4.36 (m, 1H), 3.96 (s, 1H), 3.94-3.87 (m, 1H), 3.67 (d, J=14.5 Hz, 1H), 2.29 (dd, J=16.2, 5.8 Hz, 1H), 2.14 (s, 3H), 2.03 (s, 2H), 1.64 (d, J=15.0 Hz, 1H), 1.32 (d, J=6.6 Hz, 3H).

Example 36: Preparation of (3'S,5S,7'R)-12'-hydroxy-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

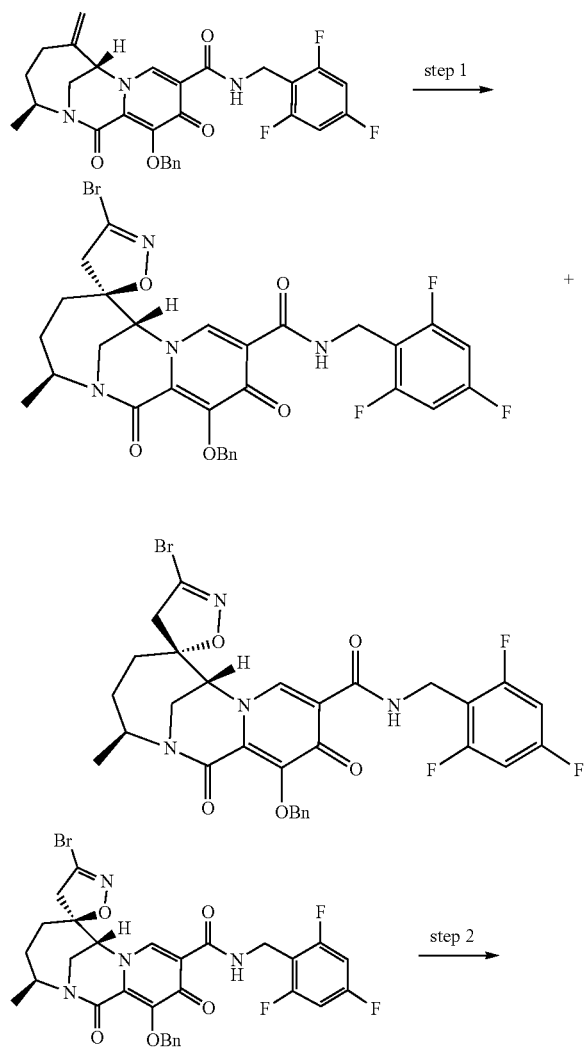

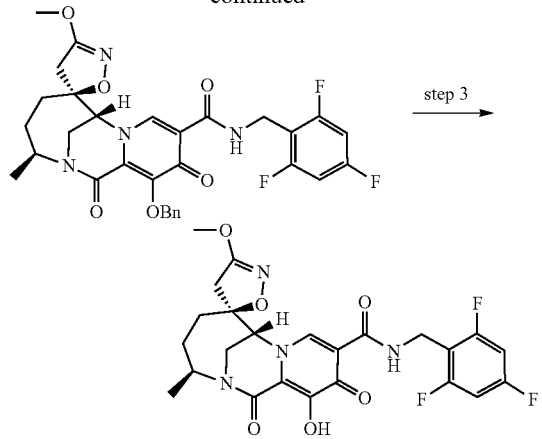

Step 1: Synthesis of (3'S,5S,7'R)-12'-(benzyloxy)-3-bromo-3'-methyl-1',1'-dioxo-N-(2,4,6-trifluorobenzyl)-1',4',5',11'-tetrahydro-3'H, 4H, 7'H-spiro[isoxazole-5,6'-[2,7]methanopyrido[1,2-a][1,4]diazonine]-10'-carboxamide and (3'S,5R,7'R)-12'-(benzyloxy)-3-bromo-3'-methyl-1',11'-dioxo-N-(2,4,6-trifluorobenzyl)-1',4',5',11'-tetrahydro-3'H,4H, 7'H-spiro[isoxazole-5,6'-[2,7]methanopyrido[(1,2-a][1,4]diazonine]-10'-carboxamide To a solution of (3S,7S)-12-(benzyloxy)-3-methyl-6-methylene-1,11-dioxo-N-(2,4,6-trifluorobenzyl)-1,4,5,6,7,11-hexahydro-3H-2,7-methanopyrido[1,2-a][1,4]diazonine-10-carboxamide (500 mg, 0.93 mmol) (Intermediate C) in EtOAc (6.4 mL) at room temperature was added potassium carbonate (642 mg, 4.65 mmol) followed by dibromomethanone oxime (189 mg, 0.93 mmol). DMF was added dropwise till the mixture became clear. The reaction was stirred for overnight before it was diluted with EtOAc. The organic layer was washed with water, brine, dried over sodium sulfate, filtered and concentrated. The residue was purified by normal phase chromatography. The first eluted peak was (3'S,5S,7'R)-12'-(benzyloxy)-3-bromo-3'-methyl-1',11'-dioxo-N-(2,4,6-trifluorobenzyl)-1',4',5',11'-tetrahydro-3'H, 4H,7'H-spiro[isoxazole-5,6'-[2,7]methanopyrido[1,2-a][1,4]diazonine]-10'-carboxamide. LCMS-ESI+(m/z): calcd H+ for C30H26BrF3N4O5, Theoretical: 658.1, Found: 659.06.

The second eluted peak was (3'S,5R,7'R)-12'-(benzyloxy)-3-bromo-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide. LCMS-ESI+(m/z): calcd H+ for C30H26BrF3N4O5, Theoretical: 658.1, Found: 659.019.

Step 2: Synthesis of (3'S,5S,7'R)-12'-(benzyloxy)-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide To a solution of (3'S,5S,7'R)-12'-(benzyloxy)-3-bromo-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (380 mg, 0.577 mmol) in MeOH (20 mL) was added potassium carbonate (478 mg, 3.46 mmol). The resulting mixture was heated at 54° C. for 1 hour. The reaction was then cooled to room temperature, diluted with water, acidified to pH~ 6 with 1N HCl. Extracted with EtOAc. The organic layer was washed with brine, dried over sodium sulfate, filtered and concentrated. LCMS-ESI+(m/z): calcd H+ for C31H29F3N4O6, Theoretical: 610.2, Found: 611.148. 1H NMR (400 MHz, CD3CN) δ 10.53 (t, J=5.9 Hz, 1H), 8.80 (s, 1H), 7.56-7.49 (m, 2H), 7.42-7.30 (m, 3H), 6.92-6.80 (m, 2H), 5.33 (d, J=10.4 Hz, 1H), 5.10 (d, J=10.4 Hz, 1H), 4.83-4.63 (m, 3H), 4.55 (dd, J=14.7, 5.6 Hz, 1H), 3.72-3.58 (m, 2H), 3.39 (d, J=18.0 Hz, 1H), 2.94 (d, J=18.0 Hz, 1H), 1.99-1.95 (m, 1H), 1.94-1.77 (m, 2H), 1.61-1.50 (m, 1H), 1.18 (d, J=6.7 Hz, 3H).

Step 3: Synthesis of (3'S,5S,7'R)-12'-hydroxy-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (3'S,5S,7'R)-12'-(benzyloxy)-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (20 mg, 0.0328 mmol) was treated with a mixture of TFA (2 mL) and toluene (2 mL) at room temperature for overnight. The reaction was concentrated, purified by reverse phase prep HPLC. LCMS-ESI+ (m/z): calcd H+ for C24H23F3N4O6, Theoretical: 520.16, Found: 521.244. 1H NMR (400 MHz, CD3CN) δ 10.40-10.31 (m, 1H), 8.47 (s, 1H), 6.93-6.79 (m, 2H), 4.69-4.56 (m, 3H), 4.44 (d, J=4.9 Hz, 1H), 3.85 (s, 3H), 3.81-3.70 (m, 2H), 2.84 (d, J=17.2 Hz, 1H), 2.61 (d, J=17.2 Hz, 1H), 2.05-1.85 (m, 3H), 1.59-1.45 (m, 1H), 1.25 (d, J=6.7 Hz, 3H).

Example 37: Preparation of (3'S,5R,7'R)-12'-hydroxy-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

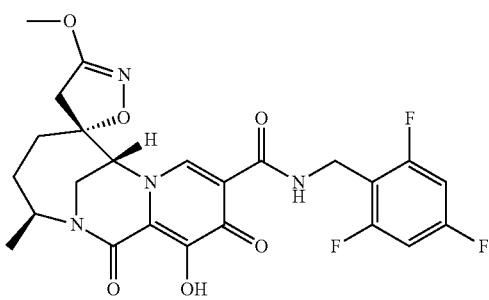 [SMILES: COC1=NO[C@]2(CC[C@H](C)N3C[C@H]2n2cc(C(=O)NCc4c(F)cc(F)cc4F)c(=O)c(O)c2C3=O)C1]

(3'S,5R,7'R)-12'-hydroxy-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide was synthesized following same method as Example 36, except using (3'S,5R,7'R)-12'-(benzyloxy)-3-bromo-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide instead of (3'S,5S,7'R)-12'-(benzyloxy)-3-bromo-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide in Step 2. LCMS-ESI+(m/z): calcd H+ for C24H23F3N4O6, Theoretical: 520.16, Found: 521.207. 1H NMR (400 MHz, CD3CN) δ 10.37 (s, 1H), 8.26 (s, 1H), 6.95-6.79 (m, 2H), 4.60 (dt, J=20.7, 5.8 Hz, 3H), 4.47-4.40 (m, 1H), 3.89 (s, 3H), 3.77-3.69 (m, 1H), 3.55 (dd, J=15.5, 1.7 Hz, 1H), 3.12 (d, J=16.6 Hz, 1H), 2.90 (d, J=16.6 Hz, 1H), 2.13 (dt, J=14.6, 7.6 Hz, 1H), 1.85 (dd, J=13.7, 7.5 Hz, 1H), 1.48-1.32 (m, 2H), 1.23 (d, J=6.6 Hz, 3H).

Example 38: Preparation of (3'S,5S,7'R)-12'-hydroxy-3-(2-methoxyethoxy)-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

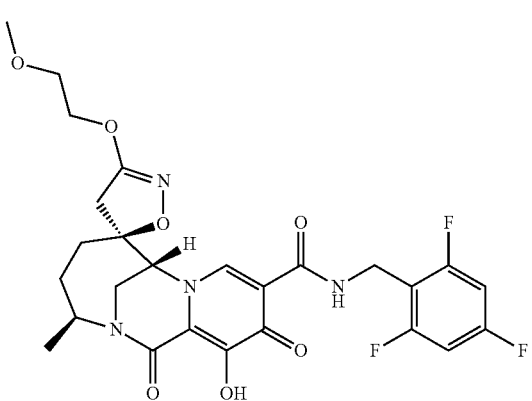 [SMILES: COCCOC1=NO[C@@]2(CC[C@H](C)N3C[C@H]2n2cc(C(=O)NCc4c(F)cc(F)cc4F)c(=O)c(O)c2C3=O)C1]

(3'S,5S,7'R)-12'-hydroxy-3-(2-methoxyethoxy)-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide was synthesized following same method as Example 36, except using 2-methoxyethanol instead of methanol in Step 2. LCMS-ESI+(m/z): calcd H+ for C26H27F3N4O7, Theoretical: 564.18, Found: 565.289. 1H NMR (400 MHz, DMSO) δ 10.35 (t, J=5.8 Hz, 1H), 8.68 (s, 1H), 7.21 (t, J=8.6 Hz, 2H), 4.73 (d, J=2.5 Hz, 1H), 4.56 (t, J=7.6 Hz, 3H), 4.20 (q, J=3.7 Hz, 2H), 3.78-3.66 (m, 2H), 3.61 (dd, J=5.2, 3.7 Hz, 2H), 3.28 (s, 3H), 2.97 (d, J=16.9 Hz, 1H), 2.69 (d, J=16.9 Hz, 1H), 1.94-1.74 (m, 3H), 1.39-1.27 (m, 1H), 1.18 (d, J=6.6 Hz, 3H).

Example 39: Preparation of (3'S,5S,7'R)-12'-hydroxy-3-(methoxy-d₃)-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-4,4-d₂-10'-carboxamide

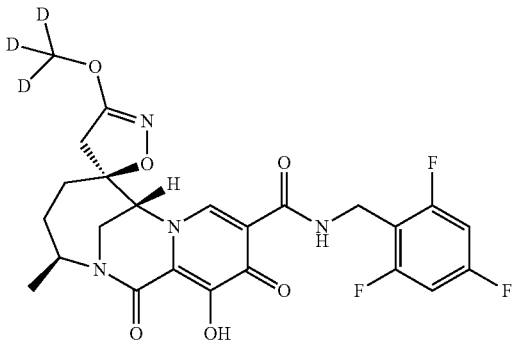 [SMILES: [2H]C([2H])([2H])OC1=NO[C@@]2(CC[C@H](C)N3C[C@H]2n2cc(C(=O)NCc4c(F)cc(F)cc4F)c(=O)c(O)c2C3=O)C1]

(3'S,5S,7'R)-12'-hydroxy-3-(methoxy-d₃)-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-4,4-d2-10'-carboxamide was synthesized following same method as Example 36, except using CD₃OD instead of methanol in Step 2. LCMS-ESI+(m/z): calcd H+ for C24H18D5F3N4O6, Theoretical: 525.48, Found: 526.32. 1H NMR (400 MHz, DMSO) δ 10.36 (t, J=5.8 Hz, 1H), 8.63 (s, 1H), 7.21 (t, J=8.6 Hz, 2H), 4.71 (d, J=2.8 Hz, 1H), 4.60-4.49 (m, 3H), 3.77-3.67 (m, 2H), 1.92-1.77 (m, 3H), 1.35 (ddd, J=15.5, 8.1, 4.9 Hz, 1H), 1.18 (d, J=6.7 Hz, 3H).

Example 40: Preparation of (3'S,5S,7'R)—N-(2,4-difluorobenzyl)-12'-hydroxy-3-methoxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

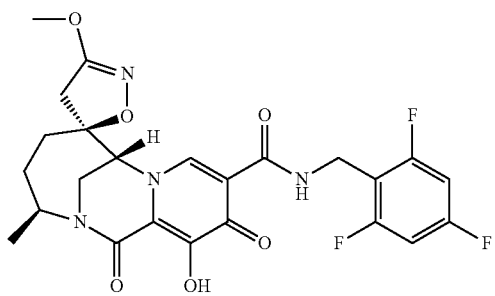 [SMILES: COC1=NO[C@@]2(CC[C@H](C)N3C[C@H]2n2cc(C(=O)NCc4c(F)cc(F)cc4F)c(=O)c(O)c2C3=O)C1]

(3'S,5S,7'R)—N-(2,4-difluorobenzyl)-12'-hydroxy-3-methoxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide was synthesized following the same method as Example 36, except using (3S,7S)-12-(benzyloxy)-N-(2,4-difluorobenzyl)-3-methyl-6-methylene-1,11-dioxo-1,4,5,6,7,11-hexahydro-3H-2,7-methanopyrido[1,2-a][1,4]diazonine-10-carboxamide (Intermediate F) instead of (3S,7S)-12-(benzyloxy)-3-methyl-6-methylene-1,11-dioxo-N-(2,4,6-trifluorobenzyl)-1,4,5,6,7,11-hexahydro-3H-2,7-methanopyrido[1,2-a][1,4]diazonine-10-carboxamide (Intermediate C) in Step 1. LCMS-ESI+(m/z): calcd H+ for C24H24F2N4O6, Theoretical: 502.17, Found: 503.326. 1H NMR (400 MHz, DMSO) δ 10.99 (s, 1H), 10.33 (t, J=5.9 Hz, 1H), 8.65 (s, 1H), 7.42 (td, J=8.6, 6.6 Hz, 1H), 7.30-7.20 (m, 1H), 7.07 (td, J=8.5, 2.6 Hz, 1H), 4.75 (s, 1H), 4.60-4.50 (m, 3H), 3.81 (s, 3H), 3.79-3.67 (m, 2H), 2.91 (s, 1H), 2.70 (d, J=16.9 Hz, 1H), 1.95-1.75 (m, 3H), 1.41-1.31 (m, 1H), 1.19 (d, J=6.7 Hz, 3H).

Example 41: Preparation of (3'S,5S,7'R)—N-(2,4-difluorobenzyl)-12'-hydroxy-3-(2-methoxyethoxy)-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

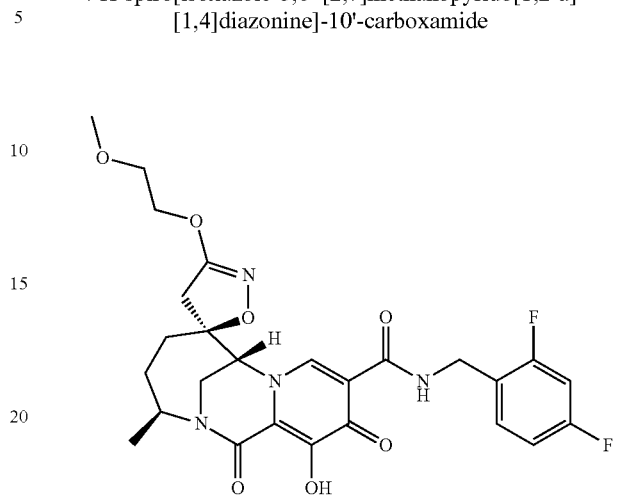

(3'S,5S,7'R)—N-(2,4-difluorobenzyl)-12'-hydroxy-3-(2-methoxyethoxy)-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide was synthesized following the same method as Example 36, except using (3S,7S)-12-(benzyloxy)-N-(2,4-difluorobenzyl)-3-methyl-6-methylene-1,11-dioxo-1,4,5,6,7,11-hexahydro-3H-2,7-methanopyrido[1,2-a][1,4]diazonine-10-carboxamide (Intermediate F) instead of (3S,7S)-12-(benzyloxy)-3-methyl-6-methylene-1,11-dioxo-N-(2,4,6-trifluorobenzyl)-1,4,5,6,7,11-hexahydro-3H-2,7-methanopyrido[1,2-a][1,4]diazonine-10-carboxamide (Intermediate C) in Step 1 and 2-methoxyethanol instead of methanol in Step 2. LCMS-ESI+(m/z): calcd H+ for C26H28F2N4O7, Theoretical: 546.19, Found: 547.570. 1H NMR (400 MHz, MeOD) δ 8.72-8.64 (m, 1H), 7.46 (q, J=7.9 Hz, 1H), 7.04-6.91 (m, 2H), 4.76-4.62 (m, 4H), 4.26 (s, 2H), 3.83 (d, J=19.2 Hz, 2H), 3.71-3.60 (m, 2H), 3.37 (s, 3H), 3.07 (d, J=17.0 Hz, 1H), 2.69 (d, J=17.1 Hz, 1H), 2.10-1.92 (m, 3H), 1.55 (dd, J=15.5, 11.2 Hz, 1H), 1.30 (d, J=6.6 Hz, 3H).

Example 42: Preparation of (3'S,5S,7'R)-3-cyano-N-(2,4-difluorobenzyl)-12'-hydroxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

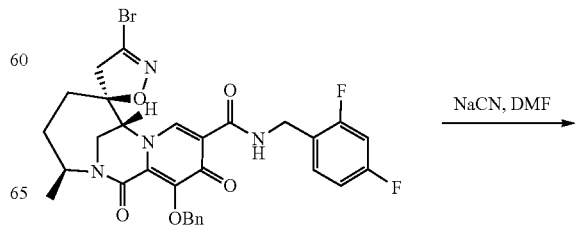

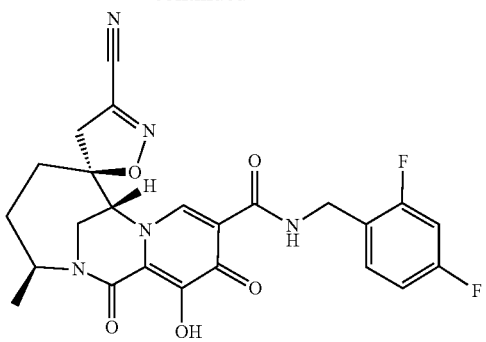

To a solution of (3'S,5S,7'R)-12'-(benzyloxy)-3-bromo-N-(2,4-difluorobenzyl)-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (30 mg, 0.0468 mmol), prepared according to Example 40, in DMF (2 ml) was added NaCN (9.36 mg, 0.187 mmol). The reaction mixture was stirred at 100° C. for 8 hours. The reaction mixture was diluted with EtOAc and washed with LiCl (5%), H$_2$O and brine. The organic phase was dried with MgSO$_4$ and concentrated in vacuo. The resulting residue was purified by prep HPLC to obtain the title compound. MS (m/z) 497.16 [M+H]+. 1H NMR (400 MHz, Methanol-d4) δ 8.78-8.58 (m, 1H), 7.54-7.28 (m, 1H), 7.07-6.82 (m, 2H), 4.62 (m, 3H), 4.47 (m, 1H), 3.73-3.53 (m, 2H), 2.99 (d, J=17.0 Hz, 1H), 2.81 (d, J=17.0 Hz, 1H), 2.05-1.81 (m, 3H), 1.64 (dd, J=13.2, 9.6 Hz, 1H), 1.29 (dd, J=8.8, 3.9 Hz, 3H).

Example 43: Preparation of (3'S,5S,7'R)-12'-hydroxy-3'-methyl-3-(methylthio)-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

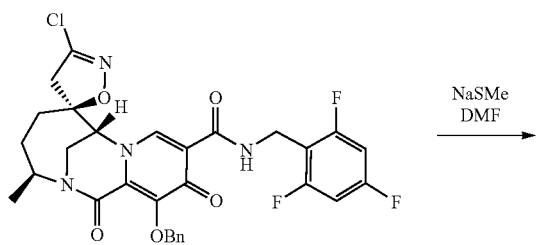

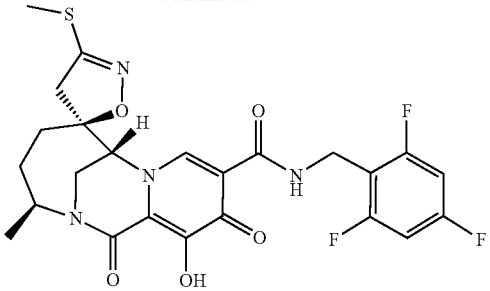

Step 1: Preparation of (3'S,5S,7'R)-12'-(benzyloxy)-3'-methyl-3-(methylthio)-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide To a solution of (3'S,5S,7'R)-12'-(benzyloxy)-3-chloro-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (0.028 g, 0.046 mmol), prepared according to Example 53, in DMF (1 mL) was added sodium methanethiolate (0.006 g, 0.082 mmol, 1.8 equiv.). The reaction mixture was stirred at rt for 3 h. The reaction mixture was diluted with EtOAc and washed with 1N HCl, brine, and 5% LiCl. The organic phase was dried over Na$_2$SO$_4$, filtered, and concentrated to afford the title compound, which was used without further purification. MS (m/z): 627.05 [M+H]+.

Step 2: Preparation of (3'S,5S,7'R)-12'-hydroxy-3'-methyl-3-(methylthio)-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (3'S,5S,7'R)-12'-(benzyloxy)-3'-methyl-3-(methylthio)-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (0.022 g, 0.035 mmol) was dissolved in 1:1 TFA/toluene (2 mL) and stirred for 2 h. The reaction mixture was concentrated and purified by reverse phase prep HPLC (5-100% MeCN/water w/0.1% TFA) to afford the desired product. MS (m/z): 537.11 [M+H]+. 1H NMR (400 MHz, DMSO-d6) δ 10.91 (s, 1H), 10.34 (t, J=5.9 Hz, 1H), 8.56 (s, 1H), 7.21 (t, J=8.6 Hz, 2H), 4.68 (s, 1H), 4.61-4.49 (m, 3H), 3.79-3.65 (m, 2H), 3.02 (d, J=17.0 Hz, 1H), 2.78 (d, J=17.0 Hz, 1H), 2.46 (s, 3H), 1.87-1.74 (m, 3H), 1.40-1.29 (m, 1H), 1.18 (d, J=6.7 Hz, 3H).

Example 44: Preparation of (3'S,5S,7'R)-3-bromo-N-(2,4-difluorobenzyl)-12'-hydroxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

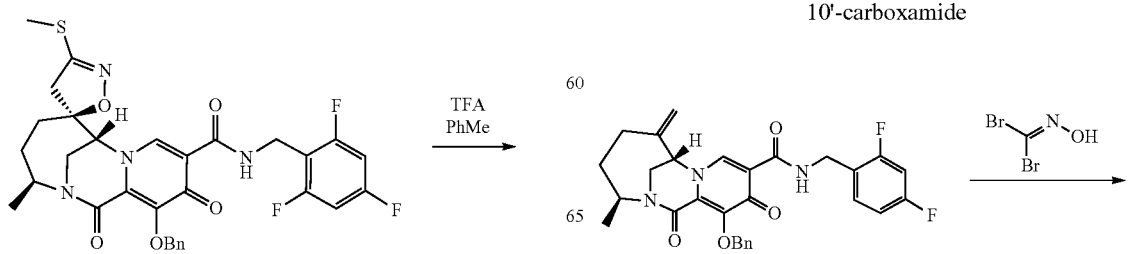

185
-continued

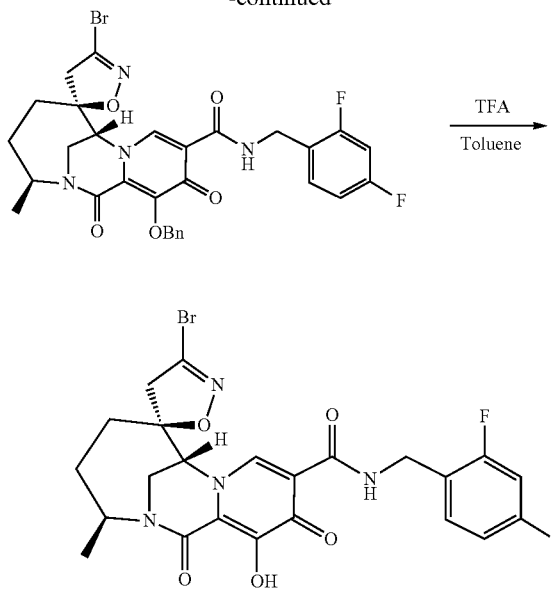

Step 1: Preparation of (3'S,5S,7'R)-12'-(benzyloxy)-3-bromo-N-(2,4-difluorobenzyl)-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide To a solution of (3S,7S)-12-(benzyloxy)-N-(2,4-difluorobenzyl)-3-methyl-6-methylene-1,11-dioxo-1,4,5,6,7,11-hexahydro-3H-2,7-methanopyrido[1,2-a][1,4]diazonine-10-carboxamide (Intermediate F) (0.55 g, 1.06 mmol) in EtOAc (5 mL) was added 1,1-dibromoformaldoxime (0.644 g, 3.18 mmol, 3 equiv.) and sodium bicarbonate (0.646 g, 10.6 mmol, 10 equiv.). The suspension was stirred at rt for 16 h. The crude reaction mixture was purified by column chromatography (0-100% EtOAc/hexanes) to afford the title compound. MS (m/z) 641.95 [M+H]+.

Step 2: Preparation of (3'S,5S,7'R)-3-bromo-N-(2,4-difluorobenzyl)-12'-hydroxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide The title compound was prepared in a manner similar to Step 5 of Example 5, except using (3'S,5S,7'R)-12'-(benzyloxy)-3-bromo-N-(2,4-difluorobenzyl)-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide instead of (3'S,4'S,5R,7'R)-12'-(benzyloxy)-N-(2,4-difluorobenzyl)-4'-fluoro-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide. MS (m/z) 551.69 [M+H]+. 1H NMR (400 MHz, Chloroform-d) δ 10.46 (t, J=5.9 Hz, 1H), 8.59 (s, 1H), 7.38 (td, J=8.7, 6.5 Hz, 1H), 6.91-6.79 (m, 2H), 4.83-4.66 (m, 2H), 4.63 (dd, J=15.2, 5.8 Hz, 1H), 4.38 (m, 1H), 3.84 (dd, J=15.0, 1.9 Hz, 1H), 3.74 (dd, J=15.0, 2.7 Hz, 1H), 3.26 (d, J=17.8 Hz, 1H), 2.81 (d, J=17.8 Hz, 1H), 2.04 (dddd, J=12.8, 9.9, 6.3, 4.3 Hz, 3H), 1.66-1.54 (m, 1H), 1.33 (d, J=6.7 Hz, 3H).

186
Example 45: Preparation of (3'S,5S,7'R)—N-(2,4-difluorobenzyl)-12'-hydroxy-3'-methyl-3-(oxetan-3-yloxy)-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

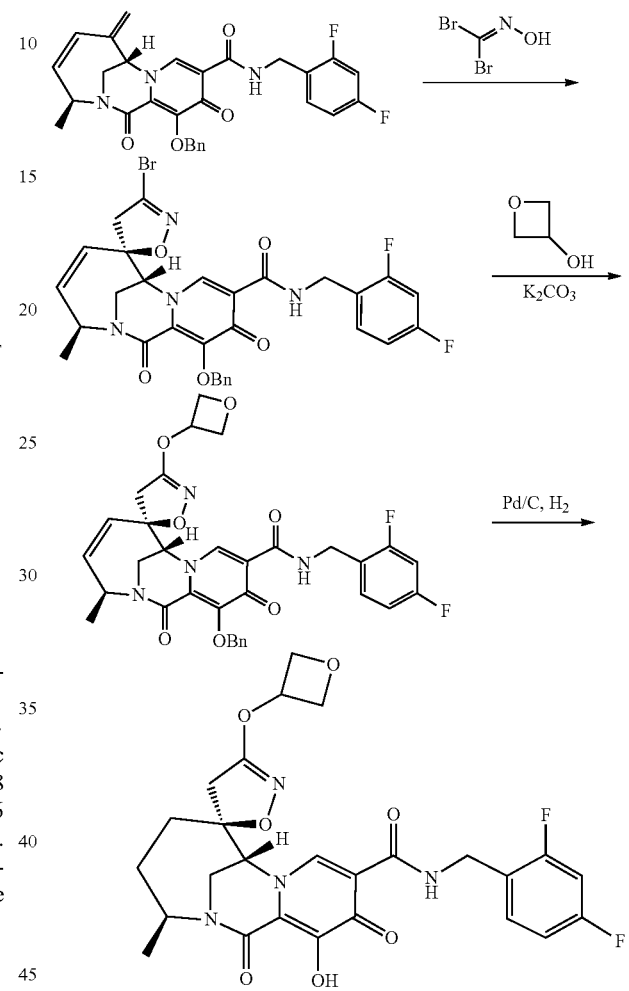

Step 1: Preparation of (3'S,5S,7'R)-12'-(benzyloxy)-3-bromo-N-(2,4-difluorobenzyl)-3'-methyl-1',11'-dioxo-1',11'-dihydro-3'H,4H,7'H-spiro[isoxazole-5,6'-[2,7]methanopyrido[1,2-a][1,4]diazonine]-10'-carboxamide To solution of (3S,7S)-12-(benzyloxy)-N-(2,4-difluorobenzyl)-3-methyl-6-methylene-1,11-dioxo-1,6,7,11-tetrahydro-3H-2,7-methanopyrido[1,2-a][1,4]diazonine-10-carboxamide (0.55 g, 1.06 mmol) (Intermediate G) in EtOAc (2 ml) was added dibromomethanone oxime (0.647 g, 3.09 mmol) then followed by NaHCO3 (0.65 g, 10.6 mmol). The reaction was stirred at room temperature overnight. The reaction mixture was diluted with EtOAc and washed with H2O and brine. The organic phase was dried over MgSO4. After removing solvent in vacuo, the residue was purified by silica gel column chromatography to obtain the title compound. MS (m/z) 640.05 [M+H]+.

Step 2: Preparation of (3'S,5S,7'R)-12'-(benzyloxy)-N-(2,4-difluorobenzyl)-3'-methyl-3-(oxetan-3-yloxy)-1',11'-dioxo-1',11'-dihydro-3'H,4H,7'H-spiro[isoxazole-5,6'-[2,7]methanopyrido[1,2-a][1,4]diazonine]-10'-carboxamide (3'S,5S,7'R)-12'-(benzyloxy)-3-bromo-N-(2,4-difluorobenzyl)-3'-methyl-1',11'-dioxo-1',11'-dihydro-3'H,4H,7'H-spiro[isoxazole-5,6'-[2,7]methanopyrido[1,2-a][1,4]diazonine]-10'-carboxamide (45 mg, 0.0702 mmol) was dissolved in oxetan-3-ol (1 ml) and $K_2CO_3$ (97 mg, 0.702 mmol) was added. The resulting mixture was stirred at room temperature overnight. The reaction mixture was diluted with EtOAc and was washed with $H_2O$, followed by brine. After organic phase was dried with $MgSO_4$ and the solvent was removed in vacuo. The resulting residue was purified by silica gel column chromatography to obtain the title compound. MS (m/z) 633.09 [M+H]+.

Step 3: Preparation of (3'S,5S,7'R)—N-(2,4-difluorobenzyl)-12'-hydroxy-3'-methyl-3-(oxetan-3-yloxy)-1',11'-dioxo-1',4',5',11'-tetrahydro-3'H,4H,7'H-spiro[isoxazole-5,6'-[2,7]methanopyrido[1,2-a][1,4]diazonine]-10'-carboxamide To a solution of (3'S,5S,7'R)-12'-(benzyloxy)-N-(2,4-difluorobenzyl)-3'-methyl-3-(oxetan-3-yloxy)-1',11'-dioxo-1',11'-dihydro-3'H,4H,7'H-spiro[isoxazole-5,6'-[2,7]methanopyrido[1,2-a][1,4]diazonine]-10'-carboxamide (0.0283 g, 0.045 mmol) in EtOH (2 ml) was added Pd/C (10% weight) (3.75 mg). Then the reaction mixture was evacuated and backfilled with $H_2$ 3 times. Reaction mixture was stirred under a $H_2$ atmosphere for 2 h. The Pd/C was filtered off through celite and rinsed with DCM. The solvent was removed in vacuo and the residue was purified by prep HPLC to obtain the title compound. MS (m/z) 545.27 [M+H]+. 1H NMR (400 MHz, Chloroform-d) δ 10.52 (s, 1H), 8.51 (s, 1H), 7.38 (td, J=8.6, 6.4 Hz, 1H), 6.91-6.79 (m, 2H), 5.40 (p, J=5.6 Hz, 1H), 4.91 (t, J=7.1 Hz, 2H), 4.80-4.64 (m, 5H), 4.25 (s, 1H), 3.82 (dd, J=15.0, 1.8 Hz, 1H), 3.69 (dd, J=14.9, 2.7 Hz, 1H), 3.05 (d, J=17.2 Hz, 1H), 2.65 (d, J=17.2 Hz, 1H), 2.14-1.91 (m, 3H), 1.65-1.53 (m, 1H), 1.31 (d, J=6.6 Hz, 3H).

Example 46: Preparation of (3'S,5S,7'R)—N-(2,4-difluorobenzyl)-12'-hydroxy-3'-methyl-1',11'-dioxo-3-(2,2,2-trifluoroethoxy)-1',4',5',11'-tetrahydro-3'H,4H,7'H-spiro[isoxazole-5,6'-[2,7]methanopyrido[1,2-a][1,4]diazonine]-10'-carboxamide

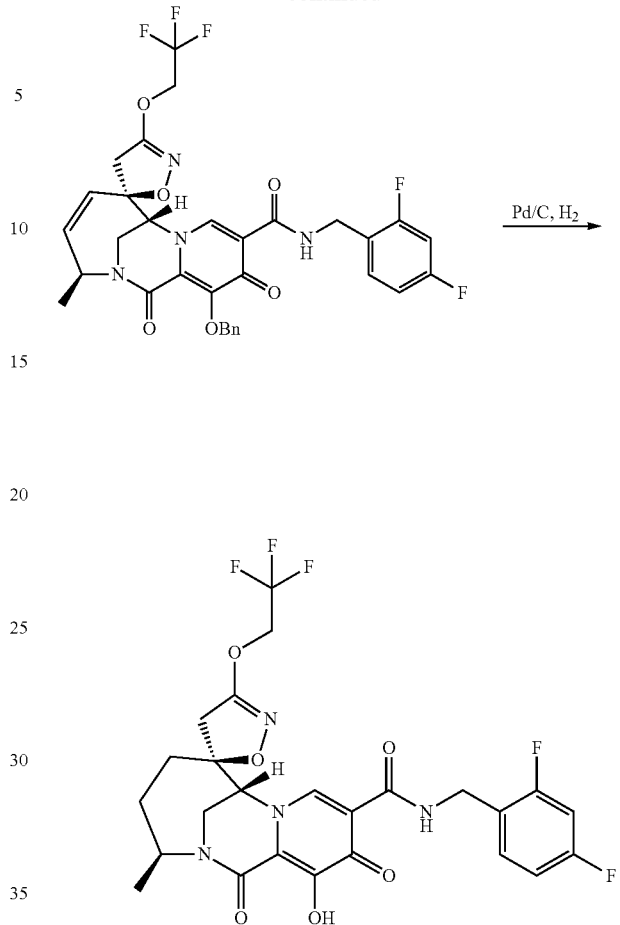

The title compound was prepared in a manner similar to Example 45, except using 2,2,2-trifluoroethan-1-ol instead of oxetan-3-ol in Step 2. MS (m/z) 571.24 [M+H]+. 1H NMR (400 MHz, Chloroform-d) δ 10.52 (t, J=5.8 Hz, 1H), 8.63 (s, 1H), 7.43-7.32 (m, 1H), 6.91-6.79 (m, 2H), 4.83-4.42 (m, 5H), 4.37 (s, 1H), 3.84 (dd, J=15.0, 1.8 Hz, 1H), 3.71 (dd, J=15.0, 2.7 Hz, 1H), 3.10 (d, J=17.3 Hz, 1H), 2.66 (d, J=17.3 Hz, 1H), 2.15-1.92 (m, 3H), 1.65-1.54 (m, 1H), 1.32 (d, J=6.7 Hz, 3H).

Example 47: Preparation of (3'S,5S,7'R)—N-(2,4-difluorobenzyl)-3-(2,2-difluoroethoxy)-12'-hydroxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

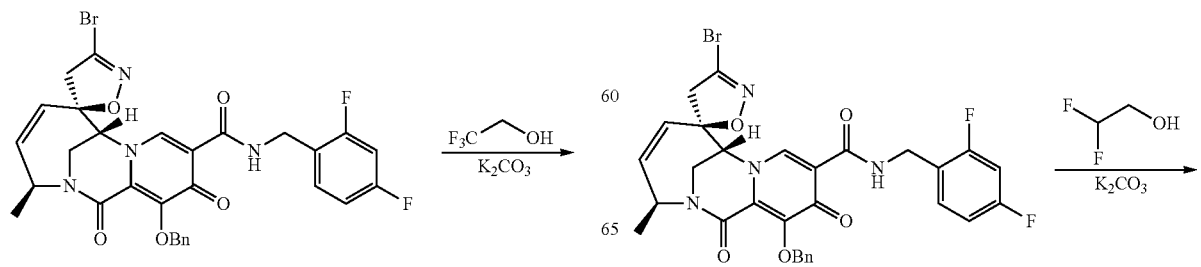

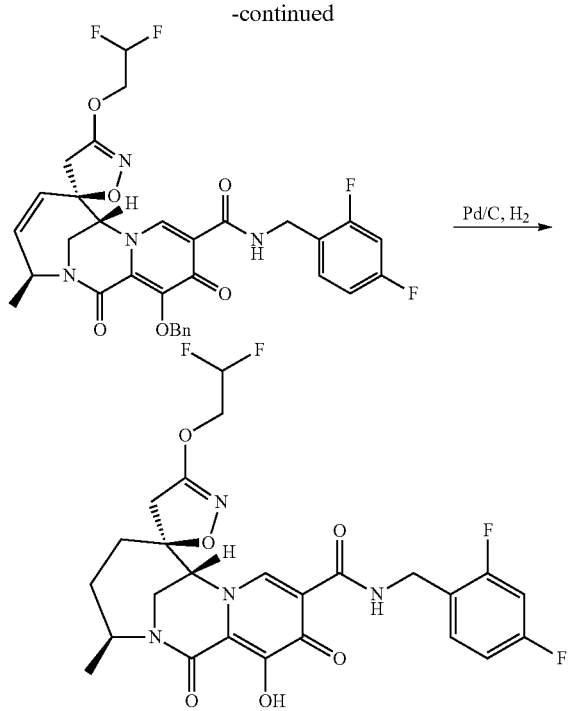
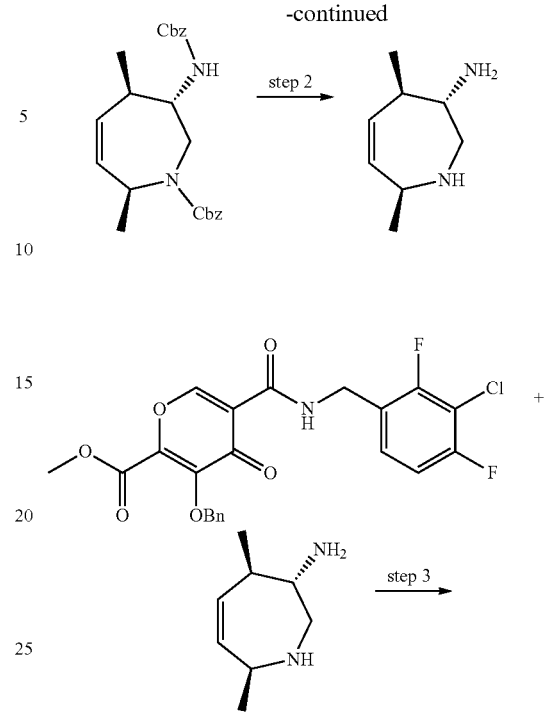

The title compound was prepared in a manner similar to Example 45, except using 2,2-difluoroethan-1-ol instead of oxetan-3-ol in Step 2. MS (m/z) 553.14 [M+H]+. 1H NMR (400 MHz, Chloroform-d) δ 10.37 (s, 1H), 8.42 (s, 1H), 7.39 (d, J=7.9 Hz, 1H), 6.84 (t, J=8.9 Hz, 2H), 6.08 (t, J=54.5 Hz, 1H), 4.75 (m, 1H), 4.67 (m, 2H), 4.38 (m, 2H), 4.23 (m, 1H), 3.84 (d, J=14.9 Hz, 1H), 3.70 (d, J=15.1 Hz, 1H), 3.05 (d, J=17.1 Hz, 1H), 2.66 (d, J=17.2 Hz, 1H), 2.07 (t, J=16.7 Hz, 2H), 2.00 (s, 1H), 1.65-1.54 (m, 1H), 1.35-1.25 (m, 3H).

Example 48: Preparation of (3'S,5R,7'R)—N-(3-chloro-2,4-difluorobenzyl)-12'-hydroxy-3-methoxy-3'-methyl-1',11'-dioxo-1',11'-dihydro-3'H,4H,7'H-spiro[isoxazole-5,6'-[2,7]methanopyrido[1,2-a][1,4]diazonine]-10'-carboxamide

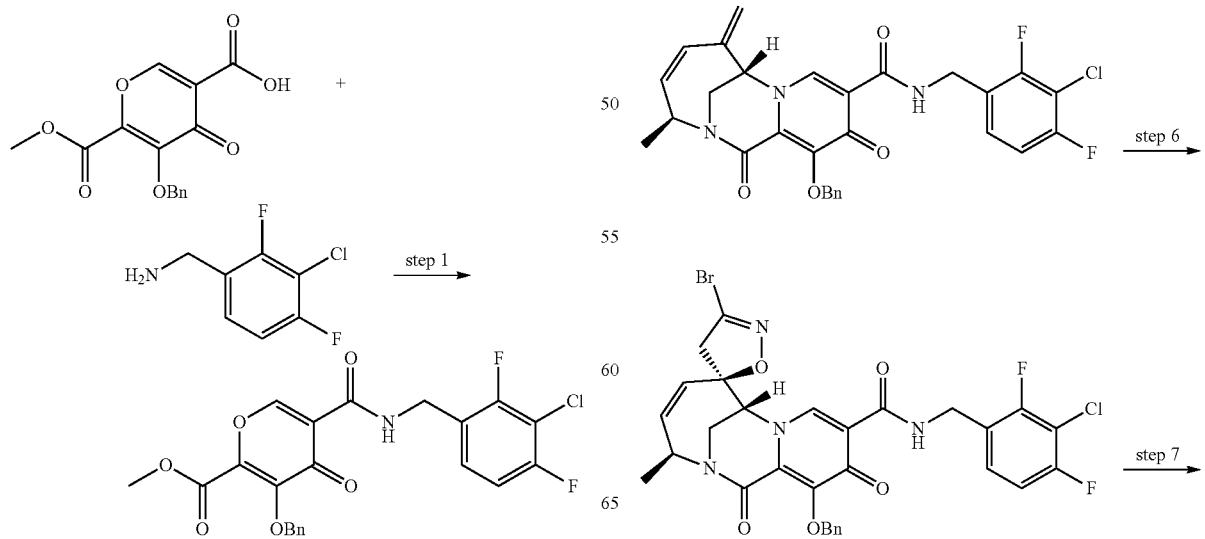

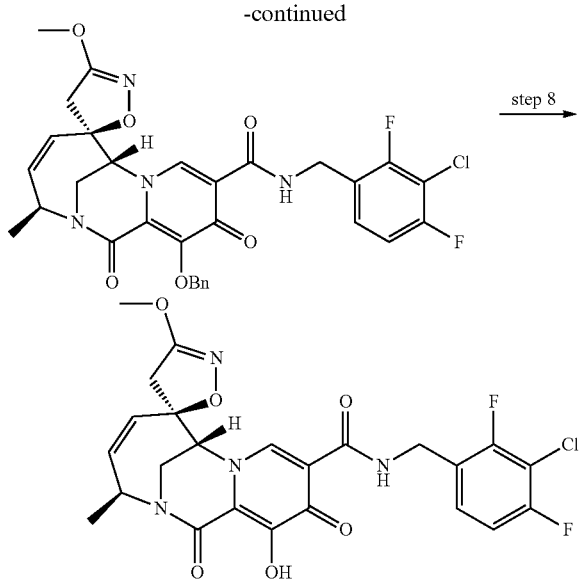

Step 1: Synthesis of methyl 3-(benzyloxy)-5-((3-chloro-2,4-difluorobenzyl)carbamoyl)-4-oxo-4H-pyran-2-carboxylate 5-(benzyloxy)-6-(methoxycarbonyl)-4-oxo-4H-pyran-3-carboxylic acid (10 g, 32.9 mmol) was dissolved in DCM (200 mL) and cooled to 0° C. Oxalyl chloride (7.926 g, 62.4 mmol) was added followed by DMF (2.40 g, 32.9 mmol) dropwise with vigorous stirring. After stirred for 30 minutes, a mixture of (3-chloro-2,4-difluoro-phenyl)methanamine (8.75 g, 49.3 mmol) and triethylamine (14.97 g, 147.8 mmol) in DCM (150 mL) was added to the cold mixture. The newly formed mixture was stirred for 1.5 h. The reaction was then poured onto 1N HCl (200 mL) and further diluted with DCM (100 mL). The organic layer was washed with 1N HCl (2×200 mL), brine (2×200 mL), dried over sodium sulfate, filtered and concentrated to give the title compound. 1H NMR (400 MHz, DMSO) δ 9.49 (t, J=6.1 Hz, 1H), 8.95 (s, 1H), 7.53-7.27 (m, 7H), 5.16 (s, 2H), 4.59 (d, J=6.0 Hz, 2H), 3.85 (s, 3H).

Step 2: Synthesis of (3S,4R,7S)-4,7-dimethyl-2,3,4,7-tetrahydro-1H-azepin-3-amine Benzyl (3S,4R,7S)-3-(((benzyloxy)carbonyl)amino)-4,7-dimethyl-2,3,4,7-tetrahydro-1H-azepine-1-carboxylate (5 g, 12.2 mmol), prepared according to WO2020197991, was treated with TFA (50 mL) at 100° C. for 4 hours. The reaction was cooled to room temperature, concentrated, coevaporated with EtOAc (4×), and used directly in next step.

Step 3: Synthesis of (3S,6R,7S)-12-(benzyloxy)-N-(3-chloro-2,4-difluorobenzyl)-3,6-dimethyl-1,11-dioxo-1,6,7,11-tetrahydro-3H-2,7-methanopyrido[1,2-a][1,4]diazonine-]0-carboxamide To a mixture of (3S,4R,7S)-4,7-dimethyl-2,3,4,7-tetrahydro-1H-azepin-3-amine (1.711 g, 12.2 mmol) in MeOH (120 mL) was added methyl 3-(benzyloxy)-5-((3-chloro-2,4-difluorobenzyl)carbamoyl)-4-oxo-4H-pyran-2-carboxylate (5.376 g, 11.6 mmol). To the resulting mixture was added water (20 mL) and sodium bicarbonate (10.248 g, 122 mmol). The newly formed mixture was stirred at 60° C. overnight. The reaction was cooled to room temperature and diluted with water and extracted with EtOAc (3×200 mL). The combined organic layer was washed with brine, dried over sodium sulfate, filtered and concentrated. The resulting residue was purified by normal phase chromatography. LCMS-ESI+(m/z): calcd H+ for C29H26ClF2N3O4, Theoretical: 553.16, Found: 554.002.

Step 4: Synthesis of (3S,6S,7R)-12-(benzyloxy)-N-(3-chloro-2,4-difluorobenzyl)-6-hydroxy-3,6-dimethyl-1,11-dioxo-1,6,7,11-tetrahydro-3H-2,7-methanopyrido[1,2-a][1,4]diazonine-10-carboxamide (3S,6R,7S)-12-(benzyloxy)-N-(3-chloro-2,4-difluorobenzyl)-3,6-dimethyl-1,11-dioxo-1,6,7,11-tetrahydro-3H-2,7-methanopyrido[1,2-a][1,4]diazonine-10-carboxamide (1.5 g, 2.71 mmol) was dissolved in dioxane (60 mL) and treated with selenium dioxide (1.19 g, 10.8 mmol) at 100° C. for 30 hours. The reaction was cooled to room temperature, filtered and concentrated. The resulting residue was purified by normal phase chromatography. LCMS-ESI+(m/z): calcd H+ for C29H26ClF2N3O5, Theoretical: 569.15, Found: 570.055.

Step 5: Synthesis of (3S,7S)-12-(benzyloxy)-N-(3-chloro-2,4-difluorobenzyl)-3-methyl-6-methylene-1,11-dioxo-1,6,7,11-tetrahydro-3H-2,7-methanopyrido[1,2-a][1,4]diazonine-10-carboxamide To a solution of (3S,6S,7R)-12-(benzyloxy)-N-(3-chloro-2,4-difluorobenzyl)-6-hydroxy-3,6-dimethyl-1,11-dioxo-1,6,7,11-tetrahydro-3H-2,7-methanopyrido[1,2-a][1,4]diazonine-10-carboxamide (610 mg, 1.07 mmol) in toluene (15 mL) at room temperature was added Martin Sulfurane dehydrating agent (1.079 g, 1.61 mmol). After 1 hour, the reaction was concentrated and resulting residue was purified by normal phase chromatography. LCMS-ESI+(m/z): calcd H+ for C29H24ClF2N3O4, Theoretical: 551.14, Found: 552.08.

Step 6: Synthesis of (3'S,5R,7'R)-12'-(benzyloxy)-3-bromo-N-(3-chloro-2,4-difluorobenzyl)-3'-methyl-1',11'-dioxo-1',11'-dihydro-3'H,4H,7'H-spiro[isoxazole-5,6'-[2,7]methanopyrido[1,2-a][1,4]diazonine]-10'-carboxamide The title compound was prepared in a manner similar to Step 1 of Example 36, except using (3S,7S)-12-(benzyloxy)-N-(3-chloro-2,4-difluorobenzyl)-3-methyl-6-methylene-1,11-dioxo-1,6,7,11-tetrahydro-3H-2,7-methanopyrido[1,2-a][1,4]diazonine-10-carboxamide instead of (3S,7S)-12-(benzyloxy)-3-methyl-6-methylene-1,11-dioxo-N-(2,4,6-trifluorobenzyl)-1,4,5,6,7,11-hexahydro-3H-2,7-methanopyrido[1,2-a][1,4]diazonine-10-carboxamide. LCMS-ESI+(m/z): calcd H+ for C30H24BrClF2N4O5, Theoretical: 672.06, Found: 672.766.

Step 7: Synthesis of (3'S,5R,7'R)-12'-(benzyloxy)-N-(3-chloro-2,4-difluorobenzyl)-3-methoxy-3'-methyl-1',11'-dioxo-1',11'-dihydro-3'H,4H,7'H-spiro[isoxazole-5,6'-[2,7]methanopyrido[1,2-a][1,4]diazonine]-10'-carboxamide The title compound was prepared in a manner similar to Step 2 of Example 36, except using (3'S,5R,7'R)-12'-(benzyloxy)-3-bromo-N-(3-chloro-2,4-difluorobenzyl)-3'-methyl-1',11'-dioxo-1',11'-dihydro-3'H,4H,7'H-spiro[isoxazole-5,6'-[2,7]methanopyrido[1,2-a][1,4]diazonine]-10'-carboxamide instead of (3'S,5S,7'R)-12'-(benzyloxy)-3-bromo-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide. LCMS-ESI+(m/z): calcd H+ for C31H27ClF2N4O6, Theoretical: 624.16, Found: 624.943.

Step 8: Synthesis of (3'S,5R,7'R)—N-(3-chloro-2,4-difluorobenzyl)-12'-hydroxy-3-methoxy-3'-methyl-1',11'-dioxo-1',11'-dihydro-3'H,4H,7'H-spiro[isoxazole-5,6'-[2,7]methanopyrido[1,2-a][1,4]diazonine]-10'-carboxamide The mixture of (3'S,5R,7'R)-12'-(benzyloxy)-N-(3-chloro-2,4-difluorobenzyl)-3-methoxy-3'-methyl-1',11'-dioxo-1',11'-dihydro-3'H,4H,7'H-spiro[isoxazole-5,6'-[2,7]methanopyrido[1,2-a][1,4]diazonine]-10'-carboxamide (71.0 mg, 0.114 mmol) and lithium chloride (48.2 mg, 1.14 mmol) in DMF (5.0 mL) was heated at 100° C. for 10 hours. The reaction mixture was cooled to room temperature and purified by reverse phase chromatography to afford the title compound. LCMS-ESI+(m/z): calcd H+ for C24H21ClF2N4O6, Theoretical: 534.11, Found: 535.125. 1H NMR (400 MHz, MeOD) δ 8.44 (s, 1H), 7.40 (td, J=8.3, 6.0 Hz, 1H), 7.11 (td, J=8.7, 1.9 Hz, 1H), 5.91 (dd, J=12.1, 2.4 Hz, 1H), 5.59 (dd, J=12.1, 2.2 Hz, 1H), 5.39 (dt, J=7.4, 2.4 Hz, 1H), 5.12 (s, 1H), 4.68 (s, 2H), 4.19 (dd, J=14.6, 2.8 Hz, 1H), 3.80 (s, 3H), 3.75 (dd, J=14.6, 1.7 Hz, 1H), 2.83 (d, J=16.2 Hz, 1H), 2.36 (d, J=16.3 Hz, 1H), 1.40 (d, J=7.2 Hz, 3H).

Example 49: Preparation of (3'S,5S,7'R)—N-(3-chloro-2,4-difluorobenzyl)-12'-hydroxy-3-methoxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (3'S,5R,7'R)—N-(3-chloro-2,4-difluorobenzyl)-12'-hydroxy-3-methoxy-3'-methyl-1',11'-dioxo-1',11'-dihydro-3'H,4H,7'H-spiro[isoxazole-5,6'-[2,7]methanopyrido[1,2-a][1,4]diazonine]-10'-carboxamide (16 mg, 0.0299 mmol), prepared according to Example 48, was dissolved in EtOH (20.0 ml) and treated with PtO2 (1.6 mg). The reaction mixture was degassed and flushed with nitrogen three times, degassed and flushed with hydrogen three times, and hydrogenated under hydrogen balloon for 10 minutes. The reaction was degassed and flushed with nitrogen, diluted with DCM (20 mL), and filtered. The filtrate was concentrated and purified by reverse phase chromatography to afford the title compound. LCMS-ESI+(m/z): calcd H+ for C24H23ClF2N4O6, Theoretical: 536.13, Found: 537.094. 1H NMR (400 MHz, DMSO) δ 11.01 (s, 1H), 10.38 (t, J=6.0 Hz, 1H), 8.64 (s, 1H), 7.40 (td, J=8.5, 6.4 Hz, 1H), 7.31 (dd, J=9.6, 7.8 Hz, 1H), 4.74 (s, 1H), 4.66-4.48 (m, J=7.4, 6.7 Hz, 3H), 3.81 (s, 3H), 3.78-3.66 (m, 2H), 2.93 (d, J=16.9 Hz, 1H), 2.70 (d, J=16.9 Hz, 1H), 1.96-1.74 (m, 3H), 1.41-1.24 (m, 1H), 1.19 (d, J=6.7 Hz, 3H).

Example 50: Preparation of (3S,3aR,3'S,7'R)-12'-hydroxy-3'-methyl-1',11'-dioxo-N-(2,4,6-trifluorobenzyl)-1',3a,4,4',5,5',6,11'-octahydro-3' H,7'H-spiro[pyrano[2,3-c]isoxazole-3,6'-[2,7]methanopyrido[1,2-a][1,4]diazonine]-10'-carboxamide

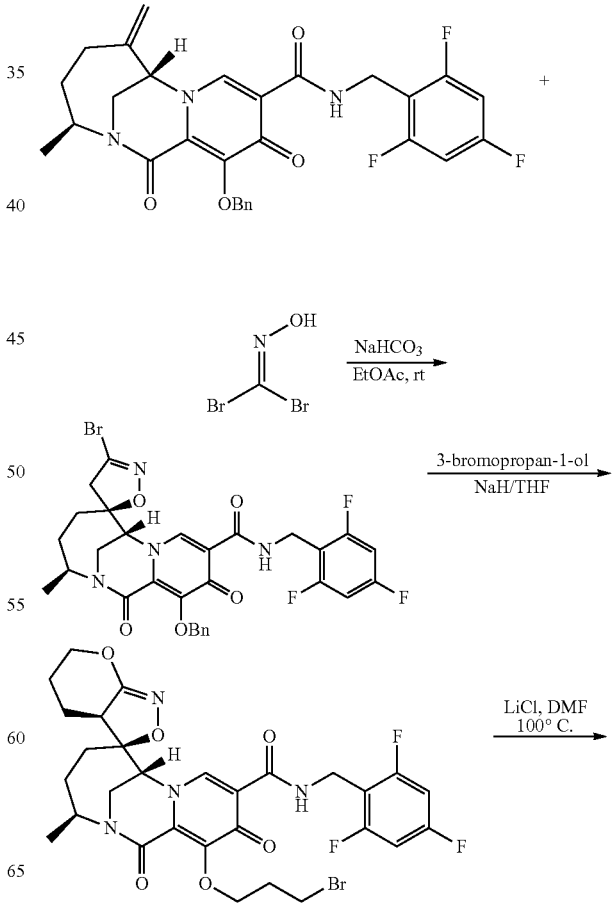

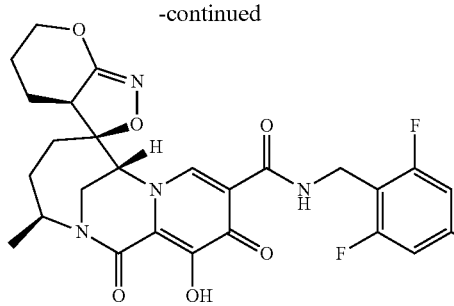

Step 1: Preparation of (3'S,5S,7'R)-12'-(benzyloxy)-3-bromo-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide Into the solution of (3S,7S)-12-(benzyloxy)-3-methyl-6-methylene-1,11-dioxo-N-(2,4,6-trifluorobenzyl)-1,4,5,6,7,11-hexahydro-3H-2,7-methanopyrido[1,2-a][1,4]diazonine-10-carboxamide (456 mg, 0.848 mmol) (Intermediate C) in EtOAc (5 ml), dibromomethanone oxime (0.516 g, 2.54 mmol) and sodium bicarbonate (0.518 g, 8.48 mmol) were added at rt. After overnight, the reaction was quenched by adding brine. The mixture was extracted with EtOAc, the organic phase was separated and dried over MgSO$_4$, filtered, concentrated down and purified by silica gel column chromatography (eluting with 0-80% EtOAc/Hexane) to give the title compound. MS (m/z) 660.978 [M+H]+.

Step 2: Preparation of (3S,3aR,3'S,7'R)-12'-(3-bromopropoxy)-3'-methyl-1',11'-dioxo-N-(2,4,6-trifluorobenzyl)-1',3a,4,4',5,5',6,11'-octahydro-3'H,7'H-spiro[pyrano[2,3-c]isoxazole-3,6'-[2,7]methanopyrido[1,2-a][1,4]diazonine]-10'-carboxamide Into the suspension of NaH (32.8 mg, 0.82 mmol) in THF (2 ml), 3-bromopropan-1-ol (203 mg, 1.46 mmol) was added at rt. After 30 min, a solution of (3'S,5S,7'R)-12'-(benzyloxy)-3-bromo-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (103 mg, 0.17 mmol) in THF (2 ml) was added. After 1 h, the reaction was quenched by adding sat. NH$_4$Cl solution. The mixture was extracted with EtOAc, the organic phase was separated and dried over MgSO$_4$, filtered, concentrated down and purified by silica gel chromatography column (eluting with 0-80% EtOAc/Hexane) to give the title compound. MS (m/z) 667.14 [M+H]+.

Step 3: Preparation of (3S,3aR,3'S,7'R)-12'-hydroxy-3'-methyl-1',11'-dioxo-N-(2,4,6-trifluorobenzyl)-1',3a,4,4',5,5',6,11'-octahydro-3'H,7'H-spiro[pyrano[2,3-c]isoxazole-3,6'-[2,7]methanopyrido[1,2-a][1,4]diazonine]-10'-carboxamide Into the solution of (3S,3aR,3'S,7'R)-12'-(3-bromopropoxy)-3'-methyl-1',11'-dioxo-N-(2,4,6-trifluorobenzyl)-1',3a,4,4',5,5',6,11'-octahydro-3'H,7'H-spiro[pyrano[2,3-c]isoxazole-3,6'-[2,7]methanopyrido[1,2-a][1,4]diazonine]-10'-carboxamide (23.2 mg, 0.0347 mmol) in DMF (2 ml), LiCl (14.7 mg, 0.347 mmol) was added at rt. After the reaction mixture was heated to 100° C. for 2 h, the mixture was extracted with EtOAc, the organic phase was separated and dried over MgSO$_4$, filtered, concentrated down and purified by reverse phase HPLC, eluting with 10-90% acetonitrile in water to give title compound. MS (m/z) 547.131 [M+H]+. $^1$H NMR (400 MHz, Chloroform-d) δ 10.36 (s, 1H), 8.44 (s, 1H), 6.69 (t, J=8.1 Hz, 2H), 6.09-5.94 (m, 1H), 5.47-5.25 (m, 3H), 4.78-4.64 (m, 3H), 4.24 (s, 1H), 3.84 (d, J=14.8 Hz, 1H), 3.73-3.65 (m, 1H), 2.99 (d, J=17.1 Hz, 1H), 2.63 (s, 1H), 2.10-2.02 (m, 3H), 1.64-1.47 (m, 2H), 1.30 (d, J=6.7 Hz, 3H).

Example 51: Preparation of (3'S,5S,7'R)-12'-hydroxy-3'-methyl-3-(methylamino)-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

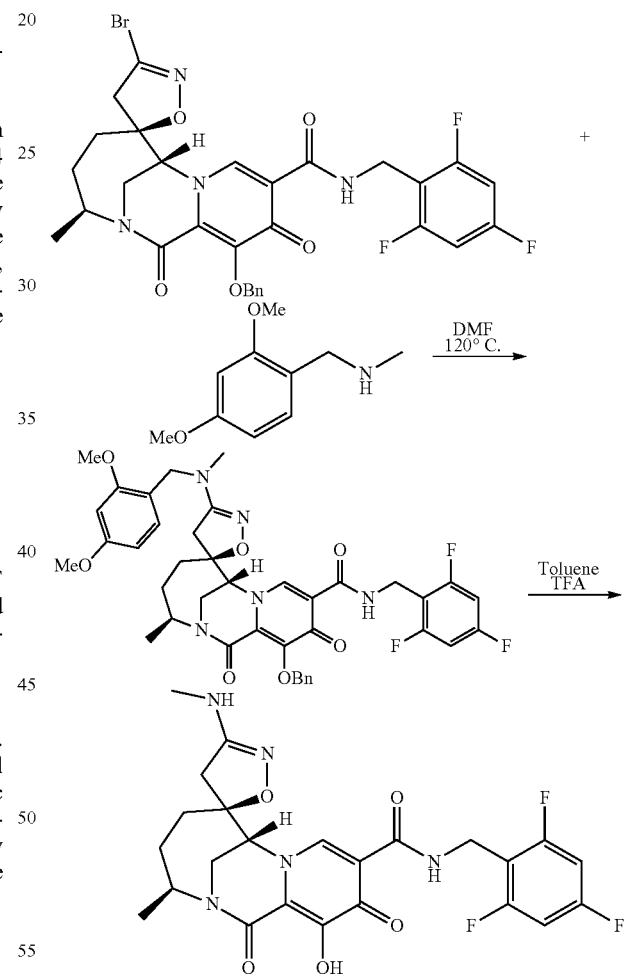

Step 1: Preparation of (3'S,5S,7'R)-12'-(benzyloxy)-3-((2,4-dimethoxybenzyl)(methyl)amino)-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide Into the solution of (3'S,5S,7'R)-12'-(benzyloxy)-3-bromo-3'-methyl-1',11'-dioxo-N-(2,4,6-trifluorobenzyl)-1', 4',5',11'-tetrahydro-3'H,4H,7'H-spiro[isoxazole-5,6'-[2,7] methanopyrido[1,2-a][1,4]diazonine]-10'-carboxamide (40 mg, 0.0607 mmol), prepared according to Example 50, in DMF (2 ml), 1-(2,4-dimethoxyphenyl)-N-methylmethanamine (33 mg, 0.182 mmol) was added. After the reaction was heated at 120° C. for 2 h, the reaction mixture was extracted with EtOAc, the organic phase was separated and dried over MgSO$_4$, filtered, concentrated down and purified by silica gel column chromatography (eluting with 0-80% EtOAc/Hexane) to give the title compound. MS (m/z) 759.946 [M+H]+.

Step 2: Preparation of (3'S,5S,7'R)-12'-hydroxy-3'-methyl-3-(methylamino)-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide To a solution of (3'S,5S,7'R)-12'-(benzyloxy)-3-((2,4-dimethoxybenzyl)(methyl)amino)-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (24 mg, 0.0316 mmol) in toluene (3 mL) was added TFA (1 mL). The reaction mixture was stirred at rt overnight. The reaction mixture was concentrated down, and the residue was purified by reverse phase HPLC, eluting with 10-90% acetonitrile in water to give title compound. MS (m/z) 520.215 [M+H]+. $^1$H NMR (400 MHz, DMSO-d$_6$) δ 11.00 (s, 1H), 10.39 (t, J=5.8 Hz, 1H), 8.43 (s, 1H), 7.22 (t, J=8.6 Hz, 2H), 6.18 (d, J=5.2 Hz, 1H), 4.57 (s, 2H), 3.75 (s, 1H), 3.39 (d, J=7.1 Hz, 2H), 2.90 (s, 1H), 2.79 (s, 1H), 2.74 (s, 1H), 2.64 (d, J=4.8 Hz, 3H), 1.80 (d, J=4.8 Hz, 2H), 1.39-1.28 (m, 1H), 1.18 (d, J=6.6 Hz, 3H).

Example 52: Preparation of (3'S,5S,7'R)-3-(dimethylamino)-12'-hydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

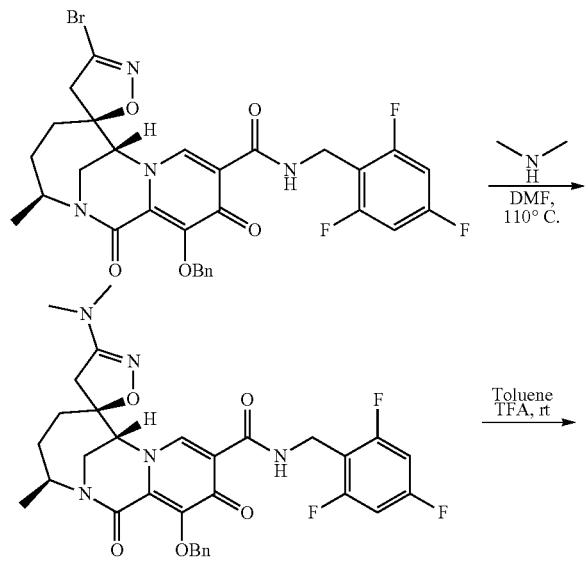

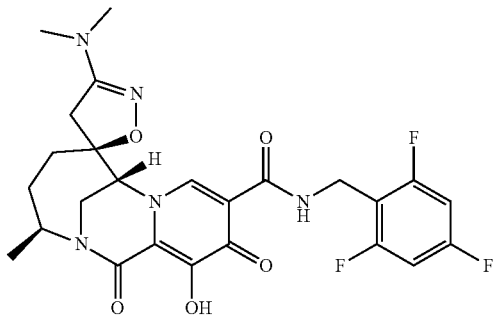

Step 1: Preparation of (3'S,5S,7'R)-12'-(benzyloxy)-3-(dimethylamino)-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide Into the solution of (3'S,5S,7'R)-12'-(benzyloxy)-3-bromo-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (40 mg, 0.0607 mmol) prepared according to Example 50, in DMF (2 ml), N-methylmethanamine (8.2 mg, 0.182 mmol) was added. After the reaction was heated at 110° C. for 2 h, the reaction mixture was extracted with EtOAc, the organic phase was separated and dried over MgSO$_4$, filtered, concentrated down and purified by silica gel column chromatography (eluting with 0-80% EtOAc/Hexane) to give the title compound. MS (m/z) 624.212 [M+H]+.

Step 2: Preparation of (3'S,5S,7'R)-3-(dimethylamino)-12'-hydroxy-3'-methyl-1',11'-dioxo-N-(2,4,6-trifluorobenzyl)-1',4',5',1'-tetrahydro-3'H,4H,7'H-spiro[isoxazole-5,6'-[2,7]methanopyrido[1,2-a][1,4]diazonine]-10'-carboxamide To a solution of (3'S,5S,7'R)-12'-(benzyloxy)-3-(dimethylamino)-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (34 mg, 0.0545 mmol) in toluene (3 mL) was added TFA (1 mL). The reaction mixture was stirred at rt overnight. The reaction mixture was concentrated down, and the residue was purified by reverse phase HPLC, eluting with 10-90% acetonitrile in water to give title compound. MS (m/z) 534.232[M+H]+. $^1$H NMR (400 MHz, Chloroform-d) δ 10.34 (t, J=5.7 Hz, 1H), 8.32 (s, 1H), 6.80-6.60 (m, 2H), 4.85-4.55 (m, 3H), 4.27 (s, 1H), 3.88 (dd, J=15.0, 1.8 Hz, 1H), 3.66 (dd, J=14.9, 2.8 Hz, 1H), 2.94 (s, 6H), 2.90 (d, J=16.3 Hz, 1H), 2.71 (d, J=16.3 Hz, 1H), 2.12-1.94 (m, 3H), 1.71-1.54 (m, 1H), 1.30 (d, J=6.7 Hz, 3H).

Example 53: Preparation of (3'S,5S,7'R)-3-chloro-12'-hydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

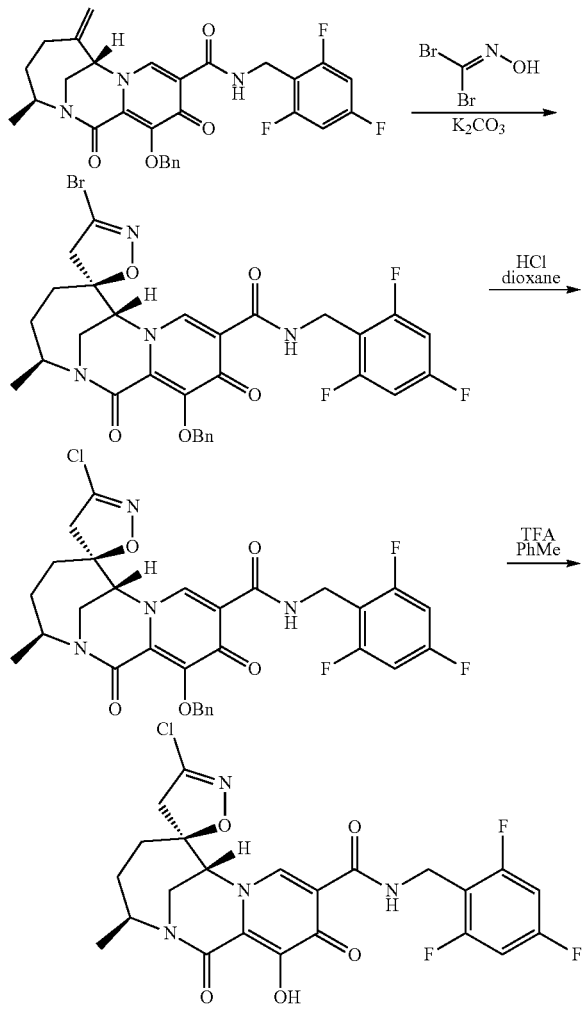

Step 1: Preparation of (3'S,5S,7'R)-12'-(benzyloxy)-3-bromo-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide To a solution of (3S,7S)-12-(benzyloxy)-3-methyl-6-methylene-1,11-dioxo-N-(2,4,6-trifluorobenzyl)-1,4,5,6,7,11-hexahydro-3H-2,7-methanopyrido[1,2-a][1,4]diazonine-10-carboxamide (1.07 g, 1.99 mmol) (Intermediate C) in EtOAc (20 mL) was added $K_2CO_3$ (0.831 g, 5.97 mmol, 3 equiv.) and dibromoformaldoxime (0.808 g, 3.98 mmol, 2 equiv.). The reaction mixture was left at rt for 6 h with high stirring. The reaction mixture was diluted with EtOAc and washed with water and brine. The aqueous phase was extracted with EtOAc and the combined organic phase was dried over $Na_2SO_4$, filtered, and concentrated. The crude residue was purified by column chromatography (0-100% EtOAc/hexanes to afford the title compound. MS (m/z): 659.06 [M+H]+.

Step 2: Preparation of (3'S,5S,7'R)-12'-(benzyloxy)-3-chloro-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (3'S,5S,7'R)-12'-(benzyloxy)-3-bromo-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (0.060 g, 0.091 mmol) was dissolved in 4M HCl in dioxane (1 mL, 0.364 mmol, 4.0 equiv.) and was stirred overnight. The reaction mixture was concentrated to yield the title compound, which was used without further purification. MS (m/z): 614.95 [M+H]+.

Step 3: Preparation of (3'S,5S,7'R)-3-chloro-12'-hydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (3'S,5S,7'R)-12'-(benzyloxy)-3-chloro-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (0.028 g, 0.046 mmol) was dissolved in 1:1 TFA/toluene (2 mL) and stirred for 2 h. The reaction mixture was concentrated and purified by reverse phase prep HPLC (5-100% MeCN/water w/0.1% TFA) to afford the title compound. MS (m/z): 525.09 [M+H]+. 1H NMR (400 MHz, DMSO-d6) δ 10.34 (t, J=5.7 Hz, 1H), 8.79 (d, J=15.2 Hz, 1H), 7.27-7.13 (m, 2H), 4.80 (d, J=10.3 Hz, 1H), 4.55 (dd, J=13.9, 6.3 Hz, 3H), 3.79 (dd, J=15.3, 2.6 Hz, 1H), 3.71 (dd, J=15.1, 1.9 Hz, 1H), 3.22 (dd, J=17.6, 5.5 Hz, 1H), 2.97 (dd, J=17.7, 7.9 Hz, 1H), 1.96-1.73 (m, 3H), 1.45-1.31 (m, 1H), 1.18 (d, J=6.7 Hz, 3H).

Example 54: Preparation of (3'R,5S,7'R)-3'-(fluoromethyl)-12'-hydroxy-3-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

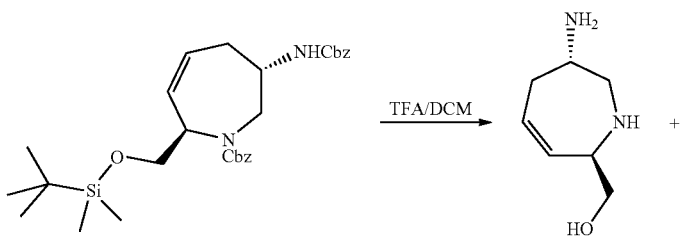

201 202
-continued
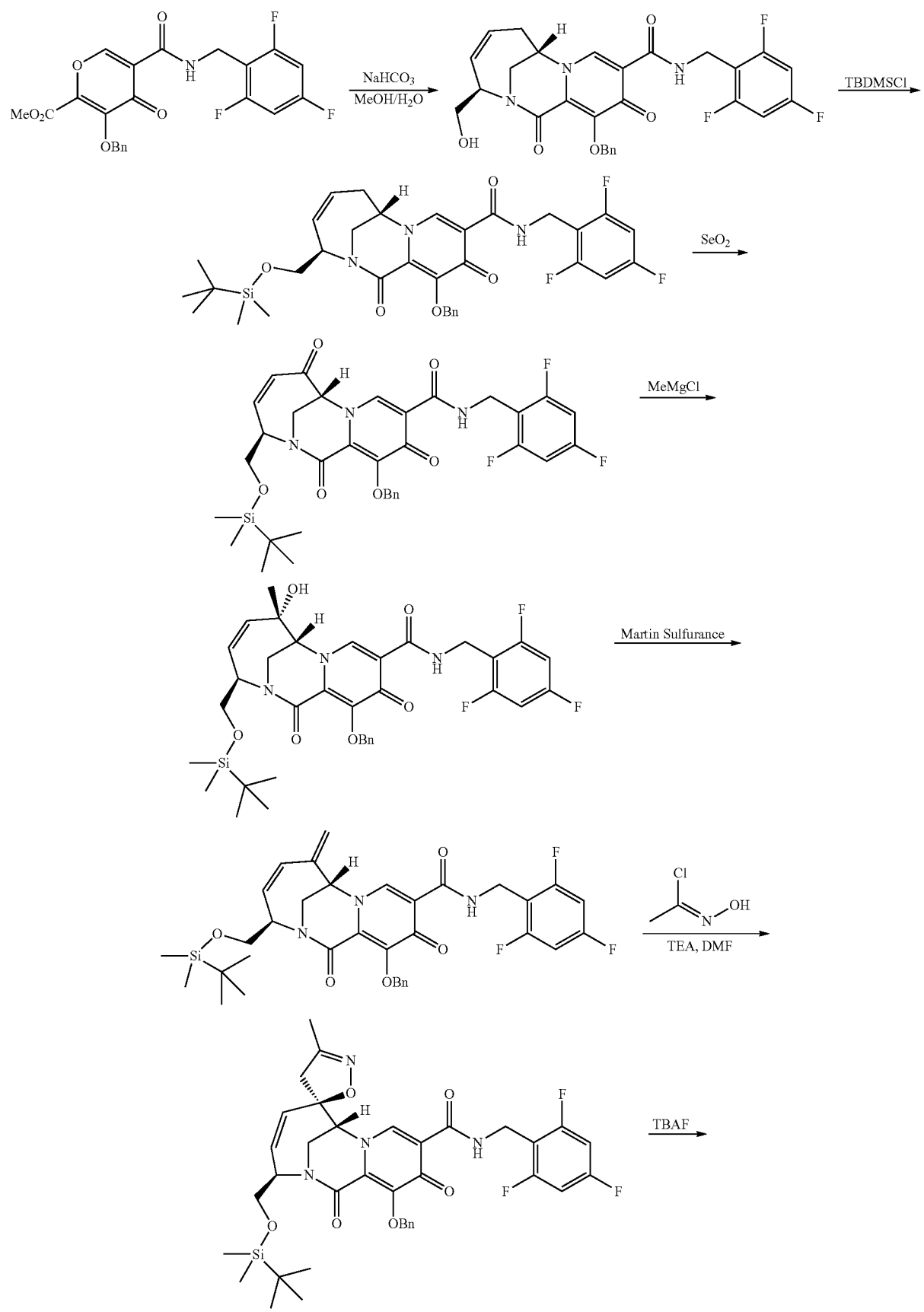

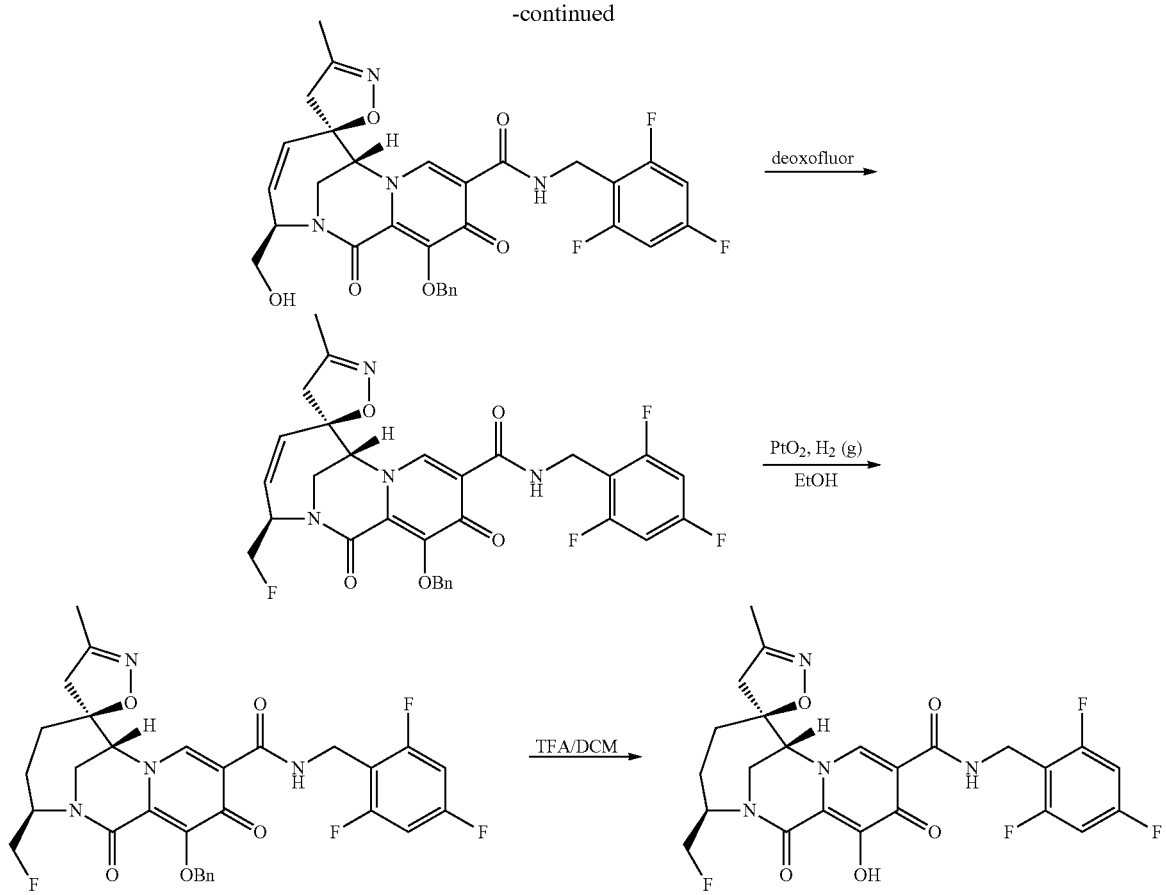

Step 1: Preparation of ((2R,6S)-6-amino-2,5,6,7-tetrahydro-1H-azepin-2-yl)methanol The reaction mixture of benzyl (3S,7R)-3-(((benzyloxy)carbonyl)amino)-7-(((tert-butyldimethylsilyl)oxy)methyl)-2,3,4,7-tetrahydro-1H-azepine-1-carboxylate (1.6 g, 3.05 mmol), prepared according to WO2020197991, in TFA (17 mL) was heated at 10° C. for 5 h. Then the reaction was cooled down to rt and the mixture was concentrated, co-evaporated with toluene and the residue was dried under high vacuum. The dried residue was used in next step without purification. MS (m/z) 142.93 [M+H]+.

Step 2: Preparation of (3R,7S)-12-(benzyloxy)-3-(hydroxymethyl)-1,11-dioxo-N-(2,4,6-trifluorobenzyl)-1,6,7,11-tetrahydro-3H-2,7-methanopyrido-[1,2-a][1,4]diazonine-10-carboxamide To a solution of ((2R,6S)-6-amino-2,5,6,7-tetrahydro-1H-azepin-2-yl)methanol trifluoroacetic acid salt (1100 mg, 2.7 mmol) in MeOH (10 mL) and water (1 mL) was added sodium bicarbonate (1.75 g, 20.8 mmol) and methyl 3-(benzyloxy)-4-oxo-5-((2,4,6-trifluorobenzyl)carbamoyl)-4H-pyran-2-carboxylate (1.14 g, 2.25 mmol). The reaction mixture was stirred at 60° C. overnight. The reaction mixture was cooled and concentrated down. The residue was washed with water and extracted with EtOAc. The organic phase was washed with brine, dried over MgSO$_4$, filtered, concentrated down and purified by silica gel chromatography, eluting with 0-100% EtOAc/hexane to give the title compound. MS (m/z) 540.10 [M+H]+.

Step 3: Preparation of (3R,7S)-12-(benzyloxy)-3-(((tert-butyldimethylsilyl)oxy)methyl)-1,11-dioxo-N-(2,4,6-trifluorobenzyl)-1,6,7,11-tetrahydro-3H-2,7-methanopyrido[1,2-a][1,4]diazonine-10-carboxamide A mixture of the (3R,7S)-12-(benzyloxy)-3-(hydroxymethyl)-1,11-dioxo-N-(2,4,6-trifluorobenzyl)-1,6,7,11-tetrahydro-3H-2,7-methanopyrido[1,2-a][1,4]diazonine-10-carboxamide (1000 mg, 1.85 mmol), tert-butyldimethylsilyl chloride (349 mg, 2.32 mmol), and imidazole (379 mg, 5.56 mmol) in CH$_2$Cl$_2$ (30 mL) was stirred at rt overnight. The reaction mixture was diluted with EtOAc, washed with 10% citric acid and water. The aqueous fractions were extracted with EtOAc and the organic fractions were combined, dried (MgSO$_4$), and concentrated. The residue was purified by silica gel column, eluting 0-100% EtOAc in hexane, concentrated, and dried to get the title compound. MS (m/z) 653.70 [M+H]+.

Step 4: Preparation of (3R,7R)-12-(benzyloxy)-3-(((tert-butyldimethylsilyl)oxy)methyl)-1,6,11-trioxo-N-(2,4,6-trifluorobenzyl)-1,6,7,11-tetrahydro-3H-2,7-methanopyrido[1,2-a][1,4]diazonine-10-carboxamide To a solution of (3R,7S)-12-(benzyloxy)-3-(((tert-butyldimethylsilyl)oxy)methyl)-1,11-dioxo-N-(2,4,6-trifluorobenzyl)-1,6,7,11-tetrahydro-3H-2,7-methanopyrido[1,2-a][1,4]diazonine-10-carboxamide (830 mg, 1.27 mmol) in dioxane (10 mL) was added selenium dioxide (423 mg, 3.8 mmol). The reaction mixture was heated at 100° C. overnight. To the mixture was added additional selenium dioxide (200 mg, 1.8 mmol). Then the reaction mixture was stirred at 100° C. for 1 day. The reaction mixture was filtered through celite, washed with brine, dried over MgSO$_4$, filtered and concentrated down. The residue was purified by silica gel chromatography, eluting with 0-100% EtOAc/hexane, to give title compound. MS (m/z) 667.96 [M+H]+.

Step 5: Preparation of (3R,6S,7R)-12-(benzyloxy)-3-(((tert-butyldimethylsilyl)oxy)methyl)-6-hydroxy-6-methyl-1,11-dioxo-N-(2,4,6-trifluorobenzyl)-1,6,7,11-tetrahydro-3H-2,7-methanopyrido[1,2-a][1,4]diazonine-10-carboxamide To a solution of MeMgCl (3M in THF, 0.45 mL, 1.35 mmol) in THF (2 mL) at 0° C., was added (3R,7R)-12-(benzyloxy)-3-(((tert-butyldimethylsilyl)oxy)methyl)-1,6,11-trioxo-N-(2,4,6-trifluorobenzyl)-1,6,7,11-tetrahydro-3H-2,7-methanopyrido[1,2-a][1,4]diazonine-10-carboxamide (150 mg, 0.25 mmol) in THF (1 mL). The reaction mixture was stirred at 0° C. for 0.5 h. The reaction was quenched by adding sat. NH$_4$Cl and extracted with EtOAc. The organic phase was separated, dried over MgSO$_4$, filtered and concentrated down. The residue was purified by silica gel column, eluting with 0-100% EtOAc/hexane, to give title compound. MS (m/z) 684.09 [M+H]+.

Step 6: Preparation of (3R,7S)-12-(benzyloxy)-3-(((tert-butyldimethylsilyl)oxy)methyl)-6-methylene-1,11-dioxo-N-(2,4,6-trifluorobenzyl)-1,6,7,11-tetrahydro-3H-2,7-methanopyrido[1,2-a][1,4]diazonine-10-carboxamide The reaction mixture of (3R,6S,7R)-12-(benzyloxy)-3-(((tert-butyldimethylsilyl)oxy)methyl)-6-hydroxy-6-methyl-1,11-dioxo-N-(2,4,6-trifluorobenzyl)-1,6,7,11-tetrahydro-3H-2,7-methanopyrido[1,2-a][1,4]diazonine-10-carboxamide (200 mg, 0.292 mmol) and Martin Sulfurane (393 mg, 0.585 mmol) in toluene (9 mL) was stirred at rt for 1 h. The reaction mixture was concentrated down. The residue was purified by silica gel chromatography, eluting with 0-100% EtOAc/hexane, to give the title compound. MS (m/z) 666.57 [M+H]+.

Step 7: Preparation of (3'R,5R,7'R)-12'-(benzyloxy)-3'-(((tert-butyldimethylsilyl)oxy)methyl)-3-methyl-1',11'-dioxo-N-(2,4,6-trifluorobenzyl)-1',11'-dihydro-3'H,4H,7'H-spiro[isoxazole-5,6'-[2,7]methanopyrido[1,2-a][1,4]diazonine]-10'-carboxamide To a solution of acetaldehyde oxime (46 mg, 0.78 mmol) in DMF (2 mL) was added N-chlorosuccinimide (104 mg, 0.78 mol). The reaction mixture was heated to 50° C. for 2 h. The reaction mixture was cooled down to rt and transferred to a flask charged with (3R,7S)-12-(benzyloxy)-3-(((tert-butyldimethylsilyl)oxy)methyl)-6-methylene-1,11-dioxo-N-(2,4,6-trifluorobenzyl)-1,6,7,11-tetrahydro-3H-2,7-methanopyrido[1,2-a][1,4]diazonine-10-carboxamide (135 mg, 0.203 mmol). To the reaction mixture was added triethylamine (103 mg, 1.01 mmol). The reaction mixture was stirred at rt overnight. The reaction was washed with brine, extracted with EtOAc, dried over MgSO$_4$, filtered and concentrated down. The residue was purified by silica gel chromatography, eluting with EtOAc in hexane from 0% to 100%, to provide the title compound. MS (m/z) 723.13 [M+H]+.

Step 8: Preparation of (3'R,5R,7'R)-12'-(benzyloxy)-3'-(hydroxymethyl)-3-methyl-1',11'-dioxo-N-(2,4,6-trifluorobenzyl)-1',11'-dihydro-3'H,4H,7'H-spiro[isoxazole-5,6'-[2,7]methanopyrido[1,2-a][1,4]diazonine]-10'-carboxamide To a solution of (3'R,5R,7'R)-12'-(benzyloxy)-3'-(((tert-butyldimethylsilyl)oxy)methyl)-3-methyl-1',11'-dioxo-N-(2,4,6-trifluorobenzyl)-1',11'-dihydro-3'H,4H,7'H-spiro[isoxazole-5,6'-[2,7]methanopyrido[1,2-a][1,4]diazonine]-10'-carboxamide (165 mg, 0.228 mmol) in THF (2 mL) at 0° C. was added 1 M tetrabutylammonium fluoride in THF (0.314 mL, 0.314 mmol). The reaction mixture was stirred at 0° C. for 1.5 h. The reaction mixture was diluted with EtOAc, washed with sat. NH$_4$Cl, extracted with EtOAc, dried over MgSO$_4$, filtered and concentrated down. The residue was purified by silica gel chromatography, eluting with 0-100% EtOAc/hexane to give the title compound. MS (m/z) 609.09 [M+H]+.

Step 9: Preparation of (3'R,5R,7'R)-12'-(benzyloxy)-3'-(fluoromethyl)-3-methyl-1',11'-dioxo-N-(2,4,6-trifluorobenzyl)-1',11'-dihydro-3'H,4H,7'H-spiro[isoxazole-5,6'-[2,7]methanopyrido[1,2-a][1,4]diazonine]-10'-carboxamide To a solution of (3'R,5R,7'R)-12'-(benzyloxy)-3'-(hydroxymethyl)-3-methyl-1',11'-dioxo-N-(2,4,6-trifluorobenzyl)-1',11'-dihydro-3'H,4H,7'H-spiro[isoxazole-5,6'-[2,7]methanopyrido[1,2-a][1,4]diazonine]-10'-carboxamide (25 mg, 0.041 mmol) in DCM (2 mL) was added [bis(2-methoxyl)amino]sulfur trifluoride (50 wt % solution in toluene, 55 mg, 0.123 mmol) at 0° C. The reaction mixture was stirred at 0° C. for 1.5 h. The reaction mixture was quenched with sat. NaHCO$_3$ solution and extracted with EtOAc. The organic phase was separated, dried over MgSO$_4$, filtered and concentrated down. The residue was purified by silica gel chromatography, eluting with 0-100% EtOAc/hexane, to give the title compound. MS (m/z) 611.05 [M+H]+.

Step 10: Preparation of (3'R,5S,7'R)-12'-(benzyloxy)-3'-(fluoromethyl)-3-methyl-1',11'-dioxo-N-(2,4,6-trifluorobenzyl)-1',4',5',1'-tetrahydro-3'H,4H,7'H-spiro[isoxazole-5,6'-[2,7]methanopyrido[1,2-a][1,4]diazonine]-10'-carboxamide To a solution of (3'R,5R,7'R)-12'-(benzyloxy)-3'-(fluoromethyl)-3-methyl-1',11'-dioxo-N-(2,4,6-trifluorobenzyl)-1',11'-dihydro-3'H,4H,7'H-spiro[isoxazole-5,6'-[2,7]methanopyrido[1,2-a][1,4]diazonine]-10'-carboxamide (20 mg, 0.033 mmol) in EtOH (2 mL) and EtOAc (0.5 mL) was added PtO$_2$ (2 mg). The reaction mixture was stirred at rt under H$_2$ balloon overnight. The reaction mixture was filtered and concentrated down. The residue was purified by silica gel chromatography, eluting with 0-100% EtOAc/hexane, to provide the title compound. MS (m/z) 613.11 [M+H]+.

Step 11: Preparation of (3'R,5S,7'R)-3'-(fluoromethyl)-12'-hydroxy-3-methyl-1',11'-dioxo-N-(2,4,6-trifluorobenzyl)-1',4',5',1'-tetrahydro-3'H,4H,7'H-spiro[isoxazole-5,6'-[2,7]methanopyrido[1,2-a][1,4]diazonine]-10'-carboxamide The solution of (3'R,5S,7'R)-12'-(benzyloxy)-3'-(fluoromethyl)-3-methyl-1',11'-dioxo-N-(2,4,6-trifluorobenzyl)-

1',4',5',11'-tetrahydro-3'H,4H,7'H-spiro[isoxazole-5,6'-[2,7]methanopyrido[1,2-a][1,4]diazonine]-10'-carboxamide (10 mg, 0.016 mmol) in DCM (1 mL) and TFA (1 mL) was stirred at rt for 2 h. The reaction mixture was concentrated down, the residue was purified by reverse phase HPLC, eluting with 5-100% acetonitrile/water to give the title compound. MS (m/z) 523.15 [M+H]+. 1H NMR (400 MHz, Methanol-d4) δ 8.49 (s, 1H), 6.92 (t, J=8.4 Hz, 2H), 4.84-4.60 (m, 4H), 4.56 (d, J=4.7 Hz, 1H), 4.50 (s, 1H), 3.97 (q, J=15.3 Hz, 2H), 3.03 (d, J=17.8 Hz, 1H), 2.65 (d, J=17.9 Hz, 1H), 2.25 (q, J=12.2 Hz, 1H), 2.04 (s, 4H), 1.96-1.86 (m, 1H), 1.61 (dd, J=15.6, 11.9 Hz, 1H).

Example 55: Preparation of (2R,3'S,7'R)-12'-hydroxy-3'-methyl-1',11'-dioxo-N-(2,4,6-trifluorobenzyl)-1',4',5',11'-tetrahydro-3'H,7'H-spiro[oxetane-2,6'-[2,7]methanopyrido[1,2-a][1,4]diazonine]-10'-carboxamide

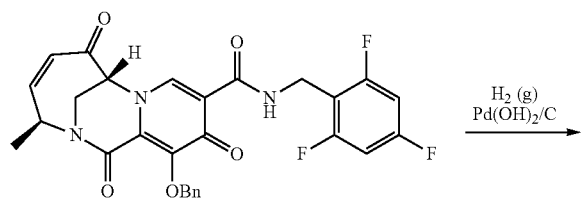

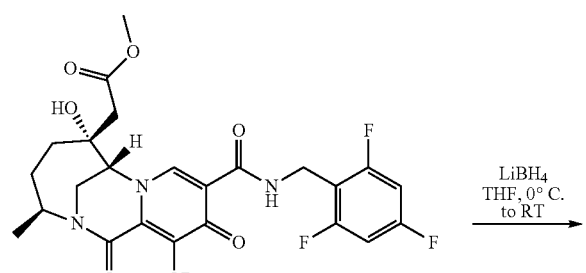

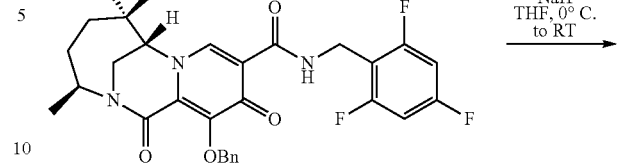

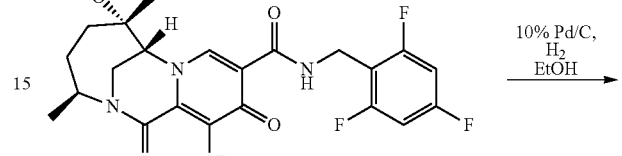

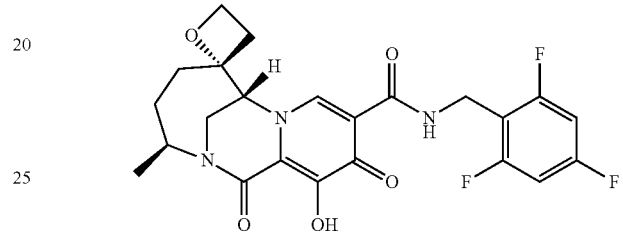

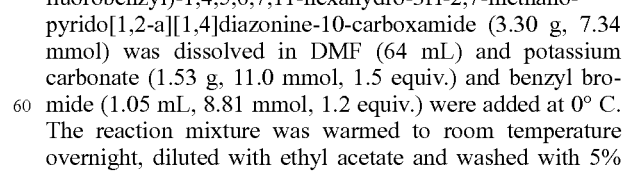

Step 1: Preparation of (3S,7R)-12-hydroxy-3-methyl-1,6,11-trioxo-N-(2,4,6-trifluorobenzyl)-1,4,5,6,7,11-hexahydro-3H-2,7-methanopyrido[1,2-a][1,4]diazonine-10-carboxamide To a suspension of (3S,7R)-12-(benzyloxy)-3-methyl-1,6,11-trioxo-N-(2,4,6-trifluorobenzyl)-1,6,7,11-tetrahydro-3H-2,7-methanopyrido[1,2-a][1,4]diazonine-10-carboxamide (Intermediate A) (5.00 g, 9.30 mmol) in EtOH (300 mL) was added 20% Pd(OH)$_2$/C (1.960 g, 2.79 mmol, 0.3 equiv.). The reaction mixture was evacuated and backfilled with hydrogen gas (3×) and sparged with H$_2$ (g) for 5 mins. The flask was sealed under hydrogen balloon atmosphere and left to stir at rt overnight. The reaction mixture was filtered through Celite and concentrated. The residue was purified by column chromatography (0-10% MeOH/DCM) and concentrated to afford the title compound. MS (m/z) 496.25 [M+EtOH+H]+.

Step 2: Preparation of (3S,7R)-12-(benzyloxy)-3-methyl-1,6,11-trioxo-N-(2,4,6-trifluorobenzyl)-1,4,5,6,7,11-hexahydro-3H-2,7-methanopyrido[1,2-a][1,4]diazonine-10-carboxamide (3S,7R)-12-hydroxy-3-methyl-1,6,11-trioxo-N-(2,4,6-trifluorobenzyl)-1,4,5,6,7,11-hexahydro-3H-2,7-methanopyrido[1,2-a][1,4]diazonine-10-carboxamide (3.30 g, 7.34 mmol) was dissolved in DMF (64 mL) and potassium carbonate (1.53 g, 11.0 mmol, 1.5 equiv.) and benzyl bromide (1.05 mL, 8.81 mmol, 1.2 equiv.) were added at 0° C. The reaction mixture was warmed to room temperature overnight, diluted with ethyl acetate and washed with 5% LiCl solution (2×). The aqueous phase was extracted with EtOAc (2×) and the combined organic phase was washed with brine, dried (Na$_2$SO$_4$) and filtered. The filtrate was concentrated and purified (0-100% EtOAc/hexanes) to give the title compound. MS (m/z) 540.06 [M+H]+.

Step 3: Preparation of methyl 2-((3S,6R,7R)-12-(benzyloxy)-6-hydroxy-3-methyl-1,11-dioxo-10-((2,4,6-trifluorobenzyl)carbamoyl)-1,4,5,6,7,11-hexahydro-3H-2,7-methanopyrido[1,2-a][1,4]diazonin-6-yl)acetate A solution of LiHMDS (1 M in THF, 2.5 equiv, 0.35 mmol, 0.35 mL) in THF (0.4 mL) was cooled to −78° C. in an oven-dried vial under argon. Methyl acetate (2.5 equiv, 0.35 mmol, 0.028 mL) was added dropwise and the reaction mixture was stirred for 15 minutes at which point a solution of (3S,7R)-12-(benzyloxy)-3-methyl-1,6,11-trioxo-N-(2,4,6-trifluorobenzyl)-1,4,5,6,7,11-hexahydro-3H-2,7-methanopyrido[1,2-a][1,4]diazonine-10-carboxamide (0.14 mmol, 75 mg) in THF (1 mL) was added dropwise. After stirring for 4 hours at −78° C., the reaction mixture was quenched with saturated aqueous ammonium chloride and extracted into EtOAx (3×), dried with sodium sulfate, filtered and concentrated. The crude residue was purified by silica gel chromatography with 0-100% EtOAc/hexanes to afford the title compound as a single diastereomer. MS (m/z) 614.16 [M+H]+. $^1$H NMR (400 MHz, Chloroform-d) δ 10.41 (t, J=5.7 Hz, 1H), 8.47 (s, 1H), 7.57 (d, J=6.9 Hz, 2H), 7.38-7.28 (m, 3H), 6.70-6.61 (m, 2H), 5.50 (d, J=10.2 Hz, 1H), 5.14 (d, J=10.2 Hz, 1H), 4.83 (dt, J=10.3, 6.7 Hz, 1H), 4.64 (qd, J=14.5, 5.5 Hz, 2H), 4.20 (s, 1H), 4.12 (s, 1H), 3.78 (s, 3H), 3.44 (dd, J=15.4, 2.9 Hz, 1H), 3.24 (d, J=15.5 Hz, 1H), 2.69 (q, J=15.5 Hz, 2H), 2.02 (dt, J=14.8, 7.0 Hz, 1H), 1.69 (dd, J=15.6, 7.3 Hz, 1H), 1.31-1.22 (m, 1H), 1.18 (d, J=6.7 Hz, 3H).

Step 4: Preparation of (3S,6R,7R)-12-(benzyloxy)-6-hydroxy-6-(2-hydroxyethyl)-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide A solution of methyl 2-((3S,6R,7R)-12-(benzyloxy)-6-hydroxy-3-methyl-1,11-dioxo-10-((2,4,6-trifluorobenzyl)carbamoyl)-1,4,5,6,7,11-hexahydro-3H-2,7-methanopyrido[1,2-a][1,4]diazonin-6-yl)acetate (0.054 mmol, 33 mg) in THF was cooled to 0° C. under argon then treated dropwise with a solution of LiBH$_4$ (2M in THF, 1.5 equiv, 40 uL) and stirred for 4 hours. The reaction mixture was quenched with saturated ammonium chloride and extracted into EtOAc (3×). The combined organic layer was washed with brine, dried with sodium sulfate, filtered and concentrated. The crude residue was purified by silica gel chromatography (0-30% MeOH in DCM) to afford the title compound, which was carried forward to Step 3 without further purification. MS (m/z) 586.11 [M+H]+.

Step 5: Preparation of (3S,6R,7R)-12-(benzyloxy)-6-(2-bromoethyl)-6-hydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide A solution of (3S,6R,7R)-12-(benzyloxy)-6-hydroxy-6-(2-hydroxyethyl)-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (0.031 mmol, 18 mg) and carbon tetrabromide (1.5 equiv, 0.046 mmol, 15.3 mg) in THF (0.1 mL) was cooled to 0° C. then treated with a solution of triphenylphosphine (1.5 equiv, 0.046 mmol, 11.4 mg) in THF (0.1 mL), slowly warmed to room temperature and stirred for ~48 hours. The reaction mixture was diluted with EtOAc and washed with brine, then further extracted into EtOAc (2×). The combined organic layer was dried with sodium sulfate, filtered and concentrated. The crude residue was purified by silica gel chromatography to afford the title compound. MS (m/z) 648.02 [M+H]+.

Step 6: Preparation of (2R,3'S,7'R)-12'-(benzyloxy)-3'-methyl-1',11'-dioxo-N-(2,4,6-trifluorobenzyl)-1',4',5',11'-tetrahydro-3'H,7'H-spiro[oxetane-2,6'-[2,7]methanopyrido[1,2-a][1,4]diazonine]-10'-carboxamide A solution of (3S,6R,7R)-12-(benzyloxy)-6-(2-bromoethyl)-6-hydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (0.012 mmol, 7.6 mg) in THF (0.4 mL) was cooled to 0° C. under argon then treated with sodium hydride (60% dispersion in mineral oil, 1.5 equiv, 0.018 mmol, 6.7 mg). The reaction mixture was slowly warmed to room temperature, stirred for 3 hours then quenched with brine and extracted into EtOAc (3×). The combined organic layer was dried with sodium sulfate, filtered and concentrated to afford the title compound which was carried forward without further purification. MS (m/z) 568.09 [M+H]+.

Step 7: Preparation of (2R,3'S,7'R)-12'-hydroxy-3'-methyl-1',11'-dioxo-N-(2,4,6-trifluorobenzyl)-1',4',5',11'-tetrahydro-3'H,7'H-spiro[oxetane-2,6'-[2,7]methanopyrido[1,2-a][1,4]diazonine]-10'-carboxamide A solution of (2R,3'S,7'R)-12'-(benzyloxy)-3'-methyl-1',11'-dioxo-N-(2,4,6-trifluorobenzyl)-1',4',5',11'-tetrahydro-3'H,7'H-spiro[oxetane-2,6'-[2,7]methanopyrido[1,2-a][1,4]diazonine]-10'-carboxamide (0.012 mmol, 6.7 mg) in EtOH (0.5 mL) was evacuated and back-filled with argon (5×cycles) then treated with 10% Pd/C (4 mg) and further evacuated with argon (5×cycles) followed by hydrogen (5×cycles). The reaction mixture was stirred at room temperature under a hydrogen balloon for 1 hour then filtered across Celite, washed with excess MeOH/DCM and concentrated. The crude residue was purified by preparative HPLC in 10-100% MeCN/water (neutral) and lyophilized to afford the title product. MS (m/z) 478.21 [M+H]+. $^1$H NMR (400 MHz, Acetonitrile-d3) δ 10.39 (s, 1H), 8.38 (s, 1H), 6.84 (t, J=8.5 Hz, 2H), 4.72-4.63 (m, 2H), 4.62-4.43 (m, 4H), 3.61 (d, J=15.8 Hz, 1H), 3.42 (d, J=15.4 Hz, 1H), 2.61-2.41 (m, 2H), 2.08-1.98 (m, 1H), 1.41-1.23 (m, 3H), 1.18 (d, J=6.7 Hz, 3H).

Example 56: Preparation of (3'S,7'R)—N-(2,4-difluorobenzyl)-12'-hydroxy-2,3'-dimethyl-1',11'-dioxo-1',4',5',11'-tetrahydro-3'H,4H,7'H-spiro[oxazole-5,6'-[2,7]methanopyrido[1,2-a][1,4]diazonine]-10'-carboxamide

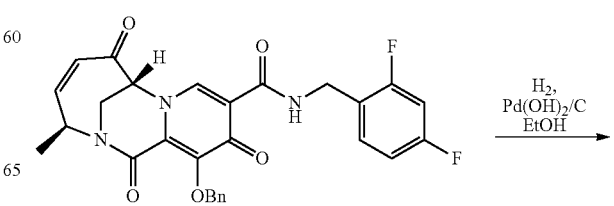

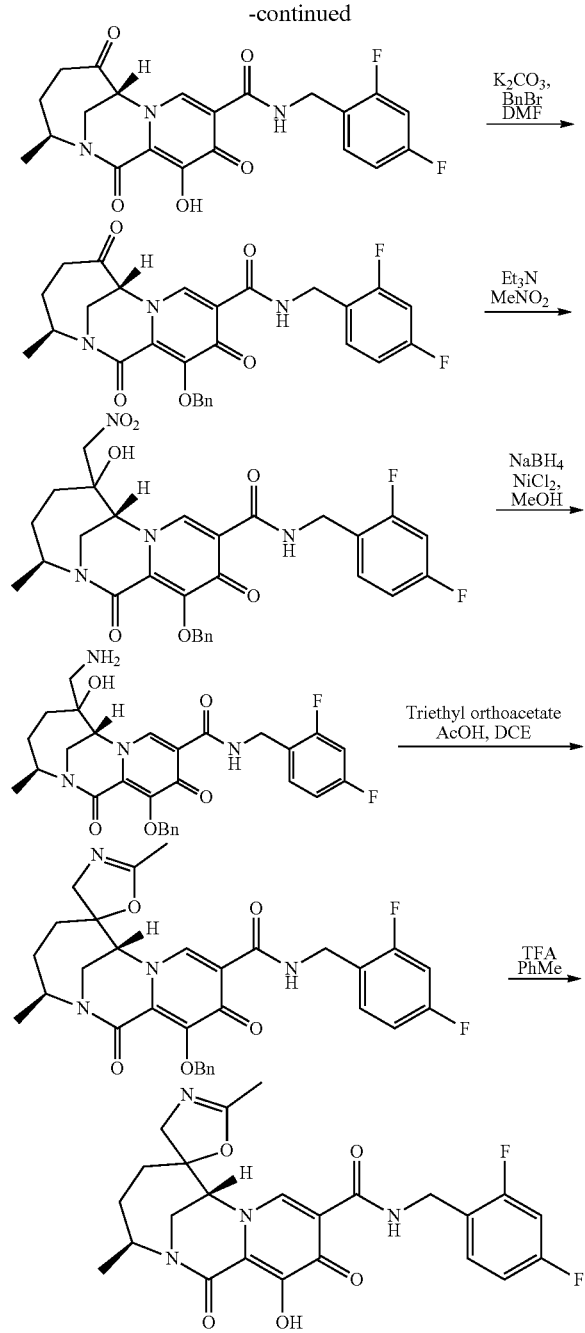

Step 1: Preparation of (3S,7R)—N-(2,4-difluorobenzyl)-12-hydroxy-3-methyl-1,6,11-trioxo-1,4,5,6,7,11-hexahydro-3H-2,7-methanopyrido[1,2-a][1,4]diazonine-10-carboxamide To a suspension of (3S,7R)-12-(benzyloxy)-N-(2,4-difluorobenzyl)-3-methyl-1,6,11-trioxo-1,6,7,11-tetrahydro-3H-2,7-methanopyrido[1,2-a][1,4]diazonine-10-carboxamide (Intermediate D) (1.00 g, 1.92 mmol) in EtOH (60 mL) was added 20% Pd(OH)$_2$/C (0.405 g, 0.577 mmol, 0.3 equiv.). The reaction mixture was evacuated and backfilled with hydrogen gas (3×) and sparged with H$_2$ (g) for 5 mins. The flask was sealed under hydrogen balloon atmosphere and left to stir at rt overnight. The reaction mixture was filtered through Celite and concentrated to afford the title compound, which was used in the subsequent step without further purification. MS (m/z): 478.20 [M+EtOH+H]+.

Step 2: Preparation of (3S,7R)-12-(benzyloxy)-N-(2,4-difluorobenzyl)-3-methyl-1,6,11-trioxo-1,4,5,6,7,11-hexahydro-3H-2,7-methanopyrido[1,2-a][1,4]diazonine-10-carboxamide (3S,7R)—N-(2,4-difluorobenzyl)-12-hydroxy-3-methyl-1,6,11-trioxo-1,4,5,6,7,11-hexahydro-3H-2,7-methanopyrido[1,2-a][1,4]diazonine-10-carboxamide (0.83 g, 1.92 mmol) was dissolved in DMF (17 mL) and potassium carbonate (0.402 g, 2.89 mmol, 1.5 equiv.) and benzyl bromide (0.275 mL, 2.31 mmol, 1.2 equiv.) were added at 0° C. The reaction mixture was warmed to room temperature overnight. The reaction mixture was diluted with ethyl acetate and washed with 5% LiCl solution (2×). The aqueous phase was extracted with EtOAc (2×) and the combined organic phase was washed with brine, dried over Na2SO4, and filtered. The filtrate was concentrated and purified (0-100% EtOAc/hexanes) to give the title product. MS (m/z): 522.05 [M+H]+.

Step 3: Preparation of (3S,7R)-12-(benzyloxy)-N-(2,4-difluorobenzyl)-6-hydroxy-3-methyl-6-(nitromethyl)-1,11-dioxo-1,4,5,6,7,11-hexahydro-3H-2,7-methanopyrido[1,2-a][1,4]diazonine-10-carboxamide To a solution of (3S,7R)-12-(benzyloxy)-N-(2,4-difluorobenzyl)-3-methyl-1,6,11-trioxo-1,4,5,6,7,11-hexahydro-3H-2,7-methanopyrido[1,2-a][1,4]diazonine-10-carboxamide (0.387 g, 0.717 mmol) in nitromethane (7.7 mL) was added Et$_3$N (0.30 mL, 2.15 mmol, 3 equiv.). The reaction mixture was stirred at rt overnight and was heated to 50° C. for 4 h. The reaction mixture was concentrated and purified by column chromatography (0-100% EtOAc/hexanes) to yield the title compound as a mixture of stereoisomers. MS (m/z): 583.07 [M+H]+.

Step 4: Preparation of (3S,7R)-6-(aminomethyl)-12-(benzyloxy)-N-(2,4-difluorobenzyl)-6-hydroxy-3-methyl-1,11-dioxo-1,4,5,6,7,11-hexahydro-3H-2,7-methanopyrido[1,2-a][1,4]diazonine-10-carboxamide To a solution of (3S,7R)-12-(benzyloxy)-N-(2,4-difluorobenzyl)-6-hydroxy-3-methyl-6-(nitromethyl)-1,11-dioxo-1,4,5,6,7,11-hexahydro-3H-2,7-methanopyrido[1,2-a][1,4]diazonine-10-carboxamide (0.025 g, 0.043 mmol) in MeOH (1 mL) at 0° C. was added nickel(II) chloride (0.0057 g, 0.044 mmol, 1.03 equiv.) and sodium borohydride (0.015 g, 0.397 mmol, 9.26 equiv.). The reaction mixture was allowed to warm to rt and stir for 3 h. The reaction mixture was quenched with water and concentrated to remove MeOH. The aqueous phase was extracted with CH$_2$Cl$_2$ (3×) and the combined organic phase was washed with brine, dried over Na$_2$SO$_4$, filtered, and concentrated to yield the title compound, which was used without further purification. MS (m/z): 553.20 [M+H]+.

Step 5: Preparation of (3'S,7'R)-12'-(benzyloxy)-N-(2,4-difluorobenzyl)-2,3'-dimethyl-1',11'-dioxo-1',4',5',11'-tetrahydro-3'H,4H,7'H-spiro[oxazole-5,6'-[2,7]methanopyrido[1,2-a][1,4]diazonine]-10'-carboxamide To a solution of (3S,7R)-6-(aminomethyl)-12-(benzyloxy)-N-(2,4-difluorobenzyl)-6-hydroxy-3-methyl-1,11-dioxo-1,4,5,6,7,11-hexahydro-3H-2,7-methanopyrido[1,2-a][1,4]diazonine-10-carboxamide (0.0237 g, 0.043 mmmol) in DCE (1 mL) was added triethyl orthoacetate (0.012 mL, 0.064 mmol, 1.5 equiv.) and 1 drop of acetic acid. The reaction mixture was heated to 85° C. for 30 min. The reaction mixture was concentrated to yield the title compound, which was used without further purification. MS (m/z): 577.15 [M+H]+.

Step 6: Preparation of (3'S,7'R)—N-(2,4-difluorobenzyl)-12'-hydroxy-2,3'-dimethyl-1',11'-dioxo-1',4',5',11'-tetrahydro-3'H,4H,7'H-spiro[oxazole-5,6'-[2,7]methanopyrido[1,2-a][1,4]diazonine]-10'-carboxamide A solution of (3'S,7'R)-12'-(benzyloxy)-N-(2,4-difluorobenzyl)-2,3'-dimethyl-1',11'-dioxo-1',4',5',11'-tetrahydro-3'H,4H,7'H-spiro[oxazole-5,6'-[2,7]methanopyrido[1,2-a][1,4]diazonine]-10'-carboxamide (0.025 g, 0.043 mmol) was dissolved in 1:1 TFA/toluene (2 mL). The solution was stirred for 2 h at rt, concentrated, and purified by RP prep HPLC (5-100% MeCN/water w/0.1% TFA). The fractions were lyophilized to afford the title compound. MS (m/z): 487.18 [M+H]+. 1H NMR (400 MHz, DMSO-d6) δ 10.31 (t, J=6.1 Hz, 1H), 8.61 (s, 1H), 7.41 (q, J=8.1 Hz, 1H), 7.25 (td, J=10.0, 2.6 Hz, 1H), 7.07 (dd, J=9.9, 7.4 Hz, 1H), 4.54 (dt, J=16.3, 6.7 Hz, 4H), 3.84 (d, J=15.8 Hz, 1H), 3.73 (d, J=15.3 Hz, 1H), 3.61 (d, J=14.3 Hz, 1H), 3.29 (d, J=14.7 Hz, 1H), 2.03 (s, 3H), 1.89-1.72 (m, 3H), 1.40 (dd, J=15.5, 11.7 Hz, 1H), 1.19 (d, J=6.9 Hz, 3H).

Example 57: Preparation of (3R,3'S,7'S)-12'-hydroxy-3'-methyl-1',5,11'-trioxo-N-(2,4,6-trifluorobenzyl)-1',4',5',11'-tetrahydro-3'H,7'H-spiro[pyrrolidine-3,6'-[2,7]methanopyrido[1,2-a][1,4]diazonine]-10'-carboxamide

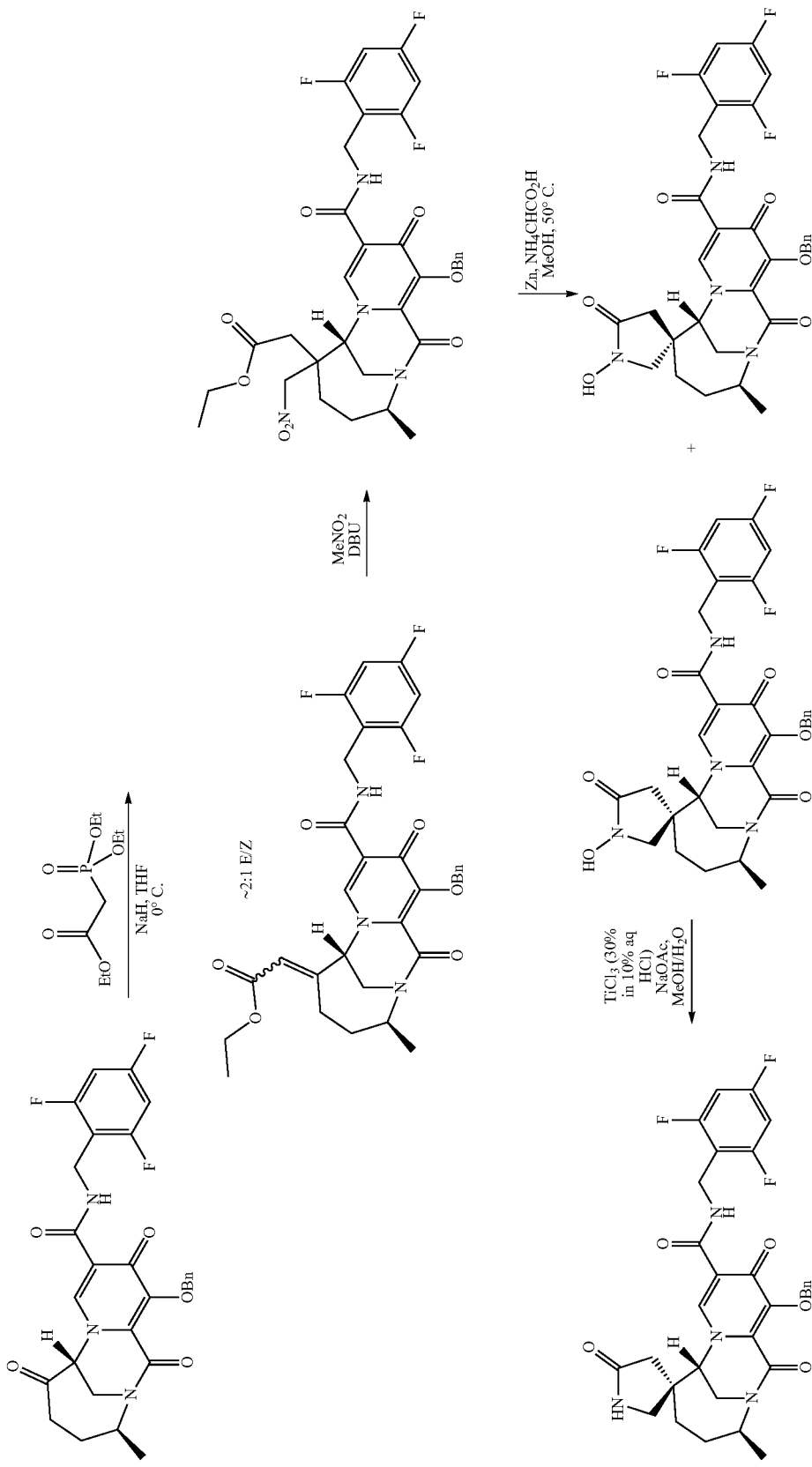

-continued
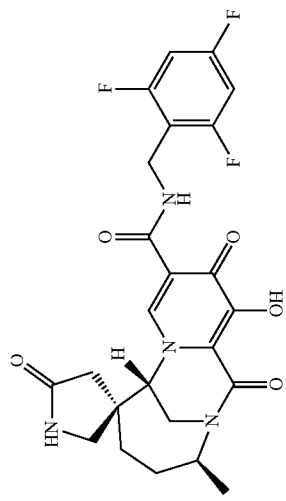

Step 1: Preparation of ethyl (E/Z)-2-((3S,7S)-12-(benzyloxy)-3-methyl-1,11-dioxo-10-((2,4,6-trifluorobenzyl)carbamoyl)-1,4,5,11-tetrahydro-3H-2,7-methanopyrido[1,2-a][1,4]diazonin-6(7H)-ylidene)acetate A suspension of sodium hydride (60% dispersion in oil, 2 equiv, 0.927 mmol, 35.5 mg) in THF (1.5 mL) was cooled to 0° C. under argon then treated with triethyl phosphonoacetate (2.2 equiv, 1.0 mmol, 200 uL). After stirring for 15 minutes, a solution of (3S,7R)-12-(benzyloxy)-3-methyl-1,6,11-trioxo-N-(2,4,6-trifluorobenzyl)-1,4,5,6,7,11-hexahydro-3H-2,7-methanopyrido[1,2-a][1,4]diazonine-10-carboxamide (0.463 mmol, 250 mg), prepared according to Example 55, in THF (3 mL) was added dropwise. After stirring for 1 hour, the reaction was quenched with brine and extracted into EtOAc (3×). The combined organic layers were dried with sodium sulfate, filtered and concentrated. The crude reaction mixture was purified by silica gel chromatography in 0-100% EtOAc/hexanes to afford the title compound as a mixture of isomers (~2:1 E/Z). MS (m/z) 610.08 (major), 610.07 (minor) [M+H]+.

Step 2: Preparation of ethyl 2-((3S,7S)-12-(benzyloxy)-3-methyl-6-(nitromethyl)-1,11-dioxo-10-((2,4,6-trifluorobenzyl)carbamoyl)-1,4,5,6,7,11-hexahydro-3H-2,7-methanopyrido[1,2-a][1,4]diazonin-6-yl)acetate A solution of ethyl 2-((3S,7S)-12-(benzyloxy)-3-methyl-1,11-dioxo-10-((2,4,6-trifluorobenzyl)carbamoyl)-1,4,5,11-tetrahydro-3H-2,7-methanopyrido[1,2-a][1,4]diazonin-6(7H)-ylidene)acetate (0.238 mmol, 145 mg) in nitromethane (75 equiv, 17.8 mmol, 0.955 mL) was treated with DBU (1.5 equiv, 0.357 mmol, 0.053 mL) then stirred at room temperature overnight. The reaction mixture was concentrated and purified by silica gel chromatography in 0-100% EtOAc/hexanes to afford the title compound as a mixture of diastereomers. MS (m/z) 671.13 (major), 671.12 (minor) [M+H]+.

Step 3: Preparation of (3R,3'S,7'S)-12'-(benzyloxy)-1-hydroxy-3'-methyl-1',5',11'-trioxo-N-(2,4,6-trifluorobenzyl)-1',4',5',11'-tetrahydro-3'H,7'H-spiro[pyrrolidine-3,6'-[2,7]methanopyrido[1,2-a][1,4]diazonine]-10'-carboxamide and (3S,3'S,7'S)-12'-(benzyloxy)-1-hydroxy-3'-methyl-1',5',11'-trioxo-N-(2,4,6-trifluorobenzyl)-1',4',5',11'-tetrahydro-3'H,7'H-spiro[pyrrolidine-3,6'-[2,7]methanopyrido[1,2-a][1,4]diazonine]-10'-carboxamide A solution of ethyl 2-((3S,7S)-12-(benzyloxy)-3-methyl-6-(nitromethyl)-1,11-dioxo-10-((2,4,6-trifluorobenzyl)carbamoyl)-1,4,5,6,7,11-hexahydro-3H-2,7-methanopyrido[1,2-a][1,4]diazonin-6-yl)acetate (0.097 mmol, 65 mg) in MeOH (1 mL) was treated with zinc (4 equiv, 0.39 mmol, 25 mg) and ammonium formate (6 equiv, 0.58 mmol, 37 mg) then heated to 50° C. The reaction mixture was concentrated, dissolved in EtOAc and washed with brine. The organic phase was dried with sodium sulfate, filtered and concentrated. The crude residue was purified by silica gel chromatography with 0-30% MeOH/DCM to afford the title compound as separate diastereomers. MS (m/z) 611.14 (major), 611.12 (minor) [M+H]+.

Step 4: Preparation of (3R,3'S,7'S)-12'-(benzyloxy)-3'-methyl-1',5,11'-trioxo-N-(2,4,6-trifluorobenzyl)-1',4',5',11'-tetrahydro-3'H,7'H-spiro[pyrrolidine-3,6'-[2,7]methanopyrido[1,2-a][1,4]diazonine]-10'-carboxamide A solution of (3R,3'S,7'S)-12'-(benzyloxy)-1-hydroxy-3'-methyl-1',5,11'-trioxo-N-(2,4,6-trifluorobenzyl)-1',4',5',11'-tetrahydro-3'H,7'H-spiro[pyrrolidine-3,6'-[2,7]methanopyrido[1,2-a][1,4]diazonine]-10'-carboxamide (0.059 mmol, 36 mg) in MeOH (0.65 mL) was treated with sodium acetate (12 equiv, 0.71 mmol, 58 mg), water (0.35 mL) and TiCl$_3$ (30% solution in 10% aqueous HCl, 0.15 mL). After 15 minutes, the reaction mixture was extracted into EtOAc (3×), washed with brine, dried with sodium sulfate, filtered and concentrated. The crude residue was purified by silica gel chromatography in 0-10% MeOH/DCM to afford the title compound. MS (m/z) 595.17 [M+H]+.

Step 5: Preparation of (3R,3'S,7'S)-12'-hydroxy-3'-methyl-1',5,11'-trioxo-N-(2,4,6-trifluorobenzyl)-1',4',5',11'-tetrahydro-3'H,7'H-spiro[pyrrolidine-3,6'-[2,7]methanopyrido[1,2-a][1,4]diazonine]-10'-carboxamide A solution of (3R,3'S,7'S)-12'-(benzyloxy)-3'-methyl-1',5,11'-trioxo-N-(2,4,6-trifluorobenzyl)-1',4',5',11'-tetrahydro-3'H,7'H-spiro[pyrrolidine-3,6'-[2,7]methanopyrido[1,2-a][1,4]diazonine]-10'-carboxamide (0.055 mmol, 33 mg) in DCM (0.5 mL) was treated with TFA (0.5 mL) and stirred at room temperature for 3 hours. The reaction mixture was concentrated, purified by preparative HPLC in 10-100% MeCN/water with 0.1% TFA and lyophilized to afford the title compound. MS (m/z) 505.18 [M+H]+. $^1$H NMR (400 MHz, Chloroform-d) δ 10.45 (t, J=5.9 Hz, 1H), 8.34 (s, 1H), 7.60 (s, 1H), 6.71-6.61 (m, 2H), 4.75-4.64 (m, 1H), 4.63-4.58 (m, 2H), 4.53 (s, 1H), 3.81 (dd, J=15.2, 2.9 Hz, 1H), 3.63 (dd, J=15.1, 1.7 Hz, 1H), 3.04 (q, J=11.4 Hz, 2H), 2.52-2.37 (m, 2H), 2.21-2.09 (m, 1H), 1.74 (dd, J=13.9, 7.6 Hz, 1H), 1.58-1.42 (m, 2H), 1.30 (d, J=6.6 Hz, 3H).

Example 58: Preparation of (3S,3'S,7'S)-12'-hydroxy-3'-methyl-1',5,11'-trioxo-N-(2,4,6-trifluorobenzyl)-1',4',5',11'-tetrahydro-3'H,7'H-spiro[pyrrolidine-3,6'-[2,7]methanopyrido[1,2-a][1,4]diazonine]-10'-carboxamide

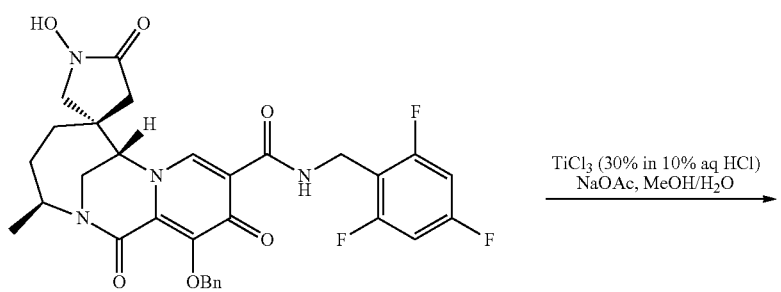

TiCl$_3$ (30% in 10% aq HCl)
NaOAc, MeOH/H$_2$O

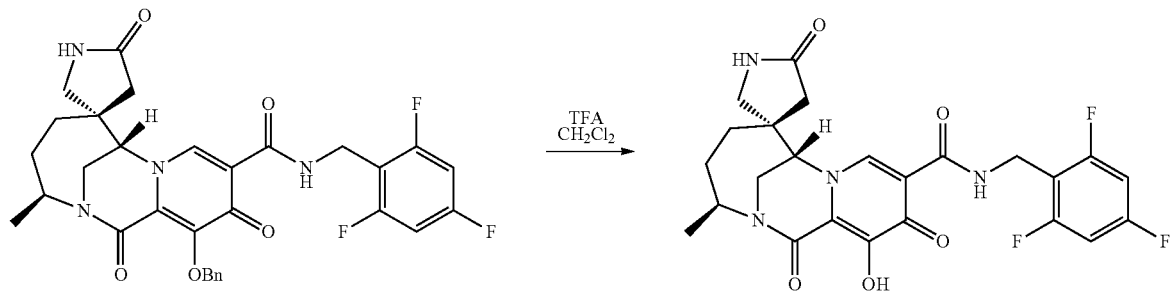

Step 1: Preparation of (3S,3'S,7'S)-12'-(benzyloxy)-3'-methyl-1',5,11'-trioxo-N-(2,4,6-trifluorobenzyl)-1',4',5',11'-tetrahydro-3'H,7'H-spiro[pyrrolidine-3,6'-[2,7]methanopyrido[1,2-a][1,4]diazonine]-10'-carboxamide A solution of (3S,3'S,7'S)-12'-(benzyloxy)-1-hydroxy-3'-methyl-1',5,11'-trioxo-N-(2,4,6-trifluorobenzyl)-1',4',5',11'-tetrahydro-3'H,7'H-spiro[pyrrolidine-3,6'-[2,7]methanopyrido[1,2-a][1,4]diazonine]-10'-carboxamide (0.012 mmol, 7.4 mg), prepared according to Step 3 of Example 57, in MeOH (0.25 mL) was treated with sodium acetate (12 equiv, 0.145 mmol, 12 mg), water (0.15 mL) and TiCl$_3$ (30% solution in 10% aqueous HCl, 30 uL). After 15 minutes, the reaction mixture was extracted into EtOAc (3×), washed with brine, dried with sodium sulfate, filtered and concentrated. The crude residue was purified by silica gel chromatography in 0-10% MeOH/DCM to afford the title compound. MS (m/z) 595.26 [M+H]+.

Step 2: Preparation of (3S,3'S,7'S)-12'-hydroxy-3'-methyl-1',5,11'-trioxo-N-(2,4,6-trifluorobenzyl)-1',4',5',11'-tetrahydro-3'H,7'H-spiro[pyrrolidine-3,6'-[2,7]methanopyrido[1,2-a][1,4]diazonine]-10'-carboxamide A solution of (3S,3'S,7'S)-12'-(benzyloxy)-3'-methyl-1',5,11'-trioxo-N-(2,4,6-trifluorobenzyl)-1',4',5',11'-tetrahydro-3'H,7'H-spiro[pyrrolidine-3,6'-[2,7]methanopyrido[1,2-a][1,4]diazonine]-10'-carboxamide (0.014 mmol, 8.2 mg) in DCM (0.2 mL) was treated with TFA (0.2 mL) and stirred at room temperature for 3 hours. The reaction mixture was concentrated, purified by preparative HPLC in 10-100% MeCN/water with 0.1% TFA and lyophilized to afford the title compound. MS (m/z) 505.31 [M+H]+. $^1$H NMR (400 MHz, Chloroform-d) δ 10.41 (t, J=5.9 Hz, 1H), 8.32 (s, 1H), 6.94 (s, 1H), 6.66 (t, J=8.1 Hz, 2H), 4.72 (dt, J=11.9, 6.5 Hz, 1H), 4.68-4.53 (m, 2H), 4.41 (s, 1H), 3.82 (dd, J=15.0, 2.4 Hz, 1H), 3.64 (d, J=15.1 Hz, 1H), 3.50-3.37 (m, 2H), 2.18-2.00 (m, 3H), 1.79 (dd, J=15.4, 7.2 Hz, 1H), 1.62-1.39 (m, 2H), 1.30 (d, J=6.6 Hz, 3H).

Example 59: Preparation of (3'S,5R,7'R)-12'-hydroxy-3'-methyl-1',2,11'-trioxo-N-(2,4,6-trifluorobenzyl)-1',4',5',11'-tetrahydro-3'H,7'H-spiro[oxazolidine-5,6'-[2,7]methanopyrido[1,2-a][1,4]diazonine]-10'-carboxamide

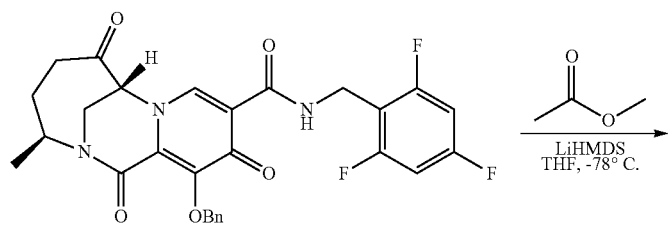

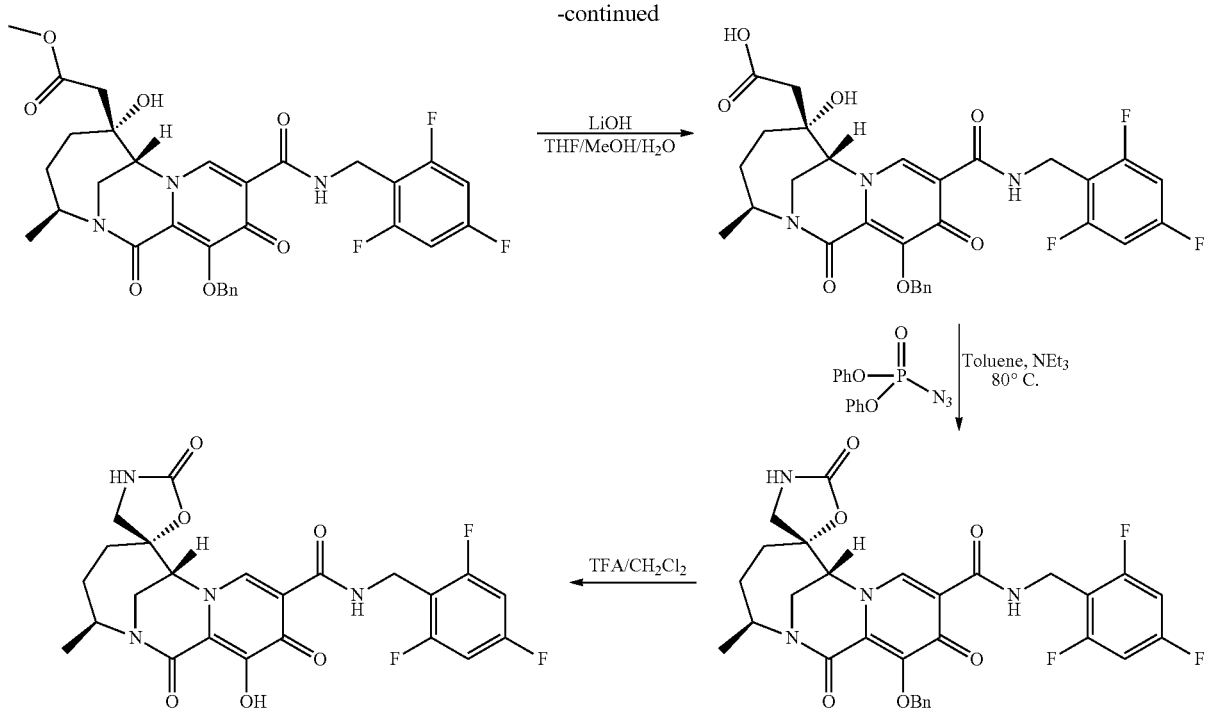

Step 1: Preparation of methyl 2-((3S,6R,7R)-12-(benzyloxy)-6-hydroxy-3-methyl-1,11-dioxo-10-((2,4,6-trifluorobenzyl)carbamoyl)-1,4,5,6,7,11-hexahydro-3H-2,7-methanopyrido[1,2-a][1,4]diazonin-6-yl)acetate A solution of LiHMDS (1 M in THF, 2.5 equiv, 0.35 mmol, 0.35 mL) in THF (0.4 mL) was cooled to −78° C. in an oven-dried vial under argon. Methyl acetate (2.5 equiv, 0.35 mmol, 0.028 mL) was added dropwise and the reaction mixture was stirred for 15 minutes, at which point a solution of (3S,7R)-12-(benzyloxy)-3-methyl-1,6,11-trioxo-N-(2,4,6-trifluorobenzyl)-1,4,5,6,7,11-hexahydro-3H-2,7-methanopyrido[1,2-a][1,4]diazonine-10-carboxamide (0.14 mmol, 75 mg), prepared according to Example 55, in THF (1 mL) was added dropwise. After stirring for 4 hours at −78° C., the reaction mixture was quenched with saturated aqueous ammonium chloride and extracted into EtOAx (3×), dried with sodium sulfate, filtered and concentrated. The crude residue was purified by silica gel chromatography with 0-100% EtOAc/hexanes to afford the title compound. MS (m/z) 614.16 [M+H]+. ¹H NMR (400 MHz, Chloroform-d) δ 10.41 (t, J=5.7 Hz, 1H), 8.47 (s, 1H), 7.57 (d, J=6.9 Hz, 2H), 7.38-7.28 (m, 3H), 6.70-6.61 (m, 2H), 5.50 (d, J=10.2 Hz, 1H), 5.14 (d, J=10.2 Hz, 1H), 4.83 (dt, J=10.3, 6.7 Hz, 1H), 4.64 (qd, J=14.5, 5.5 Hz, 2H), 4.20 (s, 1H), 4.12 (s, 1H), 3.78 (s, 3H), 3.44 (dd, J=15.4, 2.9 Hz, 1H), 3.24 (d, J=15.5 Hz, 1H), 2.69 (q, J=15.5 Hz, 2H), 2.02 (dt, J=14.8, 7.0 Hz, 1H), 1.69 (dd, J=15.6, 7.3 Hz, 1H), 1.31-1.22 (m, 1H), 1.18 (d, J=6.7 Hz, 3H).

Step 2: Preparation of 2-((3S,6R,7R)-12-(benzyloxy)-6-hydroxy-3-methyl-1,11-dioxo-O-((2,4,6-trifluorobenzyl)carbamoyl)-1,4,5,6,7,11-hexahydro-3H-2,7-methanopyrido[1,2-a][1,4]diazonin-6-yl) acetic acid A solution of methyl 2-((3S,6R,7R)-12-(benzyloxy)-6-hydroxy-3-methyl-1,11-dioxo-10-((2,4,6-trifluorobenzyl) carbamoyl)-1,4,5,6,7,11-hexahydro-3H-2,7-methanopyrido[1,2-a][1,4]diazonin-6-yl)acetate (0.077 mmol, 47 mg) in 3/2/1 THF/MeOH/water was treated with lithium hydroxide monohydrate (4 equiv, 0.31 mmol, 12.9 mg) and stirred at room temperature overnight. The reaction mixture was neutralized with 1N HCl and extracted into EtOAc (3×). The combined organic layers were washed with brine, dried with sodium sulfate, filtered and concentrated to afford the title compound, which was used without further purification. MS (m/z) 600.17 [M+H]+.

Step 3: Preparation of (3'S,5R,7'R)-12'-(benzyloxy)-3'-methyl-1',2,11'-trioxo-N-(2,4,6-trifluorobenzyl)-1',4',5',11'-tetrahydro-3'H,7'H-spiro[oxazolidine-5,6'-[2,7]methanopyrido[1,2-a][1,4]diazonine]-10'-carboxamide A solution of 2-((3S,6R,7R)-12-(benzyloxy)-6-hydroxy-3-methyl-1,11-dioxo-10-((2,4,6-trifluorobenzyl)carbamoyl)-1,4,5,6,7,11-hexahydro-3H-2,7-methanopyrido[1,2-a][1,4]diazonin-6-yl)acetic acid (0.038 mmol, 23 mg) in toluene (0.4 mL) was treated with triethylamine (1.1 equiv, 0.042 mmol, 6 uL) and diphenylphosphoryl azide (1.05 equiv, 0.04 mmol, 9 uL) then heated to 80° C. for 2 hours. The reaction mixture was concentrated and purified by silica gel chromatography with 0-100% EtOAc/hexanes followed by 0-40% MeOH/EtOAc to afford the title product. MS (m/z) 597.17 [M+H]+.

Step 4: Preparation of (3'S,5R,7'R)-12'-hydroxy-3'-methyl-1',2,11'-trioxo-N-(2,4,6-trifluorobenzyl)-1',4',5',11'-tetrahydro-3'H,7'H-spiro[oxazolidine-5,6'-[2,7]methanopyrido[1,2-a][1,4]diazonine]-10'-carboxamide A solution of (3'S,5R,7'R)-12'-(benzyloxy)-3'-methyl-1',2,11'-trioxo-N-(2,4,6-trifluorobenzyl)-1',4',5',11'-tetrahydro-3'H,7'H-spiro[oxazolidine-5,6'-[2,7]methanopyrido[1,2-a][1,4]diazonine]-10'-carboxamide (0.025 mmol, 15 mg) in DCM (0.25 mL) was treated with TFA (0.25 mL) and stirred at room temperature for 45 minutes. The reaction mixture was concentrated, purified by preparative HPLC in 10-100% MeCN/water with 0.1% TFA and lyophilized to afford the title compound. MS (m/z) 507.28 [M+H]+. $^1$H NMR (400 MHz, Acetonitrile-d3) δ 10.33 (t, J=5.0 Hz, 1H), 8.22 (s, 1H), 6.90-6.79 (m, 2H), 5.94 (s, 1H), 4.66-4.53 (m, 3H), 4.47 (s, 1H), 3.71 (dd, J=15.6, 3.1 Hz, 1H), 3.56 (dd, J=15.6, 1.7 Hz, 1H), 3.53-3.45 (m, 2H), 2.02 (dt, J=14.5, 6.9 Hz, 1H), 1.92-1.83 (m, 1H), 1.57 (dd, J=14.8, 12.1 Hz, 1H), 1.41 (dt, J=15.4, 11.3 Hz, 1H), 1.21 (d, J=6.7 Hz, 3H).

Example 60: Preparation of (3'S,5R,7'R)-12'-hydroxy-3,3'-dimethyl-1',2,11'-trioxo-N-(2,4,6-trifluorobenzyl)-1',4',5',11'-tetrahydro-3'H,7'H-spiro[oxazolidine-5,6'-[2,7]methanopyrido[1,2-a][1,4]diazonine]-10'-carboxamide

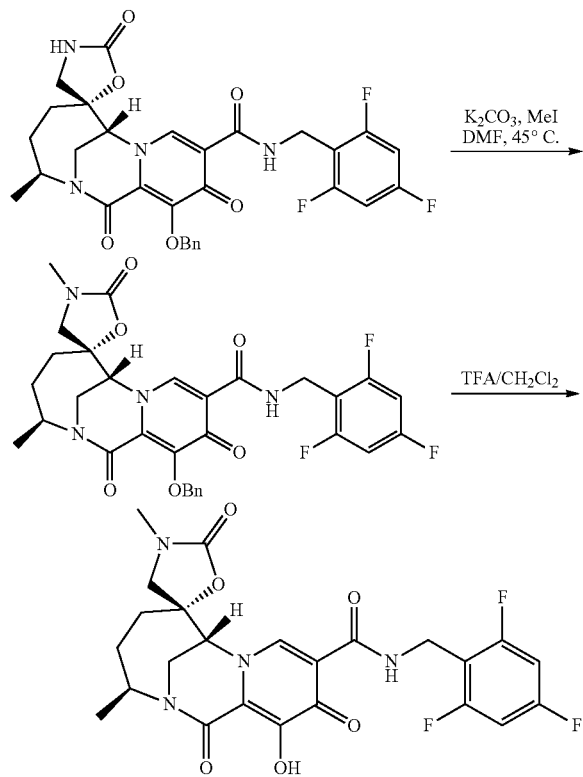

Step 1: Preparation of (3'S,5R,7'R)-12'-(benzyloxy)-3,3'-dimethyl-1',2,11'-trioxo-N-(2,4,6-trifluorobenzyl)-1',4',5',11'-tetrahydro-3'H,7'H-spiro[oxazolidine-5,6'-[2,7]methanopyrido[1,2-a][1,4]diazonine]-10'-carboxamide A solution of (3'S,5R,7'R)-12'-(benzyloxy)-3'-methyl-1',2,11'-trioxo-N-(2,4,6-trifluorobenzyl)-1',4',5',11'-tetrahydro-3'H,7'H-spiro[oxazolidine-5,6'-[2,7]methanopyrido[1,2-a][1,4]diazonine]-10'-carboxamide (0.017 mmol, 10 mg), prepared according to Example 59, in DMF (0.4 mL) was treated with potassium carbonate (2 equiv, 0.034 mmol, 5 mg) and methyl iodide (1.5 equiv, 0.025 mmol, 1.6 uL), sealed and heated to 45° C. overnight. An additional portion of potassium carbonate (2 equiv, 0.034 mmol, 5 mg) and methyl iodide (5 equiv, 0.084 mmol, 5.2 uL) were added and the reaction mixture was heated to 45° C. overnight. The reaction mixture was cooled, diluted with EtOAc, washed with 10% aqueous LiCl and brine, dried with sodium sulfate, filtered and concentrated to afford the title compound, which was used without further purification. MS (m/z) 611.09 [M+H]+.

Step 2: Preparation of (3'S,5R,7'R)-12'-hydroxy-3,3'-dimethyl-1',2,11'-trioxo-N-(2,4,6-trifluorobenzyl)-1',4',5',11'-tetrahydro-3'H,7'H-spiro[oxazolidine-5,6'-[2,7]methanopyrido[1,2-a][1,4]diazonine]-10'-carboxamide A solution of (3'S,5R,7'R)-12'-(benzyloxy)-3,3'-dimethyl-1',2,11'-trioxo-N-(2,4,6-trifluorobenzyl)-1',4',5',11'-tetrahydro-3'H,7'H-spiro[oxazolidine-5,6'-[2,7]methanopyrido[1,2-a][1,4]diazonine]-10'-carboxamide (0.025 mmol, 15 mg) in DCM (0.25 mL) was treated with TFA (0.25 mL) and stirred at room temperature for 4 hours. The reaction mixture was concentrated, purified by preparative HPLC in 10-100% MeCN/water with 0.1% TFA and lyophilized to afford the title compound. MS (m/z) 521.20 [M+H]+. $^1$H NMR (400 MHz, Chloroform-d) δ 10.44 (s, 1H), 8.51 (s, 1H), 6.66 (t, J=8.2 Hz, 2H), 4.84-4.71 (m, 1H), 4.66-4.50 (m, 3H), 3.85 (d, J=15.2 Hz, 1H), 3.61-3.38 (m, 3H), 2.90 (s, 3H), 2.19-2.09 (m, 1H), 1.94-1.80 (m, 1H), 1.81-1.68 (m, 1H), 1.44-1.32 (m, 1H), 1.29 (d, J=6.7 Hz, 3H).

Example 61: Preparation of (3R,3'S,7'S)-12'-hydroxy-1,3'-dimethyl-1',5,11'-trioxo-N-(2,4,6-trifluorobenzyl)-1',4',5',11'-tetrahydro-3'H,7'H-spiro[pyrrolidine-3,6'-[2,7]methanopyrido[1,2-a][1,4]diazonine]-10'-carboxamide

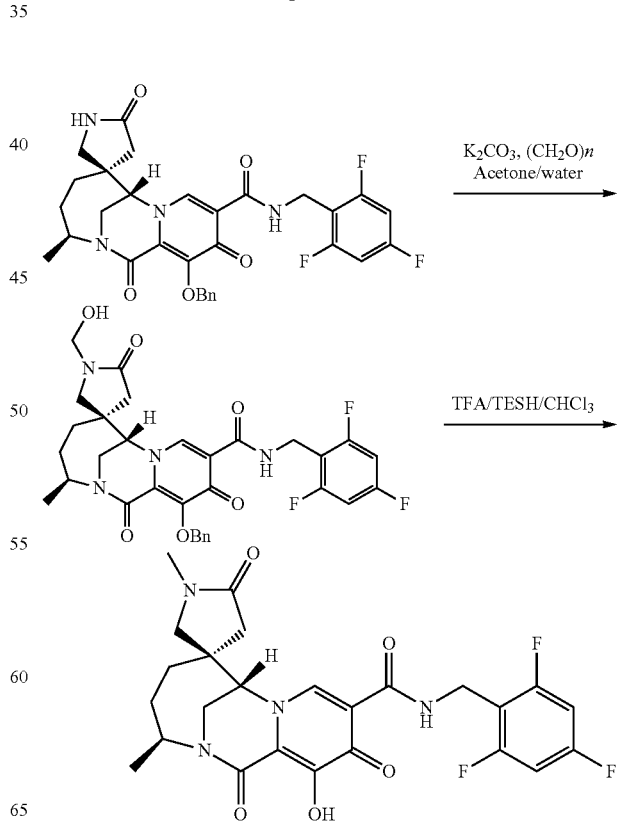

Step 1: Preparation of (3R,3'S,7'S)-12'-(benzyloxy)-1-(hydroxymethyl)-3'-methyl-1',5,11'-trioxo-N-(2,4,6-trifluorobenzyl)-1',4',5',11'-tetrahydro-3'H,7'H-spiro[pyrrolidine-3,6'-[2,7]methanopyrido[1,2-a][1,4]diazonine]-10'-carboxamide A solution of (3R,3'S,7'S)-12'-(benzyloxy)-3'-methyl-1',5,11'-trioxo-N-(2,4,6-trifluorobenzyl)-1',4',5',11'-tetrahydro-3'H,7'H-spiro[pyrrolidine-3,6'-[2,7]methanopyrido[1,2-a][1,4]diazonine]-10'-carboxamide (0.035 mmol, 21 mg), prepared according to Example 57, in 9/1 acetone/water (0.2 mL) was treated with potassium carbonate (2 equiv, 0.071 mmol, 9.8 mg) and paraformaldehyde (16 mg). After stirring at room temperature for 45 minutes, the reaction mixture was concentrated to afford the title compound which was carried on to Step 2 without further purification. MS (m/z) 625.16 [M+H]+.

Step 2: Preparation of (3R,3'S,7'S)-12'-hydroxy-1,3'-dimethyl-1',5,11'-trioxo-N-(2,4,6-trifluorobenzyl)-1',4',5',11'-tetrahydro-3'H,7'H-spiro[pyrrolidine-3,6'-[2,7]methanopyrido[1,2-a][1,4]diazonine]-10'-carboxamide The crude residue from Step 1 containing (3R,3'S,7'S)-12'-(benzyloxy)-1-(hydroxymethyl)-3'-methyl-1',5,11'-trioxo-N-(2,4,6-trifluorobenzyl)-1',4',5',11'-tetrahydro-3'H,7'H-spiro[pyrrolidine-3,6'-[2,7]methanopyrido[1,2-a][1,4]diazonine]-10'-carboxamide (0.035 mmol, 21.9 mg) was treated with CHCl$_3$ (0.6 mL), triethylsilane (0.12 mL) and TFA (0.21 mL) then stirred at room temperature overnight. The reaction mixture was concentrated then purified by prep HPLC in 10-100% MeCN/water with 0.1% TFA and lyophilized to afford the title compound. MS (m/z) 519.25 [M+H]+. $^1$H NMR (400 MHz, Chloroform-d) δ 10.33 (t, J=5.8 Hz, 1H), 8.31 (s, 1H), 6.67 (t, J=8.1 Hz, 2H), 4.81-4.53 (m, 3H), 4.13 (s, 1H), 3.77 (dd, J=14.9, 2.9 Hz, 1H), 3.55 (d, J=15.0 Hz, 1H), 3.08 (d, J=11.2 Hz, 1H), 2.98 (d, J=11.2 Hz, 1H), 2.93 (s, 3H), 2.59-2.41 (m, 2H), 2.19-2.05 (m, 1H), 1.69 (dd, J=14.0, 7.5 Hz, 1H), 1.52-1.42 (m, 2H), 1.29 (d, J=6.6 Hz, 3H).

Example 62: Preparation of (3S,3'S,7'S)-12'-hydroxy-1,3'-dimethyl-1',5,11'-trioxo-N-(2,4,6-trifluorobenzyl)-1',4',5',11'-tetrahydro-3'H,7'H-spiro[pyrrolidine-3,6'-[2,7]methanopyrido[1,2-a][1,4]diazonine]-10'-carboxamide

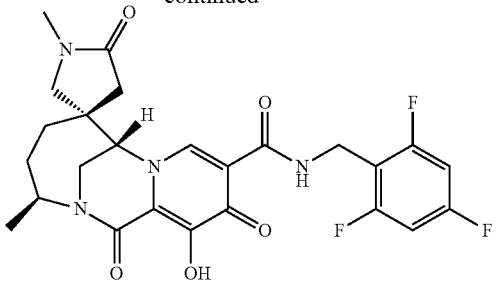

The title compound was prepared in a manner similar to Example 61, except using (3S,3'S,7'S)-12'-(benzyloxy)-3'-methyl-1',5,11'-trioxo-N-(2,4,6-trifluorobenzyl)-1',4',5',11'-tetrahydro-3'H,7'H-spiro[pyrrolidine-3,6'-[2,7]methanopyrido[1,2-a][1,4]diazonine]-10'-carboxamide, prepared according to Example 58, instead of (3R,3'S,7'S)-12'-(benzyloxy)-3'-methyl-1',5,11'-trioxo-N-(2,4,6-trifluorobenzyl)-1',4',5',11'-tetrahydro-3'H,7'H-spiro[pyrrolidine-3,6'-[2,7]methanopyrido[1,2-a][1,4]diazonine]-10'-carboxamide. MS (m/z) 519.28 [M+H]+. $^1$H NMR (400 MHz, Chloroform-d) δ 10.42 (t, J=5.3 Hz, 1H), 8.49 (s, 1H), 6.74-6.58 (m, 2H), 4.83-4.69 (m, 1H), 4.68-4.55 (m, 2H), 4.34 (s, 1H), 3.81 (d, J=14.7 Hz, 1H), 3.56 (d, J=14.9 Hz, 1H), 3.42 (d, J=10.1 Hz, 1H), 3.32 (d, J=10.5 Hz, 1H), 2.87 (s, 3H), 2.30 (d, J=17.2 Hz, 1H), 2.17-2.04 (m, 1H), 2.02 (d, J=17.2 Hz, 1H), 1.72 (dd, J=14.9, 7.1 Hz, 1H), 1.64-1.40 (m, 2H), 1.29 (d, J=6.6 Hz, 3H).

Example 63: Preparation of (3'S,5R,7'R)-3-ethyl-12'-hydroxy-3'-methyl-1',2,11'-trioxo-N-(2,4,6-trifluorobenzyl)-1',4',5',11'-tetrahydro-3'H,7'H-spiro[oxazolidine-5,6'-[2,7]methanopyrido[1,2-a][1,4]diazonine]-10'-carboxamide

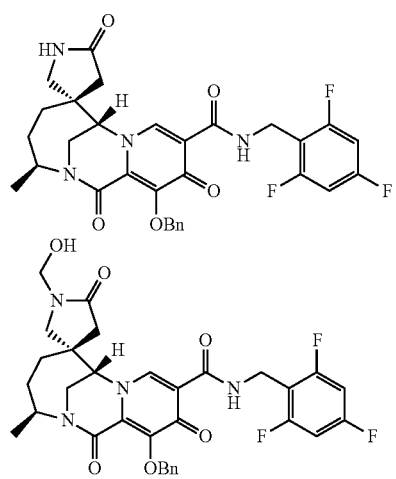

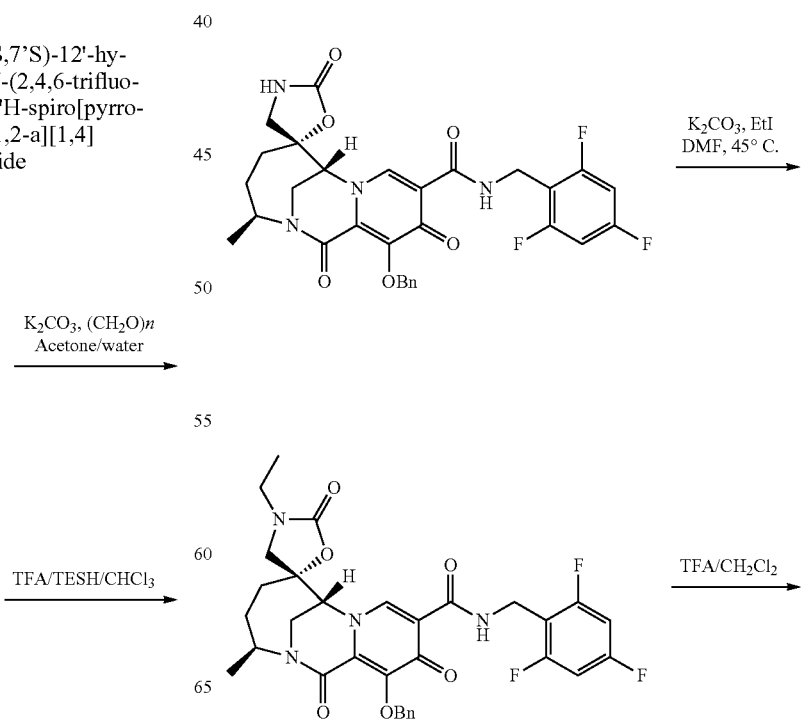

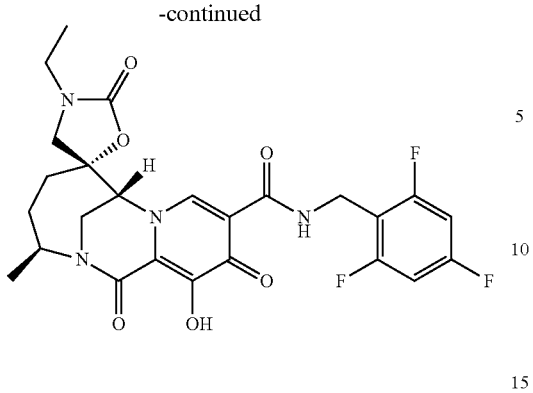

Step 1: Preparation of (3'S,5R,7'R)-12'-(benzyloxy)-3-ethyl-3'-methyl-1',2,11'-trioxo-N-(2,4,6-trifluorobenzyl)-1',4',5',11'-tetrahydro-3'H,7'H-spiro[oxazolidine-5,6'-[2,7]methanopyrido[1,2-a][1,4]diazonine]-10'-carboxamide A solution of (3'S,5R,7'R)-12'-(benzyloxy)-3'-methyl-1',2,11'-trioxo-N-(2,4,6-trifluorobenzyl)-1',4',5',11'-tetrahydro-3'H,7'H-spiro[oxazolidine-5,6'-[2,7]methanopyrido[1,2-a][1,4]diazonine]-10'-carboxamide (0.025 mmol, 15 mg), prepared according to Example 59, in DMF (0.6 mL) was treated with potassium carbonate (2 equiv, 0.05 mmol, 7 mg) and iodoethane (2 equiv, 0.05 mmol, 4 uL), sealed and heated to 45° C. overnight. An additional portion of potassium carbonate (2 equiv, 0.05 mmol, 7 mg) and iodoethane (8 equiv, 0.2 mmol, 16 uL) were added and the reaction mixture was further heated to 45° C. for 7 hours. The reaction mixture was cooled, diluted with EtOAc, washed with 10% aqueous LiCl and brine, dried with sodium sulfate, filtered and concentrated to afford the title compound, which was carried forward without further purification. MS (m/z) 625.20 [M+H]+.

Step 2: Preparation of (3'S,5R,7'R)-3-ethyl-12'-hydroxy-3'-methyl-1',2,11'-trioxo-N-(2,4,6-trifluorobenzyl)-1',4',5',11'-tetrahydro-3'H,7'H-spiro[oxazolidine-5,6'-[2,7]methanopyrido[1,2-a][1,4]diazonine]-10'-carboxamide A solution of (3'S,5R,7'R)-12'-(benzyloxy)-3-ethyl-3'-methyl-1',2,11'-trioxo-N-(2,4,6-trifluorobenzyl)-1',4',5',11'-tetrahydro-3'H,7'H-spiro[oxazolidine-5,6'-[2,7]methanopyrido[1,2-a][1,4]diazonine]-10'-carboxamide (0.025 mmol, 15.7 mg) in DCM (0.25 mL) was treated with TFA (0.25 mL) and stirred at room temperature for 4 hours. The reaction mixture was concentrated, purified by preparative HPLC in 10-100% MeCN/water with 0.1% TFA and lyophilized to afford the title compound. MS (m/z) 535.26 [M+H]+. $^1$H NMR (400 MHz, Chloroform-d) δ 10.48 (s, 1H), 8.57 (s, 1H), 6.66 (t, J=8.2 Hz, 2H), 4.78 (s, 1H), 4.60 (s, 3H), 3.85 (d, J=14.2 Hz, 1H), 3.60-3.21 (m, 5H), 2.22-2.10 (m, 1H), 1.89 (dd, J=15.4, 7.0 Hz, 1H), 1.74 (t, J=13.4 Hz, 1H), 1.40 (t, J=12.9 Hz, 1H), 1.30 (d, J=6.5 Hz, 3H), 1.18 (s, 3H).

Example 64: Preparation of (3'S,5S,7'R)—N-((4-chloro-3,5-difluoropyridin-2-yl)methyl)-12'-hydroxy-3-methoxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

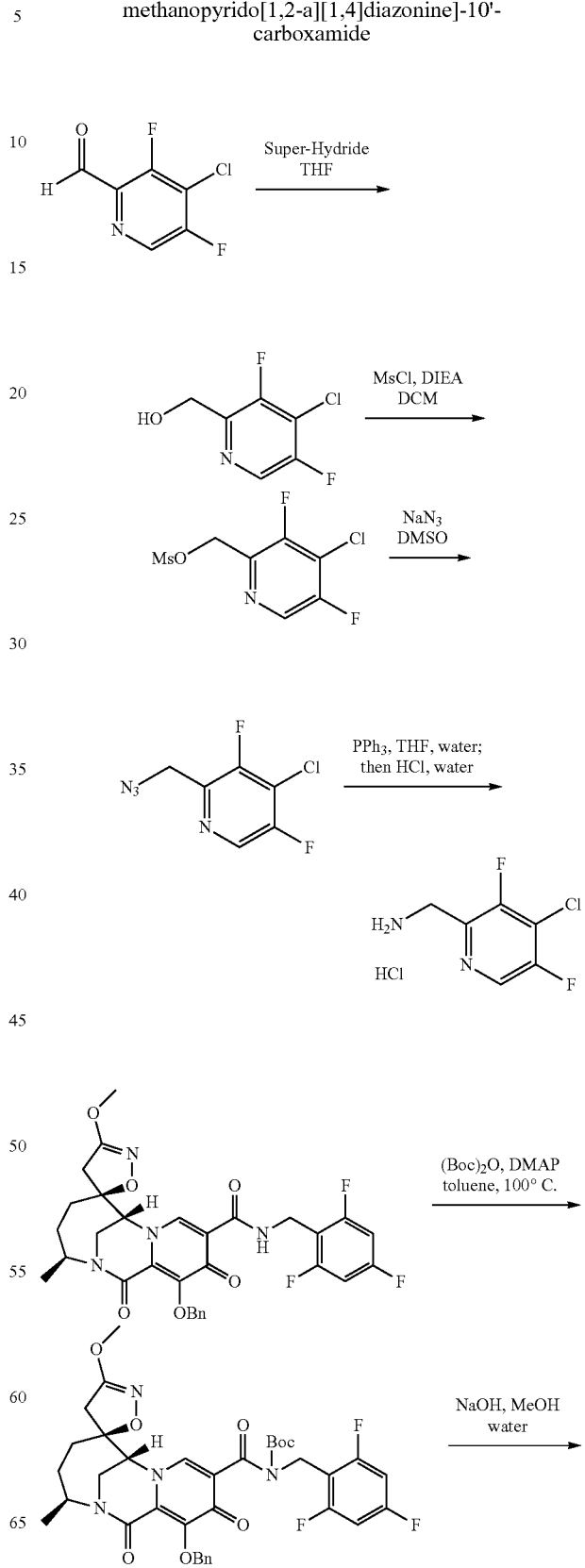

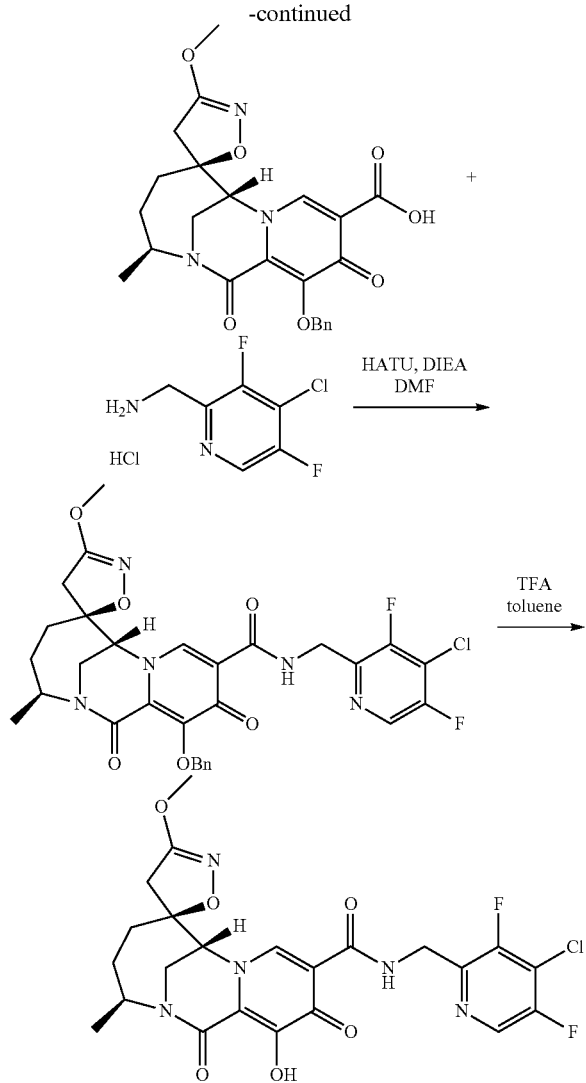

Step 1: Preparation of (4-chloro-3,5-difluoropyridin-2-yl)methanol

4-Chloro-3,5-difluoropicolinaldehyde (0.99 g, 5.58 mmol) was dissolved in anhydrous THF (15 mL) under argon atmosphere. The solution was cooled down to −60° C. 1 M Super-Hydride solution in THF (6.63 mL, 6.63 mmol) was added dropwise. The reaction was allowed to warm up to −10° C. over 3 h. The resulting reaction mixture was diluted with EtOAc and was then treated with saturated NH$_4$Cl (aq) (20 mL). The organic phase was separated and the aqueous phase was extracted with EtOAc (20 mL). The combined organic phase was washed with brine, dried over Na$_2$SO$_4$ and filtered. The filtrate was concentrated to dryness to afford the product, which was used in the next step without further purification. MS (m/z): 179.9 [M+H]+.

Step 2: Preparation of (4-chloro-3,5-difluoropyridin-2-yl)methyl methanesulfonate 4-Chloro-3,5-difluoropyridin-2-yl)methanol (1.0 g, 5.57 mmol) was dissolved in DCM (35 mL) at rt. The solution was cooled to −50 to −60° C. DIEA (1.45 mL, 8.35 mmol, 1.5 eq) was added dropwise. Then MsCl (0.56 mL, 7.24 mmol, 1.3 equiv) was added dropwise. The reaction mixture was warmed up to −15° C. with stirring over 3 h. The reaction mixture was then diluted with EtOAc (100 mL) and was treated with saturated NH$_4$Cl (aq) (30 mL). The organic phase was separated, dried over Na$_2$SO$_4$ and filtered. The filtrate was concentrated to dryness to afford the title compound, which was used in the next step without further purification. MS (m/z): 257.9 [M+H]+.

Step 3: Preparation of 2-(azidomethyl)-4-chloro-3,5-difluoropyridine (4-Chloro-3,5-difluoropyridin-2-yl)methyl methanesulfonate (1.4 g, 5.5 mmol) was dissolved in DMSO (5 mL) at rt. NaN$_3$ (0.469 g, 7.22 mmol) was added and the reaction mixture was stirred at rt for 17 h. The reaction mixture was diluted with EtOAc (10 mL) and treated with saturated NH$_4$Cl (aq) (30 mL). The organic phase was separated, dried over Na$_2$SO$_4$ and filtered. The filtrate was concentrated to dryness to afford the product, which was used in the next step without further purification. MS (m/z): 204.8 [M+H]+.

Step 4: Preparation of (4-chloro-3,5-difluoropyridin-2-yl)methanamine hydrochloride 2-(Azidomethyl)-4-chloro-3,5-difluoropyridine (1.1 g, 5.5 mmol) and PPh3 (2.19 g, 8.36 mmol) were mixed with THF (5 mL) and water (1 mL). The resulting reaction mixture was heated with stirring at 50° C. for 17 h. The resulting reaction mixture was partitioned between EtOAc (20 mL) and HCl (1N) (10 mL). The aqueous layer was separated and lyophilized to afford (4-chloro-3,5-difluoropyridin-2-yl)methanamine hydrochloride. MS (m/z): 178.9 [M+H]+.

Step 5: Preparation of tert-butyl ((3'S,5S,7'R)-12'-(benzyloxy)-3-methoxy-3'-methyl-1',11'-dioxo-1',4', 5',11'-tetrahydro-3'H,4H,7'H-spiro[isoxazole-5,6'-[2,7]methanopyrido[1,2-a][1,4]diazonine]-10'-carbonyl)(2,4,6-trifluorobenzyl)carbamate (3'S,5S,7'R)-12'-(benzyloxy)-3-methoxy-3'-methyl-1', 11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (310 mg, 0.508 mmol), prepared according to Example 36, was dissolved in toluene (3 mL) at rt. Boc2O (0.586 g, 2.69 mmol) and DMAP (248 mg, 2.03 mmol) were added and the reaction mixture was heated in sealed tube at 90-95° C. for 3 h. The reaction mixture was concentrated to dryness and the residue was purified by silica gel column chromatography (0-100% EtOAc/Hex) to afford tert-butyl ((3'S,5S,7'R)-12'-(benzyloxy)-3-methoxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carbonyl)(2,4,6-trifluorobenzyl)carbamate. MS (m/z): 710.9 [M+H]+.

Step 6: Preparation of (3'S,5S,7'R)-12'-(benzyloxy)-3-methoxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxylic acid tert-Butyl ((3'S,5S,7'R)-12'-(benzyloxy)-3-methoxy-3'-methyl-1',11'-dioxo-1',4',5',11'-tetrahydro-3'H,4H,7'H-spiro

[isoxazole-5,6'-[2,7]methanopyrido[1,2-a][1,4]diazonine]-10'-carbonyl)(2,4,6-trifluorobenzyl)carbamate (390 mg, 0.549 mmol) was mixed with MeOH (10 mL) at rt. 1N NaOH (aq) (0.853 mL, 0.853 mmol) was added dropwise and the reaction mixture was stirred at rt for 5 min. Then water (1.5 mL) was added and the resulting reaction mixture was stirred at rt for 17 h. The resulting reaction mixture was partitioned between EtOAc (10 mL) and water (10 mL). The aqueous layer was then acidified to pH=3 with 1N HCl and EtOAc (20 mL) was added. The organic phase was separated, washed with brine (10 mL) and water (10 mL), dried over $Na_2SO_4$, and filtered. The filtrate was concentrated to dryness to afford (3'S,5S,7'R)-12'-(benzyloxy)-3-methoxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxylic acid. MS (m/z): 468.2 [M+H]+.

Step 7: Preparation of (3'S,5S,7'R)-12'-(benzyloxy)-N-((4-chloro-3,5-difluoropyridin-2-yl)methyl)-3-methoxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (3'S,5S,7'R)-12'-(Benzyloxy)-3-methoxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxylic acid (26 mg, 0.0556 mmol) was dissolved in DMF (2 mL). DIEA (0.0386 mL, 0.22 mmol) and HATU (32 mg, 0.0843 mmol) were added sequentially at rt. The reaction mixture was stirred at rt for 1 h and (4-chloro-3,5-difluoropyridin-2-yl)methanamine hydrochloride (18 mg, 0.0834 mmol) was added. The reaction mixture was stirred at rt for 17 h, diluted with EtOAc (10 mL), and treated with saturated $NH_4Cl$ (aq.) (20 mL). The organic phase was separated, dried over $Na_2SO_4$, filtered, and concentrated to dryness. The crude product was purified by silica gel column chromatography (0-100% EtOAc/Hex) to afford (3'S,5S,7'R)-12'-(benzyloxy)-N-((4-chloro-3,5-difluoropyridin-2-yl)methyl)-3-methoxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide. MS (m/z): 628.0 [M+H]+.

Step 8: Preparation of (3'S,5S,7'R)—N-((4-chloro-3,5-difluoropyridin-2-yl)methyl)-12'-hydroxy-3-methoxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (3'S,5S,7'R)-12'-(Benzyloxy)-N-((4-chloro-3,5-difluoropyridin-2-yl)methyl)-3-methoxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (24 mg, 0.0382 mmol) was dissolved in toluene (1 mL) at rt. TFA (0.8 mL) was added and the reaction mixture was stirred at rt for 17 h. The reaction mixture was concentrated to dryness and the residue was purified by reverse phase prep HPLC (0-100% acetonitrile/water containing 0.1% TFA) to afford (3'S,5S,7'R)—N-((4-chloro-3,5-difluoropyridin-2-yl)methyl)-12'-hydroxy-3-methoxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide. MS (m/z): 538.1 [M+H]+. 1H NMR (400 MHz, $CD_3CN$) δ 10.58 (s, 1H), 8.48 (s, 1H), 8.44 (d, J=0.8 Hz, 1H), 4.78 (dt, J=5.5, 1.8 Hz, 2H), 4.70-4.56 (m, 1H), 4.44 (s, 1H), 3.84 (s, 3H), 3.89-3.69 (m, 2H), 2.85 (d, J=17.2 Hz, 1H), 2.62 (d, J=17.2 Hz, 1H), 2.05-1.99 (m, 1H), 1.97-1.88 (m, 2H), 1.59-1.47 (m, 1H), 1.26 (d, J=6.6 Hz, 3H).

Example 65: Preparation of (3'S,5S,7'R)-12'-hydroxy-3-methoxy-3'-methyl-1',11'-dioxo-N-(2,4,5-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

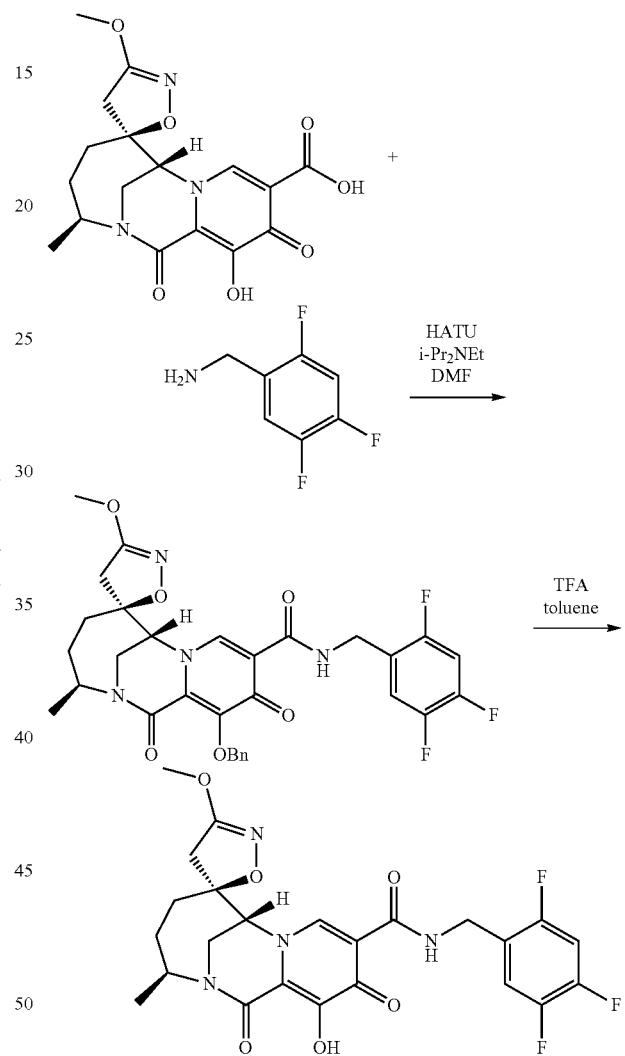

Step 1: Preparation of (3'S,5S,7'R)-12'-(benzyloxy)-3-methoxy-3'-methyl-1',11'-dioxo-N-(2,4,5-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (3'S,5S,7'R)-12'-(benzyloxy)-3-methoxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxylic acid (0.025 g, 0.054 mmol), prepared according to Step 6 of Example 64, was dissolved in DMF (2 mL). Diisopropylethylamine (0.037 mL, 0.214 mmol, 4 equiv.) and HATU (0.030 g, 0.080 mmol, 1.5 equiv.) were added sequentially at rt and stirred for 1 h. (2,4,5-trifluorophenyl)methanamine (0.013 g, 0.080 mmol, 1.5 equiv.) was added and the reaction mixture was stirred at rt for 16 h. The reaction mixture was diluted with EtOAc and washed with water and brine. The aqueous phase was extracted with EtOAc and the combined organic phase was dried over Na₂SO₄, filtered, and concentrated. The residue was purified by silica gel column chromatography using 0-100% EtOAc/hex to afford (3'S,5S,7'R)-12'-(benzyloxy)-3-methoxy-3'-methyl-1',11'-dioxo-N-(2,4,5-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide. MS (m/z) 611.03 [M+H]+.

Step 2: Preparation of (3'S,5S,7'R)-12'-hydroxy-3-methoxy-3'-methyl-1',11'-dioxo-N-(2,4,5-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (3'S,5S,7'R)-12'-(benzyloxy)-3-methoxy-3'-methyl-1',11'-dioxo-N-(2,4,5-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (0.038 g, 0.061 mmol) was dissolved in 1:1 TFA/toluene (2 mL) and stirred at rt. After 2 h, the solution was concentrated and the residue was purified by reverse phase prep HPLC (5-100% MeCN/water w/0.1% TFA). The fractions containing product were lyophilized to afford (3'S,5S,7'R)-12'-hydroxy-3-methoxy-3'-methyl-1',11'-dioxo-N-(2,4,5-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide. MS (m/z) 521.16 [M+H]+. 1H NMR (400 MHz, DMSO-d6) δ 10.34 (t, J=6.0 Hz, 1H), 8.65 (s, 1H), 7.56 (ddd, J=10.9, 9.7, 6.7 Hz, 1H), 7.43 (ddd, J=11.0, 9.0, 6.8 Hz, 1H), 4.74 (d, J=2.4 Hz, 1H), 4.55 (d, J=5.9 Hz, 3H), 3.81 (s, 3H), 3.79-3.66 (m, 2H), 2.93 (d, J=16.9 Hz, 1H), 2.70 (d, J=16.9 Hz, 1H), 1.90 (d, J=13.2 Hz, 1H), 1.87-1.77 (m, 2H), 1.43-1.28 (m, 1H), 1.19 (d, J=6.7 Hz, 3H).

Example 66: Preparation of (3'S,5S,7'R)—N-((4-chloro-3,5-difluoropyridin-2-yl)methyl)-3-(fluoromethyl)-12'-hydroxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

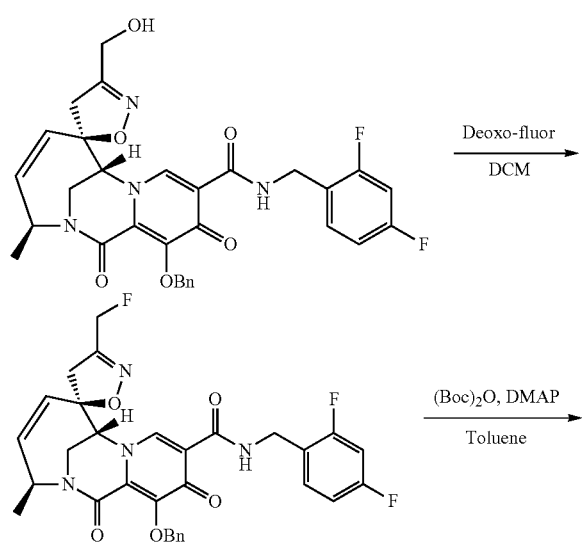

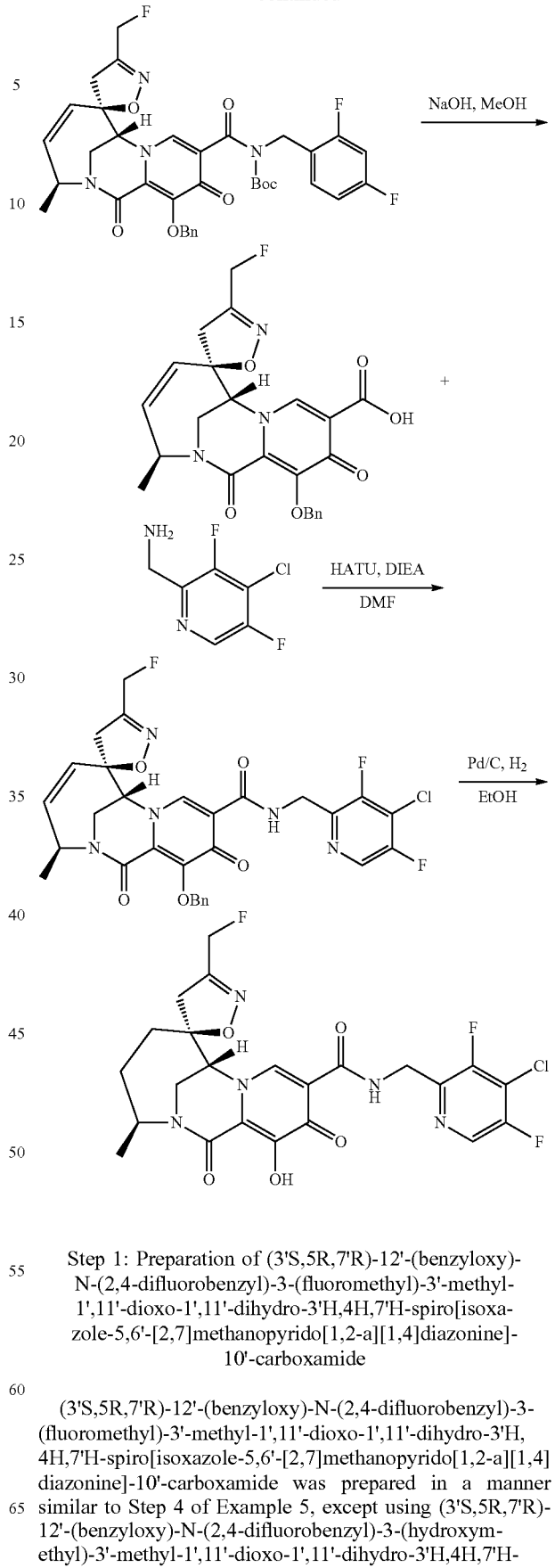

Step 1: Preparation of (3'S,5R,7'R)-12'-(benzyloxy)-N-(2,4-difluorobenzyl)-3-(fluoromethyl)-3'-methyl-1',11'-dioxo-1',11'-dihydro-3'H,4H,7'H-spiro[isoxazole-5,6'-[2,7]methanopyrido[1,2-a][1,4]diazonine]-10'-carboxamide (3'S,5R,7'R)-12'-(benzyloxy)-N-(2,4-difluorobenzyl)-3-(fluoromethyl)-3'-methyl-1',11'-dioxo-1',11'-dihydro-3'H,4H,7'H-spiro[isoxazole-5,6'-[2,7]methanopyrido[1,2-a][1,4]diazonine]-10'-carboxamide was prepared in a manner similar to Step 4 of Example 5, except using (3'S,5R,7'R)-12'-(benzyloxy)-N-(2,4-difluorobenzyl)-3-(hydroxymethyl)-3'-methyl-1',11'-dioxo-1',11'-dihydro-3'H,4H,7'H- spiro[isoxazole-5,6'-[2,7]methanopyrido[1,2-a][1,4]diazonine]-10'-carboxamide, prepared according to Example 22, instead of (3'S,4'R,5R,7'R)-12'-(benzyloxy)-N-(2,4-difluorobenzyl)-4'-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide. MS (m/z) 593.33 [M+H]+.

Step 2: Preparation of tert-butyl ((3'S,5R,7'R)-12'-(benzyloxy)-3-(fluoromethyl)-3'-methyl-1',11'-dioxo-1',11'-dihydro-3'H,4H,7'H-spiro[isoxazole-5,6'-[2,7]methanopyrido[1,2-a][1,4]diazonine]-10'-carbonyl)(2,4-difluorobenzyl)carbamate To solution of (3'S,5R,7'R)-12'-(benzyloxy)-N-(2,4-difluorobenzyl)-3-(fluoromethyl)-3'-methyl-1',11'-dioxo-1',11'-dihydro-3'H,4H,7'H-spiro[isoxazole-5,6'-[2,7]methanopyrido[1,2-a][1,4]diazonine]-10'-carboxamide (90 mg, 0.152 mmol) in toluene (1 ml) was added (Boc)$_2$O (199 mg, 0.915 mmol) and followed by the addition of DMAP (83.5 mg, 0.68 mmol). The resulting mixture was stirred at 110° C. for 4 h. Solvent was removed under vacuo and the crude material was purified by silica gel column chromatography to afford the title compound. MS (m/z) 693.19 [M+H]+.

Step 3: Preparation of (3'S,5R,7'R)-12'-(benzyloxy)-3-(fluoromethyl)-3'-methyl-1',11'-dioxo-1',11'-dihydro-3'H,4H,7'H-spiro[isoxazole-5,6'-[2,7]methanopyrido[1,2-a][1,4]diazonine]-10'-carboxylic acid To solution of tert-butyl ((3'S,5R,7'R)-12'-(benzyloxy)-3-(fluoromethyl)-3'-methyl-1',11'-dioxo-1',11'-dihydro-3'H,4H,7'H-spiro[isoxazole-5,6'-[2,7]methanopyrido[1,2-a][1,4]diazonine]-10'-carbonyl)(2,4-difluorobenzyl)carbamate (50 mg, 0.057 mmol) in MeOH (1 ml) was added NaOH (1N, 0.5 ml). The reaction mixture was stirred at room temperature for 1 h. The reaction mixture was acidified to pH=6 by HCl (1N), then it was extracted by EtOAc and the organic phase was washed H$_2$O and brine. The solvent was removed under vacuo and the crude material was used directly in next step. MS (m/z) 468.07 [M+H]+.

Step 4: Preparation of (3'S,5R,7'R)-12'-(benzyloxy)-N-((4-chloro-3,5-difluoropyridin-2-yl)methyl)-3-(fluoromethyl)-3'-methyl-1',11'-dioxo-1',11'-dihydro-3'H,4H,7'H-spiro[isoxazole-5,6'-[2,7]methanopyrido[1,2-a][1,4]diazonine]-10'-carboxamide To solution of (3'S,5R,7'R)-12'-(benzyloxy)-3-(fluoromethyl)-3'-methyl-1',11'-dioxo-1',11'-dihydro-3'H,4H,7'H-spiro[isoxazole-5,6'-[2,7]methanopyrido[1,2-a][1,4]diazonine]-10'-carboxylic acid (30 mg, 0.064 mmol) in DMF (1 ml) was added HATU (44 mg, 0.116 mmol) and (4-chloro-3,5-difluoro-2-pyridyl)methanamine (20.6 mg, 0.116 mmol), prepared according to Example 64, followed by the addition of DIEA (66 mg, 0.51 mmol). The resulting reaction mixture was stirred at rt for 2 h. The reaction mixture was diluted with EtOAc and washed with LiCl (5% aqueous), H$_2$O and brine. The organic phase was dried with MgSO$_4$, and solvent was removed under vacuo. The crude material was purified by silica gel chromatography to afford the title compound. MS (m/z) 628.00 [M+H]+.

Step 5: Preparation of (3'S,5S,7'R)—N-((4-chloro-3,5-difluoropyridin-2-yl)methyl)-3-(fluoromethyl)-12'-hydroxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide To solution of (3'S,5R,7'R)-12'-(benzyloxy)-N-((4-chloro-3,5-difluoropyridin-2-yl)methyl)-3-(fluoromethyl)-3'-methyl-1',11'-dioxo-1',11'-dihydro-3'H,4H,7'H-spiro[isoxazole-5,6'-[2,7]methanopyrido[1,2-a][1,4]diazonine]-10'-carboxamide (42 mg, 0.067 mmol) in EtOH (15 ml) was added Pd/C (10% wet) (5 mg, 0.067 mmol). The resulting mixture was purged with H$_2$ three times and the reaction mixture was stirred at room temperature under H$_2$ for 1 h. The reaction mixture was filtered through Celite to remove Pd/C, and the solvent was removed under vacuo. Crude material was purified by reverse phase prep-HPLC to afford the title compound. MS (m/z) 540.09 [M+H]+. 1H NMR (400 MHz, Chloroform-d) δ 10.89 (s, 1H), 8.56 (s, 1H), 8.41 (s, 1H), 5.22 (s, 1H), 5.10 (s, 1H), 4.87 (s, 2H), 4.78 (dt, J=10.4, 6.5 Hz, 1H), 4.26 (s, 1H), 3.89 (d, J=14.8 Hz, 1H), 3.77 (d, J=14.8 Hz, 1H), 3.14 (d, J=17.9 Hz, 1H), 2.71 (d, J=17.6 Hz, 1H), 2.11-1.98 (m, 3H), 1.69-1.58 (m, 1H), 1.34 (d, J=6.6 Hz, 3H).

Example 67: (3'S,5S,7'R)-3-ethyl-12'-hydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

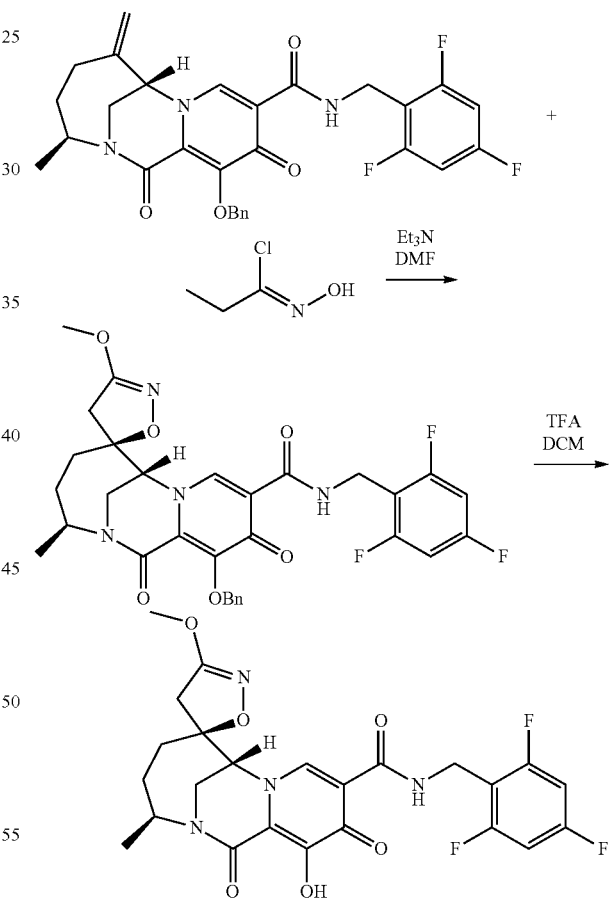

Step 1: Preparation of (3'S,5S,7'R)-12'-(benzyloxy)-3-ethyl-3'-methyl-1',11'-dioxo-N-(2,4,6-trifluorobenzyl)-1',4',5',1'-tetrahydro-3'H,4H,7'H-spiro[isoxazole-5,6'-[2,7]methanopyrido[1,2-a][1,4]diazonine]-10'-carboxamide To a solution of Intermediate C (25 mg, 0.046 mmol) in DMF (2 ml) was added N-hydroxypropionimidoyl chloride (15 mg, 0.14 mmol) followed by triethylamine (47.1 mg, 0.465 mmol). The reaction mixture was stirred at room temperature overnight. The reaction mixture was diluted with EtOAc and washed with H₂O, and brine. The organic phase was separated and dried with MgSO₄. After removing solvent in vacuo, the residue was purified by silica gel column chromatography to obtain the title compound. MS (m/z) 609.11 [M+H]+.

Step 2: Preparation of (3'S,5S,7'R)-3-ethyl-12'-hydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide The solution of (3'S,5S,7'R)-12'-(benzyloxy)-3-ethyl-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (25.0 mg, 0.0465 mmol) in DCM (1.5 mL) and TFA (1.5 mL) was stirred at rt overnight. The reaction mixture was concentrated and the residue was purified by reverse phase prep HPLC, eluting with 5-100% H₂O/ACN to give the title compound. MS (m/z) 519.15 [M+H]+. 1H NMR (400 MHz, Methanol-d4) δ 8.47 (s, 1H), 6.98-6.85 (m, 2H), 4.77-4.61 (m, 3H), 4.51 (s, 1H), 3.93-3.78 (m, 2H), 2.98 (d, J=17.8 Hz, 1H), 2.64 (d, J=17.8 Hz, 1H), 2.49-2.34 (m, 2H), 1.96 (ddt, J=28.3, 15.3, 5.0 Hz, 3H), 1.62-1.50 (m, 1H), 1.30 (d, J=6.7 Hz, 3H), 1.20 (t, J=7.5 Hz, 3H).

Example 68: Preparation (3'S,5S,7'R)-12'-hydroxy-3'-methyl-1',11'-dioxo-3-propyl-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

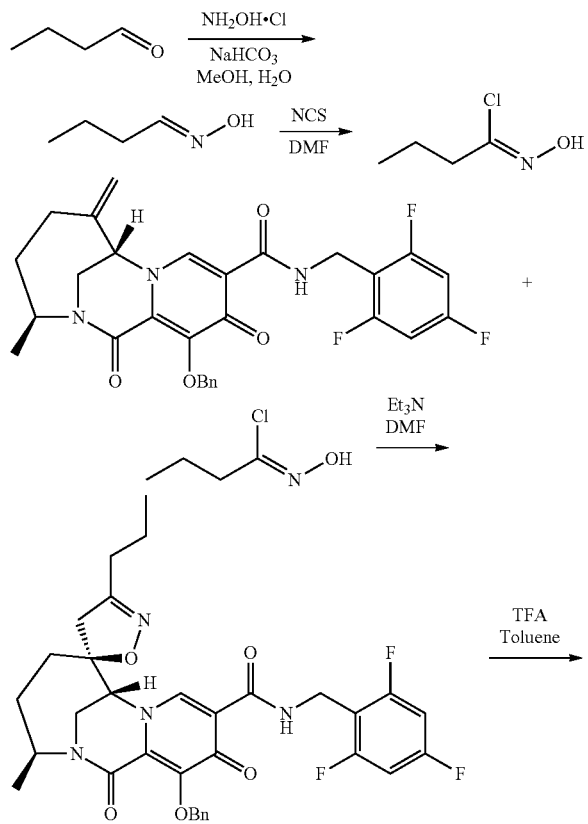

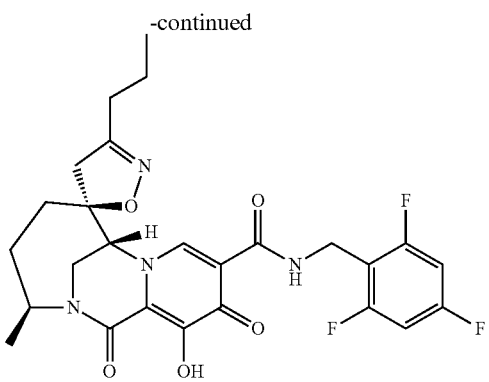

Step 1: Preparation of butyraldehyde oxime

To solution of butyraldehyde (1.5 g, 20.8 mmol) in MeOH (10 ml) and H₂O (5 ml) was added NaHCO₃ (2.1 g, 25 mmol), then followed by the addition of hydroxylamine hydrochloride (1.7 g, 25 mmol) at room temperature. The resulting mixture was stirred for 2 h. The reaction mixture was diluted with diethyl ether and washed with H₂O and brine. The organic phase was dried with MgSO₄. The solvent was removed under vacuo and the crude material was used directly in the next step.

Step 2: Preparation N-hydroxybutanimidoyl chloride

To solution of butyraldehyde oxime (1.81 g, 20.8 mmol) in DMF (5 mL) was added NCS (3.33 g, 25 mmol). The reaction mixture was stirred at 50° C. for 2 h, then reaction mixture was cooled down to room temperature and used directly in next step.

Step 3: Preparation (3'S,5S,7'R)-12'-(benzyloxy)-3'-methyl-1',11'-dioxo-3-propyl-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide To a solution of Intermediate C (0.5 g, 0.93 mmol) was added N-hydroxybutanimidoyl chloride (0.34 g, 2.8 mmol) followed by triethylamine (1.3 ml, 9.3 mmol). The reaction mixture was stirred at room temperature overnight. The reaction mixture was diluted with EtOAc and washed with LiCl (5%), H₂O and brine. The organic phase was dried with MgSO₄. The solvent was removed in vacuo and crude material was purified by silica gel column chromatography to obtain the title compound. MS (m/z) 623.07 [M+H]+.

Step 4: Preparation (3'S,5S,7'R)-12'-hydroxy-3'-methyl-1',11'-dioxo-3-propyl-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide To solution of (3'S,5S,7'R)-12'-(benzyloxy)-3'-methyl-1',11'-dioxo-3-propyl-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (69.3 mg, 0.11 mmol) in toluene (2 ml) was added TFA (2 ml). The reaction mixture was stirred at room temperature overnight. The solvent was removed in vacuo and the residue was purified by reverse phase prep HPLC to obtain the title compound. MS (m/z) 533.19 [M+H]+. 1H NMR (400 MHz, Chloroform-d) δ 10.43 (t, J=5.6 Hz, 1H), 8.38 (s, 1H), 6.76-6.63 (m, 2H), 4.79-4.58 (m, 3H), 4.12 (d, J=2.5 Hz, 1H), 3.86 (dd, J=14.9, 1.9 Hz, 1H), 3.70 (dd, J=14.9, 2.8 Hz, 1H), 2.90 (d, J=17.6 Hz, 1H), 2.53 (d, J=17.6 Hz, 1H), 2.48-2.28 (m, 2H), 2.16-1.88 (m, 3H), 1.73-1.50 (m, 3H), 1.31 (d, J=6.7 Hz, 3H), 1.02 (t, J=7.4 Hz, 3H).

Example 69: Preparation of (3'S,5S,7'R)-3-(2-fluoroethyl)-12'-hydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

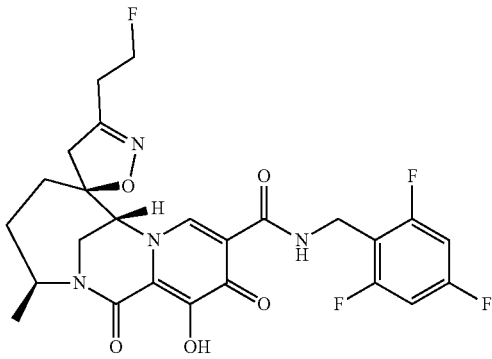 [SMILES: C[C@H]1CC[C@]2(CC(CCF)=NO2)[C@H]2CN1C(=O)c1c(O)c(=O)c(C(=O)NCc3c(F)cc(F)cc3F)cn12]

(3'S,5S,7'R)-3-(2-fluoroethyl)-12'-hydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide was prepared in a similar manner as Example 19, except using 3-((tert-butyldimethylsilyl)oxy)propanal instead of 2-((tert-butyldiphenylsilyl)oxy)acetaldehyde in Step 1. MS (m/z) 537.15 [M+H]+. 1H NMR (400 MHz, Chloroform-d) δ 10.54 (t, J=5.8 Hz, 1H), 8.52 (s, 1H), 6.76-6.64 (m, 2H), 4.82-4.69 (m, 3H), 4.71-4.61 (m, 2H), 4.20 (d, J=2.3 Hz, 1H), 3.88 (dd, J=14.9, 1.9 Hz, 1H), 3.72 (dd, J=14.9, 2.7 Hz, 1H), 3.02 (d, J=17.8 Hz, 1H), 2.82 (dtd, J=25.3, 5.8, 2.3 Hz, 2H), 2.63 (d, J=17.9 Hz, 1H), 2.14-1.92 (m, 3H), 1.65-1.53 (m, 1H), 1.32 (d, J=6.7 Hz, 3H).

Example 70: Preparation of (3'S,5S,7'R)-3-((R)-1-fluoroethyl)-12'-hydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

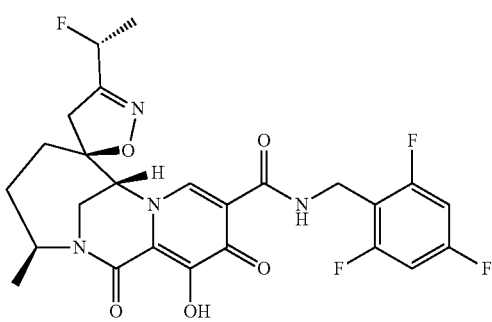 [SMILES: C[C@@H](F)C1=NO[C@@]2(CC[C@H](C)N3C[C@H]2n2cc(C(=O)NCc4c(F)cc(F)cc4F)c(=O)c(O)c2C3=O)C1]

(3'S,5S,7'R)-3-((R)-1-fluoroethyl)-12'-hydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide was prepared in a similar manner as Example 19, except using (2S)-2-[tert-butyl(dimethyl)silyl]oxypropanal instead of 2-((tert-butyldiphenylsilyl)oxy)acetaldehyde in Step 1. MS (m/z) 537.15 [M+H]+. 1H NMR (400 MHz, Chloroform-d) δ 10.43 (t, J=5.7 Hz, 1H), 8.51 (s, 1H), 6.76-6.63 (m, 2H), 5.49 (q, J=6.4 Hz, 1H), 5.42-5.30 (m, 1H), 4.78 (dd, J=14.6, 6.1 Hz, 2H), 4.62 (dd, J=14.6, 5.2 Hz, 1H), 4.21 (s, 1H), 3.87 (dd, J=14.9, 1.9 Hz, 1H), 3.72 (dd, J=14.9, 2.7 Hz, 1H), 3.09 (t, J=17.6 Hz, 1H), 2.66 (d, J=17.5 Hz, 1H), 2.09-1.96 (m, 3H), 1.67 (dd, J=24.1, 6.5 Hz, 3H), 1.33 (d, J=6.7 Hz, 3H).

Example 71: Preparation of (3'S,5S,7'R)-3-(1,1-difluoroethyl)-12'-hydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

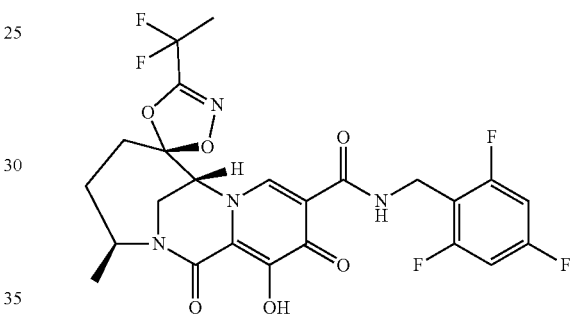

(3'S,5S,7'R)-3-(1,1-difluoroethyl)-12'-hydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide was prepared in a manner similar to Example 20, except using (2S)-2-[tert-butyl(dimethyl)silyl]oxypropanal instead of 2-((tert-butyldiphenylsilyl)oxy)acetaldehyde. MS (m/z) 555.16 [M+H]+. 1H NMR (400 MHz, Chloroform-d) δ 10.54 (t, J=5.7 Hz, 1H), 8.88 (s, 1H), 6.85-6.53 (m, 2H), 4.80 (td, J=19.7, 17.4, 8.2 Hz, 2H), 4.70-4.43 (m, 2H), 3.94-3.69 (m, 2H), 3.19 (d, J=17.9 Hz, 1H), 2.68 (d, J=17.8 Hz, 1H), 2.06-1.83 (m, 6H), 1.68-1.56 (m, 1H), 1.34 (d, J=6.6 Hz, 3H).

Example 72: Preparation of (3'S,5S,7'R)-12'-hydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

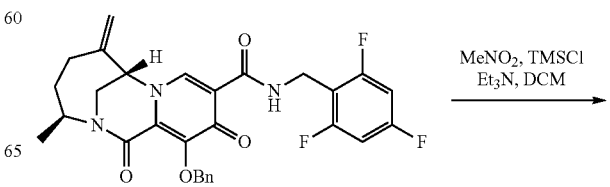

-continued

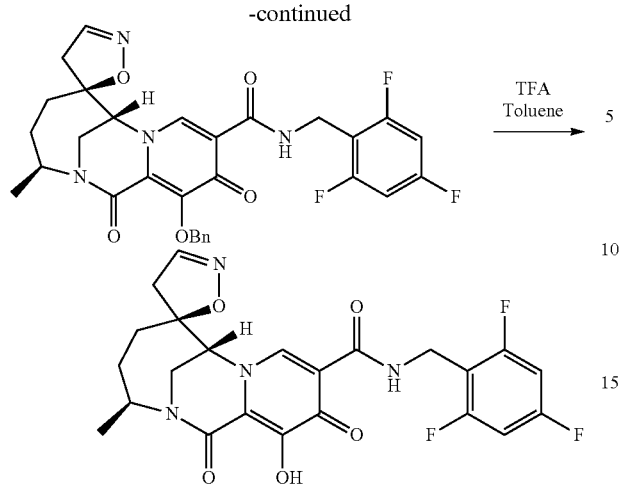

Step 1: Preparation of (3'S,5S,7'R)-12'-(benzyloxy)-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide In a vial, nitromethane (87 mg, 1.422 mmol) was dissolved in DCM (5 mL) at rt under argon atmosphere and triethylamine (144 mg, 1.422 mmol) was added dropwise. The reaction mixture was stirred at rt for 10 min and cooled to 0° C. Chlorotrimethylsilane (161 mg, 1.395 mmol) was added dropwise and the resulting reaction mixture was stirred for 2 h. To this reaction mixture was added Intermediate C (150 mg, 0.28 mmol) in one portion. The resulting reaction mixture was stirred at rt for 17 h and the reaction mixture was concentrated to dryness. The residue was purified by reverse phase prep HPLC using 0-100% acetonitrile/water (with 0.1% TFA) and lyophilized to afford (3'S,5S,7'R)-12'-(benzyloxy)-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide. MS (m/z): 581.1 [M+H]+.

Step 2: Preparation of (3'S,5S,7'R)-12'-hydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (3'S,5S,7'R)-12'-(Benzyloxy)-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (10 mg, 0.0103 mmol) was dissolved in toluene (1 mL) and TFA (0.8 mL) was added at rt. The resulting reaction mixture was stirred at rt for 17 h. The reaction mixture was concentrated to dryness and the residue was purified by reverse phase prep HPLC with 0-100% acetonitrile/water (with 0.1% TFA). Lyophilization afforded (3'S,5S,7'R)-12'-hydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide. MS (m/z): 491.2 [M+H]+; 1H NMR (400 MHz, CD3CN) δ 10.36 (s, 1H), 8.40 (s, 1H), 7.26 (s, 1H), 6.94-6.81 (m, 2H), 4.75-4.59 (m, 3H), 4.30 (s, 1H), 3.85-3.70 (m, 2H), 3.06-2.89 (m, 1H), 2.64-2.51 (m, 1H), 1.95-1.89 (m, 1H), 1.86-1.77 (m, 2H), 1.58-1.41 (m, 1H), 1.26 (d, J=6.7 Hz, 3H).

Example 73: Preparation of (3'S,5S,7'R)-12'-hydroxy-3'-methyl-1',11'-dioxo-N-(2,4,6-trifluorobenzyl)-3-(trifluoromethyl)-1',4',5',11'-tetrahydro-3'H,4H,7'H-spiro[isoxazole-5,6'-[2,7]methanopyrido[1,2-a][1,4]diazonine]-10'-carboxamide

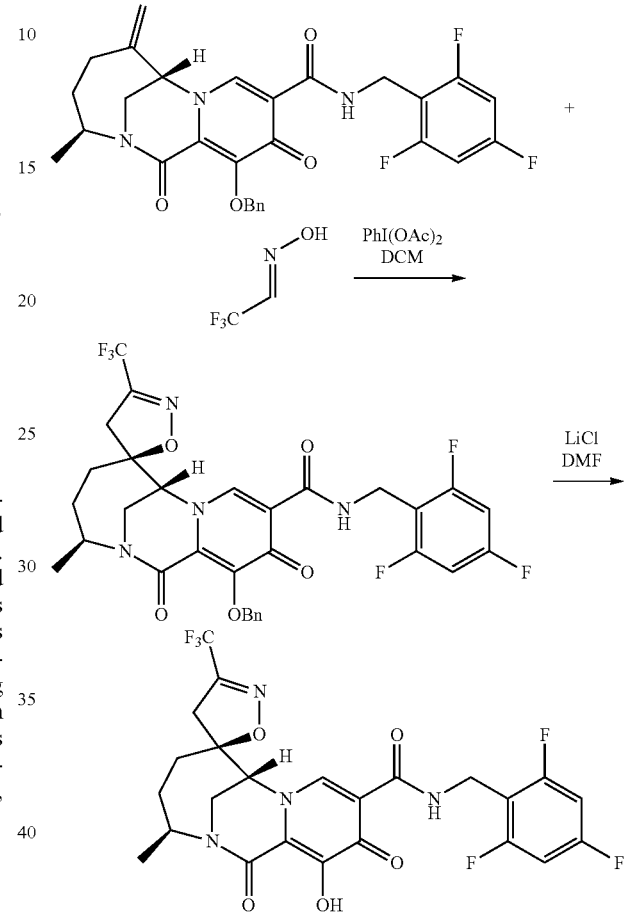

Step 1: Preparation of (3'S,5S,7'R)-12'-(benzyloxy)-3'-methyl-1',11'-dioxo-N-(2,4,6-trifluorobenzyl)-3-(trifluoromethyl)-1',4',5',1'-tetrahydro-3'H,4H,7'H-spiro[isoxazole-5,6'-[2,7]methanopyrido[1,2-a][1,4]diazonine]-10'-carboxamide Intermediate C (170 mg, 0.316 mmol) was dissolved in DCM (36 mL) and the solution was cooled to 0° C. Iodobenzene diacetate (2 g, 6.32 mmol) was added in one portion at that temperature under argon atmosphere. To the resulting slurry was added (E)-2,2,2-trifluoroacetaldehyde oxime (357 mg, 3.16 mmol) through syringe slowly. The resulting reaction mixture was stirred for 17 h. The resulting solution was then concentrated to dryness and the residue was purified by silica gel column chromatography with 0-100% EtOAc/hexanes to afford (3'S,5S,7'R)-12'-(benzyloxy)-3'-methyl-1',11'-dioxo-N-(2,4,6-trifluorobenzyl)-3-(trifluoromethyl)-1',4',5',11'-tetrahydro-3'H,4H,7'H-spiro[isoxazole-5,6'-[2,7]methanopyrido[1,2-a][1,4]diazonine]-10'-carboxamide. MS (m/z): 649.0 [M+H]+.

Step 2: Preparation of (3'S,5S,7'R)-12'-hydroxy-3'-methyl-1',11'-dioxo-N-(2,4,6-trifluorobenzyl)-3-(trifluoromethyl)-1',4',5',11'-tetrahydro-3'H,4H,7'H-spiro[isoxazole-5,6'-[2,7]methanopyrido[1,2-a][1,4]diazonine]-10'-carboxamide (3'S,5S,7'R)-12'-(benzyloxy)-3'-methyl-1',11'-dioxo-N-(2,4,6-trifluorobenzyl)-3-(trifluoromethyl)-1',4',5',11'-tetrahydro-3'H,4H,7'H-spiro[isoxazole-5,6'-[2,7]methanopyrido[1,2-a][1,4]diazonine]-10'-carboxamide (28 mg, 0.043 mg) was dissolved in DMF (1 mL). LiCl (12 mg, 0.284 mmol) was added and the reaction mixture was heated to 100° C. for 5 h. The reaction mixture was diluted with EtOAc (5 mL) and treated with 1N HCl (10 mL). The organic phase was separated and the aqueous phase was extracted with EtOAc (5 mL). The combined organic phase was washed with brine (10 mL) and water (10 mL) and the resulting organic phase was concentrated to dryness. The residue was purified by reverse phase prep HPLC with 0-100% acetonitrile/water (with 0.1% TFA) and lyophilized to afford (3'S,5S,7'R)-12'-hydroxy-3'-methyl-1',11'-dioxo-N-(2,4,6-trifluorobenzyl)-3-(trifluoromethyl)-1',4',5',11'-tetrahydro-3'H,4H,7'H-spiro[isoxazole-5,6'-[2,7]methanopyrido[1,2-a][1,4]diazonine]-10'-carboxamide. MS (m/z): 559.2 [M+H]+; 1H NMR (400 MHz, CD3CN) δ 10.32 (s, 1H), 8.54 (s, 1H), 6.94-6.81 (m, 2H), 4.72-4.56 (m, 3H), 4.54 (d, J=2.5 Hz, 1H), 3.80 (d, J=2.3 Hz, 2H), 3.23-3.13 (m, 1H), 2.89-2.79 (m, 1H), 2.06-1.85 (m, 3H), 1.63-1.51 (m, 1H), 1.26 (d, J=6.7 Hz, 3H).

Example 74: Preparation of (3'S,5S,7'R)-3-(azetidin-1-yl)-12'-hydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

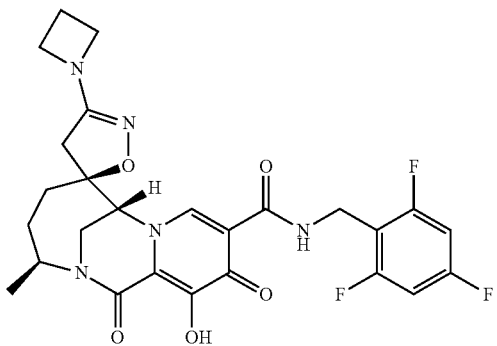

(3'S,5S,7'R)-3-(azetidin-1-yl)-12'-hydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide was prepared in a manner similar to Example 52, except using azetidine instead of dimethylamine in Step 1. MS (m/z) 546.281 [M+H]+. 1H NMR (400 MHz, Chloroform-d) δ 10.39 (s, 1H), 8.49 (s, 1H), 6.69 (dd, J=8.7, 7.5 Hz, 2H), 4.68 (ddd, J=29.8, 14.3, 5.6 Hz, 3H), 4.39 (s, 1H), 4.29-4.07 (m, 4H), 3.87 (d, J=14.9 Hz, 1H), 3.70 (d, J=14.8 Hz, 1H), 2.85 (d, J=16.3 Hz, 1H), 2.66 (d, J=16.4 Hz, 1H), 2.52 (d, J=7.5 Hz, 2H), 2.15-2.04 (m, 1H), 1.98 (s, 2H), 1.69-1.53 (m, 1H), 1.30 (d, J=6.6 Hz, 3H).

Example 75: Preparation of (3'S,5S,7'R)-12'-hydroxy-3'-methyl-1',11'-dioxo-3-(pyrrolidin-1-yl)-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

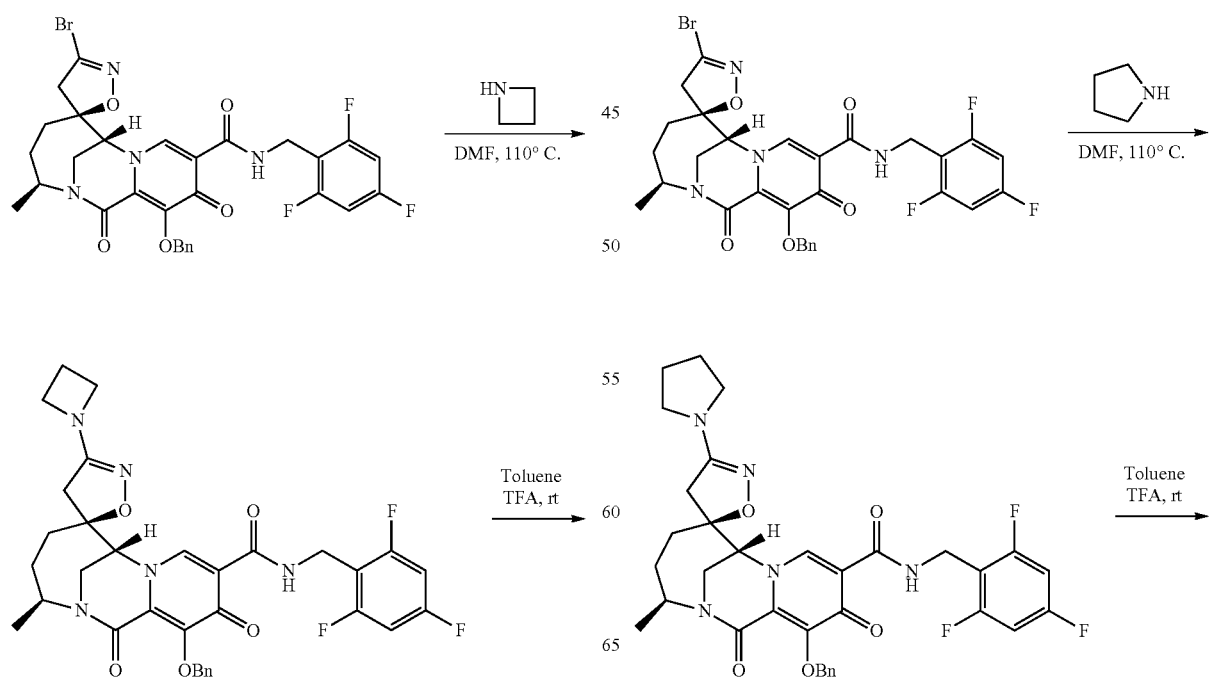

247
-continued

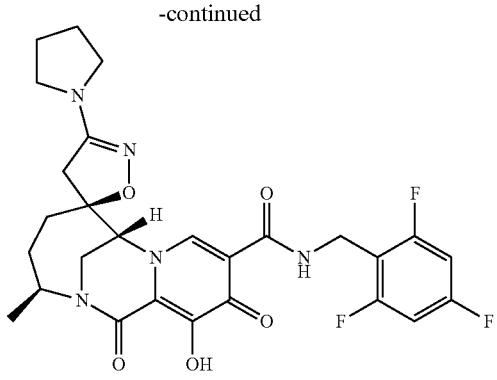

(3'S,5S,7'R)-12'-hydroxy-3'-methyl-1',11'-dioxo-3-(pyr-rolidin-1-yl)-N-(2,4,6-trifluorobenzyl)-1',4',5',11'-tetra-hydro-3'H,4'H,7'H-spiro[isoxazole-5,6'-[2,7]methanopyrido[1,2-a][1,4]diazonine]-10'-carboxamide was prepared in a manner similar to Example 52, except using pyrrolidine instead of dimethylamine in Step 1. MS (m/z) 560.221 [M+H]+. 1H NMR (400 MHz, Chloroform-d) δ 10.33 (t, J=5.7 Hz, 1H), 8.34 (s, 1H), 6.69 (dd, J=8.7, 7.5 Hz, 2H), 4.68 (dd, J=23.3, 5.8 Hz, 3H), 4.38 (s, 1H), 3.96-3.84 (m, 1H), 3.69 (dd, J=14.9, 2.6 Hz, 1H), 3.40 (d, J=23.0 Hz, 4H), 2.95 (d, J=16.4 Hz, 1H), 2.82 (d, J=16.4 Hz, 1H), 2.24-1.81 (m, 7H), 1.64 (t, J=10.5 Hz, 1H), 1.31 (d, J=6.6 Hz, 3H).

Example 76: Preparation of (3'S,5S,7'R)-12'-hydroxy-3'-methyl-1',11'-dioxo-3-(4H-1,2,4-triazol-4-yl)-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide 248
-continued

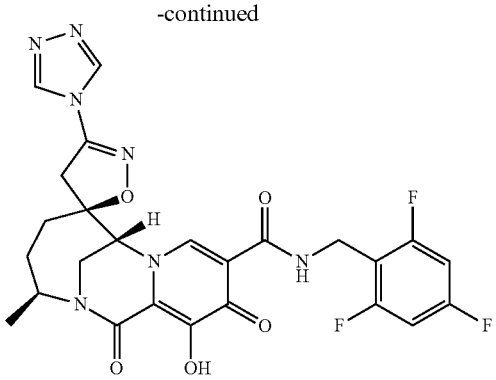

(3'S,5S,7'R)-12'-hydroxy-3'-methyl-1',11'-dioxo-3-(4H-1,2,4-triazol-4-yl)-N-(2,4,6-trifluorobenzyl)-1',4',5',11'-tetra-hydro-3'H,4H,7'H-spiro[isoxazole-5,6'-[2,7]methanopyrido[1,2-a][1,4]diazonine]-10'-carboxamide was prepared in a manner similar to Example 52, except using 1,2,4-triazole instead of dimethylamine in Step 1. MS (m/z) 558.177 [M+H]+. 1H NMR (400 MHz, Chloroform-d) δ 10.38 (s, 1H), 8.80 (s, 1H), 8.70 (s, 1H), 8.39 (s, 1H), 8.04 (d, J=16.3 Hz, 1H), 6.69 (t, J=8.1 Hz, 2H), 4.82 (d, J=10.6 Hz, 1H), 4.71 (d, J=5.7 Hz, 1H), 4.66-4.51 (m, 2H), 3.92-3.66 (m, 3H), 3.22 (d, J=18.1 Hz, 1H), 2.15-2.01 (m, 3H), 1.33 (dd, J=14.2, 6.6 Hz, 3H).

Example 77: Preparation of (3'S,5S,7'R)-12'-hydroxy-3'-methyl-1',11'-dioxo-3-(1H-pyrazol-1-yl)-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

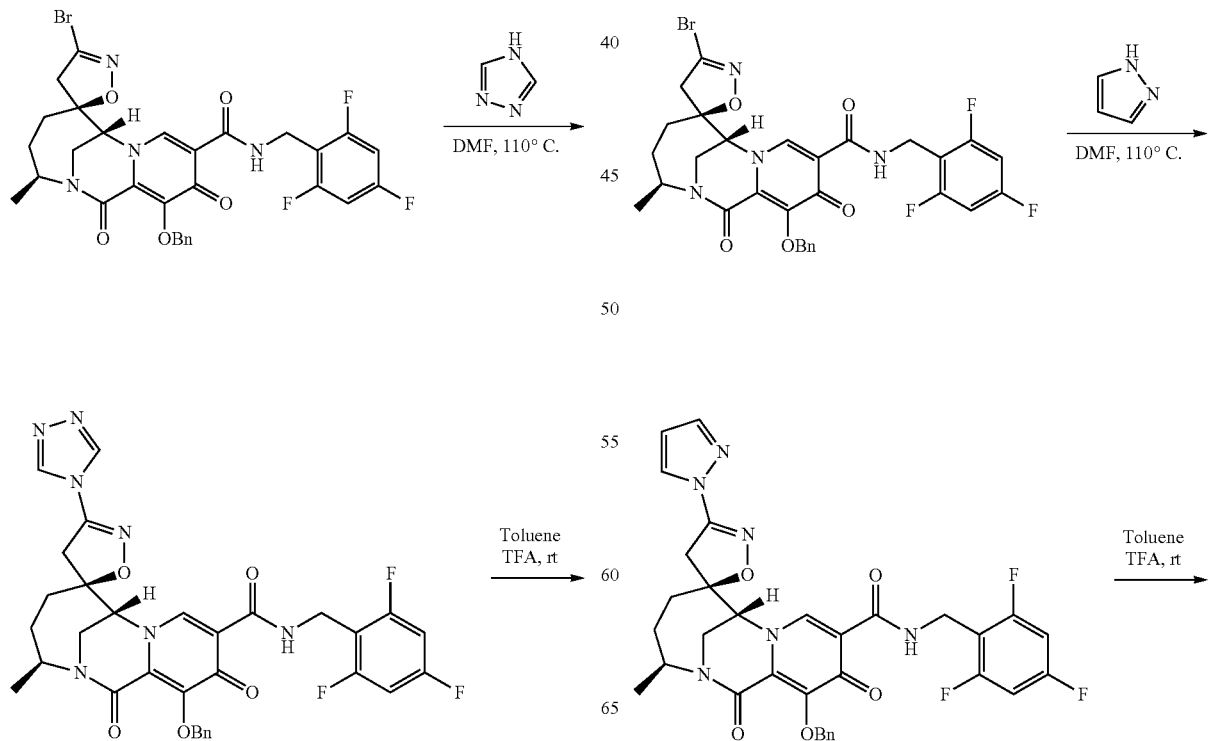

249
-continued

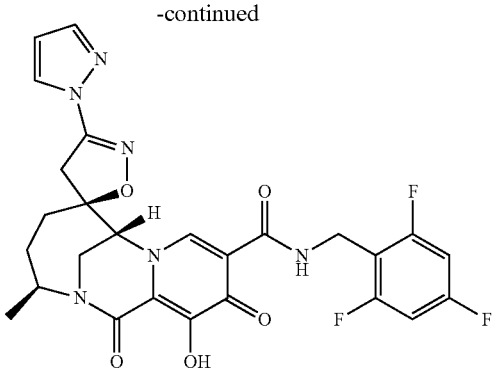

Step 1: Preparation of (3'S,5S,7'R)-12'-(benzyloxy)-3'-methyl-1',11'-dioxo-3-(1H-pyrazol-1-yl)-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (3'S,5S,7'R)-12'-hydroxy-3'-methyl-1',11'-dioxo-3-(1H-pyrazol-1-yl)-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide was prepared in a manner similar to Example 52, except using pyrazole instead of dimethylamine in Step 1. MS (m/z) 557.117 [M+H]+. 1H NMR (400 MHz, Chloroform-d) δ 10.43 (t, J=5.7 Hz, 1H), 9.17 (s, 1H), 8.05 (s, 1H), 7.35 (s, 1H), 6.67 (t, J=8.1 Hz, 2H), 6.45 (s, 1H), 5.04 (s, 1H), 4.81 (dd, J=12.6, 5.3 Hz, 2H), 4.52 (d, J=15.0 Hz, 1H), 3.87 (d, J=14.8 Hz, 1H), 3.75 (td, J=10.4, 9.0, 6.0 Hz, 2H), 3.43 (d, J=17.8 Hz, 1H), 2.11 (t, J=11.4 Hz, 2H), 2.01 (dd, J=14.7, 7.4 Hz, 1H), 1.63-1.53 (m, 1H), 1.36 (d, J=6.7 Hz, 3H).

Example 78: Preparation of (3'S,5S,7'R)-12'-hydroxy-3'-methyl-1',11'-dioxo-3-(2H-1,2,3-triazol-2-yl)-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide and (3'S,5S,7'R)-12'-hydroxy-3'-methyl-1',11'-dioxo-3-(1H-1,2,3-triazol-1-yl)-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

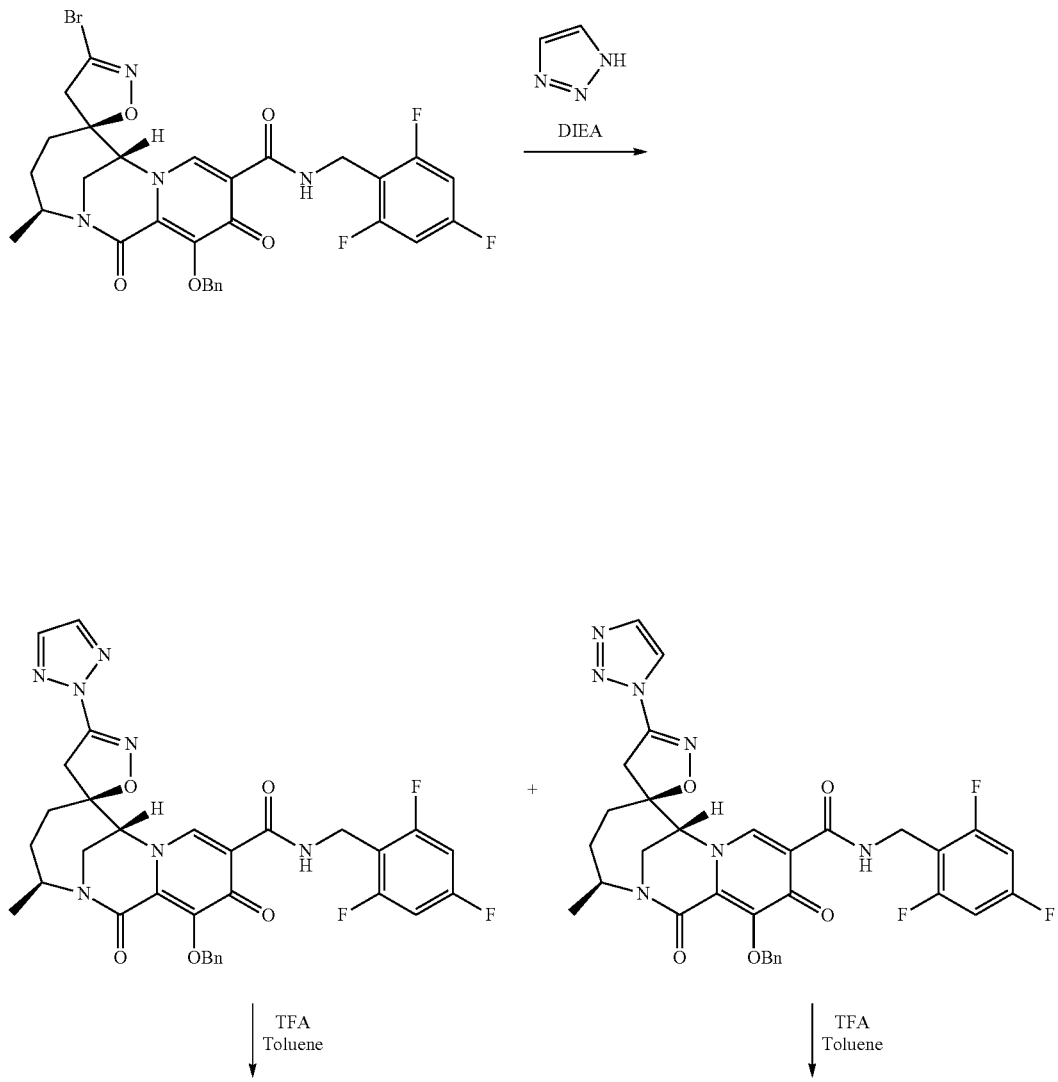

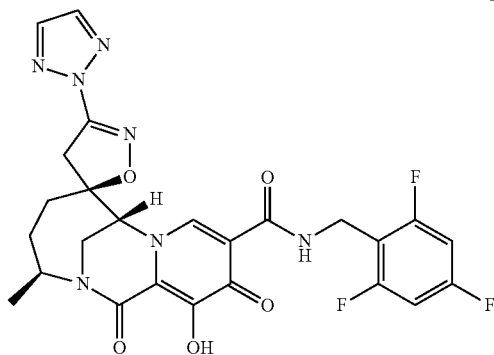
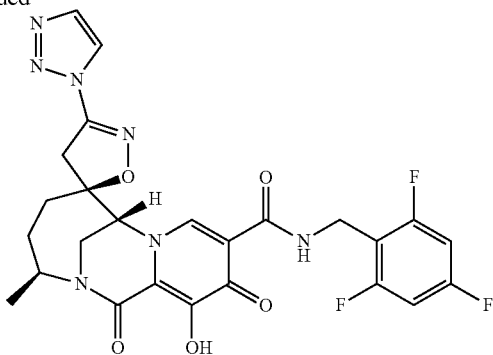

Step 1: Preparation of (3'S,5S,7'R)-12'-(benzyloxy)-3'-methyl-1',11'-dioxo-3-(2H-1,2,3-triazol-2-yl)-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide and (3'S,5S,7'R)-12'-(benzyloxy)-3'-methyl-1',11'-dioxo-3-(1H-1,2,3-triazol-1-yl)-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (3'S,5S,7'R)-12'-(Benzyloxy)-3-bromo-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (23 mg, 0.0349 mmol), prepared according to Example 36, triazole (23 mg, 0.332 mmol) and DIEA (27 mg, 0.21 mmol) were mixed with DMF (1 mL). The reaction mixture was heated at 100° C. for 17 h. The resulting reaction mixture was diluted with EtOAc (10 mL) and was treated with saturated NH4Cl (aq.) (10 mL) and water (10 mL). The organic phase was separated and the aqueous phase was extracted with EtOAc (10 mL). The combined organic phase was washed with brine (10 mL) and water (10 mL), and concentrated. The residue was purified by prep TLC with 2:1 EtOAc/Hex to afford (3'S,5S,7'R)-12'-(benzyloxy)-3'-methyl-1',11'-dioxo-3-(2H-1,2,3-triazol-2-yl)-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide and (3'S,5S,7'R)-12'-(benzyloxy)-3'-methyl-1',11'-dioxo-3-(1H-1,2,3-triazol-1-yl)-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide.

(3'S,5S,7'R)-12'-(benzyloxy)-3'-methyl-1',11'-dioxo-3-(2H-1,2,3-triazol-2-yl)-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide. MS (m/z): 648.0 [M+H]+.

(3'S,5S,7'R)-12'-(benzyloxy)-3'-methyl-1',11'-dioxo-3-(1H-1,2,3-triazol-1-yl)-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide. MS (m/z): 648.0 [M+H]+.

Step 2: Preparation of (3'S,5S,7'R)-12'-hydroxy-3'-methyl-1',11'-dioxo-3-(2H-1,2,3-triazol-2-yl)-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (3'S,5S,7'R)-12'-(Benzyloxy)-3'-methyl-1',11'-dioxo-3-(2H-1,2,3-triazol-2-yl)-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (12 mg, 0.0185 mmol) was dissolved in toluene (1.5 mL). TFA (2 mL) was added and the reaction mixture was stirred at rt for 17 h. The reaction mixture was concentrated and the residue was purified with reverse phase prep HPLC with 0-100% acetonitrile/water (with 0.1% TFA). Fractions containing product were lyophilized to afford (3'S,5S,7'R)-12'-hydroxy-3'-methyl-1',11'-dioxo-3-(2H-1,2,3-triazol-2-yl)-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide. MS (m/z): 558.2 [M+H]+. 1H NMR (400 MHz, CD3CN) δ 10.36 (s, 1H), 8.69 (s, 1H), 7.95 (br, 2H), 7.00-6.76 (m, 2H), 4.81-4.44 (m, 4H), 3.83-3.80 (m, 2H), 3.67 (d, J=17.9 Hz, 1H), 3.30 (d, J=17.8 Hz, 1H), 2.21-2.08 (m, 1H), 2.05-1.97 (m, 2H), 1.75-1.48 (m, 1H), 1.29 (d, J=6.7 Hz, 3H).

Step 3: Preparation of (3'S,5S,7'R)-12'-hydroxy-3'-methyl-1',11'-dioxo-3-(1H-1,2,3-triazol-1-yl)-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (3'S,5S,7'R)-12'-hydroxy-3'-methyl-1',11'-dioxo-3-(1H-1,2,3-triazol-1-yl)-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide was prepared in a similar manner as Step 2, except using (3'S,5S,7'R)-12'-(benzyloxy)-3'-methyl-1',11'-dioxo-3-(1H-1,2,3-triazol-1-yl)-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide instead of (3'S,5S,7'R)-12'-(benzyloxy)-3'-methyl-1',11'-dioxo-3-(2H-1,2,3-triazol-2-yl)-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide. MS (m/z): 558.2 [M+H]+; 1H NMR (400 MHz, CD3CN) δ 10.43 (s, 1H), 8.96 (s, 1H), 8.30 (br, 2H), 6.94-6.73 (m, 2H), 4.88 (s, 1H), 4.72 (d, J=12.9 Hz, 2H), 4.49 (d, J=14.3 Hz, 1H), 3.85-3.80 (m, 3H), 3.49 (d, J=16.7 Hz, 1H), 2.26-2.11 (m, 1H), 2.01 (d, J=11.2 Hz, 2H), 1.76-1.61 (m, 1H), 1.30 (d, J=6.6 Hz, 3H).

Example 79: Preparation of (3'S,5S,7'R)-12'-hydroxy-3'-methyl-3-(3-methyl-3-(methylsulfonyl)but-1-yn-1-yl)-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

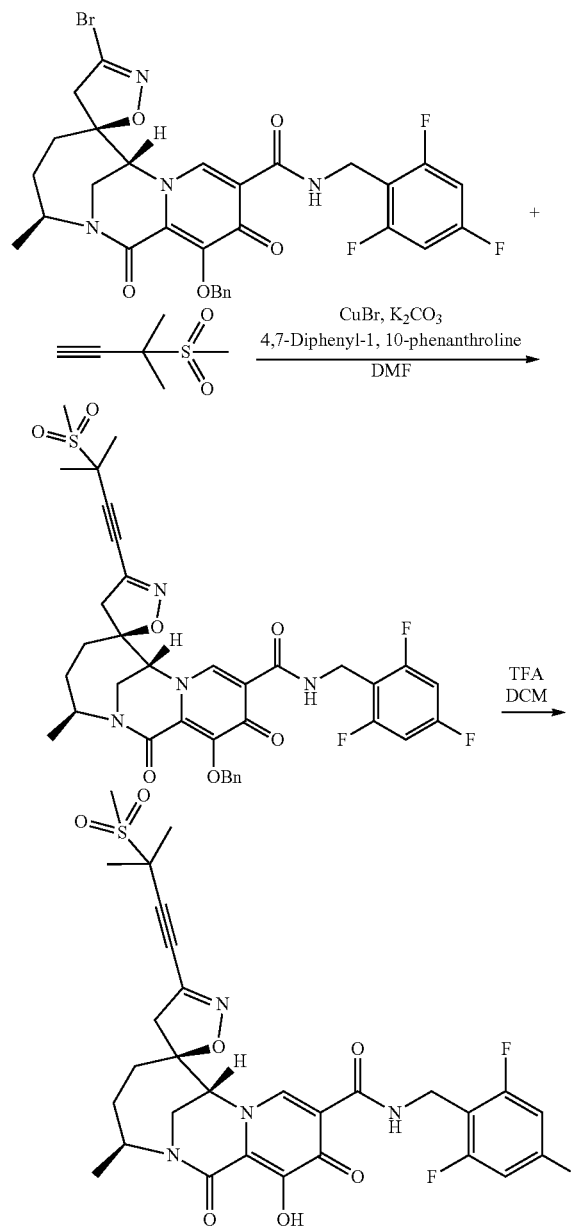

Step 1: Preparation of (3'S,5S,7'R)-12'-(benzyloxy)-3'-methyl-3-(3-methyl-3-(methylsulfonyl)but-1-yn-1-yl)-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide To a solution of (3'S,5S,7'R)-12'-(benzyloxy)-3-bromo-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (80 mg, 0.121 mmol), prepared according to Step 1 of Example 36, in DMF (3 mL), was added 3-methyl-3-methylsulfonyl-but-1-yne (99.8 mg, 0.682 mmol), K$_2$CO$_3$ (50.7 mg, 0.364 mmol), CuBr (3.48 mg, 0.024 mmol), and 4,7-diphenyl-1,10-phenanthroline (20.2 mg, 0.067 mmol). The reaction mixture was stirred at 100° C. for 17 h. The reaction was cooled down to rt. To the mixture was added sat. NaHCO$_3$, extracted with EtOAc, dried over MgSO$_4$, filtered, concentrated, and purified by silica gel column chromatography, eluting with 0-100% hexane/EtOAc to give title compound. MS (m/z) 725.00 [M+H]+.

Step 2: Preparation of (3'S,5S,7'R)-12'-hydroxy-3'-methyl-3-(3-methyl-3-(methylsulfonyl)but-1-yn-1-yl)-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide The solution of (3'S,5S,7'R)-12'-(benzyloxy)-3'-methyl-3-(3-methyl-3-(methylsulfonyl)but-1-yn-1-yl)-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (47.0 mg, 0.065 mmol) in DCM (1.5 mL) and TFA (1.5 mL) was stirred at rt overnight. The reaction mixture was concentrated and the residue was purified by reverse phase prep HPLC, eluting with 5-100% H$_2$O/ACN to give tile compound. MS (m/z) 635.10 [M+H]+. 1H NMR (400 MHz, Methanol-d4) δ 8.65 (s, 1H), 6.91 (t, J=8.5 Hz, 2H), 4.75-4.63 (m, 4H), 3.96-3.81 (m, 2H), 3.19-3.05 (m, 4H), 2.81 (d, J=17.6 Hz, 1H), 2.07-1.93 (m, 3H), 1.69 (s, 6H), 1.59 (dd, J=13.9, 11.0 Hz, 1H), 1.31 (d, J=6.6 Hz, 3H).

Example 80: Preparation of (3'S,5R,7'R)-12'-hydroxy-3'-methyl-3-(3-methyl-3-(methylsulfonyl)but-1-yn-1-yl)-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

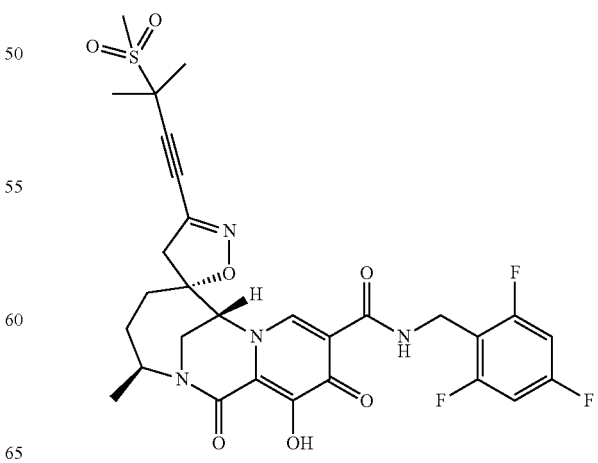

(3'S,5R,7'R)-12'-hydroxy-3'-methyl-3-(3-methyl-3-(methylsulfonyl)but-1-yn-1-yl)-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide was prepared in a similar manner as Example 79, except using (3'S,5R,7'R)-12'-(benzyloxy)-3-bromo-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide, prepared according to Example 36, instead of (3'S,5S,7'R)-12'-(benzyloxy)-3-bromo-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide. MS (m/z) 635.10 [M+H]+. 1H NMR (400 MHz, DMSO-d6) δ 10.79 (s, 1H), 10.36 (t, J=5.8 Hz, 1H), 8.16 (s, 1H), 7.31-7.13 (m, 2H), 4.78 (s, 1H), 4.59-4.48 (m, 3H), 3.84-3.69 (m, 2H), 3.29 (d, J=4.0 Hz, 2H), 3.20 (s, 3H), 2.10-1.97 (m, 1H), 1.76 (dt, J=14.1, 8.9 Hz, 1H), 1.66 (s, 6H), 1.48-1.29 (m, 2H), 1.17 (d, J=6.6 Hz, 3H).

Example 81: (3'S,5S,7'R)-12'-hydroxy-3-(3-hydroxy-3-methylbut-1-yn-1-yl)-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

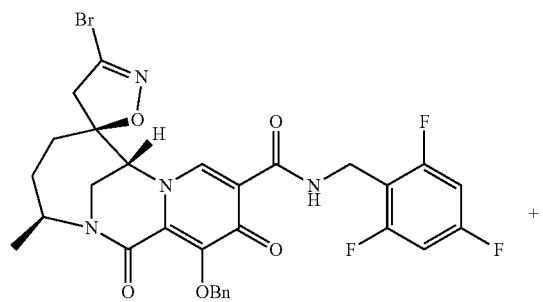

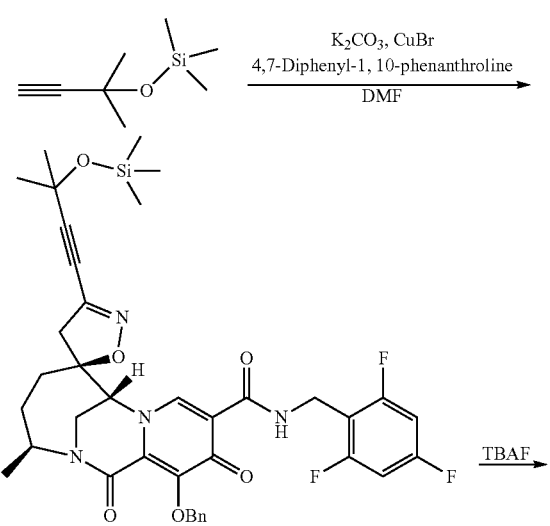

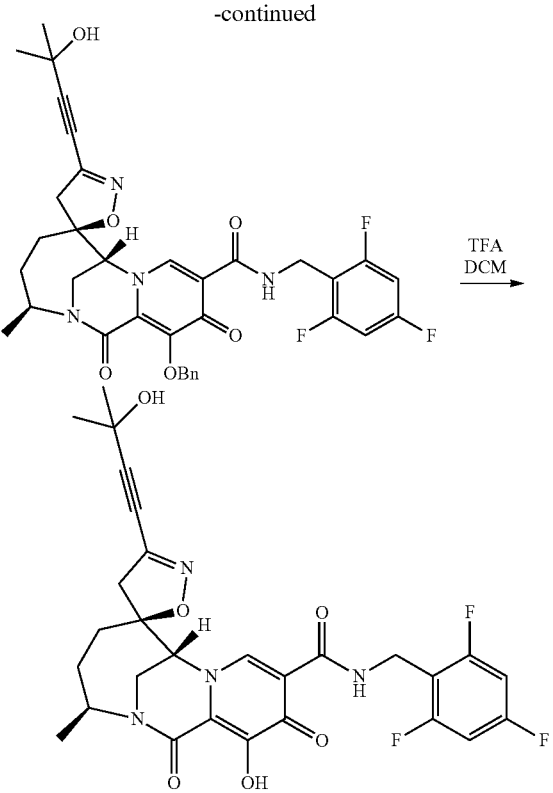

Step 1: Preparation of (3'S,5S,7'R)-12'-(benzyloxy)-3'-methyl-3-(3-methyl-3-((trimethylsilyl)oxy)but-1-yn-1-yl)-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide To a solution of (3'S,5S,7'R)-12'-(benzyloxy)-3-bromo-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (70 mg, 0.106 mmol), prepared according to Step 1 of Example 36, in DMF, was added K$_2$CO$_3$ (44 mg, 0.318 mmol), trimethyl((2-methylbut-3-yn-2-yl)oxy)silane (107 mg, 0.682 mmol), CuBr (4.5 mg, 0.0318 mmol) and 4,7-diphenyl-1,10-phenanthroline (19 mg, 0.058 mmol). The reaction mixture was stirred at 100° C. for 6 h. The reaction mixture was cooled to rt, washed with water, and extracted with EtOAc. The organic phase was dried over MgSO$_4$, filtered, concentrated, and purified by silica gel column chromatography, eluting with 0-100% hexane/EtOAc to give title compound. MS (m/z) 736.21 [M+H]+.

Step 2: Preparation of (3'S,5S,7'R)-12'-(benzyloxy)-3-(3-hydroxy-3-methylbut-1-yn-1-yl)-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide To a solution of (3'S,5S,7'R)-12'-(benzyloxy)-3'-methyl-3-(3-methyl-3-((trimethylsilyl)oxy)but-1-yn-1-yl)-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]

diazonine]-10'-carboxamide (5 mg, 0.0068 mmol) in THF (1 mL) was added tetrabutylammonium fluoride in THF (1M, 0.0935 mmol) at 0° C. The reaction mixture was stirred at 0° C. for 1 h. The reaction mixture was concentrated and the residue was purified by silica gel column chromatography, eluting with 0-100% hexane/EtOAc to give the title compound. MS (m/z) 663.06 [M+H]+.

Step 3: Preparation of (3'S,5S,7'R)-12'-hydroxy-3-(3-hydroxy-3-methylbut-1-yn-1-yl)-3'-methyl-1',11'-dioxo-N-(2,4,6-trifluorobenzyl)-1',4',5',1'-tetrahydro-3'H,4H,7'H-spiro[isoxazole-5,6'-[2,7]methanopyrido[1,2-a][1,4]diazonine]-10'-carboxamide The solution of (3'S,5S,7'R)-12'-(benzyloxy)-3-(3-hydroxy-3-methylbut-1-yn-1-yl)-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide in 1:1 TFA/DCM (2 mL) was stirred at rt overnight. The reaction mixture was concentrated down and purified by reverse phase prep HPLC, eluting with 0-100% H$_2$O/ACN to give title compound. MS (m/z) 573.14 [M+H]+. 1H NMR (400 MHz, Methanol-d4) δ 8.58 (s, 1H), 6.91 (t, J=8.5 Hz, 2H), 4.67 (d, J=18.3 Hz, 4H), 3.89 (t, J=12.3 Hz, 2H), 3.12 (d, J=17.6 Hz, 1H), 2.80-2.65 (m, 1H), 2.10-1.89 (m, 3H), 1.52 (d, J=3.6 Hz, 7H), 1.31 (d, J=6.6 Hz, 3H).

Example 82: Preparation of (3'S,5S,7'R)-3-fluoro-12'-hydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

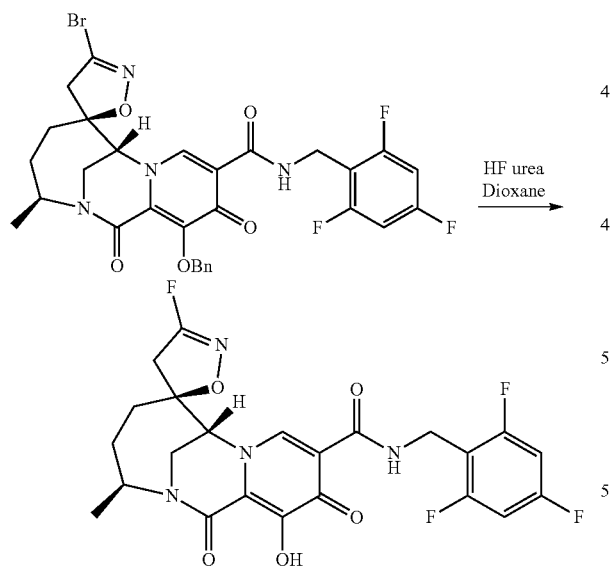

(3'S,5S,7'R)-12'-(Benzyloxy)-3-bromo-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (55 mg, 0.0834 mmol), prepared according to Example 36, was dissolved in dioxane (3 mL). HF urea (0.133 mL, 1.67 mmol) was added and the resulting reaction mixture was heated at 60-70° C. for 3 h. The reaction mixture was diluted with EtOAc (5 mL) and was treated with water (10 mL). The organic phase was separated, washed with water (10 mL), and concentrated to dryness. The residue was dissolved in ACN and purified by reverse phase prep HPLC using 0-100% acetonitrile/water with 0.1% TFA. Lyophilization afforded (3'S,5S,7'R)-3-fluoro-12'-hydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide. MS (m/z): 509.1 [M+H]+; 1H NMR (400 MHz, CD3CN) δ 10.33 (s, 1H), 8.58 (s, 1H), 6.94-6.81 (m, 2H), 4.64 (dd, J=14.7, 6.4 Hz, 3H), 4.54 (s, 1H), 3.75 (d, J=2.3 Hz, 2H), 3.14 (dd, J=18.0, 4.9 Hz, 1H), 2.77 (dd, J=17.9, 4.9 Hz, 1H), 2.19-2.05 (m, 1H), 1.94-1.88 (m, 1H), 1.60-1.48 (m, 1H), 1.25 (d, J=6.7 Hz, 3H), 1.27-1.15 (m, 1H).

Example 83: Preparation of (3'S,5S,7'R)-12'-hydroxy-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-4-d-10'-carboxamide

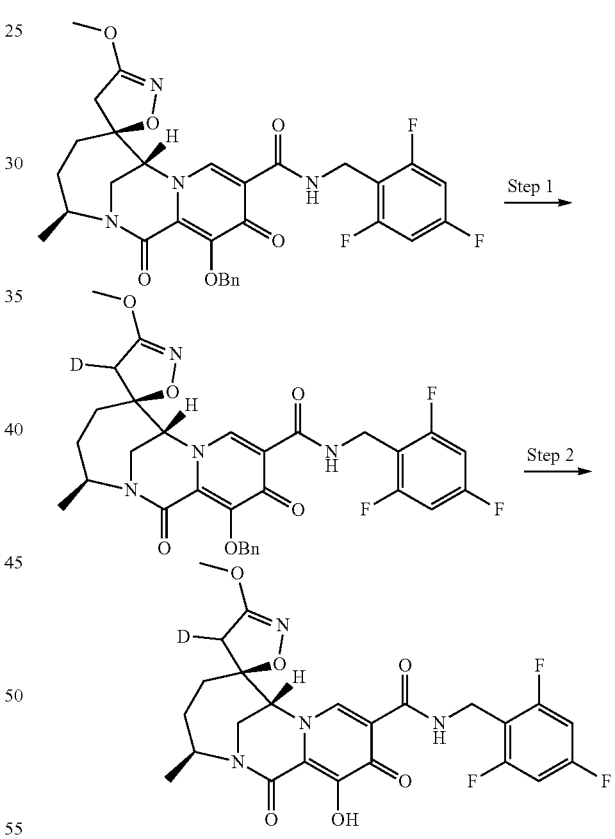

Step 1: Preparation of (3'S,5S,7'R)-12'-(benzyloxy)-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-4-d-10'-carboxamide To a mixture of (3'S,5S,7'R)-12'-(benzyloxy)-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (26.0 mg, 0.0426 mmol), prepared according to Example 36, in CD₃OD (2.0 mL) was added potassium carbonate (29.4 mg, 0.213 mmol). The resulting mixture was heated to 54° C. for 1.5 h. The reaction was cooled to room temperature, diluted with EtOAc, washed with water, brine, dried over sodium sulfate, filtered, and concentrated. The residue was used without further purification.

Step 2: Preparation of (3'S,5S,7'R)-12'-hydroxy-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-4-d-10'-carboxamide Crude (3'S,5S,7'R)-12'-(benzyloxy)-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-4-d-10'-carboxamide from Step 1 was treated with lithium chloride (17.9 mg, 0.426 mmol) in DMF (0.6 mL) at 100° C. for 3 h. The reaction mixture was cooled to room temperature, filtered, and purified by reverse phase chromatography. LCMS-ESI+(m/z): calcd H+ for C24H22DF3N4O6, Theoretical: 521.16, Found: 522.186. 1H NMR (400 MHz, CD3OD) δ 8.58 (s, 1H), 6.91 (t, J=8.5 Hz, 2H), 4.74-4.60 (m, 4H), 3.94-3.77 (m, 5H), 3.00 (s, 1H), 2.10-1.89 (m, 3H), 1.55 (dd, J=15.2, 11.5 Hz, 1H), 1.30 (d, J=6.6 Hz, 3H).

Example 84: Preparation of (3'S,4R,5R,7'R)-4,12'-dihydroxy-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

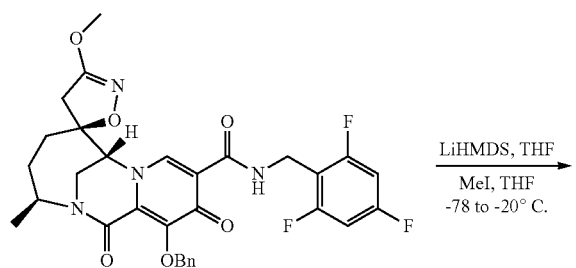

LiHMDS, THF
MeI, THF
-78 to -20° C.

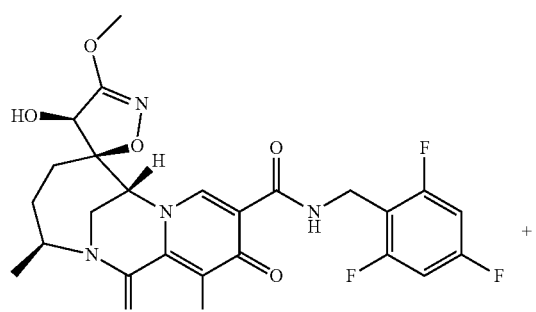

+

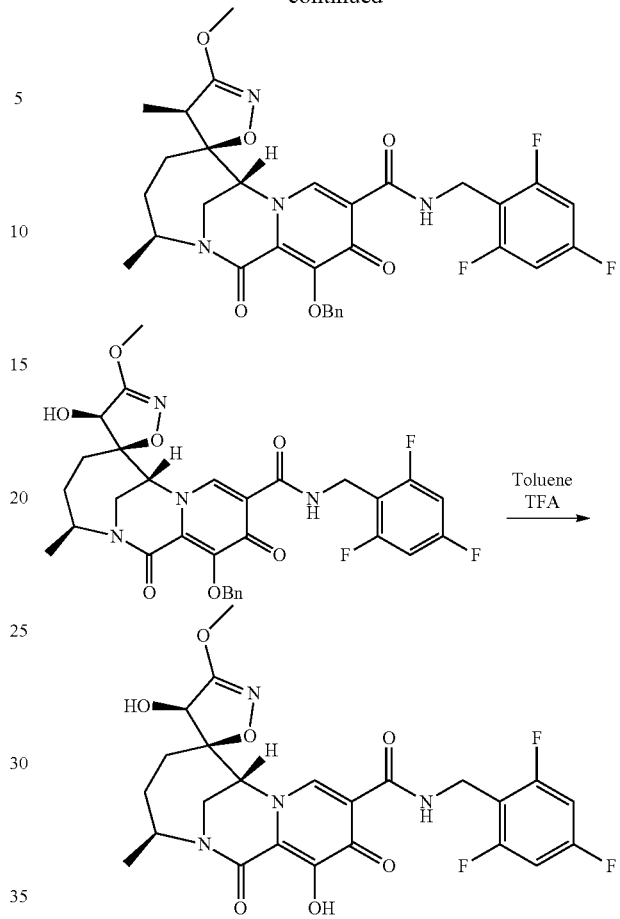

Toluene
TFA

Step 1: Preparation of (3'S,4R,5R,7'R)-12'-(benzyloxy)-4-hydroxy-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide and (3'S,4R,5S,7'R)-12'-(benzyloxy)-3-methoxy-3',4-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (3'S,4R,5R,7'R)-12'-(benzyloxy)-4-hydroxy-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide and (3'S,4R,5S,7'R)-12'-(benzyloxy)-3-methoxy-3',4-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide were prepared in a manner similar to Step 1 of Example 31, except using (3'S,5S,7'R)-12'-(benzyloxy)-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide, prepared according to Example 36, instead of (3'S,5S,7'R)-12'-(benzyloxy)-3,3'-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide. MS (m/z) 627.005 [M+H]+, and MS (m/z) 624.013 [M+H]+.

Step 2: Preparation of (3'S,4R,5R,7'R)-4,12'-dihydroxy-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (3'S,4R,5R,7'R)-4,12'-dihydroxy-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide was synthesized in a manner similar to Step 2 of Example 31, except using (3'S,4R,5R,7'R)-12'-(benzyloxy)-4-hydroxy-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide, prepared in Step 1, instead of (3'S,4S,5R,7'R)-12'-(benzyloxy)-4-hydroxy-3,3'-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide. MS (m/z) 537.115 [M+H]+. 1H NMR (400 MHz, Chloroform-d) δ 10.12 (dd, J=7.3, 4.2 Hz, 1H), 8.52 (s, 1H), 6.70 (dd, J=8.7, 7.5 Hz, 2H), 5.21 (s, 1H), 4.90 (dd, J=14.6, 7.2 Hz, 1H), 4.85-4.75 (m, 1H), 4.46-4.38 (m, 1H), 4.10 (s, 1H), 4.02 (s, 3H), 3.88 (dd, J=14.8, 1.8 Hz, 1H), 3.64 (dd, J=14.8, 2.7 Hz, 1H), 2.42 (dd, J=16.4, 5.6 Hz, 1H), 2.02 (dd, J=13.0, 7.9 Hz, 2H), 1.68-1.56 (m, 1H), 1.31 (d, J=6.6 Hz, 3H).

Example 85: Preparation of (3'S,4R,5S,7'R)-12'-hydroxy-3-methoxy-3',4-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

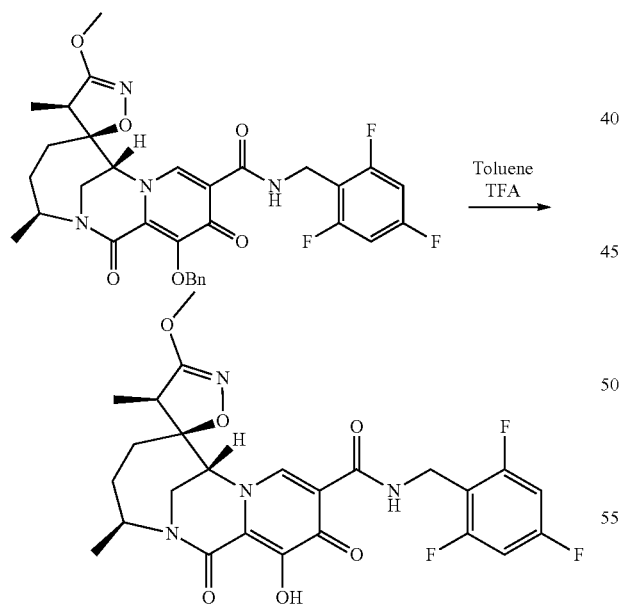

(3'S,4R,5S,7'R)-12'-hydroxy-3-methoxy-3',4-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide was synthesized in a manner similar to Step 2 of Example 23, except using (3'S,4R,5S,7'R)-12'-(benzyloxy)-3-methoxy-3',4-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide, prepared according to Example 84, instead of (3'S,5R,7'R)-12'-(benzyloxy)-N-(2,4-difluorobenzyl)-3,3',4-trimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide. MS (m/z) 535.11 [M+H]+. 1H NMR (400 MHz, Chloroform-d) δ 10.45 (s, 1H), 8.25 (s, 1H), 6.74-6.64 (m, 2H), 4.87-4.73 (m, 2H), 4.72 (d, J=6.1 Hz, 1H), 4.58 (dd, J=14.4, 5.3 Hz, 1H), 4.32 (s, 1H), 4.07 (s, 3H), 3.91-3.80 (m, 2H), 2.09 (t, J=4.4 Hz, 2H), 1.74 (d, J=5.5 Hz, 3H), 1.65 (dd, J=10.4, 2.8 Hz, 2H), 1.36 (d, J=6.7 Hz, 3H).

Example 86: Preparation of (3'S,4S,5R,7'R)-4-fluoro-12'-hydroxy-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

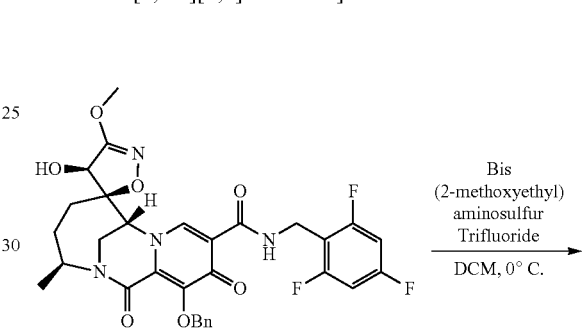

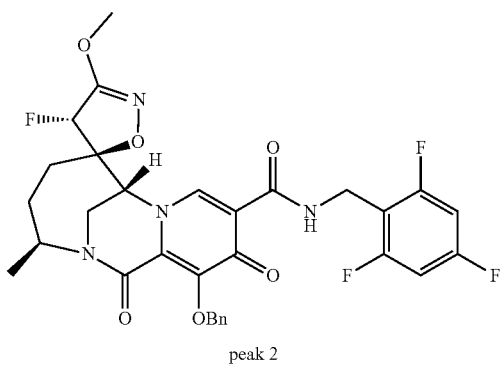

peak 2

-continued

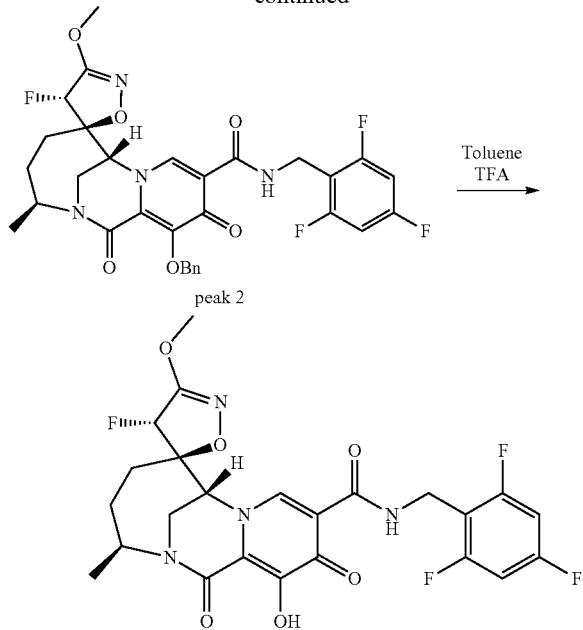

peak 2

Step 1: Preparation of (3'S,4R,5R,7'R)-12'-(benzyloxy)-N-(2,4-difluoro-6-methylbenzyl)-4-fluoro-3-methoxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide and (3'S,4S,5R,7'R)-12'-(benzyloxy)-4-fluoro-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (3'S,4R,5R,7'R)-12'-(benzyloxy)-N-(2,4-difluoro-6-methylbenzyl)-4-fluoro-3-methoxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide and (3'S,4S,5R,7'R)-12'-(benzyloxy)-4-fluoro-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide were prepared in a manner similar to Step 1 of Example 27, except using (3'S,4R,5R,7'R)-12'-(benzyloxy)-4-hydroxy-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide, prepared according to Example 84, instead of (3'S,5S,7'R)-12'-(benzyloxy)-N-(2,4-difluorobenzyl)-4-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide.
Peak 1: MS (m/z) 629.022 [M+H]+.
Peak 2: MS (m/z) 629.007 [M+H]+.

Step 2: Preparation of (3'S,4S,5R,7'R)-4-fluoro-12'-hydroxy-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (3'S,4S,5R,7'R)-4-fluoro-12'-hydroxy-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide was prepared in a manner similar to Step 2 of Example 27, except using (3'S,4S,5R,7'R)-12'-(benzyloxy)-4-fluoro-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (peak 2), prepared in Step 1, instead of (3'S,5S,7'R)-12'-(benzyloxy)-N-(2,4-difluorobenzyl)-4-fluoro-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide. MS (m/z) 539.039 [M+H]+. 1H NMR (400 MHz, Chloroform-d) δ 10.27 (t, J=5.6 Hz, 1H), 8.61 (d, J=5.6 Hz, 1H), 6.68 (dd, J=8.7, 7.5 Hz, 2H), 4.96 (d, J=54.1 Hz, 1H), 4.87-4.78 (m, 1H), 4.73 (dd, J=14.5, 5.8 Hz, 1H), 4.67 (s, 1H), 4.64 (d, J=5.4 Hz, 1H), 3.98 (s, 3H), 3.82-3.70 (m, 2H), 2.16-1.88 (m, 3H), 1.73 (dd, J=15.7, 6.2 Hz, 1H), 1.32 (d, J=6.7 Hz, 3H).

Example 87: Preparation of (3'S,4R,5R,7'R)-4-fluoro-12'-hydroxy-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

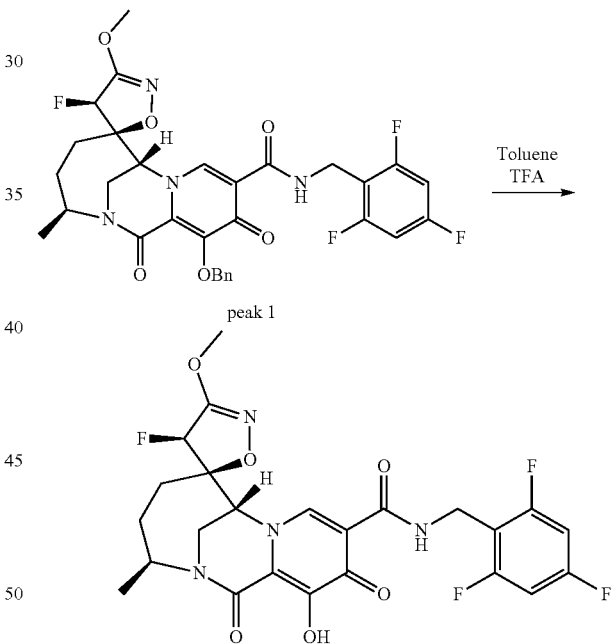

peak 1

(3'S,4R,5R,7'R)-4-fluoro-12'-hydroxy-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide was prepared in a manner similar to Step 2 of Example 27, except using (3'S,4R,5R,7'R)-12'-(benzyloxy)-4-fluoro-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (peak 2), prepared in Step 1 of Example 86, instead of (3'S,5S,7'R)-12'-(benzyloxy)-N-(2,4-difluorobenzyl)-4-fluoro-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide. MS (m/z) 539.061 [M+H]+. 1H NMR (400 MHz, Chloroform-d) δ 10.40 (s, 1H), 8.39 (s, 1H), 6.70 (dd, J=8.7, 7.5 Hz, 2H), 5.30 (s, 1H), 4.77 (d, J=6.5 Hz, 1H), 4.72 (d, J=5.9 Hz, 1H), 4.66 (d, J=5.5 Hz, 1H), 4.00 (d, J=6.8 Hz, 3H), 3.91 (d, J=1.7 Hz, 1H), 3.74 (s, 1H), 2.34-2.26 (m, 1H), 2.09 (d, J=5.6 Hz, 1H), 2.03-1.97 (m, 2H), 1.48-1.41 (m, 1H), 1.33 (d, J=6.6 Hz, 3H).

Example 88: Preparation (3'S,4S,5R,7'R)-3-(fluoromethyl)-4,12'-dihydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

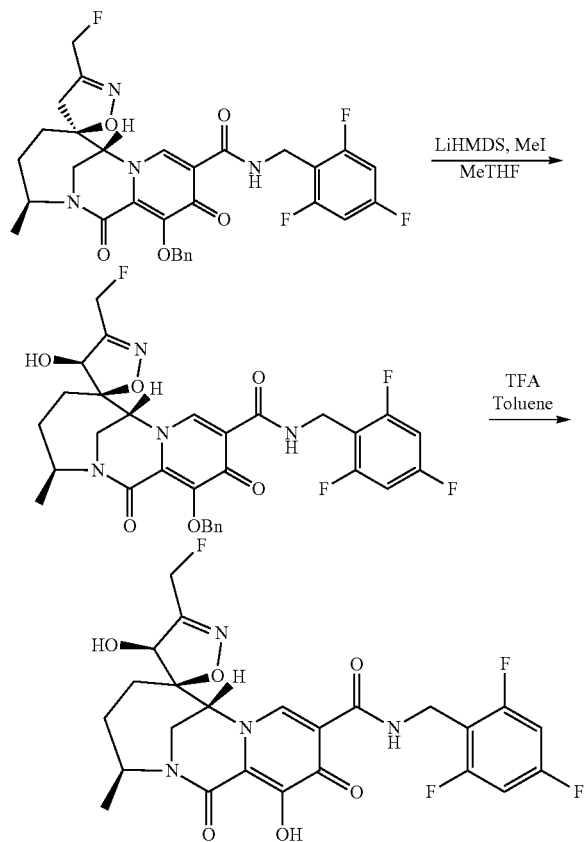

(3'S,4S,5R,7'R)-3-(fluoromethyl)-4,12'-dihydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide was prepared in a similar manner as Example 31, except using (3'S,5S,7'R)-12'-(benzyloxy)-3-(fluoromethyl)-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide, prepared according to Example 19, instead of (3'S,5S,7'R)-12'-(benzyloxy)-3,3'-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide and using 2-methyltetrahydrofuran instead of THF as solvent in Step 1. MS (m/z) 539.1 [M+H]+. 1H NMR (400 MHz, Chloroform-d) δ 10.04 (s, 1H), 8.38 (s, 1H), 6.68 (t, J=8.1 Hz, 2H), 5.50 (s, 1H), 5.38 (s, 1H), 5.26 (s, 1H), 4.84 (dt, J=12.8, 6.5 Hz, 2H), 4.32 (d, J=14.4 Hz, 1H), 3.92 (d, J=15.0 Hz, 2H), 3.68 (d, J=12.8 Hz, 1H), 2.37 (dd, J=16.3, 6.6 Hz, 1H), 2.17-1.93 (m, 3H), 1.85-1.65 (m, 1H), 1.33 (d, J=6.6 Hz, 3H).

Example 89: Preparation of (3'S,4S,5R,7'R)—N-(2,4-difluorobenzyl)-3-(fluoromethyl)-4,12'-dihydroxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

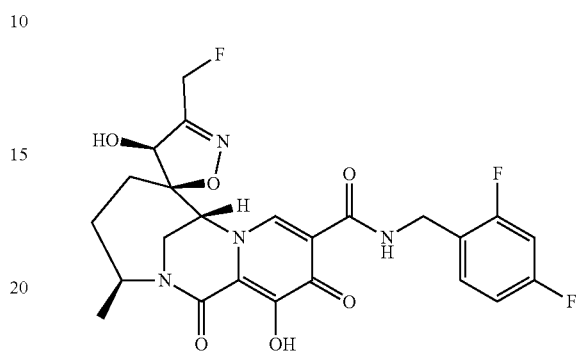

(3'S,4S,5R,7'R)—N-(2,4-difluorobenzyl)-3-(fluoromethyl)-4,12'-dihydroxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide was prepared in a similar manner as Example 88, except using (3'S,5S,7'R)-12'-(benzyloxy)-N-(2,4-difluorobenzyl)-3-(fluoromethyl)-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide, prepared according to Example 17, instead of (3'S,5S,7'R)-12'-(benzyloxy)-3-(fluoromethyl)-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide. MS (m/z) 521.66 [M+H]+. 1H NMR (400 MHz, Chloroform-d) δ 11.58 (s, 1H), 9.89 (s, 1H), 8.33 (s, 1H), 7.37 (m, 1H), 6.83 (d, J=8.4 Hz, 2H), 5.45 (s, 2H), 4.84 (dt, J=14.4, 7.5 Hz, 2H), 4.30 (d, J=14.7 Hz, 1H), 3.90 (d, J=7.5 Hz, 2H), 3.69 (dd, J=14.6, 2.6 Hz, 2H), 2.38 (dd, J=16.4, 6.7 Hz, 1H), 2.12 (dt, J=14.4, 6.7 Hz, 1H), 2.08-1.93 (m, 1H), 1.70 (d, J=16.2 Hz, 1H), 1.35 (m, 3H).

Example 90: Preparation of (3'S,7'R)-12'-hydroxy-3',5-dimethyl-1',11'-dioxo-2-phenyl-N-(2,4,6-trifluorobenzyl)-1',2,4,4',5',11'-hexahydro-3'H,7'H-spiro[pyrazole-3,6'-[2,7]methanopyrido[1,2-a][1,4]diazonine]-10'-carboxamide and (3'S,7'R)-12'-hydroxy-3',5-dimethyl-1',11'-dioxo-2-phenyl-N-(2,4,6-trifluorobenzyl)-1',2,4,4',5',11'-hexahydro-3'H,7'H-spiro[pyrazole-3,6'-[2,7]methanopyrido[1,2-a][1,4]diazonine]-10'-carboxamide

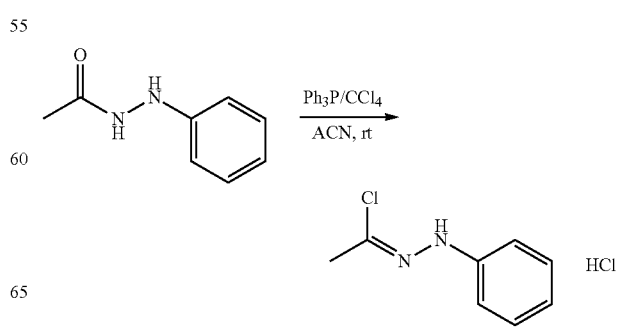

267
-continued

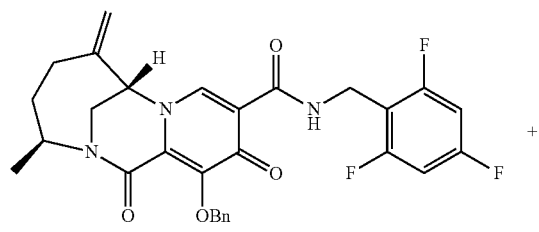

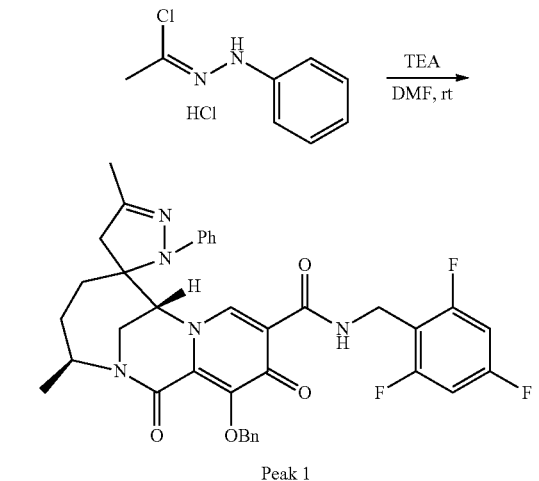

Peak 1

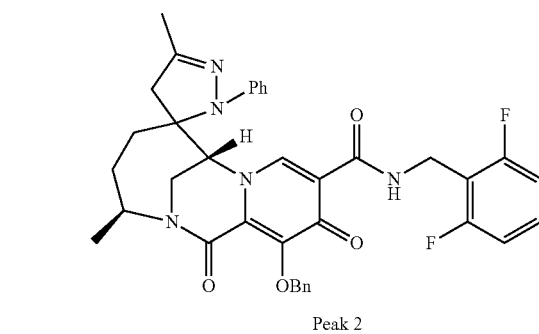

Peak 2

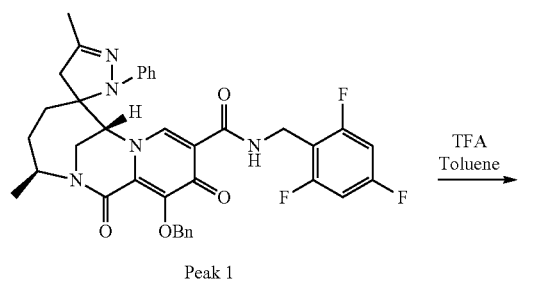

Peak 1

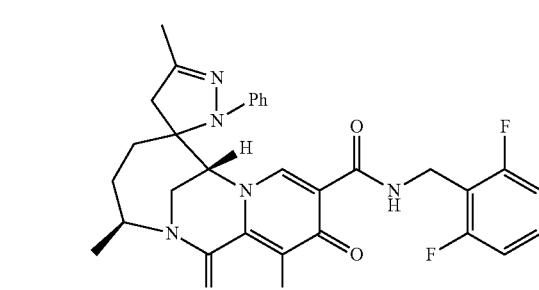

268
-continued

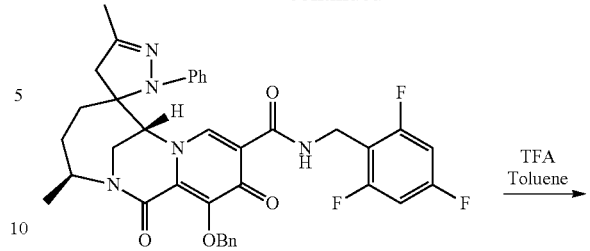

Peak 2

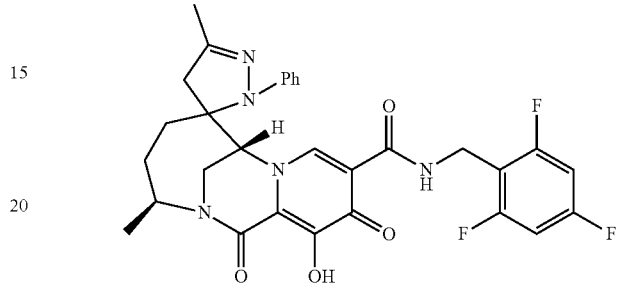

Step 1: Preparation of
(Z)—N-phenlacetohydrazonyl chloride

Into the solution of N'-phenylacetohydrazide (1.195 g, 7.96 mmol) and triphenylphosphine (2.50 g, 9.55 mmol, 1.2 equiv) in ACN (30 mL), was added carbon tetrachloride (3.67 g, 23.9 mmol, 3 equiv) at rt., After stirring overnight, the solvent was removed and the residue was used for next step without purification.

Step 2. Preparation of (3'S,7'R)-12'-(benzyloxy)-3', 5-dimethyl-1',11'-dioxo-2-phenyl-N-(2,4,6-trifluorobenzyl)-1',2,4,4',5',11'-hexahydro-3'H, 7'H-spiro[pyrazole-3,6'-[2,7]methanopyrido[1,2-a][1,4]diazonine]-10'-carboxamide and (3'S,7'R)-12'-(benzyloxy)-3',5-dimethyl-1',11'-dioxo-2-phenyl-N-(2,4,6-trifluorobenzyl)-1',2,4,4',5',11'-hexahydro-3'H, 7'H-spiro[pyrazole-3,6'-[2,7]methanopyrido[1,2-a][1,4]diazonine]-10'-carboxamide To a solution of Intermediate C (137 mg, 0.255 mmol), in DMF (3 mL) was added (Z)—N-phenylacetohydrazonoyl chloride (129 mg, 0.765 mmol) and TEA (258 mg, 2.55 mmol) at rt. The reaction mixture was stirred at rt overnight. The reaction mixture was concentrated down and the residue was purified by silica gel column chromatography to give (3'S,7'R)-12'-(benzyloxy)-3',5-dimethyl-1',11'-dioxo-2-phenyl-N-(2,4,6-trifluorobenzyl)-1',2,4,4',5',11'-hexahydro-3'H, 7'H-spiro[pyrazole-3,6'-[2,7]methanopyrido[1,2-a][1,4]diazonine]-10'-carboxamide (Peak 1) and (3'S,7'R)-12'-(benzyloxy)-3',5-dimethyl-1',11'-dioxo-2-phenyl-N-(2,4,6-trifluorobenzyl)-1',2,4,4',5',11'-hexahydro-3'H,7'H-spiro[pyrazole-3,6'-[2,7]methanopyrido[1,2-a][1,4]diazonine]-10'-carboxamide (Peak 2).

Peak 1: MS (m/z) 668.043 [M–H]—. 1H NMR (400 MHz, Chloroform-d) δ 10.32 (t, J=5.8 Hz, 1H), 8.22 (s, 1H), 7.55-7.52 (m, 2H), 7.38-7.31 (m, 5H), 7.13-7.07 (m, 2H), 7.01-6.94 (m, 1H), 6.68 (dd, J=8.7, 7.5 Hz, 2H), 5.95 (dd, J=12.0, 2.5 Hz, 1H), 5.56 (t, J=10.1 Hz, 2H), 5.45 (dd, J=12.0, 2.1 Hz, 1H), 4.90 (d, J=2.2 Hz, 1H), 4.66 (dd, J=12.0, 5.6 Hz, 2H), 4.00 (dd, J=14.4, 2.7 Hz, 1H), 3.33 (dd, J=14.5, 1.6 Hz, 1H), 2.82-2.75 (m, 1H), 2.48 (d, J=1.3 Hz, 1H), 1.88 (d, J=1.1 Hz, 3H), 1.81-1.68 (m, 1H), 1.70-1.58 (m, 1H), 1.58-1.46 (m, 1H), 1.38 (d, J=7.2 Hz, 3H).

Peak 2: MS (m/z) 668.04 [M−H]—, 1H NMR (400 MHz, Chloroform-d) δ 10.32 (t, J=5.8 Hz, 1H), 8.22 (s, 1H), 7.55-7.52 (m, 2H), 7.38-7.31 (m, 5H), 7.13-7.07 (m, 2H), 7.01-6.94 (m, 1H), 6.68 (dd, J=8.7, 7.5 Hz, 2H), 5.95 (dd, J=12.0, 2.5 Hz, 1H), 5.56 (t, J=10.1 Hz, 2H), 5.45 (dd, J=12.0, 2.1 Hz, 1H), 4.90 (d, J=2.2 Hz, 1H), 4.66 (d, J=12.0, 5.6 Hz, 2H), 4.00 (dd, J=14.4, 2.7 Hz, 1H), 3.33 (dd, J=14.5, 1.6 Hz, 1H), 2.82-2.75 (m, 1H), 2.48 (d, J=1.3 Hz, 1H), 1.88 (d, J=1.1 Hz, 3H), 1.81-1.68 (m, 1H), 1.70-1.58 (m, 1H), 1.58-1.46 (m, 1H), 1.38 (d, J=7.2 Hz, 3H).

Step 3: Preparation of (3'S,7'R)-12'-hydroxy-3',5-dimethyl-1',11'-dioxo-2-phenyl-N-(2,4,6-trifluorobenzyl)-1',2,4,4',5',11'-hexahydro-3'H,7'H-spiro[pyrazole-3,6'-[2,7]methanopyrido[1,2-a][1,4]diazonine]-10'-carboxamide (3'S,7'R)-12'-hydroxy-3',5-dimethyl-1',11'-dioxo-2-phenyl-N-(2,4,6-trifluorobenzyl)-1',2,4,4',5',11'-hexahydro-3'H,7'H-spiro[pyrazole-3,6'-[2,7]methanopyrido[1,2-a][1,4]diazonine]-10'-carboxamide was prepared in a manner similar as Step 2 of Example 3, except using (3'S,7'R)-12'-(benzyloxy)-3',5-dimethyl-1',11'-dioxo-2-phenyl-N-(2,4,6-trifluorobenzyl)-1',2,4,4',5',11'-hexahydro-3'H,7'H-spiro[pyrazole-3,6'-[2,7]methanopyrido[1,2-a][1,4]diazonine]-10'-carboxamide (Peak 1) instead of (3'S,5S,7'R)-12'-(benzyloxy)-3,3'-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide. MS (m/z) 578.001 [M−H]—. 1H NMR (400 MHz, Chloroform-d) δ 10.27 (s, 1H), 8.31 (s, 1H), 7.35 (dd, J=8.6, 7.3 Hz, 2H), 7.21-7.13 (m, 2H), 7.02 (t, J=1.0 Hz, 1H), 6.69 (dd, J=8.6, 7.5 Hz, 2H), 5.99 (dd, J=12.0, 2.4 Hz, 1H), 5.53 (dd, J=12.1, 2.2 Hz, 1H), 5.51-5.44 (m, 1H), 5.03 (s, 1H), 4.68 (d, J=5.6 Hz, 2H), 4.11 (dd, J=14.3, 2.7 Hz, 2H), 3.72-3.66 (m, 1H), 2.80-2.72 (m, 1H), 2.32-2.23 (m, 1H), 2.22-2.02 (m 1H), 1.93-1.83 (m, 3H), 1.46 (d, J=7.1 Hz, 3H).

Step 4: Preparation of (3'S,7'R)-12'-hydroxy-3',5-dimethyl-1',11'-dioxo-2-phenyl-N-(2,4,6-trifluorobenzyl)-1',2,4,4',5',11'-hexahydro-3'H,7'H-spiro[pyrazole-3,6'-[2,7]methanopyrido[1,2-a][1,4]diazonine]-10'-carboxamide (3'S,7'R)-12'-hydroxy-3',5-dimethyl-1',11'-dioxo-2-phenyl-N-(2,4,6-trifluorobenzyl)-1',2,4,4',5',11'-hexahydro-3'H,7'H-spiro[pyrazole-3,6'-[2,7]methanopyrido[1,2-a][1,4]diazonine]-10'-carboxamide was prepared in a manner similar as Step 2 of Example 3, except using (3'S,7'R)-12'-(benzyloxy)-3',5-dimethyl-1',11'-dioxo-2-phenyl-N-(2,4,6-trifluorobenzyl)-1',2,4,4',5',11'-hexahydro-3'H,7'H-spiro[pyrazole-3,6'-[2,7]methanopyrido[1,2-a][1,4]diazonine]-10'-carboxamide (Peak 2) instead of (3'S,5S,7'R)-12'-(benzyloxy)-3,3'-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide. MS (m/z) 580.125 [M+H]+. 1H NMR (400 MHz, Chloroform-d) δ 10.42 (d, J=6.1 Hz, 1H), 8.50 (s, 1H), 7.45-7.38 (m, 2H), 7.34-7.29 (m, 2H), 7.28-7.20 (m, 1H), 6.70 (dd, J=8.7, 7.5 Hz, 2H), 4.91 (s, 1H), 4.71 (t, J=4.3 Hz, 2H), 4.62 (q, J=7.0 Hz, 1H), 3.63-3.52 (m, 2H), 2.50-2.40 (m, 3H), 2.01 (d, J=1.0 Hz, 3H), 1.76 (d, J=7.7 Hz, 1H), 1.47 (dd, J=15.9, 10.5 Hz, 1H), 1.24-1.13 (m, 1H), 1.08 (d, J=6.7 Hz, 3H).

Example 91: Preparation of (3'S,5R,7'R)—N-(2,4-difluorobenzyl)-12'-hydroxy-3,3'-dimethyl-1',11'-dioxo-1',4',5',11'-tetrahydro-3' H,7'H-spiro[[1,4,2]dioxazole-5,6'-[2,7]methanopyrido[1,2-a][1,4]diazonine]-10'-carboxamide

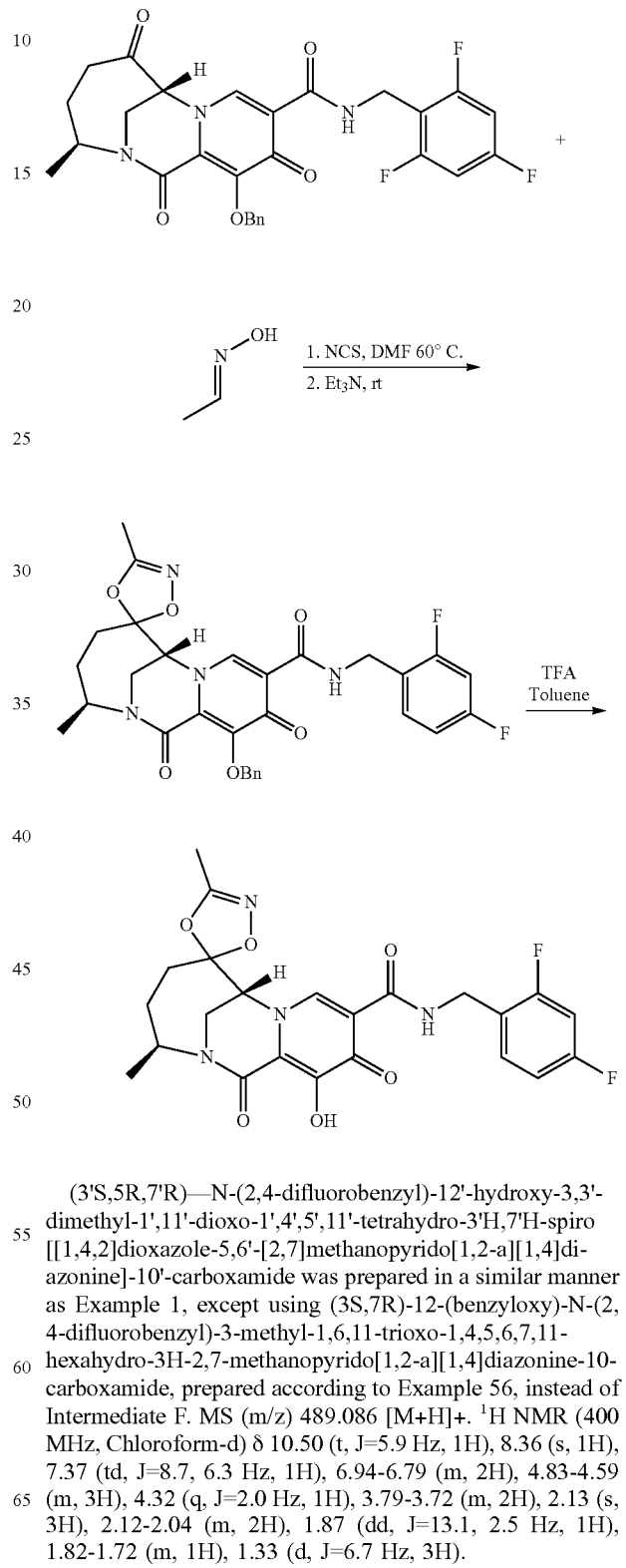

(3'S,5R,7'R)—N-(2,4-difluorobenzyl)-12'-hydroxy-3,3'-dimethyl-1',11'-dioxo-1',4',5',11'-tetrahydro-3'H,7'H-spiro[[1,4,2]dioxazole-5,6'-[2,7]methanopyrido[1,2-a][1,4]diazonine]-10'-carboxamide was prepared in a similar manner as Example 1, except using (3S,7R)-12-(benzyloxy)-N-(2,4-difluorobenzyl)-3-methyl-1,6,11-trioxo-1,4,5,6,7,11-hexahydro-3H-2,7-methanopyrido[1,2-a][1,4]diazonine-10-carboxamide, prepared according to Example 56, instead of Intermediate F. MS (m/z) 489.086 [M+H]+. 1H NMR (400 MHz, Chloroform-d) δ 10.50 (t, J=5.9 Hz, 1H), 8.36 (s, 1H), 7.37 (td, J=8.7, 6.3 Hz, 1H), 6.94-6.79 (m, 2H), 4.83-4.59 (m, 3H), 4.32 (q, J=2.0 Hz, 1H), 3.79-3.72 (m, 2H), 2.13 (s, 3H), 2.12-2.04 (m, 2H), 1.87 (dd, J=13.1, 2.5 Hz, 1H), 1.82-1.72 (m, 1H), 1.33 (d, J=6.7 Hz, 3H).

Example 92: Preparation of (3'S,5R,7'R)-12'-hydroxy-3,3'-dimethyl-1',11'-dioxo-N-(2,4,6-trifluorobenzyl)-1',4',5',11'-tetrahydro-3'H,7'H-spiro[[1,4,2]dioxazole-5,6'-[2,7]methanopyrido[1,2-a][1,4]diazonine]-10'-carboxamide

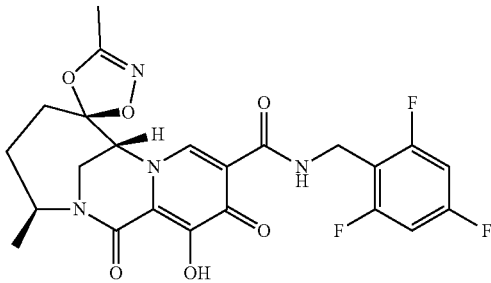 [SMILES: CC1=NO[C@@]2(CC[C@H](C)N3C[C@H]2n2cc(C(=O)NCc4c(F)cc(F)cc4F)c(=O)c(O)c2C3=O)O1]

(3'S,5R,7'R)-12'-hydroxy-3,3'-dimethyl-1',11'-dioxo-N-(2,4,6-trifluorobenzyl)-1',4',5',11'-tetrahydro-3'H,7'H-spiro[[1,4,2]dioxazole-5,6'-[2,7]methanopyrido[1,2-a][1,4]diazonine]-10'-carboxamide was prepared in a manner similar to Example 91, except using (3S,7R)-12-(benzyloxy)-3-methyl-1,6,11-trioxo-N-(2,4,6-trifluorobenzyl)-1,4,5,6,7,11-hexahydro-3H-2,7-methanopyrido[1,2-a][1,4]diazonine-10-carboxamide, prepared according to Example 55, instead of (3S,7R)-12-(benzyloxy)-N-(2,4-difluorobenzyl)-3-methyl-1,6,11-trioxo-1,4,5,6,7,11-hexahydro-3H-2,7-methanopyrido[1,2-a][1,4]diazonine-10-carboxamide. MS (m/z) 507.15 [M+H]+. 1H NMR (400 MHz, Chloroform-d) δ 10.22 (t, J=5.8 Hz, 1H), 8.25 (s, 1H), 6.75-6.54 (m, 2H), 4.88-4.66 (m, 2H), 4.58 (dd, J=14.5, 5.4 Hz, 1H), 4.28 (q, J=1.9 Hz, 1H), 3.83-3.60 (m, 2H), 2.14 (s, 3H), 2.13-2.01 (m, 2H), 1.91-1.73 (m, 2H), 1.31 (d, J=6.7 Hz, 3H).

Example 93: Preparation of (3'S,5R,7'R)-3-ethyl-12'-hydroxy-3'-methyl-1',11'-dioxo-N-(2,4,6-trifluorobenzyl)-1',4',5',11'-tetrahydro-3'H,7'H-spiro[[1,4,2]dioxazole-5,6'-[2,7]methanopyrido[1,2-a][1,4]diazonine]-10'-carboxamide

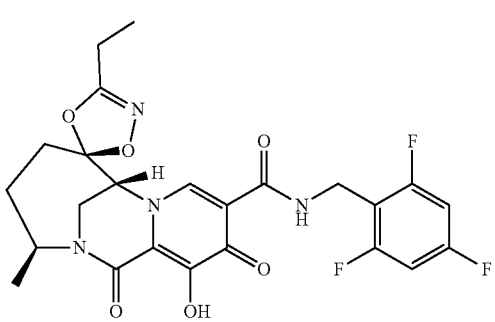 [SMILES: CCC1=NO[C@@]2(CC[C@H](C)N3C[C@H]2n2cc(C(=O)NCc4c(F)cc(F)cc4F)c(=O)c(O)c2C3=O)O1]

(3'S,5R,7'R)-3-ethyl-12'-hydroxy-3'-methyl-1',11'-dioxo-N-(2,4,6-trifluorobenzyl)-1',4',5',11'-tetrahydro-3'H,7'H-spiro[[1,4,2]dioxazole-5,6'-[2,7]methanopyrido[1,2-a][1,4]diazonine]-10'-carboxamide was prepared in a manner similar to Example 92, except using N-hydroxypropionimidoyl chloride instead of N-hydroxyacetimidoyl chloride. MS (m/z) 521.15 [M+H]+. 1H NMR (400 MHz, Chloroform-d) δ 10.35 (t, J=5.7 Hz, 1H), 8.32 (s, 1H), 6.76-6.63 (m, 2H), 4.76 (m, 2H), 4.62 (m, 1H), 4.28 (m, 1H), 3.73 (m, 2H), 2.47 (m, 2H), 2.17-1.99 (m, 2H), 1.94-1.79 (m, 1H), 1.76 (dd, J=14, 12.3 Hz, 1H), 1.32 (d, J=6.7 Hz, 3H), 1.26 (t, J=7.5 Hz, 3H).

Example 94: Preparation of (3'S,5R,7'R)—N-(2,4-difluorobenzyl)-3-ethyl-12'-hydroxy-3'-methyl-1',11'-dioxo-1',4',5',11'-tetrahydro-3'H,7'H-spiro[[1,4,2]dioxazole-5,6'-[2,7]methanopyrido[1,2-a][1,4]diazonine]-10'-carboxamide

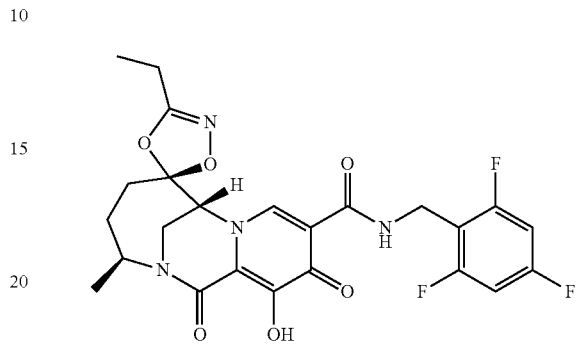

(3'S,5R,7'R)—N-(2,4-difluorobenzyl)-3-ethyl-12'-hydroxy-3'-methyl-1',11'-dioxo-1',4',5',11'-tetrahydro-3'H,7'H-spiro[[1,4,2]dioxazole-5,6'-[2,7]methanopyrido[1,2-a][1,4]diazonine]-10'-carboxamide was prepared in a manner similar to Example 91, except using N-hydroxypropionimidoyl chloride instead of N-hydroxyacetimidoyl chloride. MS (m/z) 503.18 [M+H]+. 1H NMR (400 MHz, Chloroform-d) δ 10.41 (t, J=5.9 Hz, 1H), 8.32 (s, 1H), 7.36 (td, J=8.7, 6.3 Hz, 1H), 6.90-6.78 (m, 2H), 4.82-4.57 (m, 3H), 4.31 (q, J=1.9 Hz, 1H), 3.81-3.66 (m, 2H), 2.45 (qd, J=7.5, 5.2 Hz, 2H), 2.17-1.99 (m, 2H), 1.93-1.79 (m, 1H), 1.76 (dd, J=13.9, 12.3 Hz, 1H), 1.32 (d, J=6.7 Hz, 3H), 1.24 (t, J=7.5 Hz, 3H).

Example 95: Preparation of (3'S,7'R)—N-(2,4-difluorobenzyl)-4-(dimethylamino)-12'-hydroxy-3,3'-dimethyl-1',11'-dioxo-1',4',5',11'-tetrahydro-3'H,4H,7'H-spiro[[1,2,4]oxadiazole-5,6'-[2,7]methanopyrido[1,2-a][1,4]diazonine]-10'-carboxamide

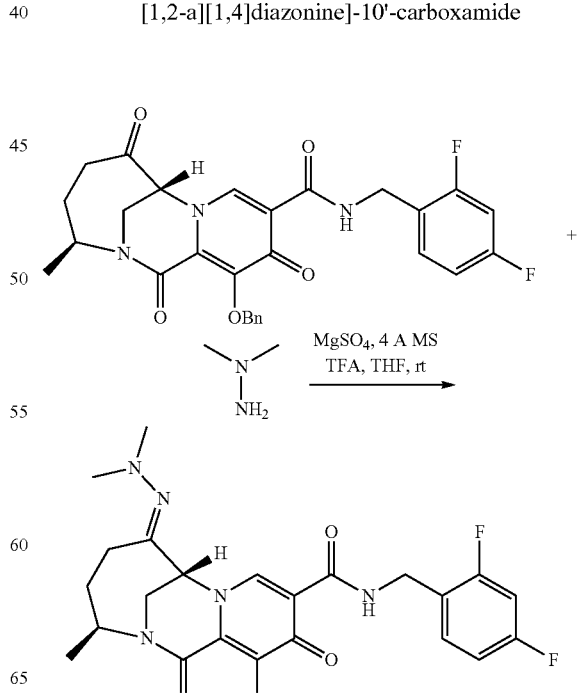

-continued

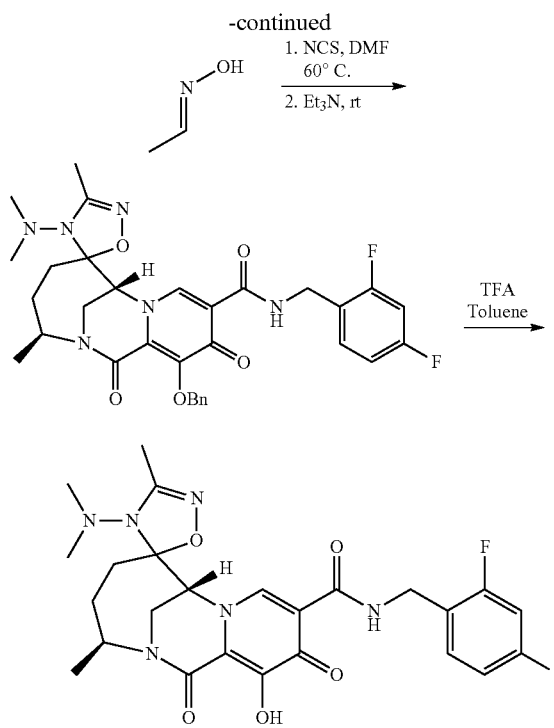

Step 1. Preparation of (3S,7R)-12-(benzyloxy)-N-(2,4-difluorobenzyl)-6-(2,2-dimethyihydrazineylidene)-3-methyl-1,11-dioxo-1,4,5,6,7,11-hexahydro-3H-2,7-methanopyrido[1,2-a][1,4]diazonine-10-carboxamide Into the mixture of (3S,7R)-12-(benzyloxy)-N-(2,4-difluorobenzyl)-3-methyl-1,6,11-trioxo-1,4,5,6,7,11-hexahydro-3H-2,7-methanopyrido[1,2-a][1,4]diazonine-10-carboxamide (666 mg, 11.3 mmol), prepared according to Step 2 of Example 56, and 1,1-dimethylhydrazine (82.3 mg, 1.37 mmol) in THF (3 mL) was added MgSO$_4$ (150 mg), 4A molecular sieves (200 mg) and TFA (0.2 mL) at rt. After 2 h, the reaction mixture was diluted with ethyl acetate (100 mL) and filtered to remove solids. The filtrate was concentrated and purified by silica gel column chromatography to give the title compound. MS (m/z) 564.205 [M+H]+.

Step 2: Preparation of (3'S,7'R)-12'-(benzyloxy)-N-(2,4-difluorobenzyl)-4-(dimethylamino)-3,3'-dimethyl-1',11'-dioxo-1',4',5',11'-tetrahydro-3'H,4H,7'H-spiro[[1,2,4]oxadiazole-5,6'-[2,7]methanopyrido[1,2-a][1,4]diazonine]-10'-carboxamide (3'S,7'R)-12'-(benzyloxy)-N-(2,4-difluorobenzyl)-4-(dimethylamino)-3,3'-dimethyl-1',11'-dioxo-1',4',5',11'-tetrahydro-3'H,4H,7'H-spiro[[1,2,4]oxadiazole-5,6'-[2,7]methanopyrido[1,2-a][1,4]diazonine]-10'-carboxamide was prepared in a similar manner as Step 1 of Example 1, except using (3S,7R)-12-(benzyloxy)-N-(2,4-difluorobenzyl)-6-(2,2-dimethylhydrazineylidene)-3-methyl-1,11-dioxo-1,4,5,6,7,11-hexahydro-3H-2,7-methanopyrido[1,2-a][1,4]diazonine-10-carboxamide from Step 1 instead of Intermediate F. MS (m/z) 621.164 [M+H]+.

Step 3: Preparation of (3'S,7'R)—N-(2,4-difluorobenzyl)-4-(dimethylamino)-12'-hydroxy-3,3'-dimethyl-1',11'-dioxo-1',4',5',11'-tetrahydro-3'H,4H,7'H-spiro[[1,2,4]oxadiazole-5,6'-[2,7]methanopyrido[1,2-a][1,4]diazonine]-10'-carboxamide (3'S,7'R)—N-(2,4-difluorobenzyl)-4-(dimethylamino)-12'-hydroxy-3,3'-dimethyl-1',11'-dioxo-1',4',5',11'-tetrahydro-3'H,4H,7'H-spiro[[1,2,4]oxadiazole-5,6'-[2,7]methanopyrido[1,2-a][1,4]diazonine]-10'-carboxamide was prepared in a similar manner as Step 2 of Example 1, except using (3'S,7'R)-12'-(benzyloxy)-N-(2,4-difluorobenzyl)-4-(dimethylamino)-3,3'-dimethyl-1',11'-dioxo-1',4',5',11'-tetrahydro-3'H,4H,7'H-spiro[[1,2,4]oxadiazole-5,6'-[2,7]methanopyrido[1,2-a][1,4]diazonine]-10'-carboxamide instead of (3'S,5S,7'R)-12'-(benzyloxy)-N-(2,4-difluorobenzyl)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide. MS (m/z) 531.073 [M+H]+. 1H NMR (400 MHz, Chloroform-d) δ 10.39 (s, 1H), 8.22 (s, 1H), 7.36 (dd, J=9.4, 6.2 Hz, 1H), 6.83 (td, J=8.1, 5.1 Hz, 2H), 4.74 (tt, J=13.2, 6.3 Hz, 2H), 4.60 (dd, J=15.3, 5.6 Hz, 1H), 3.85-3.78 (m, 2H), 3.67 (dd, J=15.3, 3.2 Hz, 1H), 2.44 (d, J=99.0 Hz, 6H), 2.27 (s, 3H), 2.10 (s, 1H), 2.01-1.97 (m, 2H), 1.73 (d, J=3.6 Hz, 1H), 1.33 (d, J=6.6 Hz, 3H).

Example 96: Preparation of (5S,7'R)-12'-hydroxy-3-methoxy-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

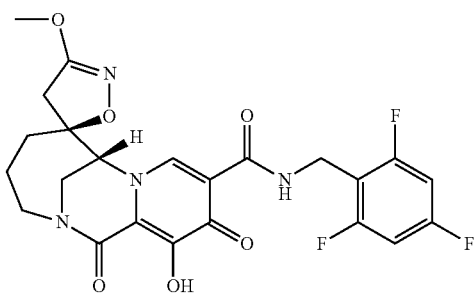 [SMILES: COC1=NO[C@@]2(CCCN3C[C@H]2n2cc(C(=O)NCc4c(F)cc(F)cc4F)c(=O)c(O)c2C3=O)C1]

(5S,7'R)-12'-hydroxy-3-methoxy-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide was synthesized in a manner similar to Example 36, except benzyl (3S)-3-(benzyloxycarbonylamino)-2,3,4,7-tetrahydroazepine-1-carboxylate was used instead of benzyl (3S,7S)-3-(benzyloxycarbonylamino)-7-methyl-2,3,4,7-tetrahydroazepine-1-carboxylate. LCMS-ESI+(m/z): calcd H+ for C23H21F3N4O6, Theoretical: 506.14, Found: 507.182. 1H NMR (400 MHz, DMSO-d6) δ 10.35 (t, J=5.8 Hz, 1H), 8.63 (s, 1H), 7.29-7.15 (m, 2H), 4.72 (d, J=2.4 Hz, 1H), 4.57 (d, J=5.7 Hz, 2H), 4.22-3.88 (m, 2H), 3.81 (s, 3H), 3.71 (dd, J=14.9, 1.8 Hz, 1H), 3.15 (dd, J=13.0, 8.0 Hz, 1H), 2.94 (d, J=16.8 Hz, 1H), 2.71 (d, J=16.9 Hz, 1H), 2.26-2.11 (m, 1H), 1.97-1.86 (m, 1H), 1.79-1.66 (m, 1H), 1.43-1.29 (m, 1H).

Example 97: Preparation of (3'R,5S,7'R)-12'-hydroxy-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

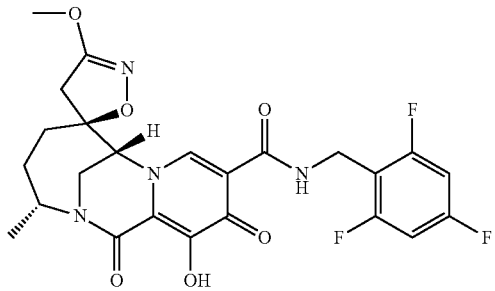 [SMILES: COC1=NO[C@@]2(CC[C@@H](C)N3C[C@H]2n2cc(C(=O)NCc4c(F)cc(F)cc4F)c(=O)c(O)c2C3=O)C1]

(3'R,5S,7'R)-12'-hydroxy-3-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide was synthesized in a manner similar to Example 36, except benzyl (3S,7R)-3-(((benzyloxy)carbonyl)amino)-7-methyl-2,3,4,7-tetrahydro-1H-azepine-1-carboxylate, prepared according to WO2022072520, was used instead of benzyl (3S,7S)-3-(((benzyloxy)carbonyl)amino)-7-methyl-2,3,4,7-tetrahydro-1H-azepine-1-carboxylate. LCMS-ESI+(m/z): calcd H+ for C24H23F3N4O6, Theoretical: 520.16, Found: 521.148. 1H NMR (400 MHz, MeOD) δ 8.50 (s, 1H), 6.97-6.86 (m, 2H), 4.78 (s, 1H), 4.73-4.61 (m, 2H), 4.00 (d, J=15.0 Hz, 1H), 3.84 (s, 3H), 3.83-3.73 (m, 2H), 3.01 (s, 1H), 2.88 (d, J=0.7 Hz, 1H), 2.41-2.28 (m, 1H), 2.22-2.11 (m, 1H), 1.93-1.80 (m, 2H), 1.75 (d, J=7.1 Hz, 3H).

Example 98: Preparation of (3'R,5S,7'R)-12'-hydroxy-3,3'-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

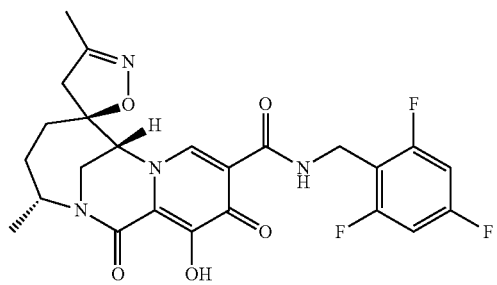 [SMILES: CC1=NO[C@@]2(CC[C@@H](C)N3C[C@H]2n2cc(C(=O)NCc4c(F)cc(F)cc4F)c(=O)c(O)c2C3=O)C1]

(3'R,5S,7'R)-12'-hydroxy-3,3'-dimethyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide was synthesized in a manner similar to Example 3, except benzyl (3S,7R)-3-(((benzyloxy)carbonyl)amino)-7-methyl-2,3,4,7-tetrahydro-1H-azepine-1-carboxylate, prepared according to WO2022072520, was used instead of benzyl (3S,7S)-3-(((benzyloxy)carbonyl)amino)-7-methyl-2,3,4,7-tetrahydro-1H-azepine-1-carboxylate.
LCMS-ESI+(m/z): calcd H+ for C24H23F3N4O5, Theoretical: 504.16, Found: 505.142. 1H NMR (400 MHz, CD3OD) δ 8.45 (s, 1H), 6.96-6.85 (m, 2H), 4.75-4.59 (m, 3H), 4.02 (d, J=14.8 Hz, 1H), 3.87-3.73 (m, 2H), 2.91 (d, J=17.7 Hz, 1H), 2.78 (d, J=17.6 Hz, 1H), 2.41-2.28 (m, 1H), 2.04 (ddd, J=15.0, 5.7, 3.3 Hz, 1H), 1.97 (s, 3H), 1.93-1.79 (m, 2H), 1.75 (d, J=7.2 Hz, 3H).

Example 99: Preparation of (3'R,5S,7'R)-3'-(fluoromethyl)-12'-hydroxy-3-methoxy-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

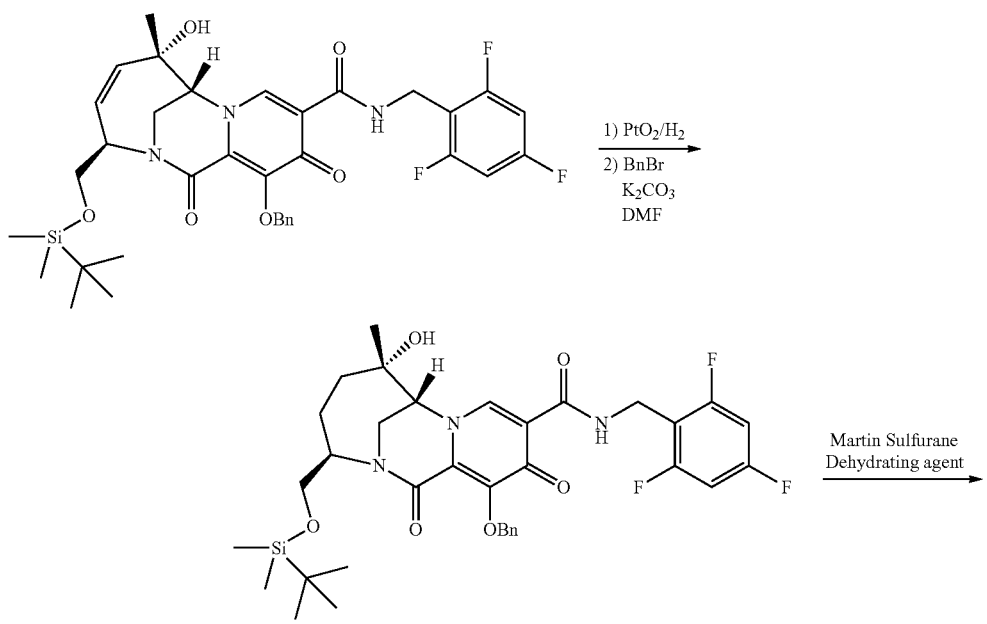

-continued
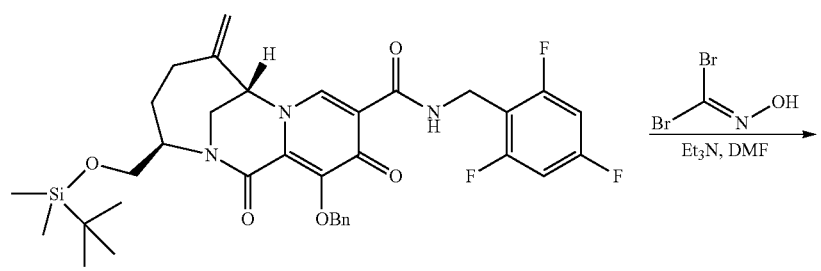
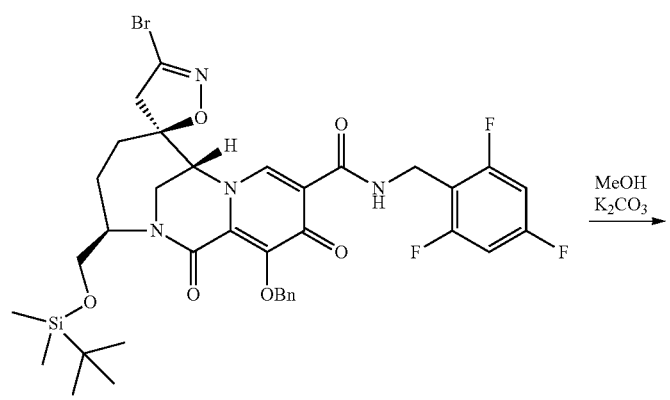
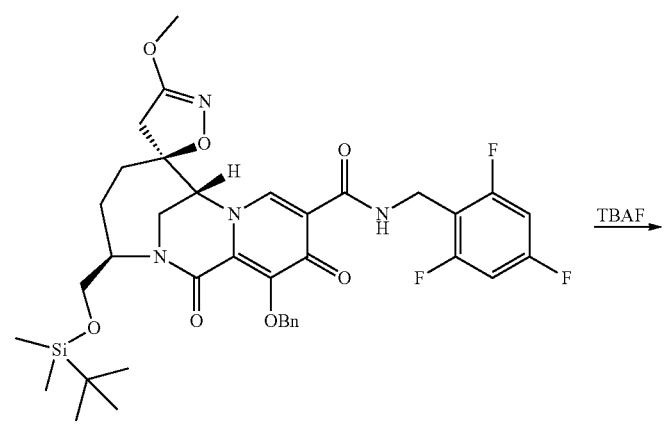
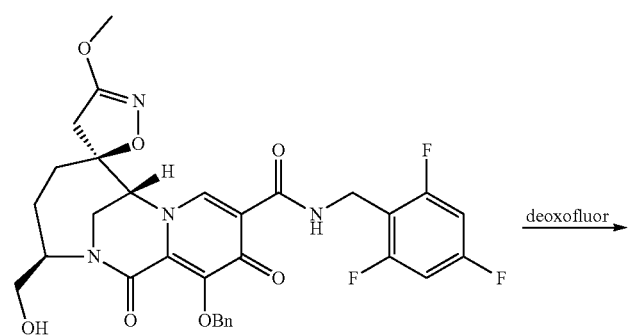

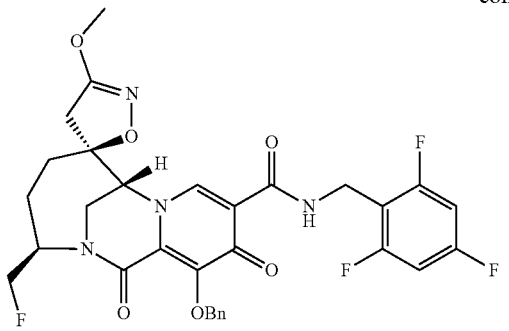 → 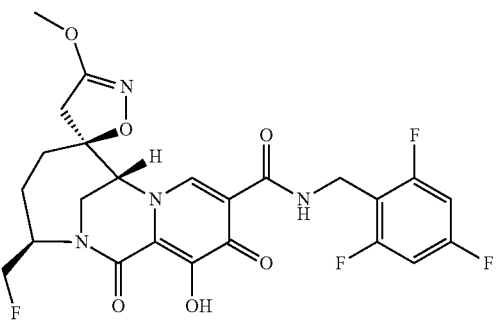

TFA
DCM

Step 1: Preparation of (3R,6S,7R)-12-(benzyloxy)-3-(((tert-butyldimethylsilyl)oxy)methyl)-6-hydroxy-6-methyl-1,11-dioxo-N-(2,4,6-trifluorobenzyl)-1,4,5,6,7,11-hexahydro-3H-2,7-methanopyrido[1,2-a][1,4]diazonine-10-carboxamide To a solution of (3R,6S,7R)-12-(benzyloxy)-3-(((tert-butyldimethylsilyl)oxy)methyl)-6-hydroxy-6-methyl-1,11-dioxo-N-(2,4,6-trifluorobenzyl)-1,6,7,11-tetrahydro-3H-2,7-methanopyrido[1,2-a][1,4]diazonine-10-carboxamide (112 mg, 0.164 mmol) in EtOH (2 mL) was added $PtO_2$ (15 mg). The reaction mixture was stirred at rt overnight under $H_2$ atmosphere. The reaction mixture was then filtered through celite and volatiles removed under vacuum. The residue was dissolved in DMF (1 mL) and $K_2CO_3$ (11.6 mg, 0.84 mmol) and benzyl bromide (8.61 mg, 0.05 mmol) were added. The reaction mixture was stirred at rt for 5 h. To the mixture was added water, extracted with EtOAc. The organic phase was separated and dried over $MgSO_4$, filtered, concentrated. The residue was purified by silica gel chromatograph, eluting with 0-100% hexane/EtOAc to give title compound. MS (m/z) 686.01 [M+H]+.

Step 2: Preparation of (3R,7S)-12-(benzyloxy)-3-(((tert-butyldimethylsilyl)oxy)methyl)-6-methylene-1,11-dioxo-N-(2,4,6-trifluorobenzyl)-1,6,7,11-tetrahydro-3H-2,7-methanopyrido[1,2-a][1,4]diazonine-10-carboxamide To a solution of (3R,6S,7R)-12-(benzyloxy)-3-(((tert-butyldimethylsilyl)oxy)methyl)-6-hydroxy-6-methyl-1,11-dioxo-N-(2,4,6-trifluorobenzyl)-1,4,5,6,7,11-hexahydro-3H-2,7-methanopyrido[1,2-a][1,4]diazonine-10-carboxamide (97 mg, 0.141 mmol) in toluene (2.0 mL) was added Martin Sulfurane dehydrating agent (190 mg, 0.382 mmol). The reaction mixture was stirred at rt for 1 h. The reaction mixture was concentrated and the residue was purified by silica gel column chromatography, eluting with 0-100% hexane/EtOAc to give the title compound. MS (m/z) 668.45 [M+H]+.

Step 3: Preparation of (3'R,5S,7'R)-12'-(benzyloxy)-3-bromo-3'-(((tert-butyldimethylsilyl)oxy)methyl)-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide To a solution of (3R,7S)-12-(benzyloxy)-3-(((tert-butyldimethylsilyl)oxy)methyl)-6-methylene-1,11-dioxo-N-(2,4,6-trifluorobenzyl)-1,6,7,11-tetrahydro-3H-2,7-methanopyrido[1,2-a][1,4]diazonine-10-carboxamide (88 mg, 0.132 mmol) in EtOAc (3 mL) was added $K_2CO_3$ (55 mg, 0.395 mmol) and dibromomethanone oxime (53 mg, 0.264 mmol). The reaction mixture was stirred at rt overnight. To the reaction mixture was added water, extracted with EtOAc, dried over $MgSO_4$, filtered, and concentrated. The residue was purified by silica gel chromatography, eluting with 0-100% hexane/EtOAc to give title compound.

Step 4: Preparation of (3'R,5S,7'R)-12'-(benzyloxy)-3'-(((tert-butyldimethylsilyl)oxy)methyl)-3-methoxy-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide To a solution of (3'R,5S,7'R)-12'-(benzyloxy)-3-bromo-3'-(((tert-butyldimethylsilyl)oxy)methyl)-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (68 mg, 0.086 mmol) in MeOH (3 mL) was added $K_2CO_3$ (48 mg, 0.34 mmol). The reaction mixture was heated at 55° C. overnight, cooled to rt, and concentrated. The residue was washed with water, extracted with EtOAc, dried over $MgSO_4$, filtered, concentrated, and purified by silica gel chromatography, eluting with 0-100% hexane/EtOAc to give title compound. MS (m/z) 740.99 [M+H]+.

Step 5: Preparation of (3'R,5S,7'R)-12'-(benzyloxy)-3'-(hydroxymethyl)-3-methoxy-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide A solution of (3'R,5S,7'R)-12'-(benzyloxy)-3'-(((tert-butyldimethylsilyl)oxy)methyl)-3-methoxy-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (34 mg, 0.046 mmol) in THF (2 mL) was stirred at 0° C. as 1 M TBAF in THF (0.063 mL, 0.063 mmol) was added. The reaction mixture was stirred at 0° C. for 2 h. The reaction mixture was diluted with EtOAc, washed with sat. NH4Cl, and extracted with EtOAc. The organic phase was separated, dried over $MgSO_4$, filtered, concentrated, and purified by silica gel chromatography, eluting with 0-100% hexane/EtOAc to give title compound. MS (m/z) 627.05 [M+H]+.

Step 6: Preparation of (3'R,5S,7'R)-12'-(benzyloxy)-3'-(fluoromethyl)-3-methoxy-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide To a solution of (3'R,5S,7'R)-12'-(benzyloxy)-3'-(hydroxymethyl)-3-methoxy-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (30 mg, 0.048 mmol) in DCM (2 mL) was added [bis(2-methoxyl)amino]sulfur trifluoride (50 wt % solution in toluene, 65 mg, 0.144 mmol) at 0° C. The reaction mixture was stirred at 0° C. for 1.5 h. The reaction mixture was quenched with sat. NaHCO₃ solution and extracted with EtOAc. The organic phase was separated, dried over MgSO₄, filtered and concentrated. The residue was purified by silica gel chromatography, eluting with 0-100% EtOAc/hexane, to give the title compound. MS (m/z) 628.98 [M+H]+.

Step 7: Preparation of (3'R,5S,7'R)-3'-(fluoromethyl)-12'-hydroxy-3-methoxy-1',11'-dioxo-N-(2,4,6-trifluorobenzyl)-1',4',5',1,1'-tetrahydro-3'H,4H,7'H-spiro[isoxazole-5,6'-[2,7]methanopyrido[1,2-a][1,4]diazonine]-10'-carboxamide The a solution of (3'R,5S,7'R)-12'-(benzyloxy)-3'-(fluoromethyl)-3-methoxy-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (13 mg, 0.021 mmol) in DCM (1 mL) and TFA (1 mL) was stirred at rt overnight. The reaction mixture was concentrated and purified by reverse phase prep HPLC, eluting with 5-100% acetonitrile/water to give the title compound. MS (m/z) 539.15 [M+H]+. 1H NMR (400 MHz, Methanol-d4) δ 8.56 (s, 1H), 6.98-6.85 (m, 2H), 4.79 (d, J=11.2 Hz, 1H), 4.67 (d, J=15.6 Hz, 4H), 4.56 (d, J=4.7 Hz, 1H), 3.98 (t, J=13.7 Hz, 2H), 3.89 (s, 3H), 3.06 (d, J=17.1 Hz, 1H), 2.71 (d, J=17.0 Hz, 1H), 2.26 (dt, J=15.1, 11.8 Hz, 1H), 2.15 (dd, J=15.9, 6.6 Hz, 1H), 1.95-1.86 (m, 1H), 1.62 (dd, J=15.8, 11.8 Hz, 1H).

Example 100: Preparation of (3'R,5S,7'R)—N-(2,4-difluorobenzyl)-3'-(fluoromethyl)-12'-hydroxy-3-methoxy-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

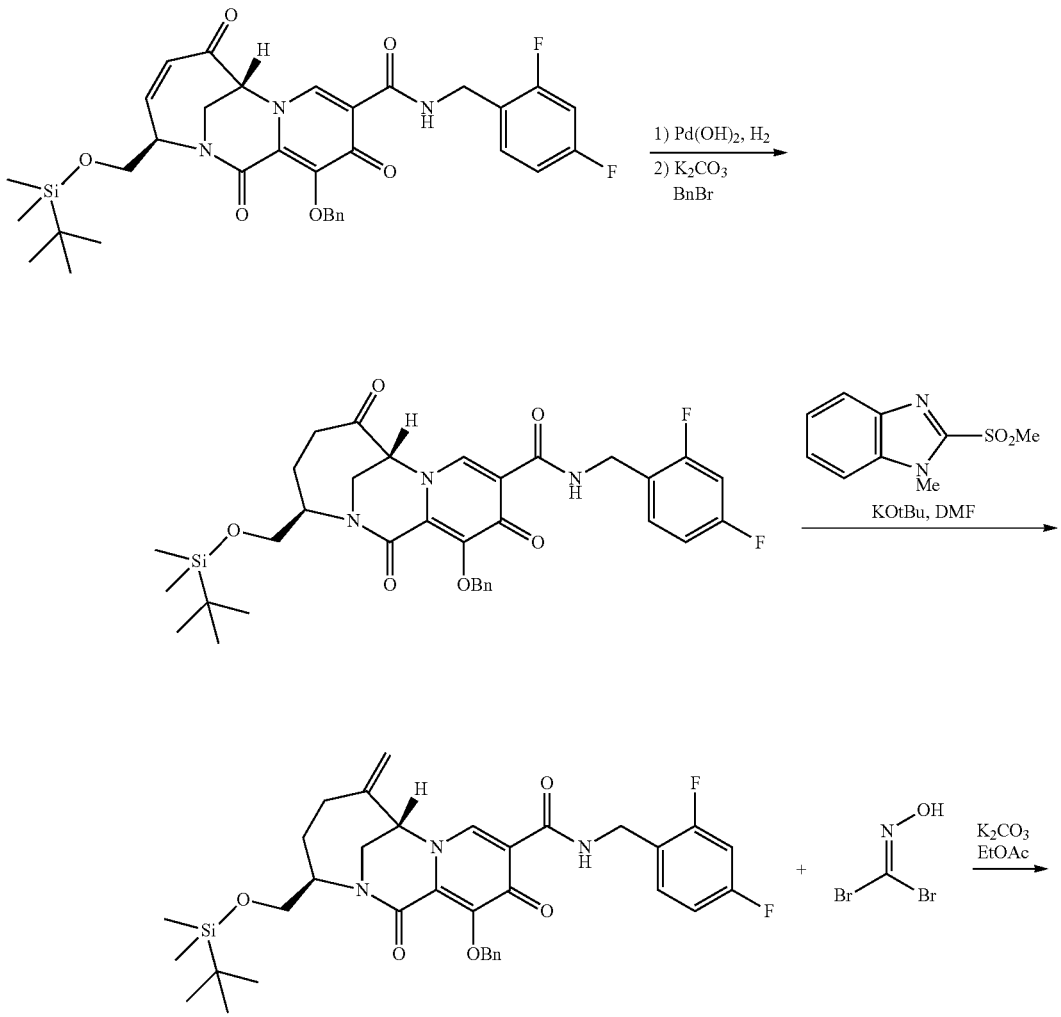

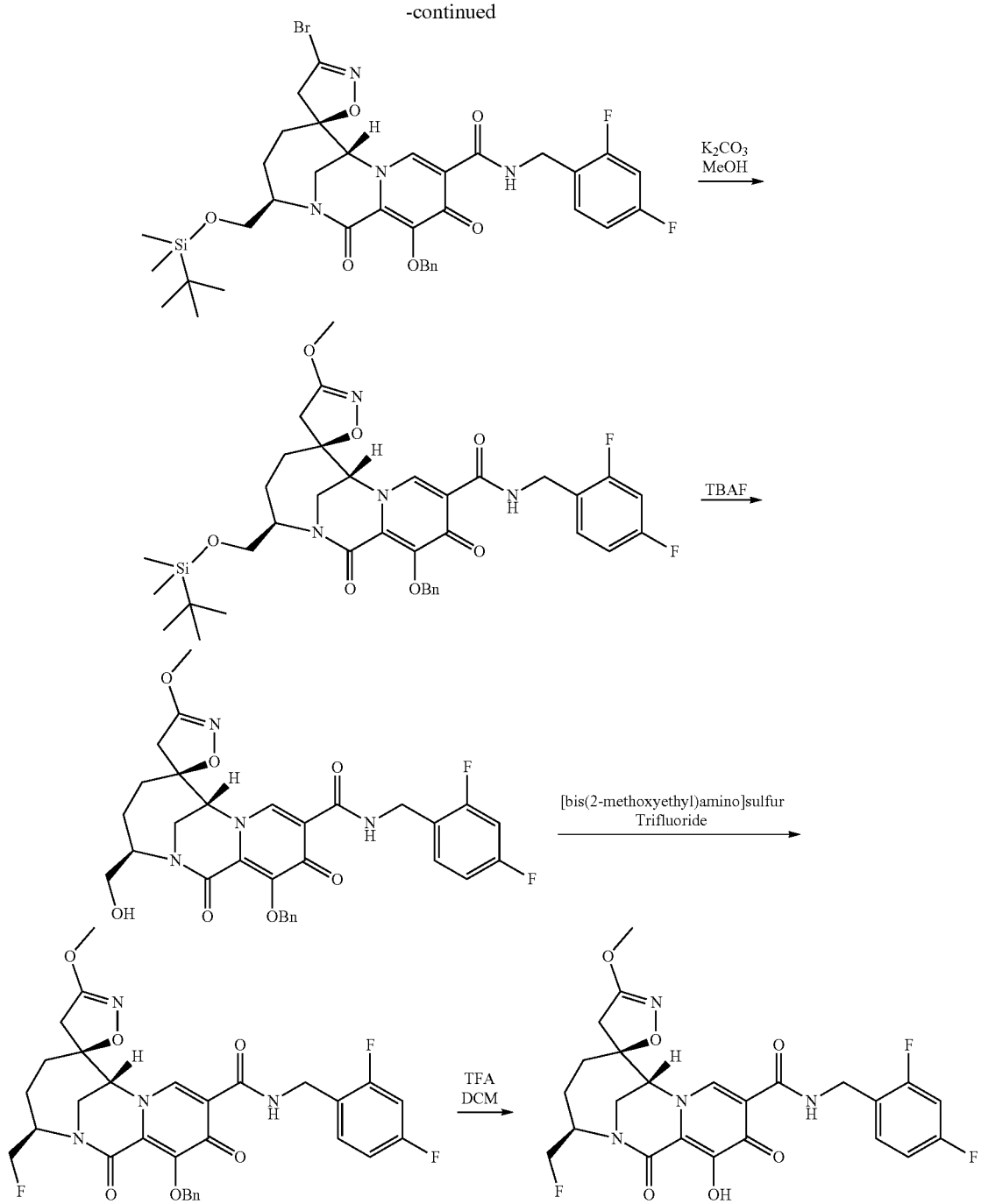

Step 1: Preparation of (3R,7R)-12-(benzyloxy)-3-(((tert-butyldimethylsilyl)oxy)methyl)-N-(2,4-difluorobenzyl)-1,6,11-trioxo-1,4,5,6,7,11-hexahydro-3H-2,7-methanopyrido[1,2-a][1,4]diazonine-10-carboxamide (3R,7R)-12-(benzyloxy)-3-(((tert-butyldimethylsilyl)oxy)methyl)-N-(2,4-difluorobenzyl)-1,6,11-trioxo-1,6,7,11-tetrahydro-3H-2,7-methanopyrido[1,2-a][1,4]diazonine-10-carboxamide (350 mg, 0.539 mmol), prepared in a similar manner as Steps 1-4 of Example 54 except using methyl 3-(benzyloxy)-5-((2,4-difluorobenzyl)carbamoyl)-4-oxo-4H-pyran-2-carboxylate instead of methyl 3-(benzyloxy)-4-oxo-5-((2,4,6-trifluorobenzyl)carbamoyl)-4H-pyran-2-carboxylate in Step 2, was dissolved in EtOH (2 mL) and Pd(OH)2 on carbon (84 mg, 0.12 mmol) was added. The reaction mixture was stirred at rt under H$_2$ balloon for 2 h. The reaction mixture was filtered through celite and the filtrate was concentrated. The residue was dissolved in DMF (3 mL). To the solution was added K$_2$CO$_3$ (113 mg, 0.819 mmol) and benzyl bromide (74 mg, 0.432 mmol). The reaction mixture was stirred at rt overnight. To the mixture was added water, then extracted with EtOAc, dried over MgSO$_4$, filtered, and concentrated. The residue was purified by silica gel column chromatography, eluting with 0-100% EtOAc/hexanes to give the title compound. MS (m/z): 651.93 [M+H]+.

Step 2: Preparation of (3R,7S)-12-(benzyloxy)-3-(((tert-butyldimethylsilyl)oxy)methyl)-N-(2,4-difluorobenzyl)-6-methylene-1,11-dioxo-1,4,5,6,7,11-hexahydro-3H-2,7-methanopyrido[1,2-a][1,4]diazonine-10-carboxamide To a solution of (3R,7R)-12-(benzyloxy)-3-(((tert-butyldimethylsilyl)oxy)methyl)-N-(2,4-difluorobenzyl)-1,6,11-trioxo-1,4,5,6,7,11-hexahydro-3H-2,7-methanopyrido[1,2-a][1,4]diazonine-10-carboxamide (352 mg, 0.54 mmol) in DMF (3 mL), was added 1-methyl-2-methylsulfonyl-benzimidazole (148 mg, 0.70 mmol) and potassium t-butoxide (152 mg, 1.35 mmol). The reaction mixture was stirred at rt for 1 h. The reaction mixture was cooled to 0° C. and quenched by adding 1N HCl slowly. The mixture was extracted with EtOAc, dried over MgSO₄, filtered, and concentrated. The residue was purified by silica gel column chromatography (0-100% EtOAc/hexanes) to give title compound. MS (m/z): 650.01 [M+H]+.

Steps 3-7: Preparation of (3'R,5S,7'R)—N-(2,4-difluorobenzyl)-3'-(fluoromethyl)-12'-hydroxy-3-methoxy-1',11'-dioxo-1',4',5',11'-tetrahydro-3'H,4H,7'H-spiro[isoxazole-5,6'-[2,7]methanopyrido[1,2-a][1,4]diazonine]-10'-carboxamide This title compound was prepared in similar manner as (3'R,5S,7'R)-3'-(fluoromethyl)-12'-hydroxy-3-methoxy-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide in Example 91, except that (3R,7S)-12-(benzyloxy)-3-(((tert-butyldimethylsilyl)oxy)methyl)-N-(2,4-difluorobenzyl)-6-methylene-1,11-dioxo-1,4,5,6,7,11-hexahydro-3H-2,7-methanopyrido[1,2-a][1,4]diazonine-10-carboxamide, K₂CO₃, and EtOAc were used instead of (3R,7S)-12-(benzyloxy)-3-(((tert-butyldimethylsilyl)oxy)methyl)-6-methylene-1,11-dioxo-N-(2,4,6-trifluorobenzyl)-1,4,5,6,7,11-hexahydro-3H-2,7-methanopyrido[1,2-a][1,4]diazonine-10-carboxamide, Et₃N, and DMF, respectively, in Step 3. MS (m/z): 521.15 [M+H]+. 1H NMR (400 MHz, Methanol-d4) δ 8.56 (s, 1H), 7.46 (q, J=8.2 Hz, 1H), 7.08-6.87 (m, 2H), 4.73-4.44 (m, 5H), 4.07-3.91 (m, 3H), 3.90 (s, 3H), 3.06 (d, J=17.0 Hz, 1H), 2.73 (d, J=17.1 Hz, 1H), 2.31-2.12 (m, 2H), 1.97-1.84 (m, 1H), 1.63 (dd, J=15.7, 11.8 Hz, 1H).

Example 101: Preparation of (3'S,5S,7'R)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide

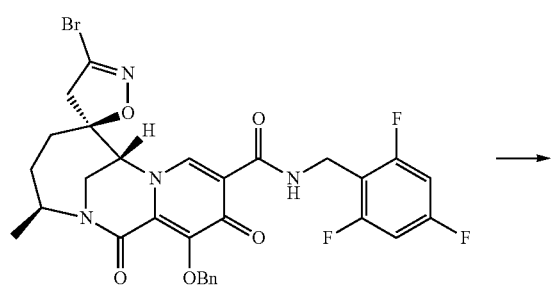

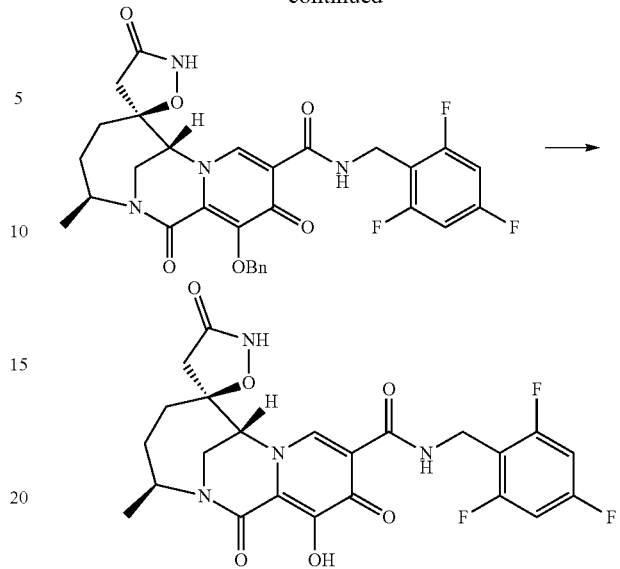

Step 1: Preparation of (3'S,5S,7'R)-12'-(benzyloxy)-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide To a mixture of (3'S,5S,7'R)-12'-(benzyloxy)-3-bromo-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (10 mg, 0.0152 mmol), prepared according to Example 36, in DMSO (0.3 mL) at room temperature was added 1N NaOH (0.1 mL). The resulting mixture was heated to 80° C. for 1 h. The reaction was then cooled to room temperature, acidified with TFA (0.2 mL), filtered, and purified by reverse phase chromatography. 1H NMR (400 MHz, CD3CN) δ 10.43 (t, J=5.8 Hz, 1H), 8.42 (s, 1H), 7.57-7.49 (m, 2H), 7.45-7.30 (m, 3H), 6.95-6.81 (m, 2H), 5.34 (d, J=10.4 Hz, 1H), 5.10 (d, J=10.4 Hz, 1H), 4.74 (dt, J=10.9, 6.6 Hz, 1H), 4.70-4.58 (m, 2H), 4.52 (q, J=2.0 Hz, 1H), 3.70-3.52 (m, 2H), 2.78 (s, 1H), 2.48 (d, J=17.1 Hz, 1H), 2.12-2.01 (m, 1H), 1.94-1.85 (m, 1H), 1.81-1.67 (m, 1H), 1.51 (ddd, J=15.9, 12.0, 1.2 Hz, 1H), 1.18 (d, J=6.7 Hz, 3H).

Step 2: Preparation of (3'S,5S,7'R)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide (3'S,5S,7'R)-12'-(benzyloxy)-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide (9 mg, 0.0152 mmol) was treated with a mixture of toluene (0.3 mL) and TFA (0.3 mL) at room temperature for overnight. The reaction was concentrated and purified by reverse phase chromatography. LCMS-ESI+(m/z): calcd H+ for C23H21F3N4O6, Theoretical: 506.14, Found: 507.167. 1H NMR (400 MHz, DMSO-D6) δ 11.42 (s, 1H), 10.90 (s, 1H), 10.35 (t, J=5.8 Hz, 1H), 8.57 (s, 1H), 7.28-7.14 (m, 2H), 4.80 (s, 1H), 4.63-4.46 (m, 3H), 3.71 (qd, J=15.0, 2.3 Hz, 2H), 2.71 (d, J=16.9 Hz, 1H), 2.47-2.30 (m, 1H), 1.97 (d, J=15.0 Hz, 1H), 1.90-1.65 (m, 2H), 1.34 (dd, J=15.8, 11.6 Hz, 1H), 1.18 (d, J=6.6 Hz, 3H).

Example 102: Preparation of (3'S,5R,7'R)-2-(4-fluorobenzyl)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide

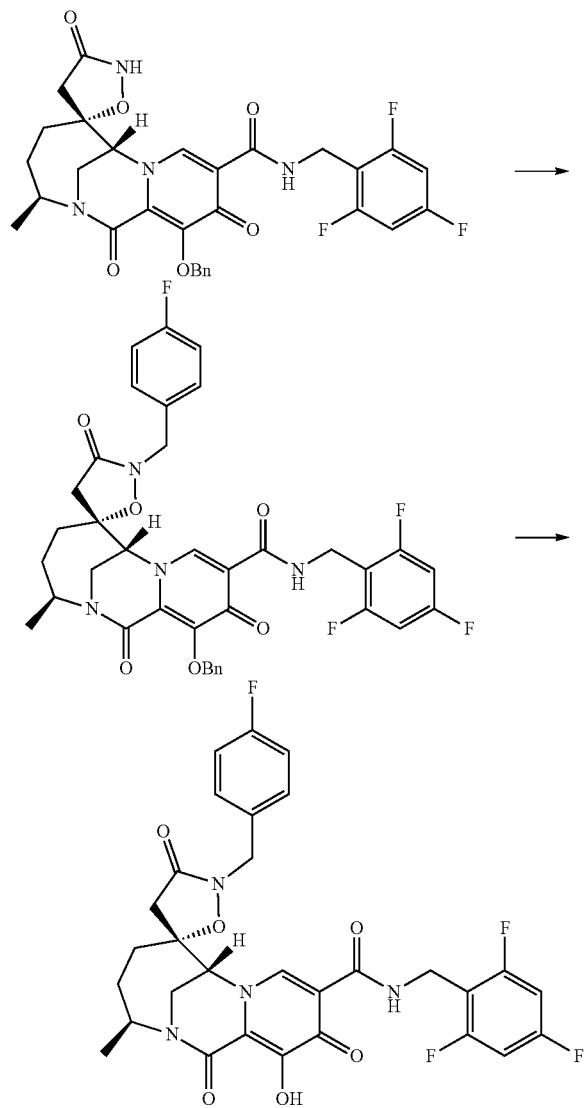

Step 1: Preparation of (3'S,5R,7'R)-12'-(benzyloxy)-2-(4-fluorobenzyl)-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide To a solution of (3'S,5R,7'R)-12'-(benzyloxy)-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide (20 mg, 0.0335 mmol), prepared in a manner similar to Step 1 of Example 101 except using (3'S,5R,7'R)-12'-(benzyloxy)-3-bromo-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide, prepared according to Example 36, instead of (3'S,5S,7'R)-12'-(benzyloxy)-3-bromo-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide, in DMF (0.5 mL) was added 1-(bromomethyl)-4-fluoro-benzene (7.6 mg, 0.0402 mmol), K₂CO₃ (13.9 mg, 0.101 mmol) and KI (1.67 mg, 0.04 mmol). The resulting mixture was heated to 110° C. for 1 h. The reaction was cooled to rt, filtered, and purified by reverse phase prep HPLC. LCMS-ESI+(m/z): calcd H+ for C37H32F4N4O6, Theoretical: 704.23, Found: 705.062.

Step 2: Preparation of (3'S,5R,7'R)-2-(4-fluorobenzyl)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide (3'S,5R,7'R)-12'-(benzyloxy)-2-(4-fluorobenzyl)-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide was treated with a mixture of Toluene (0.3 mL) and TFA (0.3 mL) at room temperature for overnight. The reaction was concentrated, purified by reverse phase prep HPLC. LCMS-ESI+ (m/z): calcd H+ for C30H26F4N4O6, Theoretical: 614.18, Found: 615.147. 1H NMR (400 MHz, CD3OD) δ 8.37 (s, 1H), 7.24-7.15 (m, 2H), 7.04-6.96 (m, 2H), 6.96-6.87 (m, 2H), 5.05 (d, J=15.6 Hz, 1H), 4.86-4.82 (m, 1H), 4.72 (s, 2H), 4.63 (dt, J=10.5, 6.6 Hz, 1H), 4.51 (d, J=15.6 Hz, 1H), 3.91-3.77 (m, 2H), 3.12-2.97 (m, 2H), 2.10 (dq, J=13.5, 6.8 Hz, 1H), 1.81 (dd, J=14.7, 7.7 Hz, 1H), 1.51 (dt, J=15.1, 11.2 Hz, 1H), 1.42-1.35 (m, 1H), 1.28 (d, J=6.7 Hz, 3H).

Example 103: Preparation of (3'S,5S,7'R)-12'-hydroxy-3'-methyl-2-((1-methyl-1H-indazol-5-yl)methyl)-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide

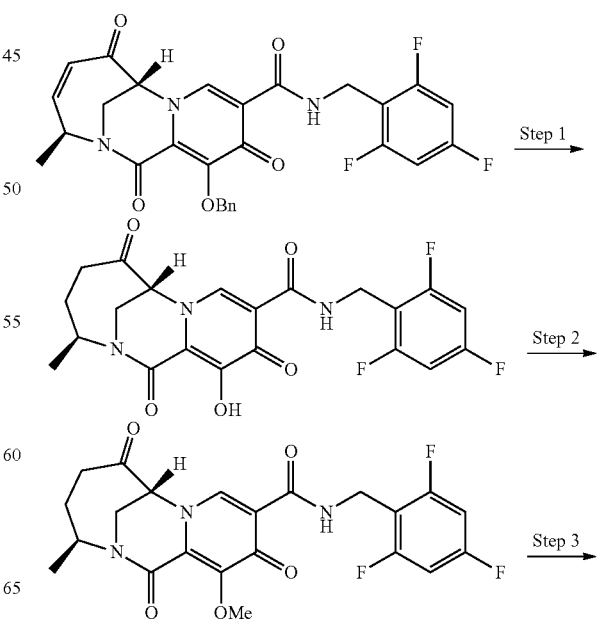

289
-continued

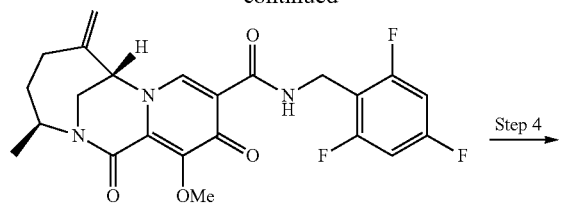

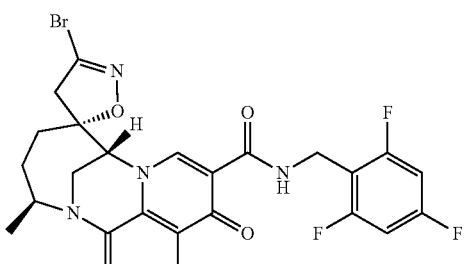

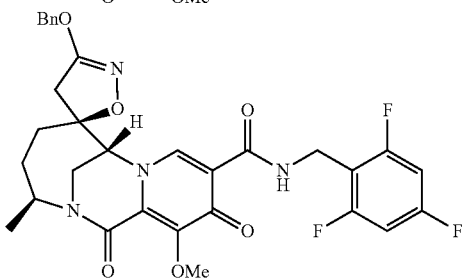

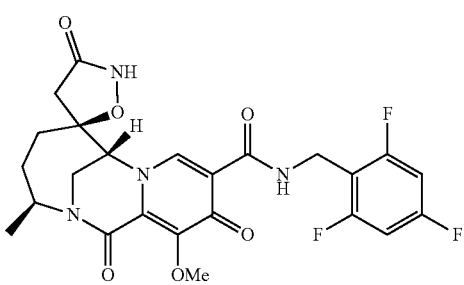

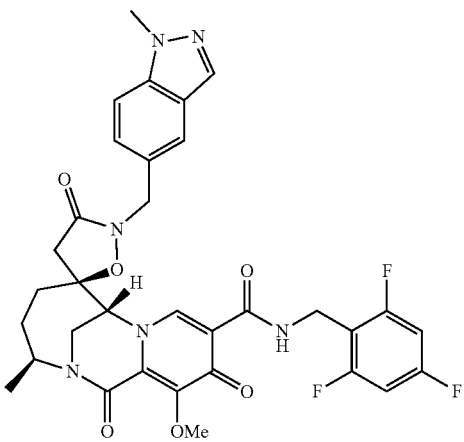

290
-continued

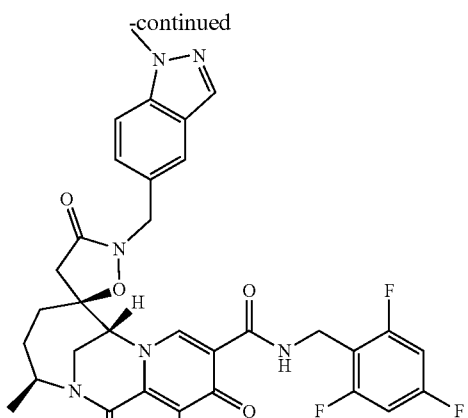

Step 1. Preparation of (3S,7R)-12-hydroxy-3-methyl-1,6,11-trioxo-N-(2,4,6-trifluorobenzyl)-1,4,5,6,7,11-hexahydro-3H-2,7-methanopyrido[1,2-a][1,4]diazonine-10-carboxamide To a solution of (3S,7R)-12-(benzyloxy)-3-methyl-1,6,11-trioxo-N-(2,4,6-trifluorobenzyl)-1,6,7,11-tetrahydro-3H-2,7-methanopyrido[1,2-a][1,4]diazonine-10-carboxamide (6.0 g, 11.2 mmol) in a mixture of EtOH (200 mL) and EtOAc (70 mL) was added 20% Pd(OH)2/C (50 wt % water, 1800 mg). The resulting mixture was degassed and flushed with nitrogen three times and then degassed and flushed with hydrogen three times before it was hydrogenated under hydrogen balloon for overnight. The reaction was then degassed and flushed with nitrogen, diluted with DCM (100 mL) and EtOAc (100 mL), stirred for 30 min, filtered and concentrate, used directly in next step. LCMS-ESI+(m/z): 496.152 [M+H+2MeOH—H$_2$O]$^+$.

Step 2: Preparation of (3S,7R)-12-methoxy-3-methyl-1,6,11-trioxo-N-(2,4,6-trifluorobenzyl)-1,4,5,6,7,11-hexahydro-3H-2,7-methanopyrido[1,2-a][1,4]diazonine-10-carboxamide To a solution of (3S,7R)-12-hydroxy-3-methyl-1,6,11-trioxo-N-(2,4,6-trifluorobenzyl)-1,4,5,6,7,11-hexahydro-3H-2,7-methanopyrido[1,2-a][1,4]diazonine-10-carboxamide from Step 1 in DMF (55 mL) at room temperature was added potassium carbonate (3081 mg, 22.3 mmol) and iodomethane (1.9 g, 13.4 mmol). The resulting mixture was stirred for overnight. The reaction was then filtered through Celite, rinsed with DMF (12 mL) and used directly in next step. LCMS-ESI+(m/z): 482.206 [M+H+H$_2$O]$^+$.

Step 3: Preparation of (3S,7S)-12-methoxy-3-methyl-6-methylene-1,11-dioxo-N-(2,4,6-trifluorobenzyl)-1,4,5,6,7,11-hexahydro-3H-2,7-methanopyrido[1,2-a][1,4]diazonine-10-carboxamide The DMF solution from Step 2 was cooled at room temperature, 1-methyl-2-methylsulfonyl-benzimidazole (2.7 g, 12.8 mmol) was added followed by potassium tert-butoxide (2.88 g, 25.7 mmol). The resulting mixture was then removed from water bath and stirred for 1.5 h. The reaction was then cooled to 0° C., quenched with 0.5N HCl (40 mL) slowly, extracted with EtOAc (3×), combined org layer was washed with water, brine, dried over sodium sulfate, filtered and concentrated, purified by normal phase chromatography. LCMS-ESI+(m/z): calcd H+ for C23H22F3N3O4, Theoretical: 461.16, Found: 462.192.

Step 4: Preparation of (3'S,5S,7'R)-3-bromo-12'-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide The title compound was prepared in a similar manner as Step 1 of Example 36, except using (3S,7S)-12-methoxy-3-methyl-6-methylene-1,11-dioxo-N-(2,4,6-trifluorobenzyl)-1,4,5,6,7,11-hexahydro-3H-2,7-methanopyrido[1,2-a][1,4]diazonine-10-carboxamide instead of (3S,7S)-12-(benzyloxy)-3-methyl-6-methylene-1,11-dioxo-N-(2,4,6-trifluorobenzyl)-1,4,5,6,7,11-hexahydro-3H-2,7-methanopyrido[1,2-a][1,4]diazonine-10-carboxamide. LCMS-ESI+(m/z): calcd H+ for C24H22BrF3N4O5, Theoretical: 582.07, Found: 583.140. Step 5: Preparation of (3'S,5S,7'R)-3-(benzyloxy)-12'-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide To a solution of (3'S,5S,7'R)-3-bromo-12'-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (2.4 g, 4.11 mmol) in DMF (8.0 mL) was added benzyl alcohol (2.22 g, 20.6 mmol) and potassium carbonate (3.4 g, 24.7 mmol). The resulting mixture was heated to 80° C. for 3 h. The reaction was cooled to room temperature, diluted with EtOAc, washed with water, brine, dried over sodium sulfate, filtered, and concentrated. The resulting residue was purified by silica gel column chromatography. LCMS-ESI+(m/z): calcd H+ for C31H29F3N4O6, Theoretical: 610.20, Found: 611.129.

Step 6: Preparation of (3'S,5S,7'R)-12'-methoxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide (3'S,5S,7'R)-3-(benzyloxy)-12'-methoxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (1.4 g, 2.29 mmol) was treated with a mixture of toluene (10 mL) and TFA (10 mL) at room temperature for 5 h. The reaction was concentrated and the resulting residue was diluted with EtOAc (10 mL) and concentrated (repeated 2x). The residue was purified by silica gel column chromatography. LCMS-ESI+(m/z): calcd H+ for C24H23F3N4O6, Theoretical: 520.16, Found: 521.202.

Step 7: Preparation of (3'S,5S,7'R)-12'-methoxy-3'-methyl-2-((1-methyl-1H-indazol-5-yl)methyl)-1',3,11'-trioxo-N-(2,4,6-trifluorobenzyl)-1',4',5',1'-tetrahydro-3'H,7'H-spiro[isoxazolidine-5,6'-[2,7]methanopyrido[1,2-a][1,4]diazonine]-10'-carboxamide To a solution of (3'S,5S,7'R)-12'-methoxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide (20 mg, 0.0384 mmol) was added 5-(bromomethyl)-1-methyl-indazole (11.2 mg, 0.05 mmol), potassium carbonate (15.9 mg, 0.115 mmol) and KI (1.91 mg, 0.0115 mmol). The resulting mixture was heated to 110° C. for 1 h before it was cooled to room temperature. The reaction was diluted with EtOAc, washed with water, brine, dried over sodium sulfate, filtered and concentrated. The crude material was used without further purification.

Step 8: Preparation of (3'S,5S,7'R)-12'-hydroxy-3'-methyl-2-((1-methyl-1H-indazol-5-yl)methyl)-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide Crude (3'S,5S,7'R)-12'-methoxy-3'-methyl-2-((1-methyl-1H-indazol-5-yl)methyl)-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide from Step 7 was dissolved in DMF (0.5 mL), treated with LiCl (16.3 mg, 0.384 mmol), and heated to 110° C. for 5 h. The reaction was then cooled to room temperature, diluted with DMF (0.1 mL), filtered, and purified by reverse phase chromatography. LCMS-ESI+(m/z): calcd H+ for C32H29F3N6O6, Theoretical: 650.21, Found: 651.319. 1H NMR (400 MHz, CD3OD) δ 8.53 (s, 1H), 8.04 (d, J=0.9 Hz, 1H), 7.82 (d, J=1.3 Hz, 1H), 7.61 (d, J=8.7 Hz, 1H), 7.49 (dd, J=8.7, 1.6 Hz, 1H), 6.96-6.86 (m, 2H), 5.03 (d, J=15.4 Hz, 1H), 4.76 (d, J=15.4 Hz, 1H), 4.72-4.65 (m, 2H), 4.65-4.49 (m, 2H), 4.09 (s, 3H), 3.75-3.61 (m, 2H), 3.02 (d, J=16.7 Hz, 1H), 2.49 (d, J=16.7 Hz, 1H), 1.98-1.88 (m, 1H), 1.59-1.49 (m, 2H), 1.39 (ddd, J=15.9, 9.9, 3.1 Hz, 1H), 1.14 (d, J=6.7 Hz, 3H).

Example 104: Preparation of (3'S,5S,7'R)-12'-hydroxy-3'-methyl-2-((2-methyl-2H-1,2,3-triazol-4-yl)methyl)-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide

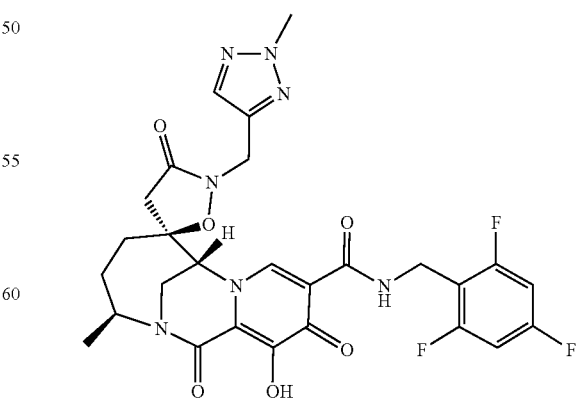

(3'S,5S,7'R)-12'-hydroxy-3'-methyl-2-((2-methyl-2H-1,2,3-triazol-4-yl)methyl)-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide was synthesized in a similar manner as Example 103, except using 4-(bromomethyl)-2-methyl-2H-1,2,3-triazole instead of 5-(bromomethyl)-1-methyl-indazole. LCMS-ESI+(m/z): calcd H+ for C27H26F3N7O6, Theoretical: 601.533, Found: 602.231. 1H NMR (400 MHz, CD3OD) δ 8.55 (s, 1H), 7.70 (s, 1H), 6.96-6.88 (m, 2H), 4.96 (d, J=16.1 Hz, 1H), 4.84-4.74 (m, 2H), 4.74-4.57 (m, 3H), 4.18 (s, 3H), 3.82-3.76 (m, 2H), 2.99 (d, J=16.9 Hz, 1H), 2.51 (d, J=16.9 Hz, 1H), 2.04 (dd, J=16.0, 5.9 Hz, 1H), 1.81-1.67 (m, 2H), 1.55-1.42 (m, 1H), 1.25 (d, J=6.7 Hz, 3H).

Example 105: Preparation of (3'S,5S,7'R)-12'-hydroxy-3'-methyl-1',3,11'-trioxo-2-phenethyl-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide

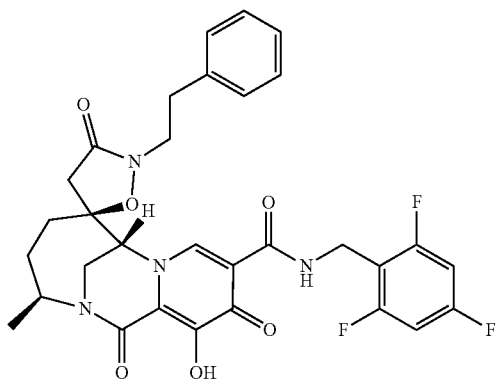 [SMILES: C[C@H]1CC[C@]2(CC(=O)N(CCc3ccccc3)O2)[C@H]2CN1C(=O)c1c(O)c(=O)c(C(=O)NCc3c(F)cc(F)cc3F)cn12]

(3'S,5S,7'R)-12'-hydroxy-3'-methyl-1',3,11'-trioxo-2-phenethyl-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide was synthesized in a similar manner as Example 103, except using 2-bromoethylbenzene instead of 5-(bromomethyl)-1-methyl-indazole. LCMS-ESI+(m/z): calcd H+ for C31H29F3N4O6, Theoretical: 610.20, Found: 611.311; 1H NMR (400 MHz, CD3OD) δ 8.31 (s, 1H), 7.41-7.20 (m, 5H), 6.96-6.87 (m, 2H), 4.75-4.58 (m, 3H), 4.30 (s, 1H), 4.04-3.88 (m, 2H), 3.69 (d, J=2.2 Hz, 2H), 3.05 (t, J=6.9 Hz, 2H), 2.69 (d, J=17.1 Hz, 1H), 2.44 (d, J=17.1 Hz, 1H), 1.97 (dd, J=17.0, 5.4 Hz, 1H), 1.93-1.73 (m, 2H), 1.50 (dd, J=16.2, 11.2 Hz, 1H), 1.27 (d, J=6.7 Hz, 3H).

Example 106: Preparation of (3'S,5S,7'R)-12'-hydroxy-3'-methyl-2-(naphthalen-1-ylmethyl)-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide

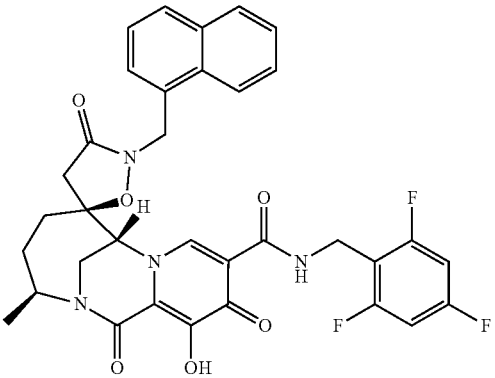 [SMILES: C[C@H]1CC[C@]2(CC(=O)N(Cc3cccc4ccccc34)O2)[C@H]2CN1C(=O)c1c(O)c(=O)c(C(=O)NCc3c(F)cc(F)cc3F)cn12]

(3'S,5S,7'R)-12'-hydroxy-3'-methyl-2-(naphthalen-1-ylmethyl)-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide was synthesized in a similar manner as Example 103, except using 1-(bromomethyl)naphthalene instead of 5-(bromomethyl)-1-methyl-indazole. LCMS-ESI+(m/z): calcd H+ for C34H29F3N4O6, Theoretical: 646.20, Found: 647.247. 1H NMR (400 MHz, CD3OD) δ 8.44 (s, 1H), 8.22 (d, J=8.5 Hz, 1H), 7.95 (dd, J=8.0, 3.9 Hz, 2H), 7.68-7.62 (m, 2H), 7.59-7.51 (m, 2H), 6.96-6.88 (m, 2H), 5.44 (d, J=15.2 Hz, 1H), 5.09 (d, J=15.1 Hz, 1H), 4.75-4.62 (m, 2H), 4.44-4.34 (m, 2H), 3.50 (dd, J=15.1, 2.7 Hz, 1H), 3.31-3.26 (m, 1H), 3.03 (d, J=16.5 Hz, 1H), 2.45 (d, J=16.5 Hz, 1H), 1.69-1.58 (m, 1H), 1.27-1.15 (m, 1H), 1.09-1.02 (m, 2H), 1.00 (d, J=6.6 Hz, 3H).

Example 107: Preparation of (3'S,5S,7'R)-12'-hydroxy-3'-methyl-2-(naphthalen-2-ylmethyl)-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide

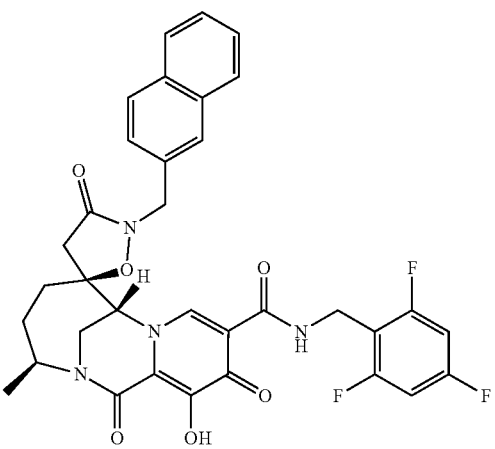 [SMILES: C[C@H]1CC[C@]2(CC(=O)N(Cc3ccc4ccccc4c3)O2)[C@H]2CN1C(=O)c1c(O)c(=O)c(C(=O)NCc3c(F)cc(F)cc3F)cn12]

(3'S,5S,7'R)-12'-hydroxy-3'-methyl-2-(naphthalen-2-yl-methyl)-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide was synthesized in a similar manner as Example 103, except using 2-(bromomethyl)naphthalene instead of 5-(bromomethyl)-1-methyl-indazole. LCMS-ESI+(m/z): calcd H+ for C34H29F3N4O6, Theoretical: 646.20, Found: 647.24. 1H NMR (400 MHz, CD3OD) δ 8.56 (s, 1H), 7.96-7.85 (m, 4H), 7.58-7.48 (m, 3H), 6.96-6.87 (m, 2H), 5.11 (d, J=15.5 Hz, 1H), 4.80 (d, J=15.5 Hz, 1H), 4.74-4.61 (m, 3H), 4.52 (dt, J=10.2, 6.8 Hz, 1H), 3.74-3.61 (m, 2H), 3.07 (d, J=16.7 Hz, 1H), 2.51 (d, J=16.7 Hz, 1H), 1.97 (dd, J=15.3, 6.2 Hz, 1H), 1.57-1.33 (m, 3H), 1.09 (d, J=6.6 Hz, 3H).

Example 108: Preparation of (3'S,5S,7'R)-12'-hydroxy-2,3'-dimethyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide

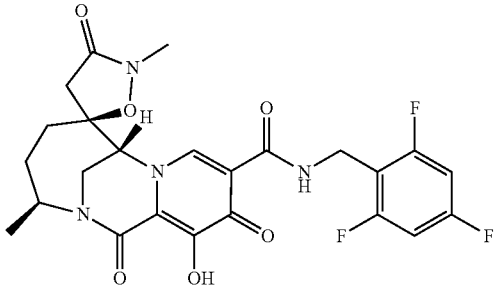 [SMILES: C[C@H]1CC[C@]2(CC(=O)N(C)O2)[C@H]2CN1C(=O)c1c(O)c(=O)c(C(=O)NCc3c(F)cc(F)cc3F)cn12]

(3'S,5S,7'R)-12'-hydroxy-2,3'-dimethyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide was synthesized in a similar manner as Example 103, except using iodomethane instead of 5-(bromomethyl)-1-methyl-indazole. LCMS-ESI+(m/z): calcd H+ for C24H23F3N4O6, Theoretical: 520.16, Found: 521.219. 1H NMR (400 MHz, CD3OD) δ 8.52 (s, 1H), 6.96-6.86 (m, 2H), 4.78 (s, 1H), 4.74-4.59 (m, 3H), 3.94-3.78 (m, 2H), 3.23 (s, 3H), 2.85 (d, J=17.0 Hz, 1H), 2.53 (d, J=17.0 Hz, 1H), 2.17-2.07 (m, 1H), 2.03-1.93 (m, 2H), 1.63-1.51 (m, 1H), 1.30 (d, J=6.7 Hz, 3H).

Example 109: Preparation of (3'S,5S,7'R)-2-(4-chlorobenzyl)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide

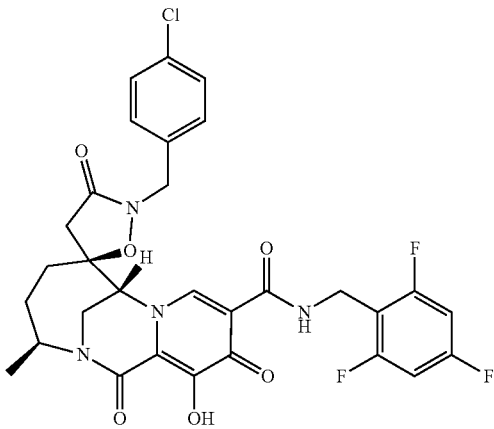 [SMILES: C[C@H]1CC[C@]2(CC(=O)N(Cc3ccc(Cl)cc3)O2)[C@H]2CN1C(=O)c1c(O)c(=O)c(C(=O)NCc3c(F)cc(F)cc3F)cn12]

(3'S,5S,7'R)-2-(4-chlorobenzyl)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide was synthesized in a similar manner as Example 103, except using 1-(bromomethyl)-4-chloro-benzene instead of 5-(bromomethyl)-1-methyl-indazole. LCMS-ESI+(m/z): calcd H+ for C30H26ClF3N4O6, Theoretical: 630.15, Found: 631.133. 1H NMR (400 MHz, CD3OD) δ 8.57 (s, 1H), 7.46-7.33 (m, 4H), 6.97-6.85 (m, 2H), 4.92 (d, J=15.5 Hz, 1H), 4.73-4.54 (m, 5H), 3.85-3.64 (m, 2H), 3.03 (d, J=16.8 Hz, 1H), 2.51 (d, J=16.8 Hz, 1H), 2.05-1.92 (m, 1H), 1.78-1.56 (m, 2H), 1.52-1.37 (m, 1H), 1.21 (d, J=6.6 Hz, 3H).

Example 110: Preparation of (3'S,5S,7'R)-2-(2,4-difluorobenzyl)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide

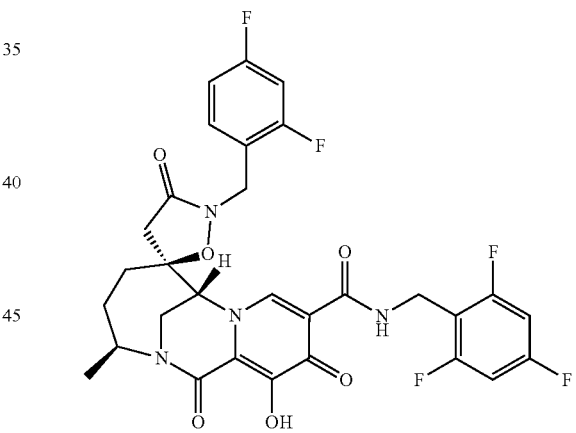

(3'S,5S,7'R)-2-(2,4-difluorobenzyl)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide was synthesized in a similar manner as Example 103, except using 1-(bromomethyl)-2,4-difluoro-benzene instead of 5-(bromomethyl)-1-methyl-indazole. LCMS-ESI+(m/z): calcd H+ for C30H25F5N4O6, Theoretical: 632.17, Found: 633.105. 1H NMR (400 MHz, CD3OD) δ 8.57 (s, 1H), 7.52 (q, J=8.9, 8.3 Hz, 1H), 7.11-6.99 (m, 2H), 6.97-6.86 (m, 2H), 4.99 (d, J=15.6 Hz, 1H), 4.75-4.57 (m, 5H), 3.85-3.65 (m, 2H), 3.04 (d, J=16.7 Hz, 1H), 2.49 (d, J=16.7 Hz, 1H), 2.02-1.92 (m, 1H), 1.70 (dt, J=13.8, 6.5 Hz, 1H), 1.65-1.53 (m, 1H), 1.49-1.39 (m, 1H), 1.21 (d, J=6.7 Hz, 3H).

Example 111: Preparation of (3'S,5S,7'R)-12'-hydroxy-3'-methyl-1',3,11'-trioxo-N-(2,4,6-trifluorobenzyl)-2-(3-(trifluoromethyl)benzyl)-1',4',5',11'-tetrahydro-3'H,7'H-spiro[isoxazolidine-5,6'-[2,7]methanopyrido[1,2-a][1,4]diazonine]-10'-carboxamide

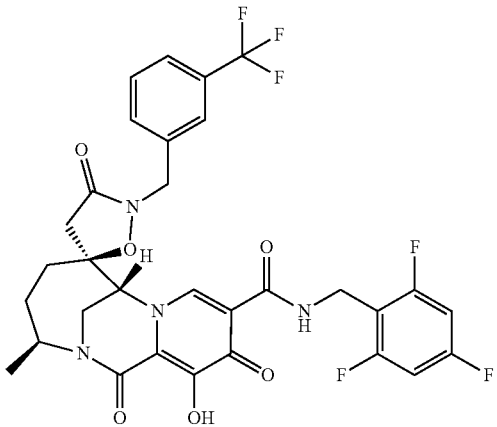 [SMILES: C[C@H]1CC[C@]2(CC(=O)N(Cc3cccc(C(F)(F)F)c3)O2)[C@H]2CN1C(=O)c1c(O)c(=O)c(C(=O)NCc3c(F)cc(F)cc3F)cn12]

(3'S,5S,7'R)-12'-hydroxy-3'-methyl-1',3,11'-trioxo-N-(2,4,6-trifluorobenzyl)-2-(3-(trifluoromethyl)benzyl)-1',4',5',11'-tetrahydro-3'H,7'H-spiro[isoxazolidine-5,6'-[2,7]methanopyrido[1,2-a][1,4]diazonine]-10'-carboxamide was synthesized in a similar manner as Example 103, except using 1-(bromomethyl)-3-(trifluoromethyl)benzene instead of 5-(bromomethyl)-1-methyl-indazole. LCMS-ESI+(m/z): calcd H+ for C31H26F6N4O6, Theoretical: 664.18, Found: 665.138. 1H NMR (400 MHz, CD3OD) δ 8.59 (s, 1H), 7.76-7.58 (m, 4H), 6.96-6.86 (m, 2H), 5.07 (d, J=15.8 Hz, 1H), 4.77-4.66 (m, 4H), 4.60 (dt, J=10.3, 7.2 Hz, 1H), 3.84-3.65 (m, 2H), 3.09 (d, J=16.7 Hz, 1H), 2.50 (d, J=16.7 Hz, 1H), 1.97 (dd, J=15.1, 6.4 Hz, 1H), 1.73-1.52 (m, 2H), 1.43 (ddd, J=16.1, 10.6, 2.3 Hz, 1H), 1.19 (d, J=6.6 Hz, 3H).

Example 112: Preparation of (3'S,5S,7'R)-2-(benzo[d]thiazol-6-ylmethyl)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide

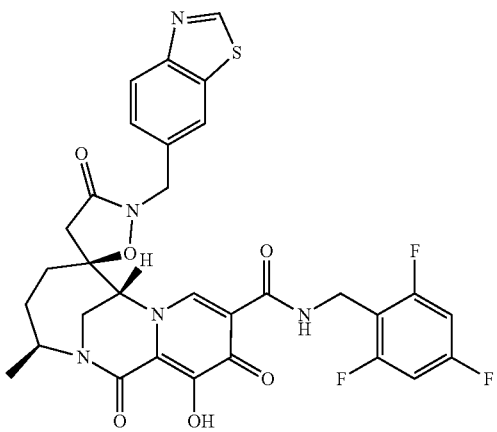 [SMILES: C[C@H]1CC[C@]2(CC(=O)N(Cc3ccc4ncsc4c3)O2)[C@H]2CN1C(=O)c1c(O)c(=O)c(C(=O)NCc3c(F)cc(F)cc3F)cn12]

(3'S,5S,7'R)-2-(benzo[d]thiazol-6-ylmethyl)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide was synthesized in a similar manner as Example 103, except using 6-(bromomethyl)benzo[d]thiazole instead of 5-(bromomethyl)-1-methyl-indazole. MS (m/z) 654.186 [M+H]+. 1H NMR (400 MHz, Chloroform-d) δ 10.37 (t, J=5.8 Hz, 1H), 9.15 (s, 1H), 8.58 (s, 1H), 8.06-7.99 (m, 1H), 7.59-7.51 (d, J=8.3 Hz, 1H), 7.52 (dd, J=8.3, 1.7 Hz, 1H), 6.69 (dd, J=8.7, 7.5 Hz, 2H), 4.92 (d, J=2.3 Hz, 2H), 4.67 (d, J=5.8 Hz, 3H), 4.32 (s, 1H), 3.59 (t, J=2.3 Hz, 2H), 2.89 (d, J=17.0 Hz, 1H), 2.41 (d, J=17.0 Hz, 1H), 2.03 (dd, J=15.7, 6.2 Hz, 1H), 1.81-1.57 (m, 2H), 1.53-1.39 (m, 1H), 1.20 (d, J=6.7 Hz, 3H).

Example 113: Preparation of (3'S,5S,7'R)-2-(benzo[d]thiazol-5-ylmethyl)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide

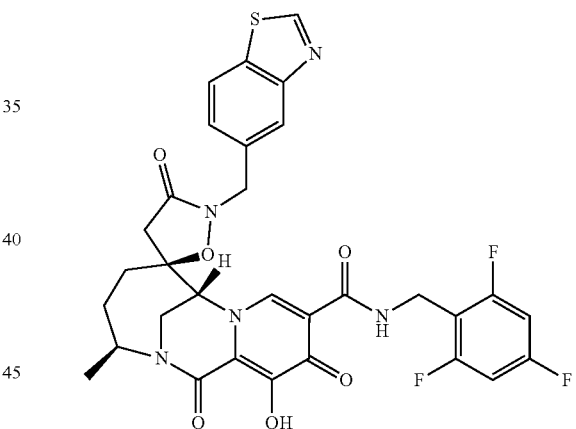

(3'S,5S,7'R)-2-(benzo[d]thiazol-5-ylmethyl)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide was synthesized in a similar manner as Example 103, except using 5-(bromomethyl)benzo[d]thiazole instead of 5-(bromomethyl)-1-methyl-indazole. MS (m/z) 654.21 [M+H]+. 1H NMR (400 MHz, Chloroform-d) δ 10.32 (t, J=5.8 Hz, 1H), 9.15 (s, 1H), 8.51 (s, 1H), 8.22-8.14 (m, 1H), 8.03 (d, J=8.3 Hz, 1H), 7.52 (dd, J=8.3, 1.7 Hz, 1H), 6.69 (dd, J=8.7, 7.5 Hz, 2H), 4.92 (d, J=2.3 Hz, 2H), 4.67 (d, J=5.8 Hz, 3H), 4.32 (s, 1H), 3.59 (t, J=2.3 Hz, 2H), 2.89 (d, J=17.0 Hz, 1H), 2.41 (d, J=17.0 Hz, 1H), 2.03 (dd, J=15.7, 6.2 Hz, 1H), 1.81-1.57 (m, 2H), 1.53-1.39 (m, 1H), 1.20 (d, J=6.7 Hz, 3H).

Example 114: Preparation of (3'S,5S,7'R)-2-((1H-benzo[d]imidazol-4-yl)methyl)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide

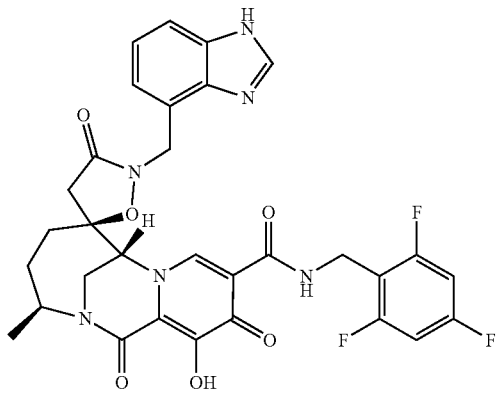 [SMILES: C[C@H]1CC[C@]2(CC(=O)N(Cc3cccc4[nH]cnc34)O2)[C@H]2CN1C(=O)c1c(O)c(=O)c(C(=O)NCc3c(F)cc(F)cc3F)cn12]

(3'S,5S,7'R)-2-((1H-benzo[d]imidazol-4-yl)methyl)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide was synthesized in a similar manner as Example 103, except using tert-butyl 4-(bromomethyl)-1H-benzo[d]imidazole-1-carboxylate instead of 5-(bromomethyl)-1-methyl-indazole. MS (m/z) 637.21 [M+H]$^+$. 1H NMR (400 MHz, Chloroform-d) δ 10.48 (s, 1H), 7.96 (d, J=8.0 Hz, 1H), 7.62-7.49 (m, 2H), 7.48 (d, J=7.3 Hz, 1H), 6.77 (s, 2H), 6.66 (t, J=8.1 Hz, 2H), 5.12 (s, 1H), 4.68 (s, 2H), 4.56 (s, 1H), 3.77 (s, 2H), 2.97 (d, J=31.5 Hz, 2H), 2.82 (d, J=17.5 Hz, 2H), 1.30 (d, J=6.7 Hz, 3H), 1.18 (d, J=6.4 Hz, 4H).

Example 115: Preparation of (3'S,5S,7'R)-2-(4-fluorobenzyl)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide and (3'S,5S,7'R)-3-((4-fluorobenzyl)oxy)-12'-hydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide Peak 1

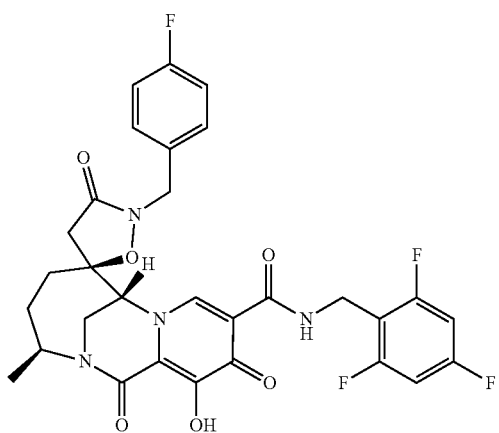

(3'S,5S,7'R)-2-(4-fluorobenzyl)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide and (3'S,5S,7'R)-3-((4-fluorobenzyl)oxy)-12'-hydroxy-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide were synthesized in a similar manner as Example 103, except using 1-(bromomethyl)-4-fluoro-benzene instead of 5-(bromomethyl)-1-methyl-indazole. After reverse phase chromatography, the title compound was obtained.

Peak 1: LCMS-ESI+(m/z): calcd H+ for C30H26F4N4O6, Theoretical: 614.18, Found: 615.146. 1H NMR (400 MHz, CD3OD) δ 8.56 (s, 1H), 7.48-7.40 (m, 2H), 7.19-7.10 (m, 2H), 6.96-6.87 (m, 2H), 4.96-4.89 (m, 1H), 4.71-4.53 (m, 5H), 3.82-3.66 (m, 2H), 3.03 (d, J=16.7 Hz, 1H), 2.50 (d, J=16.7 Hz, 1H), 2.03-1.90 (m, 1H), 1.74-1.55 (m, 2H), 1.50-1.37 (m, 1H), 1.21 (d, J=6.7 Hz, 3H).

Example 116: Preparation of (3'S,5S,7'R)-12'-hydroxy-3'-methyl-2-neopentyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide and (3'S,5S,7'R)-12'-hydroxy-3'-methyl-3-(neopentyloxy)-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide Peak 1

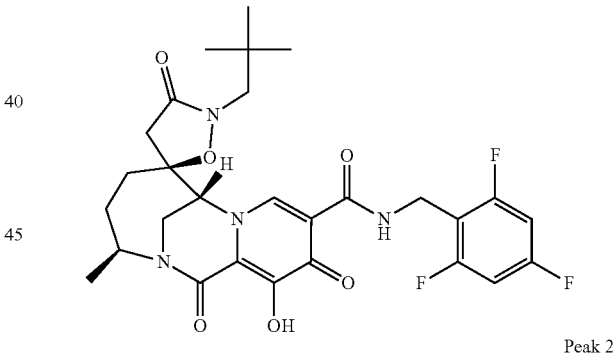

Peak 2

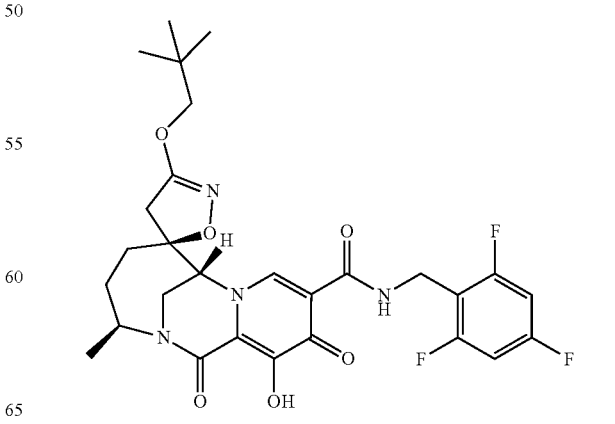

(3'S,5S,7'R)-12'-hydroxy-3'-methyl-2-neopentyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide and (3'S,5S,7'R)-12'-hydroxy-3'-methyl-3-(neopentyloxy)-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide were synthesized in a similar manner as Example 103, except using 1-bromo-2,2-dimethyl-propane instead of 5-(bromomethyl)-1-methyl-indazole. After reverse phase chromatography, the title compounds were obtained.

Peak 1: LCMS-ESI+(m/z): calcd H+ for C28H31F3N4O6, Theoretical: 576.22, Found: 577.131. 1H NMR (400 MHz, CD30D) δ 8.55 (s, 1H), 6.97-6.87 (m, 2H), 4.80-4.60 (m, 4H), 3.89-3.77 (m, 2H), 3.50 (d, J=14.7 Hz, 1H), 3.40-3.34 (m, 1H), 2.92 (d, J=16.9 Hz, 1H), 2.54 (d, J=16.9 Hz, 1H), 2.16 (dd, J=16.0, 6.1 Hz, 1H), 2.04-1.89 (m, 2H), 1.62-1.50 (m, 1H), 1.30 (d, J=6.7 Hz, 3H), 1.04 (s, 9H).

Peak 2: LCMS-ESI+(m/z): calcd H+ for C28H31F3N4O6, Theoretical: 576.22, Found: 577.002. 1H NMR (400 MHz, CD30D) δ 8.56 (s, 1H), 6.96-6.87 (m, 2H), 4.74-4.63 (m, 4H), 3.93-3.75 (m, 4H), 3.08 (d, J=17.0 Hz, 1H), 2.69 (d, J=17.0 Hz, 1H), 2.12-1.90 (m, 3H), 1.53 (dd, J=15.6, 11.0 Hz, 1H), 1.30 (d, J=6.7 Hz, 3H), 1.01 (s, 9H).

Example 117: Preparation of (3'S,5S,7'R)-12'-hydroxy-3'-methyl-1',3,11'-trioxo-2-((tetrahydro-2H-pyran-4-yl)methyl)-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide and (3'S,5S,7'R)-12'-hydroxy-3'-methyl-1',11'-dioxo-3-((tetrahydro-2H-pyran-4-yl)methoxy)-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (3'S,5S,7'R)-12'-hydroxy-3'-methyl-1',3,11'-trioxo-2-((tetrahydro-2H-pyran-4-yl)methyl)-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide and (3'S,5S,7'R)-12'-hydroxy-3'-methyl-1',11'-dioxo-3-((tetrahydro-2H-pyran-4-yl)methoxy)-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide were synthesized in a similar manner as Example 103, except using 4-(bromomethyl)tetrahydropyran instead of 5-(bromomethyl)-1-methyl-indazole. After purification by reverse phase chromatography, the title compounds were obtained.

Peak 1: LCMS-ESI+(m/z): calcd H+ for C29H31F3N4O7, Theoretical: 604.21, Found: 605.224. 1H NMR (400 MHz, CD30D) δ 8.56 (s, 1H), 6.96-6.86 (m, 2H), 4.78 (s, 1H), 4.74-4.61 (m, 3H), 4.03-3.93 (m, 2H), 3.88-3.82 (m, 2H), 3.60 (dd, J=14.5, 7.5 Hz, 1H), 3.52-3.39 (m, 3H), 2.95 (d, J=16.9 Hz, 1H), 2.54 (d, J=16.9 Hz, 1H), 2.20-1.89 (m, 4H), 1.74-1.62 (m, 2H), 1.60-1.50 (m, 1H), 1.45-1.34 (m, 2H), 1.31 (d, J=6.6 Hz, 3H).

Peak 2: LCMS-ESI+(m/z): calcd H+ for C29H31F3N4O7, Theoretical: 604.21, Found: 605.191. 1H NMR (400 MHz, CD30D) δ 8.69 (s, 1H), 6.95-6.87 (m, 2H), 4.78-4.61 (m, 4H), 4.03-3.79 (m, 7H), 3.50-3.38 (m, 2H), 3.03 (d, J=16.9 Hz, 1H), 2.68 (d, J=17.0 Hz, 1H), 2.10-1.90 (m, 5H), 1.72-1.47 (m, 2H), 1.42-1.33 (m, 1H), 1.30 (d, J=6.7 Hz, 3H).

Example 118: Preparation of (3'S,5S,7'R)-2-(4-cyanobenzyl)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide

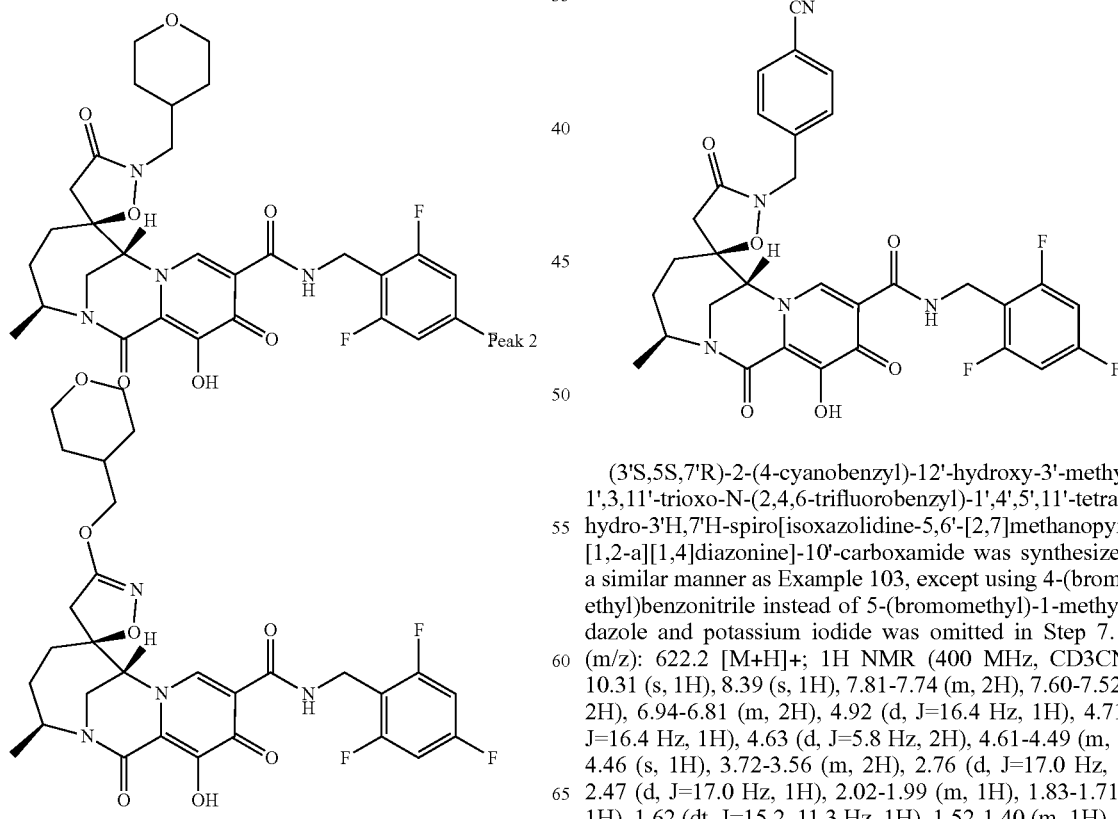

(3'S,5S,7'R)-2-(4-cyanobenzyl)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide was synthesized in a similar manner as Example 103, except using 4-(bromomethyl)benzonitrile instead of 5-(bromomethyl)-1-methyl-indazole and potassium iodide was omitted in Step 7. MS (m/z): 622.2 [M+H]+; 1H NMR (400 MHz, CD3CN) δ 10.31 (s, 1H), 8.39 (s, 1H), 7.81-7.74 (m, 2H), 7.60-7.52 (m, 2H), 6.94-6.81 (m, 2H), 4.92 (d, J=16.4 Hz, 1H), 4.71 (d, J=16.4 Hz, 1H), 4.63 (d, J=5.8 Hz, 2H), 4.61-4.49 (m, 1H), 4.46 (s, 1H), 3.72-3.56 (m, 2H), 2.76 (d, J=17.0 Hz, 1H), 2.47 (d, J=17.0 Hz, 1H), 2.02-1.99 (m, 1H), 1.83-1.71 (m, 1H), 1.62 (dt, J=15.2, 11.3 Hz, 1H), 1.52-1.40 (m, 1H), 1.18 (d, J=6.7 Hz, 3H).

Example 119: Preparation of (3'S,5S,7'R)-12'-hydroxy-2-(4-methoxybenzyl)-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide

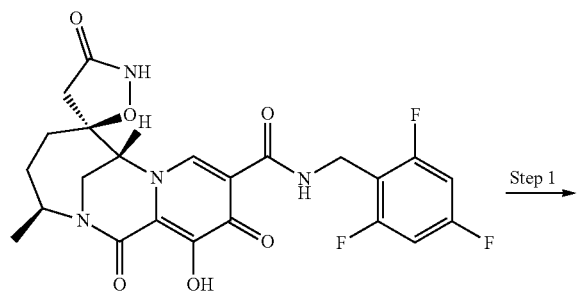

Step 1

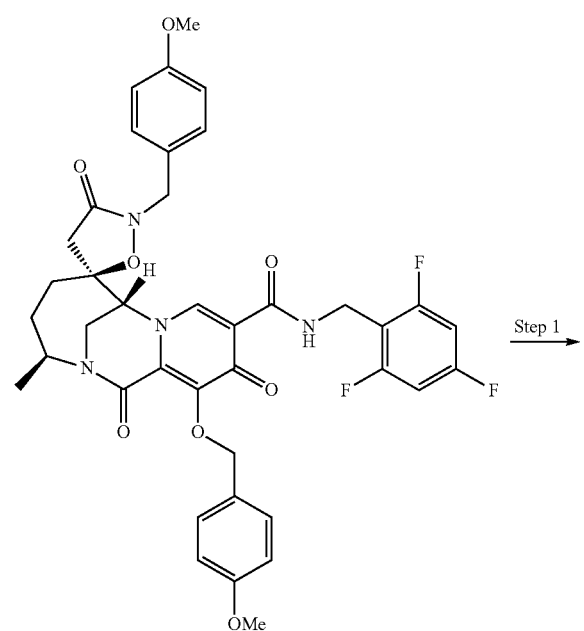

Step 1

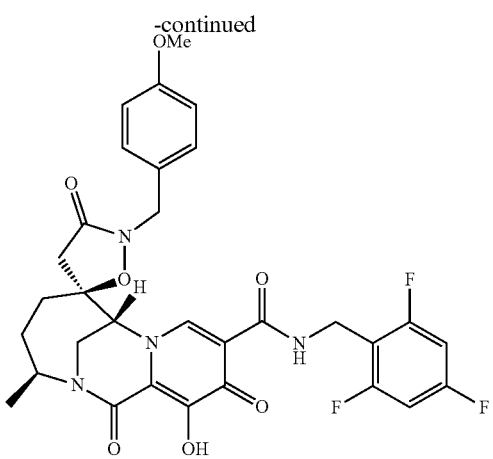

Step 1: Preparation of (3'S,5S,7'R)-2-(4-methoxybenzyl)-12'-((4-methoxybenzyl)oxy)-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide The mixture of (3'S,5S,7'R)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide (40.0 mg, 0.079 mmol), 1-(bromomethyl)-4-methoxy-benzene (41.3 mg, 0.205 mmol), potassium carbonate (65.4 mg, 0.474 mmol) and potassium iodide (3.93 mg, 0.0237 mmol) in DMF (0.5 mL) was heated at 100° C. for 1 h. The reaction was then cooled to rt, diluted with EtOAc, washed with water, brine, dried over sodium sulfate, filtered and concentrated. The residue was used without further purification.

Step 2: Preparation of (3'S,5S,7'R)-12'-hydroxy-2-(4-methoxybenzyl)-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide Crude (3'S,5S,7'R)-2-(4-methoxybenzyl)-12'-((4-methoxybenzyl)oxy)-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide from Step 1 was treated with a mixture of Toluene (0.2 mL) and TFA (0.2 mL) at room temperature for 3 h. The reaction was concentrated, redissolved in DMF, filtered, and purified by reverse phase chromatography to afford (3'S,5S,7'R)-12'-hydroxy-2-(4-methoxybenzyl)-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide. LCMS-ESI+ (m/z): calcd H+ for $C_{31}H_{29}F_3N_4O_7$, Theoretical: 626.20, Found: 627.192. 1H NMR (400 MHz, CD3OD) δ 8.52 (s, 1H), 7.33 (d, J=8.6 Hz, 2H), 7.00-6.87 (m, 4H), 4.87-4.80 (m, 1H), 4.71-4.52 (m, 5H), 3.81 (s, 3H), 3.77-3.63 (m, 2H), 3.00 (d, J=16.6 Hz, 1H), 2.48 (d, J=16.7 Hz, 1H), 2.00-1.88 (m, 1H), 1.69-1.55 (m, 2H), 1.46-1.36 (m, 1H), 1.20 (d, J=6.7 Hz, 3H).

Example 120: Preparation of (3'S,5S,7'R)-12'-hydroxy-3'-methyl-1',3,11'-trioxo-2-((R)-1-phenylethyl)-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide and (3'S,5S,7'R)-12'-hydroxy-3'-methyl-1',3,11'-trioxo-2-((S)-1-phenylethyl)-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide
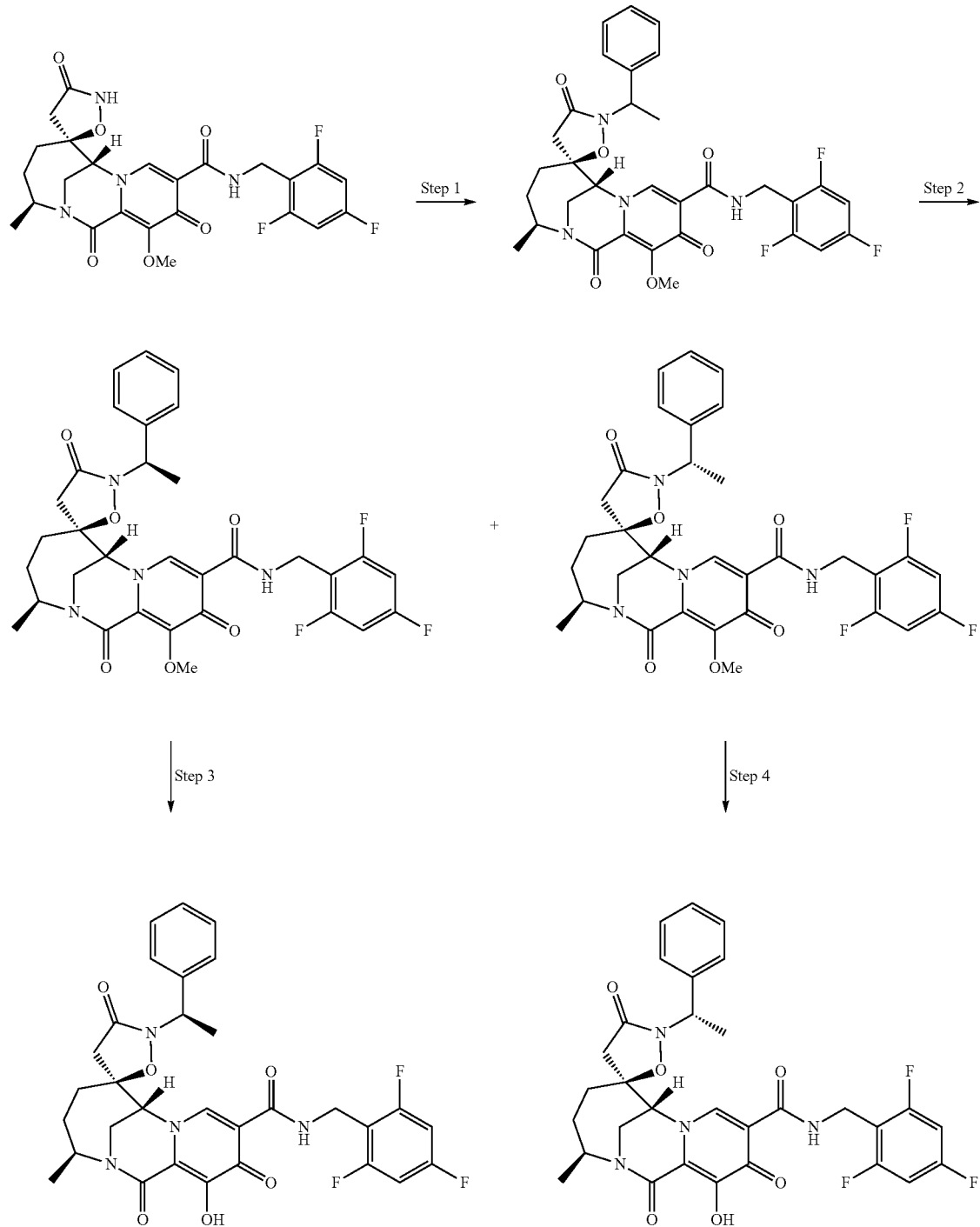

Step 1: Preparation of (3'S,5S,7'R)-12'-methoxy-3'-methyl-1',3,11'-trioxo-2-(1-phenylethyl)-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide (3'S,5S,7'R)-12'-methoxy-3'-methyl-1',3,11'-trioxo-2-(1-phenylethyl)-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide was synthesized in a similar manner as Example 103, except using 1-bromoethylbenzene instead of 5-(bromomethyl)-1-methyl-indazole. The product was purified by normal phase chromatography to give a mixture of diastereomers. LCMS-ESI+(m/z): calcd H+ for C32H31F3N4O6, Theoretical: 624.60, Found: 625.274.

Step 2: Preparation of (3'S,5S,7'R)-12'-methoxy-3'-methyl-1',3,11'-trioxo-2-((R)-1-phenylethyl)-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide and (3'S,5S,7'R)-12'-methoxy-3'-methyl-1',3,11'-trioxo-2-((S)-1-phenylethyl)-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide The diastereomeric pair obtained from Step 1 was subjected to SFC chiral separation using an AD-H column and eluting with 50% EtOH/TFA to give Peak 1 and Peak 2, (3'S,5S,7'R)-12'-methoxy-3'-methyl-1',3,11'-trioxo-2-((R)-1-phenylethyl)-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide and (3'S,5S,7'R)-12'-methoxy-3'-methyl-1',3,11'-trioxo-2-((S)-1-phenylethyl)-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide.

Step 3: Preparation of (3'S,5S,7'R)-12'-hydroxy-3'-methyl-1',3,11'-trioxo-2-((R)-1-phenylethyl)-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide (3'S,5S,7'R)-12'-methoxy-3'-methyl-1',3,11'-trioxo-2-((R)-1-phenylethyl)-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide (0.040 g, 0.064 mmol) was treated with LiCl (0.027 g, 0.64 mmol, 10 equiv) in DMF (0.5 mL) at 100° C. for 5 h, cooled to rt, and purified by reverse phase chromatography to afford the title compound. LCMS-ESI+(m/z): calcd H+ for C31H29F3N4O6, Theoretical: 610.58, Found: 611.233. 1H NMR (400 MHz, CD3OD) δ 8.42 (s, 1H), 7.58-7.49 (m, 2H), 7.47-7.30 (m, 3H), 6.90 (t, J=8.5 Hz, 2H), 5.47 (q, J=7.0 Hz, 1H), 4.74-4.57 (m, 3H), 4.30-4.20 (m, 1H), 3.65 (s, 2H), 2.93 (d, J=16.7 Hz, 1H), 2.52 (d, J=16.7 Hz, 1H), 2.21-2.09 (m, 1H), 2.01-1.87 (m, 2H), 1.70 (d, J=7.0 Hz, 3H), 1.58-1.46 (m, 1H), 1.28 (d, J=6.6 Hz, 3H).

Step 4: Preparation of (3'S,5S,7'R)-12'-hydroxy-3'-methyl-1',3,11'-trioxo-2-((S)-1-phenylethyl)-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide (3'S,5S,7'R)-12'-methoxy-3'-methyl-1',3,11'-trioxo-2-((S)-1-phenylethyl)-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide (0.027 g, 0.043 mmol) was treated with LiCl (0.018 g, 0.43 mmol, 10 equiv) in DMF (0.5 mL) at 100° C. for 5 h, cooled to rt, and purified by reverse phase chromatography to afford the title compound. LCMS-ESI+(m/z): calcd H+ for C31H29F3N4O6, Theoretical: 610.58, Found: 611.302. 1H NMR (400 MHz, DMSO-D6) δ 10.90 (s, 1H), 10.34 (t, J=5.7 Hz, 1H), 8.73 (s, 1H), 7.43-7.35 (m, 4H), 7.34-7.28 (m, 1H), 7.21 (t, J=8.7 Hz, 2H), 5.37 (q, J=7.0 Hz, 1H), 4.80 (s, 1H), 4.65-4.52 (m, 2H), 4.46 (dt, J=9.8, 6.5 Hz, 1H), 3.77 (dd, J=15.2, 2.6 Hz, 1H), 3.66 (dd, J=15.1, 1.9 Hz, 1H), 2.86 (d, J=16.6 Hz, 1H), 2.55-2.46 (m, 1H), 1.84-1.72 (m, 1H), 1.65 (d, J=7.1 Hz, 3H), 1.60-1.42 (m, 2H), 1.33-1.20 (m, 1H), 1.12 (d, J=6.6 Hz, 3H).

Example 121: Preparation of (2S,3'S,7'R)-12'-hydroxy-3'-methyl-1',5,11'-trioxo-N-(2,4,6-trifluorobenzyl)-1',4',5',11'-tetrahydro-3'H,7'H-spiro[pyrrolidine-2,6'-[2,7]methanopyrido[1,2-a][1,4]diazonine]-10'-carboxamide

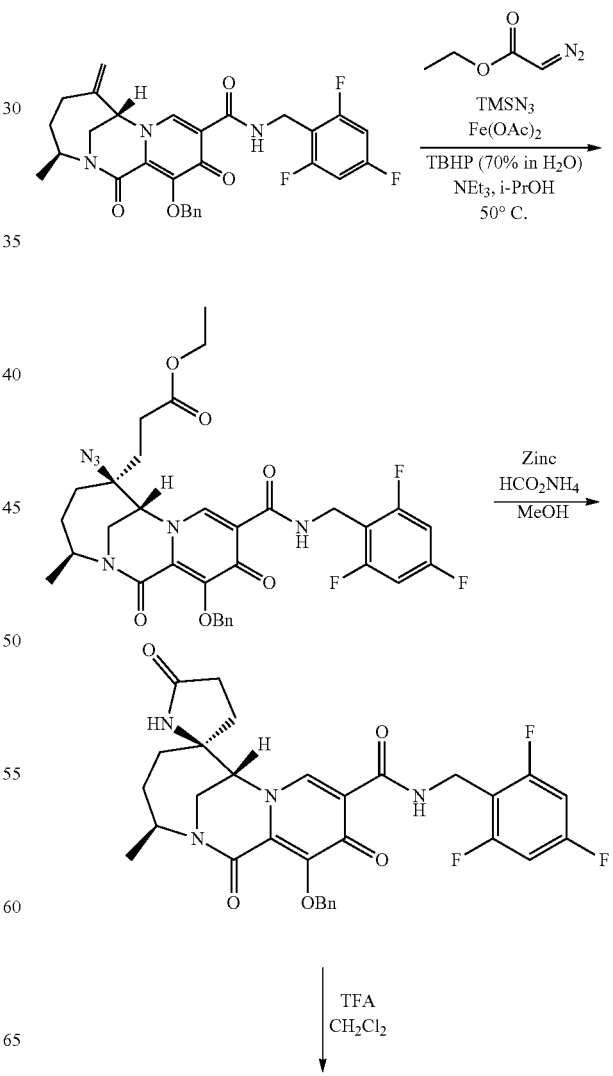

-continued

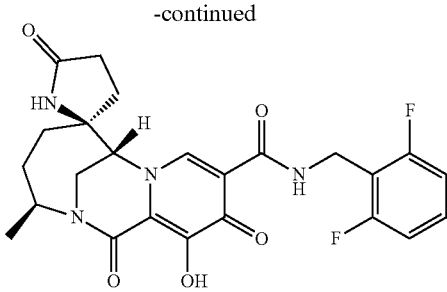

Step 1: Preparation of ethyl 3-((3S,6S,7R)-6-azido-12-(benzyloxy)-3-methyl-1,11-dioxo-10-((2,4,6-trifluorobenzyl)carbamoyl)-1,4,5,6,7,11-hexahydro-3H-2,7-methanopyrido[1,2-a][1,4]diazonin-6-yl)propanoate A suspension of Intermediate C (80 mg, 0.15 mmol) and iron(II) acetate (2.6 mg, 0.015 mmol, 0.1 equiv) in i-PrOH (2.2 mL) was sparged with argon then treated with triethylamine (42 uL, 0.30 mmol, 2 equiv), azidotrimethylsilane (40 uL, 0.30 mmol, 2 equiv), ethyl diazoacetate (36 uL, 0.30 mmol, 2 equiv), and tert-butyl hydroperoxide (60 uL, 0.45 mmol, 3 equiv). The reaction mixture was further sparged with argon for ~5 minutes then sealed and heated to 50° C. Additional portions of iron(II) acetate (0.1 equiv), triethylamine (2 equiv), azidotrimethylsilane (2 equiv), ethyl diazoacetate (2 equiv), and tert-butyl hydroperoxide (3 equiv) were added at 24 hours, on day 4, and on day 5. After 6 days, the reaction mixture was cooled to room temperature and diluted with EtOAc and saturated aqueous sodium bicarbonate. The layers were separated and the aqueous layer was further extracted with EtOAc (2×). The combined organic layer was dried with sodium sulfate, filtered and concentrated. The crude residue was purified by silica gel column chromatography (0-100% EtOAc in hexanes) to afford the title compound. MS (m/z) 667.04 [M+H]+.

Step 2: Preparation of (2S,3'S,7'R)-12'-(benzyloxy)-3'-methyl-1',5,11'-trioxo-N-(2,4,6-trifluorobenzyl)-1',4',5',11'-tetrahydro-3'H,7'H-spiro[pyrrolidine-2,6'-[2,7]methanopyrido[1,2-a][1,4]diazonine]-10'-carboxamide A solution of ethyl 3-((3S,6S,7R)-6-azido-12-(benzyloxy)-3-methyl-1,11-dioxo-10-((2,4,6-trifluorobenzyl)carbamoyl)-1,4,5,6,7,11-hexahydro-3H-2,7-methanopyrido[1,2-a][1,4]diazonin-6-yl)propanoate (35 mg, 0.053 mmol) in MeOH (1 mL) was treated with zinc (0.014 g, 0.21 mmol, 4 equiv) and ammonium formate (20 mg, 0.32 mmol, 6 equiv) and stirred at room temperature overnight. The reaction mixture was diluted with EtOAc, washed with saturated ammonium chloride and further extracted with EtOAc (2×). The combined organic layers were dried with sodium sulfate, filtered and concentrated. The crude residue was purified by silica gel column chromatography (0-100% EtOAc in hexanes) to afford the title compound. MS (m/z) 595.04 [M+H]+.

Step 3: Preparation of (2S,3'S,7'R)-12'-hydroxy-3'-methyl-1',5,11'-trioxo-N-(2,4,6-trifluorobenzyl)-1',4',5',11'-tetrahydro-3'H,7'H-spiro[pyrrolidine-2,6'-[2,7]methanopyrido[1,2-a][1,4]diazonine]-10'-carboxamide A solution of (2S,3'S,7'R)-12'-(benzyloxy)-3'-methyl-1',5,11'-trioxo-N-(2,4,6-trifluorobenzyl)-1',4',5',11'-tetrahydro-3'H,7'H-spiro[pyrrolidine-2,6'-[2,7]methanopyrido[1,2-a][1,4]diazonine]-10'-carboxamide (8.0 mg, 0.013 mmol) in DCM (0.5 mL) was treated with TFA (0.5 mL) and stirred at room temperature for 4 hours. The reaction mixture was concentrated, purified by reverse phase preparative HPLC (0-100% MeCN in water with 0.1% TFA) and lyophilized to afford the title compound as a single diastereomer. MS (m/z) 505.16 [M+H]+. 1H NMR (400 MHz, Chloroform-d) δ 10.39 (t, J=5.7 Hz, 1H), 9.11 (s, 1H), 8.50 (s, 1H), 6.74-6.60 (m, 2H), 4.75 (dt, J=10.3, 6.7 Hz, 1H), 4.66 (d, J=5.6 Hz, 2H), 4.14 (s, 1H), 3.84-3.77 (m, 1H), 3.74 (dd, J=15.3, 2.7 Hz, 1H), 2.52 (t, J=7.9 Hz, 2H), 2.18 (dt, J=13.5, 8.7 Hz, 1H), 2.11-2.00 (m, 1H), 1.75 (dd, J=15.3, 6.9 Hz, 1H), 1.70-1.55 (m, 2H), 1.48 (dd, J=15.3, 12.0 Hz, 1H), 1.33 (d, J=6.6 Hz, 3H).

Example 122: Preparation of (2R,3'S,7'R)-12'-hydroxy-3'-methyl-1',11'-dioxo-N-(2,4,6-trifluorobenzyl)-1',4',5',11'-tetrahydro-3'H,7'H-spiro[pyrrolidine-2,6'-[2,7]methanopyrido[1,2-a][1,4]diazonine]-10'-carboxamide

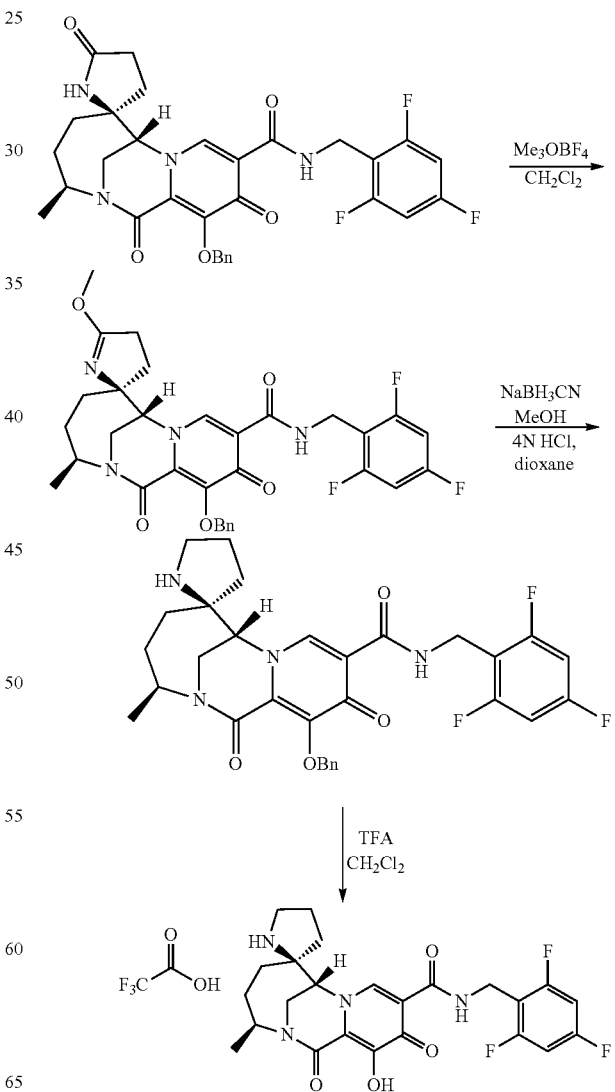

Step 1: Preparation of (2S,3'S,7'R)-12'-(benzyloxy)-5-methoxy-3'-methyl-1',11'-dioxo-N-(2,4,6-trifluorobenzyl)-1',3,4,4',5',11'-hexahydro-3'H,7'H-spiro[pyrrole-2,6'-[2,7]methanopyrido[1,2-a][1,4]diazonine]-10'-carboxamide A solution of (2S,3'S,7'R)-12'-(benzyloxy)-3'-methyl-1',5,11'-trioxo-N-(2,4,6-trifluorobenzyl)-1',4',5',11'-tetrahydro-3'H,7'H-spiro[pyrrolidine-2,6'-[2,7]methanopyrido[1,2-a][1,4]diazonine]-10'-carboxamide (4.0 mg, 0.007 mmol), prepared according to Example 121, in DCM was treated with trimethyloxonium tetrafluoroborate (1.3 mg, 1.5 mmol) and stirred at room temperature overnight. The reaction mixture was quenched with brine and extracted into EtOAc (3×). The combined organic layers were dried with sodium sulfate, filtered and concentrated to afford the title compound, which was carried on to the next step without further purification. MS (m/z) 609.11 [M+H]+.

Step 2: Preparation of (2R,3'S,7'R)-12'-(benzyloxy)-3'-methyl-1',11'-dioxo-N-(2,4,6-trifluorobenzyl)-1',4',5',11'-tetrahydro-3'H,7'H-spiro[pyrrolidine-2,6'-[2,7]methanopyrido[1,2-a][1,4]diazonine]-10'-carboxamide A solution of crude (2S,3'S,7'R)-12'-(benzyloxy)-5-methoxy-3'-methyl-1',11'-dioxo-N-(2,4,6-trifluorobenzyl)-1',3,4,4',5',11'-hexahydro-3'H,7'H-spiro[pyrrole-2,6'-[2,7]methanopyrido[1,2-a][1,4]diazonine]-10'-carboxamide from Step 1 in MeOH was treated with a small pipet tip of bromocresol green and sodium cyanoborohydride (0.8 mg, 0.013 mmol, 2 equiv) followed by careful dropwise addition of HCl/dioxane until a color change from blue to yellow first persisted. After 10 minutes, the reaction mixture was quenched with saturated aqueous sodium bicarbonate, extracted into EtOAc, dried with sodium sulfate, filtered and concentrated. The crude residue was purified by reverse phase preparative HPLC (0-100% MeCN in water with 0.1% TFA) and lyophilized to afford the title compound. MS (m/z) 581.10 [M+H]+.

Step 3: Preparation of (2R,3'S,7'R)-12'-hydroxy-3'-methyl-1',11'-dioxo-N-(2,4,6-trifluorobenzyl)-1',4',5',11'-tetrahydro-3'H,7'H-spiro[pyrrolidine-2,6'-[2,7]methanopyrido[1,2-a][1,4]diazonine]-10'-carboxamide A solution of (2R,3'S,7'R)-12'-(benzyloxy)-3'-methyl-1',11'-dioxo-N-(2,4,6-trifluorobenzyl)-1',4',5',11'-tetrahydro-3'H,7'H-spiro[pyrrolidine-2,6'-[2,7]methanopyrido[1,2-a][1,4]diazonine]-10'-carboxamide from Step 2 in DCM (0.5 mL) was treated with TFA (0.5 mL) and stirred at room temperature for 3 hours. The reaction mixture was concentrated, purified by reverse phase preparative HPLC (0-100% MeCN in water with 0.1% TFA) and lyophilized to afford the title compound as a single diastereomer. MS (m/z) 491.17 [M+H]+. 1H NMR (400 MHz, Methanol-d4) δ 10.43 (s, 1H), 8.53 (s, 1H), 6.91 (t, J=8.5 Hz, 2H), 4.80-4.55 (m, 4H), 4.06-3.77 (m, 2H), 3.69-3.51 (m, 2H), 2.36-1.88 (m, 5H), 1.79-1.50 (m, 3H), 1.30 (d, J=7.0 Hz, 3H).

Example 123: Preparation of (2R,3'S,7'R)-4,12'-dihydroxy-3'-methyl-1',11'-dioxo-N-(2,4,6-trifluorobenzyl)-1',4,4',5,5',11'-hexahydro-3H,3'H,7'H-spiro[furan-2,6'-[2,7]methanopyrido[1,2-a][1,4]diazonine]-10'-carboxamide

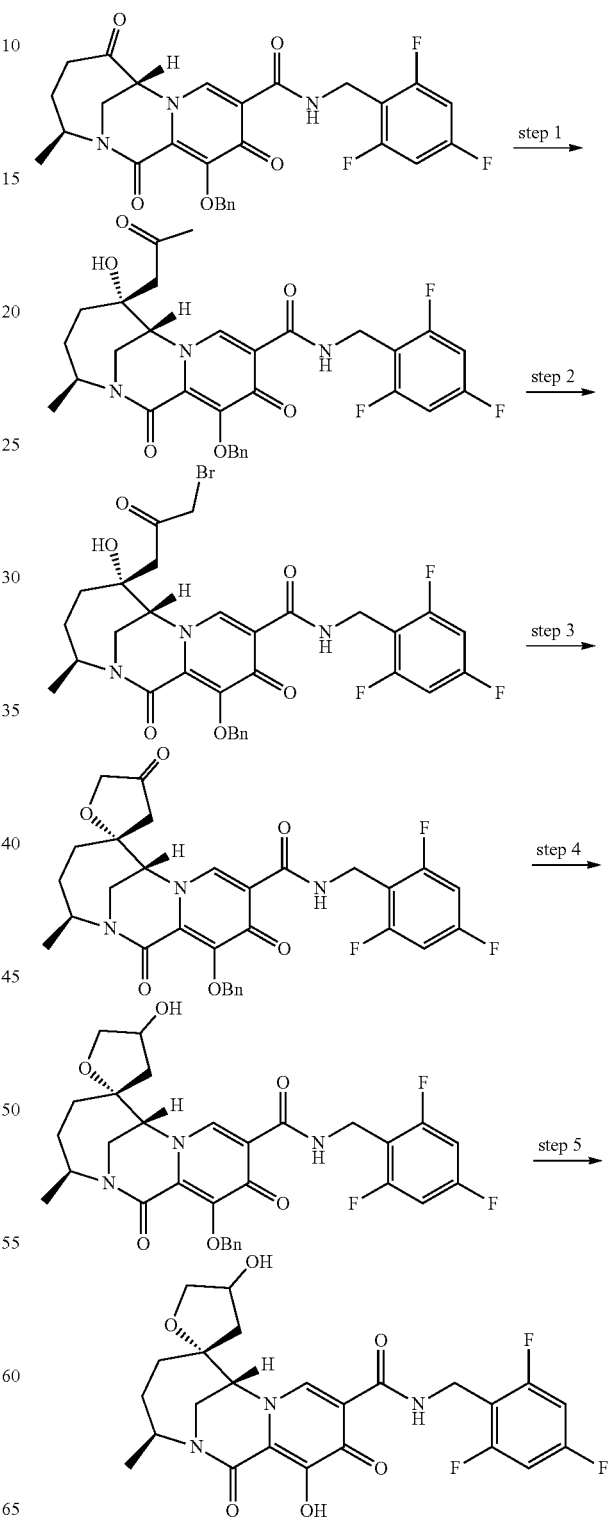

Step 1: Preparation of (3S,6R,7R)-12-(benzyloxy)-6-hydroxy-3-methyl-1,11-dioxo-6-(2-oxopropyl)-N-(2,4,6-trifluorobenzyl)-1,4,5,6,7,11-hexahydro-3H-2,7-methanopyrido[1,2-a][1,4]diazonine-10-carboxamide To a solution of (3S,7R)-12-(benzyloxy)-3-methyl-1,6,11-trioxo-N-(2,4,6-trifluorobenzyl)-1,4,5,6,7,11-hexahydro-3H-2,7-methanopyrido[1,2-a][1,4]diazonine-10-carboxamide (200 mg, 0.371 mmol), prepared according to Example 55, in THF (5.0 mL) at −78° C. under nitrogen atmosphere was added isopropenyloxy(trimethyl)silane (241 mg, 1.85 mmol) followed by 1.0N TBAF in THF (0.371 mL, 0.371 mmol) dropwise. The resulting mixture was allowed to slowly warm up to room temperature and stirred at room temperature overnight. The reaction was then quenched with water, extracted with EtOAc. The organic layer was washed with brine, dried over sodium sulfate, filtered, and concentrated. The residue was purified by silica gel column chromatography. LCMS-ESI+(m/z): calcd H+ for C31H30F3N3O6, Theoretical: 597.21, Found: 598.183.

Step 2: Preparation of (3S,6R,7R)-12-(benzyloxy)-6-(3-bromo-2-oxopropyl)-6-hydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide To a solution of (3S,6R,7R)-12-(benzyloxy)-6-hydroxy-3-methyl-1,11-dioxo-6-(2-oxopropyl)-N-(2,4,6-trifluorobenzyl)-1,4,5,6,7,11-hexahydro-3H-2,7-methanopyrido[1,2-a][1,4]diazonine-10-carboxamide (182 mg, 0.305 mmol) in MeOH (3.0 mL) at 0° C. was added bromine (73.1 mg, 0.915 mmol) dropwise. The resulting mixture was stirred at 0° C. for 5 minutes and then removed from the cooling bath and stirred at room temperature overnight. The reaction was quenched with saturated sodium bicarbonate, extracted with EtOAc, the organic layer was washed with brine, dried over sodium sulfate, filtered, and concentrated. The resulting residue was purified by silica gel column chromatography. LCMS-ESI+(m/z): calcd H+ for C31H29BrF3N3O6, Theoretical: 675.12, Found: 676.147. 1H NMR (400 MHz, CDCl3) δ 10.43 (s, 1H), 8.24 (d, J=9.4 Hz, 1H), 7.59-7.47 (m, 2H), 7.43-7.31 (m, 3H), 6.71-6.54 (m, 2H), 5.72-5.60 (m, 1H), 5.20 (d, J=10.4 Hz, 1H), 5.05 (d, J=10.4 Hz, 1H), 4.81-4.70 (m, 1H), 4.55-4.44 (m, 2H), 4.40-4.28 (m, 1H), 4.17 (s, 1H), 3.46-3.40 (m, 1H), 3.30-3.19 (m, 1H), 3.11-2.92 (m, 2H), 2.78 (d, J=13.3 Hz, 1H), 2.03-1.93 (m, 1H), 1.70-1.48 (m, 2H), 1.37-1.30 (m, 1H), 1.15 (d, J=6.7 Hz, 3H).

Step 3: Preparation of (2R,3'S,7'R)-12'-(benzyloxy)-3'-methyl-1',4,11'-trioxo-N-(2,4,6-trifluorobenzyl)-1',4,4',5,5',1'-hexahydro-3H,3'H,7'H-spiro[furan-2,6'-[2,7]methanopyrido[1,2-a][1,4]diazonine]-10'-carboxamide To a solution of (3S,6R,7R)-12-(benzyloxy)-6-(3-bromo-2-oxopropyl)-6-hydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (72 mg, 0.106 mmol) in THF (0.9 mL) at 0° C. was added DBU (19.4 mg, 0.128 mmol). The resulting mixture was stirred at 0° C. for 20 minutes before it was quenched with 1N HCl. The mixture was then diluted with EtOAc, layers were separated, the organic layer was washed with saturated sodium bicarbonate and brine, dried over sodium sulfate, filtered, and concentrated. The residue was purified by silica gel column chromatography. LCMS-ESI+(m/z): calcd H+ for C31H28F3N3O6, Theoretical: 595.19, Found: 596.073.

Step 4: Preparation of (2R,3'S,7'R)-12'-(benzyloxy)-4-hydroxy-3'-methyl-1',11'-dioxo-N-(2,4,6-trifluorobenzyl)-1',4,4',5,5',11'-hexahydro-3H,3'H,7'H-spiro[furan-2,6'-[2,7]methanopyrido[1,2-a][1,4]diazonine]-10'-carboxamide To a solution of (2R,3'S,7'R)-12'-(benzyloxy)-3'-methyl-1',4,11'-trioxo-N-(2,4,6-trifluorobenzyl)-1',4,4',5,5',11'-hexahydro-3H,3'H,7'H-spiro[furan-2,6'-[2,7]methanopyrido[1,2-a][1,4]diazonine]-10'-carboxamide (5 mg, 0.008 mmol) in MeOH (0.5 ml) at 0° C. was added sodium borohydride (0.3 mg, 0.0084 mmol). After ten minutes, the reaction was quenched with AcOH, and the resulting mixture was purified by reverse phase chromatography. Fractions containing desired product were pooled and lyophilized.

Step 5: Preparation of (2R,3'S,7'R)-4,12'-dihydroxy-3'-methyl-1',11'-dioxo-N-(2,4,6-trifluorobenzyl)-1',4,4',5,5',11'-hexahydro-3H,3'H,7'H-spiro[furan-2,6'-[2,7]methanopyrido[1,2-a][1,4]diazonine]-10'-carboxamide (2R,3'S,7'R)-12'-(benzyloxy)-4-hydroxy-3'-methyl-1',11'-dioxo-N-(2,4,6-trifluorobenzyl)-1',4,4',5,5',11'-hexahydro-3H,3'H,7'H-spiro[furan-2,6'-[2,7]methanopyrido[1,2-a][1,4]diazonine]-10'-carboxamide from Step 4, was treated with toluene (0.1 mL) and TFA (0.1 mL) at room temperature overnight. The reaction was then concentrated and purified by reverse phase chromatography to give the title product. LCMS-ESI+(m/z): calcd H+ for C24H24F3N3O6, Theoretical: 507.16, Found: 508.183. 1H NMR (400 MHz, CD3OD) δ 8.27 (s, 1H), 6.97-6.86 (m, 2H), 4.72-4.59 (m, 4H), 4.34 (s, 1H), 4.10 (dd, J=9.3, 4.9 Hz, 1H), 3.82-3.64 (m, 3H), 2.30 (dd, J=13.5, 6.6 Hz, 1H), 2.09 (dt, J=13.5, 5.8 Hz, 2H), 1.97-1.84 (m, 1H), 1.56 (dt, J=15.2, 11.2 Hz, 1H), 1.36 (dd, J=14.9, 11.7 Hz, 1H), 1.29 (d, J=6.6 Hz, 3H).

Example 124: Preparation of (3'S,4R,7'R)-12'-hydroxy-3',6-dimethyl-1',11'-dioxo-N-(2,4,6-trifluorobenzyl)-1',4',5',11'-tetrahydro-3'H,7'H-spiro[[1,3]dioxane-4,6'-[2,7]methanopyrido[1,2-a][1,4]diazonine]-10'-carboxamide

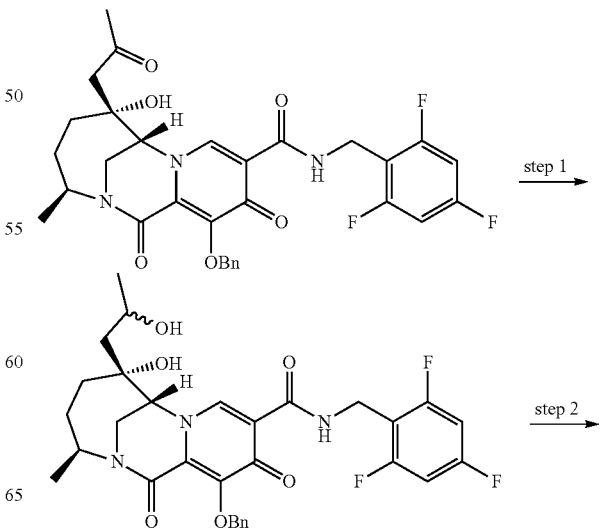

-continued

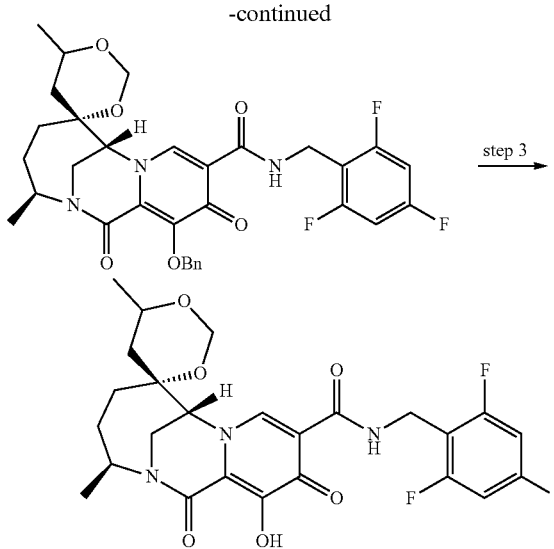

Step 1: Preparation of (3S,6R,7R)-12-(benzyloxy)-6-hydroxy-6-(2-hydroxypropyl)-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide To a solution of (3S,6R,7R)-12-(benzyloxy)-6-hydroxy-3-methyl-1,11-dioxo-6-(2-oxopropyl)-N-(2,4,6-trifluorobenzyl)-1,4,5,6,7,11-hexahydro-3H-2,7-methanopyrido[1,2-a][1,4]diazonine-10-carboxamide (25 mg, 0.0418 mmol), prepared according to Step 1 of Example 123, in MeOH (1.0 mL) at 0° C. was added sodium borohydride (1.59 mg, 0.0418 mmol). After ten minutes, the reaction was quenched with saturated ammonium chloride and extracted with EtOAc. The organic layer was washed with brine, dried over sodium sulfate, filtered and concentrated. LCMS-ESI+ (m/z): calcd H+ for C31H32F3N3O6, Theoretical: 599.22, Found: 600.200.

Step 2: Preparation of (3'S,4R,7'R)-12'-(benzyloxy)-3',6-dimethyl-1',11'-dioxo-N-(2,4,6-trifluorobenzyl)-1',4',5',11'-tetrahydro-3'H,7'H-spiro[[1,3]dioxane-4,6'-[2,7]methanopyrido[1,2-a][1,4]diazonine]-10'-carboxamide To a solution of (3S,6R,7R)-12-(benzyloxy)-6-hydroxy-6-(2-hydroxypropyl)-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (11 mg, 0.0183 mmol) in toluene (0.3 mL) at room temperature was added paraformaldehyde (18.17 mg, 0.202 mmol) and pyridinium p-toluenesulfonate (2.53 mg, 0.01 mmol). The resulting mixture was heated at 100° C. overnight. The reaction was then cooled to room temperature, concentrated, redissolved in DMF, filtered, and purified by reverse phase chromatography. Fractions containing product were pooled and lyophilized.

Step 3: Preparation of (3'S,4R,7'R)-12'-hydroxy-3',6-dimethyl-1',11'-dioxo-N-(2,4,6-trifluorobenzyl)-1',4',5',11'-tetrahydro-3'H,7'H-spiro[[1,3]dioxane-4,6'-[2,7]methanopyrido[1,2-a][1,4]diazonine]-10'-carboxamide (3'S,4R,7'R)-12'-(benzyloxy)-3',6-dimethyl-1',11'-dioxo-N-(2,4,6-trifluorobenzyl)-1',4',5',11'-tetrahydro-3'H,7'H-spiro[[1,3]dioxane-4,6'-[2,7]methanopyrido[1,2-a][1,4]diazonine]-10'-carboxamide from Step 2 was dissolved in DMF (0.2 mL) and treated with lithium chloride (7.7 mg, 0.183 mmol) at 100° C. for two hours. The reaction mixture was cooled to room temperature, filtered and purified by reverse phase chromatography to give (3'S,4R,7'R)-12'-hydroxy-3',6-dimethyl-1',11'-dioxo-N-(2,4,6-trifluorobenzyl)-1',4',5',11'-tetrahydro-3'H,7'H-spiro[[1,3]dioxane-4,6'-[2,7]methanopyrido[1,2-a][1,4]diazonine]-10'-carboxamide. LCMS-ESI+(m/z): calcd H+ for C25H26F3N3O6, Theoretical: 521.18, Found: 522.213. 1H NMR (400 MHz, MeOD) δ 8.53 (s, 1H), 6.92 (t, J=8.5 Hz, 2H), 5.00 (d, J=6.4 Hz, 1H), 4.95-4.90 (m, 2H), 4.75-4.61 (m, 3H), 4.25-4.13 (m, 1H), 3.86-3.70 (m, 2H), 2.22 (dd, J=14.5, 2.9 Hz, 1H), 2.06-1.92 (m, 1H), 1.72 (dd, J=15.1, 7.6 Hz, 1H), 1.59 (dd, J=14.5, 11.6 Hz, 2H), 1.46-1.35 (m, 1H), 1.30 (dd, J=7.6, 6.4 Hz, 6H).

Example 125: Preparation of (3'S,7'R)-12'-hydroxy-3'-methyl-1',11'-dioxo-N-(2,4,6-trifluorobenzyl)-1',4',5',11'-tetrahydro-3'H,7'H-spiro[[1,3]dioxolane-2,6'-[2,7]methanopyrido[1,2-a][1,4]diazonine]-10'-carboxamide

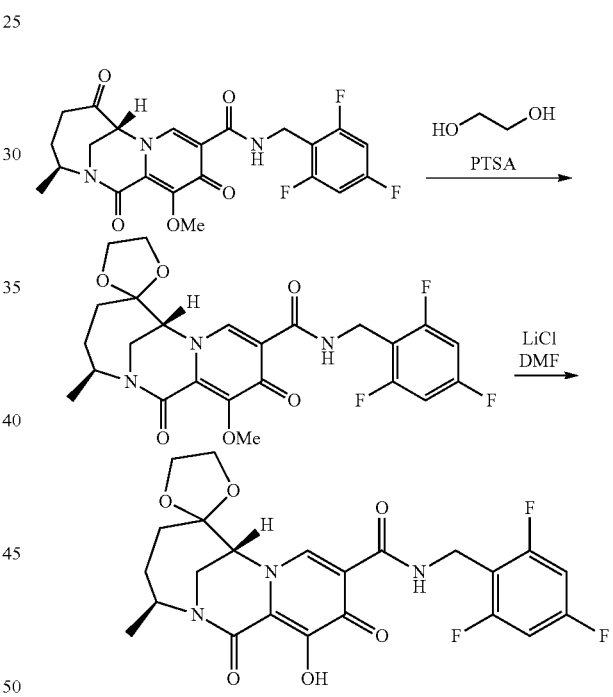

Step 1: Preparation of (3'S,7'R)-12'-methoxy-3'-methyl-1',11'-dioxo-N-(2,4,6-trifluorobenzyl)-1',4',5',1'-tetrahydro-3'H,7'H-spiro[[1,3]dioxolane-2,6'-[2,7]methanopyrido[1,2-a][1,4]diazonine]-10'-carboxamide To a solution of (3S,7R)-12-methoxy-3-methyl-1,6,11-trioxo-N-(2,4,6-trifluorobenzyl)-1,4,5,6,7,11-hexahydro-3H-2,7-methanopyrido[1,2-a][1,4]diazonine-10-carboxamide (20 mg, 0.043 mmol), prepared according to Example 103, in toluene (2 mL) was added p-toluenesulfonic acid monohydrate (2 mg, 0.0086 mmol) and 1,2-ethanediol (8.4 mg, 0.13 mmol). To the mixture was added small amount anhydrous MgSO4. The reaction mixture was stirred at 100° C. for 2 days. The reaction mixture was cooled to rt and the residue was purified by reverse phase prep HPLC, eluting with 5-100% ACN/H$_2$O. MS (m/z) 508.17 [M+H]+.

Step 2: Preparation of (3'S,7'R)-12'-hydroxy-3'-methyl-1',11'-dioxo-N-(2,4,6-trifluorobenzyl)-1',4',5',11'-tetrahydro-3'H,7'H-spiro[[1,3]dioxolane-2,6'-[2,7]methanopyrido[1,2-a][1,4]diazonine]-10'-carboxamide The solution of (3'S,7'R)-12'-methoxy-3'-methyl-1',11'-dioxo-N-(2,4,6-trifluorobenzyl)-1',4',5',11'-tetrahydro-3'H,7'H-spiro[[1,3]dioxolane-2,6'-[2,7]methanopyrido[1,2-a][1,4]diazonine]-10'-carboxamide (2.0 mg, 0.0039 mmol) and LiCl (1.67 mg, 0.094 mmol) in DMF (1 mL) was stirred at 100° C. overnight. The reaction mixture was filtered and purified by reverse phase prep HPLC, eluting with 5-100% ACN/H$_2$O to give title compound. MS (m/z) 494.14 [M+H]+. 1H NMR (400 MHz, Methanol-d4) δ 8.37 (s, 1H), 6.96-6.87 (m, 2H), 4.73-4.59 (m, 3H), 4.32 (q, J=2.0 Hz, 1H), 4.26-4.19 (m, 1H), 4.16 (dd, J=7.1, 5.0 Hz, 2H), 4.02-3.93 (m, 1H), 3.76 (t, J=2.1 Hz, 2H), 2.00 (dtd, J=15.3, 7.0, 1.3 Hz, 1H), 1.86 (dt, J=15.2, 11.3 Hz, 1H), 1.73 (dd, J=15.3, 7.2 Hz, 1H), 1.39 (ddd, J=15.5, 11.8, 1.3 Hz, 1H), 1.29 (d, J=6.7 Hz, 3H).

Example 126: Preparation of (2R,3'S,4R,7'R)-12'-hydroxy-3',4-dimethyl-1',11'-dioxo-N-(2,4,6-trifluorobenzyl)-1',4',5',11'-tetrahydro-3'H,7'H-spiro[[1,3]dioxolane-2,6'-[2,7]methanopyrido[1,2-a][1,4]diazonine]-10'-carboxamide and (2S,3'S,4R,7'R)-12'-hydroxy-3',4-dimethyl-1',11'-dioxo-N-(2,4,6-trifluorobenzyl)-1',4',5',11'-tetrahydro-3'H,7'H-spiro[[1,3]dioxolane-2,6'-[2,7]methanopyrido[1,2-a][1,4]diazonine]-10'-carboxamide To a solution of (3S,7R)-12-(benzyloxy)-3-methyl-1,6,11-trioxo-N-(2,4,6-trifluorobenzyl)-1,4,5,6,7,11-hexahydro-3H-2,7-methanopyrido[1,2-a][1,4]diazonine-10-carboxamide (50 mg, 0.093 mmol), prepared according to Example 55, in toluene (2 mL) was added p-toluenesulfonic acid monohydrate (35.3 mg, 0.185 mmol) and (R)-(−)-1,2-propanediol (21.2 mg, 0.278 mmol). To the mixture was added a small amount of MgSO$_4$. The reaction mixture was stirred at 95° C. for 2 days. The reaction mixture was cooled down to rt, concentrated, and the residue was purified by reverse phase prep HPLC to give the two titled compounds.

Peak 1: MS (m/z): 508.24 [M+H]+. 1H NMR (400 MHz, Methanol-d4) δ 8.47 (s, 1H), 6.98-6.85 (m, 2H), 4.72 (d, J=14.5 Hz, 1H), 4.69-4.57 (m, 2H), 4.32-4.19 (m, 3H), 3.83-3.70 (m, 2H), 3.70-3.62 (m, 1H), 2.03-1.91 (m, 1H), 1.90-1.72 (m, 2H), 1.41-1.29 (m, 4H), 1.28 (d, J=6.7 Hz, 3H).

Peak 2: MS (m/z): 508.21 [M+H]+. 1H NMR (400 MHz, Methanol-d4) δ 8.38 (s, 1H), 6.98-6.85 (m, 2H), 4.76-4.59 (m, 3H), 4.49 (dp, J=8.7, 5.9 Hz, 1H), 4.35-4.20 (m, 2H), 3.82-3.68 (m, 2H), 3.54-3.42 (m, 1H), 2.08-1.94 (m, 1H), 1.87 (dt, J=15.3, 11.3 Hz, 1H), 1.72 (dd, J=15.1, 7.1 Hz, 1H), 1.49-1.37 (m, 1H), 1.35 (d, J=6.0 Hz, 3H), 1.29 (d, J=6.7 Hz, 3H).

Example 127: Preparation of (2R,3'S,4S,7'R)-12'-hydroxy-3',4-dimethyl-1',11'-dioxo-N-(2,4,6-trifluorobenzyl)-1',4',5',11'-tetrahydro-3'H,7'H-spiro[[1,3]dioxolane-2,6'-[2,7]methanopyrido[1,2-a][1,4]diazonine]-10'-carboxamide

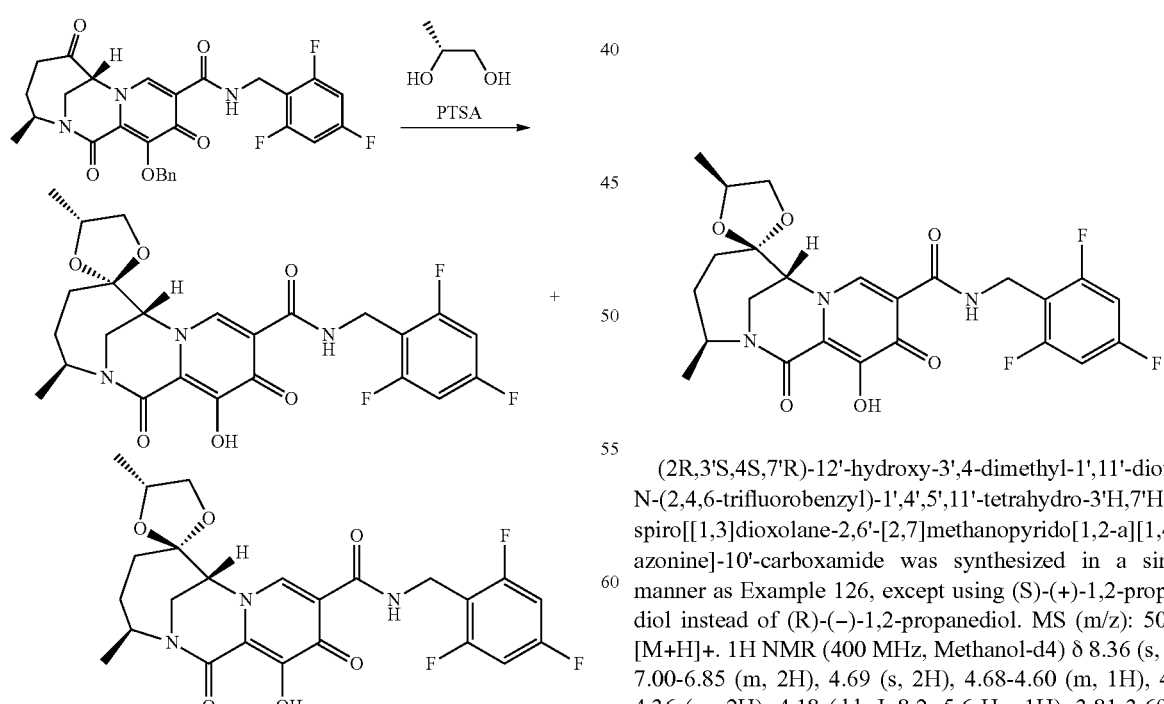

(2R,3'S,4S,7'R)-12'-hydroxy-3',4-dimethyl-1',11'-dioxo-N-(2,4,6-trifluorobenzyl)-1',4',5',11'-tetrahydro-3'H,7'H-spiro[[1,3]dioxolane-2,6'-[2,7]methanopyrido[1,2-a][1,4]diazonine]-10'-carboxamide was synthesized in a similar manner as Example 126, except using (S)-(+)-1,2-propanediol instead of (R)-(−)-1,2-propanediol. MS (m/z): 508.22 [M+H]+. 1H NMR (400 MHz, Methanol-d4) δ 8.36 (s, 1H), 7.00-6.85 (m, 2H), 4.69 (s, 2H), 4.68-4.60 (m, 1H), 4.47-4.36 (m, 2H), 4.18 (dd, J=8.2, 5.6 Hz, 1H), 3.81-3.69 (m, 3H), 2.05-1.92 (m, 1H), 1.92-1.76 (m, 2H), 1.40 (d, J=6.0 Hz, 3H), 1.31-1.26 (m, 4H).

Example 128: Preparation of (3'S,7'R)-12'-hydroxy-3'-methyl-1',11'-dioxo-N-(2,4,6-trifluorobenzyl)-1',4',5',11'-tetrahydro-3'H,7'H-spiro[[1,3]dioxane-2,6'-[2,7]methanopyrido[1,2-a][1,4]diazonine]-10'-carboxamide

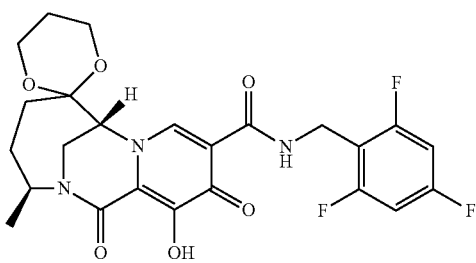 [SMILES: C[C@H]1CCC2(OCCCO2)[C@H]2CN1C(=O)c1c(O)c(=O)c(C(=O)NCc3c(F)cc(F)cc3F)cn12]

(3'S,7'R)-12'-hydroxy-3'-methyl-1',11'-dioxo-N-(2,4,6-trifluorobenzyl)-1',4',5',11'-tetrahydro-3'H,7'H-spiro[[1,3]dioxane-2,6'-[2,7]methanopyrido[1,2-a][1,4]diazonine]-10'-carboxamide was prepared in similar manner as Example 126, except that 1,3-propanediol was used instead of (R)-(−)-1,2-propanediol. MS (m/z): 508.24 [M+H]+. 1H NMR (400 MHz, Methanol-d4) δ 8.44 (s, 1H), 7.00-6.86 (m, 2H), 4.68 (s, 2H), 4.62 (dt, J=10.9, 4.4 Hz, 1H), 4.33 (dt, J=3.4, 1.6 Hz, 1H), 4.07-3.88 (m, 3H), 3.84 (ddt, J=11.9, 5.6, 1.7 Hz, 1H), 3.77-3.64 (m, 2H), 2.82 (dd, J=16.2, 7.6 Hz, 1H), 2.16-1.92 (m, 2H), 1.64 (dt, J=15.1, 11.2 Hz, 1H), 1.50 (dt, J=13.3, 2.6 Hz, 1H), 1.27 (d, J=6.7 Hz, 3H), 0.90 (dd, J=16.1, 11.5 Hz, 1H).

Example 129: Preparation of (3'S,7'R)—N-(2,4-difluorobenzyl)-12'-hydroxy-3'-methyl-1',11'-dioxo-1',4',5',11'-tetrahydro-3'H,7'H-spiro[[1,3]dioxolane-2,6'-[2,7]methanopyrido[1,2-a][1,4]diazonine]-10'-carboxamide (3'S,7'R)—N-(2,4-difluorobenzyl)-12'-hydroxy-3'-methyl-1',11'-dioxo-1',4',5',11'-tetrahydro-3'H,7'H-spiro[[1,3]dioxolane-2,6'-[2,7]methanopyrido[1,2-a][1,4]diazonine]-10'-carboxamide was prepared in similar manner as Example 126, except that (3S,7R)-12-(benzyloxy)-N-(2,4-difluorobenzyl)-3-methyl-1,6,11-trioxo-1,4,5,6,7,11-hexahydro-3H-2,7-methanopyrido[1,2-a][1,4]diazonine-10-carboxamide, prepared according to Example 56, was used instead of (3S,7R)-12-(benzyloxy)-3-methyl-1,6,11-trioxo-N-(2,4,6-trifluorobenzyl)-1,4,5,6,7,11-hexahydro-3H-2,7-methanopyrido[1,2-a][1,4]diazonine-10-carboxamide. MS (m/z): 476.23 [M+H]+. 1H NMR (400 MHz, Methanol-d4) δ 8.40 (s, 1H), 7.52-7.39 (m, 1H), 7.05-6.89 (m, 2H), 4.76-4.57 (m, 3H), 4.33 (d, J=2.0 Hz, 1H), 4.29-4.19 (m, 1H), 4.16 (dd, J=7.1, 4.9 Hz, 2H), 4.03-3.93 (m, 1H), 3.77 (t, J=2.2 Hz, 2H), 2.07-1.94 (m, 1H), 1.94-1.79 (m, 1H), 1.74 (dd, J=15.2, 7.1 Hz, 1H), 1.46-1.32 (m, 1H), 1.29 (d, J=6.7 Hz, 3H).

Example 130: Preparation of (3'S,4R,7'R)-12'-hydroxy-3'-methyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide

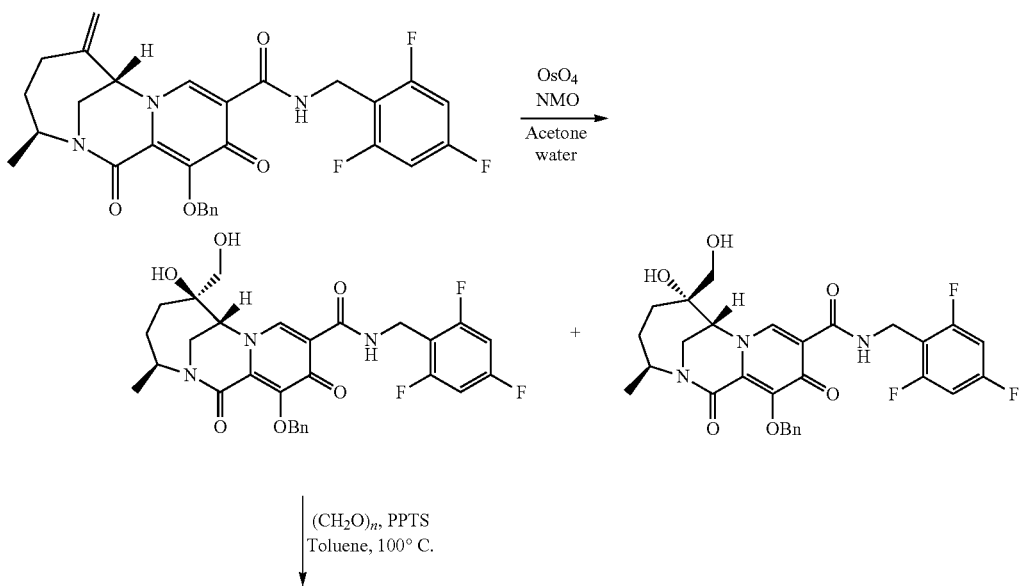

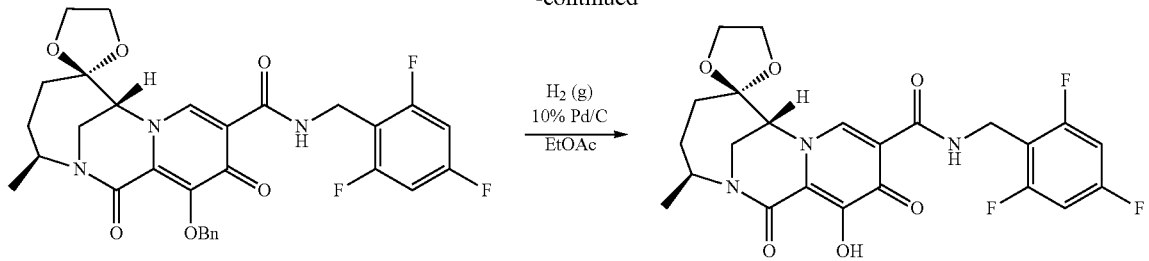

Step 1: Preparation of (3S,6R,7R)-12-(benzyloxy)-6-hydroxy-6-(hydroxymethyl)-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (major) and (3S,6S,7R)-12-(benzyloxy)-6-hydroxy-6-(hydroxymethyl)-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (minor)

A solution of Intermediate C (1.00 g, 1.86 mmol) in 8:1 acetone/water (45 mL) was cooled to 0° C. then treated with 4-methylmorpholine N-oxide (327 mg, 2.79 mmol, 1.5 equiv) and a solution of osmium tetroxide (4 wt % in water, 0.6 mL). The reaction mixture was slowly warmed to room temperature and stirred for ~72 hours then quenched with 10% aqueous sodium sulfite and extracted into EtOAc (3×). The combined organic layers were dried with sodium sulfate, filtered and concentrated. The crude reaction mixture was purified by silica gel column chromatography (0-15% MeOH in DCM) to afford the title compounds.
Peak 1 (Major): MS (m/z) 572.11 [M+H]+.
Peak 2 (Minor): MS (m/z) 572.17 [M+H]+.

Step 2: Preparation of (3'S,4R,7'R)-12'-(benzyloxy)-3'-methyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide A solution of (3S,6R,7R)-12-(benzyloxy)-6-hydroxy-6-(hydroxymethyl)-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (15 mg, 0.026 mmol) in toluene (0.35 mL) was treated with paraformaldehyde (12 mg, 0.13 mmol, 5 equiv) and pyridinium p-toluenesulfonate (1.7 mg, 0.0066 mmol, 0.25 equiv) in a microwave vial. The vial was sealed and heated to 100° C. overnight. The reaction mixture was then cooled to room temperature, adsorbed onto silica gel and purified by silica gel column chromatography (0-100% EtOAc in hexanes) to afford the title compound. MS (m/z) 584.06 [M+H]+.

Step 3: Preparation of (3'S,4R,7'R)-12'-hydroxy-3'-methyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide A solution of (3'S,4R,7'R)-12'-(benzyloxy)-3'-methyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide (5.0 mg, 0.0086 mmol) in EtOAc (1 mL) was evacuated and backfilled with argon (3×cycles) then treated with 10% Pd/C (2 mg) and further evacuated and backfilled with argon (3×cycles) then hydrogen (5×cycles). The reaction mixture was stirred at room temperature under a hydrogen balloon for 2.5 hours, then filtered across Celite, eluted with excess DCM/EtOAc, concentrated, purified by reverse phase preparative HPLC (0-100% neutral MeCN/water) and lyophilized to afford the title compound. MS (m/z) 494.16 [M+H]+. 1H NMR (400 MHz, Methanol-d4) δ 10.52 (t, J=5.8 Hz, 1H), 8.46 (s, 1H), 6.94-6.85 (m, 2H), 5.21 (s, 1H), 5.07 (s, 1H), 4.72-4.60 (m, 3H), 4.50 (s, 1H), 3.94 (d, J=9.5 Hz, 1H), 3.86 (dd, J=15.0, 1.7 Hz, 1H), 3.76 (dd, J=15.0, 2.7 Hz, 1H), 3.42 (d, J=9.6 Hz, 1H), 2.02-1.94 (m, 2H), 1.79 (dt, J=15.5, 3.9 Hz, 1H), 1.51-1.41 (m, 1H), 1.28 (d, J=6.7 Hz, 3H).

Example 131: Preparation of (3'S,4S,7'R)-12'-hydroxy-3'-methyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide

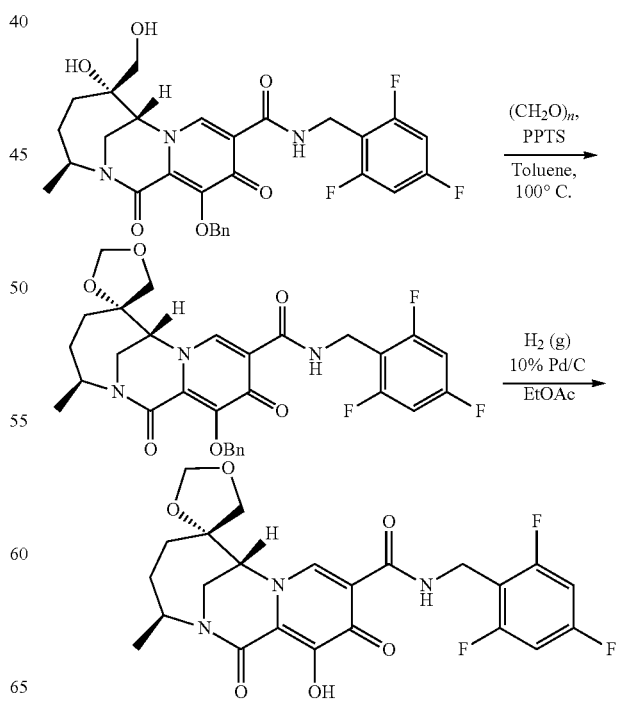

Step 1: Preparation of (3'S,4S,7'R)-12'-(benzyloxy)-3'-methyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide A solution of (3S,6S,7R)-12-(benzyloxy)-6-hydroxy-6-(hydroxymethyl)-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (15.0 mg, 0.026 mmol), prepared according to Step 1 of Example 130, in toluene (0.3 mL) was treated with paraformaldehyde (12 mg, 0.13 mmol, 5 equiv) and pyridinium p-toluenesulfonate (1.7 mg, 0.0066 mmol, 0.25 equiv) in a microwave vial. The vial was sealed and heated to 100° C. overnight. The reaction mixture was then cooled to room temperature, adsorbed onto silica gel and purified by silica gel column chromatography (0-100% EtOAc in hexanes) to afford the title compound. MS (m/z) 584.02 [M+H]+.

Step 2: Preparation of (3'S,4S,7'R)-12'-hydroxy-3'-methyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide A solution of (3'S,4S,7'R)-12'-(benzyloxy)-3'-methyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide (11.0 mg, 0.019 mmol) in EtOAc (1 mL) was evacuated and backfilled with argon (3×cycles) then treated with 10% Pd/C (2 mg) and further evacuated and backfilled with argon then hydrogen. The reaction mixture was stirred at room temperature under a hydrogen balloon for 1 hour, then filtered across Celite, eluted with excess DCM/EtOAc, concentrated, purified by reverse phase preparative HPLC (0-100% neutral MeCN/water) and lyophilized to afford the title compound. MS (m/z) 494.17 [M+H]+. 1H NMR (400 MHz, Methanol-d4) δ 10.58 (t, J=5.4 Hz, 1H), 8.25 (s, 1H), 6.94-6.85 (m, 2H), 5.29 (s, 1H), 4.83 (s, 1H), 4.71-4.57 (m, 3H), 4.32 (d, J=9.3 Hz, 1H), 4.26 (s, 1H), 3.86-3.73 (m, 2H), 3.71 (d, J=9.2 Hz, 1H), 2.12-2.03 (m, 1H), 1.81 (dd, J=14.7, 7.6 Hz, 1H), 1.57-1.35 (m, 2H), 1.27 (d, J=6.7 Hz, 3H).

Example 132: Preparation of (2S,3'S,4R,7'R)-12'-hydroxy-2,3'-dimethyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide

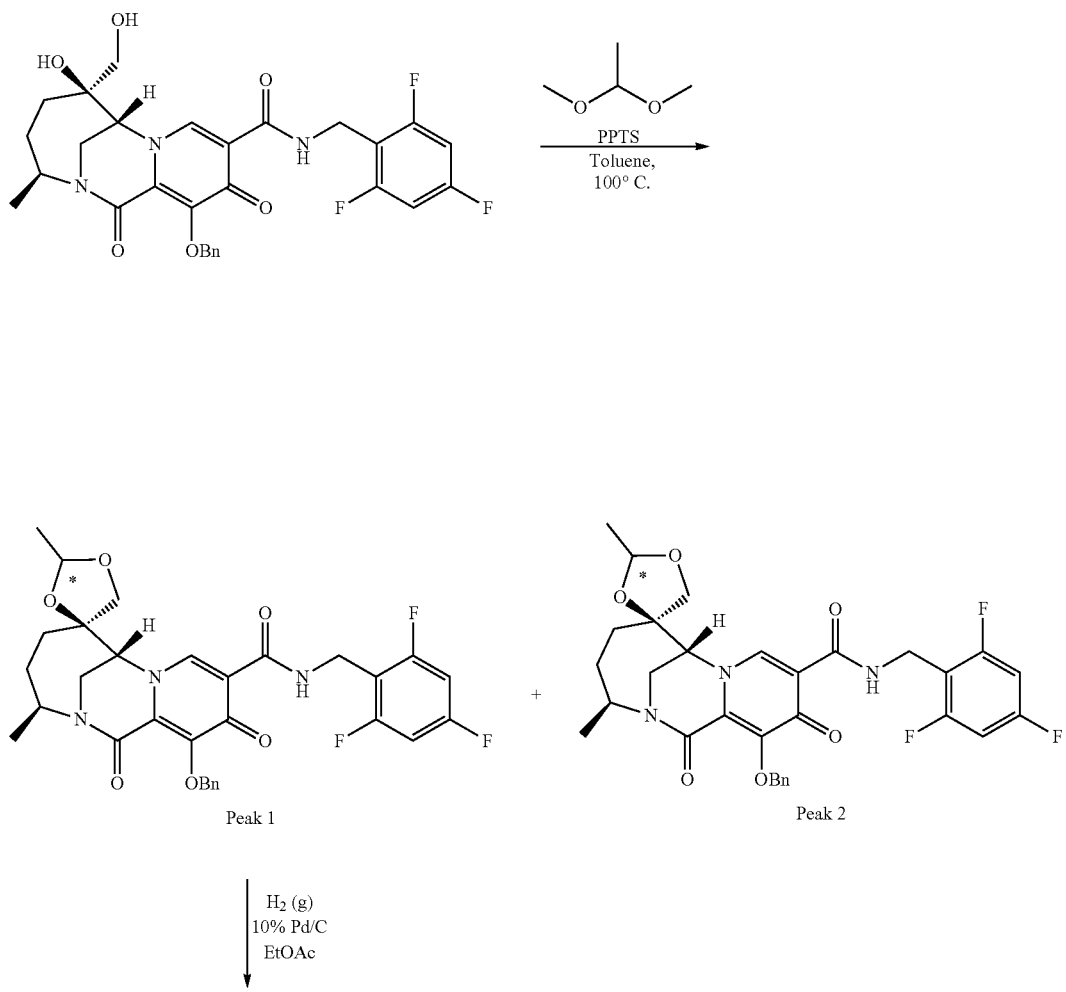

-continued

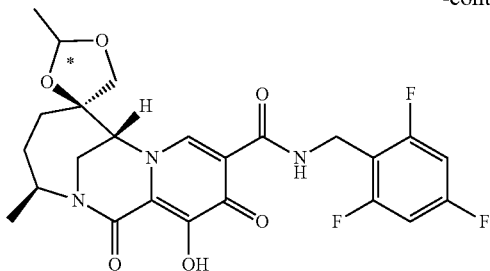

Step 1: Preparation of (2S,3'S,4R,7'R)-12'-(benzyloxy)-2,3'-dimethyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide and (2R,3'S,4R,7'R)-12'-(benzyloxy)-2,3'-dimethyl-1',11'-dioxo-N-(2,4,6-trifluorobenzyl)-1',4',5',1'-tetrahydro-3'H,7'H-spiro[[1,3]dioxolane-4,6'-[2,7]methanopyrido[1,2-a][1,4]diazonine]-10'-carboxamide A solution of (3S,6R,7R)-12-(benzyloxy)-6-hydroxy-6-(hydroxymethyl)-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (35 mg, 0.061 mmol), prepared according to Step 1 of Example 130, in toluene (1.5 mL) was treated with acetaldehyde dimethyl acetal (30 uL, 0.18 mmol, 3 equiv) and pyridinium p-toluenesulfonate (3.8 mg, 0.015 mmol, 0.25 equiv) in a microwave vial. The vial was sealed and heated to 65° C. for 2 hours then to 100° C. overnight. The reaction mixture was then cooled to room temperature, adsorbed onto silica gel and purified by silica gel column chromatography (0-100% EtOAc in hexanes) to afford the title compounds. The impure mixtures were further purified by preparative TLC (1.5:1 EtOAc/hexanes) to afford the separated diastereomers.

Peak 1: MS (m/z) 598.12 [M+H]+.
Peak 2: MS (m/z) 598.10 [M+H]+.

Step 2: Preparation of (2S,3'S,4R,7'R)-12'-hydroxy-2,3'-dimethyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide A solution of (2S,3'S,4R,7'R)-12'-(benzyloxy)-2,3'-dimethyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide (8.0 mg, 0.013 mmol) in EtOAc (1 mL) was evacuated and backfilled with argon (3×cycles) then treated with 10% Pd/C (2.4 mg) and further evacuated and backfilled with argon then hydrogen. The reaction mixture was stirred at room temperature under a hydrogen balloon for 1 hour, then filtered across Celite, eluted with excess DCM/EtOAc, concentrated, purified by reverse phase preparative HPLC (0-100% neutral MeCN/water) and lyophilized to afford the title compound. MS (m/z) 508.21 [M+H]+. 1H NMR (400 MHz, Methanol-d4) δ 8.50 (s, 1H), 6.96-6.83 (m, 2H), 5.38 (q, J=4.8 Hz, 1H), 4.74-4.60 (m, 3H), 4.51 (s, 1H), 3.93 (d, J=9.1 Hz, 1H), 3.82 (d, J=14.9 Hz, 1H), 3.74 (d, J=14.9 Hz, 1H), 3.53 (d, J=9.2 Hz, 1H), 2.00-1.89 (m, 2H), 1.80-1.70 (m, 1H), 1.51-1.42 (m, 1H), 1.37 (d, J=4.8 Hz, 3H), 1.27 (d, J=6.7 Hz, 3H).

Example 133: Preparation of (2R,3'S,4R,7'R)-12'-hydroxy-2,3'-dimethyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide

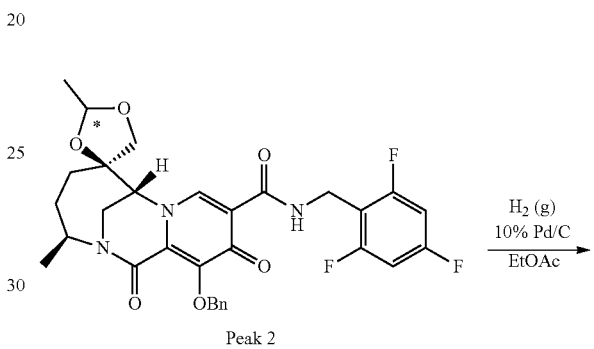

Peak 2

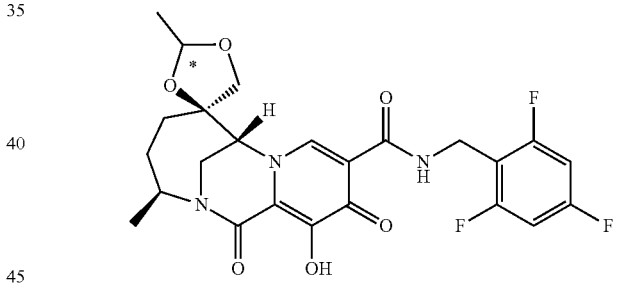

A solution of (2R,3'S,4R,7'R)-12'-(benzyloxy)-2,3'-dimethyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide (14.0 mg, 0.023 mmol), prepared according to Step 1 of Example 132, in EtOAc (1 mL) was evacuated and backfilled with argon (3×cycles) then treated with 10% Pd/C (4.2 mg) and further evacuated and backfilled with argon then hydrogen. The reaction mixture was stirred at room temperature under a hydrogen balloon for 1 hour, then filtered across Celite, eluted with excess DCM/EtOAc, concentrated, purified by reverse phase preparative HPLC (0-100% neutral MeCN/water) and lyophilized to afford the title compound. MS (m/z) 508.23 [M+H]+. 1H NMR (400 MHz, Methanol-d4) δ 8.36 (s, 1H), 6.95-6.83 (m, 2H), 5.23 (q, J=4.9 Hz, 1H), 4.75-4.56 (m, 3H), 4.41 (s, 1H), 4.02 (d, J=10.0 Hz, 1H), 3.82 (dd, J=14.9, 1.8 Hz, 1H), 3.73 (dd, J=14.9, 2.9 Hz, 1H), 3.41 (d, J=10.0 Hz, 1H), 2.07-1.91 (m, 2H), 1.87-1.77 (m, 1H), 1.48 (d, J=4.9 Hz, 3H), 1.45-1.34 (m, 1H), 1.27 (d, J=6.7 Hz, 3H).

Example 134: Preparation of (2S,3'S,4R,7'R)-2-benzyl-12'-hydroxy-3'-methyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide

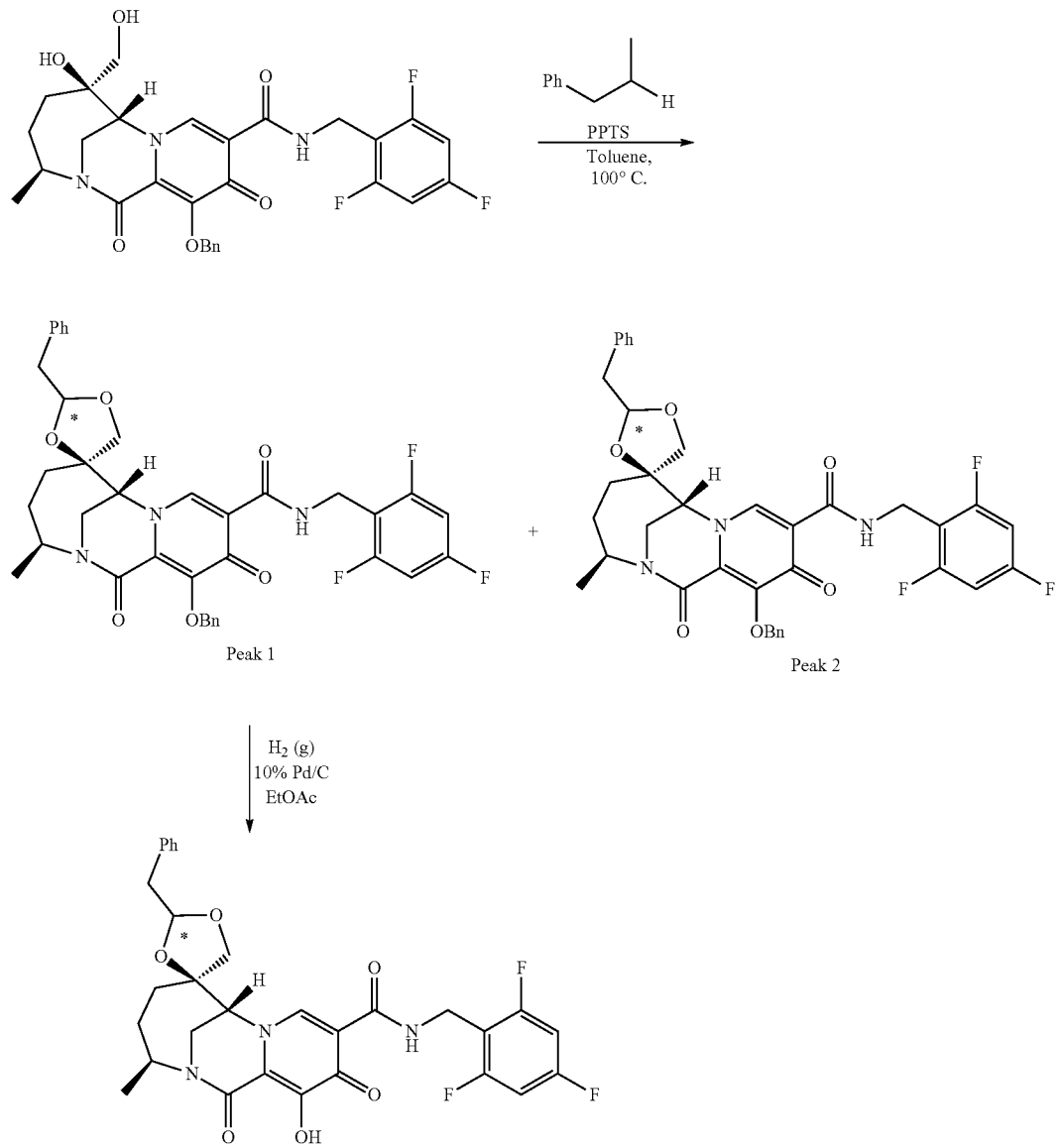

Step 1: Preparation of (2S,3'S,4R,7'R)-2-benzyl-12'-(benzyloxy)-3'-methyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide and (2R,3'S,4R,7'R)-2-benzyl-12'-(benzyloxy)-3'-methyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide A solution of (3S,6R,7R)-12-(benzyloxy)-6-hydroxy-6-(hydroxymethyl)-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (45 mg, 0.079 mmol), prepared according to Step 1 of Example 130, in toluene (1 mL) was treated with phenylacetaldehyde (47 mg, 0.39 mmol, 5 equiv) and pyridinium p-toluenesulfonate (5.0 mg, 0.020 mmol, 0.25 equiv) in a microwave vial. The vial was sealed and heated to 100° C. overnight. The reaction mixture was then cooled to room temperature, adsorbed onto silica gel and purified by silica gel column chromatography (0-100% EtOAc in hexanes) to afford the title compounds. The impure fractions were further purified by preparative TLC (1:1 EtOAc/hexanes) to afford the separated diastereomers.

Peak 1: MS (m/z) 674.07 [M+H]+.

Peak 2: MS (m/z) 674.04 [M+H]+.

Step 2: Preparation of (2S,3'S,4R,7'R)-2-benzyl-12'-hydroxy-3'-methyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide A solution of (2S,3'S,4R,7'R)-2-benzyl-12'-(benzyloxy)-3'-methyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide (25 mg, 0.037 mmol) in EtOAc (2 mL) was evacuated and backfilled with argon (3×cycles) then treated with 10% Pd/C (8 mg) and further evacuated and backfilled with argon then hydrogen. The reaction mixture was stirred at room temperature under a hydrogen balloon for 1 hour, then filtered across Celite, eluted with excess DCM/EtOAc, concentrated, purified by reverse phase preparative HPLC (0-100% neutral MeCN/water) and lyophilized to afford the title compound. MS (m/z) 584.12 [M+H]+. 1H NMR (400 MHz, Methanol-d4) δ 8.53 (s, 1H), 7.29-7.14 (m, 5H), 6.96-6.84 (m, 2H), 5.40 (t, J=4.3 Hz, 1H), 4.73-4.50 (m, 4H), 3.87-3.68 (m, 3H), 3.36-3.32 (m, 1H), 2.93 (d, J=4.3 Hz, 2H), 1.95-1.76 (m, 2H), 1.51 (dd, J=15.4, 6.3 Hz, 1H), 1.38-1.28 (m, 1H), 1.26 (d, J=6.7 Hz, 3H).

Example 135: Preparation of (2R,3'S,4R,7'R)-2-benzyl-12'-hydroxy-3'-methyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide

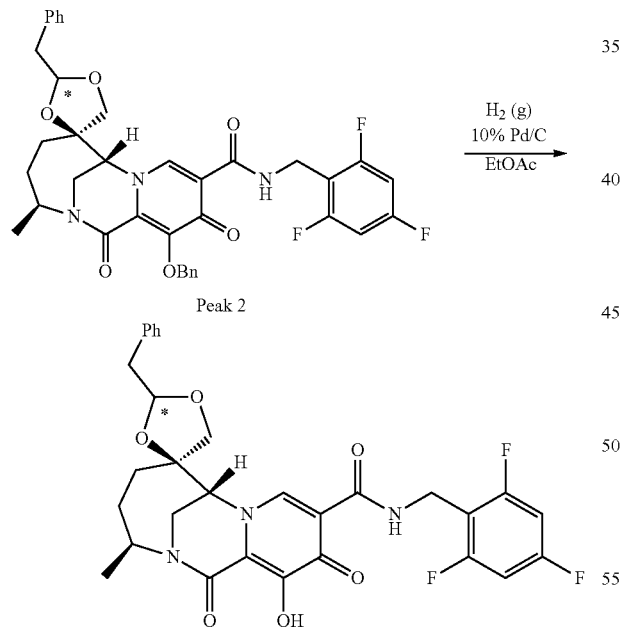

A solution of (2R,3'S,4R,7'R)-2-benzyl-12'-(benzyloxy)-3'-methyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide (20 mg, 0.030 mmol), prepared according to Step 1 of Example 134 in EtOAc (2 mL) was evacuated and backfilled with argon (3×cycles) then treated with 10% Pd/C (8 mg) and further evacuated and backfilled with argon then hydrogen. The reaction mixture was stirred at room temperature under a hydrogen balloon for 4 hours, then filtered across Celite, eluted with excess DCM/EtOAc, concentrated, purified by reverse phase preparative HPLC (0-100% neutral MeCN/water) and lyophilized to afford the title compound. MS (m/z) 584.19 [M+H]+. 1H NMR (400 MHz, Methanol-d4) δ 8.00 (s, 1H), 7.43-7.34 (m, 4H), 7.25 (tt, J=6.3, 2.2 Hz, 1H), 6.97-6.85 (m, 2H), 5.36 (t, J=3.4 Hz, 1H), 4.75-4.63 (m, 2H), 4.57 (dt, J=14.6, 7.4 Hz, 1H), 3.85 (d, J=10.1 Hz, 1H), 3.59 (dd, J=14.9, 1.9 Hz, 1H), 3.44-3.33 (m, 2H), 3.20-3.04 (m, 3H), 1.99-1.91 (m, 2H), 1.81-1.71 (m, 1H), 1.41-1.30 (m, 1H), 1.25 (d, J=6.7 Hz, 3H).

Example 136: Preparation of (3'S,4S,7'R)-2-benzyl-12'-hydroxy-3'-methyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide

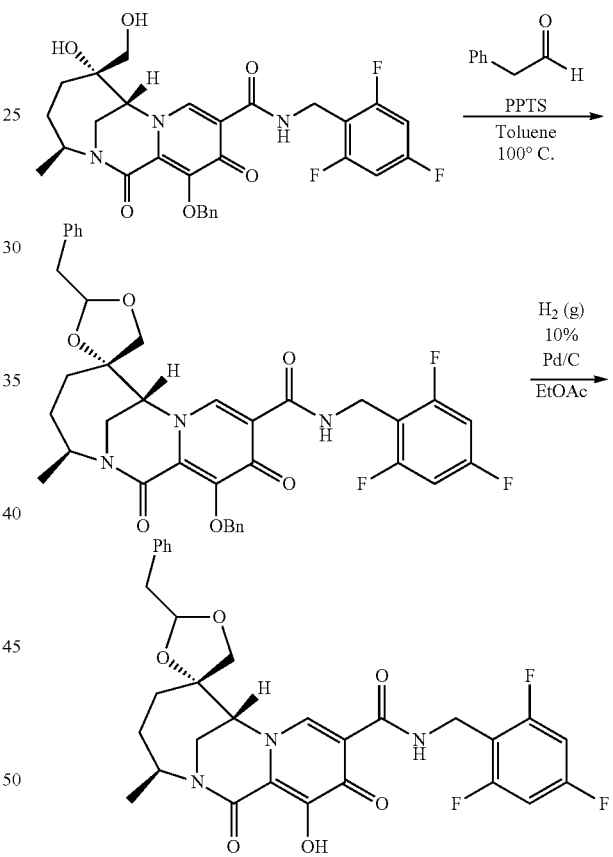

Step 1: Preparation of (3'S,4S,7'R)-2-benzyl-12'-(benzyloxy)-3'-methyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide A solution of (3S,6S,7R)-12-(benzyloxy)-6-hydroxy-6-(hydroxymethyl)-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (45 mg, 0.079 mmol), prepared according to Step 1 of Example 130, in toluene (0.9 mL) was treated with phenylacetaldehyde (47 mg, 0.39 mmol, 5 equiv) and pyridinium p-toluenesulfonate (5.0 mg, 0.020 mmol, 0.25 equiv) in a microwave vial. The vial was sealed and heated to 100° C. overnight. The reaction mixture was then cooled to room temperature, adsorbed onto silica gel and purified by silica gel chromatography (0-100% EtOAc in hexanes) to afford the title compound as a mixture of diastereomers. The impure mixture was further purified by preparative TLC (1.5:1 hexanes/EtOAc) to afford a mixture enriched in the major diastereomer (~80:20) that was carried on to the next step. MS (m/z) 674.07 [M+H]+.

Step 2: Preparation of (3'S,4S,7'R)-2-benzyl-12'-hydroxy-3'-methyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide A solution of (3'S,4S,7'R)-2-benzyl-12'-(benzyloxy)-3'-methyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide (30 mg, 0.045 mmol, ~80:20 dr) in EtOAc (3 mL) was evacuated and backfilled with argon (3×cycles) then treated with 10% Pd/C (6 mg) and further evacuated and backfilled with argon then hydrogen. The reaction mixture was stirred at room temperature under a hydrogen balloon for 3 hours, then filtered across Celite, eluted with excess DCM/EtOAc, concentrated, purified by reverse phase preparative HPLC (0-100% neutral MeCN/water) and lyophilized to afford the title compound (~85:15 dr). MS (m/z) 584.19 [M+H]+. 1H NMR (400 MHz, Methanol-d4) δ 8.52 (s, 1H), 7.20-7.08 (m, 5H), 6.95-6.84 (m, 2H), 5.05 (dd, J=6.3, 4.6 Hz, 1H), 4.77-4.56 (m, 3H), 4.35 (d, J=9.4 Hz, 1H), 4.29 (s, 1H), 3.85-3.71 (m, 3H), 3.15 (dd, J=13.8, 4.6 Hz, 1H), 3.00 (dd, J=13.8, 6.3 Hz, 1H), 2.00 (dt, J=14.9, 7.0 Hz, 1H), 1.77 (dd, J=14.5, 7.6 Hz, 1H), 1.50-1.31 (m, 2H), 1.26 (d, J=6.7 Hz, 3H).

Example 137: Preparation of (3'S,4R,7'R)-12'-hydroxy-2,2,3'-trimethyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide

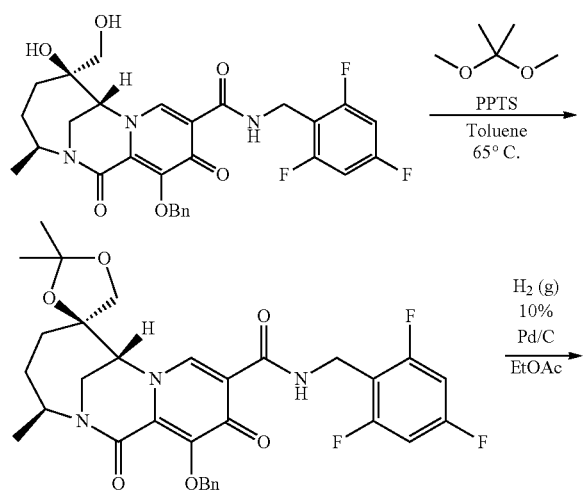

Step 1: Preparation of (3'S,4R,7'R)-12'-(benzyloxy)-2,2,3'-trimethyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide

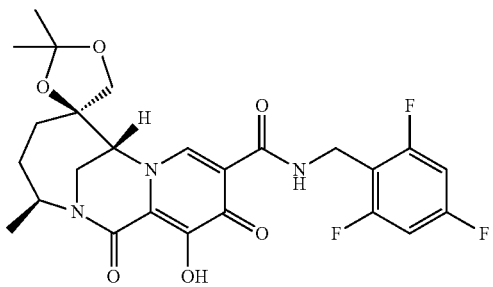

A solution of (3S,6R,7R)-12-(benzyloxy)-6-hydroxy-6-(hydroxymethyl)-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (15 mg, 0.026 mmol), prepared according to Step 1 of Example 130, in toluene (0.6 mL) was treated with 2,2-dimethoxypropane (10 uL, 0.079 mmol, 3 equiv) and pyridinium p-toluenesulfonate (1.6 mg, 0.0066 mmol, 0.25 equiv) in a microwave vial. The vial was sealed and heated to 65° C. for 3 hours. The reaction mixture was then cooled to room temperature, adsorbed onto silica gel and purified by silica gel column chromatography (0-100% EtOAc in hexanes) to afford the title compound. MS (m/z) 612.12 [M+H]+.

Step 2: Preparation of (3'S,4R,7'R)-12'-hydroxy-2,2,3'-trimethyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide A solution of (3'S,4R,7'R)-12'-(benzyloxy)-2,2,3'-trimethyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide (20 mg, 0.033 mmol) in EtOAc (2 mL) was evacuated and backfilled with argon (3×cycles) then treated with 10% Pd/C (4 mg) and further evacuated and backfilled with argon then hydrogen. The reaction mixture was stirred at room temperature under a hydrogen balloon for 2 hours, then filtered across Celite, eluted with excess DCM/EtOAc, concentrated, purified by reverse phase preparative HPLC (0-100% neutral MeCN/water) and lyophilized to afford the title compound. MS (m/z) 522.28 [M+H]+. 1H NMR (400 MHz, Methanol-d4) δ 10.53 (t, J=5.7 Hz, 1H), 8.43 (s, 1H), 6.97-6.83 (m, 2H), 4.73-4.55 (m, 3H), 4.47 (d, J=2.3 Hz, 1H), 4.03 (d, J=9.8 Hz, 1H), 3.81 (dd, J=15.0, 1.8 Hz, 1H), 3.73 (dd, J=14.9, 2.9 Hz, 1H), 3.58 (d, J=9.8 Hz, 1H), 2.01-1.93 (m, 2H), 1.80 (dt, J=15.4, 4.2 Hz, 1H), 1.55 (s, 3H), 1.46-1.35 (m, 1H), 1.40 (s, 3H), 1.27 (d, J=6.7 Hz, 3H).

Example 138: Preparation of (3'S,4S,7'R)-12'-hydroxy-2,2,3'-trimethyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide

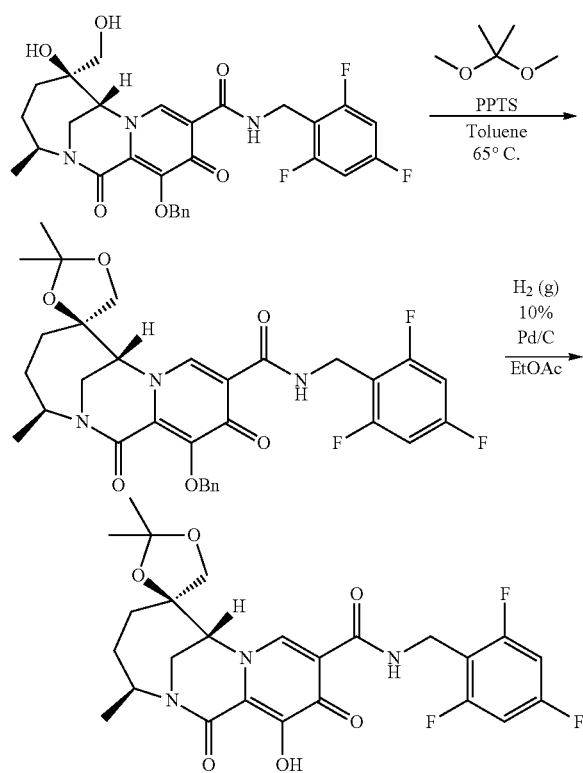

Step 1: Preparation of (3'S,4S,7'R)-12'-(benzyloxy)-2,2,3'-trimethyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide A solution of (3S,6S,7R)-12-(benzyloxy)-6-hydroxy-6-(hydroxymethyl)-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (20 mg, 0.035 mmol), prepared according to Step 1 of Example 130, in toluene (0.3 mL) was treated with 2,2-dimethoxypropane (13 uL, 0.10 mmol, 3 equiv) and pyridinium p-toluenesulfonate (2.2 mg, 0.0087 mmol, 0.25 equiv) in a microwave vial. The vial was sealed and heated to 65° C. for 3 hours. The reaction mixture was then cooled to room temperature, adsorbed onto silica gel and purified by silica gel column chromatography (0-100% EtOAc in hexanes) to afford the title compound. MS (m/z) 612.10 [M+H]+.

Step 2: Preparation (3'S,4S,7'R)-12'-hydroxy-2,2,3'-trimethyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide A solution of (3'S,4S,7'R)-12'-(benzyloxy)-2,2,3'-trimethyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide (16.3 mg, 0.027 mmol) in EtOAc was evacuated and backfilled with argon (3×cycles) then treated with 10% Pd/C (5 mg) and further evacuated and backfilled with argon then hydrogen. The reaction mixture was stirred at room temperature under a hydrogen balloon for 2 hours, then filtered across Celite, eluted with excess DCM/EtOAc, concentrated, purified by reverse phase preparative HPLC (0-100% neutral MeCN/water) and lyophilized to afford the title compound. MS (m/z) 522.22 [M+H]+. 1H NMR (400 MHz, Methanol-d4) δ 8.42 (s, 1H), 6.96-6.84 (m, 2H), 4.75-4.54 (m, 3H), 4.31 (s, 1H), 4.25 (d, J=9.6 Hz, 1H), 4.08 (d, J=9.6 Hz, 1H), 3.83-3.69 (m, 2H), 2.06 (dt, J=14.9, 6.9 Hz, 1H), 1.81 (dd, J=14.4, 7.6 Hz, 1H), 1.57 (s, 3H), 1.55-1.37 (m, 2H), 1.33 (s, 3H), 1.26 (d, J=6.7 Hz, 3H).

Example 139: Preparation of (2R,3'S,7'R)-12'-hydroxy-3'-methyl-1',11'-dioxo-N-(2,4,6-trifluorobenzyl)-1',4',5',11'-tetrahydro-3'H,7'H-spiro[[1,4]dioxane-2,6'-[2,7]methanopyrido[1,2-a][1,4]diazonine]-10'-carboxamide

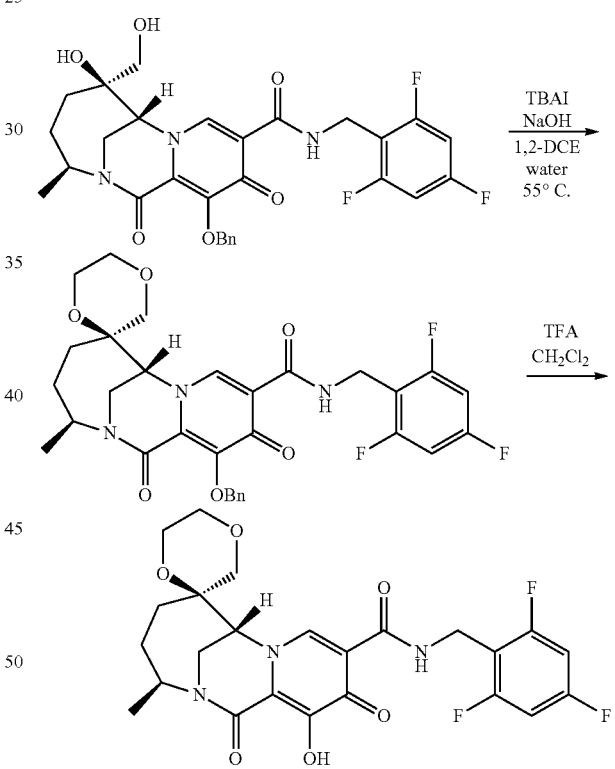

Step 1: Preparation of (2R,3'S,7'R)-12'-(benzyloxy)-3'-methyl-1',11'-dioxo-N-(2,4,6-trifluorobenzyl)-1',4',5',11'-tetrahydro-3'H,7'H-spiro[[1,4]dioxane-2,6'-[2,7]methanopyrido[1,2-a][1,4]diazonine]-10'-carboxamide A solution of (3S,6R,7R)-12-(benzyloxy)-6-hydroxy-6-(hydroxymethyl)-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (10 mg, 0.0175 mmol), prepared according to Step 1 of Example 130, in 1,2-DCE (0.1 mL) was treated with tetrabutylammonium iodide (2.6 mg, 0.007 mmol, 0.4 equiv) and sodium hydroxide (35 mg in 50 uL water, 0.88 mmol, 50 equiv). The reaction vial was sealed and heated to 55° C. Additional portions of sodium hydroxide (35 mg in 50 uL water, 0.88 mmol, 50 equiv) and 1,2-DCE (0.1 mL) were added at 24 hours, on day 4 (2×) and day 5. After 7 days, the reaction mixture was cooled to room temperature then diluted with EtOAc and water. The layers were separated and the aqueous layer was further extracted with EtOAc (2×). The combined organic layers were dried with sodium sulfate, filtered and concentrated. The crude residue was purified by silica gel column chromatography (0-100% EtOAc in hexanes) to afford the title compound. MS (m/z) 598.12 [M+H]+.

Step 2: Preparation of (2R,3'S,7'R)-12'-hydroxy-3'-methyl-1',11'-dioxo-N-(2,4,6-trifluorobenzyl)-1',4',5',11'-tetrahydro-3'H,7'H-spiro[[1,4]dioxane-2,6'-[2,7]methanopyrido[1,2-a][1,4]diazonine]-10'-carboxamide A solution of (2R,3'S,7'R)-12'-(benzyloxy)-3'-methyl-1',11'-dioxo-N-(2,4,6-trifluorobenzyl)-1',4',5',11'-tetrahydro-3'H,7'H-spiro[[1,4]dioxane-2,6'-[2,7]methanopyrido[1,2-a][1,4]diazonine]-10'-carboxamide (15.7 mg, 0.026 mmol) in DCM (0.5 mL) was treated with TFA (0.5 mL) and stirred at room temperature for 3 hours. The reaction mixture was concentrated, purified by reverse phase preparative HPLC (0-100% MeCN in water with 0.1% TFA) and lyophilized to afford the title compound. MS (m/z) 508.26 [M+H]+. 1H NMR (400 MHz, Chloroform-d) δ 10.47 (t, J=5.7 Hz, 1H), 8.68 (s, 1H), 6.75-6.59 (m, 2H), 4.79-4.49 (m, 4H), 3.94-3.85 (m, 1H), 3.83-3.63 (m, 4H), 3.59 (dd, J=14.8, 2.9 Hz, 1H), 3.49 (d, J=12.2 Hz, 1H), 3.10 (d, J=12.1 Hz, 1H), 2.13-2.00 (m, 1H), 1.94-1.70 (m, 2H), 1.27 (d, J=6.6 Hz, 3H), 1.16-0.99 (m, 1H).

Example 140: Preparation of (2S,3'S,7'R)-12'-hydroxy-3'-methyl-1',11'-dioxo-N-(2,4,6-trifluorobenzyl)-1',4',5',11'-tetrahydro-3'H,7'H-spiro[[1,4]dioxane-2,6'-[2,7]methanopyrido[1,2-a][1,4]diazonine]-10'-carboxamide

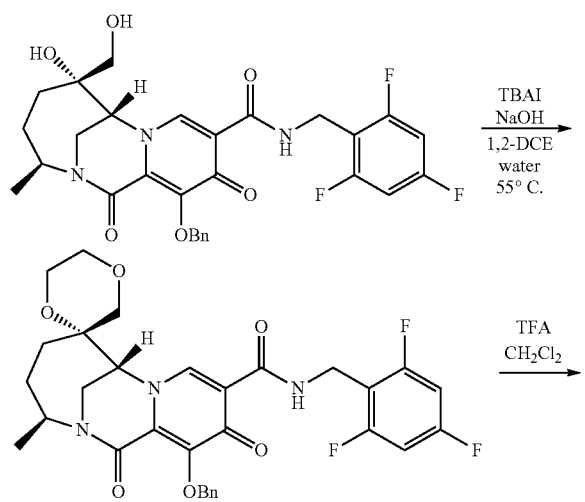

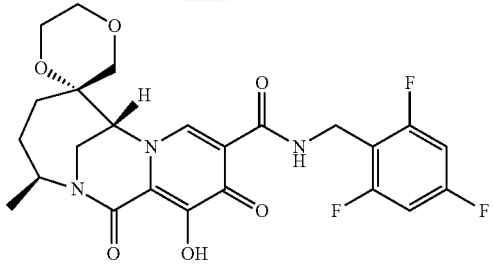

Step 1: Preparation of (2S,3'S,7'R)-12'-(benzyloxy)-3'-methyl-1',11'-dioxo-N-(2,4,6-trifluorobenzyl)-1',4',5',11'-tetrahydro-3'H,7'H-spiro[[1,4]dioxane-2,6'-[2,7]methanopyrido[1,2-a][1,4]diazonine]-10'-carboxamide A solution of (3S,6S,7R)-12-(benzyloxy)-6-hydroxy-6-(hydroxymethyl)-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (10 mg, 0.0175 mmol), prepared according to Step 1 of Example 130, in 1,2-DCE (0.1 mL) was treated with tetrabutylammonium iodide (2.6 mg, 0.007 mmol, 0.4 equiv) and sodium hydroxide (35 mg in 50 uL water, 0.88 mmol, 50 equiv). The reaction vial was sealed and heated to 55° C. Additional portions of sodium hydroxide (35 mg in 50 uL water, 0.88 mmol, 50 equiv) and 1,2-DCE (0.1 mL) were added at 24 hours, on day 4 and on day 5. After 7 days, the reaction mixture was cooled to room temperature then diluted with EtOAc and water. The layers were separated and the aqueous layer was further extracted with EtOAc (2×). The combined organic layers were dried with sodium sulfate, filtered and concentrated. The crude residue was purified by silica gel column chromatography (0-100% EtOAc in hexanes) to afford the title compound. MS (m/z) 598.06 [M+H]+.

Step 2: Preparation of (2S,3'S,7'R)-12'-hydroxy-3'-methyl-1',11'-dioxo-N-(2,4,6-trifluorobenzyl)-1',4',5',11'-tetrahydro-3'H,7'H-spiro[[1,4]dioxane-2,6'-[2,7]methanopyrido[1,2-a][1,4]diazonine]-10'-carboxamide A solution of (2S,3'S,7'R)-12'-(benzyloxy)-3'-methyl-1',11'-dioxo-N-(2,4,6-trifluorobenzyl)-1',4',5',11'-tetrahydro-3'H,7'H-spiro[[1,4]dioxane-2,6'-[2,7]methanopyrido[1,2-a][1,4]diazonine]-10'-carboxamide (10.5 mg, 0.018 mmol) in DCM (0.5 mL) was treated with TFA (0.5 mL) and stirred at room temperature for 3 hours. The reaction mixture was concentrated, purified by reverse phase preparative HPLC (0-100% MeCN in water with 0.1% TFA) and lyophilized to afford the title compound. MS (m/z) 508.20 [M+H]+. 1H NMR (400 MHz, Chloroform-d) δ 10.54 (t, J=5.2 Hz, 1H), 8.52 (s, 1H), 6.73-6.61 (m, 2H), 4.77-4.63 (m, 3H), 4.10 (s, 1H), 3.96 (d, J=11.7 Hz, 1H), 3.84-3.52 (m, 5H), 3.45 (d, J=11.6 Hz, 1H), 3.35 (dd, J=15.3, 1.6 Hz, 1H), 2.51 (dd, J=15.0, 7.9 Hz, 1H), 2.11 (dt, J=14.9, 7.4 Hz, 1H), 1.40-1.08 (m, 2H), 1.26 (d, J=6.7 Hz, 3H).

Example 141: Preparation of (3'S,4R,7'R)-2,2-difluoro-12'-hydroxy-3'-methyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide

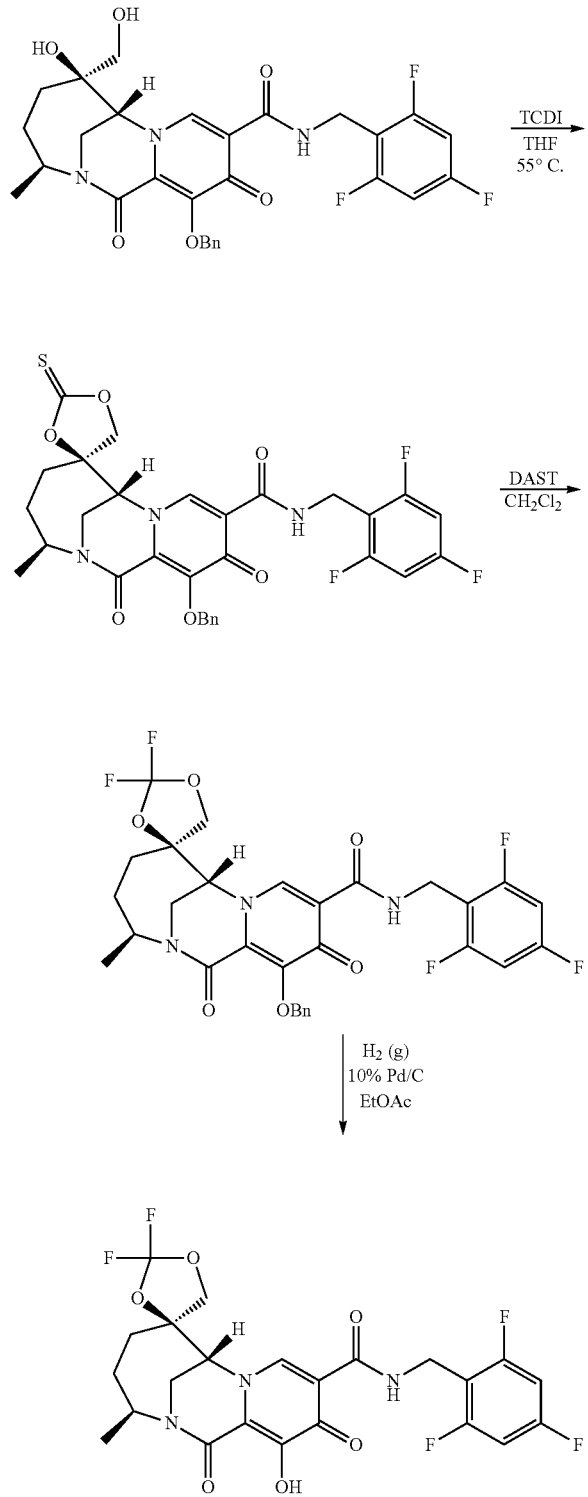

Step 1: Preparation of (3'S,4R,7'R)-12'-(benzyloxy)-3'-methyl-1',11'-dioxo-2-thioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide A solution of (3S,6R,7R)-12-(benzyloxy)-6-hydroxy-6-(hydroxymethyl)-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (50 mg, 0.087 mmol), prepared according to Step 1 of Example 130, in THF (1 mL) was treated with 1,1-thiocarbonyldiimidazole (20.3 mg, 0.11 mmol, 1.3 equiv) and heated to 55° C. overnight. The reaction mixture was cooled to room temperature and purified by silica gel column chromatography (0-100% EtOAc/hexanes) to afford the title compound. MS (m/z) 614.02 [M+H]+.

Step 2: Preparation of (3'S,4R,7'R)-12'-(benzyloxy)-2,2-difluoro-3'-methyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide A solution of (3'S,4R,7'R)-12'-(benzyloxy)-3'-methyl-1',11'-dioxo-2-thioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide (39 mg, 0.064 mmol) in DCM (3 mL) in a polypropylene tube was treated with diethylaminosulfur trifluoride (42 uL, 0.32 mmol, 5 equiv), sealed and stirred at room temperature. Additional portions diethylaminosulfur trifluoride were added at ~24 h, 48 and 72 hours. After 7 days, the reaction mixture was carefully quenched with saturated aqueous sodium bicarbonate and extracted into EtOAc (3×). The combined organic layer was dried with sodium sulfate, filtered and concentrated. The crude residue was purified by silica gel column chromatography (0-100% EtOAc in hexanes) to afford the title compound. MS (m/z) 620.03 [M+H]+.

Step 3: Preparation of (3'S,4R,7'R)-2,2-difluoro-12'-hydroxy-3'-methyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide A solution of (3'S,4R,7'R)-12'-(benzyloxy)-2,2-difluoro-3'-methyl-1',11'-dioxo-N-(2,4,6-trifluorobenzyl)-1',4',5',11'-tetrahydro-3'H,7'H-spiro[[1,3]dioxolane-4,6'-[2,7]methanopyrido[1,2-a][1,4]diazonine]-10'-carboxamide (17 mg, 0.027 mmol) in EtOAc was evacuated and backfilled with argon (3×cycles) then treated with 10% Pd/C (5 mg) and further evacuated and backfilled with argon then hydrogen. The reaction mixture was stirred at room temperature under a hydrogen balloon for 2 hours, then filtered across Celite, eluted with excess DCM/EtOAc, concentrated, purified by reverse phase preparative HPLC (0-100% MeCN/water with 0.1% TFA) and lyophilized to afford the title compound. MS (m/z) 530.18 [M+H]+. 1H NMR (400 MHz, Chloroform-d) δ 10.25 (s, 1H), 8.50 (s, 1H), 6.73-6.59 (m, 2H), 4.73 (dt, J=11.0, 6.5 Hz, 1H), 4.66 (d, J=5.5 Hz, 2H), 4.41 (s, 1H), 4.35 (d, J=9.5, 2.6 Hz, 1H), 3.87 (dd, J=9.5, 2.7 Hz, 1H), 3.76 (d, J=2.1 Hz, 2H), 2.15-2.03 (m, 2H), 1.97-1.84 (m, 1H), 1.60-1.46 (m, 1H), 1.31 (d, J=6.7 Hz, 3H).

339

Example 142: Preparation of (3'S,7'R)-12'-hydroxy-3'-methyl-1',11'-dioxo-N-(2,4,6-trifluorobenzyl)-1',4',5',11'-tetrahydro-3'H,7'H-spiro[benzo[d]imidazole-2,6'-[2,7]methanopyrido[1,2-a][1,4]diazonine]-10'-carboxamide

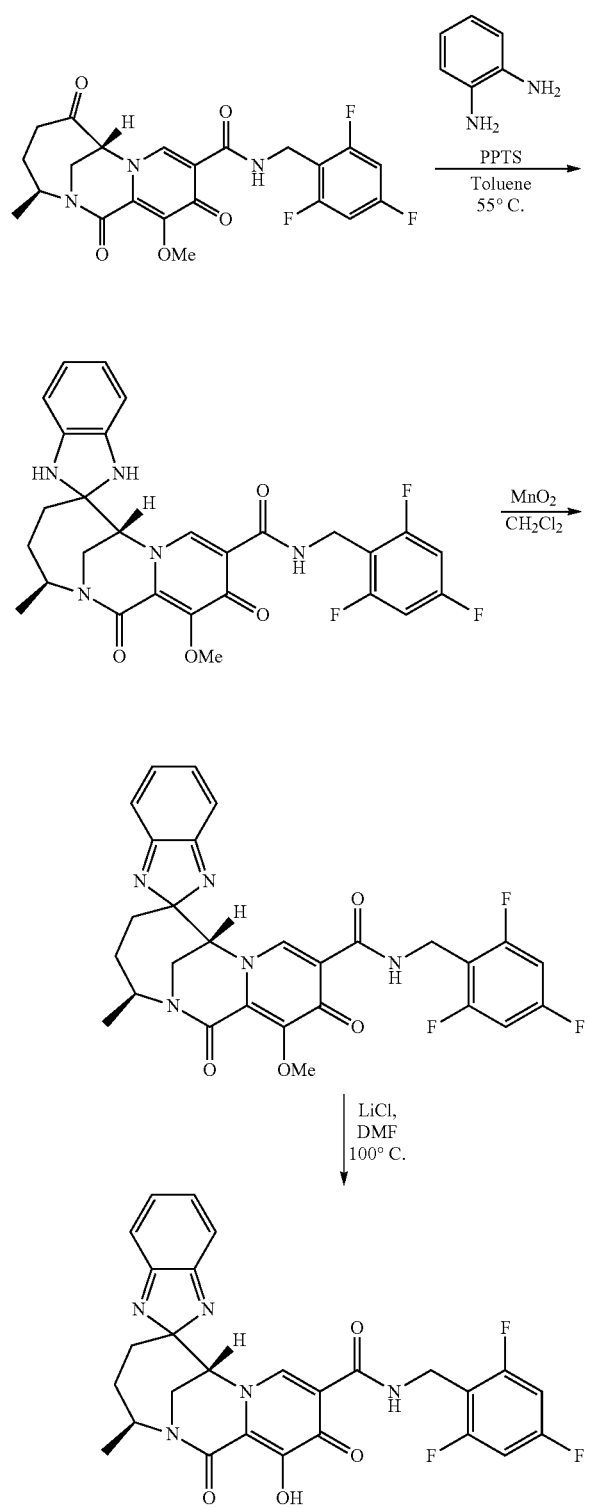

340

Step 1: Preparation of (3'S,7'R)-12'-methoxy-3'-methyl-1',11'-dioxo-N-(2,4,6-trifluorobenzyl)-1,1',3,4',5',11'-hexahydro-3'H,7'H-spiro[benzo[d]imidazole-2,6'-[2,7]methanopyrido[1,2-a][1,4]diazonine]-10'-carboxamide A solution of (3S,7R)-12-methoxy-3-methyl-1,6,11-trioxo-N-(2,4,6-trifluorobenzyl)-1,4,5,6,7,11-hexahydro-3H-2,7-methanopyrido[1,2-a][1,4]diazonine-10-carboxamide (20 mg, 0.043 mmol), prepared according to Step 2 of Example 103, in toluene (0.5 mL) was treated with benzene-1,2-diamine (9.3 mg, 0.086 mmol, 2 equiv) and pyridinium p-toluenesulfonate (5.4 mg, 0.022 mmol, 0.5 equiv), sealed and heated to 55° C. for 1 hour. The reaction mixture was cooled to room temperature and diluted with EtOAc and water. The layers were separated and the aqueous layer was further extracted with EtOAc (2×). The combined organic layer was dried with sodium sulfate, filtered and concentrated to afford the title compound, which was carried on to the next step without further purification. MS (m/z) 554.22 [M+H]+.

Step 2: Preparation of (3'S,7'R)-12'-methoxy-3'-methyl-1',11'-dioxo-N-(2,4,6-trifluorobenzyl)-1',4',5',11'-tetrahydro-3'H,7'H-spiro[benzo[d]imidazole-2,6'-[2,7]methanopyrido[1,2-a][1,4]diazonine]-10'-carboxamide A solution of crude (3'S,7'R)-12'-methoxy-3'-methyl-1',11'-dioxo-N-(2,4,6-trifluorobenzyl)-1,1',3,4',5',11'-hexahydro-3'H,7'H-spiro[benzo[d]imidazole-2,6'-[2,7]methanopyrido[1,2-a][1,4]diazonine]-10'-carboxamide from Step 1 in DCM (0.5 mL) was treated with manganese dioxide (15 mg, 0.17 mmol, 4 equiv) and stirred at room temperature overnight. The reaction mixture was filtered across Celite with excess DCM/EtOAc, concentrated and purified by silica gel column chromatography (0-100% EtOAc in hexanes) to afford the title compound. MS (m/z) 552.16 [M+H]+.

Step 3: Preparation of (3'S,7'R)-12'-hydroxy-3'-methyl-1',11'-dioxo-N-(2,4,6-trifluorobenzyl)-1',4',5',11'-tetrahydro-3'H,7'H-spiro[benzo[d]imidazole-2,6'-[2,7]methanopyrido[1,2-a][1,4]diazonine]-10'-carboxamide A solution of (3'S,7'R)-12'-methoxy-3'-methyl-1',11'-dioxo-N-(2,4,6-trifluorobenzyl)-1',4',5',11'-tetrahydro-3'H,7'H-spiro[benzo[d]imidazole-2,6'-[2,7]methanopyrido[1,2-a][1,4]diazonine]-10'-carboxamide (20 mg, 0.036 mmol) in DMF (0.5 mL) was treated with lithium chloride (15.4 mg, 0.36 mmol, 10 equiv), sealed and heated to 100° C. overnight. The reaction mixture was cooled to room temperature, passed across a syringe filter, purified by reverse phase preparative HPLC (0-100% neutral MeCN/water) and lyophilized to afford the title compound. MS (m/z) 538.20 [M+H]+. 1H NMR (400 MHz, Methanol-d4) δ 10.31 (t, J=5.6 Hz, 1H), 8.80 (s, 1H), 8.02 (d, J=8.3 Hz, 1H), 7.61 (d, J=7.9 Hz, 1H), 7.50 (t, J=7.7 Hz, 1H), 7.35 (t, J=7.6 Hz, 1H), 7.29 (s, 1H), 6.86 (t, J=8.5 Hz, 2H), 5.03-4.92 (m, 1H), 4.65 (dd, J=14.5, 5.7 Hz, 1H), 4.54 (dd, J=14.4, 5.3 Hz, 1H), 4.40 (s, 2H), 3.54-3.43 (m, 1H), 2.55-2.36 (m, 2H), 1.91 (q, J=11.8 Hz, 1H), 1.33 (d, J=6.7 Hz, 3H).

Example 143: Preparation of (2S,3'S,7'R)-12'-hydroxy-3'-methyl-1',11'-dioxo-N-(2,4,6-trifluorobenzyl)-1',4',5',11'-tetrahydro-3H,3'H,7'H-spiro[benzofuran-2,6'-[2,7]methanopyrido[1,2-a][1,4]diazonine]-10'-carboxamide

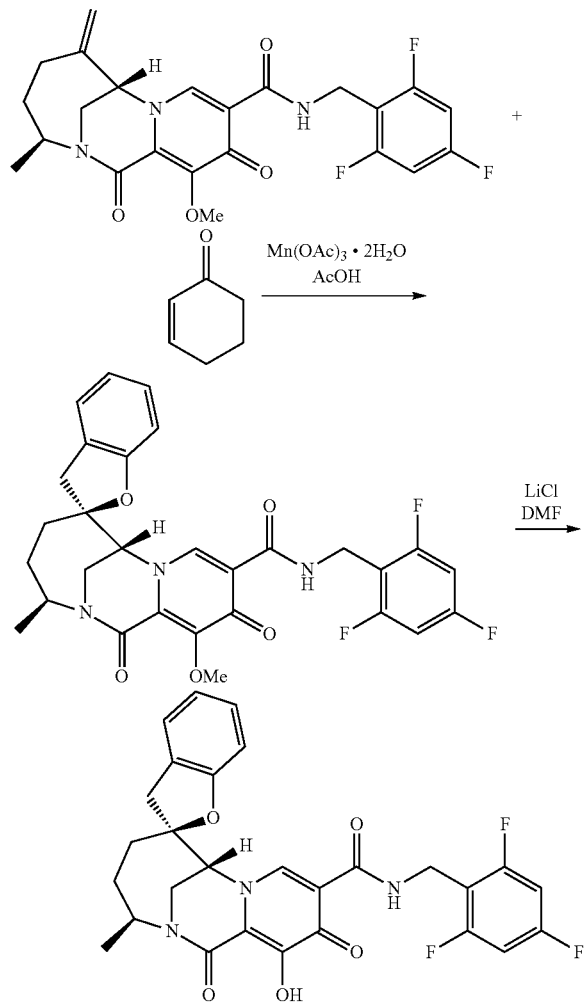

Step 1: Preparation of (2S,3'S,7'R)-12'-methoxy-3'-methyl-1',11'-dioxo-N-(2,4,6-trifluorobenzyl)-1',4',5',11'-tetrahydro-3H,3'H,7'H-spiro[benzofuran-2,6'-[2,7]methanopyrido[1,2-a][1,4]diazonine]-10'-carboxamide (3S,7S)-12-Methoxy-3-methyl-6-methylene-1,11-dioxo-N-(2,4,6-trifluorobenzyl)-1,4,5,6,7,11-hexahydro-3H-2,7-methanopyrido[1,2-a][1,4]diazonine-10-carboxamide (123 mg, 0.27 mmol), prepared according to Example 103, was dissolved in AcOH (5 mL). Ar (g) was bubbled through the reaction mixture for 10 min and Mn(OAc)$_3$·2H$_2$O (289 mg, 1.08 mmol) was added. Cyclohex-2-en-1-one (52 mg, 0.54 mmol) was added, and the reaction mixture was heated at 80° C. for 17 h. The reaction mixture was then concentrated to dryness and the residue was purified by silica gel column chromatography using 0-100% EtOAc/Hex to afford (2S,3'S,7'R)-12'-methoxy-3'-methyl-1',11'-dioxo-N-(2,4,6-trifluorobenzyl)-1',4',5',11'-tetrahydro-3H,3'H,7'H-spiro[benzofuran-2,6'-[2,7]methanopyrido[1,2-a][1,4]diazonine]-10'-carboxamide. MS (m/z): 554.2 [M+H]+.

Step 2: Preparation of (2S,3'S,7'R)-12'-hydroxy-3'-methyl-1',11'-dioxo-N-(2,4,6-trifluorobenzyl)-1',4',5',11'-tetrahydro-3H,3'H,7'H-spiro[benzofuran-2,6'-[2,7]methanopyrido[1,2-a][1,4]diazonine]-10'-carboxamide (2S,3'S,7'R)-12'-Methoxy-3'-methyl-1',11'-dioxo-N-(2,4,6-trifluorobenzyl)-1',4',5',11'-tetrahydro-3H,3'H,7'H-spiro[benzofuran-2,6'-[2,7]methanopyrido[1,2-a][1,4]diazonine]-10'-carboxamide (18 mg, 0.0325 mmol) was dissolved in DMF (1 mL) and LiCl (11 mg, 0.26 mmol) was added. The reaction mixture was stirred at 100° C. for 5 h, diluted with EtOAc (5 mL), and treated with 1N HCl (10 mL). The organic phase was separated and the aqueous phase was extracted with EtOAc (5 mL). The combined organic phase was washed with brine (10 mL) and water (10 mL). The resulting organic phase was concentrated to dryness, purified by reverse phase prep HPLC using 0-100% acetonitrile/water (with 0.1% TFA), and lyophilized to afford (2S,3'S,7'R)-12'-hydroxy-3'-methyl-1',11'-dioxo-N-(2,4,6-trifluorobenzyl)-1',4',5',11'-tetrahydro-3H,3'H,7'H-spiro[benzofuran-2,6'-[2,7]methanopyrido[1,2-a][1,4]diazonine]-10'-carboxamide. MS (m/z): 540.1 [M+H]+; 1H NMR (400 MHz, CD3CN) δ 10.35 (s, 1H), 8.36 (s, 1H), 7.21 (t, J=7.8 Hz, 2H), 6.95 (t, J=7.4 Hz, 1H), 6.91-6.82 (m, 3H), 4.71-4.63 (m, 1H), 4.61 (d, J=5.6 Hz, 2H), 4.48 (s, 1H), 3.87 (dd, J=14.9, 1.9 Hz, 1H), 3.77 (dd, J=14.8, 2.8 Hz, 1H), 3.17 (d, J=16.3 Hz, 1H), 2.73 (d, J=16.3 Hz, 1H), 2.12-1.99 (m, 2H), 1.94-1.86 (m, 1H), 1.60-1.45 (m, 1H), 1.29 (d, J=6.7 Hz, 3H).

Example 144: Preparation of (2R,3'S,7'R)-12'-hydroxy-3'-methyl-1',11'-dioxo-N-(2,4,6-trifluorobenzyl)-1',4',5',11'-tetrahydro-3H,3'H,7'H-spiro[benzofuran-2,6'-[2,7]methanopyrido[1,2-a][1,4]diazonine]-10'-carboxamide

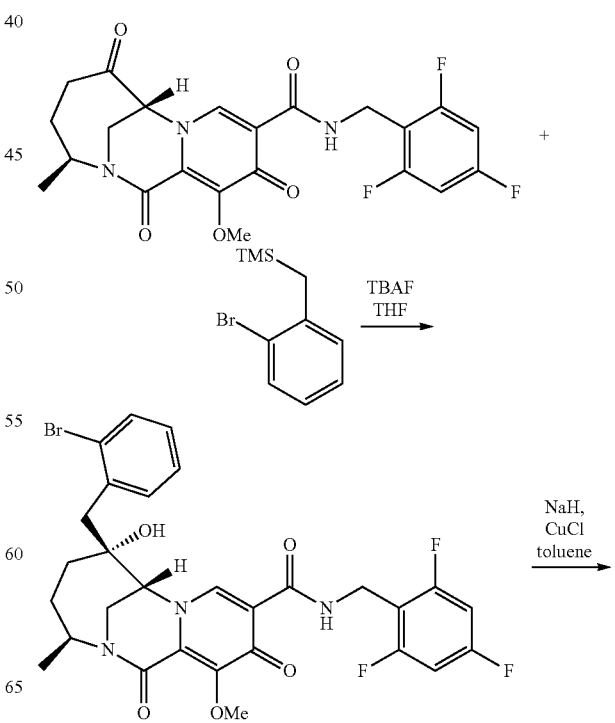

343

-continued

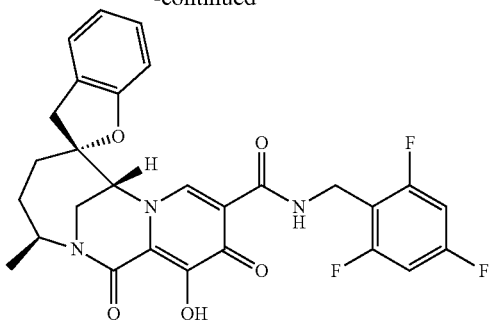

Step 1: Preparation of (3S,6R,7R)-6-(2-bromobenzyl)-6-hydroxy-12-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (3S,7R)-12-Methoxy-3-methyl-1,6,11-trioxo-N-(2,4,6-trifluorobenzyl)-1,4,5,6,7,11-hexahydro-3H-2,7-methanopyrido[1,2-a][1,4]diazonine-10-carboxamide (128 mg, 0.276 mmol), prepared according to Example 103, was dissolved in THF (2 mL) at rt under argon atmosphere. (2-Bromobenzyl)trimethylsilane (212 mg, 0.83 mmol) was added dropwise followed by 1N TBAF solution in THF (13 mg, 0.041 mmol). The resulting reaction mixture was stirred at 40-45° C. for 2 h. Additional (2-Bromobenzyl)trimethylsilane (212 mg, 0.83 mmol) and TBAF (1N in THF) (13 mg, 0.041 mmol) were added and heating continued at 40-45° C. for 8 h. The reaction mixture was then treated with additional 1N TBAF solution in THF (0.276 mL, 0.276 mmol) with stirring at rt for 30 min. The reaction mixture was diluted with EtOAc (20 mL) and treated with saturated NH4Cl (aq). The organic phase was separated and the aqueous phase was extracted with EtOAc (10 mL). The combined organic phases were washed with water and brine and the solvent was removed in vacuo. The residue was purified by silica gel column chromatography using 0-100% EtOAc/Hex to afford (3S,6R,7R)-6-(2-bromobenzyl)-6-hydroxy-12-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide. MS (m/z): 634.2 [M+H]+.

Step 2: Preparation of (2R,3'S,7'R)-12'-hydroxy-3'-methyl-1',11'-dioxo-N-(2,4,6-trifluorobenzyl)-1',4',5',11'-tetrahydro-3H,3'H,7'H-spiro[benzofuran-2,6'-[2,7]methanopyrido[1,2-a][1,4]diazonine]-10'-carboxamide (3S,6R,7R)-6-(2-Bromobenzyl)-6-hydroxy-12-methoxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (43 mg, 0.0678 mmol) was mixed with anhydrous toluene (1.5 mL) at rt. Ar (g) was bubbled through the reaction mixture for 5 min. NaH (60% in mineral oil) (5.7 mg, 0.149 mmol) was added and the resulting reaction mixture was then stirred at 35° C. for 30 min. CuCl (7.38 mg, 0.0746 mmol) was added and the resulting reaction mixture was stirred at 100° C. for 10 h. The reaction mixture was concentrated to dryness and the residue was purified by reverse phase prep HPLC with 0-100% acetonitrile/water (with 0.1% TFA) to afford (2R,

344

3'S,7'R)-12'-hydroxy-3'-methyl-1',11'-dioxo-N-(2,4,6-trifluorobenzyl)-1',4',5',11'-tetrahydro-3H,3'H,7'H-spiro[benzofuran-2,6'-[2,7]methanopyrido[1,2-a][1,4]diazonine]-10'-carboxamide. MS (m/z): 540.1 [M+H]+; 1H NMR (400 MHz, CD3CN) δ 10.35 (s, 1H), 7.98 (s, 1H), 7.32 (d, J=7.4 Hz, 1H), 7.23 (t, J=7.7 Hz, 1H), 7.00 (td, J=7.5, 1.0 Hz, 1H), 6.96-6.83 (m, 2H), 6.69 (t, J=8.1 Hz, 1H), 4.81-4.47 (m, 3H), 4.34 (s, 1H), 3.78-3.63 (m, 2H), 3.35-3.20 (m, 2H), 2.20-2.06 (m, 1H), 1.90 (d, J=10.6 Hz, 1H), 1.70-1.52 (m, 2H), 1.28 (d, J=6.6 Hz, 3H).

Example 145: Preparation of (3'S,5R,7'R)—N-(2,4-difluorobenzyl)-12'-hydroxy-3-methoxy-3'-methyl-1',11'-dioxo-1',4',5',11'-tetrahydro-3'H,4H,7'H-spiro[isothiazole-5,6'-[2,7]methanopyrido[1,2-a][1,4]diazonine]-10'-carboxamide

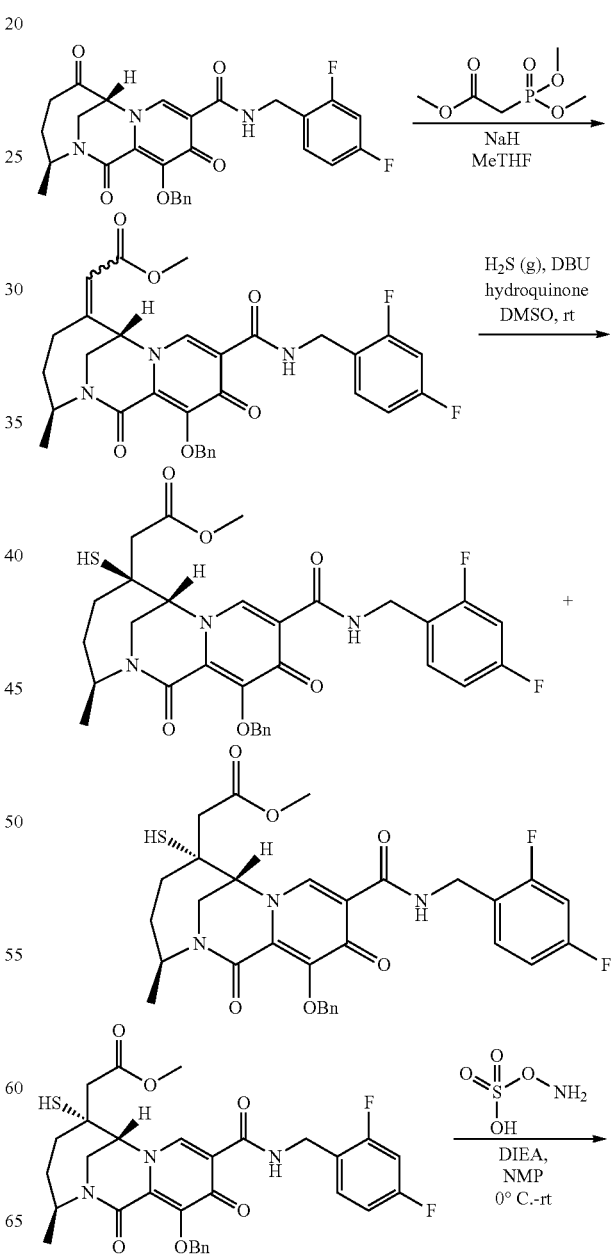

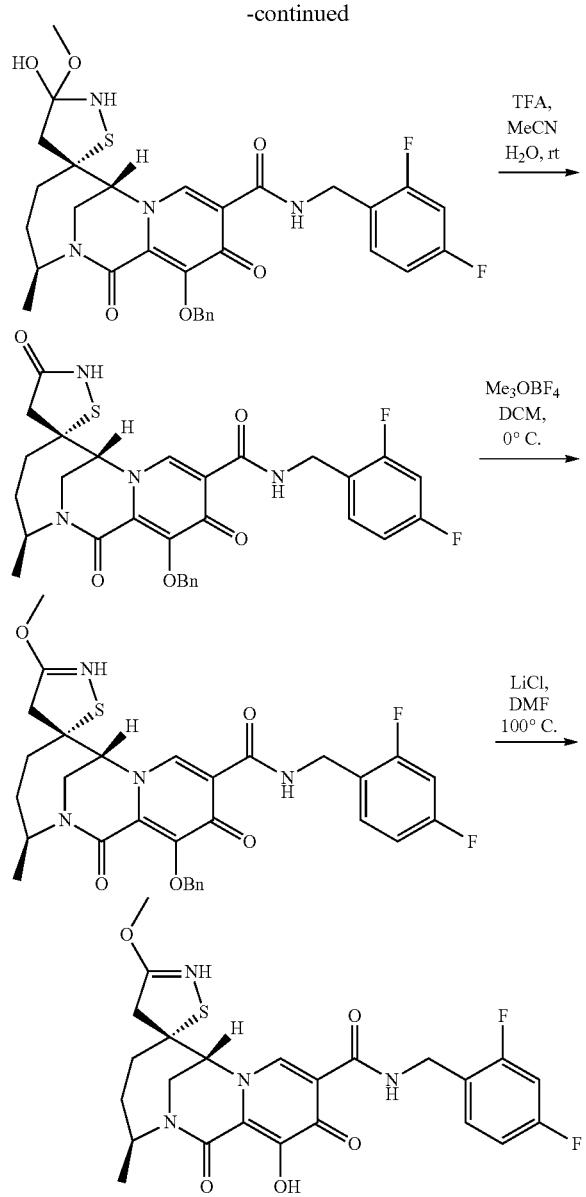

Step 1: Preparation of methyl 2-((3S,7S)-12-(benzyloxy)-10-((2,4-difluorobenzyl)carbamoyl)-3-methyl-1,11-dioxo-1,4,5,11-tetrahydro-3H-2,7-methanopyrido[1,2-a][1,4]diazonin-6(7H)-ylidene)acetate NaH (60% in mineral oil) (151 mg, 3.95 mmol) was mixed with anhydrous Me-THF (40 mL) and the suspension was cooled to 0° C. under argon atmosphere. Trimethyl phosphonoacetate (807 mg, 4.35 mmol) was added and the resulting reaction was stirred at 0° C. for 15 minutes. A solution of (3S,7R)-12-(Benzyloxy)-N-(2,4-difluorobenzyl)-3-methyl-1,6,11-trioxo-1,4,5,6,7,11-hexahydro-3H-2,7-methanopyrido[1,2-a][1,4]diazonine-10-carboxamide (807 mg, 4.35 mmol), prepared according to Example 56, in Me-THF (7 mL) was added dropwise. The reaction mixture was stirred at the same temperature for 30 minutes. The reaction mixture was treated with 1 mL saturated ammonium chloride solution at 0° C. and partitioned between brine (30 mL) and EtOAc (30 mL). The organic phase was separated and the aqueous phase was extracted with EtOAc (20 mL). The combined organic phase was dried over sodium sulfate, filtered and concentrated. The residue was purified by silica gel column chromatography using 0-100% EtOAc/hexanes to afford methyl 2-((3S,7S)-12-(benzyloxy)-10-((2,4-difluorobenzyl)carbamoyl)-3-methyl-1,11-dioxo-1,4,5,11-tetrahydro-3H-2,7-methanopyrido[1,2-a][1,4]diazonin-6(7H)-ylidene)acetate. MS (m/z): 578.0 [M+H]+.

Step 2: Preparation of methyl 2-((3S,6S,7R)-12-(benzyloxy)-10-((2,4-difluorobenzyl)carbamoyl)-6-mercapto-3-methyl-1,11-dioxo-1,4,5,6,7,11-hexahydro-3H-2,7-methanopyrido[1,2-a][1,4]diazonin-6-yl)acetate and methyl 2-((3S,6R,7R)-12-(benzyloxy)-10-((2,4-difluorobenzyl)carbamoyl)-6-mercapto-3-methyl-1,11-dioxo-1,4,5,6,7,11-hexahydro-3H-2,7-methanopyrido[1,2-a][1,4]diazonin-6-yl)acetate Methyl 2-((3S,7S)-12-(benzyloxy)-10-((2,4-difluorobenzyl)carbamoyl)-3-methyl-1,11-dioxo-1,4,5,11-tetrahydro-3H-2,7-methanopyrido[1,2-a][1,4]diazonin-6(7H)-ylidene)acetate (870 mg, 1.51 mmol) was dissolved in DMSO (5 mL) at room temperature. Hydroquinone (16.6 mg, 0.151 mmol) and DBU (22.9 mg, 0.151 mmol) were added sequentially and $H_2S$ (g) was bubbled through the reaction mixture for 60 min. The reaction mixture was diluted with EtOAc (15 mL) and treated with saturated NH4Cl (aq) (15 mL). The organic phase was separated and the aqueous phase was extracted with EtOAc (15 mL). The combined organic phase was washed with water (15 mL) and brine (15 mL). The organic phase was concentrated and the residue was purified by silica gel column chromatography using 0-100% EtOAc/Hex to afford methyl 2-((3S,6S,7R)-12-(benzyloxy)-10-((2,4-difluorobenzyl)carbamoyl)-6-mercapto-3-methyl-1,11-dioxo-1,4,5,6,7,11-hexahydro-3H-2,7-methanopyrido[1,2-a][1,4]diazonin-6-yl)acetate (Peak 1) and methyl 2-((3S,6R,7R)-12-(benzyloxy)-10-((2,4-difluorobenzyl)carbamoyl)-6-mercapto-3-methyl-1,11-dioxo-1,4,5,6,7,11-hexahydro-3H-2,7-methanopyrido[1,2-a][1,4]diazonin-6-yl)acetate (Peak 2).

Peak 1: MS (m/z): 612.1 [M+H]+.
Peak 2: MS (m/z): 612.1 [M+H]+.

Step 3: Preparation of (3'S,5R,7'R)-12'-(benzyloxy)-N-(2,4-difluorobenzyl)-3-hydroxy-3-methoxy-3'-methyl-1',11'-dioxo-1',4',5',11'-tetrahydro-3'H,7'H-spiro[isothiazolidine-5,6'-[2,7]methanopyrido[1,2-a][1,4]diazonine]-10'-carboxamide Methyl 2-((3S,6R,7R)-12-(benzyloxy)-10-((2,4-difluorobenzyl)carbamoyl)-6-mercapto-3-methyl-1,11-dioxo-1,4,5,6,7,11-hexahydro-3H-2,7-methanopyrido[1,2-a][1,4]diazonin-6-yl)acetate (300 mg, 0.48 mmol) was dissolved in NMP (10 mL) at room temperature. Argon was bubbled through for 10 min and (aminooxy)sulfonic acid (1.13 g, 9.65 mmol) was added. Bubbling with Ar (g) was continued for 10 min and the reaction mixture was cooled down to 0° C. Bubbling with Ar (g) was continued for 5 min, then anhydrous DIEA (1.84 mL, 10.6 mmol) was added dropwise at 0° C. under argon atmosphere. Ar (g) was bubbled through the reaction mixture for 10 min and the reaction mixture was allowed to warm to rt and stirred for 17 h. The reaction mixture was purified by reverse phase prep HPLC with 0-100% acetonitrile/water (with 0.1% TFA) to afford (3'S,5R,7'R)-12'-(benzyloxy)-N-(2,4-difluorobenzyl)-3-hydroxy-3-methoxy-3'-methyl-1',11'-dioxo-1',4',5',11'-tetrahydro-3'H,7'H-spiro[isothiazolidine-5,6'-[2,7]methanopyrido[1,2-a][1,4]diazonine]-10'-carboxamide. MS (m/z): 627.1 [M+H]+.

Step 4: Preparation of (3'S,5R,7'R)-12'-(benzyloxy)-N-(2,4-difluorobenzyl)-3'-methyl-1',3,11'-trioxo-1',4',5',11'-tetrahydro-3'H,7'H-spiro[isothiazolidine-5,6'-[2,7]methanopyrido[1,2-a][1,4]diazonine]-10'-carboxamide A solution of (3'S,5R,7'R)-12'-(Benzyloxy)-N-(2,4-difluorobenzyl)-3-hydroxy-3-methoxy-3'-methyl-1',11'-dioxo-1',4',5',11'-tetrahydro-3'H,7'H-spiro[isothiazolidine-5,6'-[2,7]methanopyrido[1,2-a][1,4]diazonine]-10'-carboxamide in acetonitrile/water containing 0.1% TFA was left at room temperature for 24 h. The reaction mixture was lyophilized under vacuum and the residue was purified by reverse phase prep HPLC using 0-100% acetonitrile/water (with 0.1% TFA) to afford (3'S,5R,7'R)-12'-(benzyloxy)-N-(2,4-difluorobenzyl)-3'-methyl-1',3,11'-trioxo-1',4',5',11'-tetrahydro-3'H,7'H-spiro[isothiazolidine-5,6'-[2,7]methanopyrido[1,2-a][1,4]diazonine]-10'-carboxamide. MS (m/z): 595.1 [M+H]+.

Step 5: Preparation of (3'S,5R,7'R)-12'-(benzyloxy)-N-(2,4-difluorobenzyl)-3-methoxy-3'-methyl-1',11'-dioxo-1',4',5',11'-tetrahydro-3'H,4H,7'H-spiro[isothiazole-5,6'-[2,7]methanopyrido[1,2-a][1,4]diazonine]-10'-carboxamide (3'S,5R,7'R)-12'-(Benzyloxy)-N-(2,4-difluorobenzyl)-3'-methyl-1',3,11'-trioxo-1',4',5',11'-tetrahydro-3'H,7'H-spiro[isothiazolidine-5,6'-[2,7]methanopyrido[1,2-a][1,4]diazonine]-10'-carboxamide (66 mg, 0.11 mmol) was dissolved in DCM (3 mL) at rt. Under Ar (g), the solution was cooled down to 0° C. and Me$_3$OBF$_4$ (21 mg, 0.16 mmol) was added in one portion. The reaction mixture was stirred at 0° C. for 4-5 h, allowed to warm to rt, and stirred for 17 h. The reaction mixture was then cooled down to 0° C. and NMP (2 mL) was added. The resulting reaction mixture was concentrated to remove volatiles and the residue was purified by reverse phase prep HPLC using 0-100% acetonitrile/water (with 0.1% TFA) to afford (3'S,5R,7'R)-12'-(benzyloxy)-N-(2,4-difluorobenzyl)-3-methoxy-3'-methyl-1',11'-dioxo-1',4',5',11'-tetrahydro-3'H,4H,7'H-spiro[isothiazole-5,6'-[2,7]methanopyrido[1,2-a][1,4]diazonine]-10'-carboxamide. MS (m/z): 609.0 [M+H]+.

Step 6: Preparation of (3'S,5R,7'R)—N-(2,4-difluorobenzyl)-12'-hydroxy-3-methoxy-3'-methyl-1',11'-dioxo-1',4',5',11'-tetrahydro-3'H,4H,7'H-spiro[isothiazole-5,6'-[2,7]methanopyrido[1,2-a][1,4]diazonine]-10'-carboxamide (3'S,5R,7'R)-12'-(Benzyloxy)-N-(2,4-difluorobenzyl)-3-methoxy-3'-methyl-1',11'-dioxo-1',4',5',11'-tetrahydro-3'H,4H,7'H-spiro[isothiazole-5,6'-[2,7]methanopyrido[1,2-a][1,4]diazonine]-10'-carboxamide (10 mg, 0.016 mmol) was dissolved in DMF (0.5 mL) and LiCl (6 mg, 0.14 mmol) was added. The resulting reaction mixture was heated at 100° C. for 5 h. The reaction mixture was purified by reverse phase prep HPLC using 0-100% acetonitrile/water to afford (3'S,5R,7'R)—N-(2,4-difluorobenzyl)-12'-hydroxy-3-methoxy-3'-methyl-1',11'-dioxo-1',4',5',11'-tetrahydro-3'H,4H,7'H-spiro[isothiazole-5,6'-[2,7]methanopyrido[1,2-a][1,4]diazonine]-10'-carboxamide. MS (m/z): 519.1 [M+H]+; 1H NMR (500 MHz, CD3CN) δ 10.4 (s, 1H), 8.38 (s, 1H), 7.43 (m, 1H), 6.95 (m, 2H), 4.75 (dt, J=10.4, 6.5 Hz, 1H), 4.62 (d, J=6.0 Hz, 2H), 4.40 (s, 1H), 3.87 (s, 3H), 3.76-3.49 (m, 2H), 3.16-2.99 (m, 2H), 2.25-2.04 (m, 2H), 1.95-1.90 (m, 1H), 1.67-1.41 (m, 1H), 1.25 (d, J=6.8 Hz, 3H).

Example 146: Preparation of (3'S,5S,7'R)-12'-hydroxy-3,3'-dimethyl-1',11'-dioxo-N-(2,4,6-trifluorobenzyl)-1',4',5',11'-tetrahydro-3'H,7'H-spiro[[1,4,2]oxathiazole-5,6'-[2,7]methanopyrido[1,2-a][1,4]diazonine]-10'-carboxamide

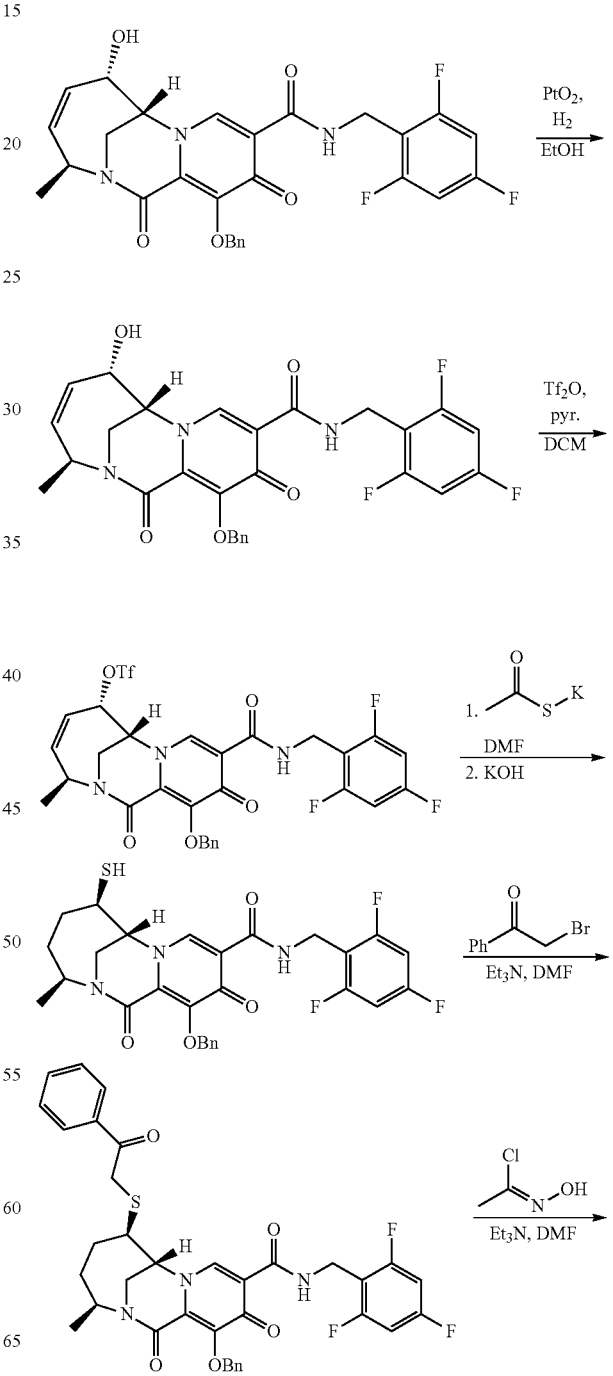

-continued

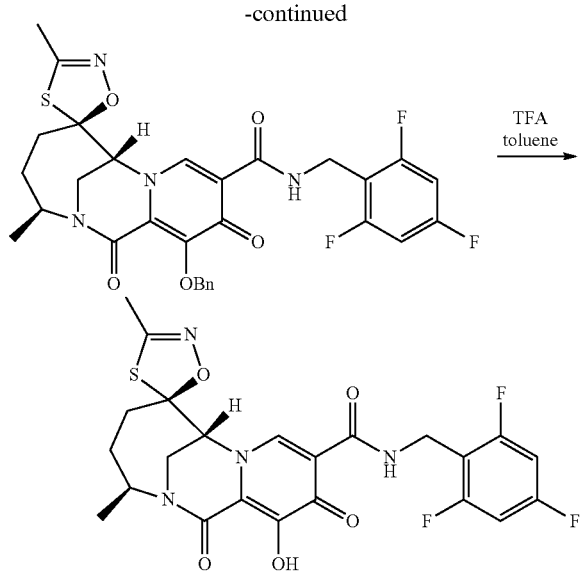

Step 1: Preparation of (3S,6S,7R)-12-(benzyloxy)-6-hydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (3S,6S,7R)-12-(benzyloxy)-6-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide (0.84 g, 1.56 mmol), prepared according to WO2022072520, was dissolved in EtOH (30 mL) and platinum(IV) oxide (35.4 mg, 0.156 mmol) was added. The resulting mixture was purged with $H_2$ (g) and stirred under $H_2$ atmosphere for 5 h. The reaction mixture was filtered and concentrated, and the resulting crude material was taken forward to next step without further purification. MS (m/z) 541.9 [M+H]+.

Step 2: Preparation of (3S,6S,7R)-12-(benzyloxy)-3-methyl-1,11-dioxo-O-((2,4,6-trifluorobenzyl)carbamoyl)-1,4,5,6,7,11-hexahydro-3H-2,7-methanopyrido[1,2-a][1,4]diazonin-6-yl trifluoromethanesulfonate Trifluoromethanesulfonic anhydride (0.96 g, 3.39 mmol) in $CH_2Cl_2$ (10 mL) was added to a solution of (3S,6S,7R)-12-(benzyloxy)-6-hydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (0.8 g, 2.83 mmol) and pyridine (0.47 g, 5.95 mmol) in $CH_2Cl_2$ (10 mL) at 0° C. The reaction mixture was stirred at 0° C. for 3 h. The reaction mixture was diluted with DCM (10 mL) and $H_2O$ at 0° C. The phases were separated, and the organic phase was dried over MgSO4, filtered, and concentrated. The crude material was purified by silica gel column chromatography (0-100% EtOAc/hexanes) to afford the title compound. MS (m/z) 674.07 [M+H]+.

Step 3: Preparation of (3S,6R,7R)-12-(benzyloxy)-6-mercapto-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide To a solution of (3S,6S,7R)-12-(benzyloxy)-3-methyl-1,11-dioxo-10-((2,4,6-trifluorobenzyl)carbamoyl)-1,4,5,6,7,11-hexahydro-3H-2,7-methanopyrido[1,2-a][1,4]diazonin-6-yl trifluoromethanesulfonate (0.65 g, 0.96 mmol) in DMF (5 mL) at rt was added potassium thioacetate (0.22 g, 1.93 mmol). The reaction mixture was stirred at rt for 30 min and 1N NaOH (1 mL) was added. After 20 min, the reaction mixture was diluted with EtOAc and washed with 5% LiCl (aq) solution followed by brine. The phases were separated, and the organic phase was dried over MgSO4, filtered, and concentrated. The crude material was purified by silica gel column chromatography (0-100% EtOAc/hexanes) to afford the title compound. MS (m/z) 558.08 [M+H]+.

Step 4: Preparation of (3S,6R,7R)-12-(benzyloxy)-3-methyl-1,11-dioxo-6-((2-oxo-2-phenylethyl)thio)-N-(2,4,6-trifluorobenzyl)-1,4,5,6,7,11-hexahydro-3H-2,7-methanopyrido[1,2-a][1,4]diazonine-10-carboxamide (3S,6R,7R)-12-(benzyloxy)-6-mercapto-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (0.48 g, 0.86 mmol) was dissolved in DMF (5 mL) followed by the addition of 2-bromo-1-phenyl-ethanone (0.19 g, 0.94 mmol) and triethylamine (0.11 g, 1.04 mmol). The reaction mixture was stirred at rt for 30 min. The reaction mixture was diluted with EtOAc and washed with 5% LiCl (aq) solution followed by brine. The phases were separated, and the organic phase was dried over MgSO4, filtered, and concentrated. The crude material was purified by silica gel column chromatography (0-100% EtOAc/hexanes) to afford the title compound. MS (m/z) 676.06 [M+H]+.

Step 5: Preparation of (3'S,5S,7'R)-12'-(benzyloxy)-3,3'-dimethyl-1',11'-dioxo-N-(2,4,6-trifluorobenzyl)-1',4',5',11'-tetrahydro-3'H,7'H-spiro[[1,4,2]oxathiazole-5,6'-[2,7]methanopyrido[1,2-a][1,4]diazonine]-10'-carboxamide (3S,6R,7R)-12-(benzyloxy)-3-methyl-1,11-dioxo-6-((2-oxo-2-phenylethyl)thio)-N-(2,4,6-trifluorobenzyl)-1,4,5,6,7,11-hexahydro-3H-2,7-methanopyrido[1,2-a][1,4]diazonine-10-carboxamide (0.02 g, 0.003 mmol) was dissolved in DCM (1 mL) followed by the addition N-hydroxyacetimidoyl chloride (0.0055 g, 0.006 mmol). After the addition of triethylamine (0.009 g, 0.0089 mol), the reaction mixture was immediately placed in a photoreactor and irradiated using a 365 nm LED-UV light. The photoreactor was equipped with a built-in fan to maintain ambient temperature during the course of the reaction. After 1 h, the reaction mixture was diluted with EtOAc and washed with 5% LiCl (aq) and brine. The phases were separated, and the organic phase was dried over MgSO4, filtered, and concentrated. The crude material was purified by silica gel column chromatography (0-100% EtOAc/hexanes) to afford the title compound. MS (m/z) 612.98 [M+H]+.

Step 6: Preparation of (3'S,5S,7'R)-12'-hydroxy-3,3'-dimethyl-1',11'-dioxo-N-(2,4,6-trifluorobenzyl)-1',4',5',11'-tetrahydro-3'H,7'H-spiro[[1,4,2]oxathiazole-5,6'-[2,7]methanopyrido[1,2-a][1,4]diazonine]-10'-carboxamide (3'S,5S,7'R)-12'-(benzyloxy)-3,3'-dimethyl-1',11'-dioxo-N-(2,4,6-trifluorobenzyl)-1',4',5',11'-tetrahydro-3'H,7'H-spiro[[1,4,2]oxathiazole-5,6'-[2,7]methanopyrido[1,2-a][1,4]diazonine]-10'-carboxamide (15 mg, 0.0025 mmol) was dissolved in toluene (1 mL) and TFA (0.5 mL) was added. The reaction mixture was stirred at rt overnight and concentrated. The crude material was purified by reverse phase preparative HPLC (5-100% MeCN/water containing 0.1%

TFA) to afford the title compound. MS (m/z) 523.11 [M+H]+. 1H NMR (400 MHz, Chloroform-d) δ 10.38 (d, J=6.0 Hz, 1H), 8.47 (s, 1H), 6.78-6.57 (m, 2H), 4.86-4.70 (m, 2H), 4.62 (dd, J=14.5, 5.2 Hz, 1H), 4.35 (s, 1H), 3.86 (dd, J=15.1, 1.9 Hz, 1H), 3.73 (dd, J=15.1, 2.7 Hz, 1H), 2.66-2.53 (m, 1H), 2.28 (s, 3H), 2.17-2.01 (m, 2H), 1.98-1.82 (m, 1H), 1.32 (d, J=6.7 Hz, 3H).
Example 147: Preparation of (3'S,5R,7'R)—N-(2,4-difluorobenzyl)-12'-hydroxy-4-(4-methoxybenzyl)-3, 3'-dimethyl-1',11'-dioxo-1',4',5',11'-tetrahydro-3'H, 4H,7'H-spiro[[1,2,4]oxadiazole-5,6'-[2,7] methanopyrido[1,2-a][1,4]diazonine]-10'-carboxamide
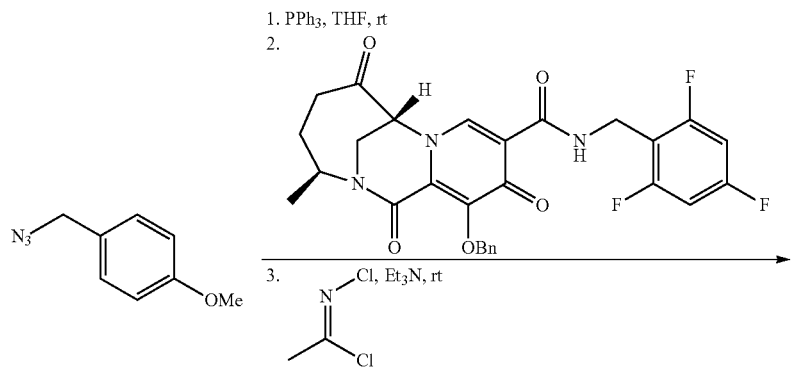
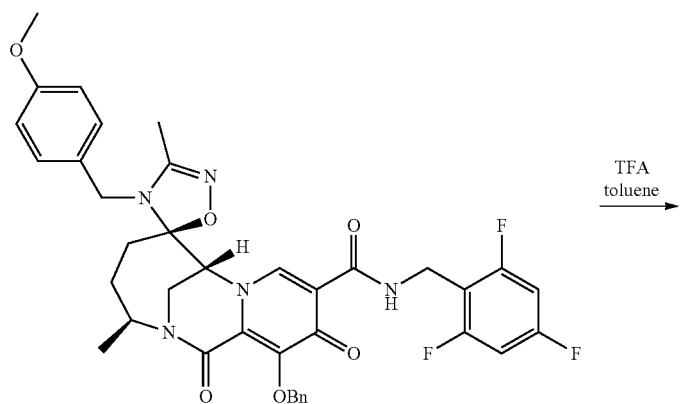
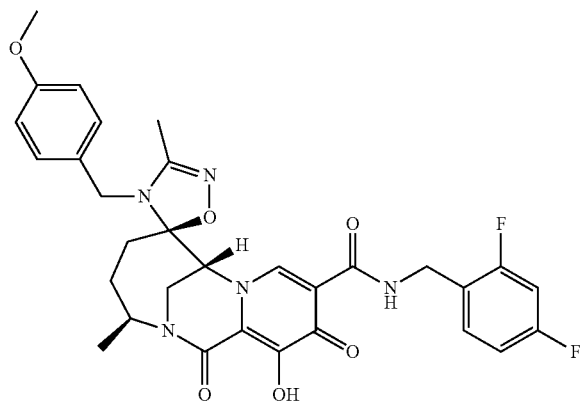

Step 1: Preparation of (3'S,5R,7'R)-12'-(benzyloxy)-N-(2,4-difluorobenzyl)-4-(4-methoxybenzyl)-3,3'-dimethyl-1',11'-dioxo-1',4',5',11'-tetrahydro-3'H,4H,7'H-spiro[[1,2,4]oxadiazole-5,6'-[2,7]methanopyrido[1,2-a][1,4]diazonine]-10'-carboxamide Into the solution of 1-(azidomethyl)-4-methoxy-benzene (120 mg, 0.735 mmol) in THF (10 ml) was added triphenylphosphine (218 mg, 0.882 mmol) at rt. After 4 h stirring, (3S,7R)-12-(benzyloxy)-N-(2,4-difluorobenzyl)-3-methyl-1,6,11-trioxo-1,4,5,6,7,11-hexahydro-3H-2,7-methano-pyrido[1,2-a][1,4]diazonine-10-carboxamide (307 mg, 0.588 mmol), prepared according to Step 2 of Example 56, was added and heated to 60° C. overnight. After cooling down to rt, N-hydroxyacetimidoyl chloride (317 mg, 3.39 mmol) and triethylamine (0.295 g, 2.91 mmol) were added at rt. After stirring at rt overnight, the reaction mixture was extracted with EtOAc. The organic phase was separated and dried over MgSO₄, filtered, concentrated and purified by silica gel column chromatography (eluting with 0-100% EtOAc/hexanes) to give the title compound. MS (m/z) 698.156 [M+H]+.

Step 2: Preparation of (3'S,5R,7'R)—N-(2,4-difluorobenzyl)-12'-hydroxy-4-(4-methoxybenzyl)-3,3'-dimethyl-1',11'-dioxo-1',4',5',11'-tetrahydro-3'H,4H,7'H-spiro[[1,2,4]oxadiazole-5,6'-[2,7]methanopyrido[1,2-a][1,4]diazonine]-10'-carboxamide A solution of (3'S,5R,7'R)-12'-(benzyloxy)-N-(2,4-difluorobenzyl)-4-(4-methoxybenzyl)-3,3'-dimethyl-1',11'-dioxo-1',4',5',11'-tetrahydro-3'H,4H,7'H-spiro[[1,2,4]oxadiazole-5,6'-[2,7]methanopyrido[1,2-a][1,4]diazonine]-10'-carboxamide (0.203 g, 0.291 mmol) in 1:1 toluene/TFA (1.5 mL) was stirred at rt overnight. The reaction mixture was concentrated, purified by reverse phase preparative HPLC (5-100% MeCN/water w/0.1% TFA), and lyophilized to afford the title compound. MS (m/z) 608.117 [M+H]+. ¹H NMR (400 MHz, Chloroform-d) δ 10.35 (t, J=5.9 Hz, 1H), 8.16 (s, 1H), 7.65-7.58 (m, 1H), 7.41 (td, J=8.7, 6.4 Hz, 1H), 6.87 (dd, J=9.2, 6.7 Hz, 3H), 6.80-6.75 (m, 2H), 4.80-4.58 (m, 3H), 4.25-4.14 (m, 2H), 3.78 (s, 4H), 3.64 (dd, J=15.2, 2.8 Hz, 1H), 3.43 (d, J=17.3 Hz, 1H), 2.12 (s, 3H), 2.03 (ddt, J=23.6, 16.9, 8.4 Hz, 3H), 1.70-1.59 (m, 1H), 1.31 (d, J=6.7 Hz, 3H).

Example 148: Preparation of (3'S,5R,7'R)—N-(2,4-difluorobenzyl)-12'-hydroxy-3,3'-dimethyl-1',11'-dioxo-1',4',5',11'-tetrahydro-3' H,4H,7'H-spiro[[1,2,4]oxadiazole-5,6'-[2,7]methanopyrido[1,2-a][1,4]diazonine]-10'-carboxamide

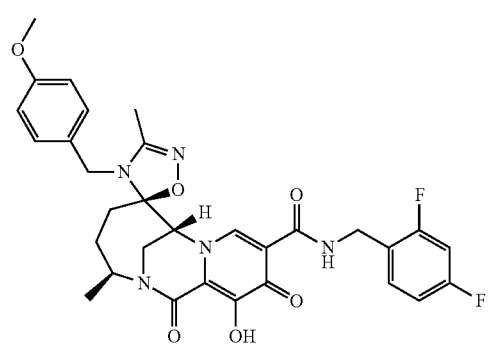

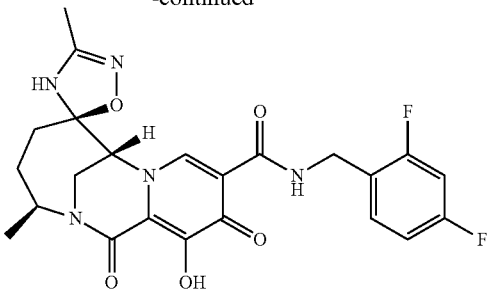

To a solution of (3'S,5R,7'R)—N-(2,4-difluorobenzyl)-12'-hydroxy-4-(4-methoxybenzyl)-3,3'-dimethyl-1',11'-dioxo-1',4',5',11'-tetrahydro-3'H,4H,7'H-spiro[[1,2,4]oxadiazole-5,6'-[2,7]methanopyrido[1,2-a][1,4]diazonine]-10'-carboxamide (43.5 mg, 0.0717 mmol) in 1,2-dichloroethane (2 mL) was added TFA (0.5 mL). The reaction mixture was stirred at 70° C. overnight. The reaction mixture was concentrated and the residue was purified by reverse phase preparative HPLC (eluting with 10-90% acetonitrile in water) to give the title compound. MS (m/z) 488.198 [M+H]+. ¹H NMR (400 MHz, Chloroform-d) δ 9.89 (s, 1H), 8.30 (s, 1H), δ 7.50-7.40 (m, 1H), 6.85 (m, 3H), 4.85 (m, 2H), 4.32 (m, 1H), 3.90-3.51 (m, 3H), 2.17-1.97 (m, 3H), 1.94 (s, 3H), 1.79 (m, 1H), 1.31 (d, J=6.5 Hz, 3H).

Example 149: Preparation of (3'S,5R,7'R)—N-(2,4-difluorobenzyl)-12'-hydroxy-3,3',4-trimethyl-1',11'-dioxo-1',4',5',11'-tetrahydro-3' H,4H,7'H-spiro[[1,2,4]oxadiazole-5,6'-[2,7]methanopyrido[1,2-a][1,4]diazonine]-10'-carboxamide and (3'S,5R,7'R)—N-(2,4-difluorobenzyl)-12'-hydroxy-2,3,3'-trimethyl-1',11'-dioxo-1',4',5',11'-tetrahydro-2H,3'H,7'H-spiro[[1,2,4]oxadiazole-5,6'-[2,7]methanopyrido[1,2-a][1,4]diazonine]-10'-carboxamide

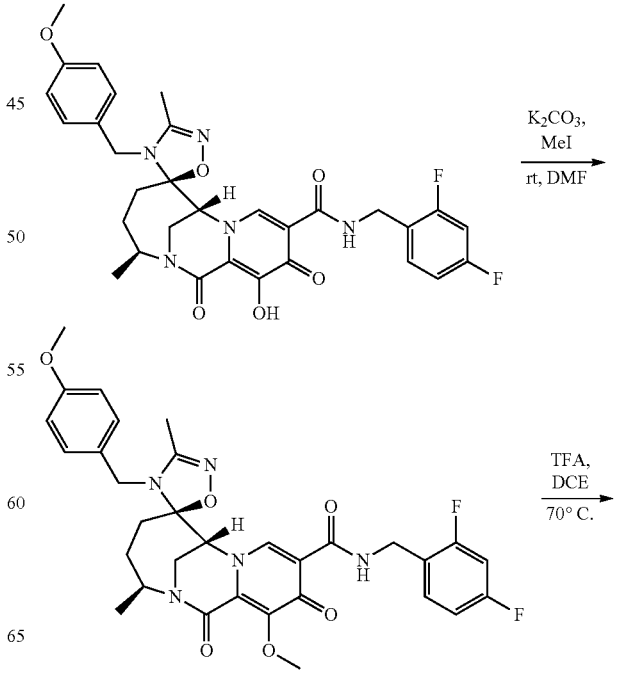

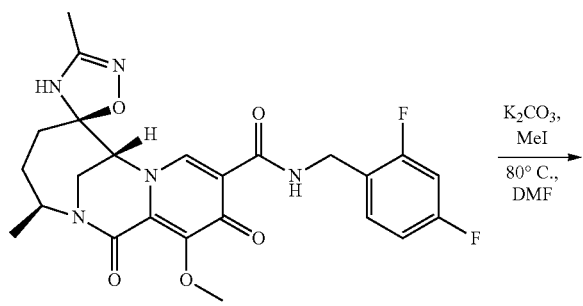
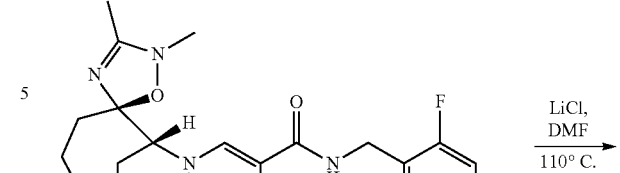

Step 1: Preparation of (3'S,5R,7'R)—N-(2,4-difluorobenzyl)-12'-methoxy-4-(4-methoxybenzyl)-3,3'-dimethyl-1',11'-dioxo-1',4',5',11'-tetrahydro-3'H,4H,7'H-spiro[[1,2,4]oxadiazole-5,6'-[2,7]methanopyrido[1,2-a][1,4]diazonine]-10'-carboxamide (3'S,5R,7'R)—N-(2,4-difluorobenzyl)-12'-methoxy-4-(4-methoxybenzyl)-3,3'-dimethyl-1',11'-dioxo-1',4',5',11'-tetrahydro-3'H,4H,7'H-spiro[[1,2,4]oxadiazole-5,6'-[2,7]methanopyrido[1,2-a][1,4]diazonine]-10'-carboxamide was prepared in a manner similar to Step 2 of Example 103, except using (3'S,5R,7'R)—N-(2,4-difluorobenzyl)-12'-hydroxy-4-(4-methoxybenzyl)-3,3'-dimethyl-1',11'-dioxo-1',4',5',11'-tetrahydro-3'H,4H,7'H-spiro[[1,2,4]oxadiazole-5,6'-[2,7]methanopyrido[1,2-a][1,4]diazonine]-10'-carboxamide, prepared according to Example 147, instead of (3S,7R)-12-hydroxy-3-methyl-1,6,11-trioxo-N-(2,4,6-trifluorobenzyl)-1,4,5,6,7,11-hexahydro-3H-2,7-methanopyrido[1,2-a][1,4]diazonine-10-carboxamide. MS (m/z) 622.128 [M+H]⁺.

Step 2: Preparation of (3'S,5R,7'R)—N-(2,4-difluorobenzyl)-12'-methoxy-3,3'-dimethyl-1',11'-dioxo-1',4',5',11'-tetrahydro-3'H,4H,7'H-spiro[[1,2,4]oxadiazole-5,6'-[2,7]methanopyrido[1,2-a][1,4]diazonine]-10'-carboxamide (3'S,5R,7'R)—N-(2,4-difluorobenzyl)-12'-methoxy-3,3'-dimethyl-1',11'-dioxo-1',4',5',11'-tetrahydro-3'H,4H,7'H-spiro[[1,2,4]oxadiazole-5,6'-[2,7]methanopyrido[1,2-a][1,4]diazonine]-10'-carboxamide was prepared in a manner similar to Example 148, except using (3'S,5R,7'R)—N-(2,4-difluorobenzyl)-12'-methoxy-4-(4-methoxybenzyl)-3,3'-dimethyl-1',11'-dioxo-1',4',5',11'-tetrahydro-3'H,4H,7'H-spiro[[1,2,4]oxadiazole-5,6'-[2,7]methanopyrido[1,2-a][1,4]diazonine]-10'-carboxamide instead of (3'S,5R,7'R)—N-(2,4-difluorobenzyl)-12'-hydroxy-4-(4-methoxybenzyl)-3,3'-dimethyl-1',11'-dioxo-1',4',5',11'-tetrahydro-3'H,4H,7'H-spiro[[1,2,4]oxadiazole-5,6'-[2,7]methanopyrido[1,2-a][1,4]diazonine]-10'-carboxamide. MS (m/z) 502.188 [M+H]+.

Step 3: Preparation of (3'S,5R,7'R)—N-(2,4-difluorobenzyl)-12'-methoxy-3,3',4-trimethyl-1',11'-dioxo-1',4',5',11'-tetrahydro-3'H,4H,7'H-spiro[[1,2,4]oxadiazole-5,6'-[2,7]methanopyrido[1,2-a][1,4]diazonine]-10'-carboxamide and (3'S,5R,7'R)—N-(2,4-difluorobenzyl)-12'-methoxy-2,3,3'-trimethyl-1',11'-dioxo-1',4',5',11'-tetrahydro-2H,3'H,7'H-spiro[[1,2,4]oxadiazole-5,6'-[2,7]methanopyrido[1,2-a][1,4]diazonine]-10'-carboxamide To a solution of (3'S,5R,7'R)—N-(2,4-difluorobenzyl)-12'-methoxy-3,3'-dimethyl-1',11'-dioxo-1',4',5',11'-tetrahydro-3'H,4H,7'H-spiro[[1,2,4]oxadiazole-5,6'-[2,7]methanopyrido[1,2-a][1,4]diazonine]-10'-carboxamide (66 mg, 0.132 mmol) in DMF was added iodomethane (28 mg, 0.197 mmol) and anhydrous potassium carbonate (81.6 mg, 1.32 mmol) at rt. The reaction flask was sealed and heated to 80° C. overnight. The reaction mixture was extracted with ethyl acetate and washed with brine. After drying over Na$_2$SO$_4$, the solvent was removed, and the residue was purified by silica gel column chromatography (0-40% MeOH/EtOAc) to obtain the two title compounds.

Peak 1: MS (m/z) 516.134 [M+H]$^+$
Peak 2: MS (m/z) 516.192 [M+H]$^+$

Step 4: Preparation of (3'S,5R,7'R)—N-(2,4-difluorobenzyl)-12'-hydroxy-3,3',4-trimethyl-1',11'-dioxo-1',4',5',11'-tetrahydro-3'H,4H,7'H-spiro[[1,2,4]oxadiazole-5,6'-[2,7]methanopyrido[1,2-a][1,4]diazonine]-10'-carboxamide (149a)

(3'S,5R,7'R)—N-(2,4-difluorobenzyl)-12'-hydroxy-3,3',4-trimethyl-1',11'-dioxo-1',4',5',11'-tetrahydro-3'H,4H,7'H-spiro[[1,2,4]oxadiazole-5,6'-[2,7]methanopyrido[1,2-a][1,4]diazonine]-10'-carboxamide was prepared in a manner similar to Step 8 of Example 103, except using (3'S,5R,7'R)—N-(2,4-difluorobenzyl)-12'-methoxy-3,3',4-trimethyl-1',11'-dioxo-1',4',5',11'-tetrahydro-3'H,4H,7'H-spiro[[1,2,4]oxadiazole-5,6'-[2,7]methanopyrido[1,2-a][1,4]diazonine]-10'-carboxamide instead of (3'S,5S,7'R)-12'-methoxy-3'-methyl-2-((1-methyl-1H-indazol-5-yl)methyl)-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide. MS (m/z) 502.153 [M+H]+. $^1$H NMR (400 MHz, Chloroform-d) δ 10.51 (t, J=6.0 Hz, 1H), 8.23 (s, 1H), 7.37 (d, J=6.6 Hz, 1H), 6.83 (dd, J=8.4, 2.2 Hz, 2H), 4.72-4.65 (m, 3H), 4.21 (s, 1H), 3.69 (td, J=14.8, 2.3 Hz, 2H), 3.12 (s, 3H), 2.05 (s, 3H), 2.03-1.95 (m, 3H), 1.45 (d, J=7.0 Hz, 1H), 1.32 (d, J=6.6 Hz, 3H).

Step 5: Preparation of (3'S,5R,7'R)—N-(2,4-difluorobenzyl)-12'-hydroxy-2,3,3'-trimethyl-1',11'-dioxo-1',4',5',11'-tetrahydro-2H,3'H,7'H-spiro[[1,2,4]oxadiazole-5,6'-[2,7]methanopyrido[1,2-a][1,4]diazonine]-10'-carboxamide (149b)

(3'S,5R,7'R)—N-(2,4-difluorobenzyl)-12'-hydroxy-2,3,3'-trimethyl-1',11'-dioxo-1',4',5',11'-tetrahydro-2H,3'H,7'H-spiro[[1,2,4]oxadiazole-5,6'-[2,7]methanopyrido[1,2-a][1,4]diazonine]-10'-carboxamide was prepared in a manner similar to Step 8 of Example 103, except using (3'S,5R,7'R)—N-(2,4-difluorobenzyl)-12'-methoxy-2,3,3'-trimethyl-1',11'-dioxo-1',4',5',11'-tetrahydro-2H,3'H,7'H-spiro[[1,2,4]oxadiazole-5,6'-[2,7]methanopyrido[1,2-a][1,4]diazonine]-10'-carboxamide instead of (3'S,5S,7'R)-12'-methoxy-3'-methyl-2-((1-methyl-1H-indazol-5-yl)methyl)-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide. MS (m/z) 502.123 [M+H]+. $^1$H NMR (400 MHz, Chloroform-d) δ 10.37 (t, J=5.9 Hz, 1H), 8.31 (s, 1H), 7.38 (td, J=8.7, 6.2 Hz, 1H), 6.90-6.80 (m, 2H), 4.77-4.61 (m, 3H), 4.19 (s, 1H), 3.78 (dd, J=15.1, 1.9 Hz, 1H), 3.66 (dd, J=15.1, 2.8 Hz, 1H), 2.34 (s, 3H), 2.06 (s, 1H), 2.04 (s, 3H), 1.99 (d, J=5.4 Hz, 2H), 1.72-1.66 (m, 1H), 1.33 (d, J=6.7 Hz, 3H).

Example 150: Preparation of (3'S,5S,7'R)—N-((4-chloro-3,5-difluoropyridin-2-yl)methyl)-12'-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

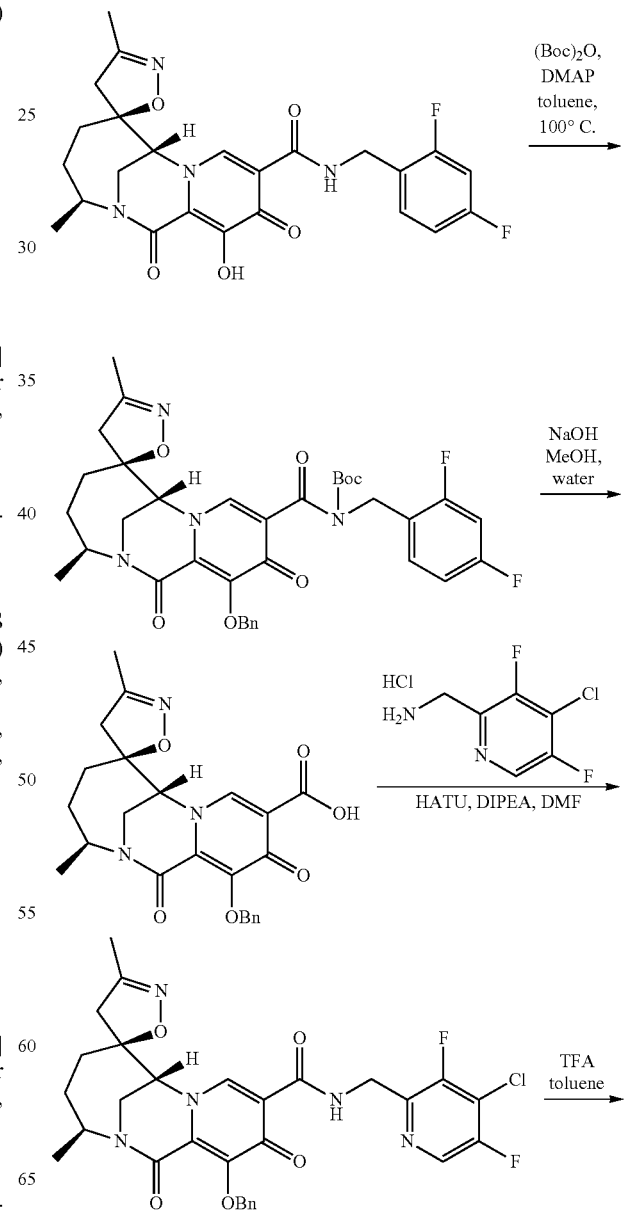

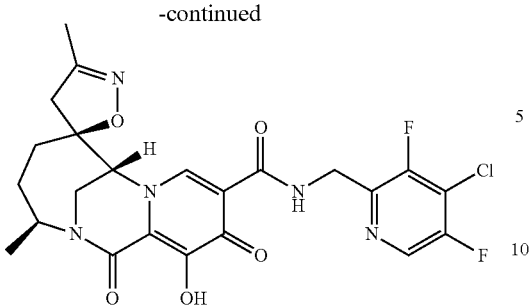

Step 1: Preparation of tert-butyl ((3'S,5S,7'R)-12'-(benzyloxy)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carbonyl)(2,4-difluorobenzyl)carbamate (3'S,5S,7'R)-12'-(Benzyloxy)-N-(2,4-difluorobenzyl)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (5 g, 8.67 mmol), prepared according to Step 1 of Example 1, was dissolved in toluene (80 mL) at rt. Boc$_2$O (10 g, 45.9 mmol) and DMAP (4.24 g, 34.7 mmol) were added. The reaction mixture was heated in sealed tube at 105° C. for 3 h. The reaction mixture was concentrated to dryness and the residue was purified by silica gel column chromatography using 0-100% EtOAc/hexanes to afford the title product. MS (m/z): 677.1 [M+H]+.

Step 2: Preparation of (3'S,5S,7'R)-12'-(benzyloxy)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxylic acid Tert-butyl ((3'S,5S,7'R)-12'-(benzyloxy)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carbonyl)(2,4-difluorobenzyl)carbamate (2.92 g, 4.32 mmol) was mixed with MeOH (100 mL) at rt. 1N NaOH (8.63 mL, 8.63 mmol) was added dropwise. The reaction was stirred at rt for 5 min and water (15 mL) was added. The resulting reaction mixture was stirred at rt for 17 h. The resulting reaction mixture was partitioned between EtOAc (10 mL) and water (10 mL). The aqueous layer was then acidified to pH 3 with 1N HCl. EtOAc (20 mL) was added and the phases separated. The organic phase was washed with brine (10 mL) and water (10 mL), then dried over Na$_2$SO$_4$ and filtered. The filtrate was concentrated to dryness to afford the title product. MS (m/z): 452.1 [M+H]+.

Step 3: Preparation of (3'S,5S,7'R)-12'-(benzyloxy)-N-((4-chloro-3,5-difluoropyridin-2-yl)methyl)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (3'S,5S,7'R)-12'-(Benzyloxy)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxylic acid (32.5 mg, 0.072 mmol) was dissolved in DMF (2 mL). DIPEA (0.05 mL, 0.288 mmol) and HATU (41.1 mg, 0.108 mmol) were added sequentially at rt. Reaction mixture was stirred at rt for 1 h and (4-chloro-3,5-difluoropyridin-2-yl)methanamine hydrochloride (18 mg, 0.0834 mmol) was added. Reaction mixture was then stirred at rt for 17 h. Reaction mixture was then diluted with EtOAc (10 mL) and treated with saturated aqueous NH$_4$Cl (20 mL). The organic phase was separated, dried over Na$_2$SO$_4$ and filtered. The filtrate was concentrated to dryness to afford the product. MS (m/z): 612.0 [M+H]+.

Step 4: Preparation of (3'S,5S,7'R)—N-((4-chloro-3,5-difluoropyridin-2-yl)methyl)-12'-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (3'S,5S,7'R)-12'-(Benzyloxy)-N-((4-chloro-3,5-difluoropyridin-2-yl)methyl)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (44 mg, 0.072 mmol) was dissolved in toluene (1 mL) at rt. TFA (0.8 mL) was added and the reaction mixture was stirred at rt for 17 h. The reaction mixture was concentrated to dryness and the residue was purified by reverse phase prep-HPLC (with 0-100% acetonitrile containing 0.1% TFA in water containing 0.1% TFA) to afford the title product. MS (m/z): 522.1 [M+H]+. $^1$H NMR (400 MHz, CD$_3$CN) δ 10.58 (s, 1H), 8.45 (s, 1H), 8.44 (s, 1H), 4.78 (d, J=4.1 Hz, 2H), 4.64 (td, J=8.3, 6.5 Hz, 1H), 4.36 (d, J=2.5 Hz, 1H), 3.77 (d, J=2.3 Hz, 2H), 2.90 (d, J=17.8 Hz, 1H), 2.54 (d, J=17.8 Hz, 1H), 1.97-1.81 (m, 3H), 1.94 (s, 3H), 1.54-1.42 (m, 1H), 1.26 (d, J=6.6 Hz, 3H).

Example 151: Preparation of (3'S,5S,7'R)—N-((2,4-difluorophenyl)methyl-d2)-12'-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide-N'-$^{15}$N

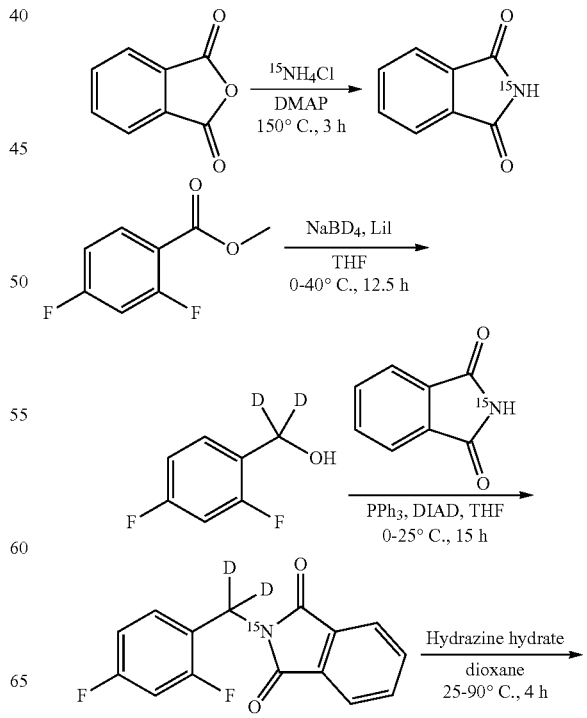

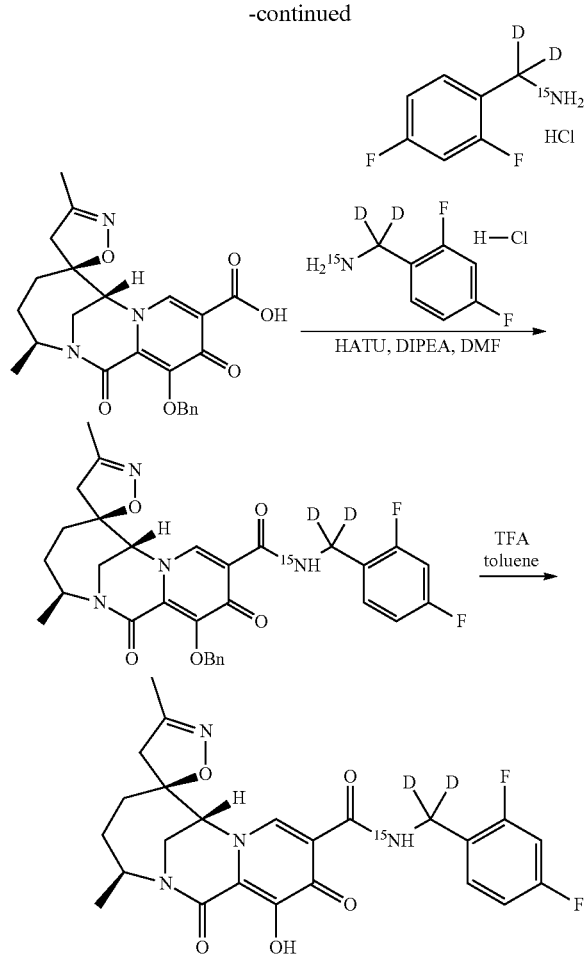

give (2,4-difluorophenyl)methan-$d_2$-ol. $^1$H NMR (CDCl$_3$ 400 MHz): δ 7.43-7.33 (m, 1H), 6.92-6.84 (m, 1H), 6.84-6.75 (m, 1H).

Step 3: Preparation of 2-((2,4-difluorophenyl)methyl-$d_2$)isoindoline-1,3-dione-$^{15}$N (2,4-difluorophenyl)methan-$d_2$-ol (22.4 g, 84.4 mmol), isoindoline-1,3-dione-$^{15}$N (12.5 g, 84.4 mmol) and PPh$_3$ (26.5 g, 101 mmol) were mixed with THF (300 mL) at rt. DIAD (19.7 mL, 101 mmol) was added at 0° C. under N$_2$. Reaction mixture was stirred it at 25° C. for 15 h and was then concentrated under reduced pressure to remove THF. The residue was purified by column chromatography (SiO$_2$, Petroleum ether/Ethyl acetate=86/14) to afford the product which was then further triturated with methanol (100 mL) at 25° C. for 30 min to afford 2-((2,4-difluorophenyl)methyl-$d_2$)isoindoline-1,3-dione-$^{15}$N. MS (m/z): 277.10 [M+H]+. $^1$H NMR: (CDCl$_3$ 400 MHz): δ 7.90-7.83 (m, 2H), 7.77-7.70 (m, 2H), 7.38 (dt, J=6.4, 8.6 Hz, 1H), 6.88-6.76 (m, 2H).

Step 4: Preparation of (2,4-difluorophenyl)methan-$d_2$-amine-$^{15}$N hydrochloride 2-((2,4-difluorophenyl)methyl-$d_2$)isoindoline-1,3-dione-$^{15}$N (4-b) (20.3 g, 73.5 mmol) was dissolved in dioxane (400 mL) at rt. Hydrazine hydrate (14.4 mL, 236 mmol) was added at 25° C. The reaction mixture was then heated with stirring at 90° C. for 4 h. H$_2$O (300 mL) and 2M HCl (50 mL) were added to bring the pH between 2-3. The reaction mixture was then filtered. The filtrate was extracted with EtOAc (300 mL×2). The aqueous layer was treated with 2M NaOH to pH 8-9 and extracted with EtOAc (300 mL×2). The organic layer was treated with H$_2$O (500 mL) and 2M HCl (50 mL) to pH 2-3. The aqueous layer was concentrated under reduced pressure to give a residue. The residue was triturated with ethyl acetate (100 mL) at 25° C. for 30 min to afford (2,4-difluorophenyl)methan-$d_2$-amine-$^{15}$N hydrochloride. MS (m/z): 147.10 [M+H]+. $^1$H NMR: (MeOD-$d_4$ 400 MHz): δ 7.66-7.56 (m, 1H), 7.14-7.02 (m, 2H).

Step 5: Preparation of (3'S,5S,7'R)-12'-(benzyloxy)-N-((2,4-difluorophenyl)methyl-$d_2$)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide-N'-$^{15}$N (3'S,5S,7'R)-12'-(Benzyloxy)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxylic acid (800 mg, 1.77 mmol), prepared according to Step 2 of Example 150, was dissolved in DMF (7 mL). DIPEA (1.08 mL, 6.2 mmol) and HATU (1.03 g, 2.63 mmol) were added sequentially at rt. Reaction mixture was stirred at rt for 1 h. Then (2,4-difluorophenyl)methan-$d_2$-amine-$^{15}$N hydrochloride (550 mg, 3.01 mmol) was added. Reaction mixture was then stirred at rt for 17 hr. Reaction mixture was then diluted with EtOAc (10 mL) and was treated with 0.5N HCl ((20 mL). Organic phase was separated, dried over Na$_2$SO$_4$ and filtered. The filtrate was concentrated to dryness. The crude product was purified by silica gel column chromatography using 0-100% EtOAc/hexanes to afford the title product. MS (m/z): 580.1 [M+H]+.

Step 6: Preparation of (3'S,5S,7'R)—N-((2,4-difluorophenyl)methyl-$d_2$)-12'-hydroxy-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide-N'-$^{15}$N (3'S,5S,7'R)-12'-(benzyloxy)-N-((2,4-difluorophenyl)methyl-$d_2$)-3,3'-dimethyl-1',11'-dioxo-1',4',5',11'-tetra- Step 1: Preparation of isoindoline-1,3-dione-$^{15}$N Isobenzofuran-1,3-dione (5.00 g, 33.8 mmol, 1.00 eq), $^{15}$NH$_4$Cl (2.53 g, 47.3 mmol, 1.40 eq) and DMAP (5.77 g, 47.3 mmol, 1.40 eq) were mixed in a microwave tube and was heated at 150° C. for 3 h. The reaction mixture was diluted with dichloromethane and methanol (10/1, v/v, 300 mL) and the mixture was washed with 1M HCl (100 mL). The organic layer was washed with H$_2$O (100 mL×2), dried over Na$_2$SO$_4$, filtered and concentrated under reduced pressure to give isoindoline-1,3-dione-$^{15}$N. MS (m/z): 149.1 [M+H]+. $^1$H NMR (CDCl$_3$ 400 MHz): δ 7.89 (br dd, J=2.8, 4.8 Hz, 2H), 7.82-7.70 (m, 2H).

Step 2: Preparation of (2,4-difluorophenyl)methan-$d_2$-ol

A solution of methyl 2,4-difluorobenzoate (25.0 g, 145 mmol) in THF (100 mL) was added dropwise to a pre-mixed reaction mixture of NaBD$_4$ (16.5 g, 436 mmol, 3.00 eq) and LiI (58.3 g, 436 mmol, 3.00 eq) in THF (250 mL) 0° C. under N$_2$. The reaction mixture was stirred at 40° C. for 12 h. 1M DCl (270 mL) was added slowly at 0° C. Reaction mixture was stirred at 25° C. for 10 h and was filtered, diluted with H$_2$O (600 mL), and extracted with ethyl acetate (300 mL×3). The combined organic layer was dried over Na$_2$SO$_4$, filtered and concentrated under reduced pressure to hydro-3'H,4H,7'H-spiro[isoxazole-5,6'-[2,7]methanopyrido[1,2-a][1,4]diazonine]-10'-carboxamide-N'-$^{15}$N (810 mg, 1.4 mmol) was dissolved in toluene (38 mL) at rt. TFA (37 mL) was added. The reaction mixture was stirred at rt for 17 h. The reaction mixture was concentrated to dryness. The residue was triturated with diethyl ether to afford the title product. MS (m/z): 490.2 [M+H]+. 1H NMR (400 MHz, CD3CN) δ 11.41 (s, 1H), 10.37 (d, J=90 Hz, 1H), 8.42 (s, 1H), 7.45 (td, J=8.7, 6.5 Hz, 1H), 6.97 (ddt, J=10.0, 8.4, 2.8 Hz, 2H), 4.64 (dq, J=14.6, 6.8 Hz, 1H), 4.33 (s, 1H), 3.82-3.69 (m, 2H), 2.90 (d, J=17.7 Hz, 1H), 2.53 (d, J=17.7 Hz, 1H), 1.93 (s, 3H), 1.97-1.82 (m, 3H), 1.48 (dt, J=15.6, 6.4 Hz, 1H), 1.26 (d, J=6.7 Hz, 3H).

Example 152: Preparation of (3'S,5S,7'R)-12'-hydroxy-3,3'-dimethyl-10'-(5-(2,4,6-trifluorobenzyl)-1,3,4-thiadiazol-2-yl)-4',5'-dihydro-3'H,4H,7'H-spiro[isoxazole-5,6'-[2,7]methanopyrido[1,2-a][1,4]diazonine]-1',11'-dione

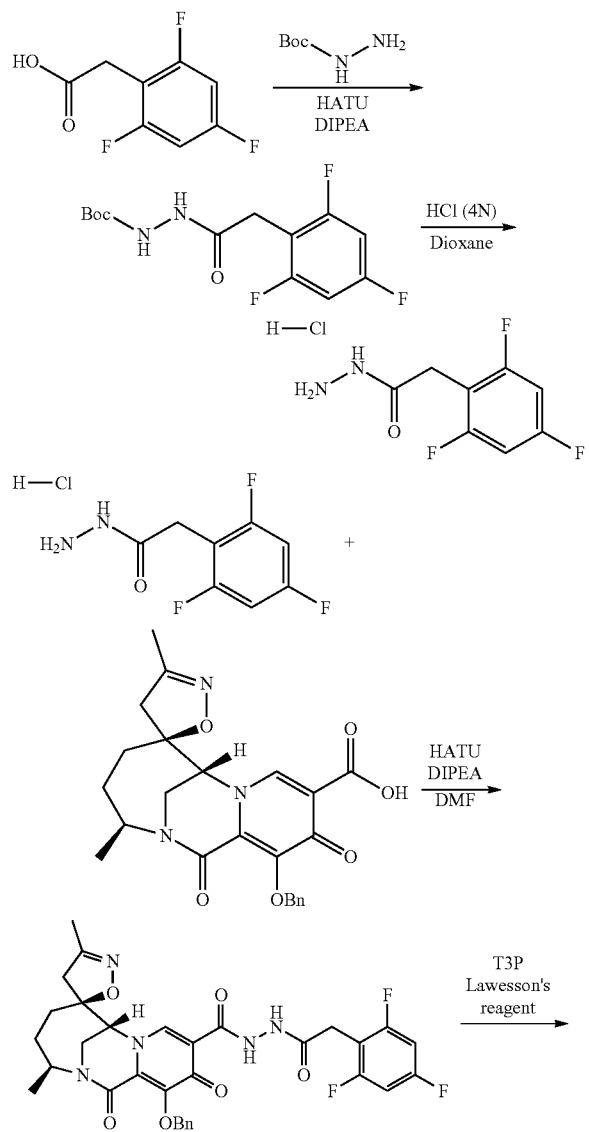

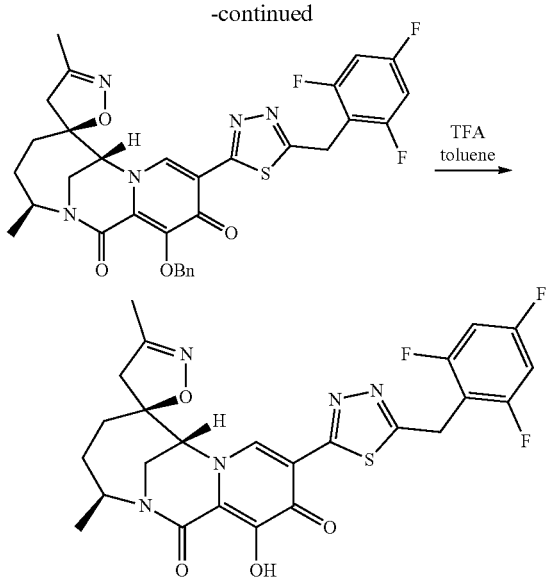

Step 1: Preparation of tert-butyl 2-(2-(2,4,6-trifluorophenyl)acetyl)hydrazine-1-carboxylate 2-(2,4,6-Trifluorophenyl)acetic acid (1.72 g, 9.05 mmol) was dissolved in DMF (20 mL) at rt. DIPEA (3.15 mL, 18.1 mmol) and HATU (2.77 g, 11.8 mmol) were added sequentially. The reaction mixture was stirred at rt for 1 h. Then tert-butyl carbazate (1.37 g, 10.4 mmol) was added. The reaction mixture was stirred at rt for 17 h. Reaction mixture was then diluted with EtOAc (100 mL) and treated with NH4Cl (saturated aq) (50 mL) and water (50 mL). The organic phase was separated, and the aqueous layer was extracted with EtOAc (50 mL). The combined organic phase was washed with water (50 mL) and brine (50 mL). The organic phase was separated and concentrated. The residue was purified by silica gel column chromatography with 0-100% EtOAc/hexanes to afford the title compound. MS (m/z): 305.2 [M+H]+.

Step 2: Preparation of 2-(2,4,6-trifluorophenyl)acetohydrazide hydrochloride

Tert-butyl 2-(2-(2,4,6-trifluorophenyl)acetyl)hydrazine-1-carboxylate (0.7 g, 2.3 mmol) was mixed with HCl (4N in dioxane) (7.63 mL, 30.5 mmol) at rt. The reaction mixture was stirred at rt for 17 h. The reaction mixture was concentrated to dryness and the residue was triturated with diethyl ether. Filtration afforded the title compound. MS (m/z): 205.1 [M+H]+.

Step 3: Preparation of (3'S,5S,7'R)-12'-(benzyloxy)-3,3'-dimethyl-1',11'-dioxo-N'-(2-(2,4,6-trifluorophenyl)acetyl)-1',4',5',11'-tetrahydro-3'H,4H,7'H-spiro[isoxazole-5,6'-[2,7]methanopyrido[1,2-a][1,4]diazonine]-10'-carbohydrazide (3'S,5S,7'R)-12'-(benzyloxy)-3,3'-dimethyl-1',11'-dioxo-1',4',5',11'-tetrahydro-3'H,4H,7'H-spiro[isoxazole-5,6'-[2,7]methanopyrido[1,2-a][1,4]diazonine]-10'-carboxylic acid (82.5 mg, 0.146 mmol), prepared according to Step 2 of Example 150, was dissolved in DMF (2 mL) at rt. DIPEA (0.14 mL, 0.804 mmol) and HATU (70.2 mg, 0.175 mmol) were added sequentially. The resulting reaction mixture was stirred at rt for 1 h. 2-(2,4,6-trifluorophenyl)acetohydrazide hydrochloride (45.7 mg, 0.19 mmol) was added and the reaction mixture was stirred at rt for 48 h. The reaction mixture was then partitioned between EtOAc (10 mL) and NH$_4$Cl (sat. aqueous solution) (10 mL) and the organic phase was separated. The aqueous phase was diluted with water (10 mL) and was then extracted with EtOAc (20 mL). The combined organic phase was washed with water (10 mL) and brine (10 mL). The organic phase was separated and concentrated to dryness. The residue was purified by silica gel column chromatography using 0-100% EtOAc/hexanes to afford the title compound. MS (m/z): 638.1 [M+H]+.

Step 4: Preparation of (3'S,5S,7'R)-12'-(benzyloxy)-3,3'-dimethyl-10'-(5-(2,4,6-trifluorobenzyl)-1,3,4-thiadiazol-2-yl)-4',5'-dihydro-3'H,4H,7'H-spiro [isoxazole-5,6'-[2,7]methanopyrido[1,2-a][1,4] diazonine]-1',11'-dione (3'S,5S,7'R)-12'-(benzyloxy)-3,3'-dimethyl-1',11'-dioxo-N'-(2-(2,4,6-trifluorophenyl)acetyl)-1',4',5',11'-tetrahydro-3'H,4H,7'H-spiro[isoxazole-5,6'-[2,7]methanopyrido[1,2-a] [1,4]diazonine]-10'-carbohydrazide (69 mg, 0.0753 mmol) was dissolved in THF (2.1 mL) at rt. 1-Propanephosphonic acid cyclic anhydride (50% w in DCM) (340 mg, 0.377 mmol) and Lawesson's reagent (304 mg, 0.753 mmol) were added sequentially. The resulting reaction mixture was stirred at rt for 48 h. The resulting slurry was concentrated to dryness. The residue was partitioned between EtOAc (10 mL) and NaHCO$_3$ (sat. aqueous solution) (10 mL). The organic phase was separated and concentrated. The residue was purified by silica gel column chromatography using 0-100% EtOAc/hexanes to afford the title compound. MS (m/z): 636.2 [M+H]+.

Step 5: Preparation of (3'S,5S,7'R)-12'-hydroxy-3,3'-dimethyl-10'-(5-(2,4,6-trifluorobenzyl)-1,3,4-thiadiazol-2-yl)-4',5'-dihydro-3'H,4H,7'H-spiro[isoxazole-5,6'-[2,7]methanopyrido[1,2-a][1,4]diazonine]-1',11'-dione (3'S,5S,7'R)-12'-(Benzyloxy)-3,3'-dimethyl-10'-(5-(2,4,6-trifluorobenzyl)-1,3,4-thiadiazol-2-yl)-4',5'-dihydro-3'H,4H,7'H-spiro[isoxazole-5,6'-[2,7]methanopyrido[1,2-a][1,4] diazonine]-1',11'-dione (20 mg, 0.031 mmol) was dissolved in toluene (5 mL) at rt. TFA (5 mL) was added and the reaction mixture was stirred at rt for 17 h. The reaction mixture was concentrated to dryness. The residue was triturated with diethyl ether to afford the title compound. MS (m/z): 546.2 [M+H]+. 1H NMR (400 MHz, Acetonitrile-d$_3$) δ 8.76 (s, 1H), 7.02-6.87 (m, 2H), 4.66 (q, J=7.9 Hz, 1H), 4.48 (s, 2H), 4.40 (s, 1H), 3.80 (d, J=2.1 Hz, 2H), 2.99 (d, J=17.8 Hz, 1H), 2.55 (d, J=17.8 Hz, 1H), 1.96 (s, 3H), 1.94-1.82 (m, 3H), 1.52 (dt, J=15.4, 6.2 Hz, 1H), 1.27 (d, J=6.6 Hz, 3H).

Example 153: Preparation of (3'S,5S,7'R)—N-(2,4-difluorobenzyl)-12'-hydroxy-3-(methoxy-d$_3$)-3'-methyl-1',11'-dioxo-1',4',5',11'-tetrahydro-3' H,4H, 7'H-spiro[isoxazole-5,6'-[2,7]methanopyrido[1,2-a] [1,4]diazonine]-10'-carboxamide

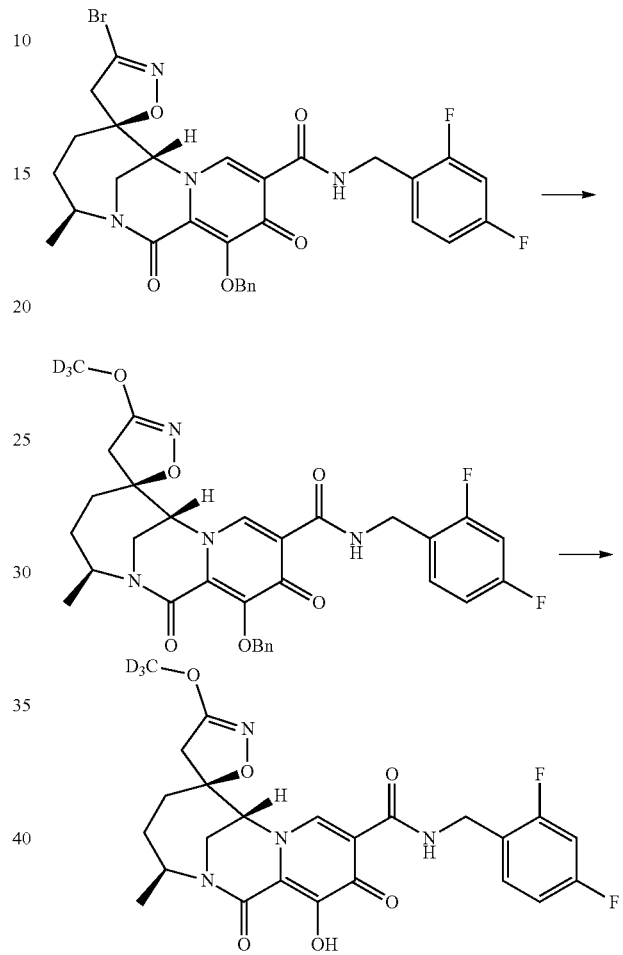

Step 1: Preparation of (3'S,5S,7'R)-12'-(benzyloxy)-N-(2,4-difluorobenzyl)-3-(methoxy-d$_3$)-3'-methyl-1', 11'-dioxo-1',4',5',11'-tetrahydro-3'H,4H,7'H-spiro [isoxazole-5,6'-[2,7]methanopyrido[1,2-a][1,4] diazonine]-10'-carboxamide To a mixture of (3'S,5S,7'R)-12'-(benzyloxy)-3-bromo-N-(2,4-difluorobenzyl)-3'-methyl-1',11'-dioxo-1',4',5',11'-tetrahydro-3'H,4H,7'H-spiro[isoxazole-5,6'-[2,7]methanopyrido [1,2-a][1,4]diazonine]-10'-carboxamide (1.0 g, 1.56 mmol) and CD$_3$OH (4.37 g, 125 mmol) in DMF (2.0 mL) at room temperature was added potassium carbonate (645 mg, 4.68 mmol). The resulting mixture was heated at 54° C. for 1.5 h. The reaction was then cooled to room temperature. Water (32 mL) was added and the mixture was stirred for 20 minutes before it was filtered. The filter cake was rinsed with water and vacuum dried to give the title compound. LCMS-ESI+(m/z): calcd H+ for C$_{31}$H27D3F2N4O6, Theoretical: 595.62, Found: 596.12.

367

Step 2: Preparation of (3'S,5S,7'R)—N-(2,4-difluorobenzyl)-12'-hydroxy-3-(methoxy-d₃)-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (3'S,5S,7'R)-12'-(benzyloxy)-N-(2,4-difluorobenzyl)-3-(methoxy-d₃)-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (868 mg, 1.46 mmol) was treated with a mixture of toluene (3.2 mL) and TFA (1.6 mL) at room temperature overnight. The reaction was then concentrated and the resulting residue was dissolved in EtOAc and evaporated (2 cycles). The residue was suspended in a mixture of toluene (2.1 mL), MeOH (2.1 mL) and EtOAc (2.1 mL) and heated to 70° C. for one hour. The mixture was removed from the heat and allowed to stir at room temperature for 2 h before it was filtered. The filter cake was rinsed with EtOAc and vacuum dried to afford the title compound. 1H NMR (400 MHz, DMSO-d6) δ 10.99 (s, 1H), 10.34 (t, J=5.9 Hz, 1H), 8.64 (s, 1H), 7.42 (td, J=8.7, 6.6 Hz, 1H), 7.25 (ddd, J=10.5, 9.3, 2.6 Hz, 1H), 7.11-7.02 (m, 1H), 4.74 (s, 1H), 4.64-4.46 (m, 3H), 3.80-3.63 (m, 2H), 2.93 (d, J=16.8 Hz, 1H), 2.70 (d, J=17.0 Hz, 1H), 1.95-1.77 (m, 3H), 1.36 (dt, J=15.4, 5.9 Hz, 1H), 1.19 (d, J=6.7 Hz, 3H). LCMS-ESI+(m/z): calcd H+ for C24H21D3F2N4O6, Theoretical: 505.49, Found: 506.22.

Example 154: Preparation of (3'S,5S,7'R)-12'-hydroxy-3'-methyl-3-(methylsulfonyl)-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

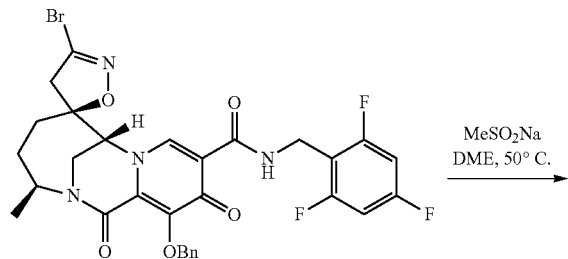

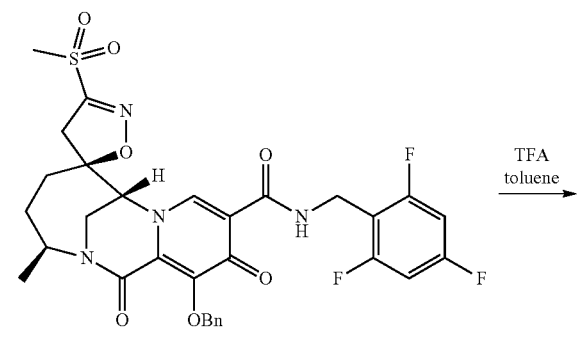

Step 1: Preparation of (3'S,5S,7'R)-12'-(benzyloxy)-3'-methyl-3-(methylsulfonyl)-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide

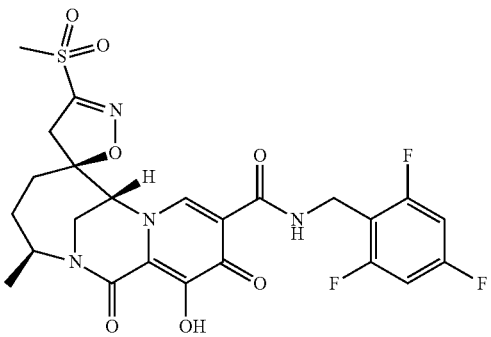

(3'S,5S,7'R)-12'-(benzyloxy)-3-bromo-3'-methyl-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (0.015 g, 0.023 mmol) and sodium methanesulfinate (0.002 g, 0.023 mmol) were suspended in 1,2-dimethoxyethane (1 mL) and heated to 50° C. for 7 d. The reaction mixture was cooled to rt and water was added. The solution was purified by reverse phase preparative HPLC (5-100% MeCN/water w/0.1% TFA) and lyophilized to afford the title compound. MS (m/z): 659.11 [M+H]+.

Step 2: Preparation of (3'S,5S,7'R)-12'-hydroxy-3'-methyl-3-(methylsulfonyl)-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (3'S,5S,7'R)-12'-(benzyloxy)-3'-methyl-3-(methylsulfonyl)-1',11'-dioxo-N-(2,4,6-trifluorobenzyl)-1',4',5',11'-tetrahydro-3'H,4H,7'H-spiro[isoxazole-5,6'-[2,7]methanopyrido[1,2-a][1,4]diazonine]-10'-carboxamide (0.009 g, 0.013 mmol) was dissolved in a 1:1 TFA/toluene mixture (2 mL) and stirred at rt overnight. The reaction mixture was concentrated, purified by reverse phase preparative HPLC (5-100% MeCN/water w/0.1% TFA), and lyophilized to afford the title compound. MS (m/z): 569.16 [M+H]+. 1H NMR (400 MHz, DMSO-d6) δ 10.33 (t, J=5.7 Hz, 1H), 8.82 (s, 1H), 7.21 (t, J=8.6 Hz, 2H), 4.90 (d, J=2.3 Hz, 1H), 4.58 (tt, J=14.6, 7.4 Hz, 3H), 3.80 (qd, J=15.2, 2.3 Hz, 2H), 3.39 (s, 3H), 3.34 (d, J=17.7 Hz, 1H), 3.10 (d, J=17.7 Hz, 1H), 1.99-1.75 (m, 3H), 1.49-1.32 (m, 1H), 1.19 (d, J=6.7 Hz, 3H).

369

Example 155: Preparation of (3'R,5S,7'R)—N-(2,4-difluorobenzyl)-3'-(fluoromethyl)-12'-hydroxy-3-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide

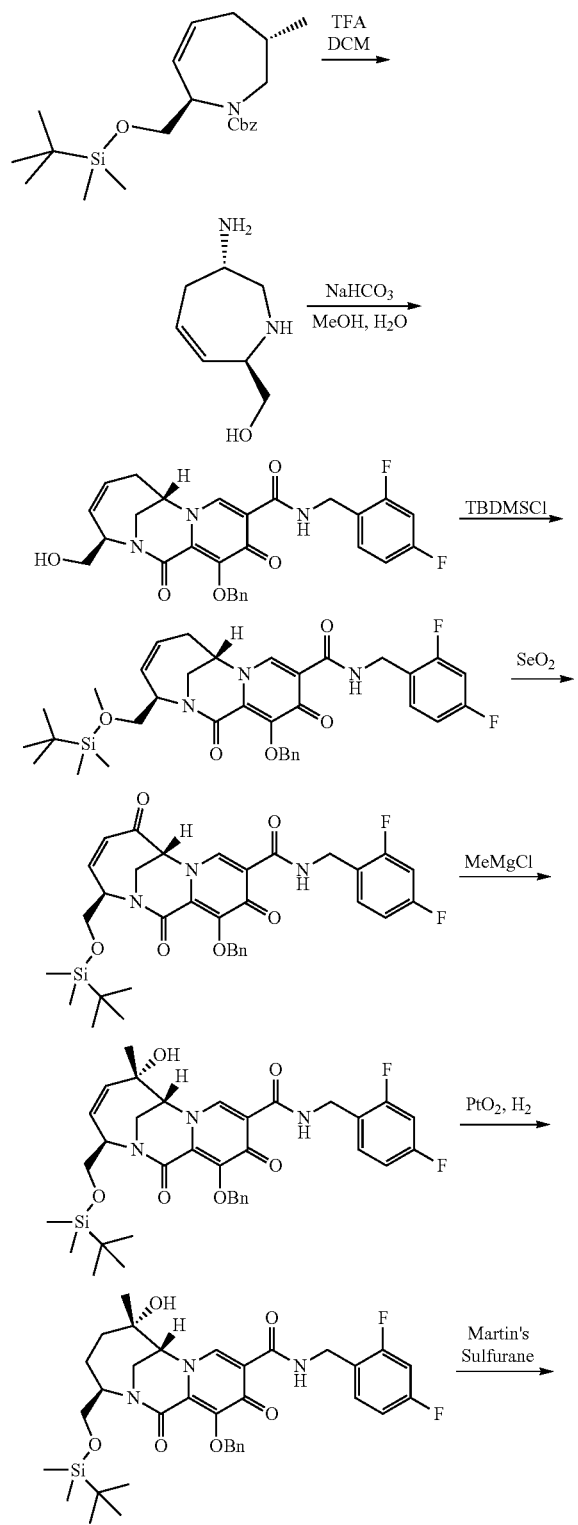

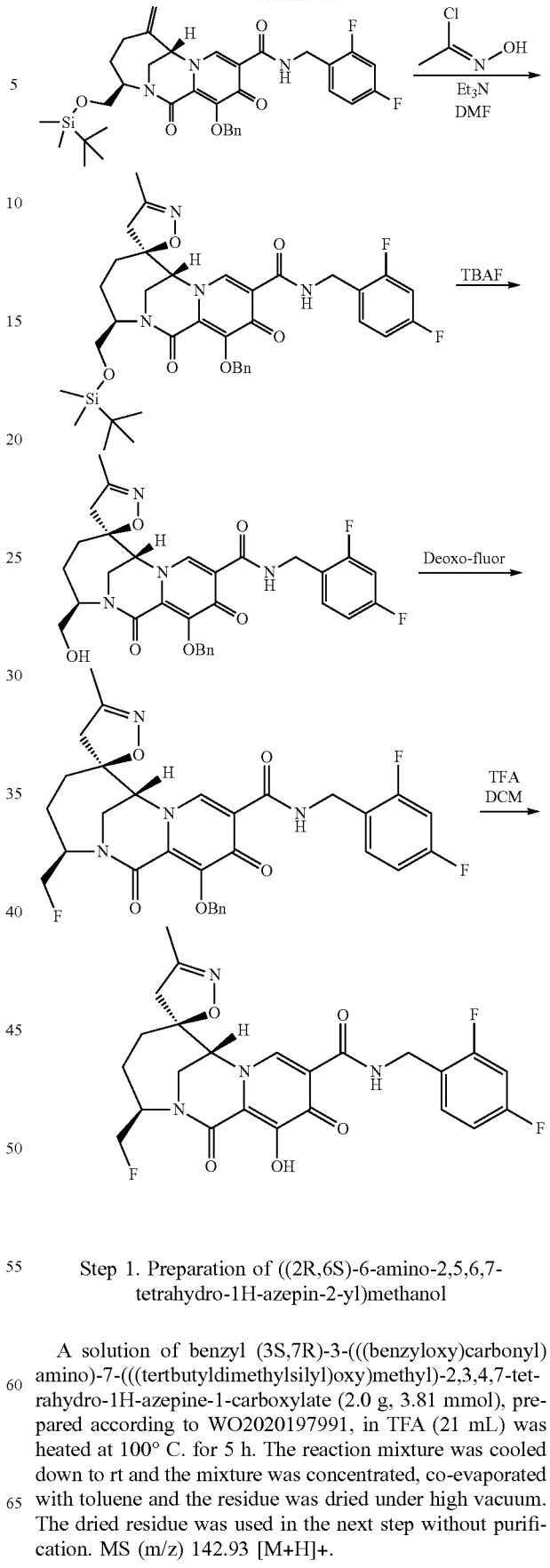

Step 1. Preparation of (((2R,6S)-6-amino-2,5,6,7-tetrahydro-1H-azepin-2-yl)methanol A solution of benzyl (3S,7R)-3-(((benzyloxy)carbonyl)amino)-7-(((tertbutyldimethylsilyl)oxy)methyl)-2,3,4,7-tetrahydro-1H-azepine-1-carboxylate (2.0 g, 3.81 mmol), prepared according to WO2020197991, in TFA (21 mL) was heated at 100° C. for 5 h. The reaction mixture was cooled down to rt and the mixture was concentrated, co-evaporated with toluene and the residue was dried under high vacuum. The dried residue was used in the next step without purification. MS (m/z) 142.93 [M+H]+.

Step 2: Preparation of (3R,7S)-12-(benzyloxy)-N-(2,4-difluorobenzyl)-3-(hydroxymethyl)-1,11-dioxo-1,6,7,11-tetrahydro-3H-2,7-methanopyrido[1,2-a][1,4]diazonine-10-carboxamide To a solution of ((2R,6S)-6-amino-2,5,6,7-tetrahydro-1H-azepin-2-yl)methanol trifluoroacetic acid salt (1410 mg, 3.81 mmol) in MeOH (10 mL) and water (1 mL) was added sodium bicarbonate (2.24 g, 26.7 mmol) and methyl 3-(benzyloxy)-4-oxo-5-((2,4-difluorobenzyl)carbamoyl)-4H-pyran-2-carboxylate (1.55 g, 3.62 mmol). The reaction mixture was stirred at 60° C. overnight. The reaction mixture was cooled and concentrated. The residue was washed with water and extracted with EtOAc. The organic phase was washed with brine, dried over $MgSO_4$, filtered, concentrated and purified by silica gel chromatography, eluting with 0-100% EtOAc/hexane, to give the title compound. MS (m/z) 522.12 [M+H]+.

Step 3: Preparation of (3R,7S)-12-(benzyloxy)-3-(((tert-butyldimethylsilyl)oxy)methyl)-N-(2,4-difluorobenzyl)-1,11-dioxo-1,6,7,11-tetrahydro-3H-2,7-methanopyrido[1,2-a][1,4]diazonine-10-carboxamide A mixture of (3R,7S)-12-(benzyloxy)-N-(2,4-difluorobenzyl)-3-(hydroxymethyl)-1,11-dioxo-1,6,7,11-tetrahydro-3H-2,7-methanopyrido[1,2-a][1,4]diazonine-10-carboxamide (950 mg, 1.82 mmol), tert-butyldimethylsilyl chloride (349 mg, 2.32 mmol), and imidazole (379 mg, 5.56 mmol) in $CH_2Cl_2$ (30 mL) was stirred at rt overnight. The reaction mixture was diluted with EtOAc, washed with 10% citric acid, and water. The aqueous phase was extracted with EtOAc and the combined organic phase was combined, dried over $MgSO_4$, and concentrated. The residue was purified by silica gel column chromatography, eluting with 0-100% EtOAc/hexane, concentrated, and dried to afford the title compound. MS (m/z) 635.98 [M+H]+.

Step 4: Preparation of (3R,7R)-12-(benzyloxy)-3-(((tert-butyldimethylsilyl)oxy)methyl)-N-(2,4-difluorobenzyl)-1,6,11-trioxo-1,6,7,11-tetrahydro-3H-2,7-methanopyrido[1,2-a][1,4]diazonine-10-carboxamide To a solution of (3R,7S)-12-(benzyloxy)-3-(((tert-butyldimethylsilyl)oxy)methyl)-N-(2,4-difluorobenzyl)-1,11-dioxo-1,6,7,11-tetrahydro-3H-2,7-methanopyrido[1,2-a][1,4]diazonine-10-carboxamide (960 mg, 1.51 mmol) in dioxane (10 mL) was added selenium dioxide (500 mg, 4.5 mmol). The reaction mixture was heated at 100° C. overnight. To the mixture was added additional selenium dioxide (200 mg, 1.8 mmol). Then the reaction mixture was stirred at 100° C. for 1 day. The reaction mixture was filtered through celite, washed with brine, dried over $MgSO_4$, filtered and concentrated. The residue was purified by silica gel chromatography, eluting with 0-100% EtAOc/hexane, to give the title compound. MS (m/z) 650.00 [M+H]+.

Step 5: Preparation of (3R,6S,7R)-12-(benzyloxy)-3-(((tert-butyldimethylsilyl)oxy)methyl)-N-(2,4-difluorobenzyl)-6-hydroxy-6-methyl-1,11-dioxo-1,6,7,11-tetrahydro-3H-2,7-methanopyrido[1,2-a][1,4]diazonine-10-carboxamide To a solution of (3R,7R)-12-(benzyloxy)-3-(((tert-butyldimethylsilyl)oxy)methyl)-N-(2,4-difluorobenzyl)-1,6,11-trioxo-1,6,7,11-tetrahydro-3H-2,7-methanopyrido[1,2-a][1,4]diazonine-10-carboxamide (500 mg, 0.77 mmol) in THF (2 mL) was added a solution of MeMgCl (3M in THF, 1.0 mL, 3.08 mmol) at 0° C. The reaction mixture was stirred at 0° C. for 0.5 h. The reaction was quenched with saturated aqueous $NH_4Cl$ and extracted with EtOAc. The organic phase was separated, dried over $MgSO_4$, filtered and concentrated. The residue was purified by silica gel column chromatography, eluting with 0-100% EtOAc/hexane, to give the title compound. MS (m/z) 666.13 [M+H]+.

Step 6: Preparation of (3R,6S,7R)-12-(benzyloxy)-3-(((tert-butyldimethylsilyl)oxy)methyl)-N-(2,4-difluorobenzyl)-6-hydroxy-6-methyl-1,11-dioxo-1,4,5,6,7,11-hexahydro-3H-2,7-methanopyrido[1,2-a][1,4]diazonine-10-carboxamide To a solution of (3R,6S,7R)-12-(benzyloxy)-3-(((tert-butyldimethylsilyl)oxy)methyl)-N-(2,4-difluorobenzyl)-6-hydroxy-6-methyl-1,11-dioxo-1,6,7,11-tetrahydro-3H-2,7-methanopyrido[1,2-a][1,4]diazonine-10-carboxamide (210 mg, 0.315 mmol) in EtOH (2 mL) was added $PtO_2$ (30 mg). The reaction mixture was stirred at rt under $H_2$ balloon atmosphere for 4 h. The reaction mixture was filtered through celite and the filtrate was concentrated. The residue was used without purification. MS (m/z) 668.16 [M+H]+.

Step 7: Preparation of (3R,7S)-12-(benzyloxy)-3-(((tert-butyldimethylsilyl)oxy)methyl)-N-(2,4-difluorobenzyl)-6-methylene-1,11-dioxo-1,4,5,6,7,11-hexahydro-3H-2,7-methanopyrido[1,2-a][1,4]diazonine-10-carboxamide To a solution of (3R,6S,7R)-12-(benzyloxy)-3-(((tert-butyldimethylsilyl)oxy)methyl)-N-(2,4-difluorobenzyl)-6-hydroxy-6-methyl-1,11-dioxo-1,4,5,6,7,11-hexahydro-3H-2,7-methanopyrido[1,2-a][1,4]diazonine-10-carboxamide (210 mg, 0.31 mmol) in toluene (9.0 mL) was added Martin's Sulfurane dehydrating agent (423 mg, 0.63 mmol). The reaction mixture was stirred at rt for 1 h. The reaction mixture was concentrated and the residue was purified by silica gel chromatography, eluting with 0-100% hexane/EtOAc, to give the title compound. MS (m/z) 650.17 [M+H]+.

Step 8: Preparation of (3'R,5S,7'R)-12'-(benzyloxy)-3'-(((tert-butyldimethylsilyl)oxy)methyl)-N-(2,4-difluorobenzyl)-3-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide To a solution of (3R,7S)-12-(benzyloxy)-3-(((tert-butyldimethylsilyl)oxy)methyl)-N-(2,4-difluorobenzyl)-6-methylene-1,11-dioxo-1,4,5,6,7,11-hexahydro-3H-2,7-methanopyrido[1,2-a][1,4]diazonine-10-carboxamide (130 mg, 0.2 mmol) in EtOAc (2 mL) was added $K_2CO_3$ (139 mg, 1 mmol) and N-hydroxyacetimidoyl chloride (56 mg, 0.6 mmol). The reaction mixture was stirred at rt overnight. To the reaction mixture was added water and the aqueous phase was extracted with EtOAc. The combined organic phase was dried over $MgSO_4$, filtered, and concentrated. The residue was purified by silica gel chromatography, eluting with 0-100% hexane/EtOAc, to give the title compound. MS (m/z) 707.16 [M+H]+.

Step 9: Preparation of (3'R,5S,7'R)-12'-(benzyloxy)-N-(2,4-difluorobenzyl)-3'-(hydroxymethyl)-3-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide A solution of (3'R,5S,7'R)-12'-(benzyloxy)-3'-(((tert-butyldimethylsilyl)oxy)methyl)-N-(2,4-difluorobenzyl)-3-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (50 mg, 0.071 mmol) in THF (2 mL) was stirred at 0° C. as 1 M TBAF in THF (0.097 mL, 0.097 mmol) was added. The reaction mixture was stirred at 0° C. for 2 h. The reaction mixture was diluted with EtOAc, washed with sat. NH4Cl, and the aqueous phase was extracted with EtOAc. The combined organic phase was dried over MgSO$_4$, filtered, concentrated, and purified by silica gel chromatography, eluting with 0-100% hexane/EtOAc, to give the title compound. MS (m/z) 593.18 [M+H]+.

Step 10: Preparation of (3'R,5S,7'R)-12'-(benzyloxy)-N-(2,4-difluorobenzyl)-3'-(fluoromethyl)-3-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide To a solution of (3'R,5S,7'R)-12'-(benzyloxy)-N-(2,4-difluorobenzyl)-3'-(hydroxymethyl)-3-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (15 mg, 0.025 mmol) in DCM (2 mL) was added bis(2-methoxyethyl)aminosulfur trifluoride (50 wt % solution in toluene, 35 mg, 0.076 mmol) at 0° C. The reaction mixture was stirred at 0° C. for 1.5 h. The reaction mixture was quenched with sat. NaHCO$_3$ solution and extracted with EtOAc. The organic phase was separated, dried over MgSO$_4$, filtered and concentrated. The residue was purified by silica gel chromatography, eluting with 0-100% EtOAc/hexane, to give the title compound. MS (m/z) 595.17 [M+H]+.

Step 11: Preparation of (3'R,5S,7'R)—N-(2,4-difluorobenzyl)-3'-(fluoromethyl)-12'-hydroxy-3-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide A solution of (3'R,5S,7'R)-12'-(benzyloxy)-N-(2,4-difluorobenzyl)-3'-(fluoromethyl)-3-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (13 mg, 0.021 mmol) in DCM (1 mL) and TFA (1 mL) was stirred at rt overnight. The reaction mixture was concentrated and the residue was purified by reverse phase preparative HPLC, eluting with 5-100% acetonitrile/water, to give the title compound. MS (m/z) 505.23 [M+H]+. 1H NMR (400 MHz, Methanol-d4) δ 8.51 (s, 1H), 7.46 (td, J=8.5, 6.4 Hz, 1H), 7.03-6.92 (m, 2H), 4.80 (dd, J=11.1, 5.9 Hz, 1H), 4.67 (dd, J=11.4, 5.2 Hz, 1H), 4.56 (d, J=4.8 Hz, 1H), 4.51 (s, 1H), 4.05-3.90 (m, 2H), 3.04 (d, J=17.9 Hz, 1H), 2.66 (d, J=17.8 Hz, 1H), 2.25 (dt, J=15.3, 11.9 Hz, 1H), 2.04 (s, 4H), 1.98-1.86 (m, 1H), 1.62 (dd, J=15.5, 11.8 Hz, 1H).

Example 156: Preparation of (3'S,5S,7'R)—N-(2,4-difluorobenzyl)-12'-hydroxy-3'-methyl-1',3,11'-trioxo-1',4',5',11'-tetrahydro-3'H,7'H-spiro[isoxazolidine-5,6'-[2,7]methanopyrido[1,2-a][1,4]diazonine]-10'-carboxamide

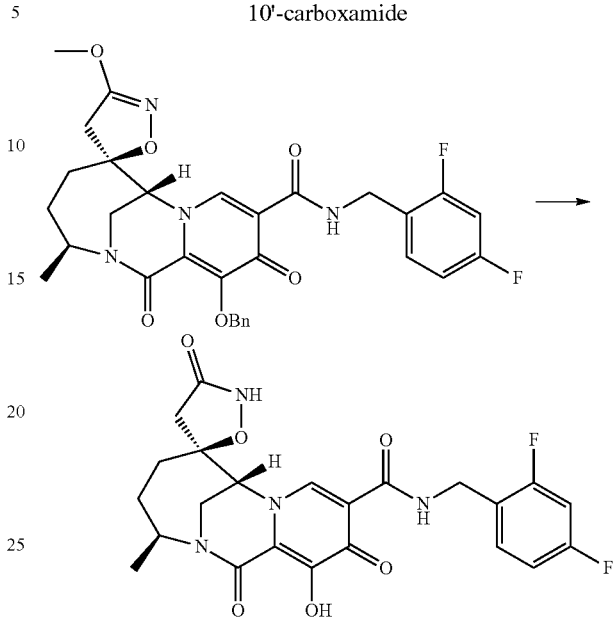

(3'S,5S,7'R)-12'-(benzyloxy)-N-(2,4-difluorobenzyl)-3-methoxy-3'-methyl-1',11'-dioxo-1',4',5',11'-tetrahydro-3'H,4H,7'H-spiro[isoxazole-5,6'-[2,7]methanopyrido[1,2-a][1,4]diazonine]-10'-carboxamide (30 mg, 0.051 mmol), prepared according to Example 40, was treated with a mixture of toluene (0.3 mL) and TFA (0.3 mL) at room temperature for overnight before it was concentrated. The residue was coevaporated with EtOAc (3×2.0 mL), then it was dissolved in DMF (1.0 mL) and heated with LiCl (10 mg, 0.24 mmol) at 125° C. overnight. The reaction was cooled to room temperature, diluted with DMF, filtered, and purified by reverse phase preparative HPLC (5-100% acetonitrile/water containing 0.1% TFA) to afford the title compound. 1H NMR (400 MHz, DMSO) δ 10.94 (s, 1H), 10.33 (q, J=6.3 Hz, 1H), 8.59 (s, 1H), 7.42 (td, J=8.7, 6.6 Hz, 1H), 7.29-7.20 (m, 1H), 7.08 (td, J=8.4, 2.7 Hz, 1H), 4.83 (s, 1H), 4.54 (dt, J=16.7, 5.6 Hz, 3H), 3.72 (qd, J=15.1, 2.2 Hz, 2H), 2.76-2.67 (m, 1H), 2.44 (d, J=16.6 Hz, 1H), 1.98 (dd, J=15.7, 6.4 Hz, 1H), 1.90-1.66 (m, 2H), 1.35 (dd, J=15.8, 11.6 Hz, 1H), 1.18 (d, J=6.6 Hz, 3H). LCMS-ESI+(m/z): calcd H+ for C23H22F2N4O6, Theoretical: 488.45, Found: 489.22.

Example 157: Preparation of (3'S,5S,7'R)-2-ethyl-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide

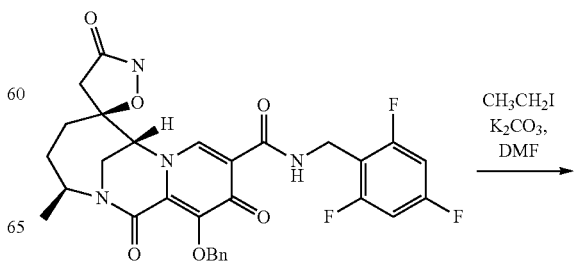

-continued

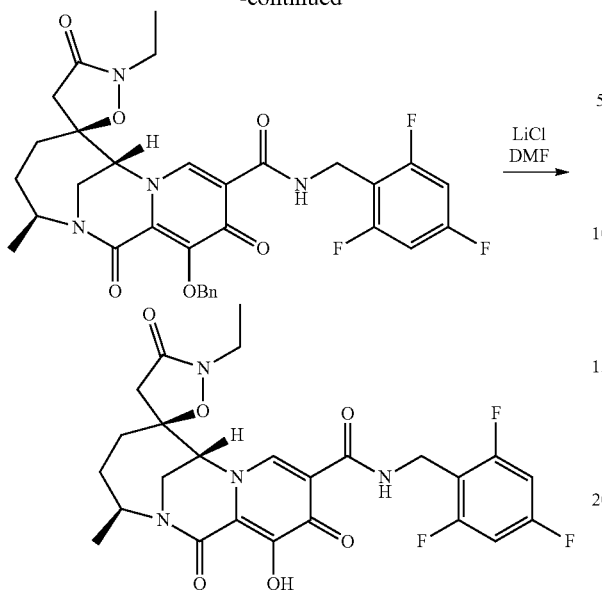

Step 1: Preparation of (3'S,5S,7'R)-12'-(benzyloxy)-2-ethyl-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide (3'S,5S,7'R)-12'-(benzyloxy)-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide (20 mg, 0.0335 mmol), prepared according to Step 1 of Example 101, was dissolved in DMF (2.5 mL). K₂CO₃ (18.5 mg, 0.134 mmol) and iodoethane (5.23 mg, 0.0335 mmol) were added sequentially. The reaction mixture was then stirred at rt for 17 h. The reaction mixture was diluted with EtOAc (10 mL) and treated with saturated aqueous NH₄Cl (10 mL). The organic phase was separated and the aqueous phase was extracted with EtOAc (5 mL). The combined organic phase was washed with brine (10 mL) and water (10 mL) and the resulting organic phase was concentrated to dryness. The residue was used directly in next step. MS (m/z): 625.2. [M+H]+.

Step 2: Preparation of (3'S,5S,7'R)-2-ethyl-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide Crude (3'S,5S,7'R)-12'-(benzyloxy)-2-ethyl-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide (21 mg, 0.0336 mmol) was dissolved in DMF (1.5 mL). LiCl (12 mg, 0.283 mmol) was added and the resulting reaction mixture was heated at 100° C. for 5 h. The reaction mixture was then purified directly on reverse phase preparative HPLC using 0-100% acetonitrile (with 0.1% TFA) in water (with 0.1% TFA) to afford the desired product. MS (m/z): 535.3 [M+H]+. 1H NMR (400 MHz, CD3CN) δ 10.32 (s, 1H), 8.35 (s, 1H), 6.94-6.81 (m, 2H), 4.61 (ddd, J=14.8, 8.4, 4.9 Hz, 3H), 4.52 (s, 1H), 3.83-3.68 (m, 2H), 3.60 (qd, J=7.2, 2.3 Hz, 2H), 2.63 (d, J=17.0 Hz, 1H), 2.41 (d, J=17.0 Hz, 1H), 2.04 (dd, J=15.9, 6.2 Hz, 1H), 1.97-1.80 (m, 2H), 1.51 (ddd, J=15.9, 10.9, 2.2 Hz, 1H), 1.28-1.16 (m, 6H).

Example 158: Preparation of (3'S,5S,7'R)-2-(4-bromobenzyl)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide

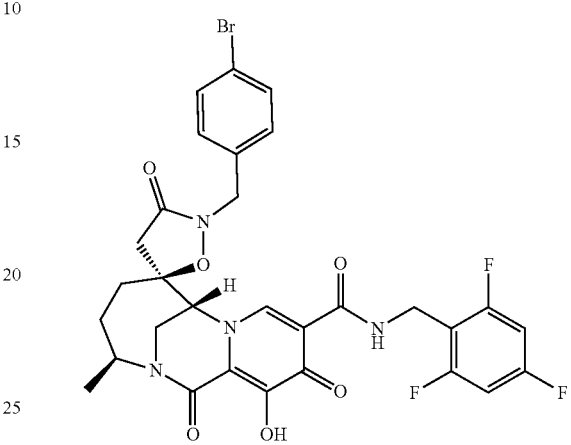

(3'S,5S,7'R)-2-(4-bromobenzyl)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide was synthesized in a similar manner as Example 103, except using 4-bromobenzyl bromide instead of 5-(bromomethyl)-1-methyl-indazole. MS (m/z) 675.24 [M+H]+. 1H NMR (400 MHz, Chloroform-d) δ 10.33 (t, J=5.7 Hz, 1H), 8.52 (s, 1H), 7.58-7.50 (m, 2H), 7.29-7.20 (m, 2H), 6.76-6.63 (m, 2H), 4.74 (d, J=15.6 Hz, 1H), 4.73-4.59 (m, 4H), 4.31 (s, 1H), 3.68-3.52 (m, 2H), 2.88 (d, J=16.9 Hz, 1H), 2.38 (d, J=17.0 Hz, 1H), 1.99 (dd, J=15.7, 6.7 Hz, 1H), 1.77 (dt, J=13.6, 6.5 Hz, 1H), 1.68-1.54 (m, 1H), 1.52-1.37 (m, 1H), 1.24 (d, J=6.6 Hz, 3H).

Example 159: Preparation of (3'S,5S,7'R)-12'-hydroxy-3'-methyl-1',3,11'-trioxo-2-(pyridin-2-ylmethyl)-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide

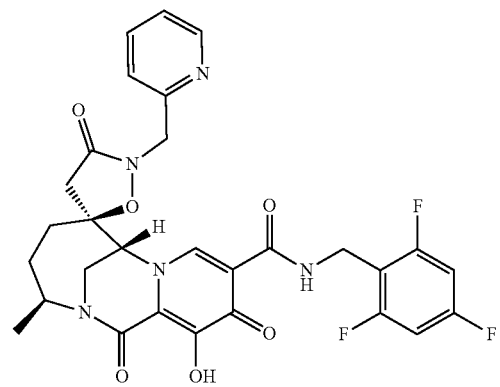 [SMILES: C[C@H]1CC[C@]2(CC(=O)N(Cc3ccccn3)O2)[C@H]2CN1C(=O)c1c(O)c(=O)c(C(=O)NCc3c(F)cc(F)cc3F)cn12]

(3'S,5S,7'R)-12'-hydroxy-3'-methyl-1',3,11'-trioxo-2-(pyridin-2-ylmethyl)-N-(2,4,6-trifluorobenzyl)-1',4',5',11'- tetrahydro-3'H,7'H-spiro[isoxazolidine-5,6'-[2,7]methanopyrido[1,2-a][1,4]diazonine]-10'-carboxamide was synthesized in a similar manner as Example 103, except using 2-(bromomethyl)pyridine instead of 5-(bromomethyl)-1-methyl-indazole. MS (m/z) 598.29 [M+H]+. 1H NMR (400 MHz, Chloroform-d) δ 10.28 (t, J=5.8 Hz, 1H), 8.76-8.65 (m, 1H), 8.47 (s, 1H), 7.99 (td, J=7.7, 1.7 Hz, 1H), 7.59-7.43 (m, 2H), 6.75-6.63 (m, 2H), 5.07 (d, J=16.1 Hz, 1H), 4.94 (d, J=16.1 Hz, 1H), 4.67 (q, J=5.3, 4.7 Hz, 3H), 4.53 (s, 1H), 3.70-3.63 (m, 2H), 2.88 (m, 1H), 2.46 (m, 1H), 2.09 (dd, J=16.1, 6.4 Hz, 1H), 1.95-1.68 (m, 2H), 1.58-1.46 (m, 1H), 1.34-1.21 (m, 3H).

Example 160: Preparation of (3'S,5S,7'R)-12'-hydroxy-3'-methyl-1',3,11'-trioxo-2-(pyridin-3-ylmethyl)-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide

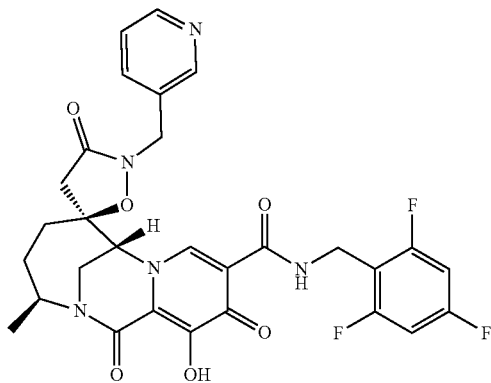 [SMILES: C[C@H]1CC[C@]2(CC(=O)N(Cc3cccnc3)O2)[C@H]2CN1C(=O)c1c(O)c(=O)c(C(=O)NCc3c(F)cc(F)cc3F)cn12]

(3'S,5S,7'R)-12'-hydroxy-3'-methyl-1',3,11'-trioxo-2-(pyridin-3-ylmethyl)-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide was synthesized in a similar manner as Example 103, except using 3-(bromomethyl)pyridine instead of 5-(bromomethyl)-1-methyl-indazole. MS (m/z) 598.29 [M+H]+. 1H NMR (400 MHz, Chloroform-d) δ 10.22 (t, J=5.8 Hz, 1H), 8.98-8.92 (m, 1H), 8.69 (dd, J=5.2, 1.5 Hz, 1H), 8.40 (s, 1H), 8.06 (d, J=8.0 Hz, 1H), 7.67 (dd, J=7.8, 5.2 Hz, 1H), 6.69 (dd, J=8.7, 7.5 Hz, 2H), 4.90 (d, J=16.0 Hz, 1H), 4.81 (d, J=15.9 Hz, 1H), 4.68 (dd, J=13.8, 6.0 Hz, 3H), 4.35 (s, 1H), 3.79-3.63 (m, 2H), 2.94-2.83 (m, 1H), 2.42 (d, J=17.3 Hz, 1H), 2.15-2.01 (m, 1H), 1.75-1.65 (m, 2H), 1.53 (dd, J=15.8, 11.4 Hz, 1H), 1.29 (d, J=6.7 Hz, 3H).

Example 161: Preparation of (3'S,5S,7'R)-2-(benzo[d]thiazol-2-ylmethyl)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide

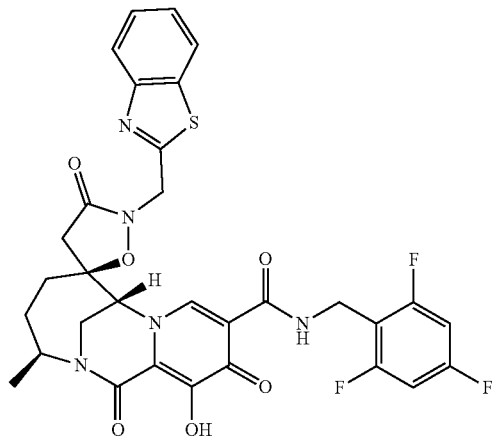 [SMILES: C[C@H]1CC[C@]2(CC(=O)N(Cc3nc4ccccc4s3)O2)[C@H]2CN1C(=O)c1c(O)c(=O)c(C(=O)NCc3c(F)cc(F)cc3F)cn12]

(3'S,5S,7'R)-2-(benzo[d]thiazol-2-ylmethyl)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide was synthesized in a similar manner as Example 103, except using 2-(bromomethyl)benzo[d]thiazole instead of 5-(bromomethyl)-1-methyl-indazole in Step 7. MS (m/z) 654.242 [M+H]+. 1H NMR (400 MHz, Chloroform-d) δ 10.57 (t, J=5.8 Hz, 1H), 8.82 (s, 1H), 8.08 (d, J=8.1 Hz, 1H), 8.01-7.91 (m, 1H), 7.62-7.47 (m, 2H), 6.72-6.62 (m, 2H), 4.72 (s, 2H), 4.69-4.63 (m, 1H), 4.61 (d, J=5.8 Hz, 1H), 3.94 (d, J=14.8 Hz, 1H), 3.77 (dd, J=14.8, 2.7 Hz, 1H), 2.97-2.86 (m, 1H), 2.20 (d, J=15.5 Hz, 2H), 1.98 (d, J=16.0 Hz, 4H), 1.47 (dd, J=14.1, 11.3 Hz, 1H), 1.37-1.25 (m, 3H).

Example 162: Preparation of (3'S,5S,7'R)-2-((1H-benzo[d]imidazol-2-yl)methyl)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide

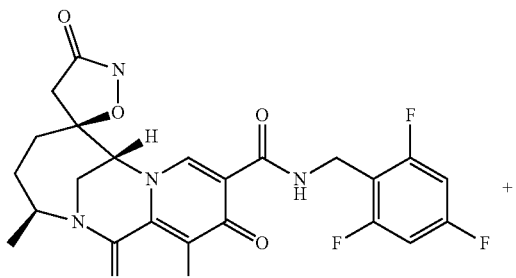

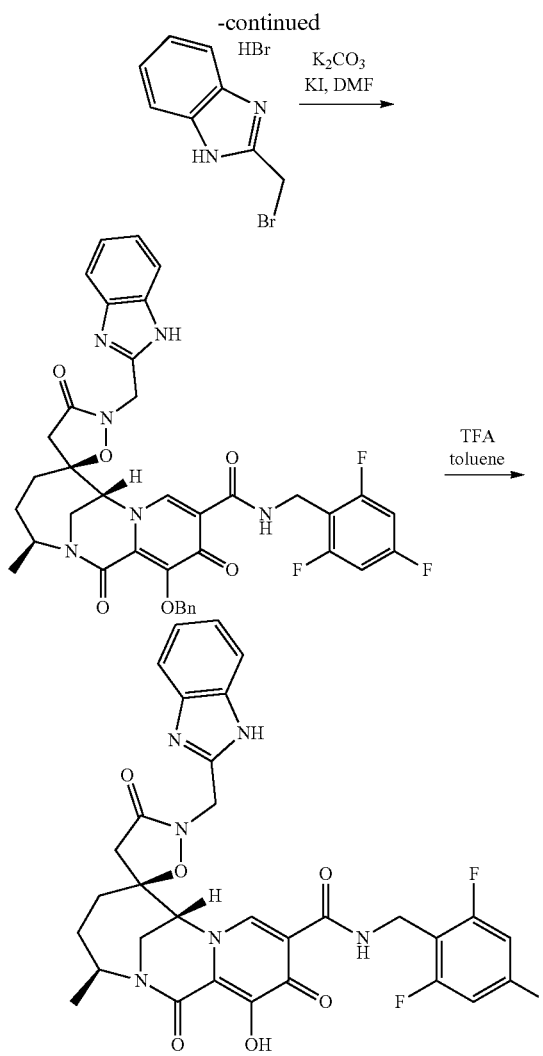

Step 1: Preparation of (3'S,5S,7'R)-2-((1H-benzo[d]imidazol-2-yl)methyl)-12'-(benzyloxy)-3'-methyl-1', 3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide (3'S,5S,7'R)-2-((1H-benzo[d]imidazol-2-yl)methyl)-12'-(benzyloxy)-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide was prepared in a similar manner as Step 7 of Example 103, except using (3'S,5S,7'R)-12'-(benzyloxy)-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide instead of (3'S,5S,7'R)-12'-methoxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide and 2-(bromomethyl)-1H-benzo[d]imidazole hydrobromide instead of 5-(bromomethyl)-1-methyl-indazole. MS (m/z) 727.29 [M+H]+.

Step 2: Preparation of (3'S,5S,7'R)-2-((1H-benzo[d]imidazol-2-yl)methyl)-12'-hydroxy-3'-methyl-1',3, 11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide (3'S,5S,7'R)-2-((1H-benzo[d]imidazol-2-yl)methyl)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide was prepared in a similar manner as Step 2 of Example 101, except using (3'S,5S,7'R)-2-((1H-benzo[d]imidazol-2-yl)methyl)-12'-(benzyloxy)-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide instead of (3'S,5S,7'R)-12'-(benzyloxy)-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide. MS (m/z) 637.297 [M+H]+. $^1$H NMR (400 MHz, Chloroform-d) δ 10.57 (s, 1H), 8.31 (s, 1H), 7.70 (dd, J=6.5, 3.0 Hz, 2H), 7.56-7.44 (m, 2H), 6.63 (t, J=8.3 Hz, 2H), 5.41 (d, J=17.1 Hz, 1H), 5.28 (s, 1H), 4.87 (s, 1H), 4.66 (d, J=9.1 Hz, 1H), 4.53 (s, 2H), 3.90-3.73 (m, 2H), 3.00 (s, 1H), 2.61 (d, J=17.6 Hz, 1H), 2.46 (s, 1H), 2.14 (d, J=15.4 Hz, 2H), 1.57 (d, J=13.2 Hz, 1H), 1.28 (d, J=6.5 Hz, 3H).

Example 163: Preparation of (3'S,5S,7'R)-12'-hydroxy-3'-methyl-2-((1-methyl-1H-benzo[d]imidazol-2-yl)methyl)-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide

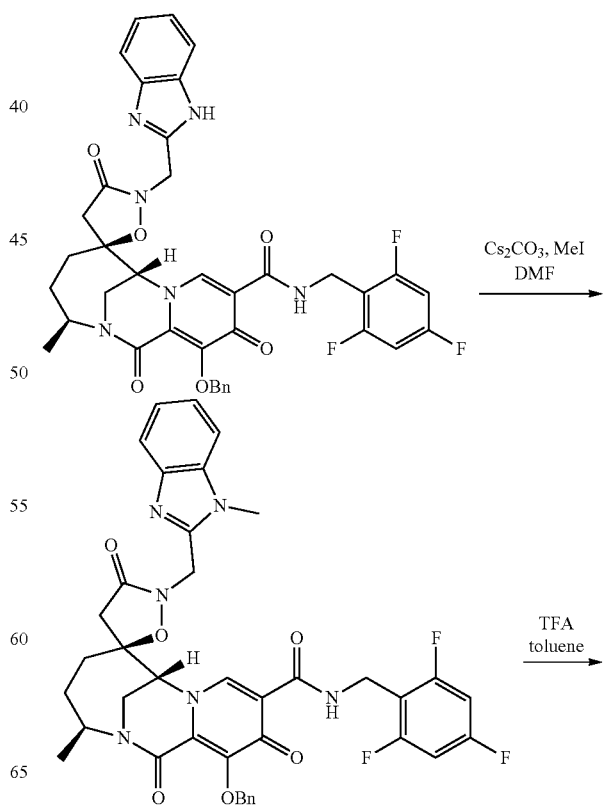

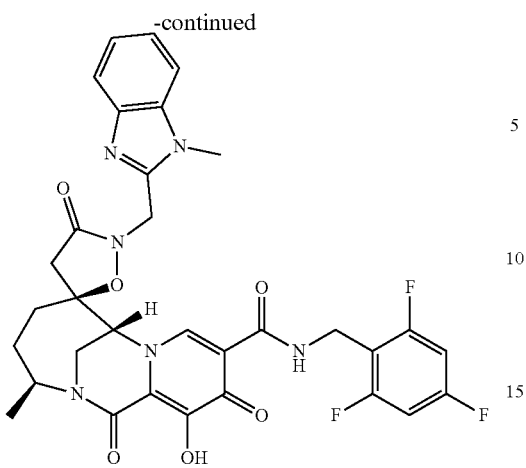

Step 1: Preparation of (3'S,5S,7'R)-12'-(benzyloxy)-3'-methyl-2-((1-methyl-1H-benzo[d]imidazol-2-yl)methyl)-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide To a solution of (3'S,5S,7'R)-2-((1H-benzo[d]imidazol-2-yl)methyl)-12'-(benzyloxy)-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide (19 mg, 0.261 mmol), prepared according to Step 1 of Example 162, in DMF (1 mL) was added iodomethane (3.7 mg, 0.0261 mmol) and cesium carbonate (25.6 mg, 0.0784 mmol) at rt. The reaction mixture was stirred at rt overnight. The reaction mixture was extracted with ethyl acetate. After the solvent was removed, the residue was used in the next step without further purification. MS (m/z) 741.235 [M+H]+.

Step 2: Preparation of (3'S,5S,7'R)-12'-hydroxy-3'-methyl-2-((1-methyl-1H-benzo[d]imidazol-2-yl)methyl)-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide (3'S,5S,7'R)-12'-hydroxy-3'-methyl-2-((1-methyl-1H-benzo[d]imidazol-2-yl)methyl)-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide was prepared in a manner similar to Step 2 of Example 162, except using (3'S,5S,7'R)-12'-(benzyloxy)-3'-methyl-2-((1-methyl-1H-benzo[d]imidazol-2-yl)methyl)-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide instead of (3'S,5S,7'R)-2-((1H-benzo[d]imidazol-2-yl)methyl)-12'-(benzyloxy)-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide. MS (m/z) 651.307 [M+H]+. $^1$H NMR (400 MHz, Chloroform-d) δ 10.56 (t, J=5.8 Hz, 1H), 8.78 (s, 1H), 7.94 (dd, J=7.8, 1.3 Hz, 1H), 7.63-7.50 (m, 3H), 6.75-6.68 (m, 1H), 6.47 (s, 1H), 4.79-4.59 (m, 3H), 4.29 (s, 1H), 3.99 (d, J=11.5 Hz, 2H), 3.78 (d, J=15.1 Hz, 2H), 3.63 (dd, J=14.9, 2.8 Hz, 2H), 3.05 (d, J=16.4 Hz, 1H), 2.76 (s, 3H), 2.21-2.07 (m, 2H), 1.79 (d, J=11.8 Hz, 1H), 1.29 (d, J=6.6 Hz, 3H).

Example 164: Preparation of (3'S,5S,7'R)-2-((1-ethyl-1H-benzo[d]imidazol-2-yl)methyl)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide

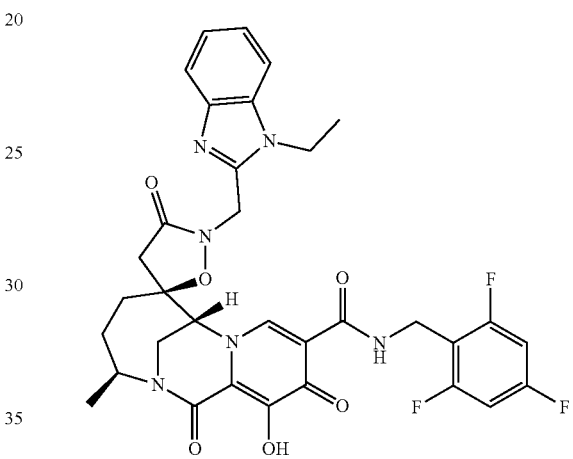

(3'S,5S,7'R)-2-((1-ethyl-1H-benzo[d]imidazol-2-yl)methyl)-12'-hydroxy-3'-methyl-1',3,11'-trioxo-N-(2,4,6-trifluorobenzyl)-1',4',5',11'-tetrahydro-3'H,7'H-spiro[isoxazolidine-5,6'-[2,7]methanopyrido[1,2-a][1,4]diazonine]-10'-carboxamide was prepared in a manner similar to Example 163, except using iodoethane instead of iodomethane in Step 1. MS (m/z) 665.33 [M+H]+. $^1$H NMR (400 MHz, Chloroform-d) δ 10.40 (t, J=5.8 Hz, 1H), 8.61 (s, 1H), 8.08-7.92 (m, 1H), 7.71-7.51 (m, 2H), 6.67 (dd, J=8.7, 7.5 Hz, 2H), 5.73 (s, 1H), 4.71 (s, 1H), 4.66 (t, J=6.1 Hz, 1H), 4.54-4.40 (m, 2H), 3.83 (dd, J=15.1, 1.9 Hz, 1H), 3.69 (dd, J=14.9, 2.7 Hz, 1H), 3.07-2.96 (m, 1H), 2.81-2.68 (m, 2H), 2.40-2.29 (m, 2H), 2.19 (s, 1H), 2.08 (s, 2H), 1.99 (s, 2H), 1.62 (t, J=7.3 Hz, 3H), 1.30 (dd, J=6.7, 2.5 Hz, 3H).

Example 165: Preparation of (2R,3'S,7'R)-12'-hydroxy-3'-methyl-1',11'-dioxo-N-(2,4,6-trifluorobenzyl)-1',4',5',11'-tetrahydro-3'H,7'H-spiro[oxirane-2,6'-[2,7]methanopyrido[1,2-a][1,4]diazonine]-10'-carboxamide

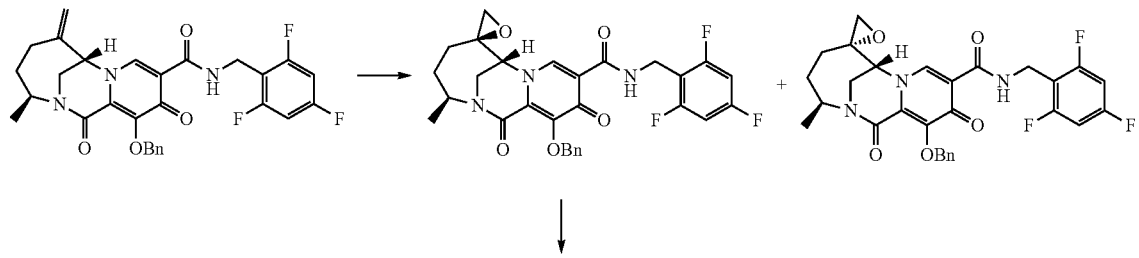

-continued

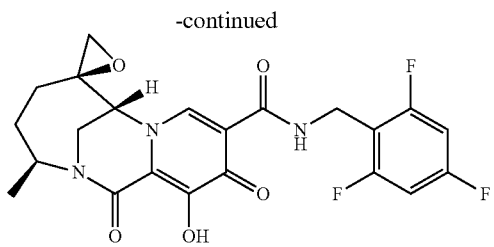

Step 1: Preparation of (2R,3'S,7'R)-12'-(benzyloxy)-3'-methyl-1',11'-dioxo-N-(2,4,6-trifluorobenzyl)-1',4',5',11'-tetrahydro-3'H,7'H-spiro[oxirane-2,6'-[2,7]methanopyrido[1,2-a][1,4]diazonine]-10'-carboxamide (Peak 1) and (2S,3'S,7'R)-12'-(benzyloxy)-3'-methyl-1',11'-dioxo-N-(2,4,6-trifluorobenzyl)-1',4',5',11'-tetrahydro-3'H,7'H-spiro[oxirane-2,6'-[2,7]methanopyrido[1,2-a][1,4]diazonine]-10'-carboxamide (Peak 2)

To a solution of Intermediate C (100 mg, 0.186 mmol) in DCE (4.0 mL) was added m-CPBA (96.3 mg, 0.558 mmol) and heated at 60° C. for 2 h. The reaction was then cooled to room temperature and diluted with DCM. 1N sodium thiosulfate (10 mL) and saturated sodium bicarbonate (10 mL) were added and stirred vigorously for 10 minutes. The phases were separated and the organic phase was washed with brine, dried over sodium sulfate, filtered and concentrated. The residue was purified by silica gel column chromatography (0-100% EtOAc/hexanes then 0-10% MeOH/EtOAc) to afford the title compounds.

Peak 1: (2R,3'S,7'R)-12'-(benzyloxy)-3'-methyl-1',11'-dioxo-N-(2,4,6-trifluorobenzyl)-1',4',5',11'-tetrahydro-3'H,7'H-spiro[oxirane-2,6'-[2,7]methanopyrido[1,2-a][1,4]diazonine]-10'-carboxamide. LCMS-ESI+(m/z): calcd H+ for C29H26F3N3O5, Theoretical: 553.54, Found: 554.07.

Peak 2: (2S,3'S,7'R)-12'-(benzyloxy)-3'-methyl-1',11'-dioxo-N-(2,4,6-trifluorobenzyl)-1',4',5',11'-tetrahydro-3'H,7'H-spiro[oxirane-2,6'-[2,7]methanopyrido[1,2-a][1,4]diazonine]-10'-carboxamide. LCMS-ESI+(m/z): calcd H+ for C29H26F3N3O5, Theoretical: 553.54, Found: 554.11.

Step 2: Preparation of (2R,3'S,7'R)-12'-hydroxy-3'-methyl-1',11'-dioxo-N-(2,4,6-trifluorobenzyl)-1',4',5',11'-tetrahydro-3'H,7'H-spiro[oxirane-2,6'-[2,7]methanopyrido[1,2-a][1,4]diazonine]-10'-carboxamide (2R,3'S,7'R)-12'-(benzyloxy)-3'-methyl-1',11'-dioxo-N-(2,4,6-trifluorobenzyl)-1',4',5',11'-tetrahydro-3'H,7'H-spiro[oxirane-2,6'-[2,7]methanopyrido[1,2-a][1,4]diazonine]-10'-carboxamide (15 mg, 0.027 mmol) was treated with a mixture of toluene (0.3 mL) and TFA (0.3 mL) at room temperature overnight. The reaction was concentrated and purified by reverse phase preparative HPLC (10-100% MeCN/water containing 0.1% TFA) to afford the title compound. 1H NMR (400 MHz, DMSO-d6) δ 10.36 (t, J=5.7 Hz, 1H), 8.54 (s, 1H), 7.26-7.15 (m, 2H), 4.65-4.49 (m, 3H), 4.18 (d, J=2.4 Hz, 1H), 3.87 (dd, J=15.1, 1.9 Hz, 1H), 3.76 (dd, J=15.0, 2.6 Hz, 1H), 3.21 (d, J=4.5 Hz, 1H), 2.72 (d, J=4.5 Hz, 1H), 2.00-1.88 (m, 1H), 1.79-1.51 (m, 2H), 1.23 (d, J=6.7 Hz, 3H), 1.16 (dd, J=15.2, 6.7 Hz, 1H). LCMS-ESI+(m/z): calcd H+ for C22H20F3N3O5, Theoretical: 463.41, Found: 464.15.

Example 166: Preparation of (2S,3'S,7'R)-12'-hydroxy-3'-methyl-1',11'-dioxo-N-(2,4,6-trifluorobenzyl)-1',4',5',11'-tetrahydro-3'H,7'H-spiro[oxirane-2,6'-[2,7]methanopyrido[1,2-a][1,4]diazonine]-10'-carboxamide

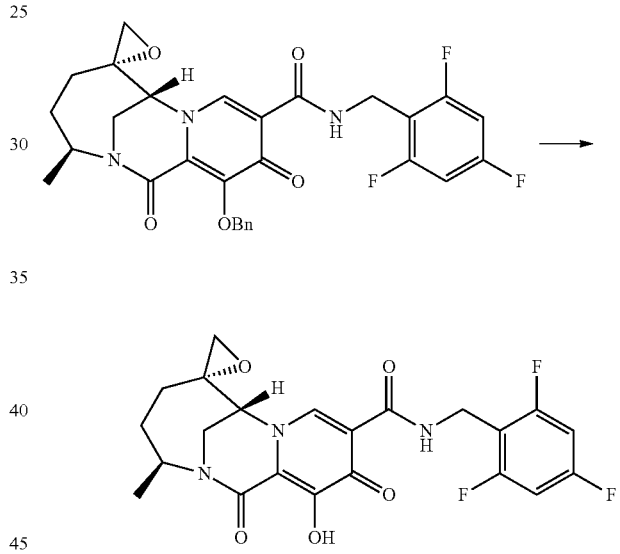

(2S,3'S,7'R)-12'-(benzyloxy)-3'-methyl-1',11'-dioxo-N-(2,4,6-trifluorobenzyl)-1',4',5',11'-tetrahydro-3'H,7'H-spiro[oxirane-2,6'-[2,7]methanopyrido[1,2-a][1,4]diazonine]-10'-carboxamide (20 mg, 0.036 mmol), prepared according to Step 1 of Example 165, was treated with a mixture of toluene (0.2 mL) and TFA (0.2 mL) at room temperature overnight. The reaction was concentrated and purified by reverse phase preparative HPLC (10-100% MeCN/water containing 0.1% TFA) to afford the title compound. 1H NMR (400 MHz, DMSO-d6) δ 10.35 (t, J=5.8 Hz, 1H), 8.22 (s, 1H), 7.21 (t, J=8.7 Hz, 2H), 4.63-4.51 (m, 3H), 4.33 (d, J=2.2 Hz, 1H), 3.94 (dd, J=15.1, 1.8 Hz, 1H), 3.76 (dd, J=15.1, 2.9 Hz, 1H), 3.06 (dd, J=5.2, 1.7 Hz, 1H), 2.77 (d, J=5.2 Hz, 1H), 2.00 (dt, J=14.1, 6.9 Hz, 1H), 1.77-1.62 (m, 1H), 1.59-1.47 (m, 1H), 1.21 (d, J=6.7 Hz, 3H), 1.09 (dd, J=14.7, 7.4 Hz, 1H). LCMS-ESI+(m/z): calcd H+ for C22H20F3N3O5, Theoretical: 463.41, Found: 464.19.

Example 167: Preparation of (2R,3'S,4S,7'R)-12'-hydroxy-4-(methoxymethyl)-3'-methyl-1',11'-dioxo-N-(2,4,6-trifluorobenzyl)-1',4',5',11'-tetrahydro-3'H,7'H-spiro[[1,3]dioxolane-2,6'-[2,7]methanopyrido[1,2-a][1,4]diazonine]-10'-carboxamide

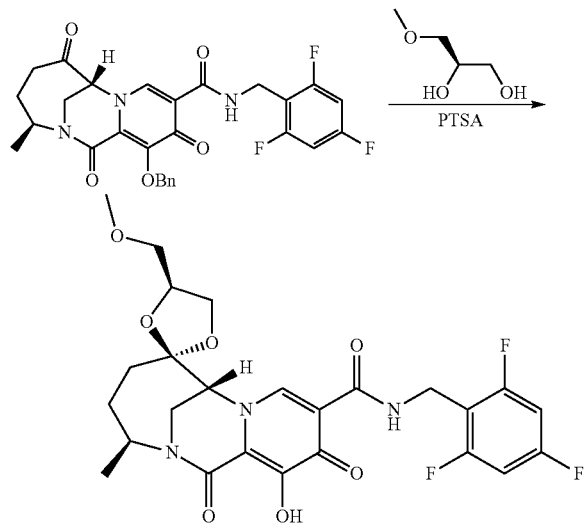

To a solution of (3S,7R)-12-(benzyloxy)-3-methyl-1,6,11-trioxo-N-(2,4,6-trifluorobenzyl)-1,4,5,6,7,11-hexahydro-3H-2,7-methanopyrido[1,2-a][1,4]diazonine-10-carboxamide (40 mg, 0.071 mmol), prepared according to Example 55, in toluene (2 mL) was added p-toluenesulfonic acid monohydrate (28.2 mg, 0.145 mmol) and (R)-3-methoxypropane-1,2-diol (23.2 mg, 0.22 mmol). To the mixture was added small amount of MgSO₄. The reaction mixture was stirred at 95° C. for 2 d. The reaction mixture was cooled to rt and concentrated. The residue was purified by reverse phase preparative HPLC (5-100% MeCN/water containing 0.1% TFA) to afford the title compound. MS (m/z): 538.18 [M+H]+. 1H NMR (400 MHz, Methanol-d4) δ 8.41 (s, 1H), 6.97-6.87 (m, 2H), 4.72-4.58 (m, 3H), 4.55 (q, J=2.1 Hz, 1H), 4.47 (ddt, J=9.9, 6.5, 3.7 Hz, 1H), 4.16-4.05 (m, 2H), 3.77 (d, J=2.4 Hz, 2H), 3.68 (dd, J=10.6, 3.3 Hz, 1H), 3.56 (dd, J=10.6, 4.1 Hz, 1H), 3.50 (s, 3H), 2.04-1.93 (m, 1H), 1.91-1.75 (m, 2H), 1.30 (d, J=1.1 Hz, 1H), 1.28 (dd, J=6.7, 2.4 Hz, 3H).

Example 168: Preparation of (2S,3'S,4R,7'R)-12'-hydroxy-4-(methoxymethyl)-3'-methyl-1',11'-dioxo-N-(2,4,6-trifluorobenzyl)-1',4',5',11'-tetrahydro-3'H,7'H-spiro[[1,3]dioxolane-2,6'-[2,7]methanopyrido[1,2-a][1,4]diazonine]-10'-carboxamide and (2R,3'S,4R,7'R)-12'-hydroxy-4-(methoxymethyl)-3'-methyl-1',11'-dioxo-N-(2,4,6-trifluorobenzyl)-1',4',5',11'-tetrahydro-3'H,7'H-spiro[[1,3]dioxolane-2,6'-[2,7]methanopyrido[1,2-a][1,4]diazonine]-10'-carboxamide

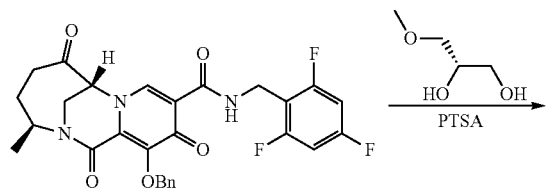

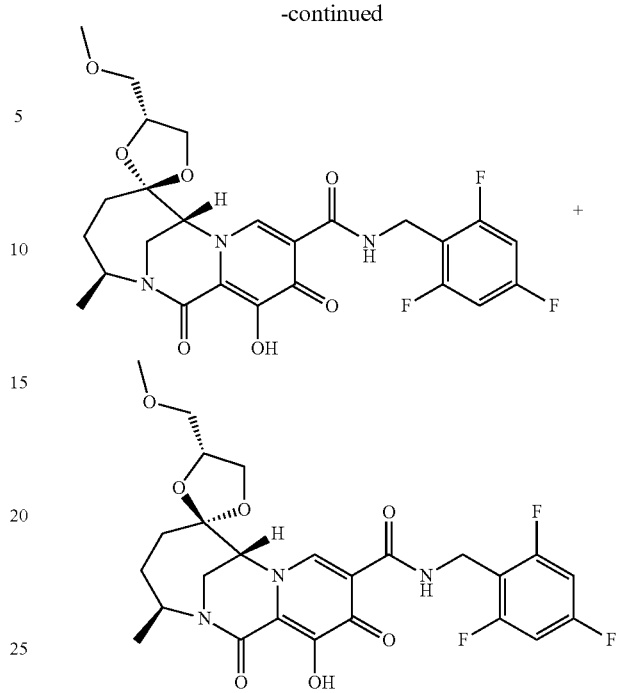

The title compounds were prepared in a manner similar to Example 167, except using (S)-3-methoxypropane-1,2-diol instead of (R)-3-methoxypropane-1,2-diol. Two compounds were isolated during reverse phase preparative HPLC.

Peak 1: MS (m/z): 538.23 [M+H]+. 1H NMR (400 MHz, Methanol-d4) δ 8.38 (s, 1H), 6.96-6.86 (m, 2H), 4.71-4.61 (m, 3H), 4.59-4.50 (m, 1H), 4.38 (s, 1H), 4.31 (dd, J=8.3, 6.3 Hz, 1H), 3.82-3.74 (m, 3H), 3.56 (dd, J=4.8, 1.1 Hz, 2H), 3.43 (s, 3H), 2.01 (dt, J=14.0, 6.9 Hz, 1H), 1.94-1.83 (m, 1H), 1.76 (dd, J=15.1, 7.1 Hz, 1H), 1.47-1.37 (m, 1H), 1.29 (d, J=6.7 Hz, 3H).

Peak 2: MS (m/z): 538.24 [M+H]+. 1H NMR (400 MHz, Methanol-d4) δ 8.64 (s, 1H), 6.98-6.86 (m, 2H), 4.73-4.61 (m, 3H), 4.34 (q, J=3.5 Hz, 2H), 4.21 (dd, J=8.3, 6.3 Hz, 1H), 4.07 (dd, J=8.3, 7.3 Hz, 1H), 3.81-3.68 (m, 3H), 3.59-3.49 (m, 2H), 2.05-1.70 (m, 4H), 1.44-1.31 (m, 2H), 1.28 (d, J=6.6 Hz, 3H).

Example 169: Preparation of (2S,3'S,4R,7'R)-4-benzyl-12'-hydroxy-3'-methyl-1',11'-dioxo-N-(2,4,6-trifluorobenzyl)-1',4',5',11'-tetrahydro-3'H,7'H-spiro[[1,3]dioxolane-2,6'-[2,7]methanopyrido[1,2-a][1,4]diazonine]-10'-carboxamide and (2R,3'S,4R,7'R)-4-benzyl-12'-hydroxy-3'-methyl-1',11'-dioxo-N-(2,4,6-trifluorobenzyl)-1',4',5',11'-tetrahydro-3'H,7'H-spiro[[1,3]dioxolane-2,6'-[2,7]methanopyrido[1,2-a][1,4]diazonine]-10'-carboxamide

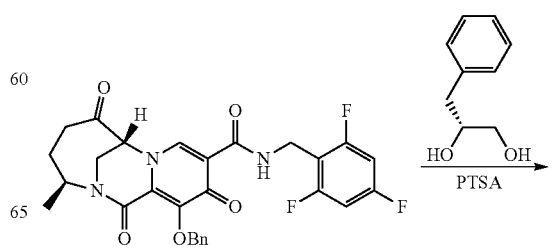

-continued

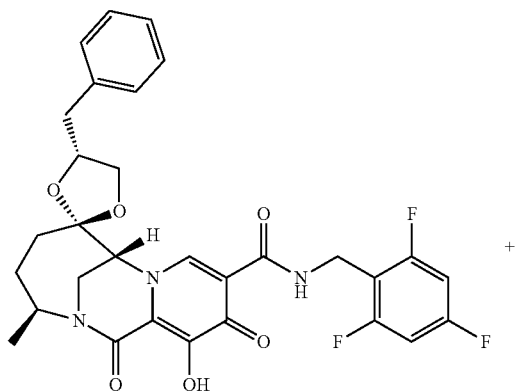

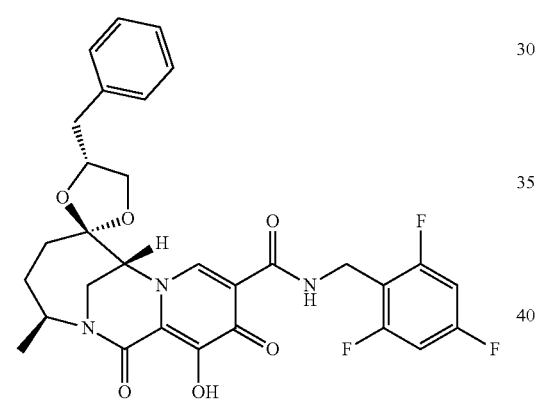

The title compounds were prepared in a manner similar to Example 167, except using (R)-3-phenylpropane-1,2-diol instead of (R)-3-methoxypropane-1,2-diol. Two compounds were isolated during reverse phase preparative HPLC.

Peak 1: MS (m/z): 584.20 [M+H]+. 1H NMR (400 MHz, Methanol-d4) δ 8.62 (s, 1H), 7.20 (dd, J=6.5, 3.0 Hz, 2H), 7.16-7.07 (m, 3H), 6.99-6.87 (m, 2H), 4.82-4.68 (m, 2H), 4.68-4.57 (m, 2H), 4.39-4.27 (m, 2H), 4.22 (dd, J=8.2, 5.2 Hz, 1H), 3.85 (t, J=8.7 Hz, 1H), 3.77 (t, J=2.5 Hz, 2H), 2.99 (d, J=6.6 Hz, 2H), 1.94 (dt, J=14.2, 6.9 Hz, 1H), 1.88-1.77 (m, 1H), 1.73 (dt, J=15.3, 7.4 Hz, 1H), 1.27 (d, J=6.6 Hz, 3H).

Peak 2: MS (m/z): 584.26 [M+H]+. 1H NMR (400 MHz, Methanol-d4) δ 8.39 (s, 1H), 7.34-7.22 (m, 5H), 6.95-6.86 (m, 2H), 4.72-4.55 (m, 4H), 4.34 (q, J=2.1 Hz, 1H), 4.20 (dd, J=8.2, 5.6 Hz, 1H), 3.75-3.69 (m, 2H), 3.65 (t, J=8.3 Hz, 1H), 3.05-2.89 (m, 2H), 2.06-1.95 (m, 1H), 1.87 (dt, J=15.4, 11.3 Hz, 1H), 1.64 (dd, J=15.1, 7.0 Hz, 1H), 1.38 (ddd, J=15.1, 11.7, 1.3 Hz, 1H), 1.28 (d, J=6.6 Hz, 3H).

Example 170: Preparation of (2S,3'S,5R,7'R)-12'-hydroxy-5-methoxy-3'-methyl-1',11'-dioxo-N-(2,4,6-trifluorobenzyl)-1',4',5',11'-tetrahydro-3'H,7'H-spiro[[1,3]oxathiolane-2,6'-[2,7]methanopyrido[1,2-a][1,4]diazonine]-10'-carboxamide, (2S,3'S,5S,7'R)-12'-hydroxy-5-methoxy-3'-methyl-1',11'-dioxo-N-(2,4,6-trifluorobenzyl)-1',4',5',11'-tetrahydro-3'H,7'H-spiro[[1,3]oxathiolane-2,6'-[2,7]methanopyrido[1,2-a][1,4]diazonine]-10'-carboxamide, (2R,3'S,5R,7'R)-12'-hydroxy-5-methoxy-3'-methyl-1',11'-dioxo-N-(2,4,6-trifluorobenzyl)-1',4',5',11'-tetrahydro-3'H,7'H-spiro[[1,3]oxathiolane-2,6'-[2,7]methanopyrido[1,2-a][1,4]diazonine]-10'-carboxamide, and (2R,3'S,5S,7'R)-12'-hydroxy-5-methoxy-3'-methyl-1',11'-dioxo-N-(2,4,6-trifluorobenzyl)-1',4',5',11'-tetrahydro-3'H,7'H-spiro[[1,3]oxathiolane-2,6'-[2,7]methanopyrido[1,2-a][1,4]diazonine]-10'-carboxamide

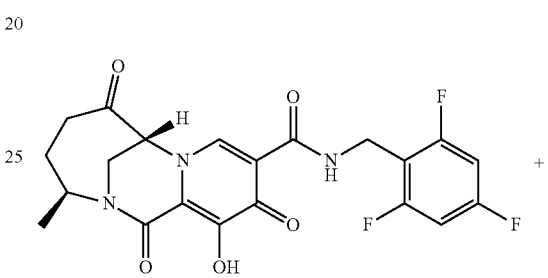

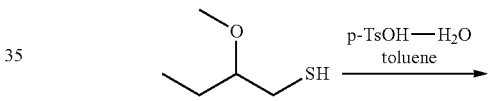

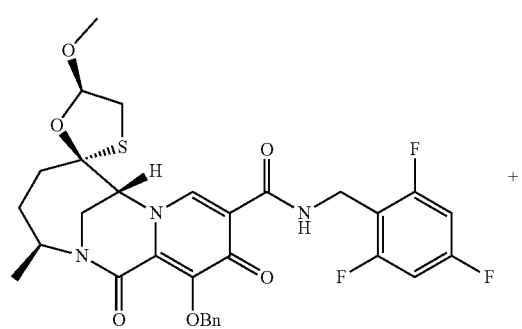

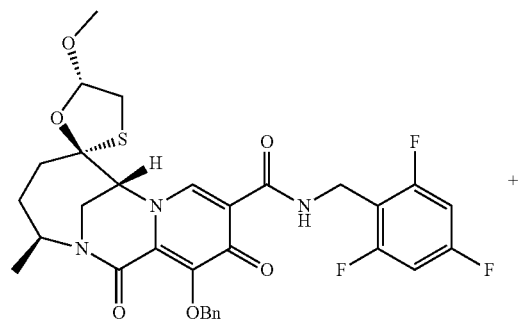

389
-continued
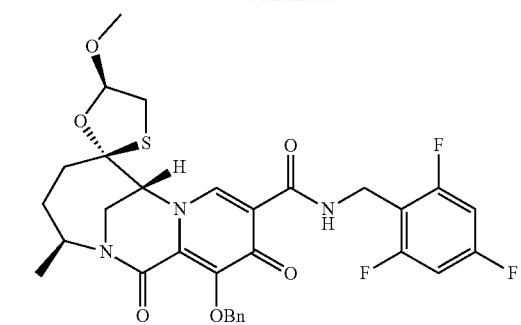
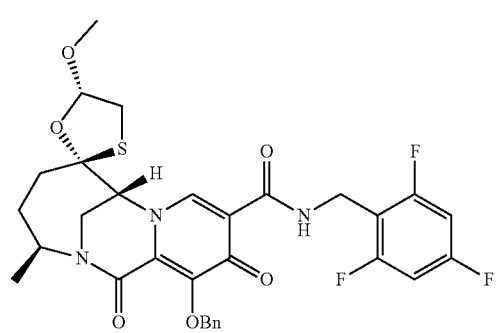
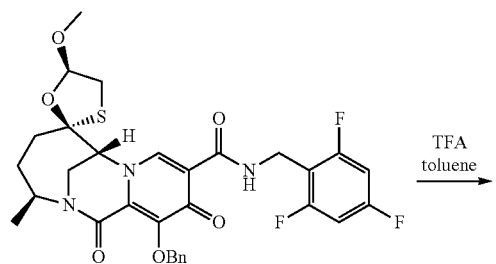
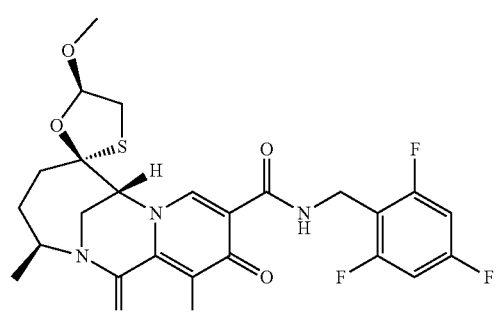
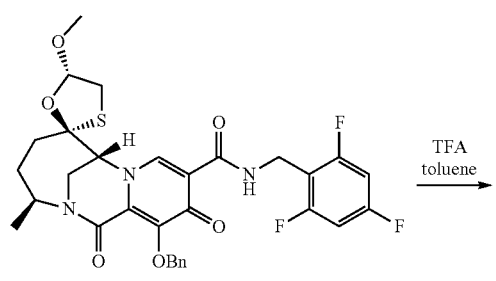
390
-continued
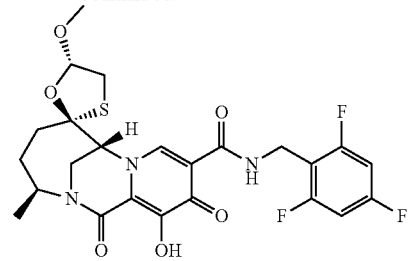
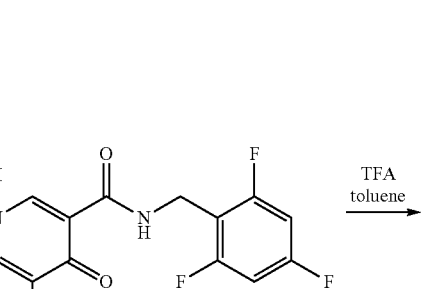 TFA toluene →
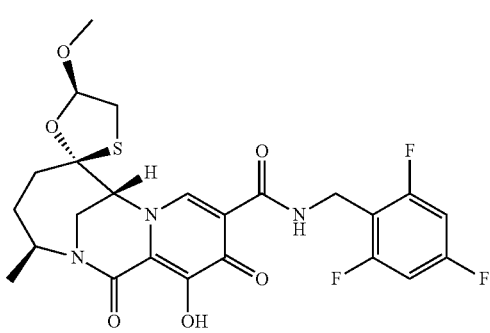
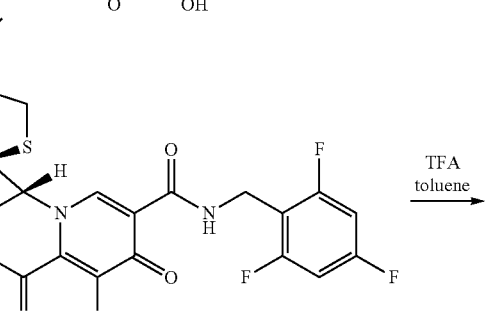 TFA toluene →
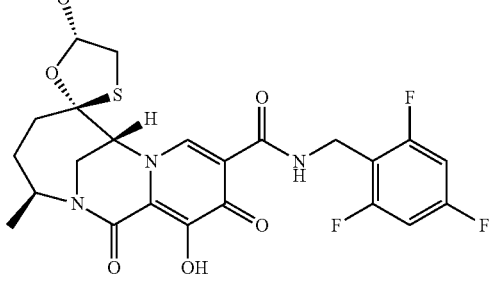

Step 1. Preparation of (2S,3'S,5R,7'R)-12'-(benzyloxy)-5-methoxy-3'-methyl-1',11'-dioxo-N-(2,4,6-trifluorobenzyl)-1',4',5',7'-tetrahydro-3'H, 7'H-spiro[[1,3 oxathiolane-2,6'-[2,7]methanopyrido[1,2-a][1,4]diazonine]-10'-carboxamide, (2S,3'S,5S,7'R)-12'-(benzyloxy)-5-methoxy-3'-methyl-1',1]'-dioxo-N-(2,4,6-trifluorobenzyl)-1',4',5',11'-tetrahydro-3'H, 7'H-spiro[[1,3]oxathiolane-2,6'-[2,7]methanopyrido[1,2-a][1,4]diazonine]-10-carboxamide, (2R,3'S,5R,7'R)-12'-(benzyloxy)-5-methoxy-3'-methyl-1',11'-dioxo-N-(2,4,6-trifluorobenzyl)-1',4',5',11'-tetrahydro-3'H, 7'H-spiro[[1,3]oxathiolane-2,6'-[2,7]methanopyrido[1,2-a][1,4]diazonine]-10'-carboxamide, and (2R,3'S,5S,7'R)-12'-(benzyloxy)-5-methoxy-3'-methyl-1',11'-dioxo-N-(2,4,6-trifluorobenzyl)-1',4',5',1'-tetrahydro-3'H,7'H-spiro[[1,3]oxathiolane-2,6'-[2,7]methanopyrido[1,2-a][1,4]diazonine]-10'-carboxamide To a solution of (3S,7R)-12-(benzyloxy)-3-methyl-1,6,11-trioxo-N-(2,4,6-trifluorobenzyl)-1,4,5,6,7,11-hexahydro-3H-2,7-methanopyrido[1,2-a][1,4]diazonine-10-carboxamide (152 mg, 0.282 mmol), prepared according to Example 55, in toluene (4 mL) was added 2,2-dimethoxyethanethiol (103 mg, 0.845 mmol) and p-toluenesulfonic acid monohydrate (4.85 mg, 0.0282 mmol) at rt. The reaction flask was sealed and heated to 130° C. for 4 h. The reaction mixture was extracted with ethyl acetate, washed with brine. After drying over $Na_2SO_4$, the solvent was removed and the residue was purified by silica gel column chromatography to obtain four isomers.

Peak 1: MS (m/z) 630.164 [M+H]+.
Peak 2: MS (m/z) 630.072 [M+H]+.
Peak 3: MS (m/z) 630.166 [M+H]+.
Peak 4: MS (m/z) 630.052 [M+H]+.

Step 2-5: Preparation of (2S,3'S,5R,7'R)-12'-hydroxy-5-methoxy-3'-methyl-1',11'-dioxo-N-(2,4,6-trifluorobenzyl)-1',4',5',11'-tetrahydro-3'H,7'H-spiro[[1,3]oxathiolane-2,6'-[2,7]methanopyrido[1,2-a][1,4]diazonine]-10'-carboxamide, (2S,3'S,5S,7'R)-12'-hydroxy-5-methoxy-3'-methyl-1',11'-dioxo-N-(2,4,6-trifluorobenzyl)-1',4',5',11'-tetrahydro-3'H,7'H-spiro[[1,3]oxathiolane-2,6'-[2,7]methanopyrido[1,2-a][1,4]diazonine]-10'-carboxamide, (2R,3'S,5R,7'R)-12'-hydroxy-5-methoxy-3'-methyl-1',11'-dioxo-N-(2,4,6-trifluorobenzyl)-1',4',5',11'-tetrahydro-3'H,7'H-spiro[[1,3]oxathiolane-2,6'-[2,7]methanopyrido[1,2-a][1,4]diazonine]-10'-carboxamide, and (2R,3'S,5S,7'R)-12'-hydroxy-5-methoxy-3'-methyl-1',11'-dioxo-N-(2,4,6-trifluorobenzyl)-1',4',5',11'-tetrahydro-3'H,7'H-spiro[[1,3]oxathiolane-2,6'-[2,7]methanopyrido[1,2-a][1,4]diazonine]-10'-carboxamide A solution of each isomer from Step 1 in 3:1 toluene/TFA (2 mL) was stirred at rt overnight. The reaction mixture was concentrated and purified by reverse phase preparative HPLC (5-100% MeCN/water containing 0.1% TFA) to yield the four title compounds.

From Peak 1: MS (m/z) 540.172 [M+H]+. $^1$H NMR (400 MHz, Chloroform-d) δ 10.64 (t, J=5.8 Hz, 1H), 8.42 (s, 1H), 6.70 (dd, J=8.7, 7.5 Hz, 2H), 5.50 (d, J=3.8 Hz, 1H), 4.76-4.64 (m, 3H), 4.26 (s, 1H), 3.67 (qd, J=15.3, 2.4 Hz, 2H), 3.48-3.40 (m, 1H), 3.33 (s, 3H), 3.27 (d, J=11.7 Hz, 1H), 2.23-2.08 (m, 2H), 1.84 (dd, J=14.7, 11.5 Hz, 1H), 1.55 (dt, J=14.8, 11.0 Hz, 1H), 1.31 (d, J=6.7 Hz, 3H).

From Peak 2: MS (m/z) 540.289 [M+H]+. $^1$H NMR (400 MHz, Chloroform-d) δ 10.54 (d, J=5.8 Hz, 1H), 8.70 (s, 1H), 6.73-6.67 (m, 2H), 5.52-5.47 (m, 1H), 4.72 (t, J=5.2 Hz, 2H), 3.77 (d, J=2.0 Hz, 1H), 3.72-3.68 (m, 1H), 3.48-3.40 (m, 3H), 3.33-3.24 (m, 2H), 3.21 (dd, J=11.6, 1.3 Hz, 2H), 2.42-2.33 (m, 1H), 2.23-2.14 (m, 1H), 1.84 (dd, J=14.7, 11.6 Hz, 1H), 1.76-1.68 (m, 1H), 1.31 (dd, J=6.7, 2.2 Hz, 3H).

From Peak 3: MS (m/z) 540.226 [M+H]+. $^1$H NMR (400 MHz, Chloroform-d) δ 10.45 (t, J=5.8 Hz, 1H), 8.69 (s, 1H), 6.69 (dd, J=8.7, 7.5 Hz, 2H), 5.48 (t, J=2.6 Hz, 1H), 4.71 (dq, J=23.7, 7.1, 5.7 Hz, 4H), 4.46 (s, 1H), 3.84-3.68 (m, 2H), 3.46 (s, 2H), 3.30 (d, J=2.7 Hz, 2H), 2.17-2.09 (m, 1H), 2.03-1.91 (m, 2H), 1.72 (ddd, J=15.6, 9.7, 3.2 Hz, 1H), 1.31 (d, J=6.7 Hz, 3H).

From Peak 4: MS (m/z) 540.218 [M+H]+. $^1$H NMR (400 MHz, Chloroform-d) δ 10.40 (t, J=5.5 Hz, 1H), 8.73 (s, 1H), 6.67 (dd, J=8.7, 7.5 Hz, 2H), 5.45 (t, J=4.5 Hz, 1H), 4.80-4.59 (m, 3H), 4.43 (s, 1H), 3.70-3.55 (m, 2H), 3.51 (s, 3H), 3.37 (dd, J=12.2, 4.7 Hz, 1H), 3.26 (d, J=4.2 Hz, 1H), 2.25-2.14 (m, 2H), 1.85 (d, J=6.9 Hz, 1H), 1.64-1.58 (m, 1H), 1.30 (d, J=6.7 Hz, 3H).

Example 171: HIV MT-4 Antiviral and Cytotoxicity Assay

Antiviral Assay in MT-4 Cells

Compounds were tested in a high-throughput 384-well assay format for their ability to inhibit the replication of HIV-1 (IIIB) in MT-4 cells. Compounds were serially diluted (1:3) in DMSO on 384-well polypropylene plates and further diluted 200-fold into complete RPMI media (10% FBS, 1% P/S) using the Biotek Micro Flow and Labcyte ECHO acoustic dispenser. Each plate contained up to 8 test compounds, with negative (No Drug Control) and 5 μM AZT positive controls. MT-4 cells were pre-infected with 10 μL of either RPMI (mock-infected) or a fresh 1:250 dilution of HIV-1 IIIB concentrated virus stock. Infected and uninfected MT-4 cells were further diluted in complete RPMI media and added to each plate using a Micro Flow dispenser. After 5 days incubation in a humidified and temperature controlled incubator (37° C.), Cell Titer Glo (Promega) was added to the assay plates and chemiluminescence read using an Envision plate-reader. $EC_{50}$ values were defined as the compound concentration that causes a 50% decrease in luminescence signal, and were calculated using a sigmoidal dose-response model to generate curve fits. The data for exemplary compounds, as well as for Reference compounds A, B, C, and D is shown in Table 1-3. The structures of Reference compounds A, B, C, and D are shown below. These compounds are described in WO2020/197991.

Reference Compound A

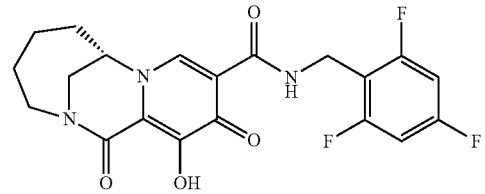

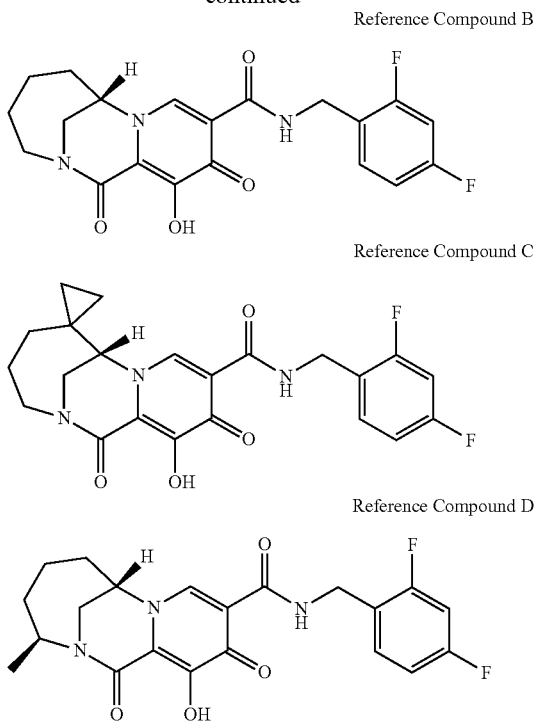

Cytotoxicity Assay in MT-4 Cells

Assays were performed as above except uninfected MT-4 cells were added to each well containing test compound. In addition, 10 μM puromycin was added to the last column of each assay plate to assess a base level of cytotoxicity. The data for exemplary compounds is shown in Table 1 and 2.

Example 172: HIV MT-4 Serum Shift Antiviral Reporter Assay

To quantify the amount of protein binding to human serum, test compounds and controls are prediluted (1:3) and spotted in replicates into 384 well black assay plates via acoustic transfer (Labcyte Echo). Replicate sets of plates are made for CCM media (RPMI/10% FBS) and each serum concentration to be tested. MT-4 cells grown in batch are centrifuged and resuspended in fresh CCM media at $2\times10^6$ cells/ml. Cells are batch infected with pLAI reporter virus at 50 ul/ml, aliquoted into large nutation tubes and incubated 2 hrs at 37 degrees with continuous mixing. The infection mixes are pooled and divided into centrifuge tubes for CCM and 50% human serum media conditions. The tubes are pelleted and resuspended to 375,000 cells/ml in each media condition, then added to assay plates at 40 ul per well using a Viaflo 384 pipettor. After 3 days incubation at 37 degrees in a $CO_2$ incubator, assay plates are processed with Renilla-glo reagent using a ViaFlo 384 with an addition/mixing program. Plates are read immediately on an Envision reader. Assay signals are plotted and dose response curves generated to determine compound potency in CCM and 50% human serum media conditions. To compare the level of protein binding, fold shifts are calculated by dividing $EC_{50}$ (50% HS)/$EC_{50}$ (CCM). The data for exemplary compounds, as well as for Reference compounds A, B, C, and D is shown in Table 1-3.

Compounds of the present disclosure demonstrate antiviral activity in this assay as depicted in Table 1 below. Accordingly, the compounds of the embodiments disclosed herein may be useful for treating the proliferation of the HIV virus, treating AIDS, or delaying the onset of AIDS or ARC symptoms.

Example 173: High Throughput Microsomal Stability Assay

Metabolic stability of compounds was assessed using Human, or Rat Liver Microsomal assays (Corning). In this assay, 10 nL compounds at concentration of 1 mM in 100% DMSO were dispensed into 384-well polypropylene plates using the Echo 550 acoustic liquid dispenser (Labcyte®). Each plate contained 384 wells with a single test compound in each well.

A solution of human (Corning® Gentest™ Human Mixed Pooled Microsomes), or rat (Corning® Gentest™ Rat [Sprague-Dawley] Pooled Liver Microsomes) liver microsomes at 2 mg/ml in 100 mM $K_2HPO_4/KH_2PO_4$ pH 7.4 with Alamethicin from *Trichoderma viride* (Sigma-Aldrich) 0.0225 mg/ml were incubated on ice for 15 minutes. 5 uL of this solution was added to individual wells following 15 minute incubation at room temperature; and supplemented with 5 uL NADPH Regenerating Solution of cofactors (Corning® Gentest™ UGT Reaction Mix) containing 100 mM $K_2HPO_4/KH_2PO_4$ pH 7.4, 2.6 mM NADP+, 6.6 mM glucose-6-phosphate, 6.6 mM $MgCl_2$, 0.8 U/mL glucose-6-phosphate dehydrogenase, 0.1 mM Sodium Citrate, 6.8 mM uridine diphosphate-glucuronic acid. Final concentration of analyte compounds at the beginning of the reaction was 1 uM. The reactions were incubated at 37° C. and time points of 0, 5, 15, 30, 40, 50, 60, and 70 minutes were collected for further analysis. Background data were collected using reactions without analyte compounds.

Upon collection of the reaction time points, samples were quenched with 30 uL of a solution of 72% acetonitrile, 8% methanol, 0.1% formic acid, 19.9% water, and internal standard (IS). Reaction plates were span in a centrifuge at speed of 4,000 rcf for 30 minutes and 4° C., following a dilution of the 10 uL quenched reaction into 40 uL de-ionized water, yielding assay plates.

Assay plates were analyzed using solid-state extraction coupled with quadrupole time-of-flight mass spectrometer, using Agilent QToF 6530 RapidFire 360 system, with $C_4$ type A solid state cartridges. Analysis was performed in either positive or negative ionization modes. Mobile phases contained 0.1% formic acid in water for loading analytes onto solid state extraction cartridges, and 0.1% formic acid in acetonitrile for elution into mass spectrometer in positive ionization mode, or 0.1% acetic acid in water for loading and 0.1% acetic acid in acetonitrile for extraction in negative ionization mode. Peak-area ratios of integrated counts for individual compounds to IS were plotted as semi-logarithmic chart of log vs time. Initial, linear portion of decay was fitted to a linear regression equation to derive half time of a compound decay.

Pharmacological parameters for an analyte compound metabolism were calculated using the following equations:

| Parameter | Equation |
|---|---|
| Half Life | $T_{1/2} = \dfrac{\mathrm{Ln}(2)}{-1 * \mathrm{Slope}}$ |
| Intrinsic Clearance (in vitro) | $Cl_{int,\,in\,vitro} = \dfrac{\ln 2}{T_{1/2} * Conc}$ |
| Intrinsic Clearance | $Cl_{int} = \dfrac{Cl_{int,\,in\,vitro} * \text{Liver Mass} * \text{Yield}}{\text{Body Weight}}$ |
| Predicted Hepatic Clearance | $Cl = \dfrac{Cl_{int} * Q_H}{Cl_{int} + Q_H}$ |
| Hepatic Extraction | $E = \dfrac{Cl}{Q_H} * 100\%$ |

Where:

Calculation of in vitro intrinsic clearance $$CL_{int,in,vitro} = \dfrac{\ln 2}{\text{Half-Life} * \text{Concentration}}$$

Concentration refers to the protein concentration (mg/mL) in the reaction.

| System | Concentration |
|---|---|
| "Mixed cofactor" Hepatic microsomes (+UDPGA +NADPH) | 1.0 mg protein/mL |

Calculation of In Vivo Intrinsic Clearance

This scales the in vitro intrinsic clearance up to the value that would be predicted for the entire mass of liver tissue (but with no restriction by blood flow). The value depends upon the size of the liver (species-dependent) and the yield of microsomal protein as appropriate (assumed to be species-independent).

$$CL_{int} = \dfrac{CL_{int,in,vitro} * \text{Liver mass} * \text{Yield}}{\text{Body weight}}$$

| Matrix | Yield |
|---|---|
| Microsomal fraction | 45 mg/g liver |

| Species | Body weight kg | Liver weight g |
|---|---|---|
| Human | 70 | 1800 |

Calculation of Predicted Clearance

Hepatic clearance will depend upon the inter-relationship of intrinsic clearance and hepatic blood flow and can be predicted from in vitro data using a variety of approaches.

$$CL = \dfrac{CL_{int} * Q_H}{CL_{int} + Q_H}$$

| Species | Hepatic blood flow L/hr/kg |
|---|---|
| Human | 1.3 |

Calculation of Hepatic Extraction

This is simply the predicted clearance expressed as a proportion of hepatic blood flow.

$$E = CL/Q_H * 100\%$$

Intrinsic clearance of the instant compounds, as well as for reference compounds, were calculated following the procedure above.

Example 174: Half Life

Nonclinical In Vivo Studies

All nonclinical studies were conducted in accordance with the Guide for the Care and Use of Laboratory Animals as adopted and promulgated by the U.S. National Institutes of Health, and were approved by the Institution's Animal Care and Use Committee or local equivalent.

Test compound PK was determined in monkeys (Labcorp, Madison, WI) following a single-dose intravenous infusion for 30 minutes. The dosing vehicle was a mixture of N-methylpyrrolidone, polyethylene glycol 300, and water for intravenous administration in monkeys. Serial blood samples were collected at predose, 0.25, 0.48 (before end of infusion), 0.58, 0.75, 1, 1.5, 2, 4, 8, 12, 24, 48, 72, 96, 120, 144, and 168 hours postdose (based on start of infusion) and plasma test compound concentrations were quantified using an LC-MS/MS method.

Cyno half lives for selected exemplary compounds as well as Reference Compounds A, B, C, and D are presented below.

| Compound | Cyno half-life (h) |
|---|---|
| Example 40 | 12 |
| Example 1 | 29 |
| Reference Compound A | 3 |
| Reference Compound B | 5 |
| Reference Compound D | 3 |

Plasma Bioanalysis

Nonclinical plasma samples were prepared by addition of 200 µl cold acetonitrile/internal standard solution to 96-well plates containing 50 µl aliquots of each plasma sample. After protein precipitation, each of the supernatants (50 µl) were transferred to clean 96-well plates and diluted with 450 µl of water. The sample injection volume was 2 µl. Samples were analyzed by a multiple reaction monitoring LC-MS/MS method. LC-MS system consisted of a Cohesive LX-2 multiplex with two identical DIONEX UltiMate 3000 RS pumps, Hypersil Gold C18 HPLC column (50×2.1 mm, 1.9 µm particle size; Thermo Fisher Scientific), and the ABSciex QTRAP5500 Mass Spectrometer LC-MS/MS system. Chromatography was performed using 0.1% formic acid and 1% isopropyl alcohol in aqueous solution (MP A), and 0.1% formic acid and 1% isopropyl alcohol in acetonitrile (MP B). The flow rate was maintained at 0.5 mL/min (gradient: 0-0.5 minutes, 5% MP B; 1.83 minutes, 30% MP B; 2.83-3.50 minutes, 95% MP B; 3.5-5 minutes, 5% MP B).

Pharmacokinetic Analysis

Plasma PK parameters for test compounds in monkeys were estimated via noncompartmental analysis using the software program Phoenix WinNonlin, version 6.3 (Pharsight Corporation, Mountain View, CA). The following plasma PK parameters were estimated in nonclinical species (as appropriate): observed peak plasma concentration ($C_{max}$), time to reach Cmax ($T_{max}$), last quantifiable plasma concentration (Clast), $t_{1/2}$, time of Clast ($T_{last}$), area under the plasma concentration-time curve (AUC) from time 0 to Clast ($AUC_{last}$), AUC from time 0 to infinity ($AUC_{inf}$), CL, mean residence time (MRT), and volume of distribution at steady state ($V_{ss}$).

Abbreviations

AUC: area under the plasma concentration-time curve;
$AUC_{inf}$: area under the plasma concentration-time curve from time 0 to infinity;
CL: clearance;
$C_{max}$: observed peak plasma concentration;
HPLC: high-performance liquid chromatography;
LC-MS/MS: liquid chromatography-tandem mass spectrometry;
PK: pharmacokinetic(s);
$T_{max}$: time to reach peak plasma concentration;
$V_{ss}$: volume of distribution at steady state;

TABLE 1

| Example No. | MT4 EC$_{50}$ (nM) | CC$_{50}$ (nM) | RLUC CCM EC$_{50}$ (nM) | RLUC 50% HS EC$_{50}$ (nM) | RLUC 50% HS Shift |
|---|---|---|---|---|---|
| 1 | 0.8 | 20406 | 0.3 | 92.0 | 307× |
| 2 | 11.2 | 50000 | 2.6 | 9.2 | 4× |
| 3 | 0.9 | 20060 | 0.2 | 71.2 | 356× |
| 4 | 5.7 | 50000 | 3.0 | 4.6 | 2× |
| 5 | 1.6 | 25752 | 0.4 | 27.4 | 69× |
| 6 | 0.5 | 9276 | 0.2 | 543.3 | 2717× |
| 7 | 1.9 | 38172 | 0.5 | 1.6 | 3× |
| 8 | 0.8 | 14817 | 0.2 | 75.2 | 376× |
| 9 | 0.8 | 10150 | 0.5 | 145.8 | 292× |
| 10 | 1.7 | 5859 | 1.0 | 5.5 | 6× |
| 11 | 1.8 | 8732 | 1.7 | 15.4 | 9× |
| 12 | 1.7 | 23451 | 1.1 | 35.6 | 32× |
| 13 | 4.3 | 50000 | 1.5 | 2.1 | 1× |
| 14 | 1.6 | 16746 | 0.8 | 4.1 | 5× |
| 15 | 2.4 | 50000 | 0.8 | 3.8 | 5× |
| 16 | 2.6 | 49437 | 2.8 | 52.9 | 19× |
| 17 | 0.6 | 20503 | 0.2 | 225.5 | 1128× |
| 18 | 4.5 | 50000 | 1.6 | 2.4 | 2× |
| 19 | 1.0 | 22903 | 0.2 | 162.6 | 813× |
| 20 | 1.2 | 12434 | 0.3 | 168.4 | 561× |
| 21 | 1.4 | 29270 | 0.3 | 72.7 | 242× |
| 22 | 1.3 | 23662 | | | |
| 23 | 1.2 | 50000 | 0.5 | 0.9 | 2× |
| 24 | 5.9 | 50000 | 2.8 | 4.9 | 2× |
| 25 | 100.0 | 50000 | 34.0 | 58.1 | 2× |
| 26 | 0.5 | 12990 | 0.3 | 9.5 | 32× |
| 27 (peak 1) | 1.3 | 33130 | 0.2 | 175.4 | 877× |
| 27 (peak 2) | 0.6 | 45624 | 0.3 | 160.3 | 534× |
| 28 | 0.9 | 46956 | 0.4 | 51.5 | 129× |
| 29 | 1.7 | 50000 | 0.8 | 167.7 | 210× |
| 30 | 1.2 | 39965 | 0.5 | 79.4 | 159× |
| 31 | 1.4 | 29996 | 0.3 | 47.2 | 157× |
| 32 | 1.5 | 21182 | 0.4 | 260.7 | 652× |
| 33 | 0.7 | 14070 | 0.4 | 341.6 | 854× |
| 34 | 0.6 | 13560 | 0.2 | 76.7 | 384× |
| 35 | 0.9 | 20264 | 0.3 | 102.0 | 340× |
| 36 | 0.7 | 19470 | 0.2 | 27.6 | 138× |
| 37 | 1.6 | 49891 | 0.7 | 8.3 | 12× |
| 38 | 1.2 | 22097 | 0.3 | 1.5 | 5× |
| 39 | 1.0 | 23479 | 0.3 | 35.4 | 118× |
| 40 | 0.8 | 34094 | 0.2 | 22.5 | 113× |
| 41 | 0.6 | 21488 | 0.4 | 0.5 | 1× |
| 42 | 100.0 | 50000 | 157.1 | 550.4 | 4× |
| 43 | 6.1 | 33411 | 1.5 | 279.1 | 186× |
| 44 | 0.7 | 24378 | 0.1 | 160.0 | 1600× |
| 45 | 2.0 | 50000 | 0.4 | 1.8 | 5× |
| 46 | 1.7 | 7715 | 0.1 | 2.3 | 23× |
| 47 | 1.8 | 27456 | 0.5 | 6.5 | 13× |
| 48 | 0.4 | 22903 | 0.2 | 8.1 | 41× |
| 49 | 0.7 | 29839 | 0.3 | 124.4 | 415× |
| 50 | 0.8 | 50000 | 0.5 | 10.3 | 21× |
| 51 | 1.3 | 41061 | 0.3 | 5.2 | 17× |
| 52 | 0.9 | 27016 | 0.3 | 6.2 | 21× |
| 53 | 1.7 | 9469 | 0.3 | 166.1 | 554× |
| 54 | 0.7 | 27277 | 0.3 | 53.7 | 179× |
| 55 | 1.7 | 50000 | 1.1 | 51.0 | 46× |
| 56 | 6.2 | 50000 | 3.4 | 5.0 | 1× |
| 57 | 27.9 | 50000 | 13.8 | 6.0 | <1× |
| 58 | 77.4 | 50000 | | | |
| 59 | 51.4 | 50000 | 22.8 | 49.1 | 2× |
| 60 | 78.6 | 50000 | 25.2 | 31.2 | 1× |
| 61 | 7.6 | 50000 | 1.9 | 3.4 | 2× |
| 62 | 31.1 | 50000 | 7.8 | 13.4 | 2× |
| 63 | 45.9 | 50000 | 11.1 | 15.5 | 1× | x in Table above indicates times. For examples "2×" means 2 times.

TABLE 2

| Example No. | MT4 EC$_{50}$ (nM) | CC$_{50}$ (nM) | RLUC CCM EC$_{50}$ (nM) | RLUC 50% HS EC$_{50}$ (nM) | RLUC 50% HS Shift |
|---|---|---|---|---|---|
| 64 | 2.9 | 22903 | 0.6 | 299.7 | 500× |
| 65 | 1.6 | 26331 | 0.6 | 107.0 | 178× |
| 66 | 3.9 | 30072 | 0.8 | 561.2 | 702× |
| 67 | 1.3 | 20017 | 0.3 | 190.2 | 634× |
| 68 | 1.2 | 15739 | 0.3 | 85.4 | 285× |
| 69 | 1.3 | 26260 | 0.2 | 94.1 | 471× |
| 70 | 1.3 | 26565 | 0.4 | 176.2 | 441× |
| 71 | 3.3 | 32102 | 0.2 | 82.4 | 412× |
| 72 | 1.2 | 31909 | 0.3 | 108.3 | 361× |
| 73 | 1.1 | 31210 | 0.2 | 65.2 | 326× |
| 74 | 2.1 | 22325 | 0.4 | 4.9 | 12× |
| 75 | 1.8 | 14072 | 0.3 | 1.8 | 6× |
| 76 | 2.2 | 10109 | 0.4 | 3.3 | 8× |
| 77 | 2.9 | 1484 | 0.5 | 17.7 | 35× |
| 78 | 1.0 | 3185 | 0.3 | 3.6 | 12× |
| 78 | 1.4 | 1367 | 0.2 | 8.6 | 43× |
| 79 | 4.8 | 50000 | 1.0 | 1.4 | 1× |
| 80 | 81.5 | 50000 | 15.7 | 30.1 | 2× |
| 81 | 2.1 | 19627 | 0.5 | 0.6 | 1× |
| 82 | 7.1 | 5463 | 1.3 | 186.1 | 143× |
| 83 | 2.3 | 16190 | 0.3 | 41.1 | 137× |
| 84 | 1.6 | 25831 | 0.3 | 22.3 | 74× |
| 85 | 1.0 | 29643 | 0.2 | 28.7 | 144× |
| 86 | 1.2 | 11909 | 0.3 | 68.4 | 228× |
| 87 | 1.2 | 10509 | 0.2 | 31.8 | 159× |
| 88 | 2.6 | 50000 | 0.3 | 279.8 | 933× |
| 89 | 1.3 | 50000 | 0.4 | 63.8 | 160× |
| 90 | 4.3 | 22304 | 1.3 | 22.1 | 17× |
| 90 | 3.2 | 20007 | 1.2 | 10.7 | 9× |
| 91 | 1.4 | 19971 | 0.2 | 157.7 | 789× |
| 92 | 0.7 | 24909 | 0.2 | 409.4 | 2047× |
| 93 | 0.7 | 13620 | 0.2 | 621.8 | 3109× |
| 94 | 1.0 | 30154 | 0.2 | 684.3 | 3422× |
| 95 | 0.6 | 24132 | | | |
| 96 | 1.1 | 31441 | 0.2 | 1.2 | 6× |
| 97 | 2.5 | 10363 | 0.5 | 1.8 | 4× |
| 98 | 3.0 | 12679 | 0.5 | 7.4 | 15× |
| 99 | 1.5 | 36511 | 0.2 | 19.7 | 99× |

TABLE 2-continued

| Example No. | MT4 EC$_{50}$ (nM) | CC$_{50}$ (nM) | RLUC CCM EC$_{50}$ (nM) | RLUC 50% HS EC$_{50}$ (nM) | RLUC 50% HS Shift |
|---|---|---|---|---|---|
| 100 | 1.5 | 50000 | 0.3 | 13.5 | 45× |
| 101 | 98.1 | 50000 | 34.0 | 408.4 | 12× |
| 102 | 11.5 | 8792 | 2.0 | 30.0 | 15× |
| 103 | 1.5 | 50000 | 0.2 | 0.4 | 2× |
| 104 | 2.6 | 50000 | 0.9 | 0.3 | 0× |
| 105 | 1.2 | 50000 | 0.3 | 15.5 | 52× |
| 106 | 0.9 | 50000 | 0.2 | 64.2 | 321× |
| 107 | 0.8 | 50000 | 0.3 | 10.2 | 34× |
| 108 | 3.5 | 50000 | 0.5 | 7.8 | 16× |
| 109 | 1.6 | 2887 | 0.3 | 3.9 | 13× |
| 110 | 1.2 | 11968 | 0.3 | 2.9 | 10× |
| 111 | 2.3 | 7232 | 0.4 | 1.9 | 5× |
| 112 | 0.7 | 50000 | 0.2 | 0.4 | 2× |
| 113 | 0.7 | 50000 | 0.1 | 0.7 | 7× |
| 114 | 6.1 | 50000 | 1.9 | 5.9 | 3× |
| 115 | 1.2 | 50000 | 0.3 | 5.1 | 17× |
| 116 | 5.8 | 50000 | | | |
| 116 | 1.8 | 50000 | 0.3 | 1.0 | 3× |
| 117 | 2.3 | 32180 | 0.4 | 0.6 | 2× |
| 117 | 5.5 | 50000 | 0.8 | 0.5 | 1× |
| 118 | 2.6 | 50000 | 0.4 | 0.4 | 1× |
| 119 | 1.5 | 50000 | 0.5 | 2.3 | 5× |
| 120 | 0.9 | 49355 | 0.2 | 188.7 | 944× |
| 120 | 0.8 | 50000 | 0.2 | 2.6 | 13× |
| 121 | 86.5 | 50000 | 16.9 | 19.9 | 1× |
| 122 | 6.4 | 38022 | 0.9 | 7.6 | 8× |
| 123 | 8.4 | 50000 | 2.1 | 1.4 | 1× |
| 124 | 0.8 | 29829 | 0.2 | 0.4 | 2× |
| 125 | 0.7 | 24211 | 0.2 | 30.2 | 151× |
| 126 | 0.5 | 31882 | 0.1 | 10.7 | 107× |
| 126 | 0.7 | 32577 | 0.1 | 4.7 | 47× |
| 127 | 1.2 | 49862 | 0.1 | 13.3 | 133× |
| 128 | 1.1 | 20521 | 0.2 | 18.4 | 92× |
| 129 | 0.5 | 27404 | 0.2 | 8.0 | 40× |
| 130 | 0.9 | 9839 | 0.2 | 362.9 | 1815× |
| 131 | 1.9 | 28926 | 0.5 | 8.1 | 16× |
| 132 | 1.4 | 30319 | | | |
| 133 | 1.7 | 20212 | 0.5 | 102.5 | 205× |
| 134 | 4.8 | 8499 | 1.9 | 6.3 | 3× |
| 135 | 7.1 | 6883 | 2.6 | 581.3 | 224× |
| 136 | 5.8 | 16562 | 1.7 | 8.7 | 5× |
| 137 | 1.5 | 42420 | 0.3 | 13.3 | 44× |
| 138 | 2.0 | 23228 | 0.5 | 13.1 | 26× |
| 139 | 1.4 | 30893 | 0.1 | 83.7 | 837× |
| 140 | 1.8 | 22823 | 0.1 | 1.7 | 17× |
| 141 | 0.9 | 30359 | 0.2 | 263.4 | 1317× |
| 142 | 3.9 | 50000 | 0.5 | 0.7 | 1× |
| 143 | 1.4 | 24392 | 0.1 | 78.4 | 784× |
| 144 | 1.3 | 4811 | 0.1 | 2.3 | 23× |
| 145 | 3.8 | 50000 | 1.1 | 7.5 | 7× | x in Table above indicates times. For examples "2×" means 2 times.

TABLE 2A

| Example No. | MT4 EC$_{50}$ (nM) | CC$_{50}$ (nM) | RLUC CCM EC$_{50}$ (nM) | RLUC 50% HS EC$_{50}$ (nM) | RLUC 50% HS Shift |
|---|---|---|---|---|---|
| 146 | 1.3 | 16888 | | | |
| 147 | 4.1 | 7532 | 1.3 | 12.3 | 10× |
| 148 | 3.4 | 50000 | 1.1 | 21.0 | 19× |
| 149a | 2.0 | 50000 | 0.8 | 4.8 | 6× |
| 149b | 1.4 | 39091 | 0.4 | 5.7 | 16× |
| 150 | 2.1 | 26970 | | | |
| 151 | 1.8 | 13843 | 0.3 | 69.2 | 203× |
| 152 | 4.2 | 14153 | | | |
| 153 | 0.9 | 17633 | 0.2 | 16.1 | 67× |
| 154 | 4.2 | 4143 | 1.2 | 22.1 | 18× |
| 155 | 1.0 | 28423 | 0.5 | 59.8 | 129× |
| 156 | 18.1 | 50000 | 25.0 | 79.8 | 3× |

TABLE 2A-continued

| Example No. | MT4 EC$_{50}$ (nM) | CC$_{50}$ (nM) | RLUC CCM EC$_{50}$ (nM) | RLUC 50% HS EC$_{50}$ (nM) | RLUC 50% HS Shift |
|---|---|---|---|---|---|
| 157 | 1.1 | 50000 | 0.3 | 4.1 | 12× |
| 158 | 1.7 | 2115 | 0.8 | 3.2 | 4× |
| 159 | 1.8 | 50000 | 0.8 | 1.1 | 1× |
| 160 | 1.5 | 50000 | 1.6 | 0.5 | 0× |
| 161 | 1.4 | 50000 | 0.4 | 0.9 | 2× |
| 162 | 3.6 | 50000 | 1.4 | 5.7 | 4× |
| 163 | 1.5 | 50000 | 0.9 | 2.0 | 2× |
| 164 | 3.0 | 45714 | | | |
| 165 | 1.4 | 6591 | 0.3 | 5.4 | 19× |
| 166 | 0.9 | 4599 | 0.2 | 1.3 | 7× |
| 167 | 1.7 | 35779 | 0.6 | 8.7 | 15× |
| 168 (peak 1) | 1.1 | 28944 | 0.4 | 2.0 | 5× |
| 168 (peak 2) | 2.0 | 37042 | 0.6 | 16.4 | 26× |
| 169 (peak 1) | 4.9 | 39008 | 1.4 | 10.0 | 7× |
| 169 (peak 2) | 4.3 | 45128 | 2.0 | 4.0 | 2× |
| 170 (peak 1) | 1.3 | 42043 | 0.3 | 5.0 | 16× |
| 170 (peak 2) | 1.7 | 42554 | 0.2 | 2.6 | 15× |
| 170 (peak 3) | 1.2 | 8241 | 0.3 | 43.4 | 132× |
| 170 (peak 4) | 1.7 | 33117 | 0.3 | 14.5 | 52× | x in Table above indicates times. For examples "2×" means 2 times.

TABLE 3

| Compound | MT4 EC$_{50}$ (nM) | RLUC CCM EC$_{50}$ (nM) | RLUC 50% HS EC$_{50}$ (nM) | RLUC 50% HS Shift |
|---|---|---|---|---|
| Example 40 | 0.8 | 0.2 | 22.5 | 112× |
| Example 1 | 0.8 | 0.25 | 92.0 | 368× |
| Reference Compound A | 1.1 | 0.35 | 2.0 | 6× |
| Reference Compound B | 1.5 | 0.28 | 1.1 | 4× |
| Reference Compound C | 1.2 | 0.25 | 2.0 | 8× |
| Reference Compound D | 1.3 | 0.22 | 7.5 | 34× | x in Table above indicates times. For examples "2×" means times.

Example 150: Double Mutant Shift (Fold Over Wild Type)

The HIV double mutant assay assesses the changes in efficacy of antiviral compounds against viral mutants compared to wild type. Each of the three mutant virus strains in this panel contain two amino acid substitutions (G140S/Q140R, E138K/Q148K and E92Q/N155H) of the parental HXB2. Test compounds and controls were serially diluted and spotted in replicates into 384 well black assay plates using acoustic transfer (Echo). Replicate sets of plates were made for each strain. MT-4 cells were grown in batch, centrifuged and resuspended in fresh CCM media (RPMI w/10% FBS, 1% PS) at 2×10$^6$ cells/ml. Cells were batch infected with each mutant strain at optimized volumes (currently HXB2 25 ul/ml; G140S/Q140R, E138K/Q148K and E92Q/N155H at 40 ul/ml cells). The size of each infection mix was based on number of sample plates to be tested. Each infection mix was transferred into 5 ml closed tubes and nutated rapidly on a shaker at 37 deg. incubator for 1 hour. The infection mixes were then diluted 25× in fresh CCM media then added to assay plates at 40 ul per well using a Viaflo 384 pipettor. After 5 day incubation at 37 degrees in a CO$_2$ incubator, assay plates were processed with Cell-titer glo reagent using a ViaFlo 384 with an addition/mixing program. Plates were read immediately on Envision reader. Assay signals were plotted and dose response curves generated to determine individual compound $EC_{50}$s. The effect of each mutation was assessed by comparing $EC_{50}$s of wild type and mutant strains.

TABLE 4

| Compound | Double Mutant Shift (fold over wild type) | | |
|---|---|---|---|
| | E92Q/ N155H | G140S/ Q148R | E138K/ Q148K |
| Example 40 | 1× | 5× | 4× |
| Example 1 | 1× | 4× | 3× |
| Reference Compound A | 2× | 10× | 13× |
| Reference Compound B | 3× | 12× | 18× |
| Reference Compound C | 2× | 5× | 3× |
| Reference Compound D | 1× | 5× | 6× | x in Table above indicates times. For examples "2×" means 2 times.

All of the U.S. patents, U.S. patent application publications, U.S. patent applications, foreign patents, foreign patent applications and non-patent publications referred to in this specification are incorporated herein by reference, in their entirety to the extent non inconsistent with the present description.

From the forgoing it will be appreciated that, although specific embodiments have been described herein for purposes of illustration, various modifications may be made without deviating from the spirit and scope of the disclosure. Accordingly, the disclosure is not limited except as by the appended claims.

We claim:

1. A compound, or a pharmaceutically acceptable salt thereof, wherein the compound is selected from the group consisting of:

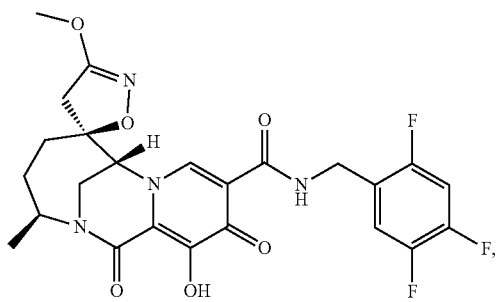

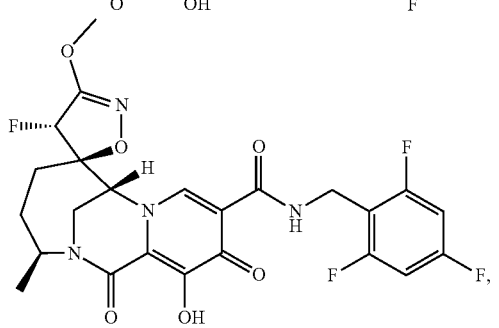

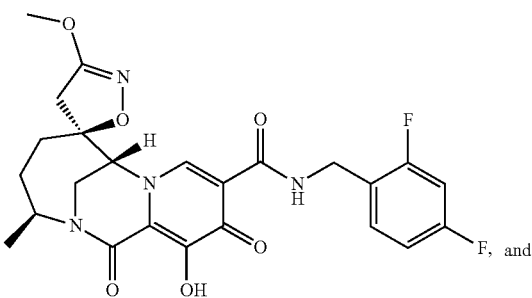

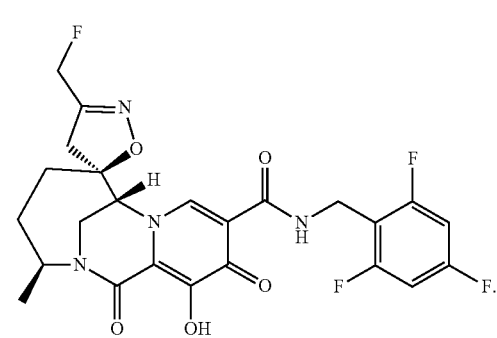

2. The compound of claim 1, or the pharmaceutically acceptable salt thereof, wherein the compound is:

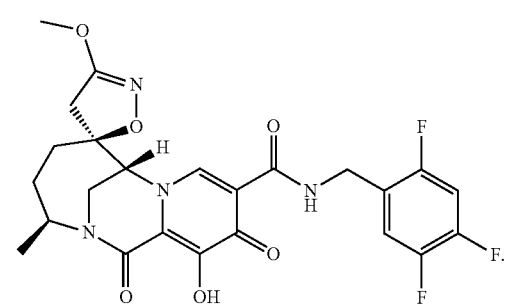 [SMILES: COC1=NO[C@@]2(CC[C@H](C)N3C[C@H]2n2cc(C(=O)NCc4cc(F)c(F)cc4F)c(=O)c(O)c2C3=O)C1]

3. The compound of claim 1, or the pharmaceutically acceptable salt thereof, wherein the compound is:

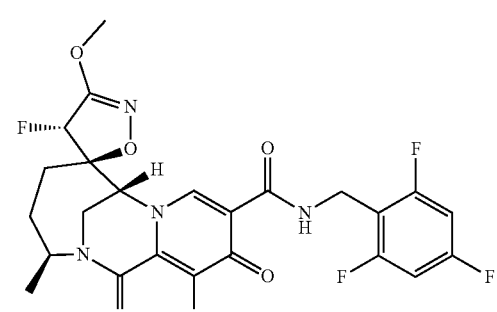

4. The compound of claim 1, or the pharmaceutically acceptable salt thereof, wherein the compound is:

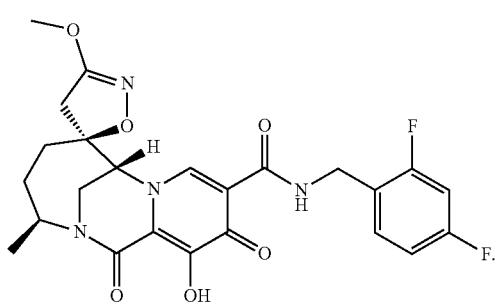 [SMILES: COC1=NO[C@@]2(CC[C@H](C)N3C[C@H]2n2cc(C(=O)NCc4ccc(F)cc4F)c(=O)c(O)c2C3=O)C1]

5. The compound of claim 1, or the pharmaceutically acceptable salt thereof, wherein the compound is:

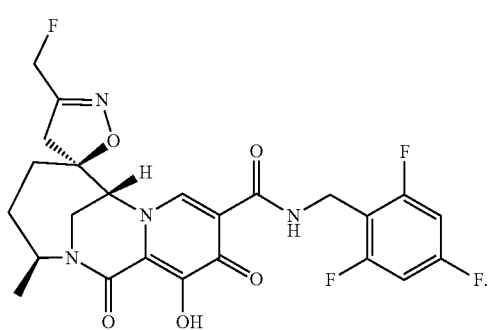 [SMILES: C[C@H]1CC[C@]2(CC(CF)=NO2)[C@H]2CN1C(=O)c1c(O)c(=O)c(C(=O)NCc3c(F)cc(F)cc3F)cn12]

6. The compound of claim 1, wherein the compound is:

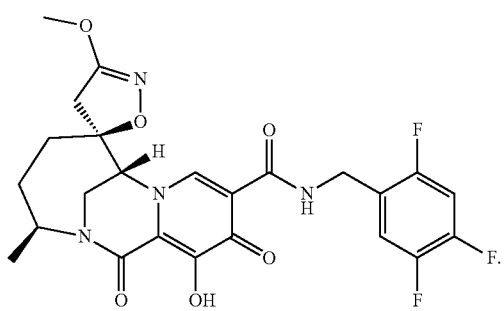 [SMILES: COC1=NO[C@@]2(CC[C@H](C)N3C[C@H]2n2cc(C(=O)NCc4cc(F)c(F)cc4F)c(=O)c(O)c2C3=O)C1]

7. The compound of claim 1, wherein the compound is:

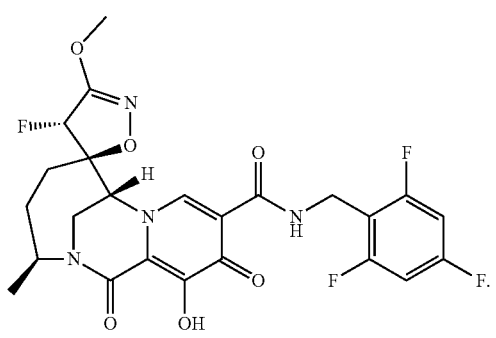 [SMILES: COC1=NO[C@@]2(CC[C@H](C)N3C[C@H]2n2cc(C(=O)NCc4c(F)cc(F)cc4F)c(=O)c(O)c2C3=O)[C@@H]1F]

8. The compound of claim 1, wherein the compound is:

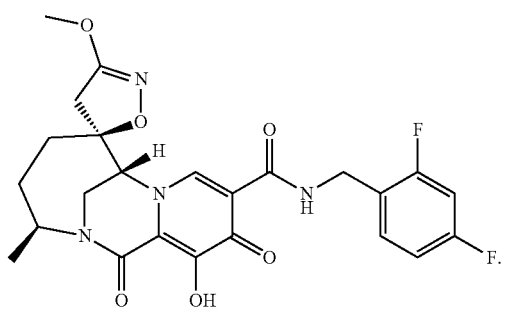 [SMILES: COC1=NO[C@@]2(CC[C@H](C)N3C[C@H]2n2cc(C(=O)NCc4ccc(F)cc4F)c(=O)c(O)c2C3=O)C1]

9. The compound of claim 1, wherein the compound is:

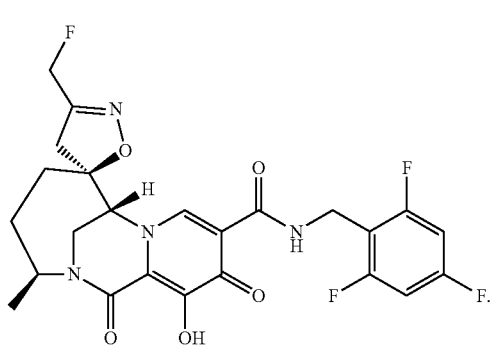

10. A pharmaceutical composition comprising a therapeutically effective amount of a compound selected from the group consisting of:

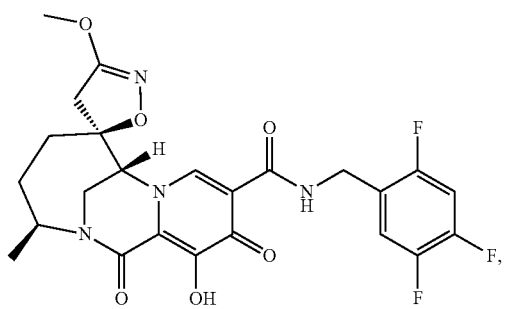

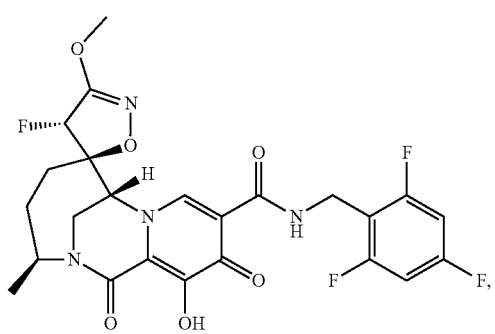

-continued

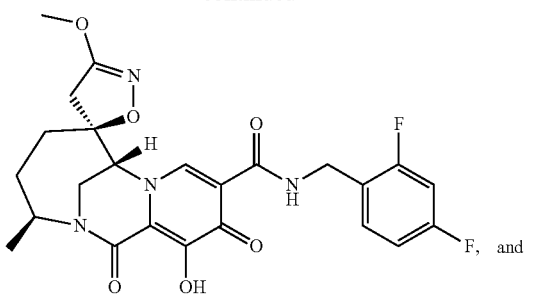

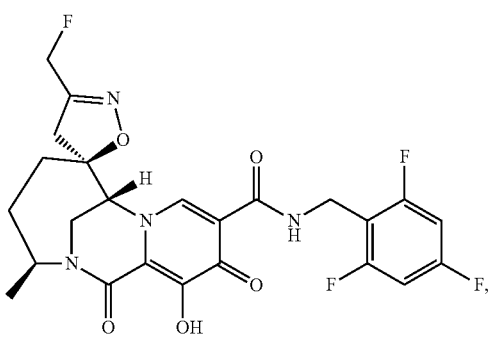 [SMILES: C[C@H]1CC[C@]2(CC(CF)=NO2)[C@H]2CN1C(=O)c1c(O)c(=O)c(C(=O)NCc3c(F)cc(F)cc3F)cn12]

or a pharmaceutically acceptable salt thereof.

11. The pharmaceutical composition of claim 10, further comprising an additional therapeutic agent.

12. The pharmaceutical composition of claim 11, wherein the additional therapeutic agent is an anti-HIV agent.

13. The pharmaceutical composition of claim 10, wherein the pharmaceutical composition is for oral or parenteral administration.

14. The pharmaceutical composition of claim 10, wherein the compound is:

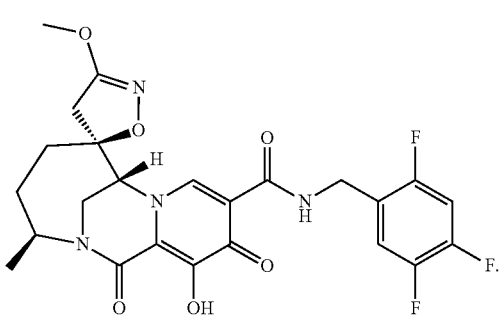 [SMILES: COC1=NO[C@@]2(CC[C@H](C)N3C[C@H]2n2cc(C(=O)NCc4cc(F)c(F)cc4F)c(=O)c(O)c2C3=O)C1]

15. The pharmaceutical composition of claim 10, wherein the compound is:

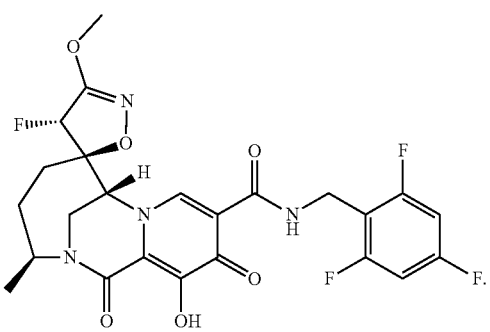 [SMILES: COC1=NO[C@@]2(CC[C@H](C)N3C[C@H]2n2cc(C(=O)NCc4c(F)cc(F)cc4F)c(=O)c(O)c2C3=O)[C@@H]1F]

16. The pharmaceutical composition of claim 10, wherein the compound is:

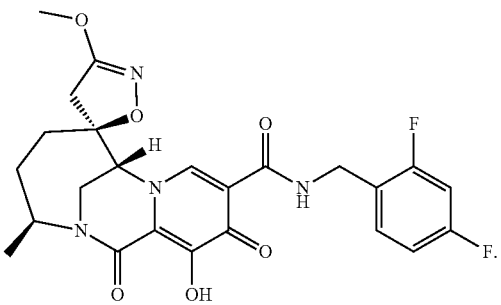 [SMILES: COC1=NO[C@@]2(CC[C@H](C)N3C[C@H]2n2cc(C(=O)NCc4ccc(F)cc4F)c(=O)c(O)c2C3=O)C1]

17. The pharmaceutical composition of claim 10, wherein the compound is:

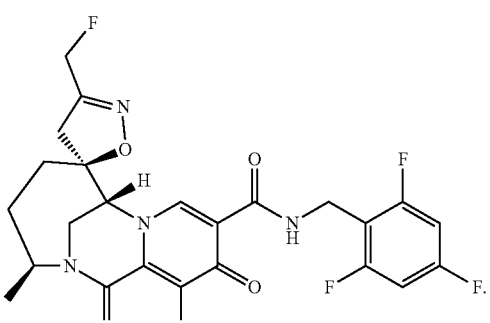

18. A kit comprising a compound selected from the group consisting of:

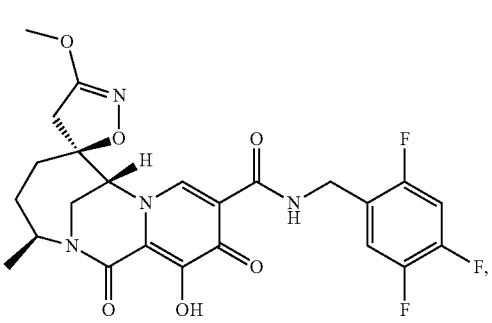

407
-continued

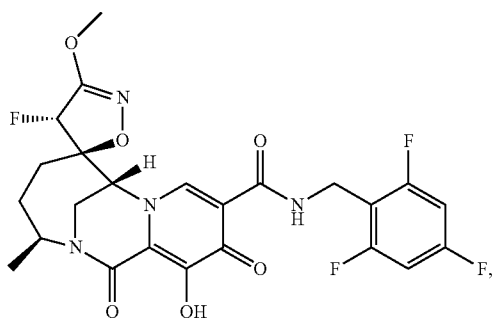

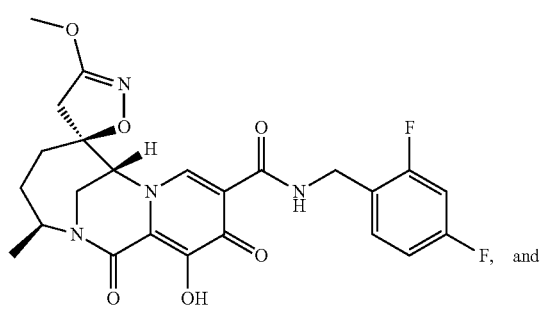

and

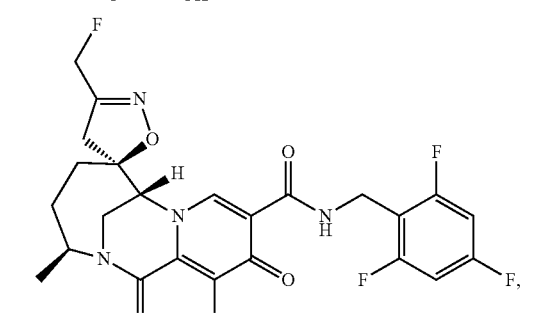

or a pharmaceutically acceptable salt thereof, and instructions for use.

19. The kit of claim 18, further comprising an additional therapeutic agent.

20. The kit of claim 19, wherein the additional therapeutic agent is an anti-HIV agent.

21. A method of treating an HIV infection in a human having the HIV infection, comprising administering to the human a therapeutically effective amount of a compound selected from the group consisting of:

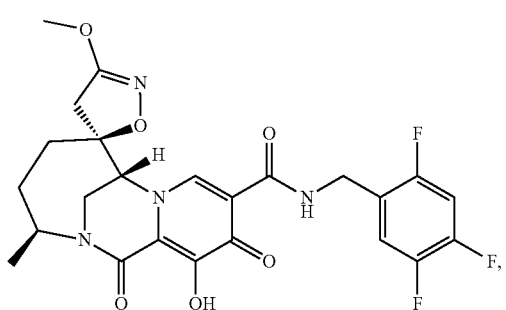

408
-continued

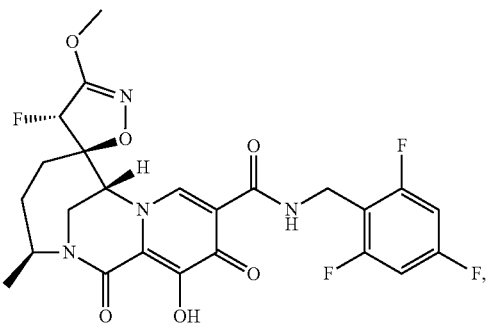

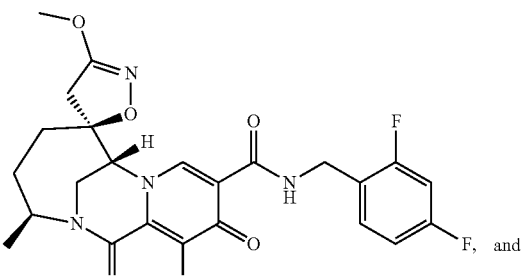

and

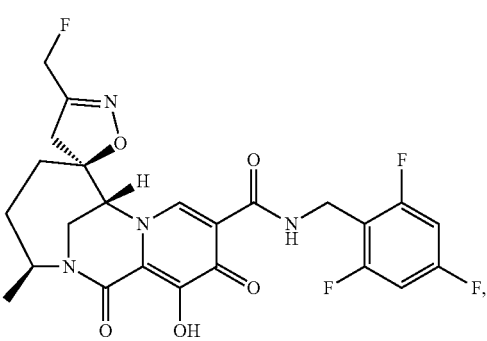

or a pharmaceutically acceptable salt thereof.

22. The method of claim 21, further comprising administering to the human a therapeutically effective amount of one, two, three, or four additional therapeutic agents.

23. The method of claim 22, wherein the additional therapeutic agent or agents are anti-HIV agents.

24. The method of claim 21, wherein the compound, or the pharmaceutically acceptable salt thereof, is administered to the human by oral, intravenous, subcutaneous, or intramuscular administration.

25. The method of claim 21, wherein the compound is:
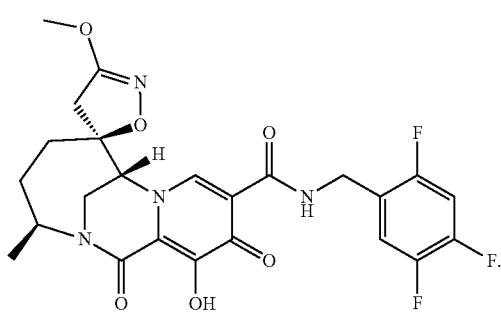 [SMILES: COC1=NO[C@@]2(CC[C@H](C)N3C[C@H]2n2cc(C(=O)NCc4cc(F)c(F)cc4F)c(=O)c(O)c2C3=O)C1]
26. The method of claim 21, wherein the compound is:
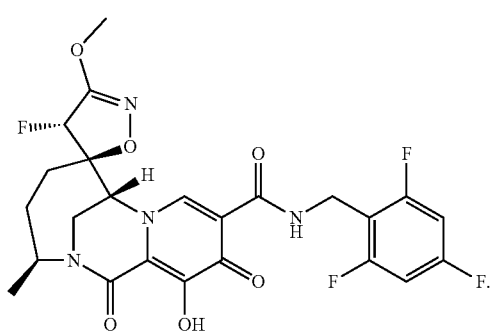 [SMILES: COC1=NO[C@@]2(CC[C@H](C)N3C[C@H]2n2cc(C(=O)NCc4c(F)cc(F)cc4F)c(=O)c(O)c2C3=O)[C@@H]1F]
27. The method of claim 21, wherein the compound is:
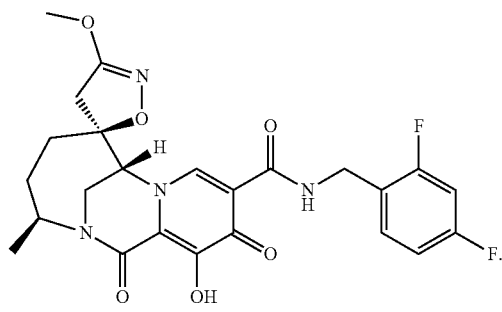 [SMILES: COC1=NO[C@@]2(CC[C@H](C)N3C[C@H]2n2cc(C(=O)NCc4ccc(F)cc4F)c(=O)c(O)c2C3=O)C1]
28. The method of claim 21, wherein the compound is:
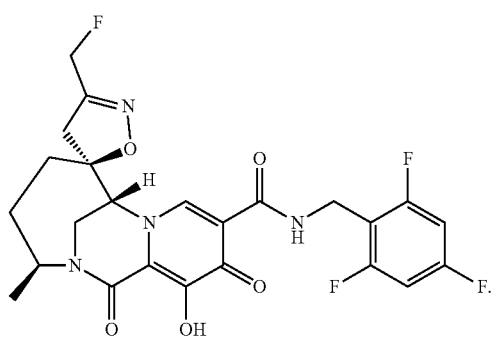 [SMILES: C[C@H]1CC[C@]2(CC(CF)=NO2)[C@H]2CN1C(=O)c1c(O)c(=O)c(C(=O)NCc3c(F)cc(F)cc3F)cn12]
* * * * *